US012433158B2

(12) United States Patent
Xu et al.

(10) Patent No.: US 12,433,158 B2
(45) Date of Patent: Sep. 30, 2025

(54) NITROGEN-CONTAINING COMPOUND, ORGANIC ELECTROLUMINESCENT DEVICE, AND ELECTRONIC APPARATUS

(71) Applicant: Shaanxi Lighte Optoelectronics Material Co., Ltd., Xi'an (CN)

(72) Inventors: Xianbin Xu, Xi'an (CN); Lei Yang, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 18/870,554

(22) PCT Filed: Sep. 15, 2023

(86) PCT No.: PCT/CN2023/119238
§ 371 (c)(1),
(2) Date: Nov. 29, 2024

(87) PCT Pub. No.: WO2024/183260
PCT Pub. Date: Sep. 12, 2024

(65) Prior Publication Data
US 2025/0176427 A1     May 29, 2025

(30) Foreign Application Priority Data

Mar. 7, 2023    (CN) .......................... 202310215156.0

(51) Int. Cl.
| | | |
|---|---|---|
| C07D 413/04 | (2006.01) | |
| C07D 413/10 | (2006.01) | |
| C07D 413/14 | (2006.01) | |
| C09K 11/02 | (2006.01) | |
| H10K 85/60 | (2023.01) | |
| H10K 50/11 | (2023.01) | |

(52) U.S. Cl.
CPC ......... *H10K 85/654* (2023.02); *C07D 413/04* (2013.01); *C07D 413/10* (2013.01); *C07D 413/14* (2013.01); *C09K 11/02* (2013.01); *H10K 85/615* (2023.02); *H10K 85/622* (2023.02); *H10K 85/626* (2023.02); *H10K 85/657* (2023.02); *H10K 85/6572* (2023.02); *H10K 85/6574* (2023.02); *H10K 85/6576* (2023.02); *H10K 50/11* (2023.02)

(58) Field of Classification Search
None
See application file for complete search history.

(56) References Cited

U.S. PATENT DOCUMENTS

| | | | |
|---|---|---|---|
| 2019/0148645 A1 | 5/2019 | Moon | |
| 2019/0214572 A1* | 7/2019 | Cho | ..................... H10K 85/657 |
| 2021/0083197 A1 | 3/2021 | Moon | |
| 2021/0320263 A1 | 10/2021 | Jung et al. | |
| 2023/0002332 A1* | 1/2023 | Jung | ..................... C07F 7/0812 |
| 2023/0008185 A1 | 1/2023 | Ma et al. | |
| 2023/0371374 A1* | 11/2023 | Cho | ..................... H10K 85/633 |
| 2024/0057475 A1* | 2/2024 | Kang | ................... C07D 209/88 |
| 2024/0090321 A1* | 3/2024 | Jung | ..................... C07C 211/61 |
| 2024/0276872 A1* | 8/2024 | Jung | ..................... H10K 85/342 |

FOREIGN PATENT DOCUMENTS

| | | |
|---|---|---|
| CN | 113582997 A | 11/2021 |
| CN | 113999220 A | 2/2022 |
| CN | 114105992 A | 3/2022 |
| KR | 20150136033 A | 12/2015 |
| WO | 2022206389 A1 | 10/2022 |

OTHER PUBLICATIONS

Hun Min Kang et al., "Synthesis, physical and electroluminescent properties of [1,2,4]-triazolo[4,3-a]-pyridine based bipolar red host materials and their applications in organic light emitting diodes," Journal of Luminescence, vol. 196, Dec. 31, 2018, pp. 470-476.
International Search Report from corresponding International Application No. PCT/CN2023/119238, mailed Jan. 3, 2024, 4 pages with translation.

\* cited by examiner

*Primary Examiner* — Robert S Loewe
(74) *Attorney, Agent, or Firm* — Tucker Ellis LLP

(57) ABSTRACT

The disclosure relates to the technical field of organic electroluminescent materials, and provides a nitrogen-containing compound and an organic electroluminescent device comprising the same, and an electronic apparatus. The compound of the disclosure adopts naphtho[2,1-d]oxazole as a core structure, and the compound of the disclosure used as a host material of an emitting layer can improve the carrier balance in the emitting layer, broaden the carrier recombination region, improve exciton generation and utilization efficiency, and improve the luminous efficiency and lifetime of a device.

12 Claims, 1 Drawing Sheet

NITROGEN-CONTAINING COMPOUND, ORGANIC ELECTROLUMINESCENT DEVICE, AND ELECTRONIC APPARATUS

CROSS REFERENCE TO RELATED APPLICATIONS

The present application claims priority to Chinese Patent Application No. 202310215156.0 filed on Mar. 7, 2023, the entire content of which is incorporated herein by reference.

TECHNICAL FIELD

The present disclosure relates to the technical field of organic electroluminescent materials, in particular to a nitrogen-containing compound, an organic electroluminescent device, and an electronic apparatus.

BACKGROUND

With the development of electronic technology and the progress of material science, the application scope of electronic components for achieving electroluminescence or photoelectric conversion is increasingly wide. An organic electroluminescent device (OLED) typically includes a cathode and an anode arranged opposite, and a functional layer arranged between the cathode and the anode. The functional layer is composed of a plurality of organic or inorganic film layers, and generally includes an organic emitting layer, a first hole transport layer, an electron transport layer, etc. When a voltage is applied to the cathode and the anode, the two electrodes generate an electric field. Under the action of the electric field, electrons on the cathode side move to the organic emitting layer, holes on the anode side also move to the organic emitting layer, the electrons and the holes combine in the organic emitting layer to form excitons, and the excitons are in an excited state to release energy outwards, so that the organic emitting layer emits light outwards.

In existing organic electroluminescent devices, the main problems are embodied in lifetime and efficiency. With the increasing size of displays, the driving voltage also increases, and the luminous efficiency and current efficiency need to be improved. Therefore, it is necessary to continue developing novel materials to further improve the performance of organic electroluminescent devices.

SUMMARY

In view of the above problems existing in the prior art, the objective of the present disclosure is to provide a nitrogen-containing compound and an organic electroluminescent device containing the same, and an electronic apparatus. The nitrogen-containing compound can be used in an organic electroluminescent device to improve the performance of the device.

According to a first aspect of the disclosure, a nitrogen-containing compound is provided. The nitrogen-containing compound has a structure represented by formula 1 below:

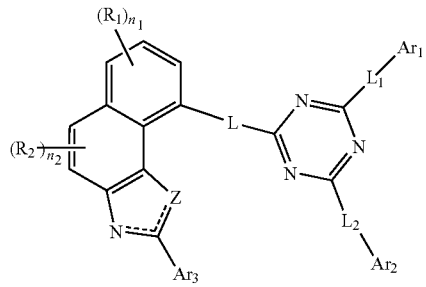

formula 1 where one of X and Z is —N═, and the other is O or S;

$L_1$ and $L_2$ are the same or different, and are each independently selected from a single bond, substituted or unsubstituted arylene with 6 to 20 carbon atoms, and substituted or unsubstituted heteroarylene with 3 to 18 carbon atoms;

L is selected from a single bond, substituted or unsubstituted arylene with 6 to 20 carbon atoms, and substituted or unsubstituted heteroarylene with 3 to 12 carbon atoms;

the substituent(s) in L, $L_1$, and $L_2$ are the same or different, and are each independently selected from deuterium, cyano, a halogen group, alkyl with 1 to 5 carbon atoms, haloalkyl with 1 to 5 carbon atoms, deuterated alkyl with 1 to 5 carbon atoms, trialkylsilyl with 3 to 8 carbon atoms, aryl with 6 to 14 carbon atoms, deuterated aryl with 6 to 14 carbon atoms, heteroaryl with 3 to 12 carbon atoms, and cycloalkyl with 5 to 10 carbon atoms;

$Ar_1$ and $Ar_2$ are the same or different, and are each independently selected from substituted or unsubstituted aryl with 6 to 30 carbon atoms, a group represented by formula 2, and a group represented by formula 3;

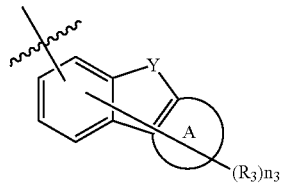

formula 2

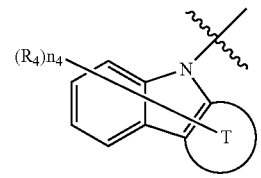

formula 3 ring A and ring T are each independently selected from a benzene ring and a naphthalene ring;

Y is selected from O, S, and N(Ar);

Ar is selected from substituted or unsubstituted aryl with 6 to 18 carbon atoms, and substituted or unsubstituted heteroaryl with 3 to 12 carbon atoms;

the substituent(s) in Ar are the same or different, and are each independently selected from deuterium, cyano, a halogen group, alkyl with 1 to 5 carbon atoms, deuterated alkyl with 1 to 5 carbon atoms, haloalkyl with 1 to 5 carbon atoms, trialkylsilyl with 3 to 8 carbon atoms, aryl with 6 to 12 carbon atoms, deuterated aryl with 6 to 12 carbon atoms, heteroaryl with 3 to 12 carbon atoms, and cycloalkyl with 5 to 10 carbon atoms;

$Ar_3$ is selected from substituted or unsubstituted aryl with 6 to 30 carbon atoms, substituted or unsubstituted heteroaryl with 3 to 30 carbon atoms, alkyl with 1 to 10 carbon atoms, and cycloalkyl with 5 to 10 carbon atoms;

the substituent(s) in $Ar_1$, $Ar_2$, and $Ar_3$ are the same or different, and are each independently selected from hydrogen, deuterium, cyano, a halogen group, alkyl with 1 to 10 carbon atoms, haloalkyl with 1 to 10 carbon atoms, deuterated alkyl with 1 to 10 carbon atoms, trialkylsilyl with 3 to 12 carbon atoms, aryl with 6 to 18 carbon atoms, deuterated aryl with 6 to 18 carbon atoms, heteroaryl with 3 to 18 carbon atoms, and cycloalkyl with 5 to 10 carbon atoms; optionally, any two adjacent substituents form a saturated or unsaturated 5- to 13-membered ring;

$R_1$, $R_2$, $R_3$, and $R_4$ are the same or different, and are each independently selected from hydrogen, deuterium, cyano, a halogen group, alkyl with 1 to 10 carbon atoms, haloalkyl with 1 to 10 carbon atoms, deuterated alkyl with 1 to 10 carbon atoms, trialkylsilyl with 3 to 12 carbon atoms, triphenylsilyl, aryl with 6 to 18 carbon atoms, deuterated aryl with 6 to 18 carbon atoms, heteroaryl with 3 to 18 carbon atoms, and cycloalkyl with 5 to 10 carbon atoms;

$n_1$ represents the number of $R_1$, and $n_1$ is selected from 0, 1, 2, and 3;

$n_2$ represents the number of $R_2$, and $n_2$ is selected from 0, 1, and 2;

$n_3$ represents the number of $R_3$, and $n_3$ is selected from 0, 1, 2, 3, 4, 5, 6, and 7; and $n_4$ represents the number of $R_4$, and $n_4$ is selected from 0, 1, 2, 3, 4, 5, 6, 7, and 8.

According to a second aspect of the disclosure, an organic electroluminescent device is provided, including an anode and a cathode arranged opposite, and a functional layer arranged between the anode and the cathode, where the functional layer contains the nitrogen-containing compound described above.

According to a third aspect of the disclosure, an electronic apparatus is provided, including the organic electroluminescent device described in the second aspect.

The compound in the disclosure adopts naphtho[2,1-d] oxazole as a parent nucleus structure, which is connected to substituted triazine at position 9 as an electron transport type red light host material. On the one hand, the special connection maintains a high first triplet energy level value ($T_1$) of the material while enabling the material to have strong carrier transport capability and high energy transfer efficiency. On the other hand, the special connection enables the compound structure to have some torsion, which suppresses excessive stacking between compound molecules and suppresses compound crystallization, thereby endowing a compound film with high stability. When the compound of the disclosure is used as an electron transport material in a hybrid host material, the compound can improve the carrier balance in the light-emitting layer, broaden the carrier recombination region, improve exciton generation and utilization efficiency, and improve the luminous efficiency and lifetime of a device.

BRIEF DESCRIPTION OF THE DRAWINGS

The accompanying drawings are used to provide a further understanding of the disclosure, constitute a part of the description, and are used for interpreting the disclosure together with the following specific embodiments, rather than limiting the disclosure.

REFERENCE NUMERALS

Figure 1:
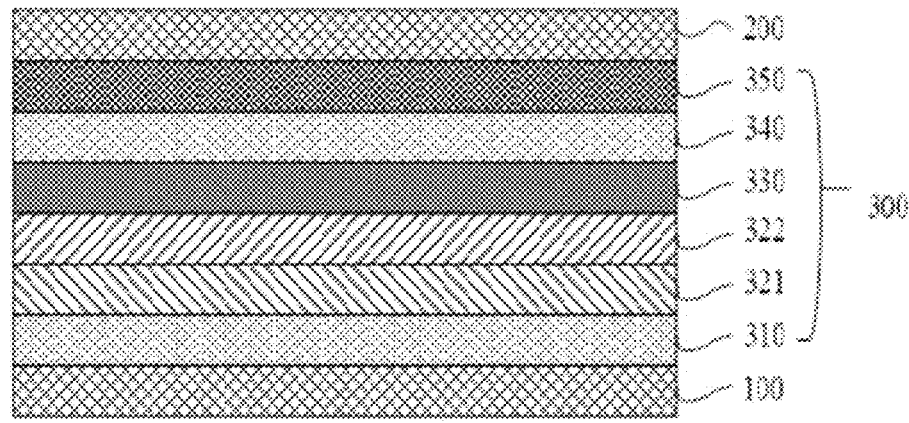
FIG. 1 is a schematic structural diagram of an organic electroluminescent device in an embodiment of the disclosure.

100. Anode 200. Cathode 300. Functional layer 310. Hole injection layer 321. First hole 322. Second hole 330. Organic light-340. Electron transport layer transport layer emitting layer transport layer 350. Electron 400. Electronic injection layer apparatus

DETAILED DESCRIPTION

Exemplary embodiments are now described more comprehensively with reference to the accompanying drawings. However, the exemplary embodiments can be implemented in various forms, and should not be construed as being limited to the examples set forth herein. On the contrary, these embodiments are provided to make the disclosure more comprehensive and complete, and fully convey the concept of the exemplary embodiments to those skilled in the art. The described features, structures, or characteristics may be incorporated in one or more embodiments in any suitable manner. In the following description, many specific details are provided to provide a sufficient understanding of the embodiments of the present disclosure.

In a first aspect, the disclosure provides a nitrogen-containing compound. The nitrogen-containing compound has a structure represented by formula 1 below:

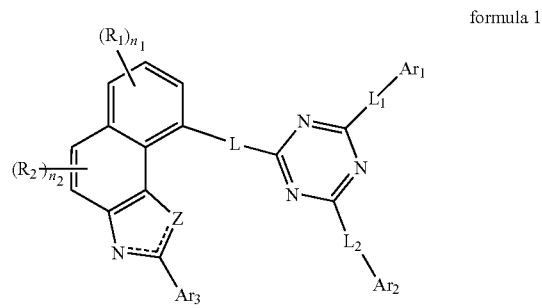

formula 1 where one of X and Z is —N═, and the other is O or S;

$L_1$ and $L_2$ are the same or different, and are each independently selected from a single bond, substituted or unsubstituted arylene with 6 to 20 carbon atoms, and substituted or unsubstituted heteroarylene with 3 to 18 carbon atoms;

L is selected from a single bond, substituted or unsubstituted arylene with 6 to 20 carbon atoms, and substituted or unsubstituted heteroarylene with 3 to 12 carbon atoms;

the substituent(s) in L, $L_1$, and $L_2$ are the same or different, and are each independently selected from deuterium, cyano, a halogen group, alkyl with 1 to 5 carbon atoms, haloalkyl with 1 to 5 carbon atoms, deuterated alkyl with 1 to 5 carbon atoms, trialkylsilyl with 3 to 8 carbon atoms, aryl with 6 to 14 carbon atoms, deuterated aryl with 6 to 14 carbon atoms, heteroaryl with 3 to 12 carbon atoms, and cycloalkyl with 5 to 10 carbon atoms;

$Ar_1$ and $Ar_2$ are the same or different, and are each independently selected from substituted or unsubstituted aryl with 6 to 30 carbon atoms, a group represented by formula 2, and a group represented by formula 3;

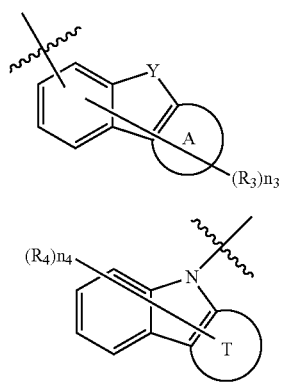

formula 2 formula 3 ring A and ring T are each independently selected from a benzene ring and a naphthalene ring;

Y is selected from O, S, and N(Ar);

Ar is selected from substituted or unsubstituted aryl with 6 to 18 carbon atoms, and substituted or unsubstituted heteroaryl with 3 to 12 carbon atoms;

the substituent(s) in Ar are the same or different, and are each independently selected from deuterium, cyano, a halogen group, alkyl with 1 to 5 carbon atoms, deuterated alkyl with 1 to 5 carbon atoms, haloalkyl with 1 to 5 carbon atoms, trialkylsilyl with 3 to 8 carbon atoms, aryl with 6 to 12 carbon atoms, deuterated aryl with 6 to 12 carbon atoms, heteroaryl with 3 to 12 carbon atoms, and cycloalkyl with 5 to 10 carbon atoms;

$Ar_3$ is selected from substituted or unsubstituted aryl with 6 to 30 carbon atoms, substituted or unsubstituted heteroaryl with 3 to 30 carbon atoms, alkyl with 1 to 10 carbon atoms, and cycloalkyl with 5 to 10 carbon atoms;

the substituent(s) in $Ar_1$, $Ar_2$, and $Ar_3$ are the same or different, and each is independently selected from hydrogen, deuterium, cyano, a halogen group, alkyl with 1 to 10 carbon atoms, haloalkyl with 1 to 10 carbon atoms, deuterated alkyl with 1 to 10 carbon atoms, trialkylsilyl with 3 to 12 carbon atoms, aryl with 6 to 18 carbon atoms, deuterated aryl with 6 to 18 carbon atoms, heteroaryl with 3 to 18 carbon atoms, and cycloalkyl with 5 to 10 carbon atoms; optionally, any two adjacent substituents form a saturated or unsaturated 5- to 13-membered ring;

$R_1$, $R_2$, $R_3$, and $R_4$ are the same or different, and each is independently selected from hydrogen, deuterium, cyano, a halogen group, alkyl with 1 to 10 carbon atoms, haloalkyl with 1 to 10 carbon atoms, deuterated alkyl with 1 to 10 carbon atoms, trialkylsilyl with 3 to 12 carbon atoms, triphenylsilyl, aryl with 6 to 18 carbon atoms, deuterated aryl with 6 to 18 carbon atoms, heteroaryl with 3 to 18 carbon atoms, and cycloalkyl with 5 to 10 carbon atoms;

$n_1$ represents the number of $R_1$, and $n_1$ is selected from 0, 1, 2, and 3;

$n_2$ represents the number of $R_2$, and $n_2$ is selected from 0, 1, and 2;

$n_3$ represents the number of $R_3$, and $n_3$ is selected from 0, 1, 2, 3, 4, 5, 6, and 7; and $n_4$ represents the number of $R_4$, and $n_4$ is selected from 0, 1, 2, 3, 4, 5, 6, 7, and 8.

In the disclosure, the terms "optional" and "optionally" mean that the subsequently described events or circumstance may or may not occur. For example, "optionally, any two adjacent substituents form a ring" means that the two substituents may or may not form a ring, including: a scenario where the two adjacent substituents form a ring and a scenario where the two adjacent substituents do not form a ring. For another example, "in $Ar_1$, $Ar_2$, and $Ar_3$, optionally, any two adjacent substituents form a ring" means that any two adjacent substituents in $Ar_1$, $Ar_2$, and $Ar_3$ are interconnected to form a ring, or any two adjacent substituents in $Ar_1$, $Ar_2$, and $Ar_3$ may each independently exist. "Any two adjacent" may include two substituents on the same atom, and may also include one substituent on each of two adjacent atoms, where when two substituents are on the same atom, the two substituents can form a saturated or unsaturated spiro ring together with an atom to which they are connected together; and when one substituent is on each of two adjacent atoms, the two substituents can be fused into a ring.

In the disclosure, the saturated or unsaturated 5- to 13-membered ring refers to a carbon ring or heterocycle containing 5 to 13 ring atoms, such as but not limited to cyclopentane, cyclohexane, benzene ring, fluorene ring, pyran ring, tetrahydropyran ring, piperidine ring, tetrahydropyridine ring, etc.

In the disclosure, the adopted descriptions of "each of . . . is independently", " . . . each is respectively", and " . . . are (is) each independently" can be interchanged, and should be understood in a broad sense, indicating that specific options expressed between the same symbols in different groups do not affect each other, or specific options expressed between the same symbols in the same group do not affect each other. For example,

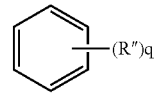

Formula Q-1

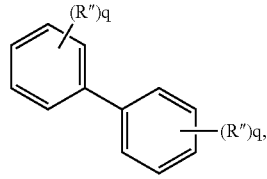

Formula Q-2 where each q is independently 0, 1, 2 or 3, and each R" is independently selected from hydrogen, deuterium, fluorine, or chlorine" means: a formula Q-1 represents that the benzene ring has q substituent(s) R", each R" can be the same or different, and the options of each R" do not affect each other; and a formula Q-2 represents that each benzene ring of biphenyl has q substituent(s) R", the numbers q of R" substituent(s) on the two benzene rings can be the same or different, each R" may be the same or different, and the options of each R" do not affect each other.

In the disclosure, the term "substituted or unsubstituted" indicates that the functional group described behind the term may or may not have a substituent (hereinafter, for the convenience of description, the substituents are collectively referred to as Rc). For example, "substituted or unsubstituted aryl" indicates aryl with a substituent Rc or aryl without a substituent. The above substituent, namely Rc, may be, for example, deuterium, a halogen group, cyano, heteroaryl, aryl, trialkylsilyl, alkyl, halogenated alkyl, deuterated alkyl, deuterated aryl, halogenated aryl, cycloalkyl, etc. The number of substituent(s) may be one or more.

In the disclosure, "a plurality of" refers to two or more, such as 2, 3, 4, 5, 6, etc.

The hydrogen atom in the compound structure of the disclosure includes various isotopic atoms of hydrogen, such as hydrogen (H), deuterium (D), or tritium (T).

In the disclosure, the number of carbon atoms of a substituted or unsubstituted functional group refers to the number of all carbon atoms. For example, if L is substituted arylene with 12 carbon atoms, the number of all carbon atoms of the arylene and substituent(s) on the arylene is 12.

In the disclosure, aryl refers to an optional functional group or substituent derived from an aromatic carbocyclic ring. The aryl may be monocyclic aryl (such as phenyl) or polycyclic aryl. In other words, the aryl may be monocyclic aryl, fused-ring aryl, two or more monocyclic aryls connected by a carbon-carbon single bond(s), monocyclic aryl and fused-ring aryl connected by a carbon-carbon single bond, or two or more fused-ring aryls connected by a carbon-carbon single bond(s). That is, unless otherwise specified, two or more aromatic groups connected by a carbon-carbon single bond(s) may also be considered as aryl of the disclosure. The fused-ring aryl may include, for example, bicyclic fused aryl (such as naphthyl), tricyclic fused aryl (such as phenanthryl, fluorenyl, and anthryl). The aryl does not contain heteroatoms such as B, N, O, S, P, Se, and Si. Examples of the aryl may include, but are not limited to, phenyl, naphthyl, fluorenyl, phenyl-naphthyl, spirobifluorenyl

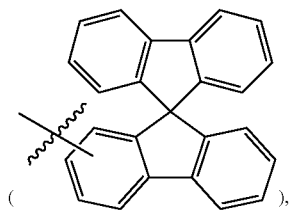

(                                                              ), anthryl, phenanthryl, biphenyl, terphenyl, triphenylene, perylenyl, benzo[9,10]phenanthryl, pyrenyl, benzofluoranthenyl, chrysenyl, etc.

In the disclosure, the arylene referred to refers to a divalent or multivalent group formed by further loss of one or more hydrogen atoms from the aryl.

In the disclosure, the terphenyl includes

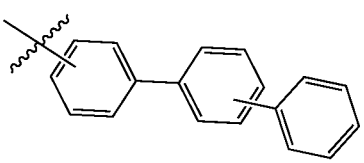

and

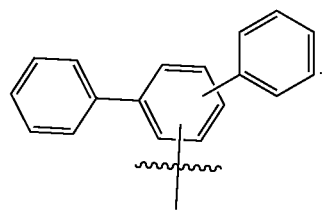

.

In the disclosure, the number of carbon atoms in the substituted aryl refers to the total number of carbon atoms in the aryl and the substituents on the aryl, for example, the substituted aryl with 18 carbon atoms indicates that the total number of carbon atoms of the aryl and the substituents on the aryl is 18.

In the disclosure, the number of carbon atoms in the substituted or unsubstituted aryl (arylene) may be 6, 8, 10, 12, 13, 14, 15, 16, 17, 18, 19, 20, 21, 22, 23, 24, 25, 26, 28, or 30. In some embodiments, the substituted or unsubstituted aryl is substituted or unsubstituted aryl with 6 to 30 carbon atoms. In other embodiments, the substituted or unsubstituted aryl is substituted or unsubstituted aryl with 6 to 20 carbon atoms. In other embodiments, the substituted or unsubstituted aryl is substituted or unsubstituted aryl with 6 to 25 carbon atoms. In other embodiments, the substituted or unsubstituted aryl is substituted or unsubstituted aryl with 6 to 18 carbon atoms. In other embodiments, the substituted or unsubstituted aryl is substituted or unsubstituted aryl with 6 to 15 carbon atoms.

In the disclosure, the fluorenyl may be substituted with one or more substituents. When the fluorenyl is substituted, the substituted fluorenyl may be, but is not limited to,

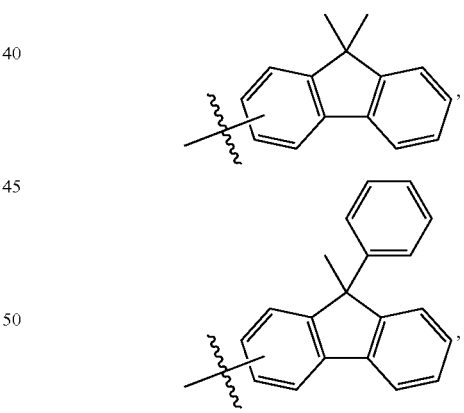

,

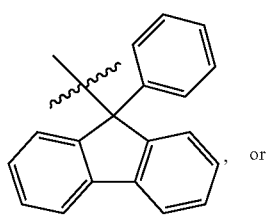

, or

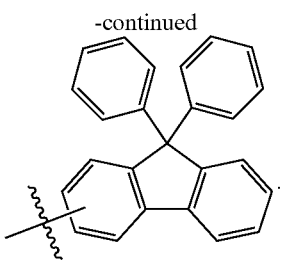

In the disclosure, the aryl as substituents of L, $L_1$, $L_2$, $Ar_1$, $Ar_2$, and $Ar_3$ includes, but is not limited to, phenyl, naphthyl, phenanthryl, biphenyl, fluorenyl, etc.

In the disclosure, the heteroaryl refers to a monovalent aromatic ring containing 1, 2, 3, 4, 5, or 6 heteroatoms or derivatives thereof, and the heteroatoms may be one or more of B, O, N, P, Si, Se, and S. The heteroaryl may be monocyclic heteroaryl or polycyclic heteroaryl. In other words, the heteroaryl may be a system of a single aromatic ring or a system of multiple aromatic rings connected by carbon-carbon single bonds, and any aromatic ring system is one aromatic monocyclic ring or one aromatic fused ring. For example, the heteroaryl may include, but is not limited to, thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolinyl, quinazolinyl, quinoxalinyl, phenoxazinyl, phthalazinyl, pyridopyrimidinyl, pyridopyrazinyl, pyrazinopyrazinyl, isoquinolinyl, indolyl, carbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, phenothiazinyl, silafluorenyl, dibenzofuranyl, N-phenylcarbazolyl, N-pyridylcarbazolyl, N-methylcarbazolyl, etc.

In the disclosure, the heteroarylene referred to refers to a divalent or multivalent group formed by further loss of one or more hydrogen atoms from the heteroaryl.

In the disclosure, the number of carbon atoms in the substituted or unsubstituted heteroaryl (heteroarylene) may be selected from 3, 4, 5, 6, 7, 8, 9, 10, 11, 12, 13, 14, 15, 16, 17, 18, 19, 20, 21, 22, 23, 24, 25, 26, 27, 28, 29, 30, etc. In some embodiments, the substituted or unsubstituted heteroaryl is substituted or unsubstituted heteroaryl having a total carbon atoms number of 3 to 18. In other embodiments, the substituted or unsubstituted heteroaryl is substituted or unsubstituted heteroaryl having a total carbon atoms number of 3 to 12. In other embodiments, the substituted or unsubstituted heteroaryl is substituted or unsubstituted heteroaryl having a total carbon atoms number of 5 to 12.

In the disclosure, the heteroaryl as substituents of L, $L_1$, $L_2$, $Ar_1$, $Ar_2$, and $Ar_3$ includes, but is not limited to, pyridyl, carbazolyl, quinolyl, isoquinolyl, phenanthrolinyl, benzoxazolyl, benzothiazolyl, benzimidazolyl, dibenzothiophenyl, and dibenzofuranyl.

In the disclosure, the substituted heteroaryl may indicate that one or more hydrogen atoms in the heteroaryl is substituted with groups such as a deuterium atom, a halogen group, cyano, aryl, heteroaryl, trialkylsilyl, alkyl, cycloalkyl, haloalkyl, etc. It should be understood that the number of carbon atoms in the substituted heteroaryl refers to the total number of carbon atoms of the heteroaryl and the substituents on the heteroaryl.

In the disclosure, the alkyl with 1 to 10 carbon atoms may include linear alkyl with 1 to 10 carbon atoms and branched alkyl with 3 to 10 carbon atoms. The number of carbon atoms in the alkyl is, for example, 1, 2, 3, 4, 5, 6, 7, 8, 9, or 10. Specific examples of the alkyl include, but are not limited to, methyl, ethyl, n-propyl, isopropyl, n-butyl, isobutyl, tert-butyl, n-pentyl, isopentyl, neopentyl, n-hexyl, etc.

In the disclosure, the halogen group is, for example, fluorine, chlorine, bromine, or iodine.

In the disclosure, specific examples of the trialkylsilyl include, but are not limited to, trimethylsilyl, triethylsilyl, etc.

In the disclosure, specific examples of the haloalkyl include, but are not limited to, trifluoromethyl.

In the disclosure, specific examples of the deuterated alkyl include, but are not limited to, trideuteromethyl.

In the disclosure, the deuterated aryl refers to aryl containing deuterium, such as but not limited to pentadeuterophenyl, heptadeuteronaphthyl, deuterobiphenyl, etc.

In the disclosure, the haloaryl refers to aryl with a halogen substituent, such as but not limited to fluorophenyl, fluoronaphthyl, fluorobiphenyl, etc.

In the disclosure, the number of carbon atoms in the cycloalkyl with 5 to 10 carbon atoms is, for example, 5, 6, 7, 8, or 10. Specific examples of the cycloalkyl include, but are not limited to, cyclopentyl, cyclohexyl, and adamantyl.

In the disclosure, an unpositioned connecting bond refers to a single bond

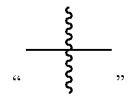

extending from a ring system, which means that that one end of the connecting bond can be connected to any position through which the bond penetrates in the ring system, and the other end can be connected to the rest of the compound molecule. For example, as shown in the following formula (f), the naphthyl represented by formula (f) is connected to other positions of a molecule by two unpositioned connecting bonds penetrating a dicyclic ring, which includes any possible connecting mode as shown in formulae (f-1) to (f-10):

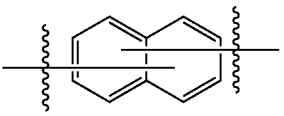

(f)

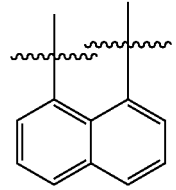

(f-1)

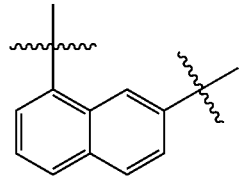

(f-2)

-continued (f-3) 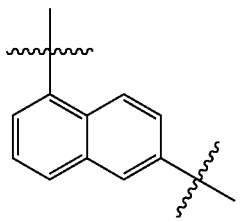

(f-4) 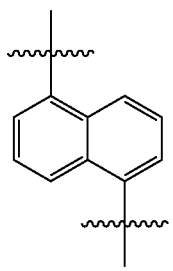

(f-5) 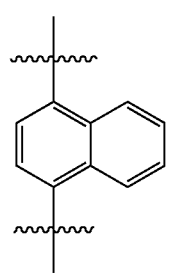

(f-6) 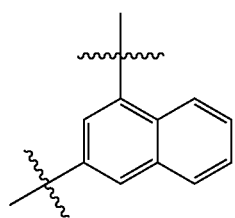

(f-7) 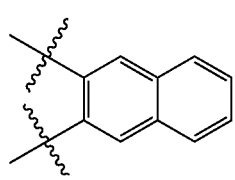

(f-8) 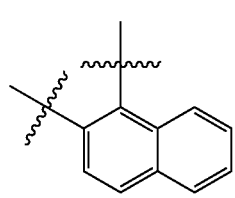

(f-9) 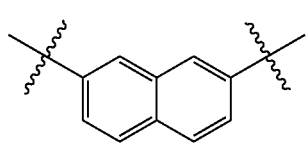

-continued (f-10) 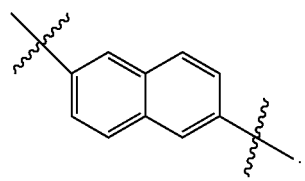

For another example, as shown in the following formula (X'), the dibenzofuranyl represented by formula (X') is connected to other positions of a molecule by an unpositioned connecting bond extending from the middle of a benzene ring on one side, which includes any possible connecting mode as shown in formulae (X'-1) to (X'-4):

(X')

(X'-1) 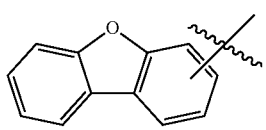

(X'-2) 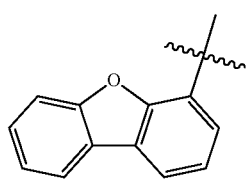

(X'-3) 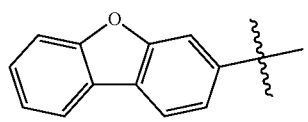

(X'-4) 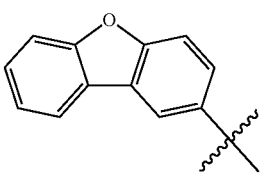

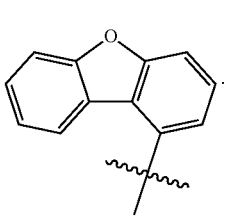

The unpositioned substituent in the disclosure refers to a substituent connected by a single bond extending from the center of a ring system, indicating that the substituent can be connected to any possible position in the ring system. For example, as shown in the following formula (Y), the substituent R' represented by formula (Y) is connected to a quinoline ring through an unpositioned connecting bond, which includes any possible connecting mode as shown in formulae (Y-1) to (Y-7):

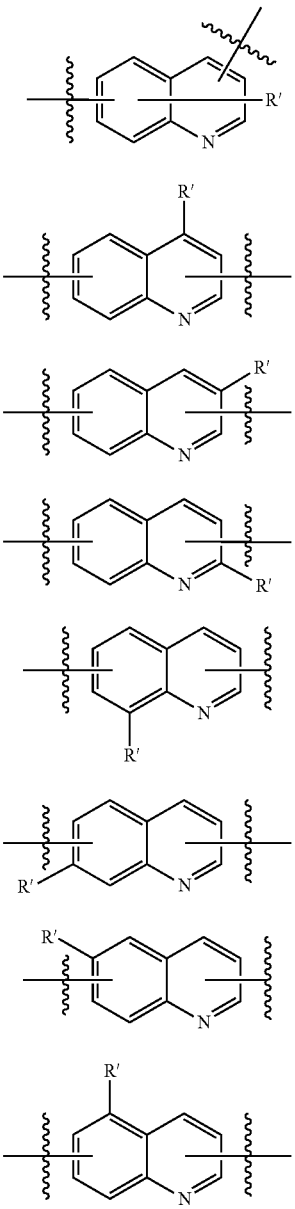

In some embodiments, the compound represented by formula 1 is selected from the structure shown in the following formula (1-1) or formula (1-2):

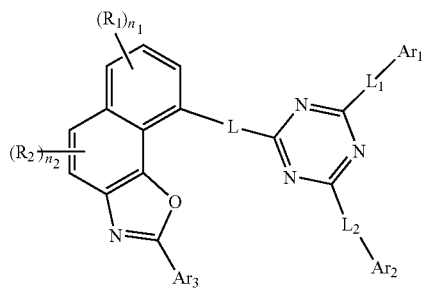

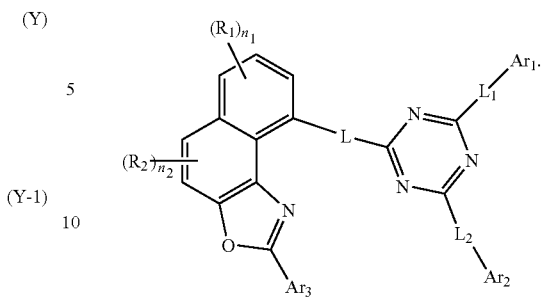

In some embodiments, $L_1$ and $L_2$ are the same or different, and each is independently selected from a single bond, substituted or unsubstituted arylene with 6, 7, 8, 9, 10, 11, 12, 13, 14, 15, 16, 17, 18, 19, or 20 carbon atoms, and substituted or unsubstituted heteroarylene with 3, 4, 5, 6, 7, 8, 9, 10, 11, 12, 13, 14, 15, 16, 17, or 18 carbon atoms.

Optionally, the substituent(s) in $L_1$ and $L_2$ are each independently selected from deuterium, fluorine, cyano, alkyl with 1 to 5 carbon atoms, fluoroalkyl with 1 to 5 carbon atoms, deuterated alkyl with 1 to 5 carbon atoms, trialkylsilyl with 3 to 8 carbon atoms, pentadeuterophenyl, phenyl, and naphthyl.

In some embodiments, $L_1$ and $L_2$ are each independently selected from a single bond, substituted or unsubstituted phenylene, substituted or unsubstituted naphthylene, substituted or unsubstituted biphenylene, substituted or unsubstituted triphenylene, substituted or unsubstituted fluorenylene, substituted or unsubstituted phenanthrylene, substituted or unsubstituted dibenzothiophenylene, substituted or unsubstituted dibenzofuranylene, substituted or unsubstituted carbazolylene, and substituted or unsubstituted pyridylidene.

Optionally, the substituent(s) in $L_1$ and $L_2$ are the same or different, and each is independently selected from deuterium, fluorine, cyano, methyl, ethyl, isopropyl, tert-butyl, trifluoromethyl, trideuteromethyl, trimethylsilyl, pentadeuterophenyl, and phenyl.

Optionally, $L_1$ and $L_2$ are each independently selected from a single bond and a substituted or unsubstituted group Q, where the unsubstituted group Q is selected from the following groups:

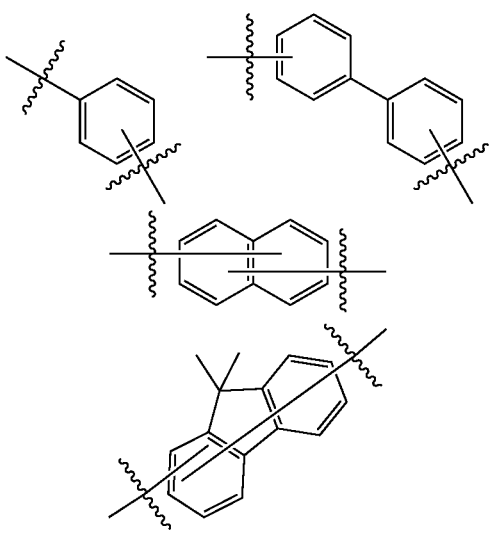

-continued

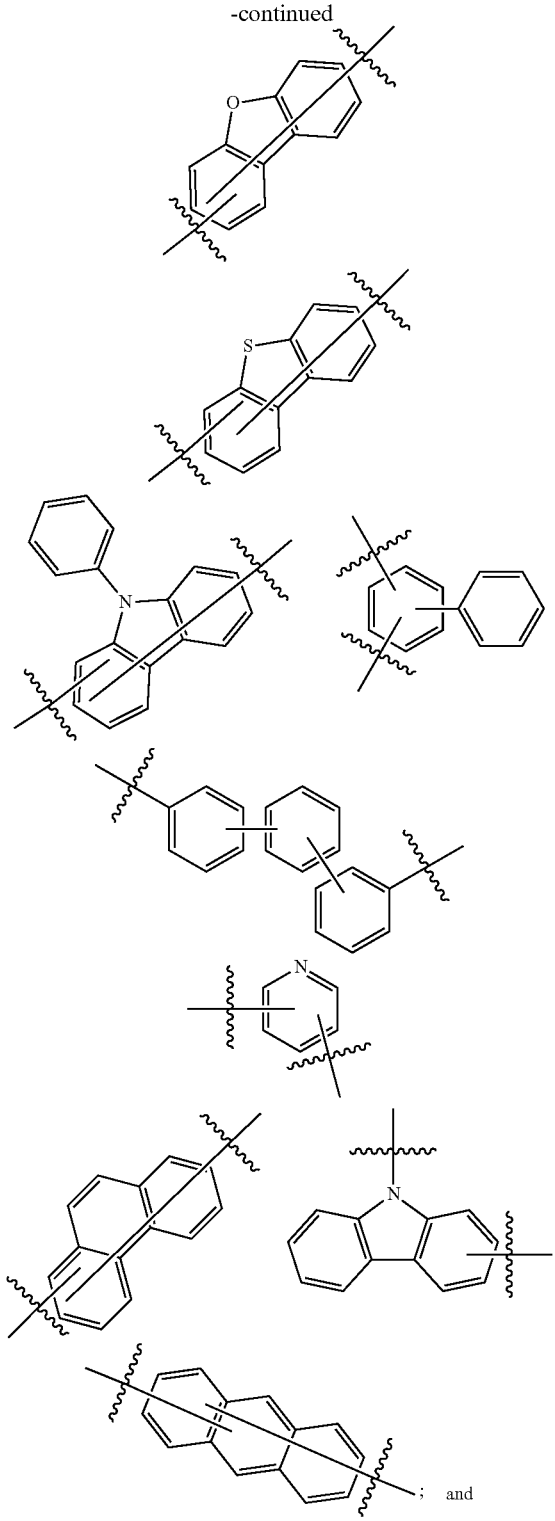

; and the substituted group Q is a group formed by substituting the unsubstituted group Q with one or more substituents; the substituen(s) on the substituted group Q are each independently selected from deuterium, fluorine, cyano, trideuteromethyl, trimethylsilyl, trifluoromethyl, methyl, ethyl, isopropyl, tert-butyl, phenyl, or pentadeuterophenyl; when the number of substituents on the group Q is greater than 1, the substituents are the same or different.

In some embodiments, $L_1$ and $L_2$ are each independently selected from a single bond and the group consisting of the following groups:

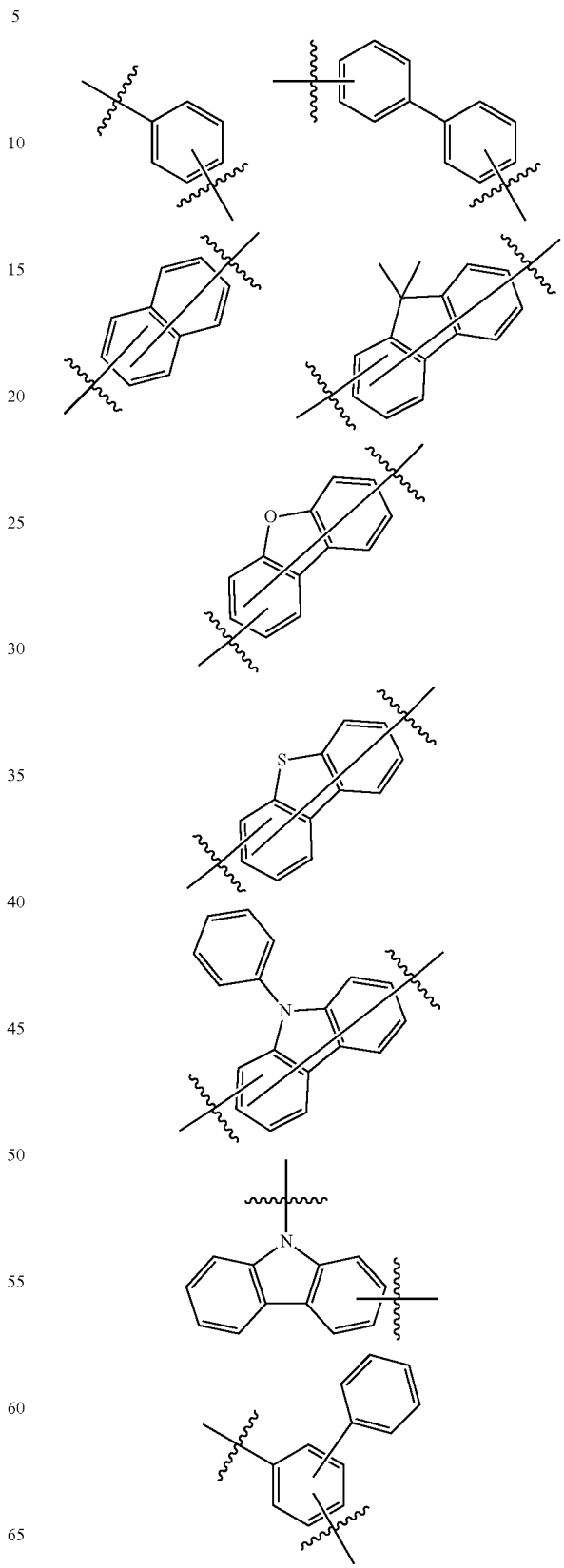

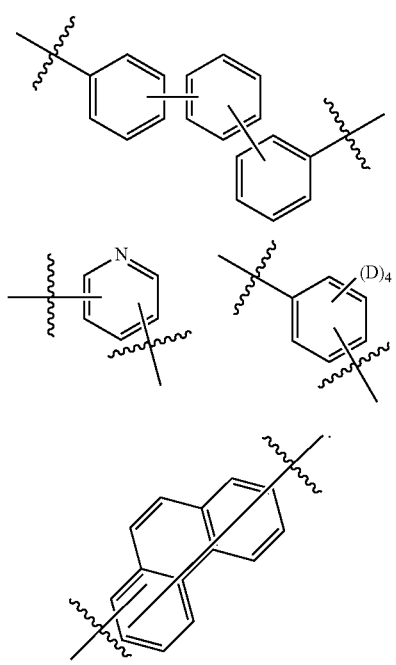
In some embodiments, $L_1$ and $L_2$ are each independently selected from a single bond and the group consisting of the following groups:
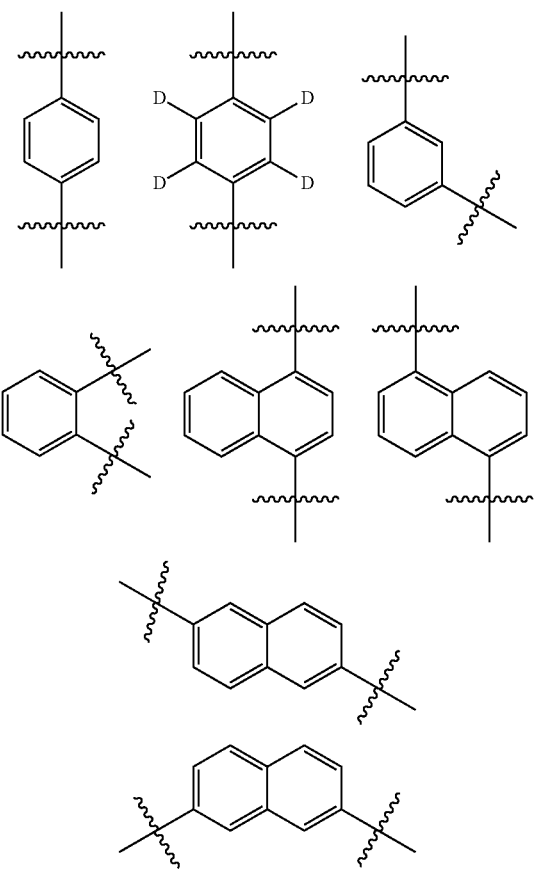
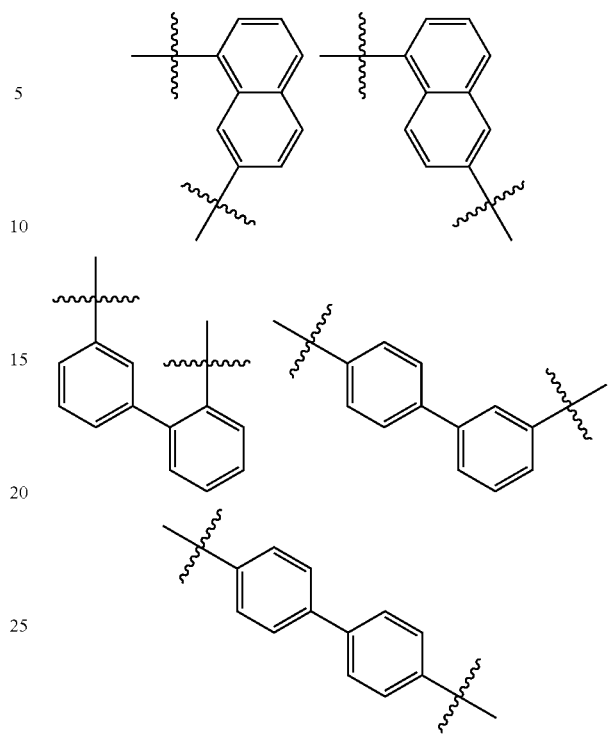
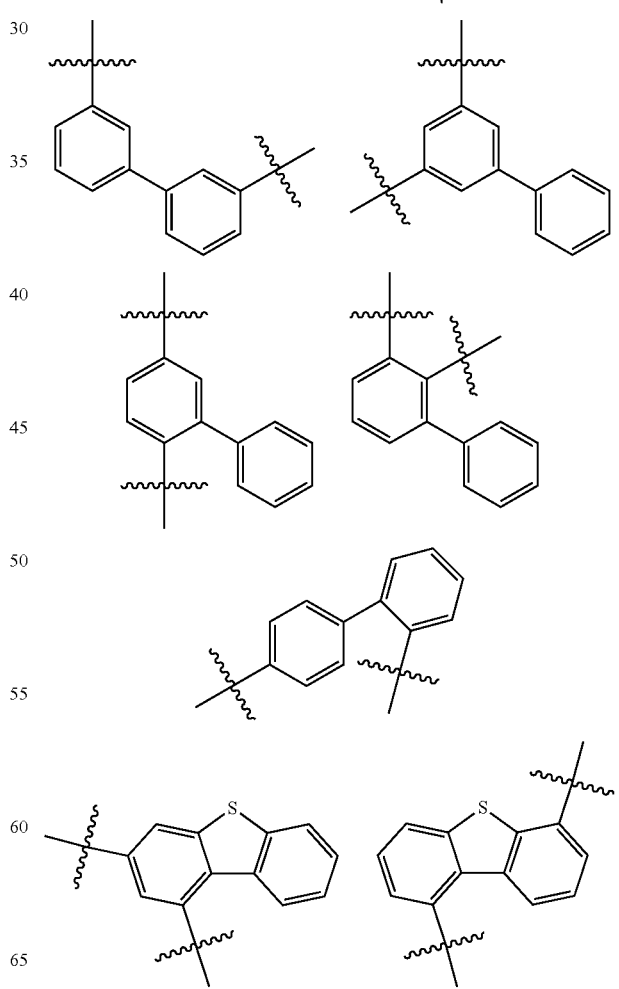

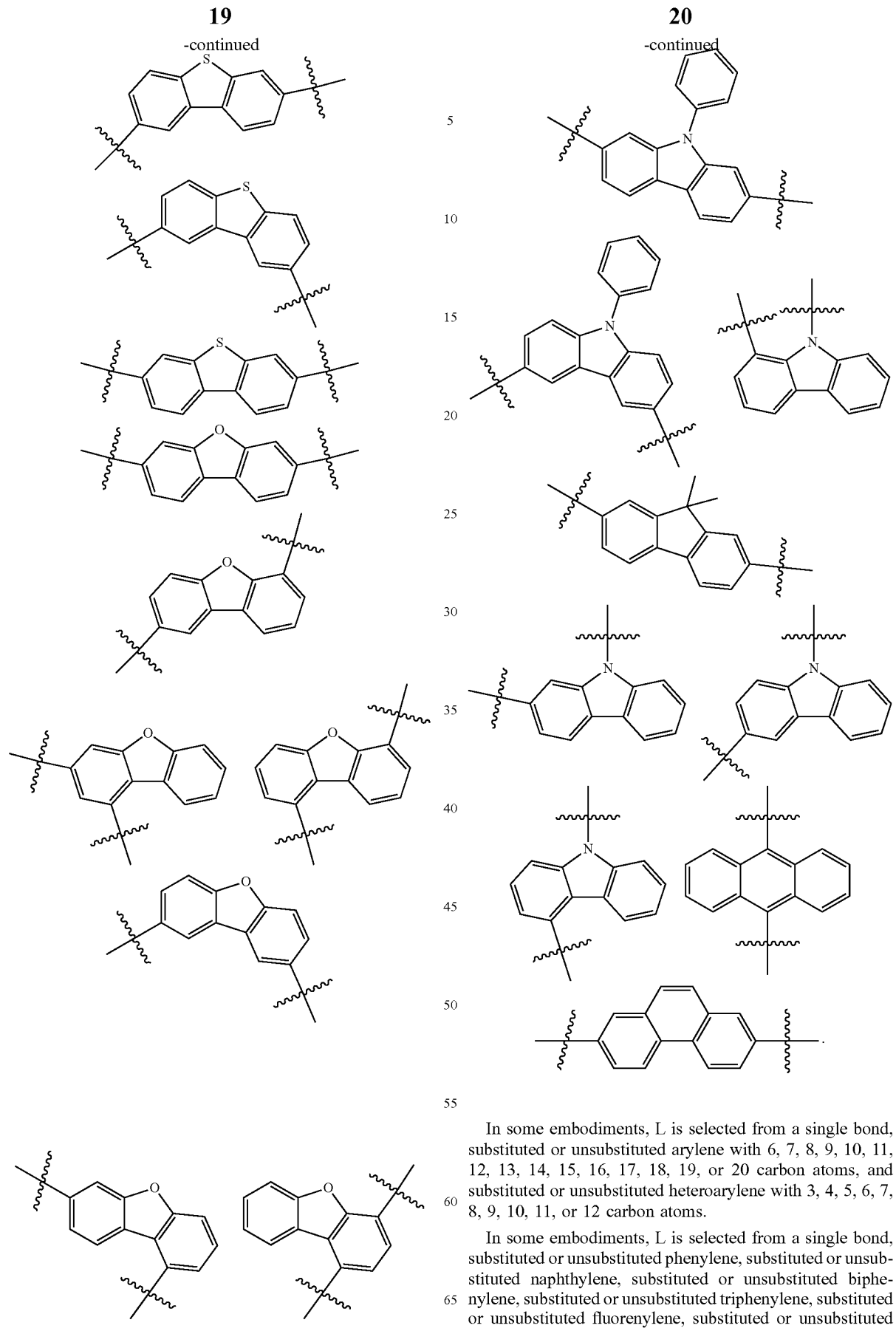

In some embodiments, L is selected from a single bond, substituted or unsubstituted arylene with 6, 7, 8, 9, 10, 11, 12, 13, 14, 15, 16, 17, 18, 19, or 20 carbon atoms, and substituted or unsubstituted heteroarylene with 3, 4, 5, 6, 7, 8, 9, 10, 11, or 12 carbon atoms.

In some embodiments, L is selected from a single bond, substituted or unsubstituted phenylene, substituted or unsubstituted naphthylene, substituted or unsubstituted biphenylene, substituted or unsubstituted triphenylene, substituted or unsubstituted fluorenylene, substituted or unsubstituted phenanthrylene, substituted or unsubstituted pyridylidene, substituted or unsubstituted dibenzothiophenylene, substituted or unsubstituted dibenzofuranylene, and substituted or unsubstituted carbazolylene.

Optionally, the substituent(s) in L are the same or different, and each is independently selected from deuterium, fluorine, cyano, methyl, ethyl, isopropyl, tert-butyl, trifluoromethyl, trideuteromethyl, trimethylsilyl, pentadeuterophenyl, and phenyl.

In some embodiments, L is selected from a single bond or the group consisting of the following groups:

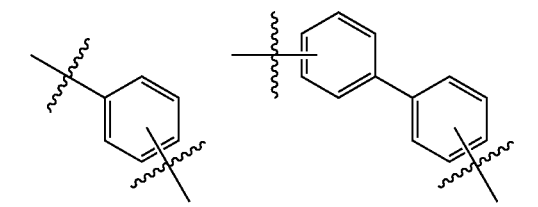

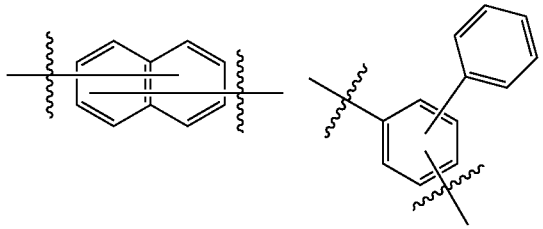

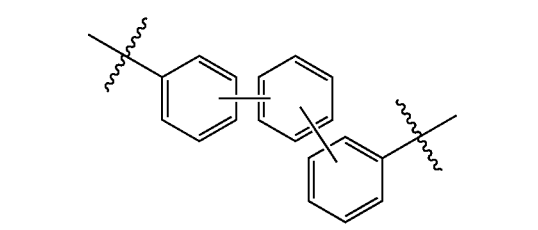

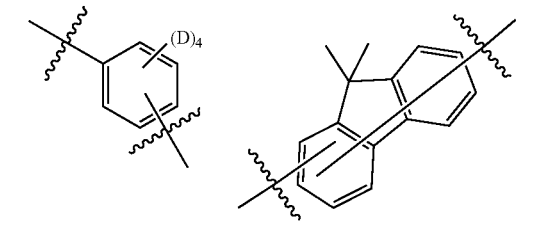

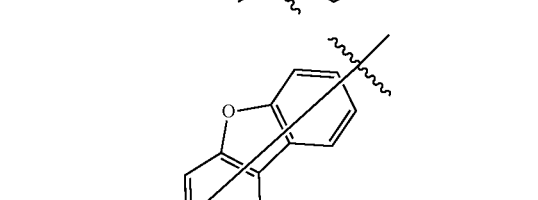

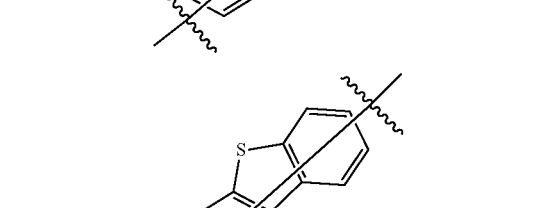

-continued

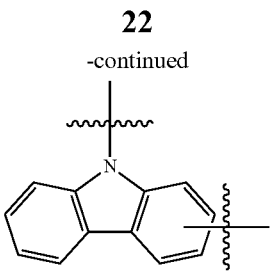

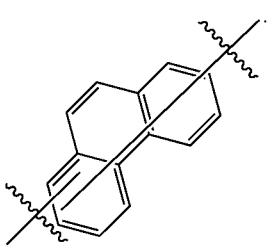

In some embodiments, L is selected from a single bond or the group consisting of the following groups:

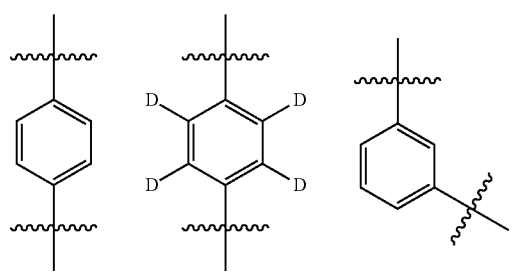

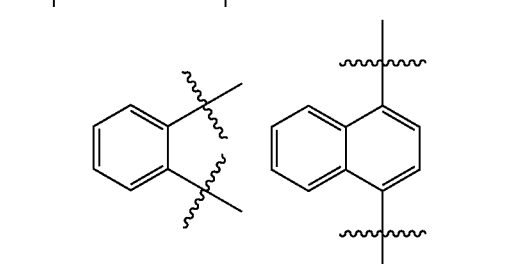

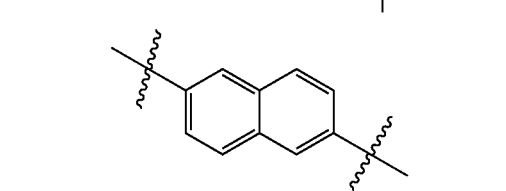

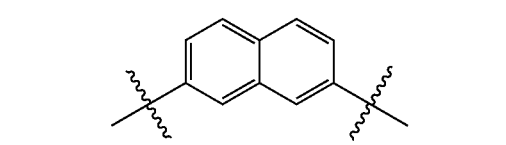

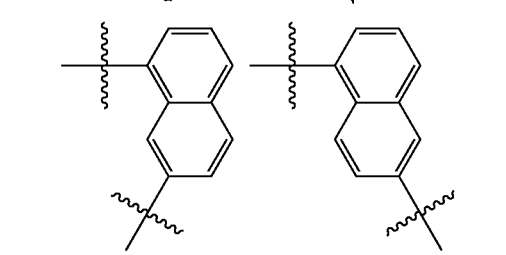

-continued

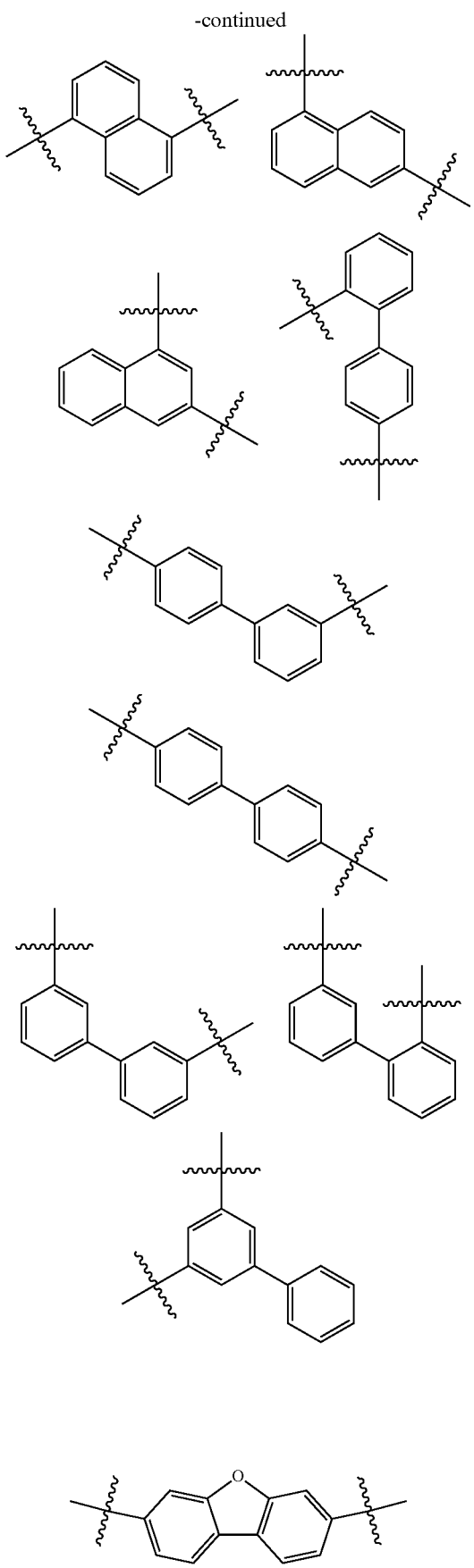

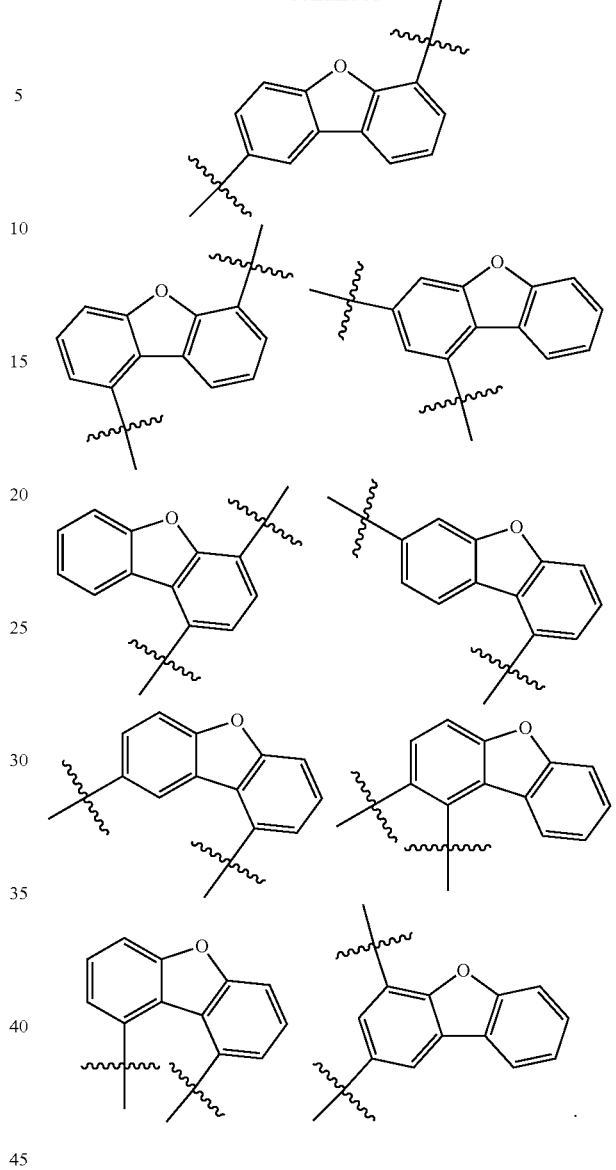

In some embodiments, $Ar_1$ and $Ar_2$ are the same or different, and are each independently selected from substituted or unsubstituted aryl with 6 to 25 carbon atoms, a group represented by formula 2, and a group represented by formula 3.

In some embodiments, $Ar_3$ is selected from substituted or unsubstituted aryl with 6 to 25 carbon atoms, and substituted or unsubstituted heteroaryl with 12 to 18 carbon atoms.

Optionally, the substituents in $Ar_1$, $Ar_2$, and $Ar_3$ are each independently selected from deuterium, a halogen group, cyano, haloalkyl with 1 to 5 carbon atoms, deuterated alkyl with 1 to 5 carbon atoms, alkyl with 1 to 5 carbon atoms, cycloalkyl with 5 to 10 carbon atoms, aryl with 6 to 12 carbon atoms, deuterated aryl with 6 to 12 carbon atoms, heteroaryl with 5 to 12 carbon atoms, and trialkylsilyl with 3 to 8 carbon atoms; and optionally, any two adjacent substituents form a benzene ring or a fluorene ring.

In some embodiments, $Ar_1$, $Ar_2$, and $Ar_3$ are the same or different, and each is independently selected from substituted or unsubstituted phenyl, substituted or unsubstituted naphthyl, substituted or unsubstituted biphenyl, substituted or unsubstituted terphenyl, substituted or unsubstituted fluorenyl, substituted or unsubstituted phenanthryl, substituted or unsubstituted anthryl, substituted or unsubstituted pyrenyl, substituted or unsubstituted triphenylene, substituted or unsubstituted spirobifluorenyl, and the following groups:

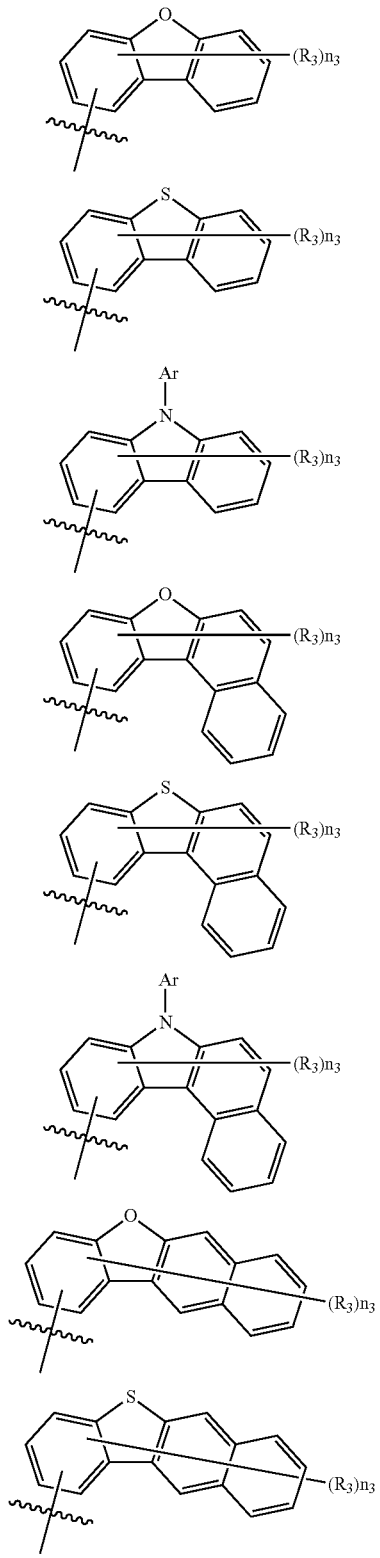

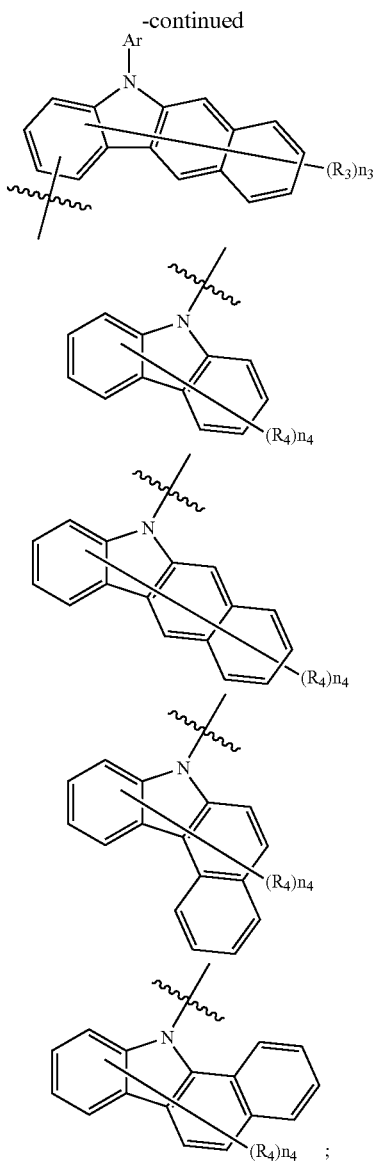

each Ar is independently selected from substituted or unsubstituted phenyl, substituted or unsubstituted naphthyl, substituted or unsubstituted biphenyl, substituted or unsubstituted terphenyl, substituted or unsubstituted fluorenyl, substituted or unsubstituted phenanthryl, substituted or unsubstituted dibenzofuranyl, and substituted or unsubstituted dibenzothiophenyl;

each of $R_3$ and $R_4$ is independently selected from hydrogen, deuterium, fluorine, cyano, trimethylsilyl, trideuteromethyl, trifluoromethyl, cyclopentyl, cyclohexyl, methyl, ethyl, isopropyl, tert-butyl, phenyl, pentadeuterophenyl, naphthyl, biphenyl, dibenzofuranyl, and dibenzothiophenyl;

$n_3$ represents the number of $R_3$, and $n_3$ is selected from 0, 1, 2, 3, 4, 5, 6, and 7;

$n_4$ represents the number of $R_4$, and $n_4$ is selected from 0, 1, 2, 3, 4, 5, 6, 7, and 8; and the substituents in $Ar_1$, $Ar_2$, and $Ar_3$ are the same or different, and are each independently selected from deuterium, fluorine, cyano, trimethylsilyl, trideuteromethyl, trifluoromethyl, cyclopentyl, cyclohexyl, methyl, ethyl, isopropyl, tert-butyl, phenyl, pentadeuterophenyl, naphthyl, biphenyl, dibenzofuranyl, dibenzothiophenyl, and carbazolyl.

In some embodiments, $Ar_1$ and $Ar_2$ are the same or different, and each is independently selected from substituted or unsubstituted phenyl, substituted or unsubstituted naphthyl, substituted or unsubstituted biphenyl, substituted or unsubstituted terphenyl, substituted or unsubstituted fluorenyl, substituted or unsubstituted phenanthryl, substituted or unsubstituted anthryl, substituted or unsubstituted pyrenyl, substituted or unsubstituted triphenylene, substituted or unsubstituted spirobifluorenyl, and the following groups:

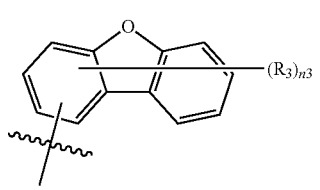

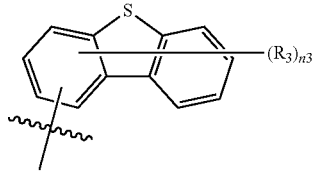

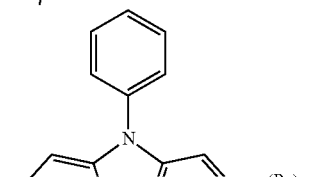

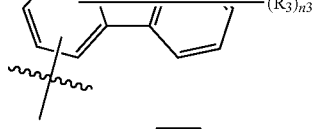

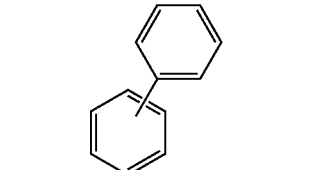

-continued

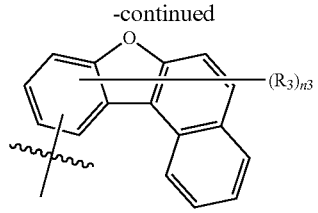

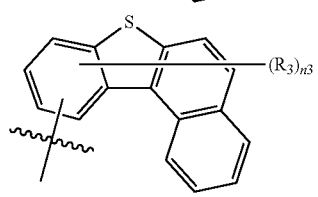

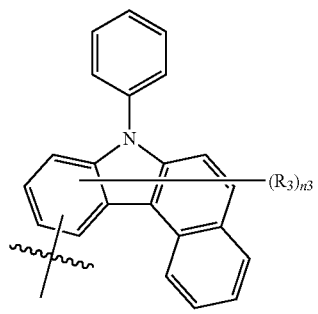

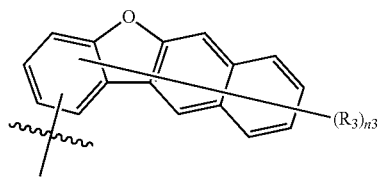

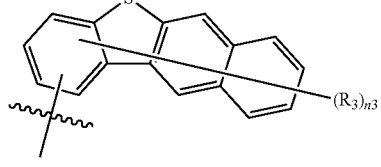

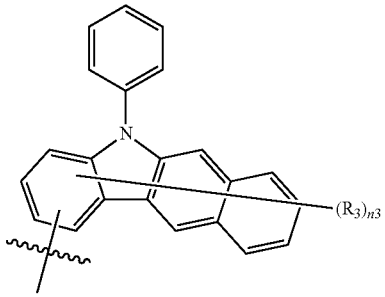

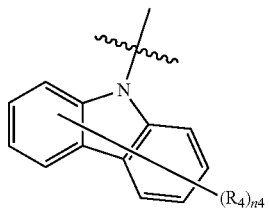

-continued

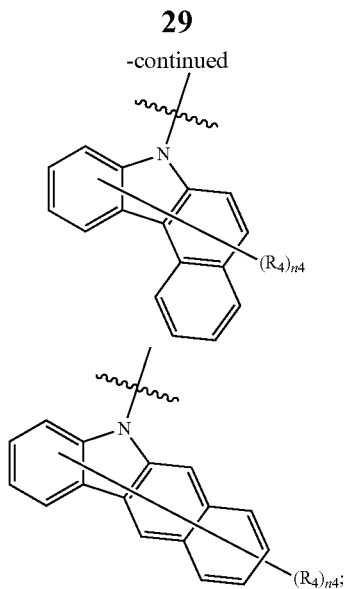

the substituent(s) in $Ar_1$ and $Ar_2$ are the same as or different from those in each $R_3$ and $R_4$, and are each independently selected from deuterium, fluorine, cyano, trimethylsilyl, trideuteromethyl, trifluoromethyl, methyl, ethyl, isopropyl, tert-butyl, phenyl, pentadeuterophenyl, and naphthyl;

$n_3$ represents the number of $R_3$, and $n_3$ is selected from 0, 1, 2, 3, 4, 5, 6, and 7; and $n_4$ represents the number of $R_4$, and $n_4$ is selected from 0, 1, 2, 3, 4, 5, 6, 7, and 8.

In some embodiments, $Ar_3$ is selected from substituted or unsubstituted phenyl, substituted or unsubstituted naphthyl, substituted or unsubstituted biphenyl, substituted or unsubstituted terphenyl, substituted or unsubstituted fluorenyl, substituted or unsubstituted dibenzofuranyl, or substituted or unsubstituted dibenzothiophenyl; the substituent(s) in $Ar_3$ are the same or different, and are each independently selected from deuterium, fluorine, cyano, trimethylsilyl, trideuteromethyl, trifluoromethyl, methyl, ethyl, isopropyl, tert-butyl, phenyl, pentadeuterophenyl, and naphthyl.

In some embodiments, $Ar_1$ and $Ar_2$ are the same or different, and are each independently selected from the following groups:

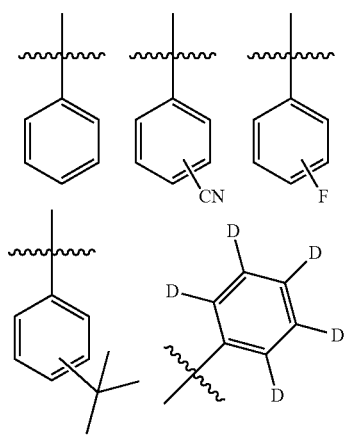

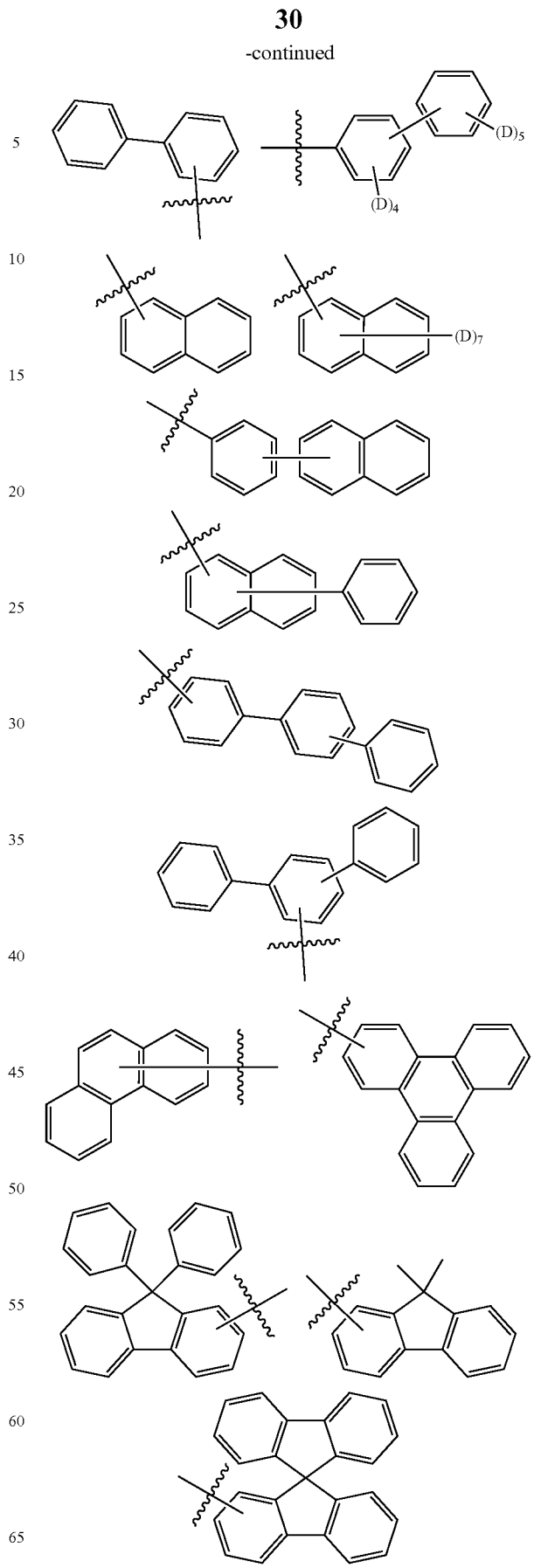

-continued
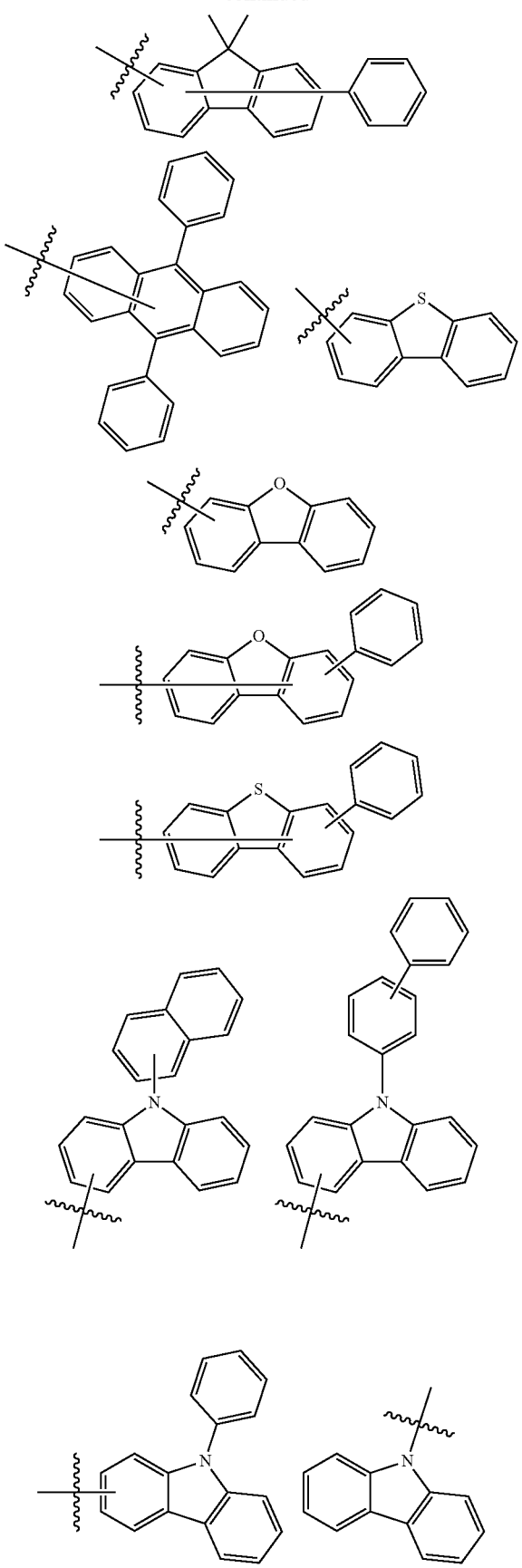
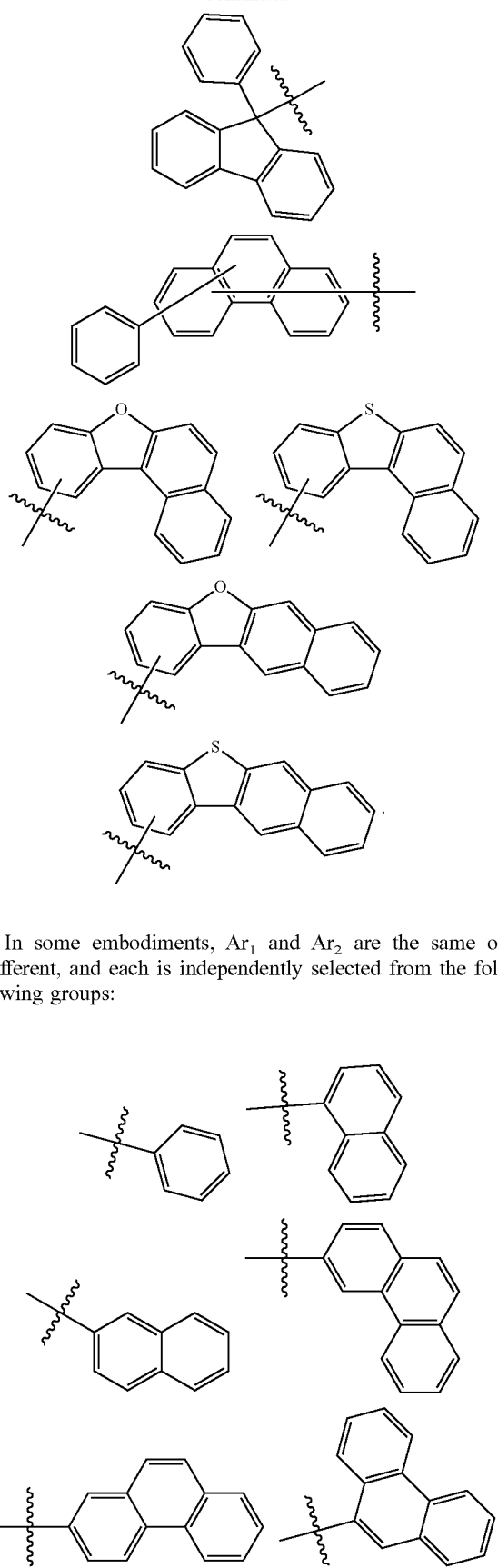
In some embodiments, $Ar_1$ and $Ar_2$ are the same or different, and each is independently selected from the following groups:

-continued
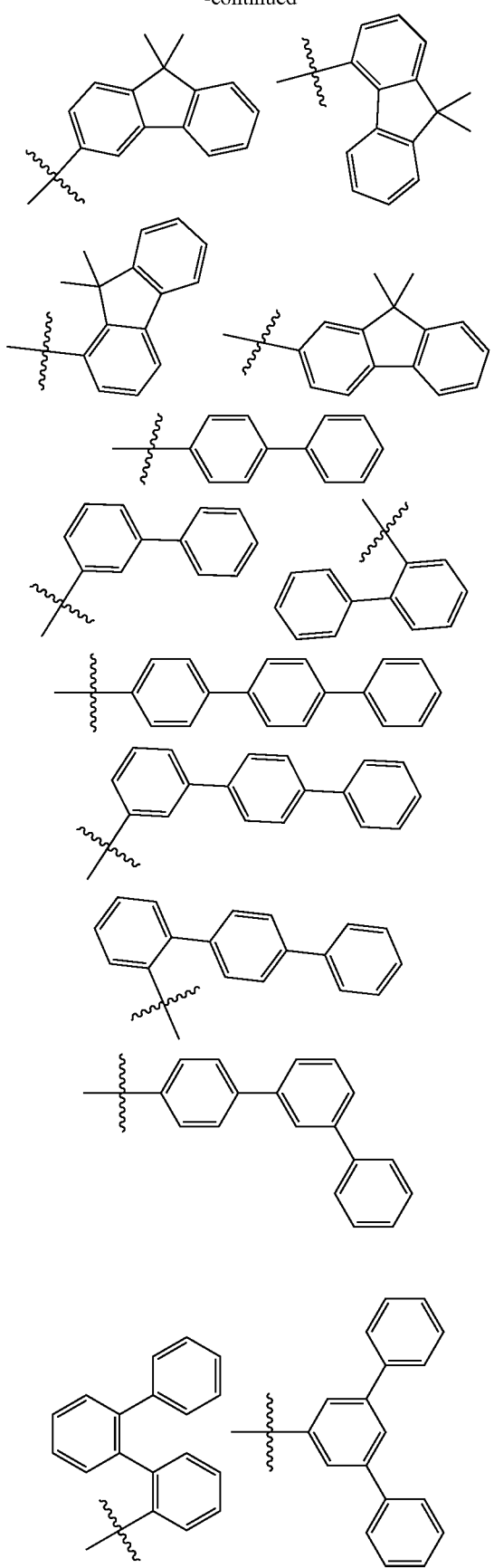
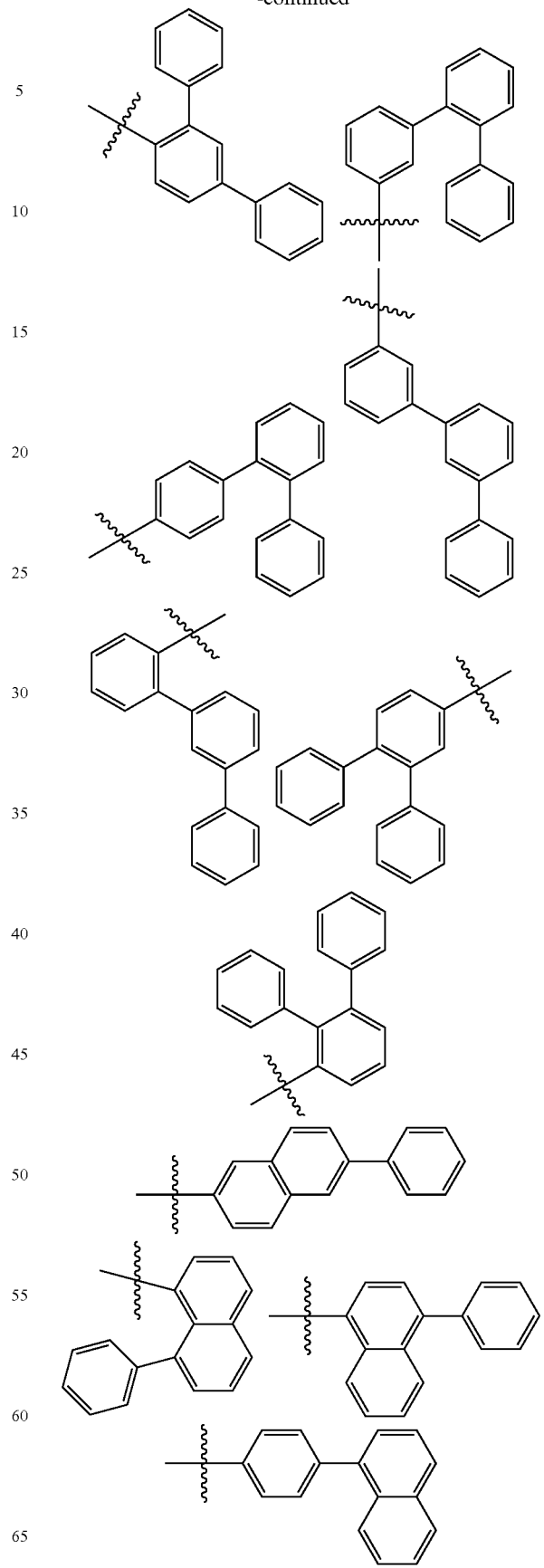

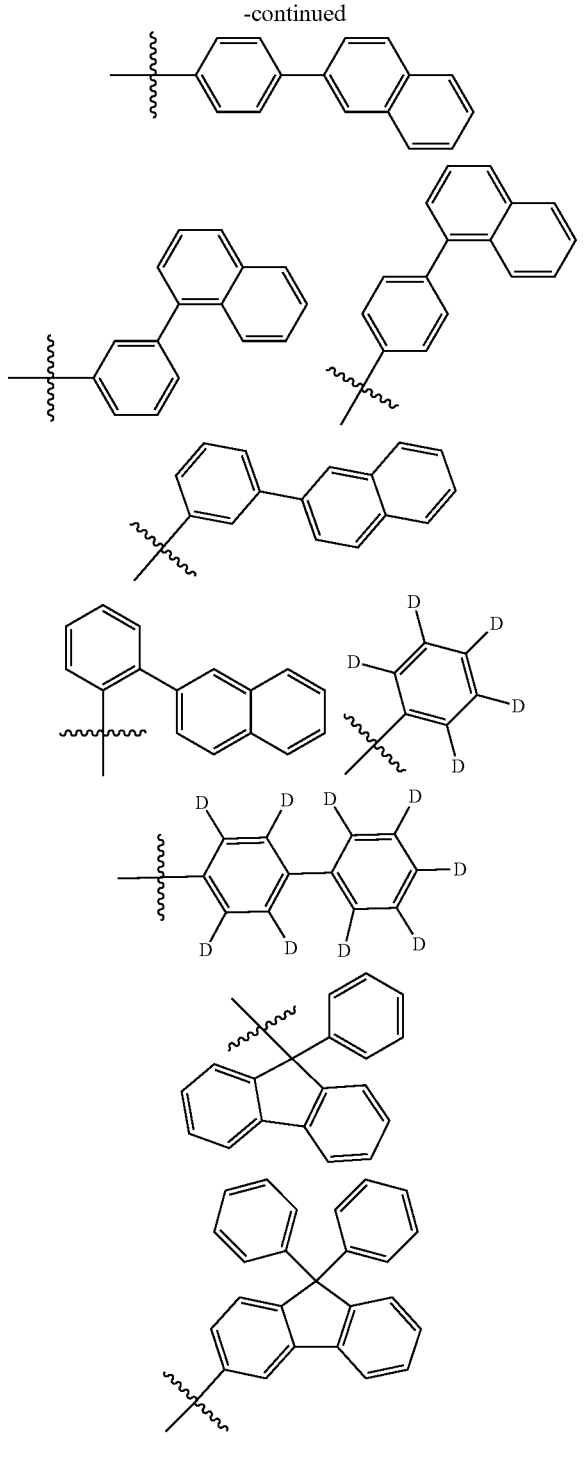
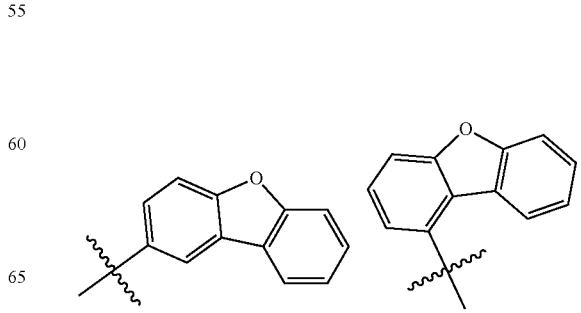

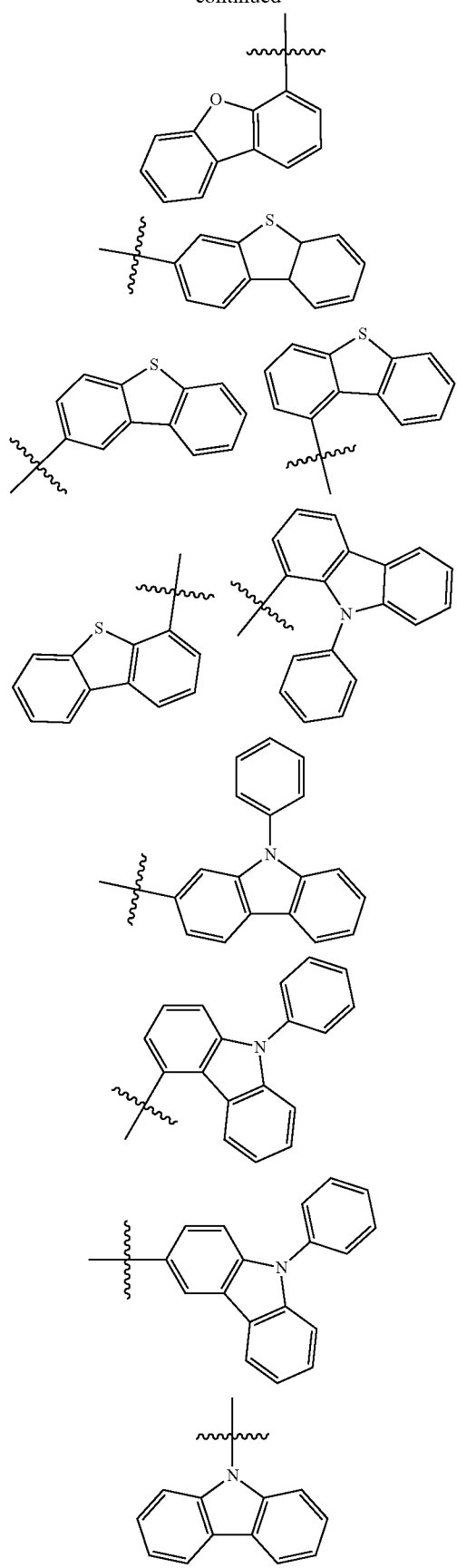
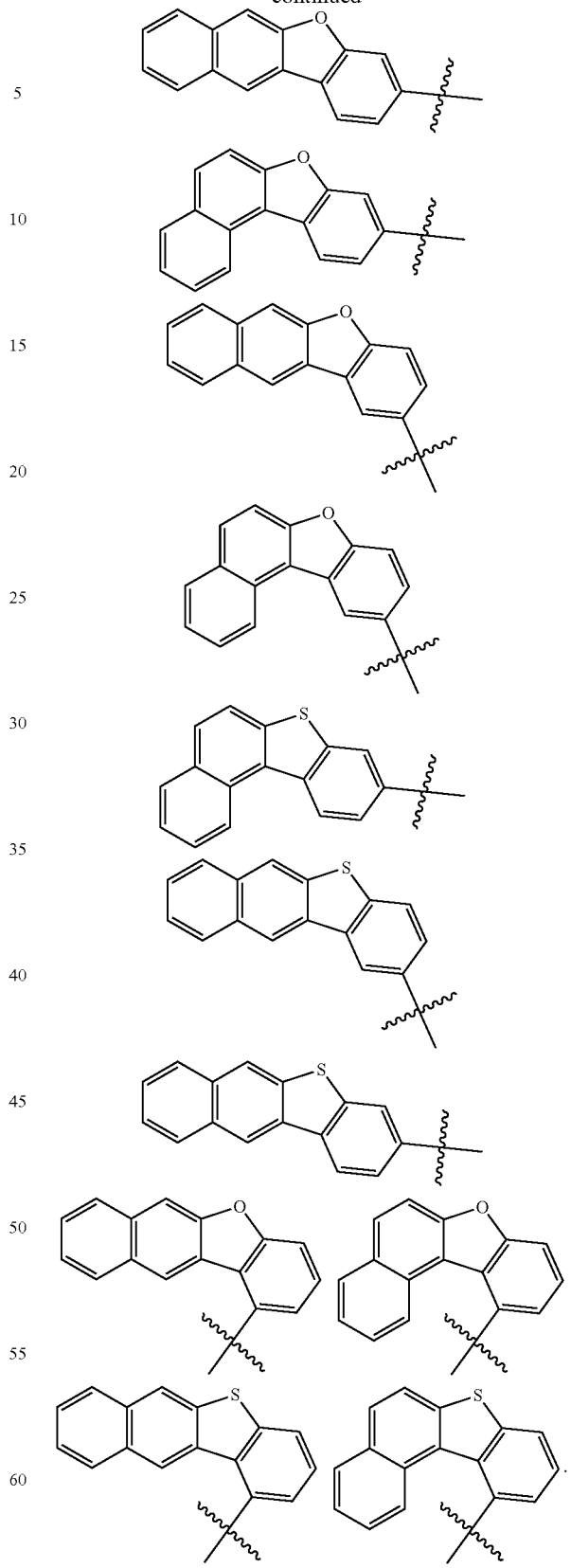
In some embodiments, $Ar_3$ is selected from the following groups:

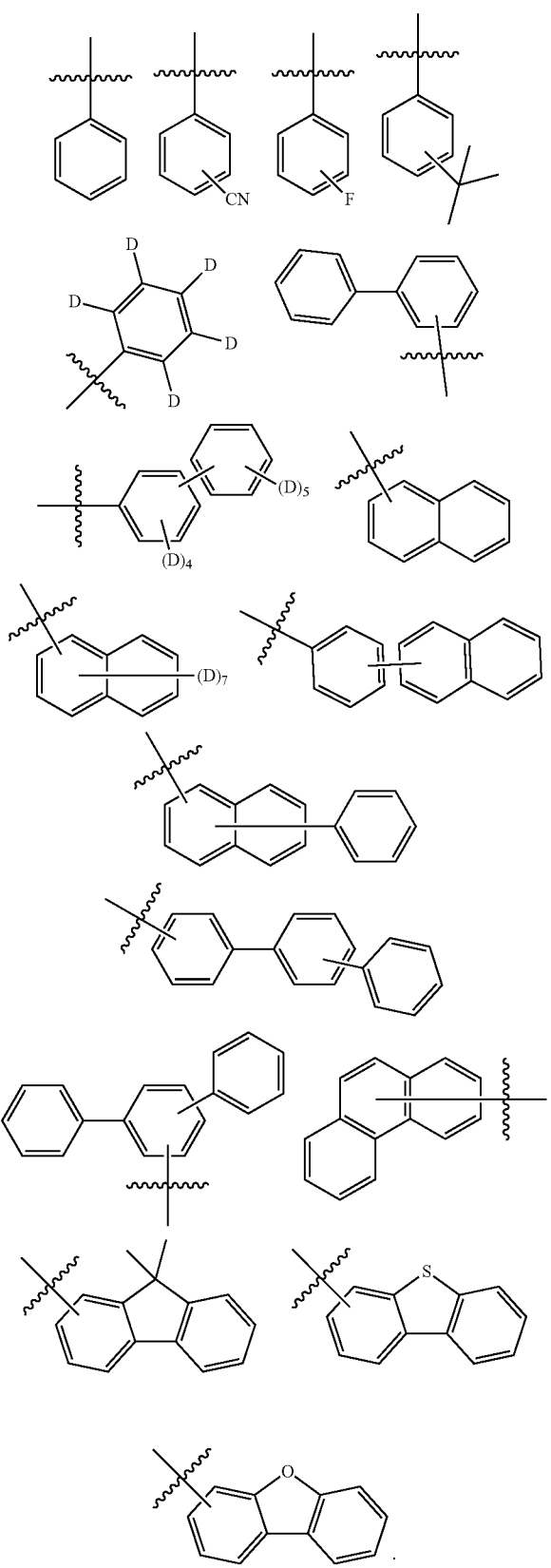
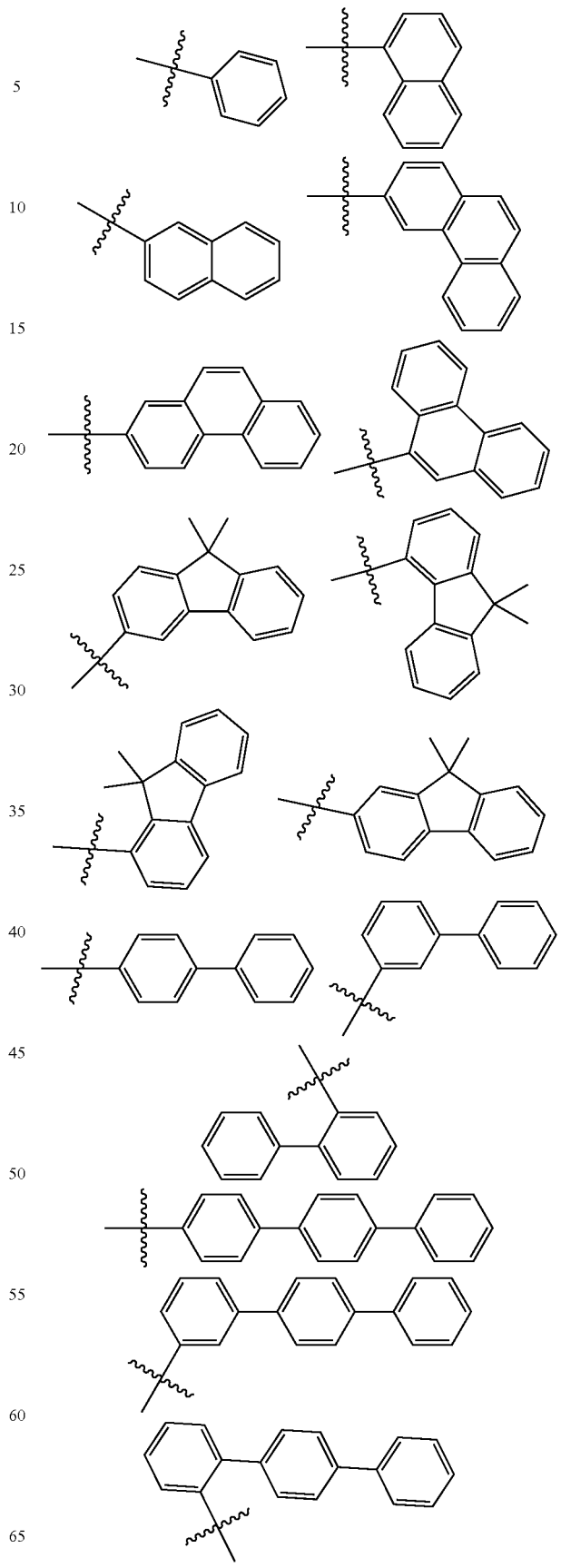
In some embodiments, Ar₃ is selected from the following groups:

-continued
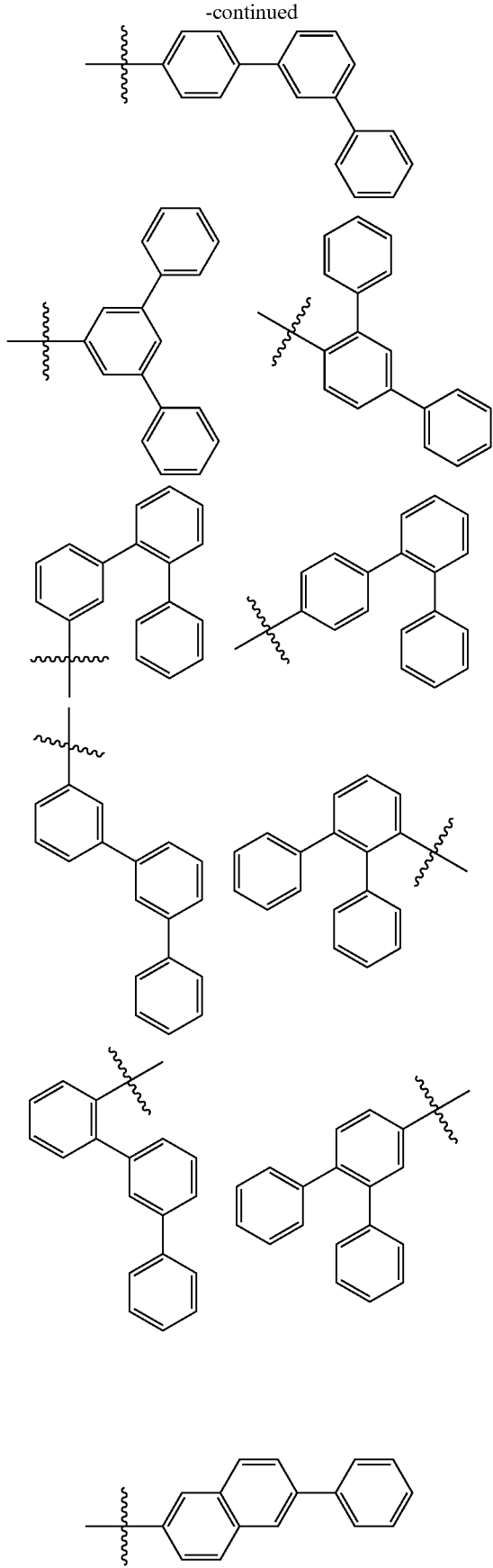
-continued
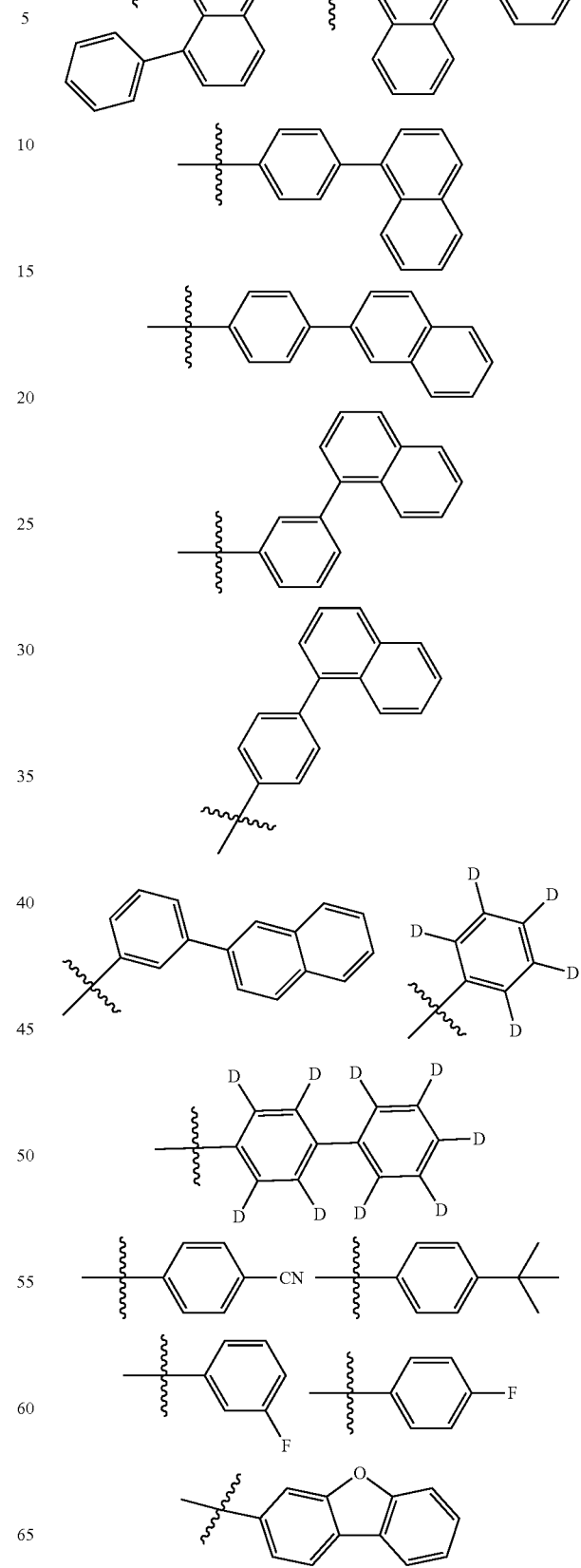

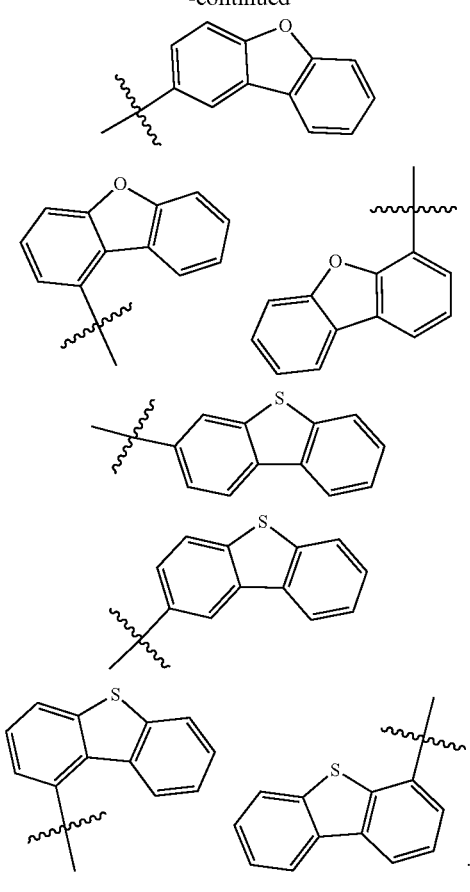
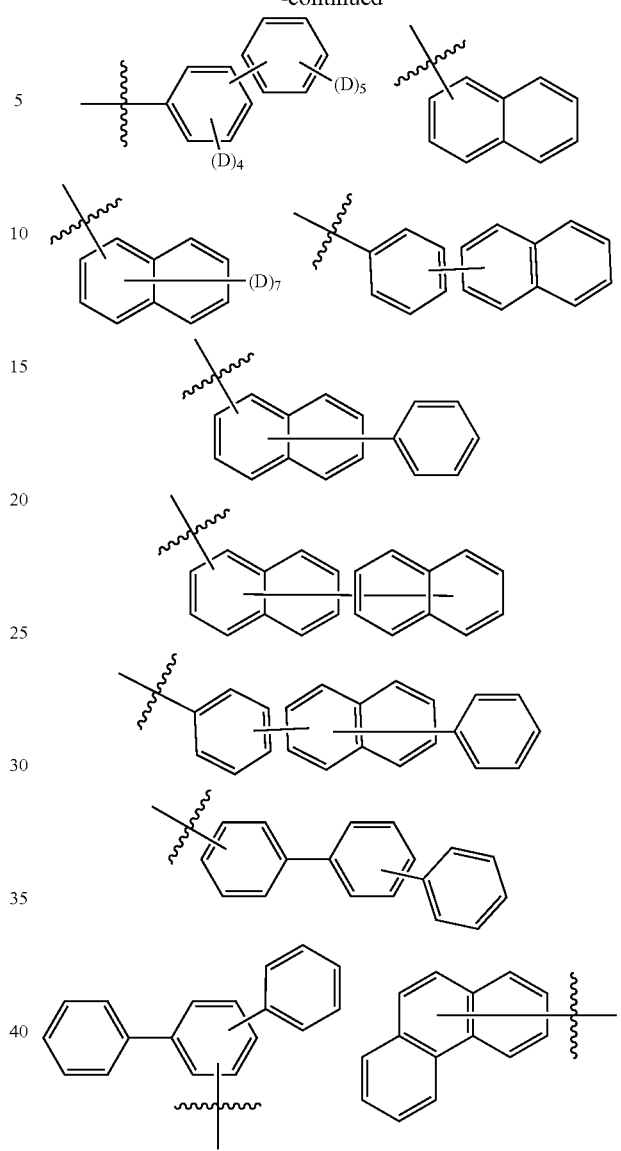
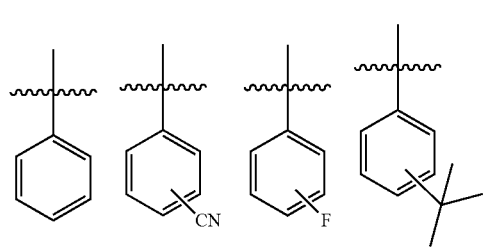
In some embodiments, are the same or different, and are each independently selected from the following groups:
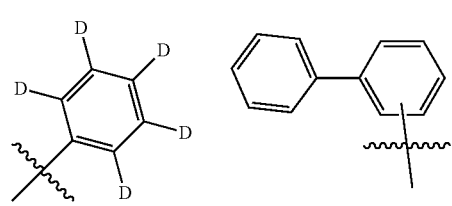
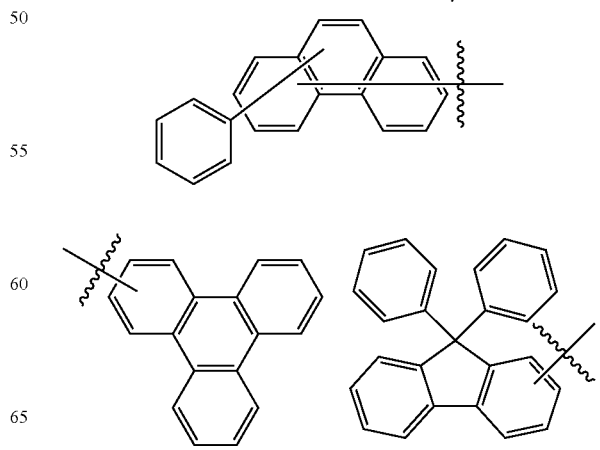

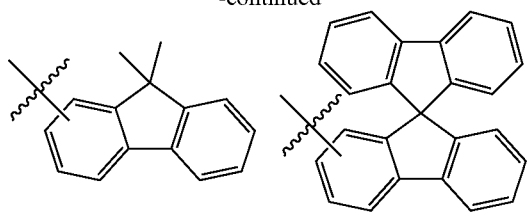
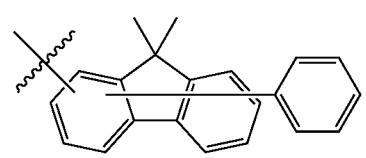
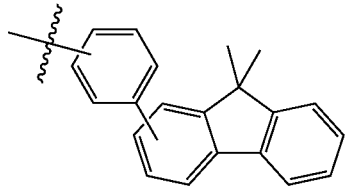
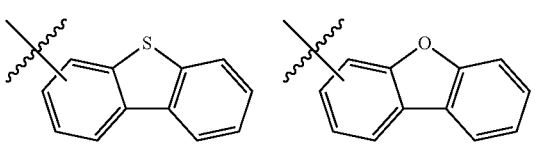
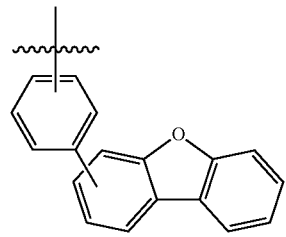
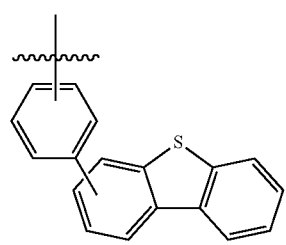
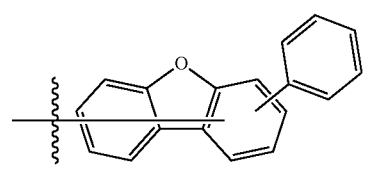
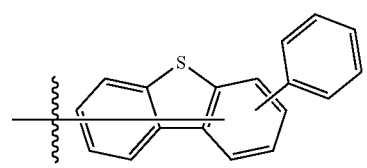

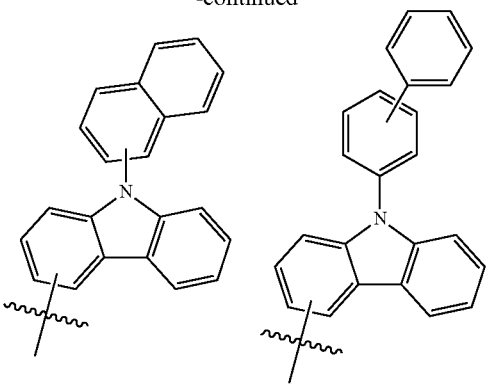
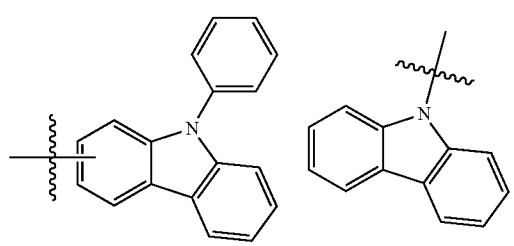
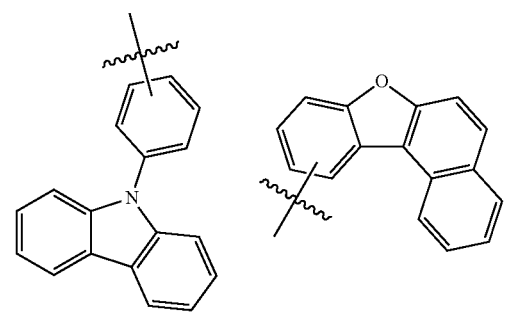
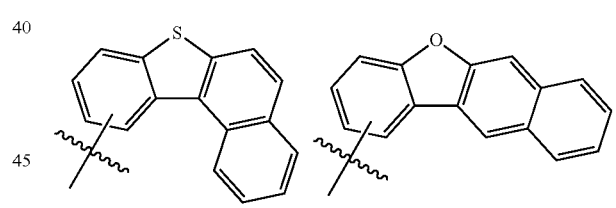
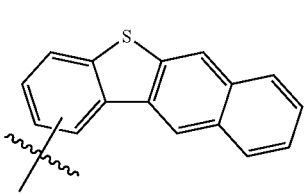

In some embodiments, each of $R_1$ and $R_2$ is independently selected from hydrogen, deuterium, fluorine, cyano, trimethylsilyl, trideuteromethyl, trifluoromethyl, cyclopentyl, cyclohexyl, methyl, ethyl, isopropyl, tert-butyl, phenyl, pentadeuterophenyl, and naphthyl.

In some embodiments, the nitrogen-containing compound is selected from the group consisting of the following compounds:

1
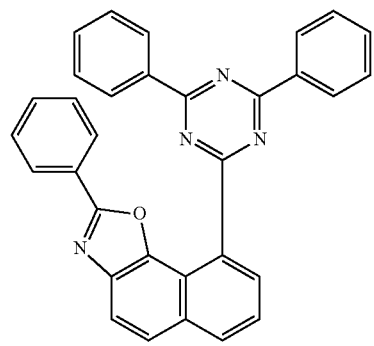
2
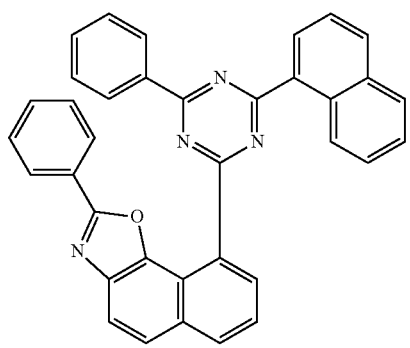
3
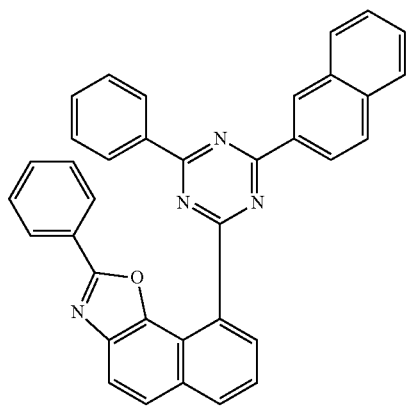
4
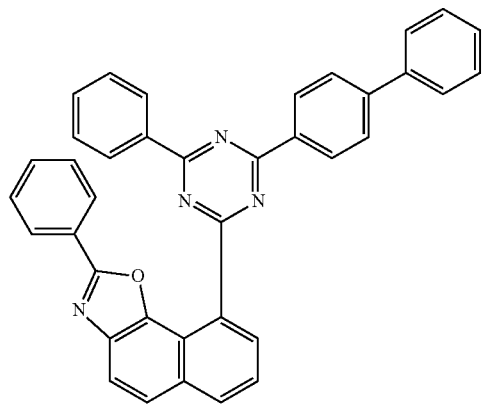
-continued
5
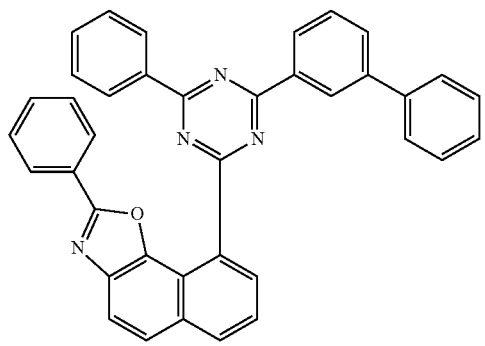
6
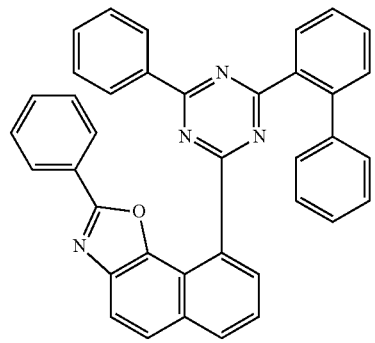
7
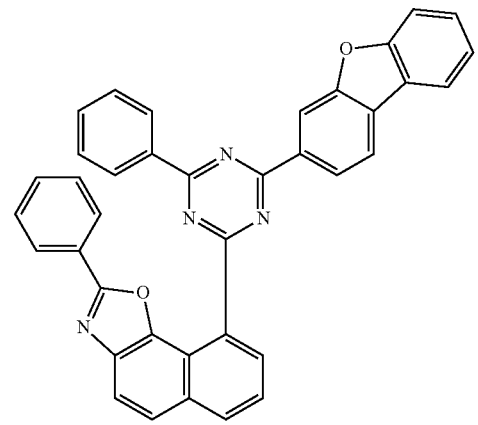
8
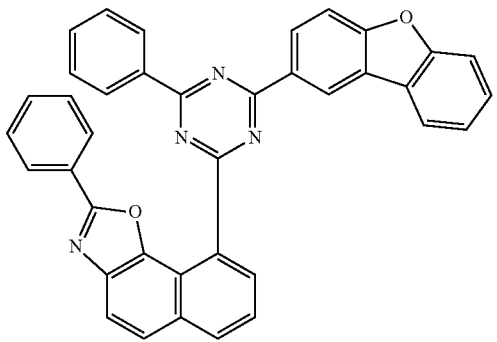

9
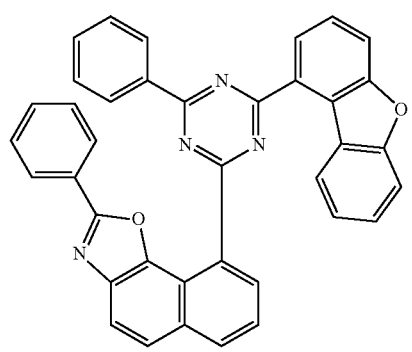
10
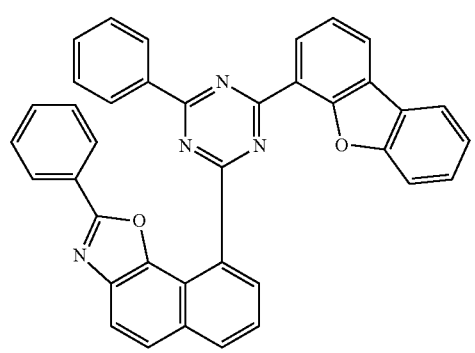
11
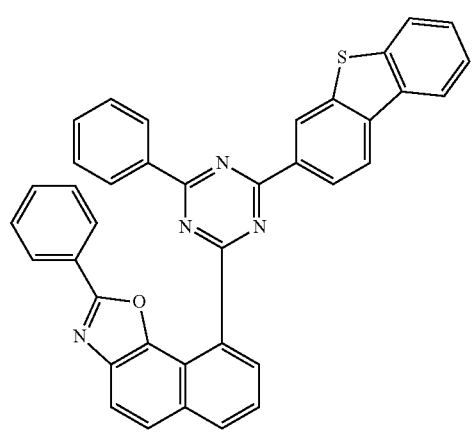
12
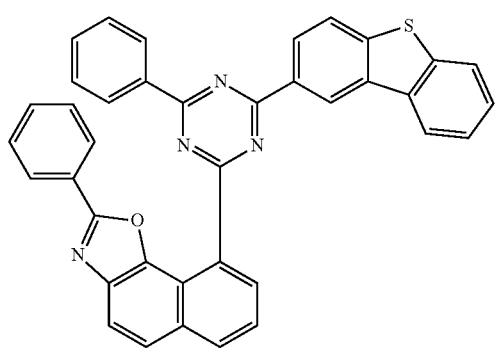
13
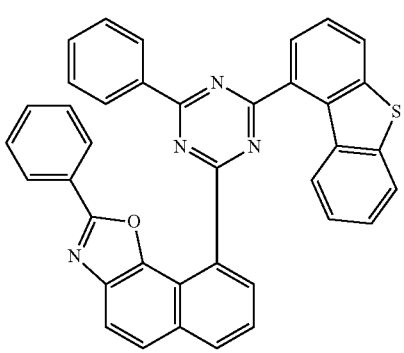
14
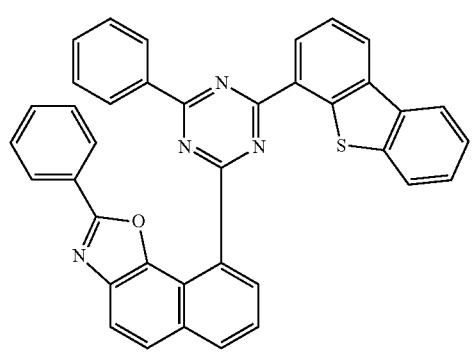
15
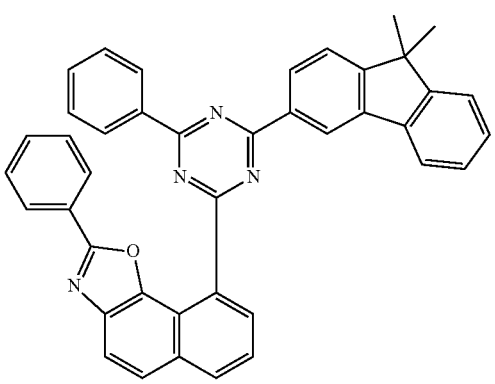
16
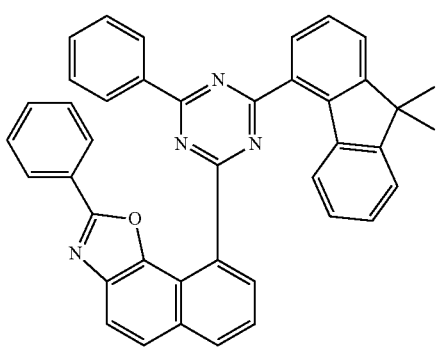

17
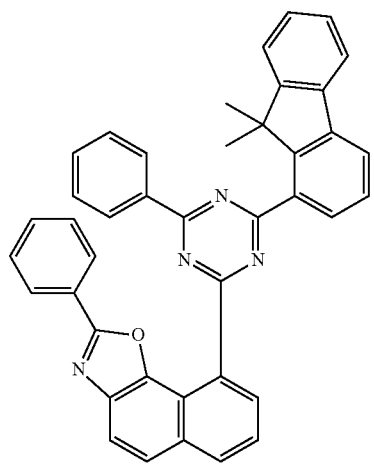
18
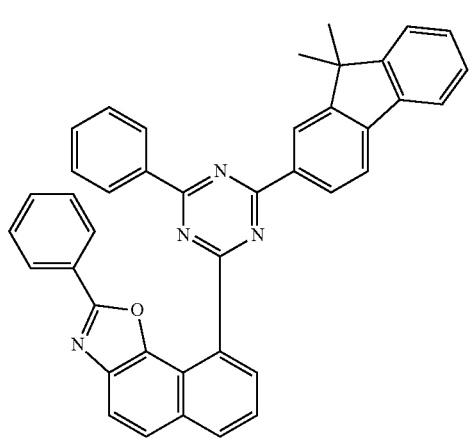
19
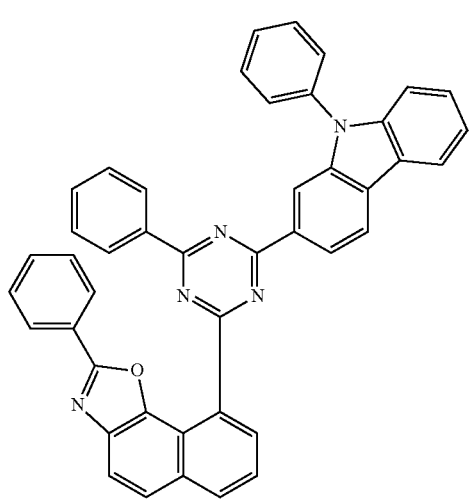
20
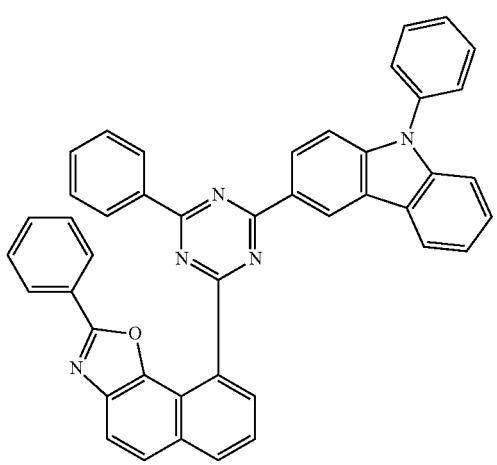
21
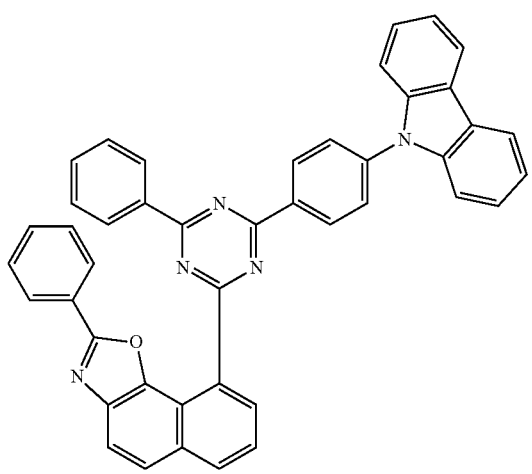
22
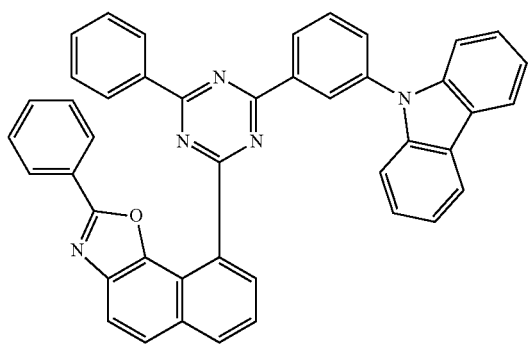

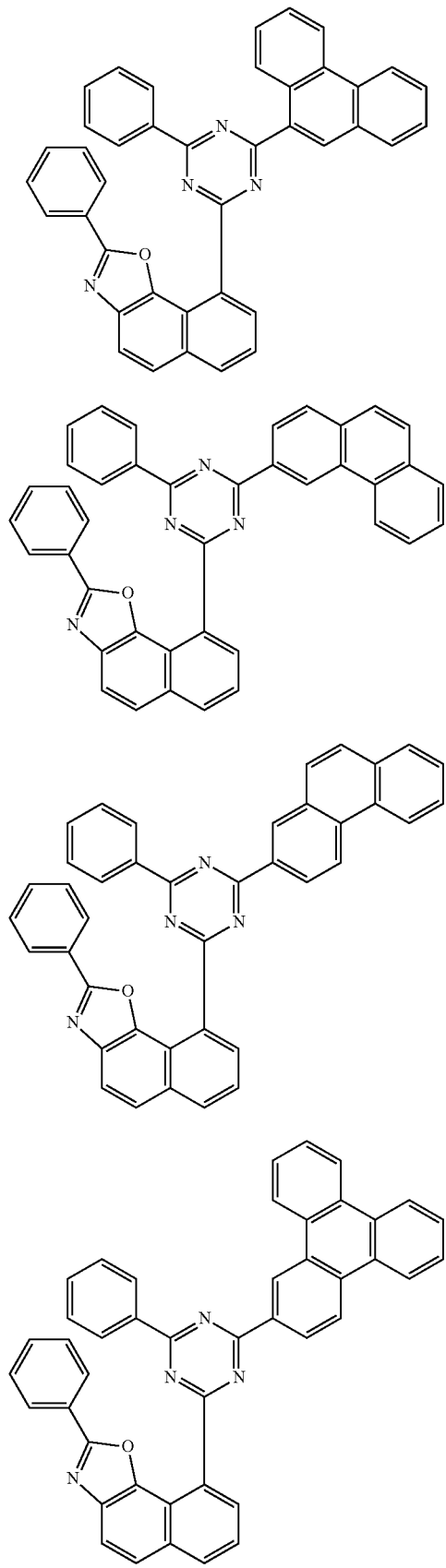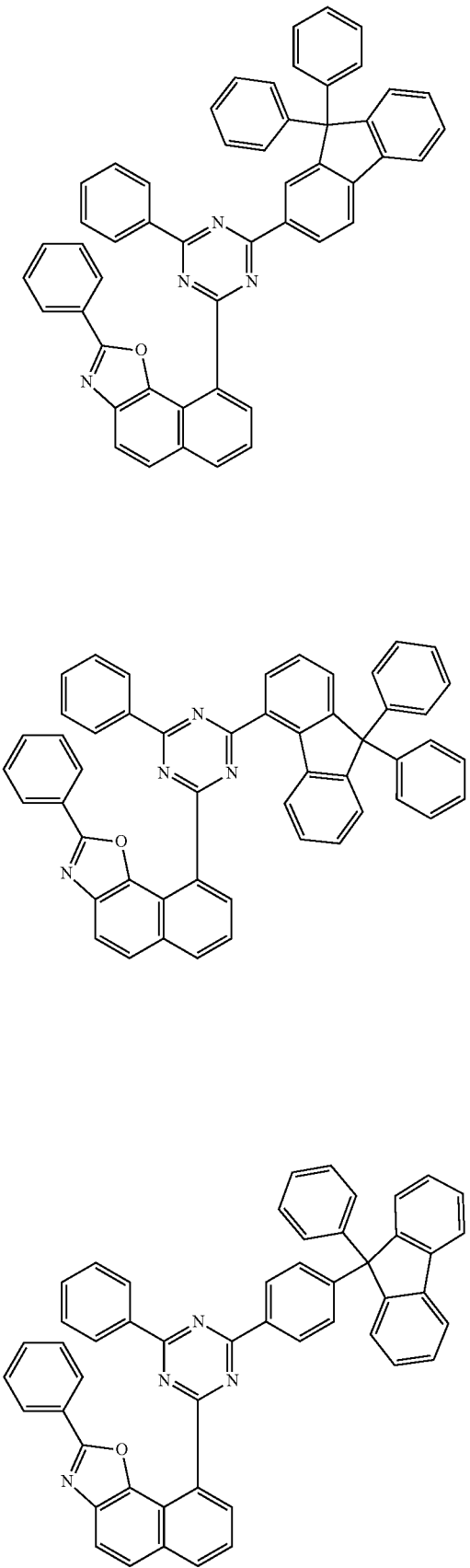

30
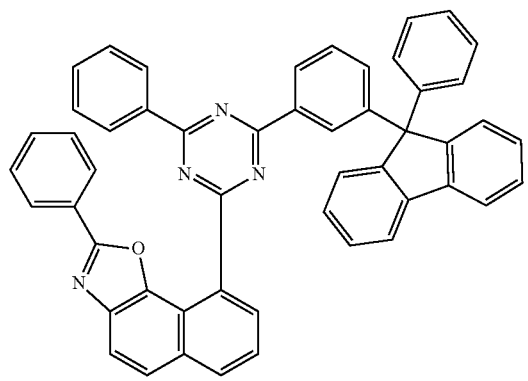
31
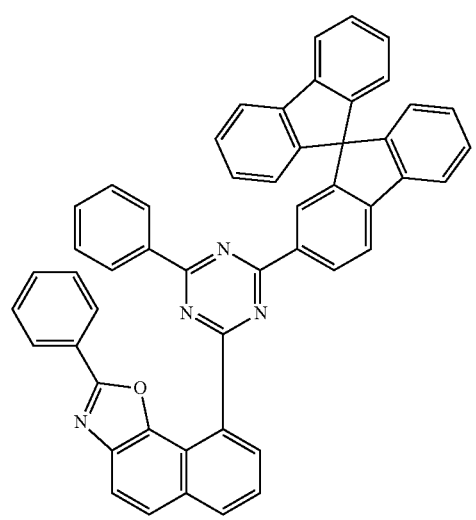
32
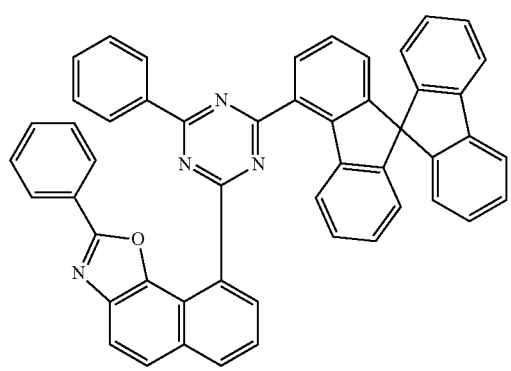
33
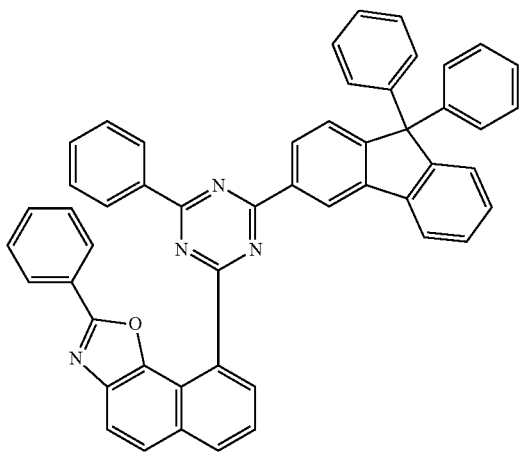
34
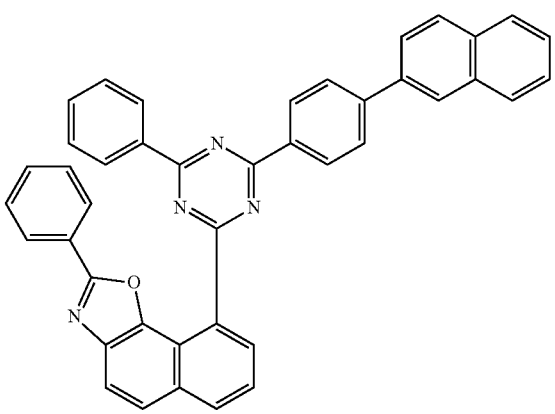
35

36
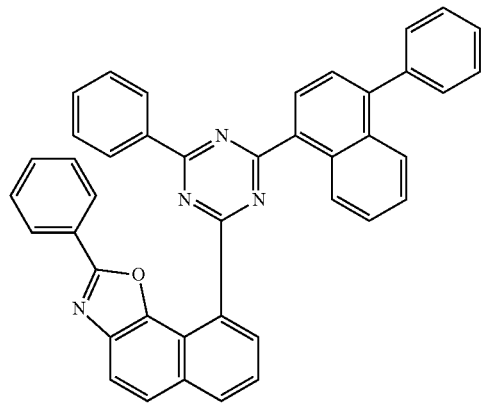
37
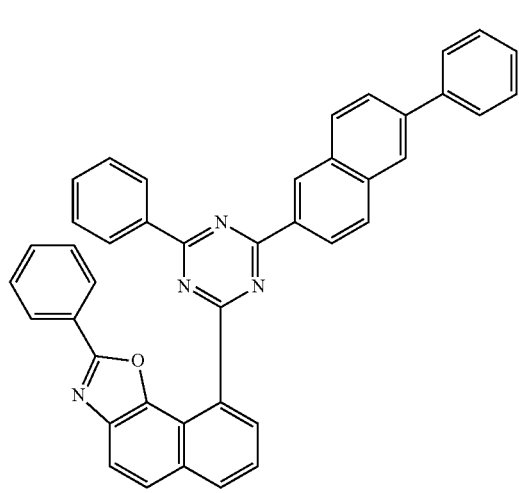
38
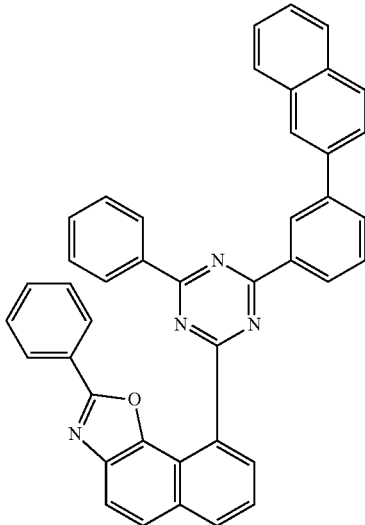
39
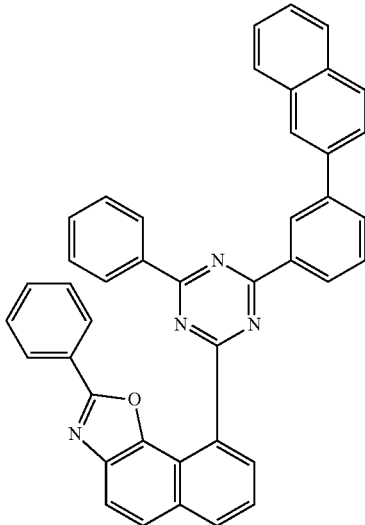
40
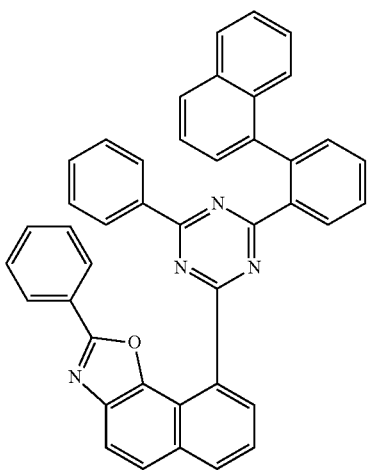
41
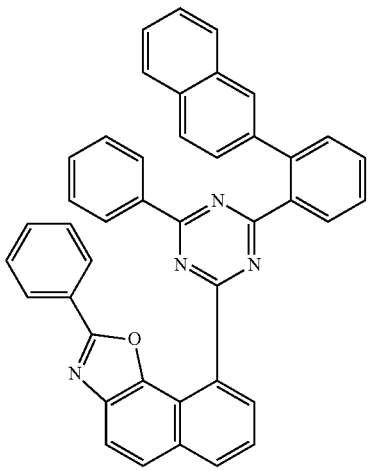

42
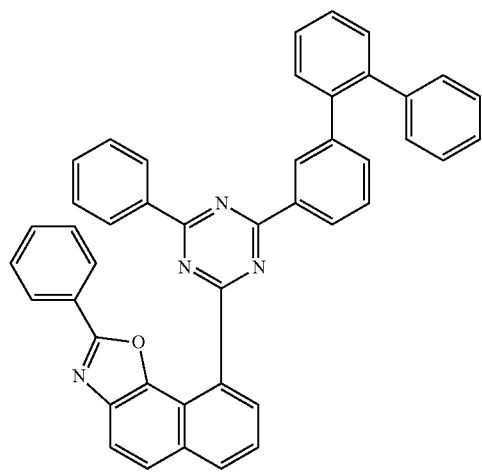
43
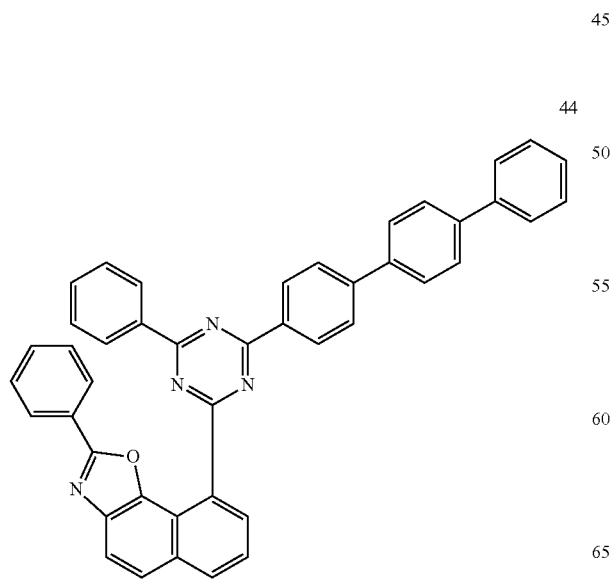
44
45
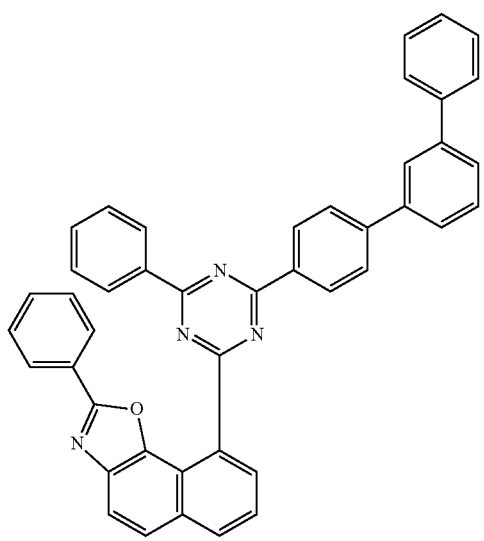
46
47
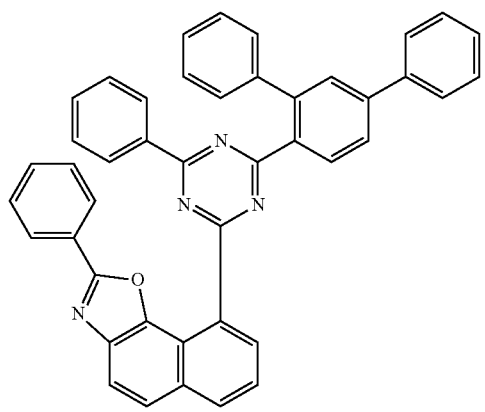

61
-continued
48
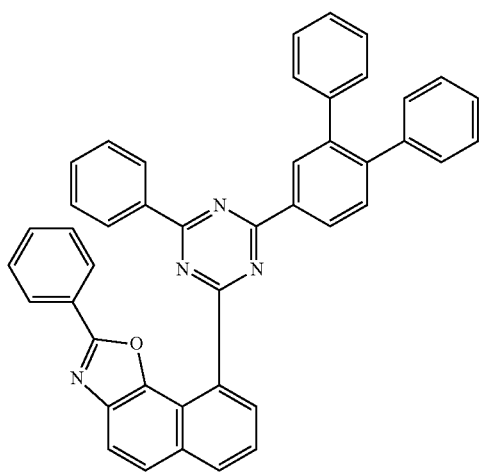
49
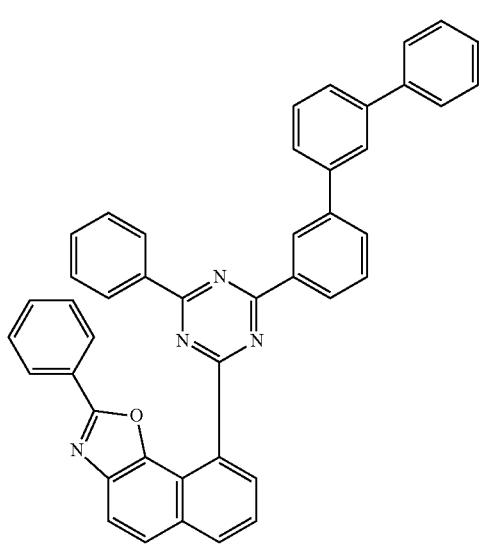
50
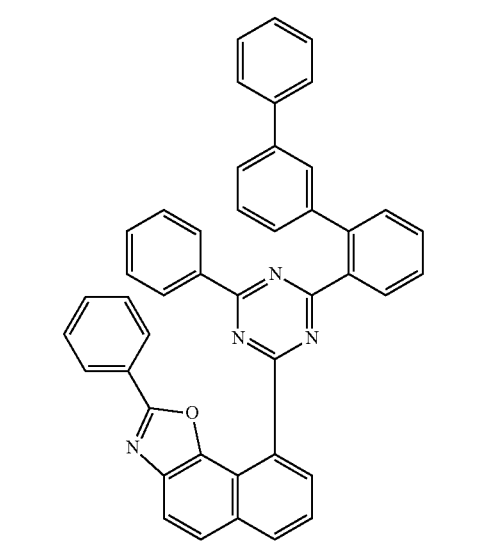
62
-continued
51
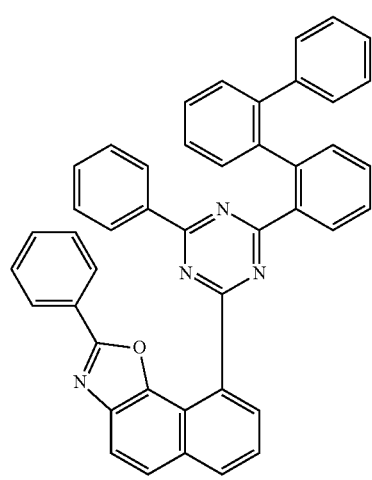
52
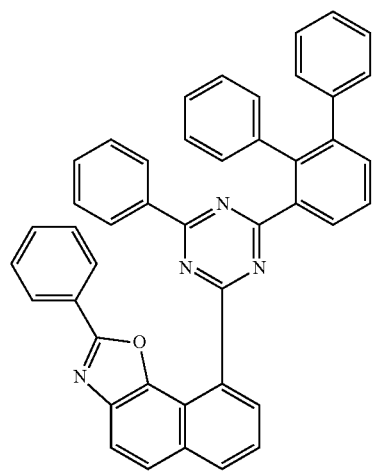
53
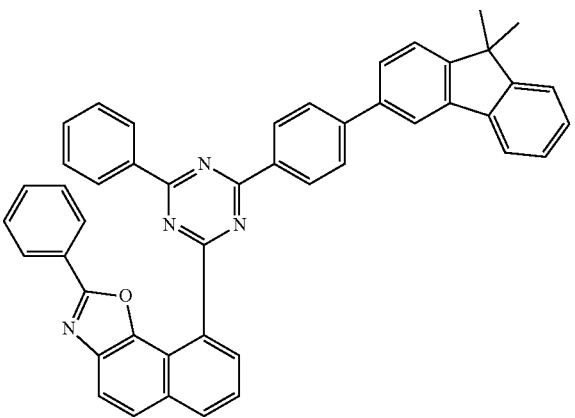

54
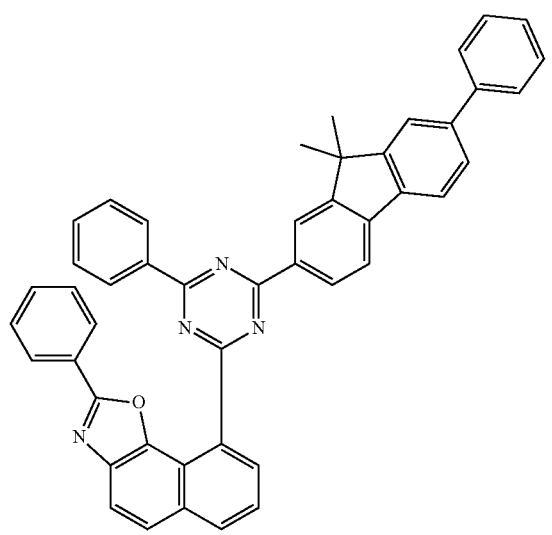
57
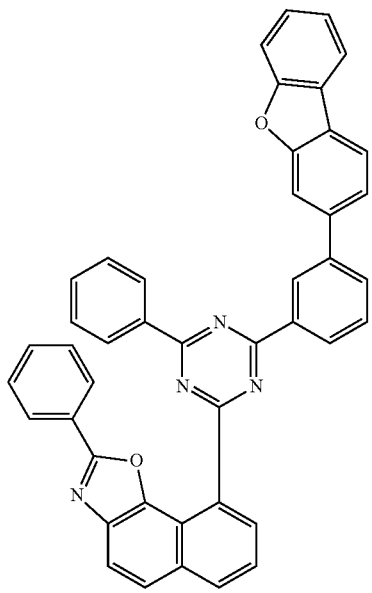
55
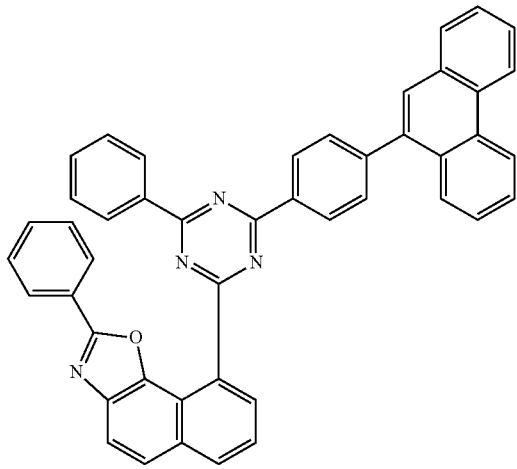
58
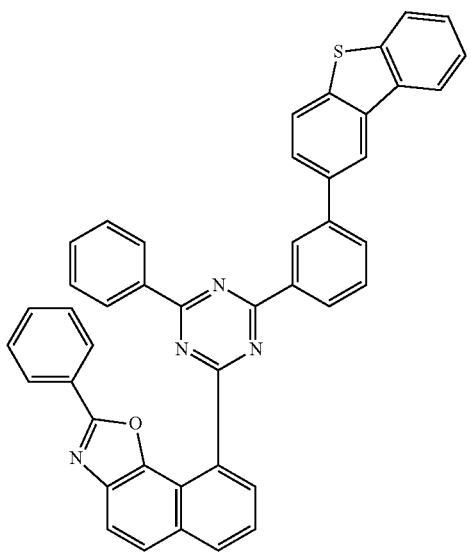
56
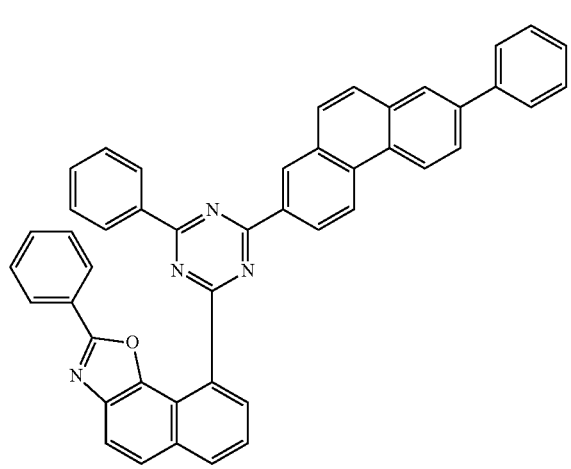
59
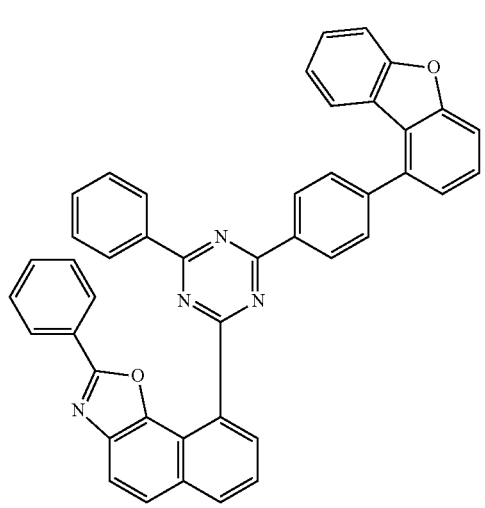

60
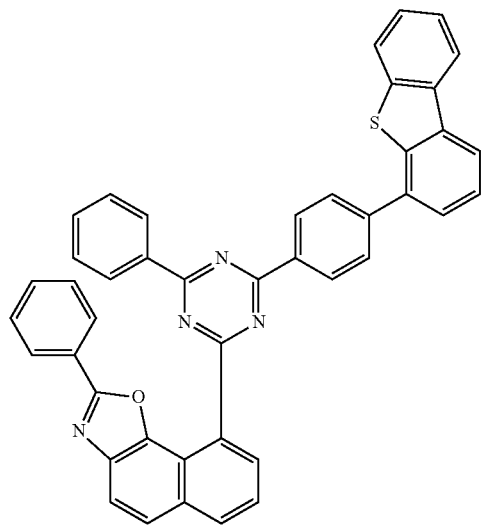
61
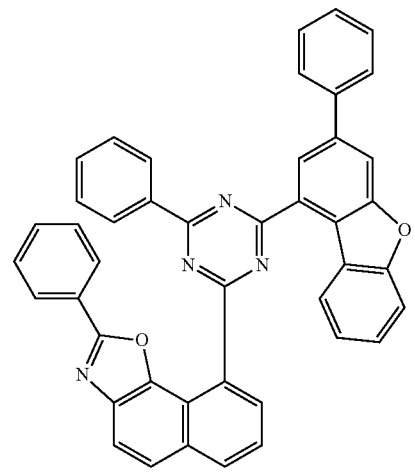
62
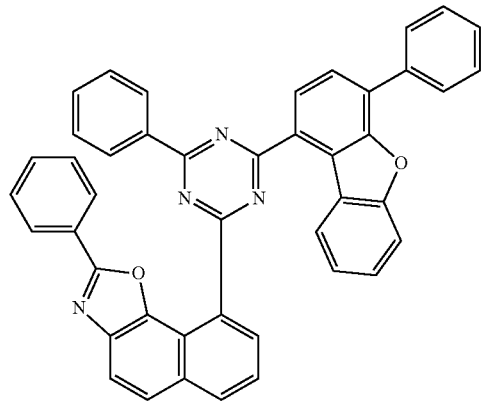
63
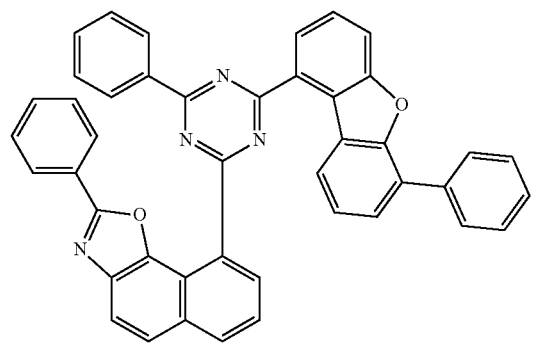
64
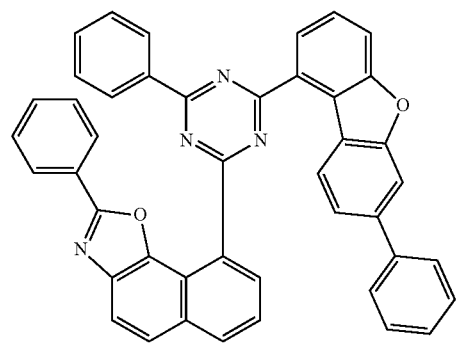
65
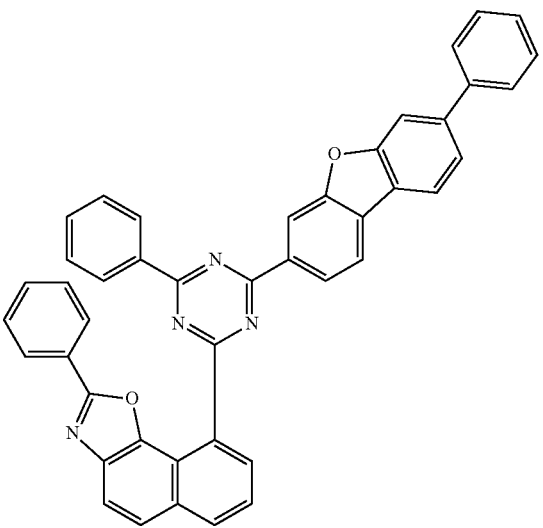

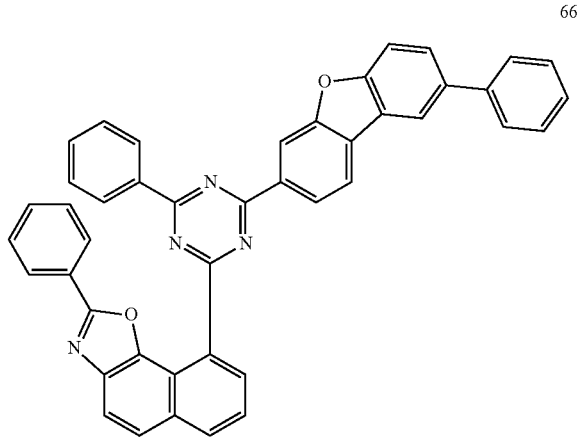
66
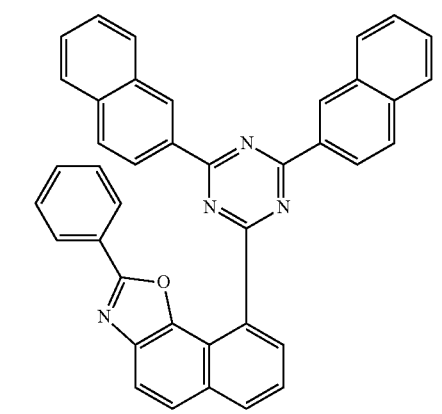
67
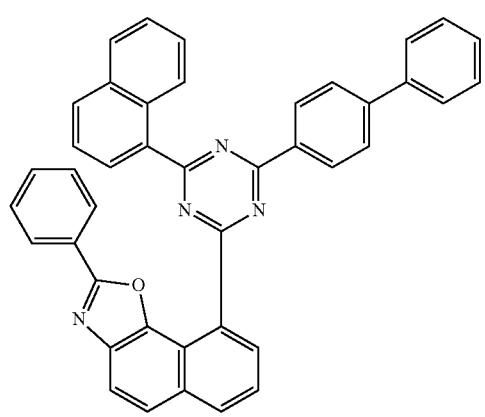
68
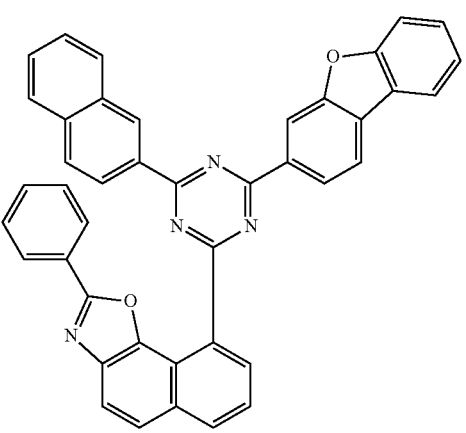
69
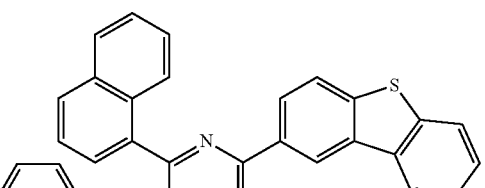
70
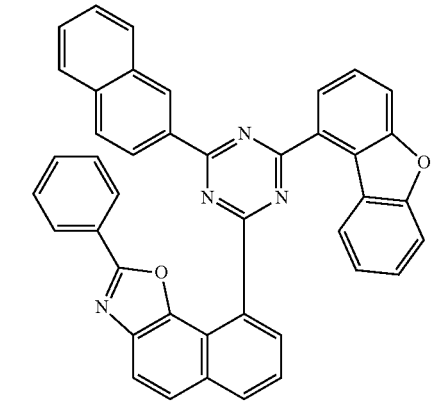
71
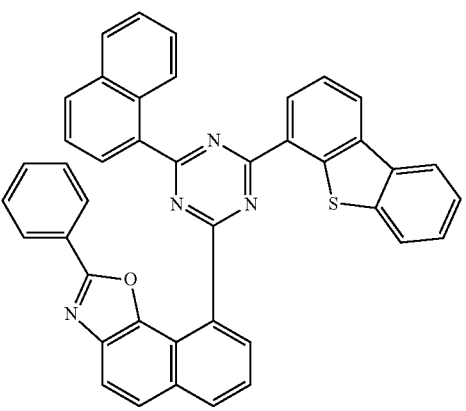
72

73
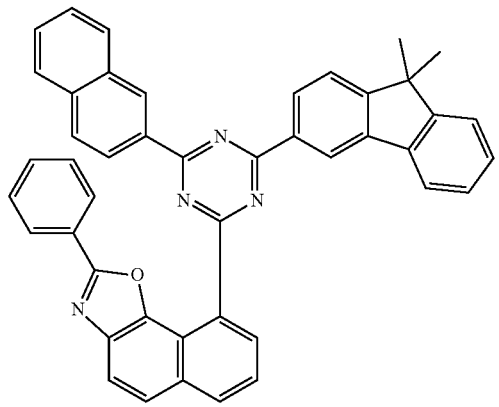
74
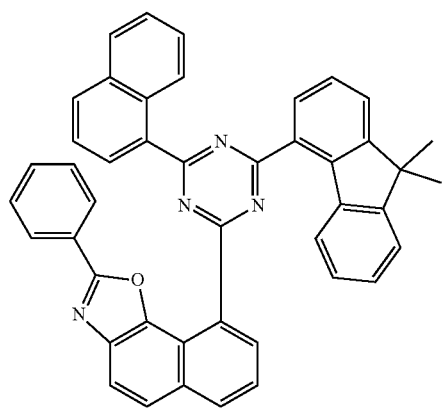
75
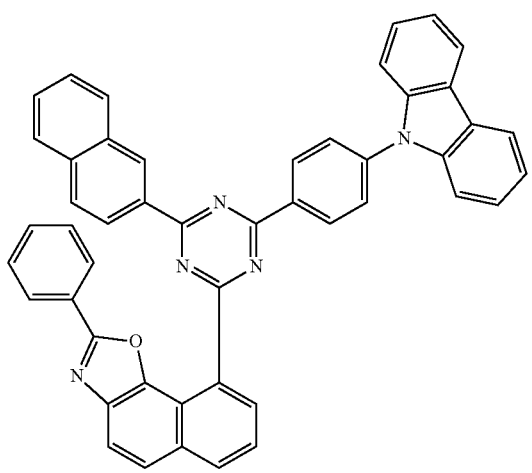
76
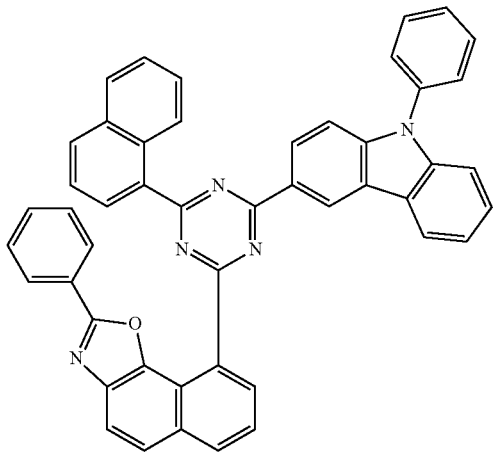
77
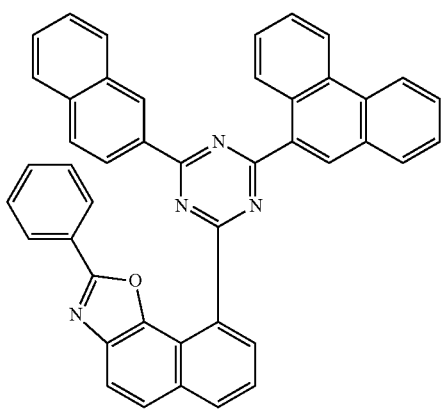
78
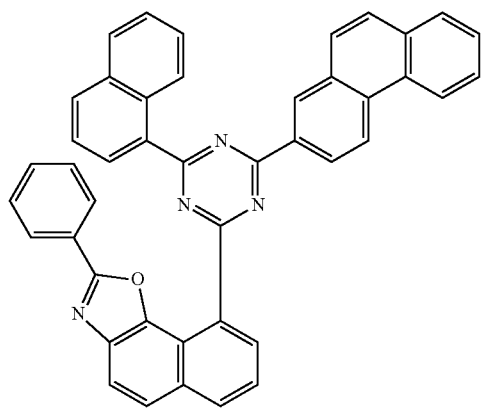

71
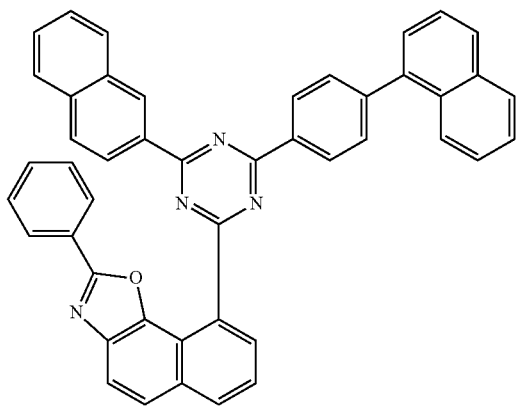
79
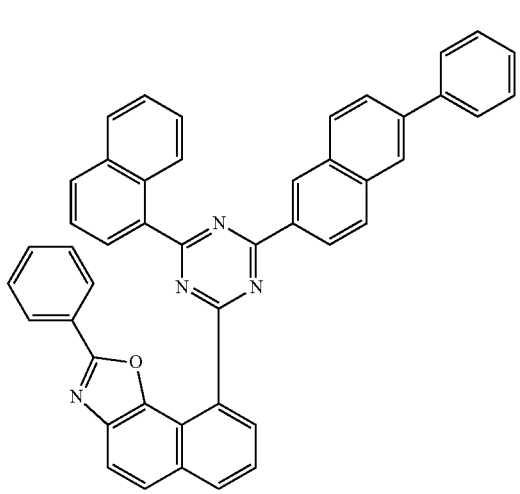
80
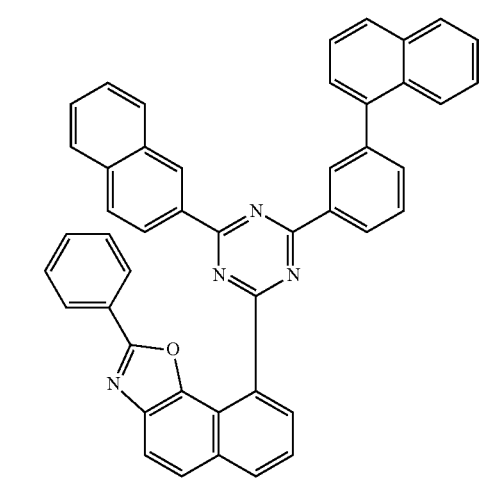
81
72
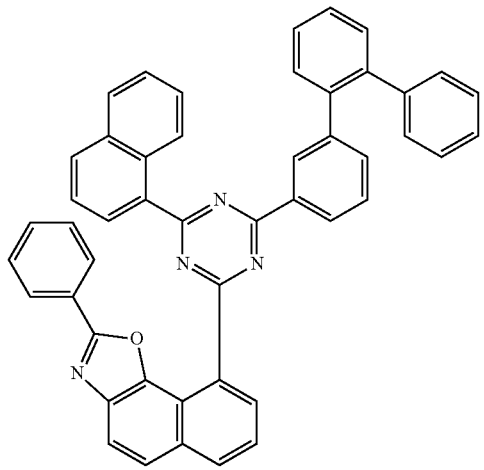
82
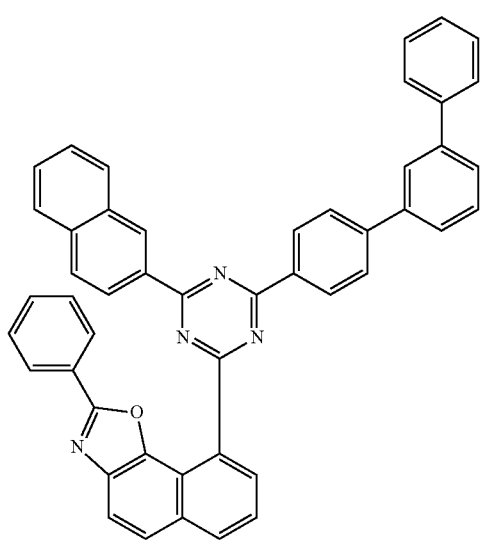
83
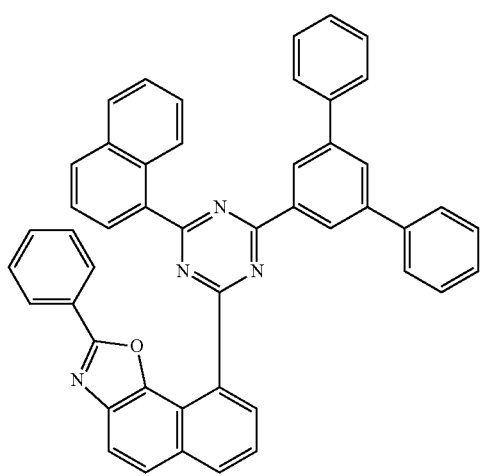
84

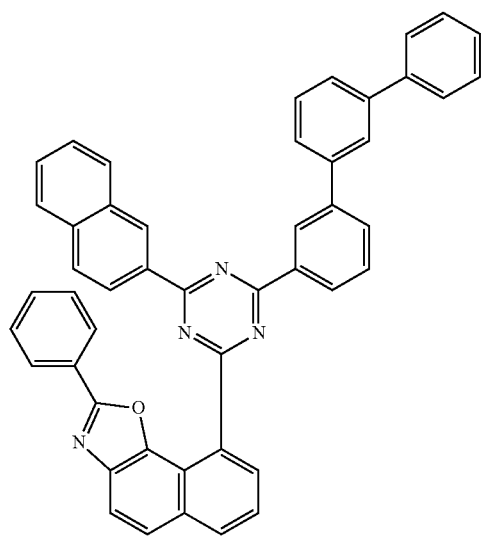
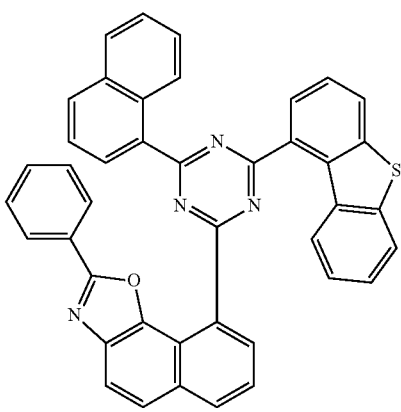
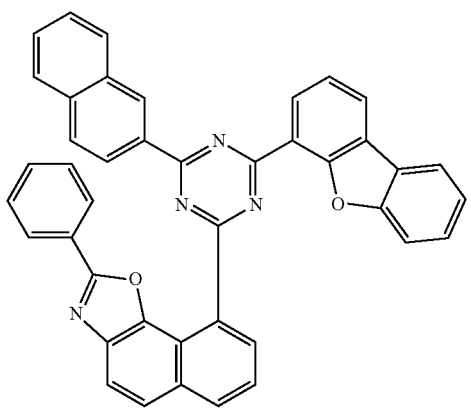

91
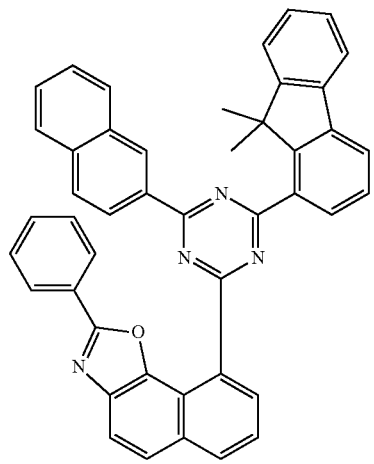
92
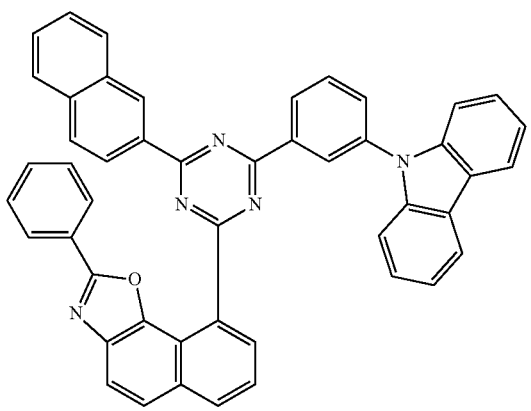
94
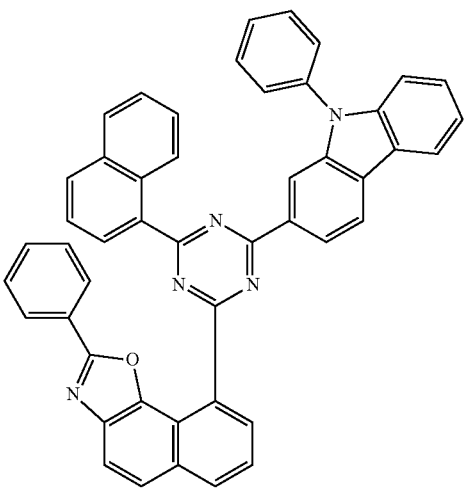
95
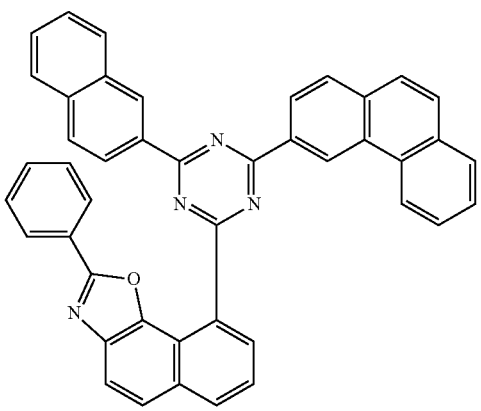
96
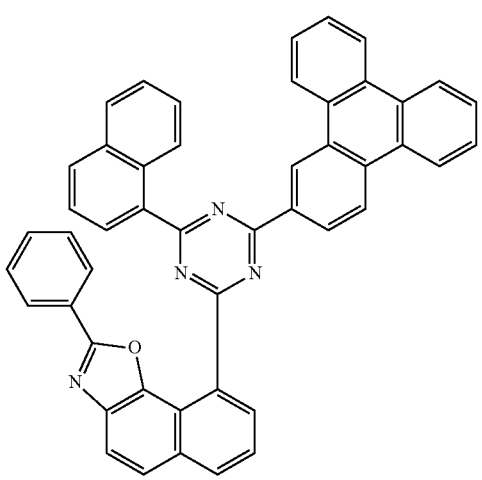

97
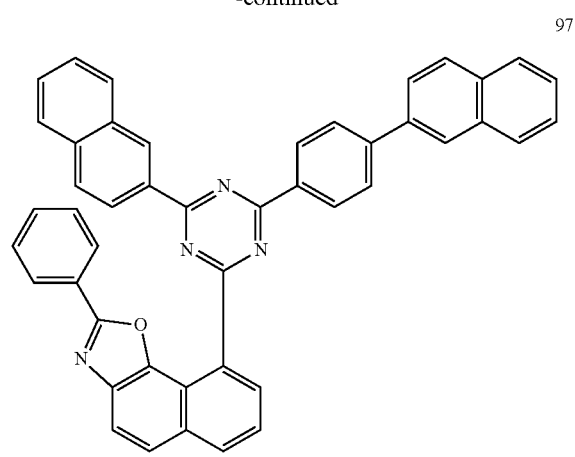
98
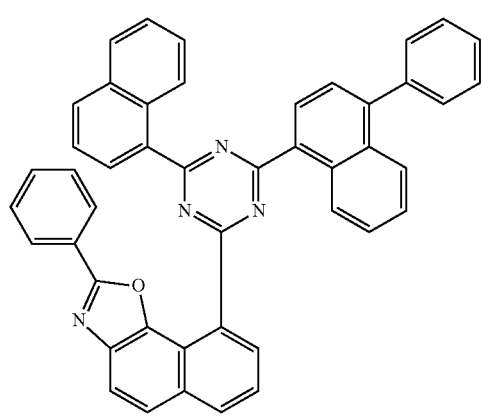
99
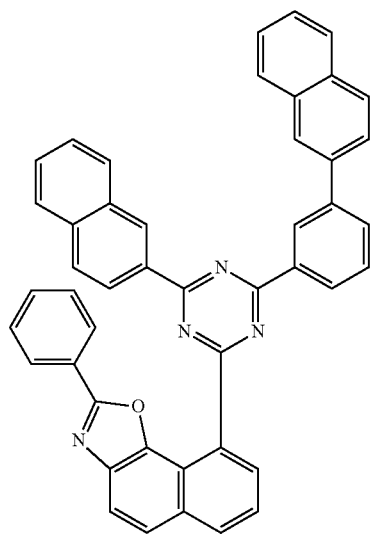
100
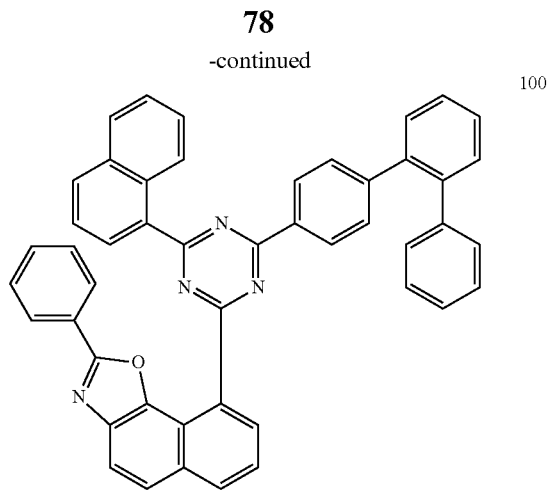
101
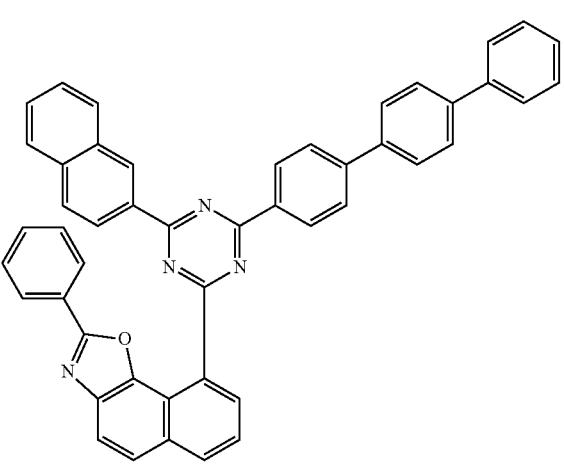
102
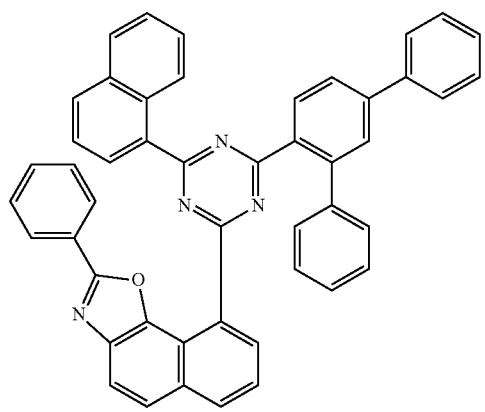

103
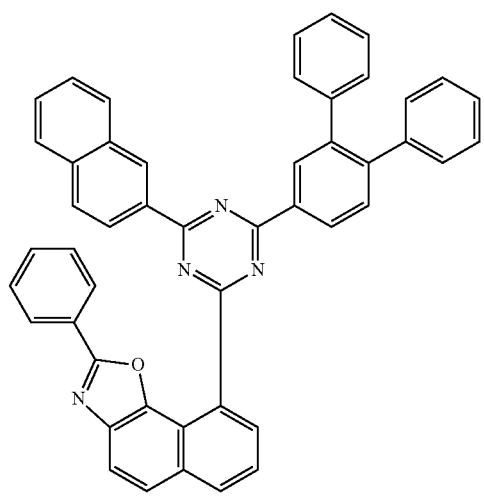
104
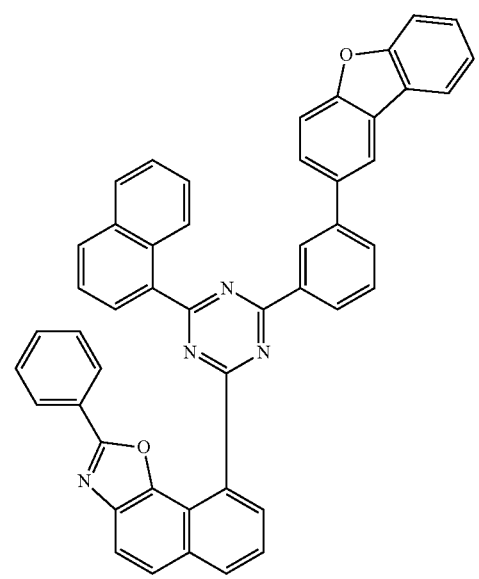
105
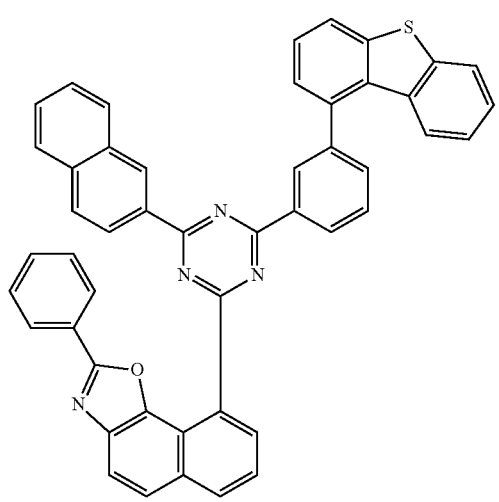
106
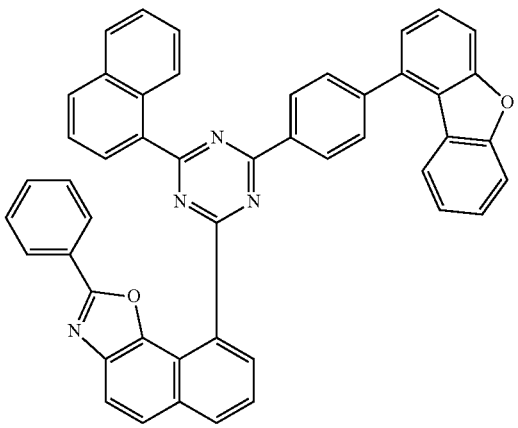
107
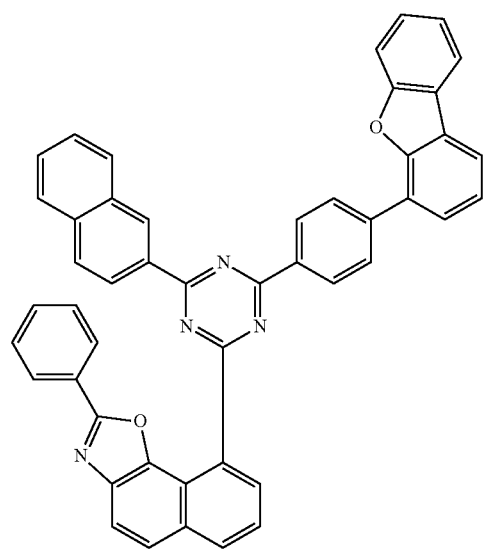
108
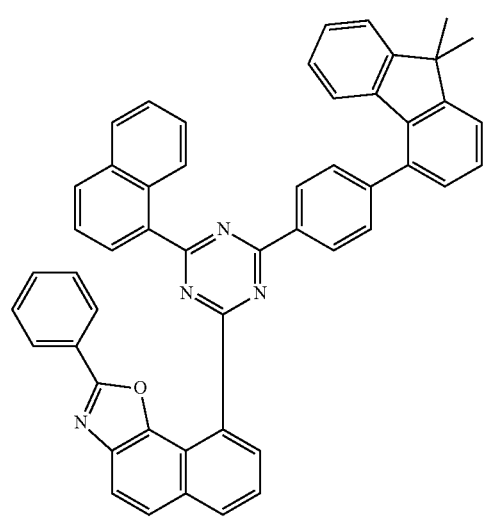

109
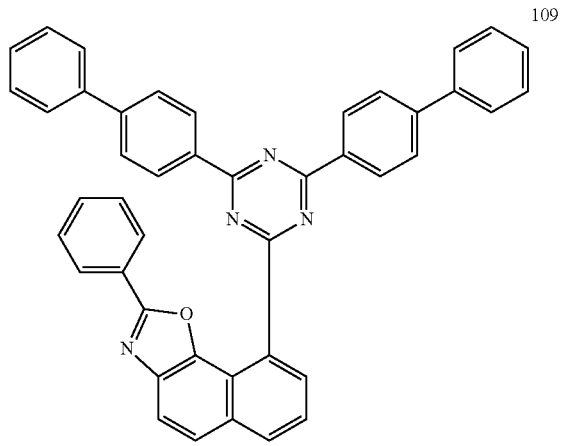
110
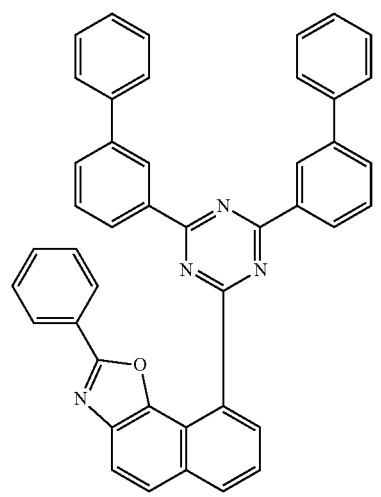
111
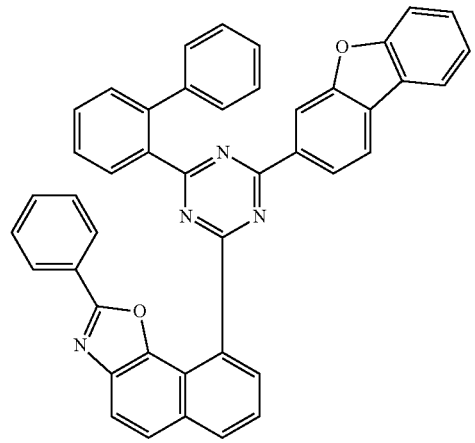
112
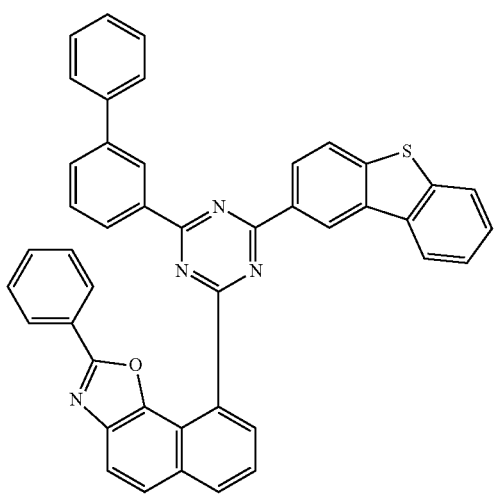
113
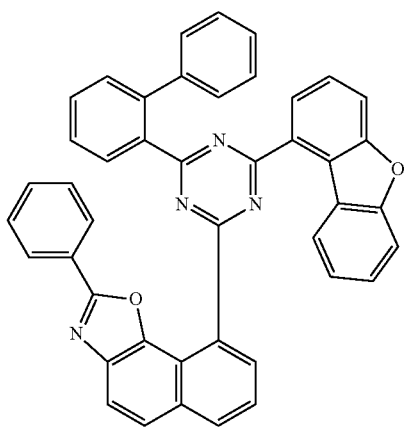
114
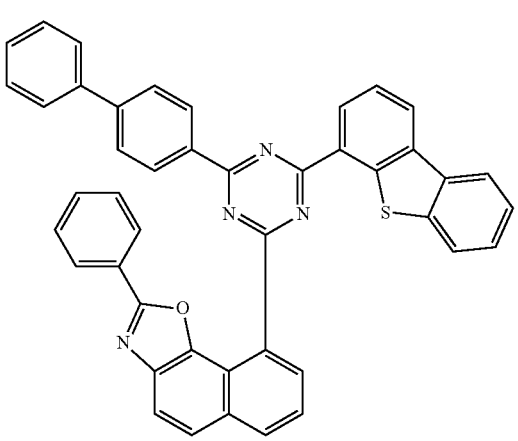

115
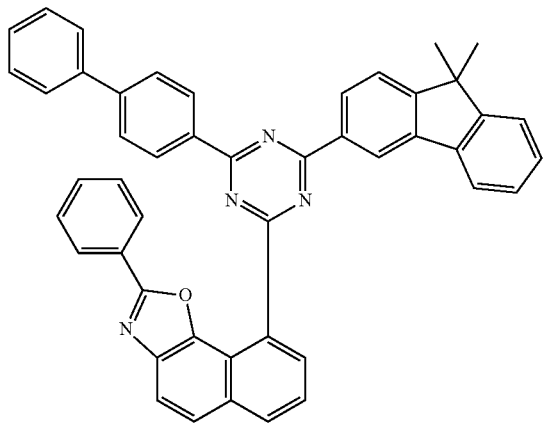
116
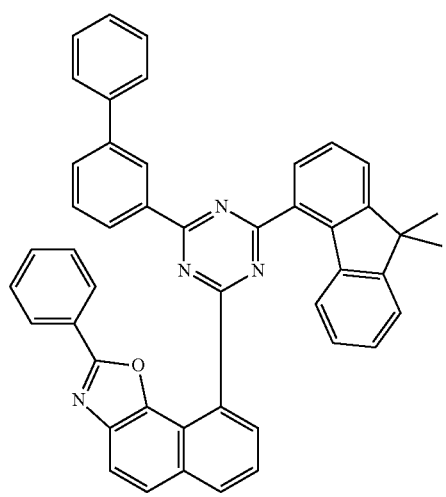
117
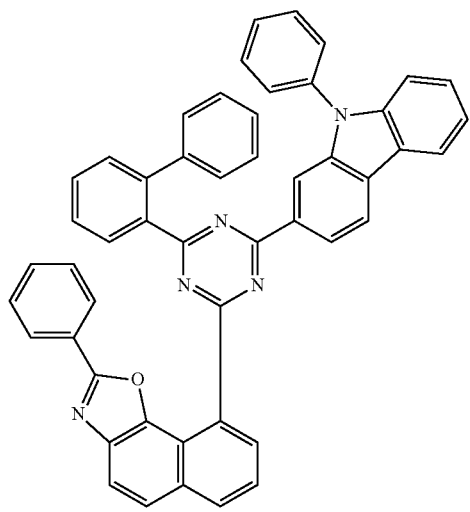
118
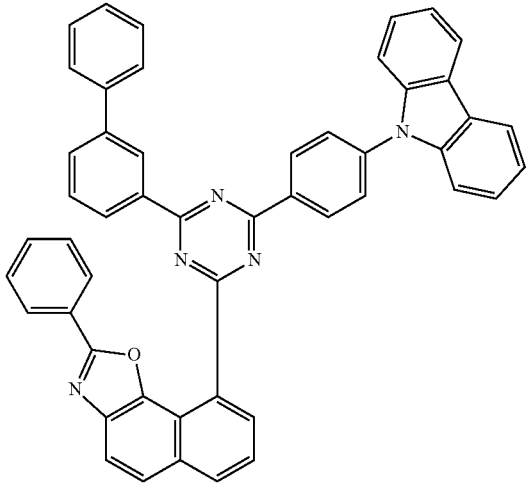
119
120
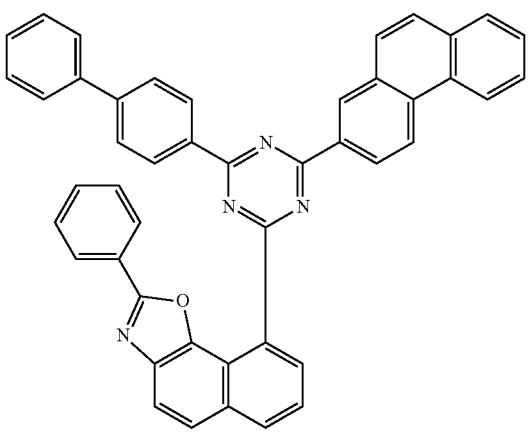

85
-continued
121
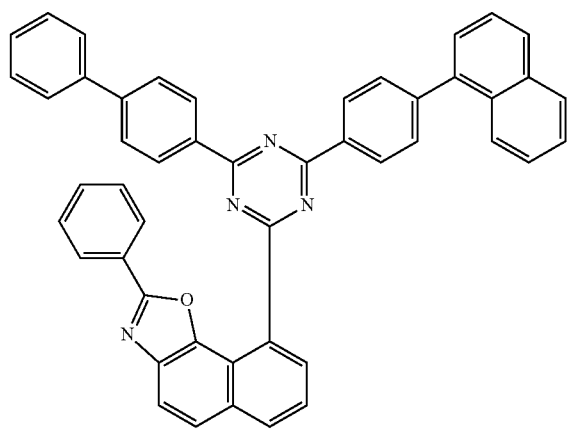
122
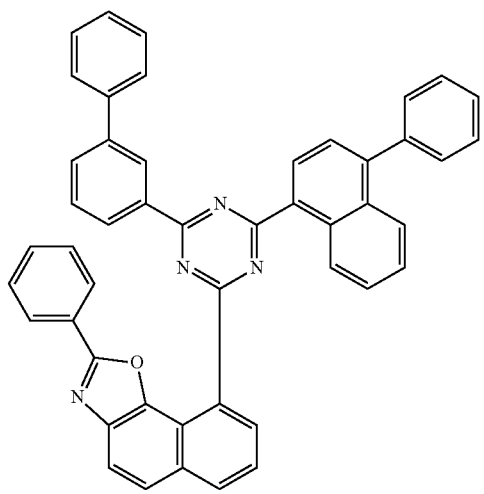
123
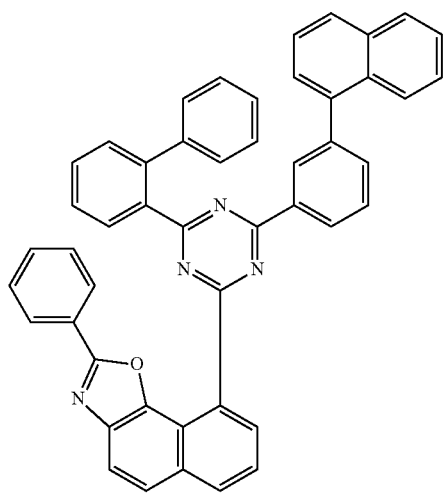
86
-continued
124
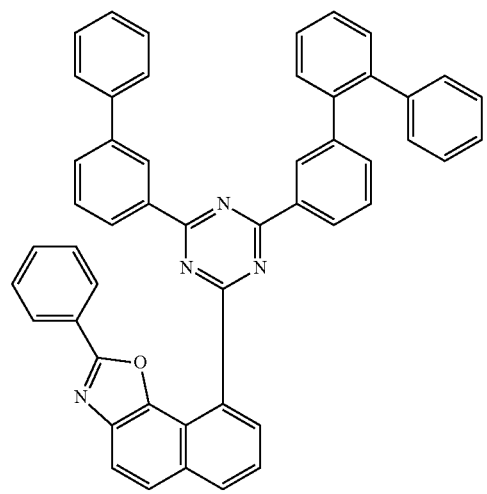
125
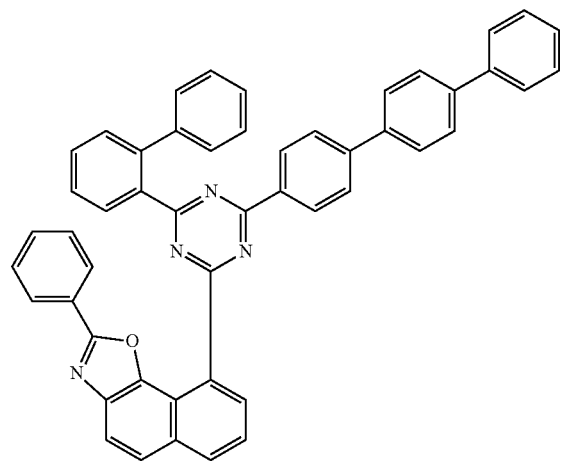
126
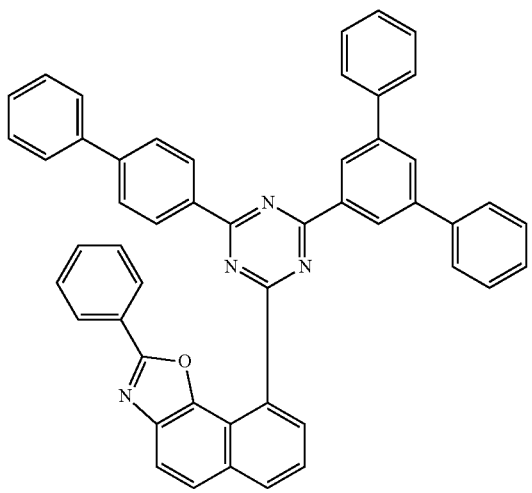

127
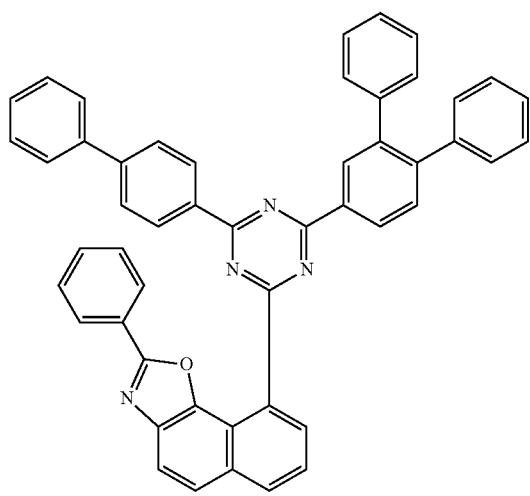
128
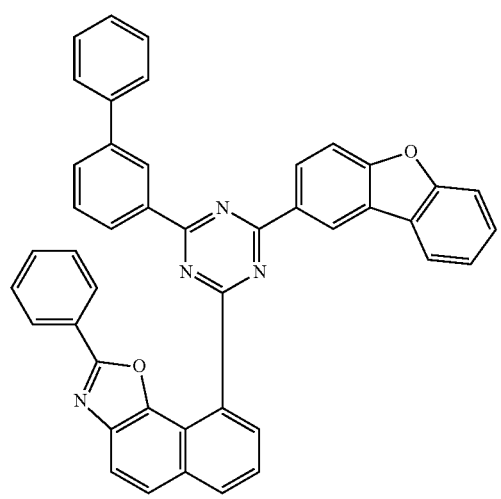
129
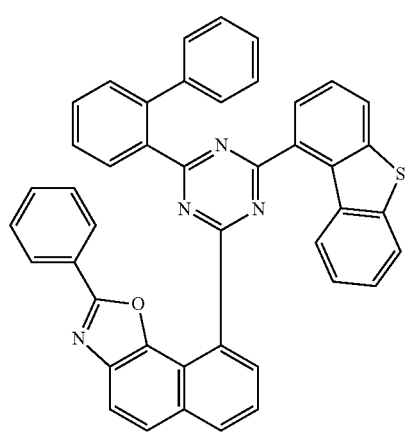
130
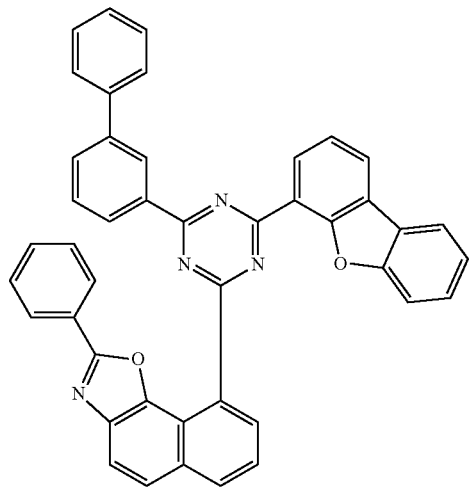
131
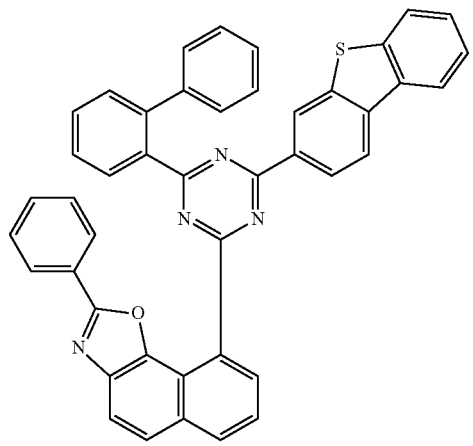
132
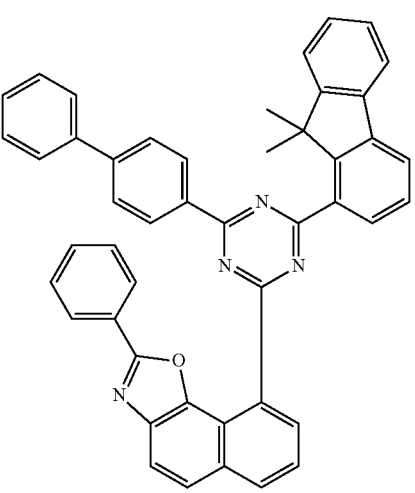

133
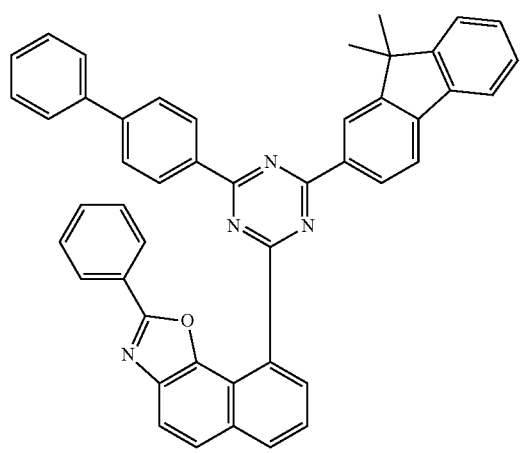
134
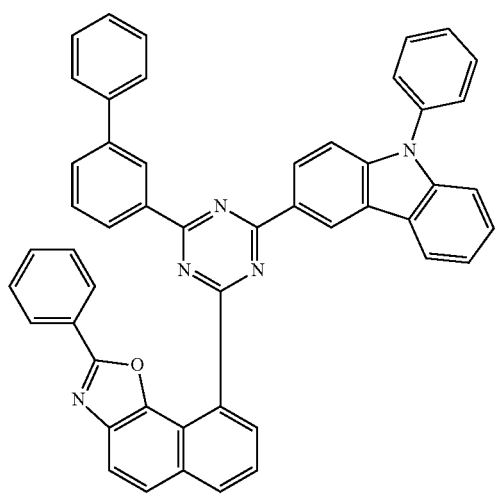
135
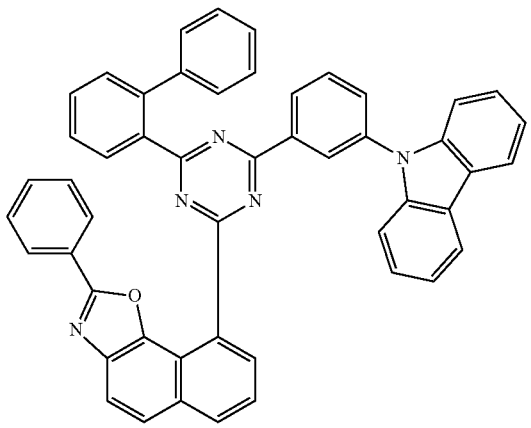
136
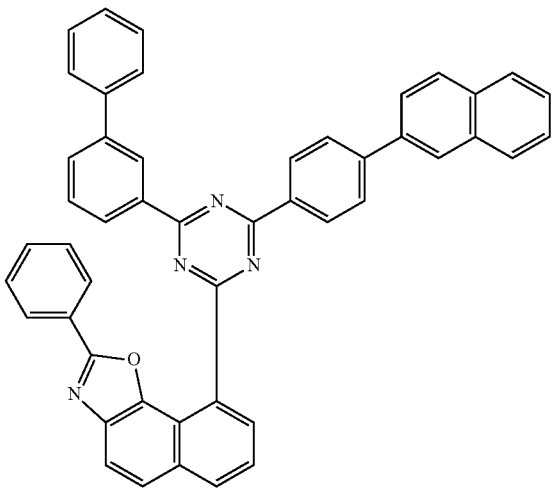
137
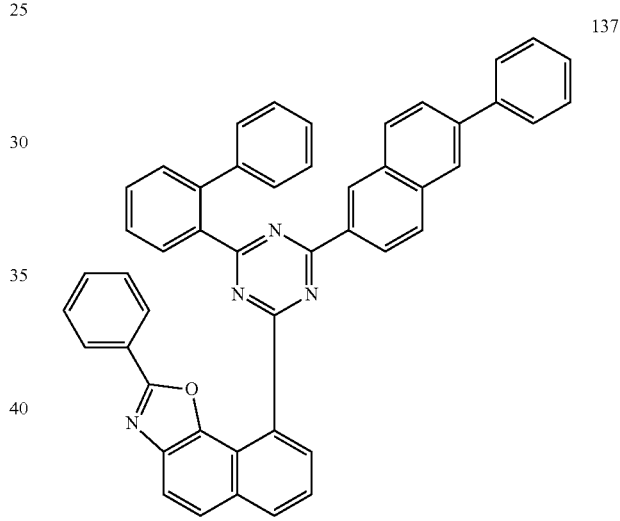
138
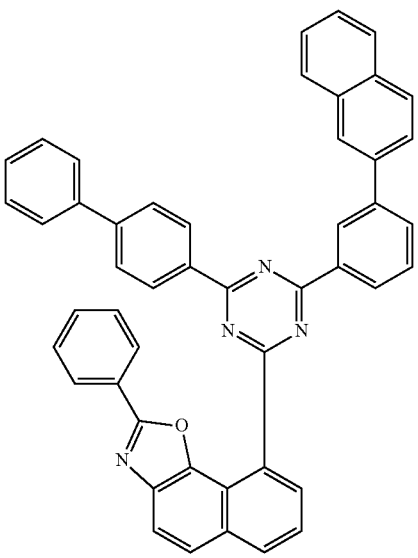

-continued
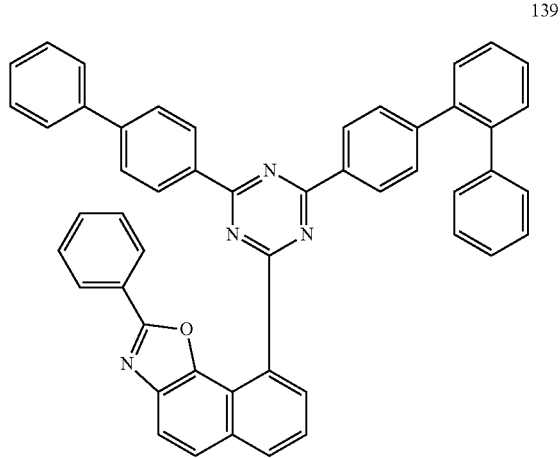
139
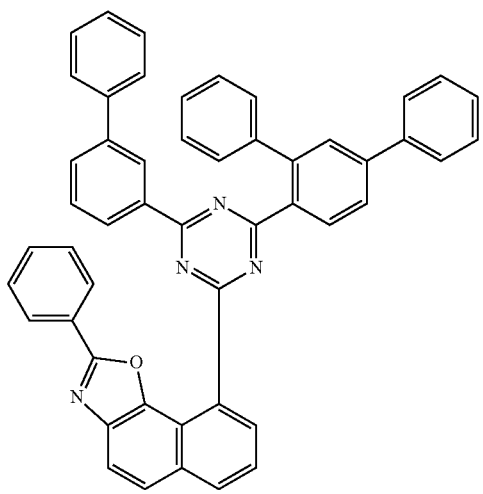
142
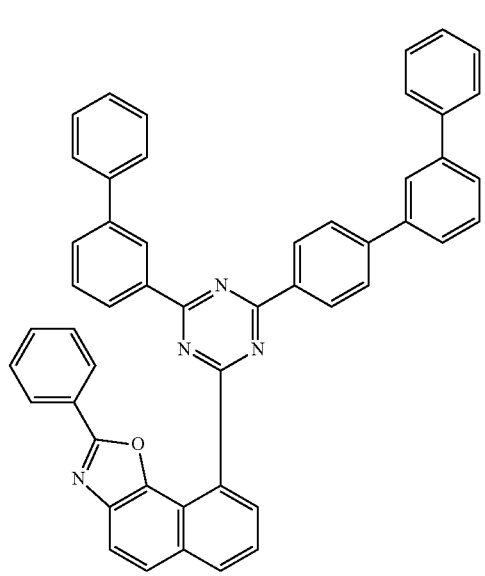
140
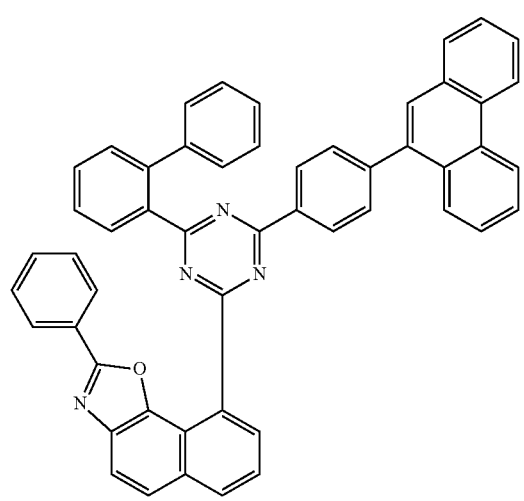
143
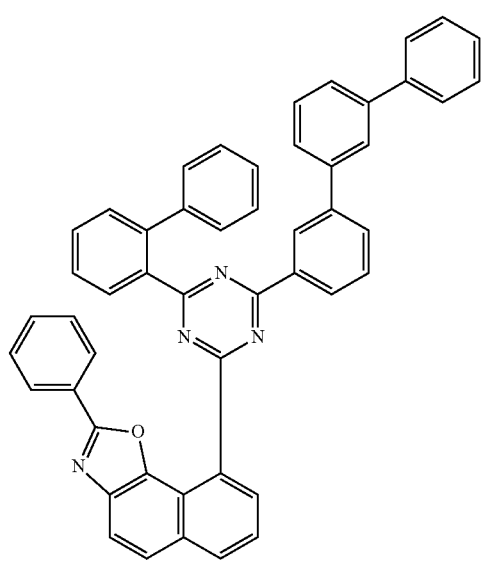
141
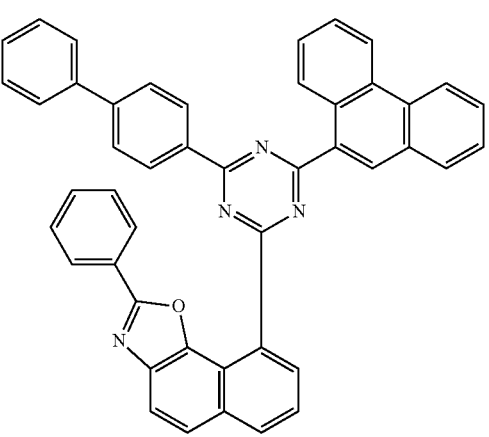
144

145
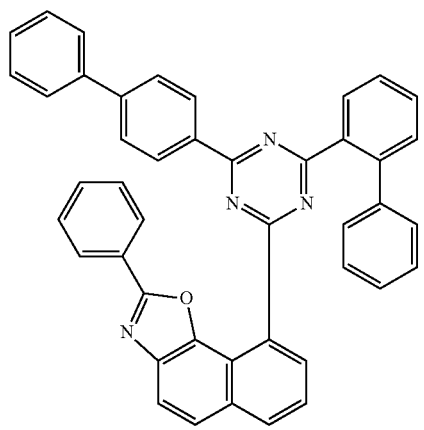
146
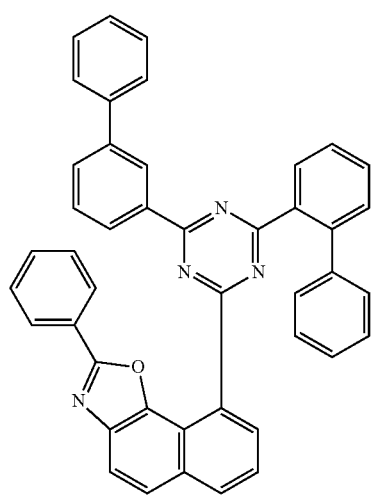
147
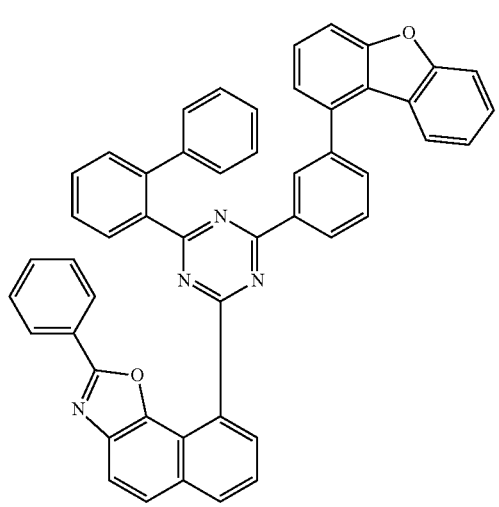
148
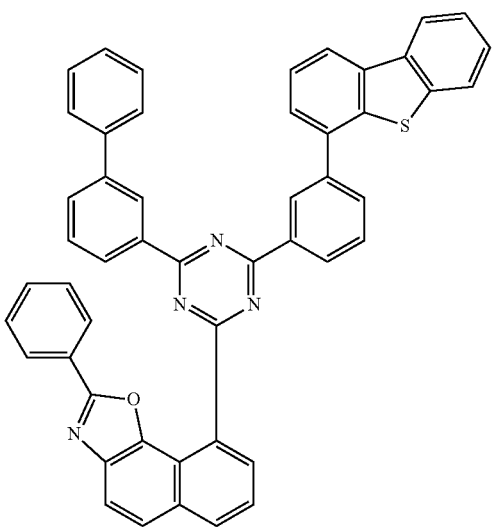
149
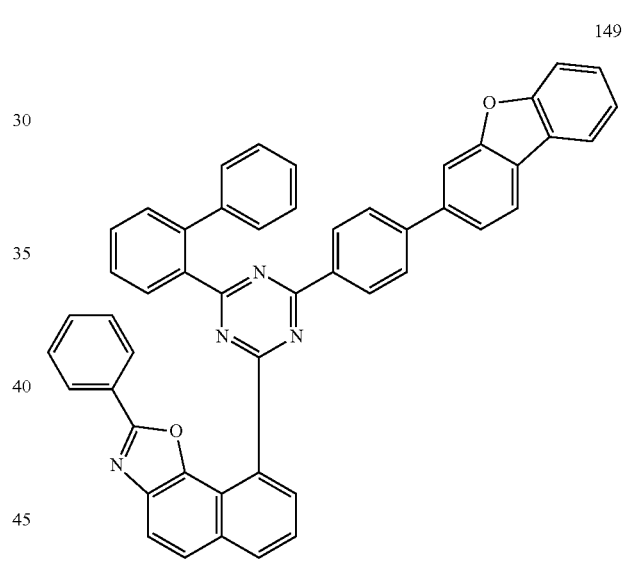
150
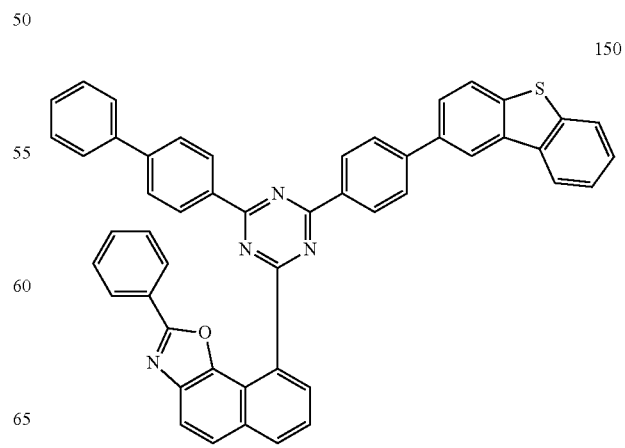

151 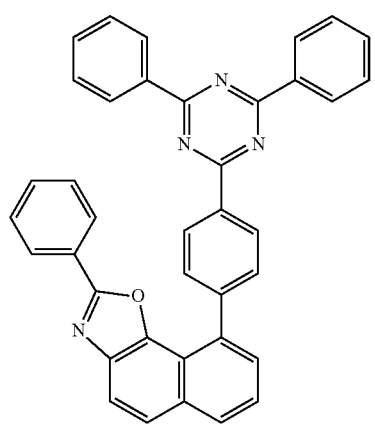
152 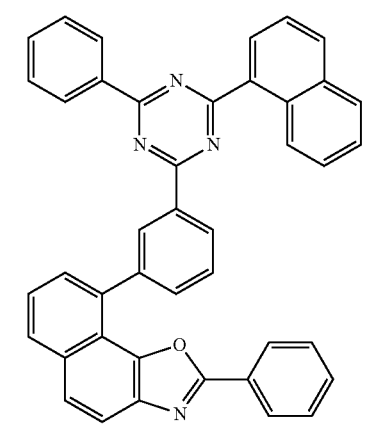
153 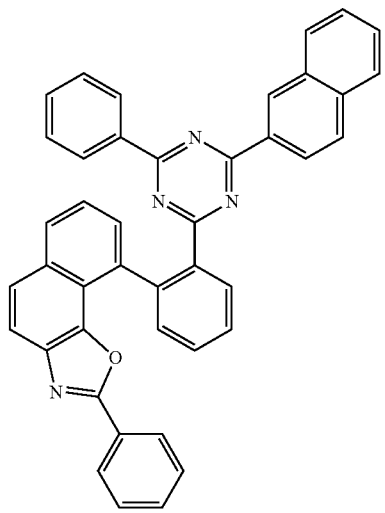
154 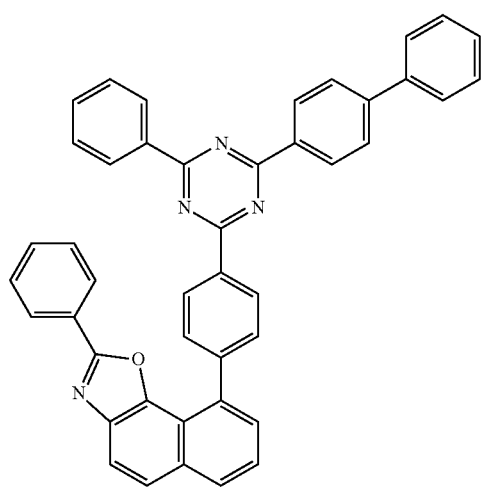
155 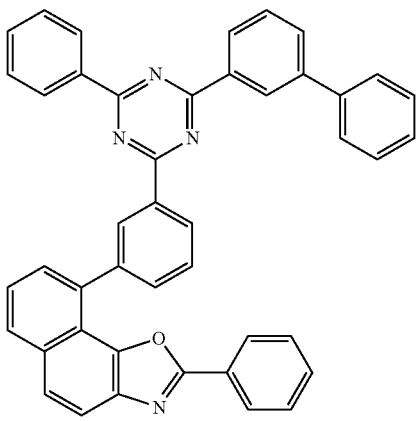
156 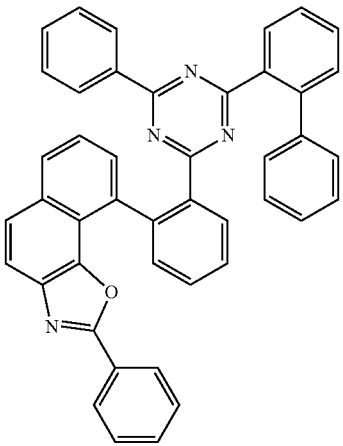

157
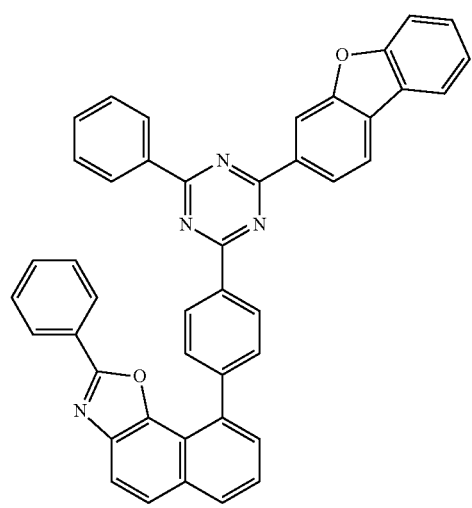
158
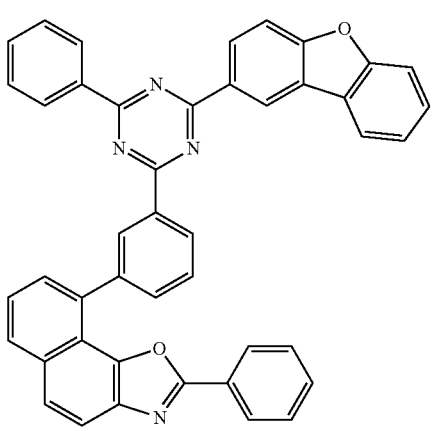
159
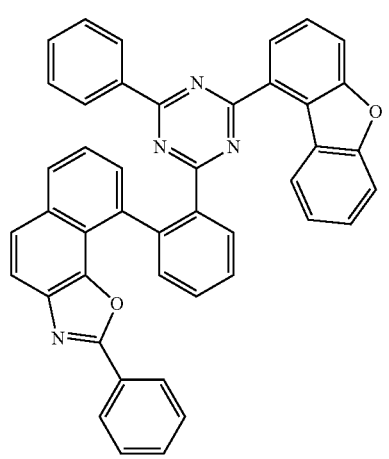
160
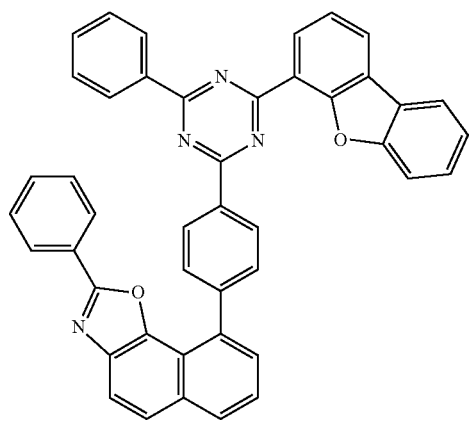
161
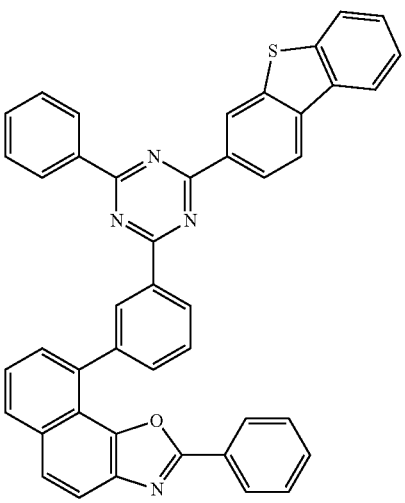
162
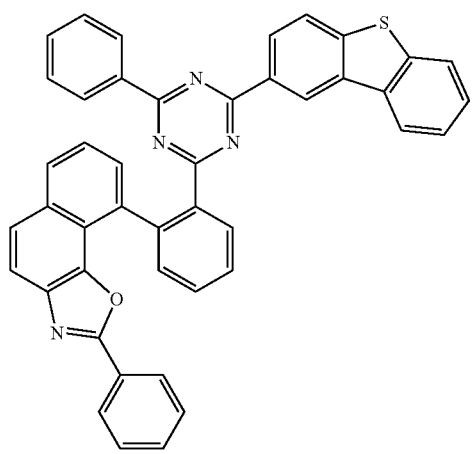

163
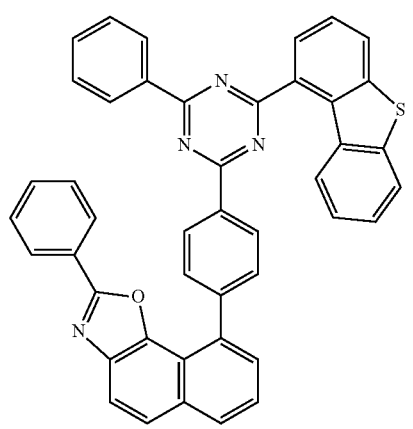
164
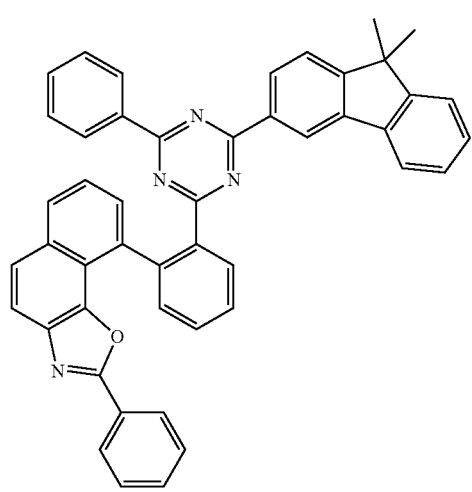
166
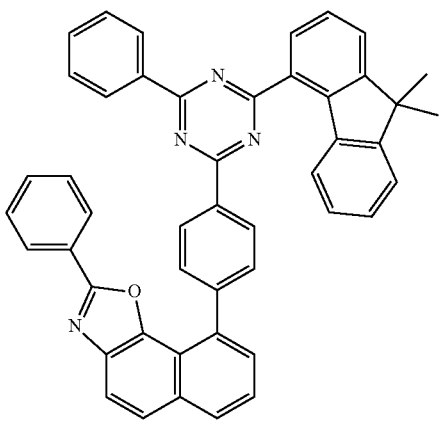
167
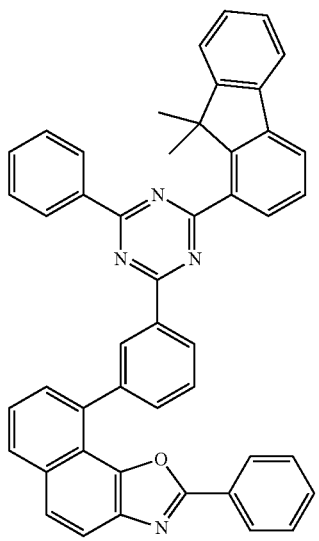
165
168

169
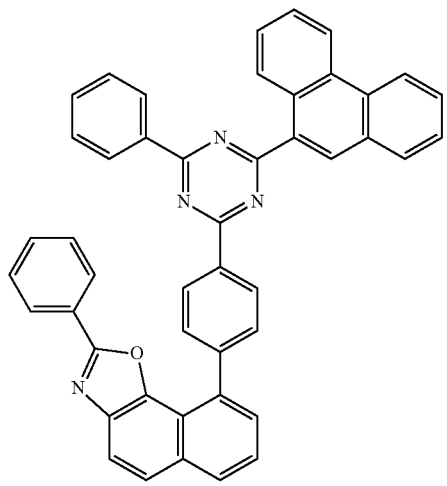
170
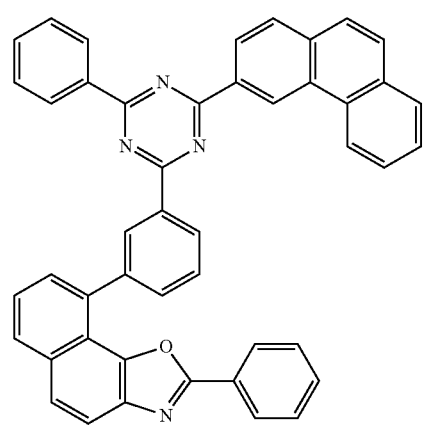
171
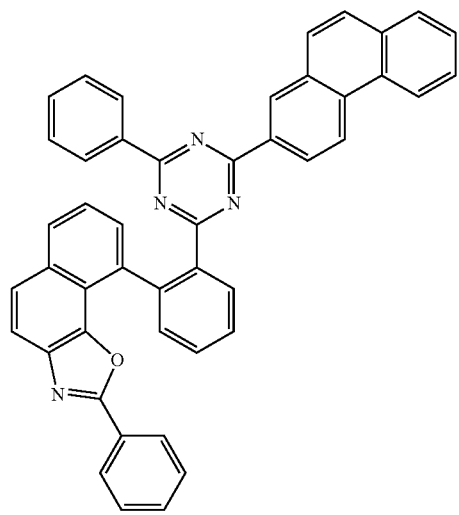
172
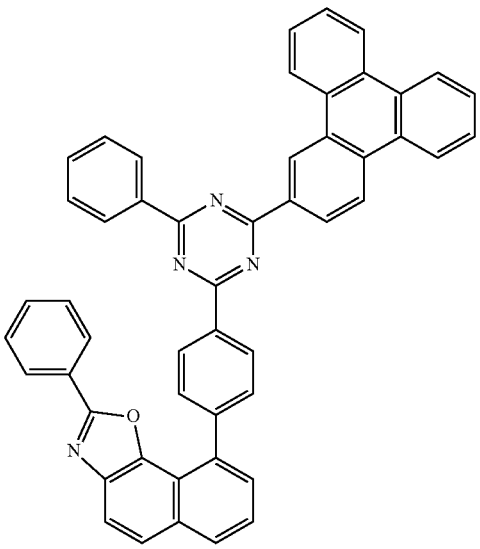
173
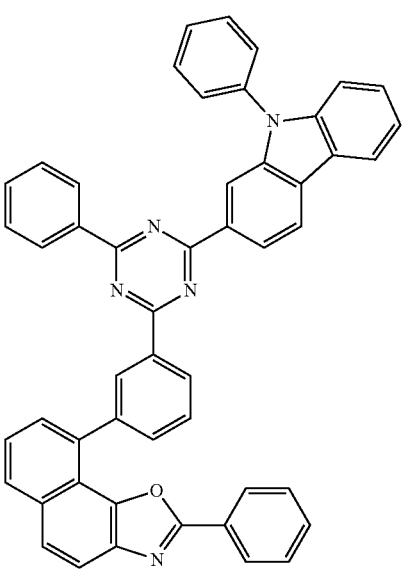
174
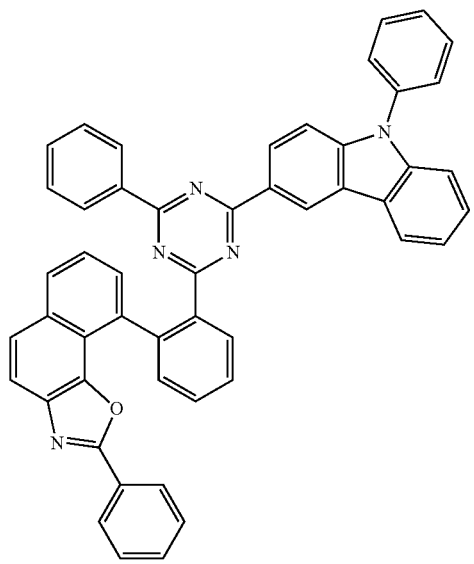

175
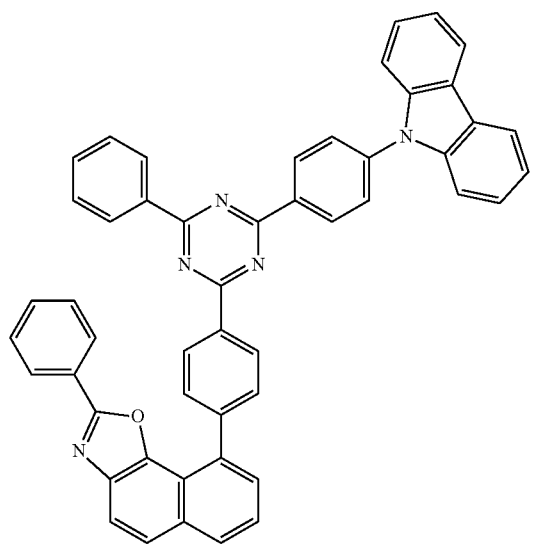
176
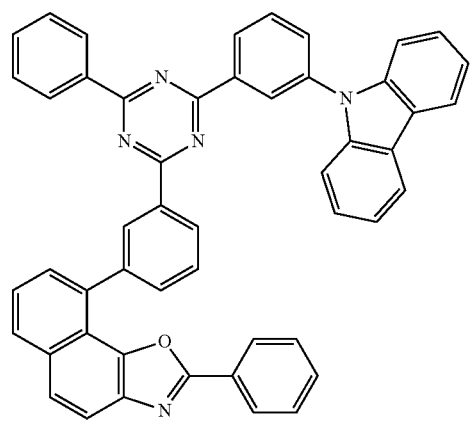
177
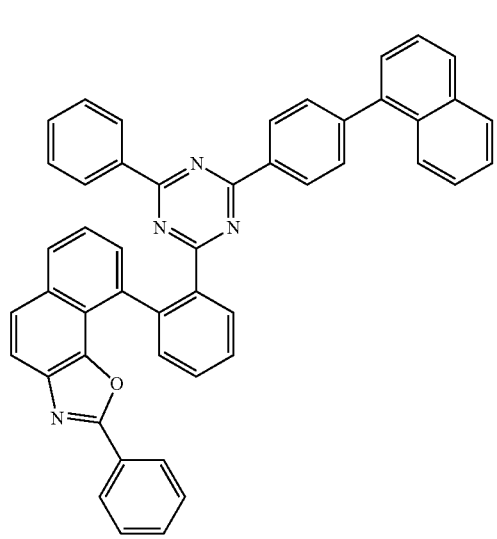
178
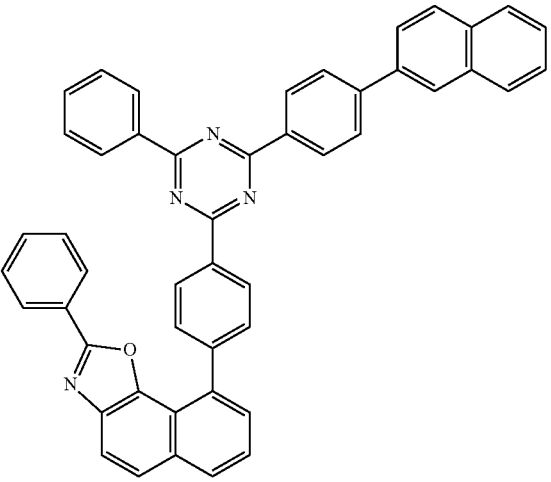
179
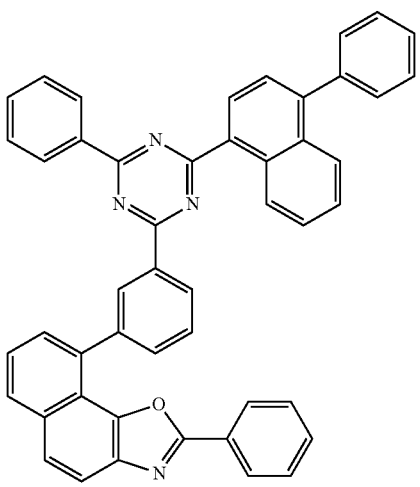
180
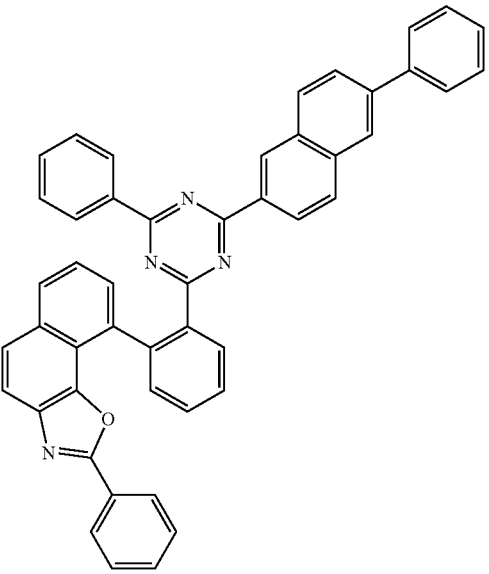

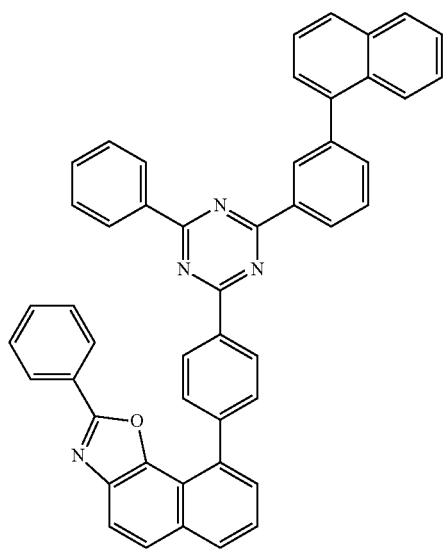
181
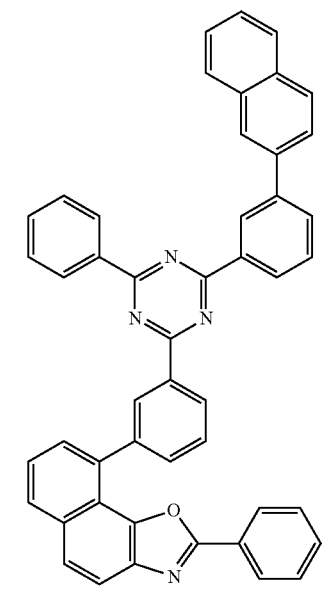
182
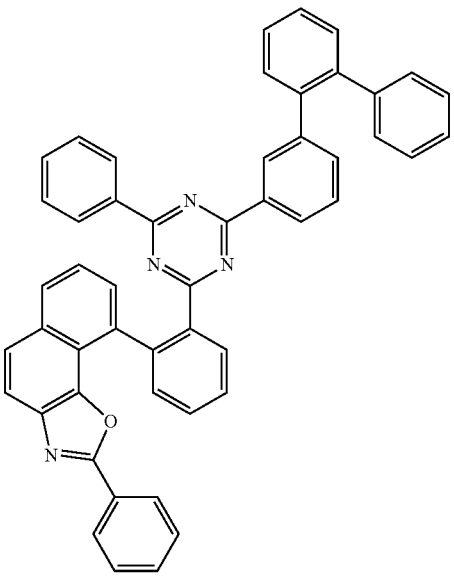
183
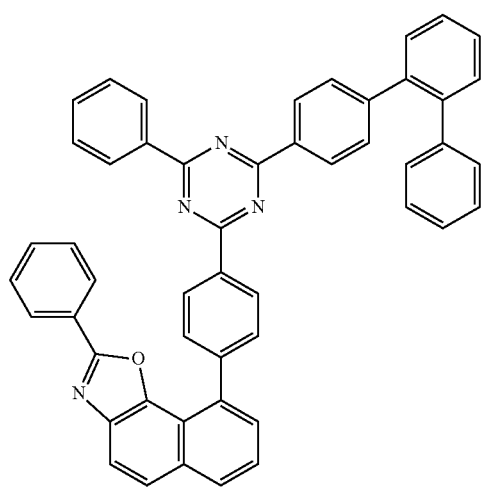
184
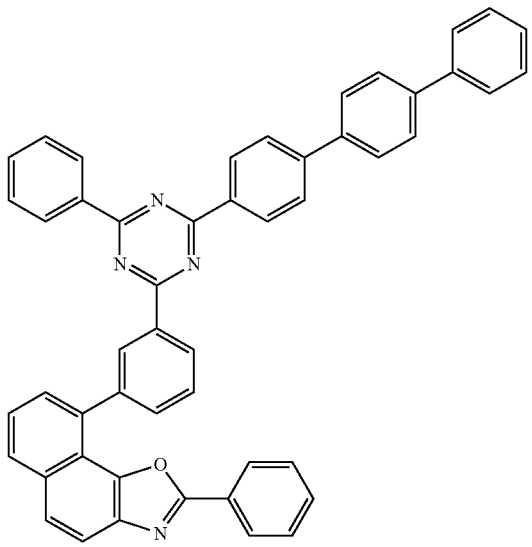
185

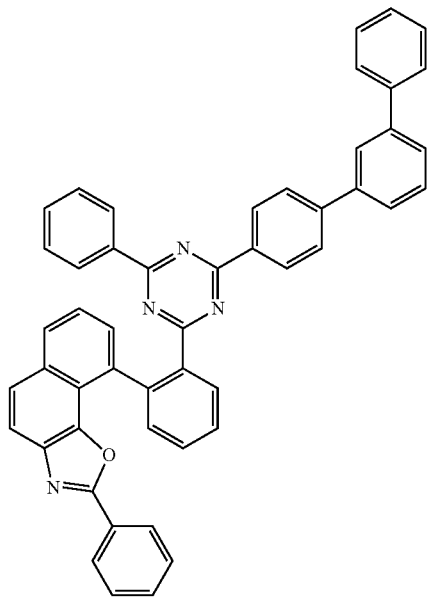
186
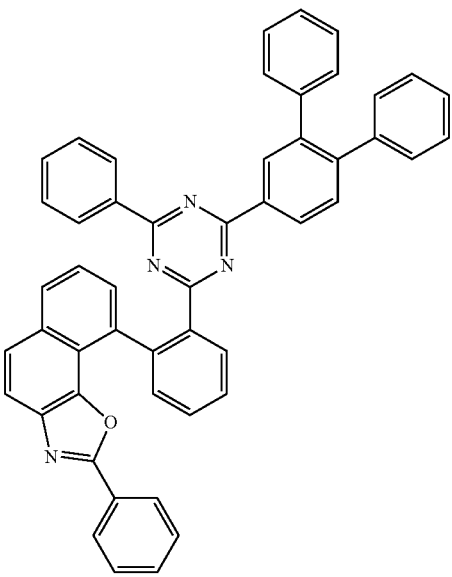
189
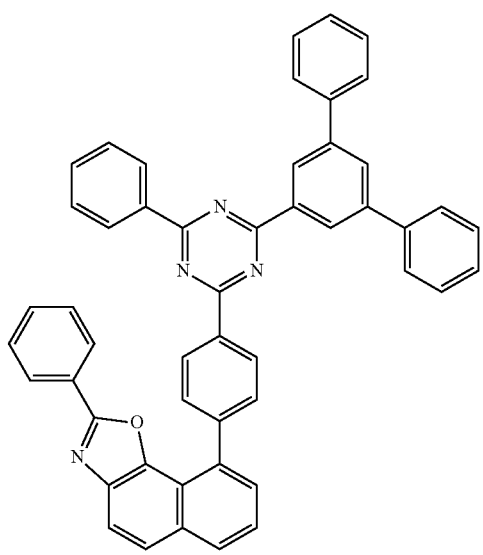
187
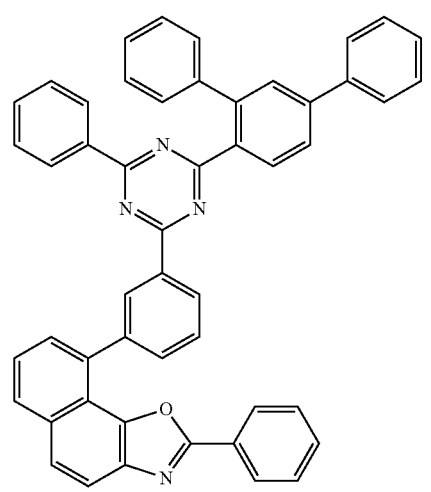
188
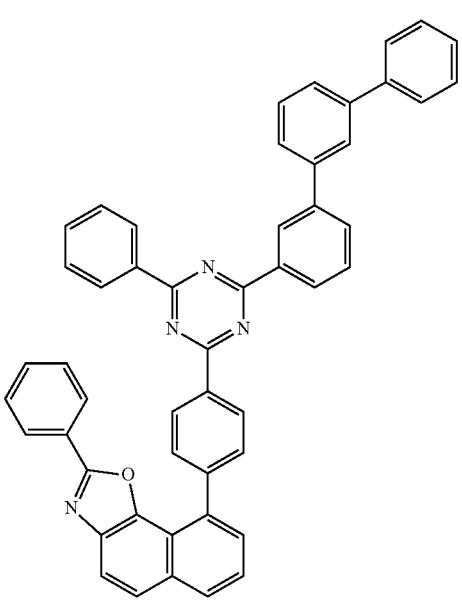
190

191
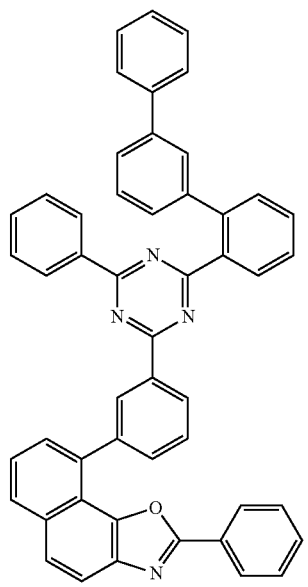
192
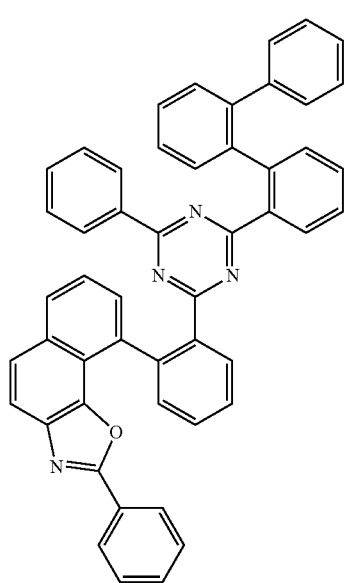
193
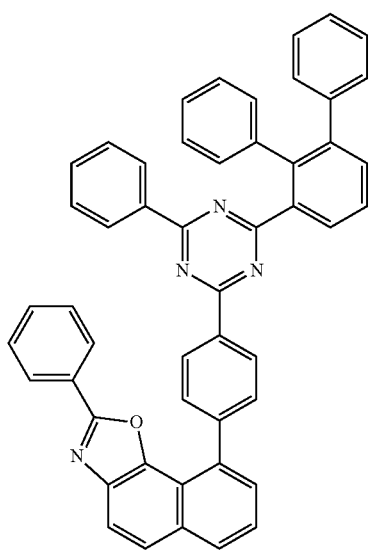
194
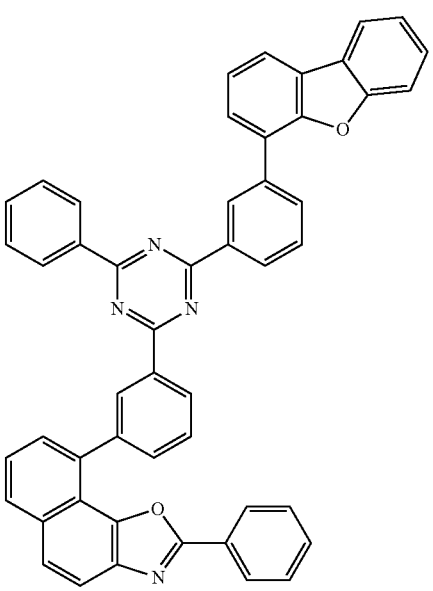

111
-continued
195
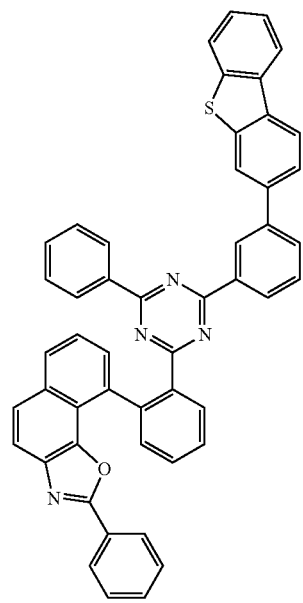
196
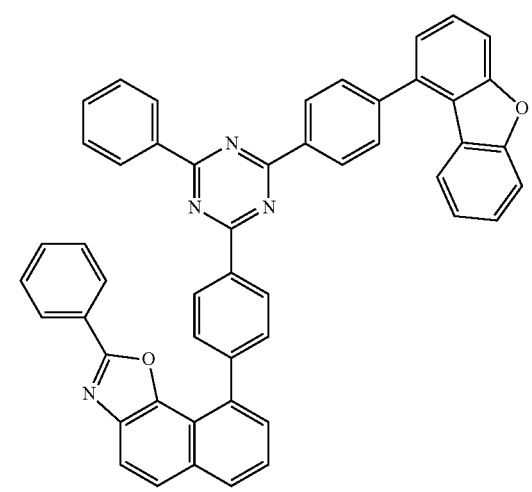
197
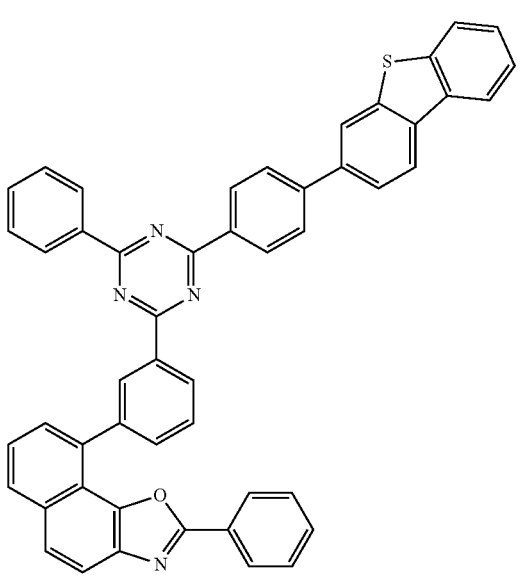
112
-continued
198
199
200
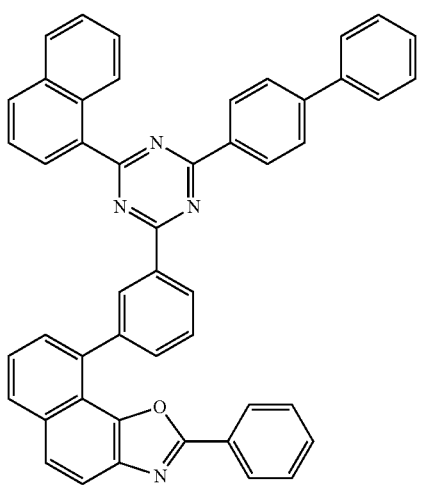

201
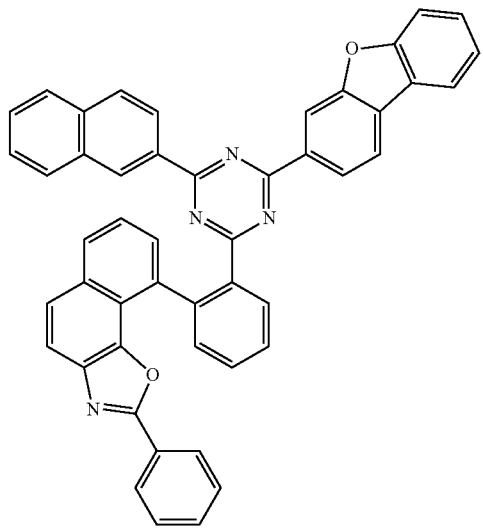
202
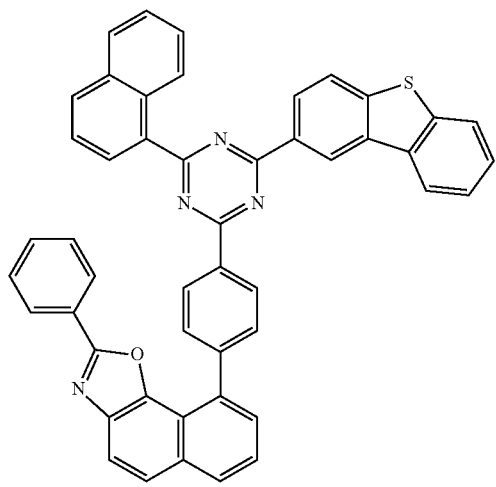
203
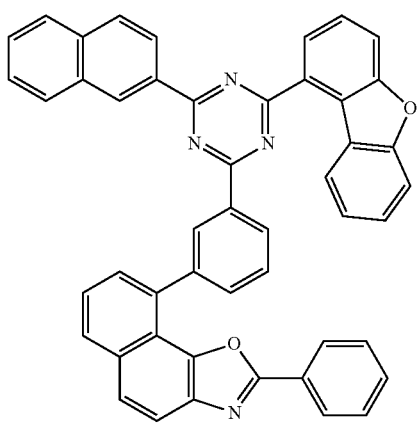
204
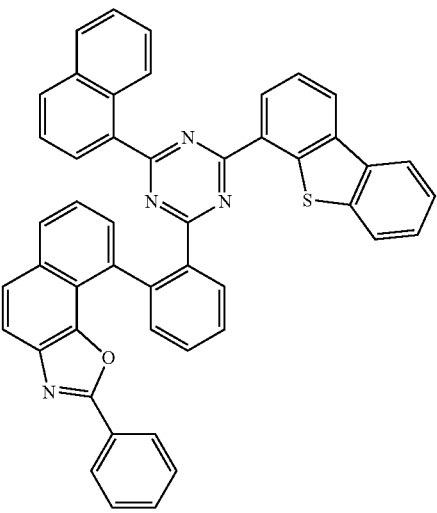
205
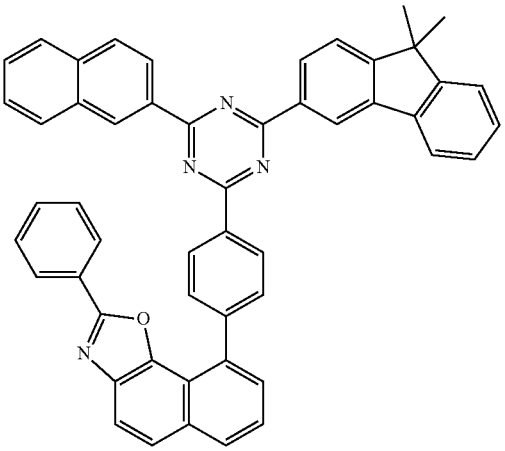
206
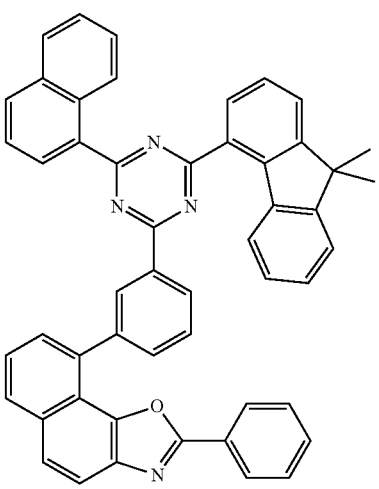

207
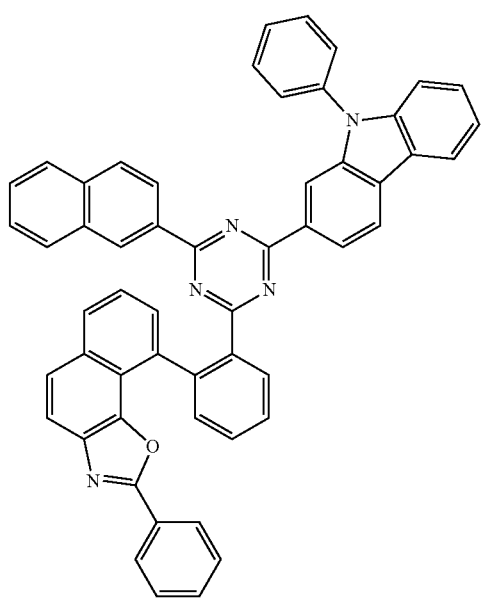
208
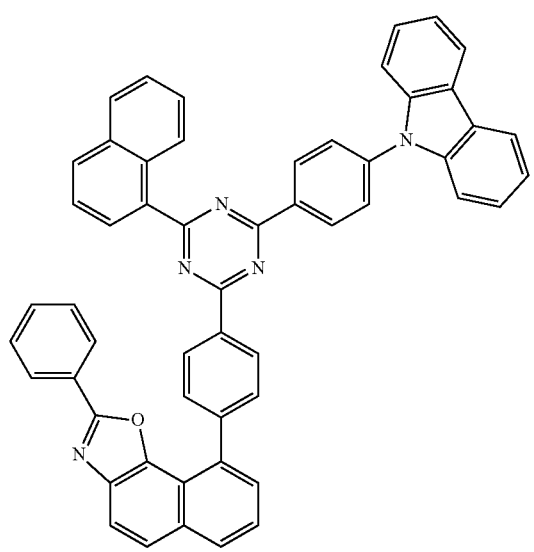
209
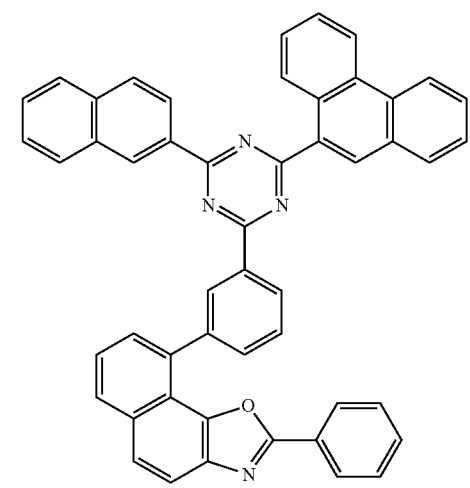
210
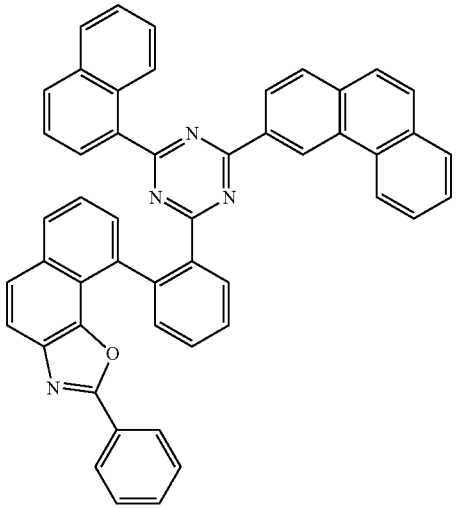
211
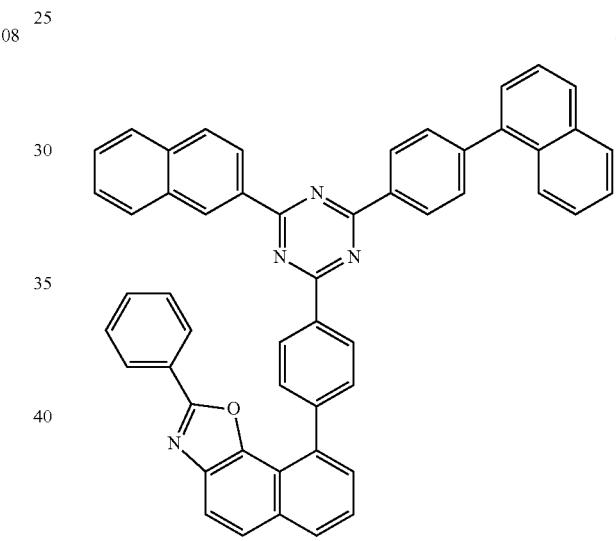
212
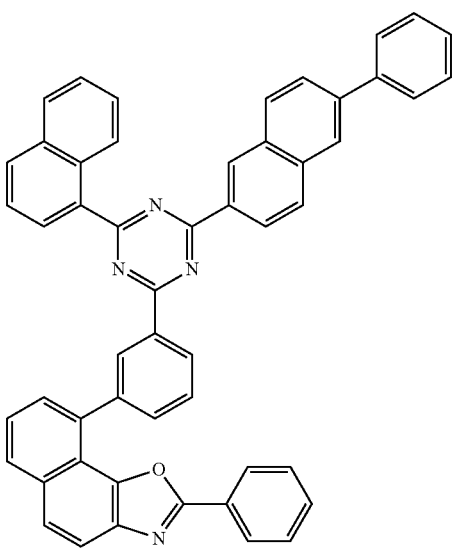

117
-continued
213
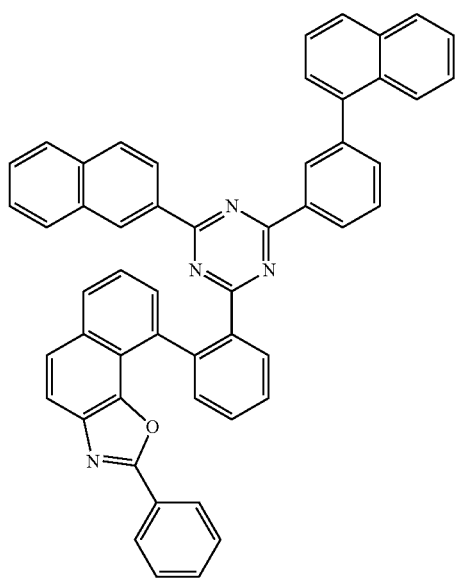
214
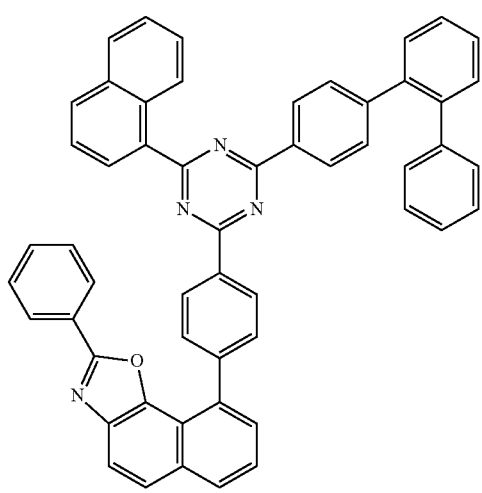
215
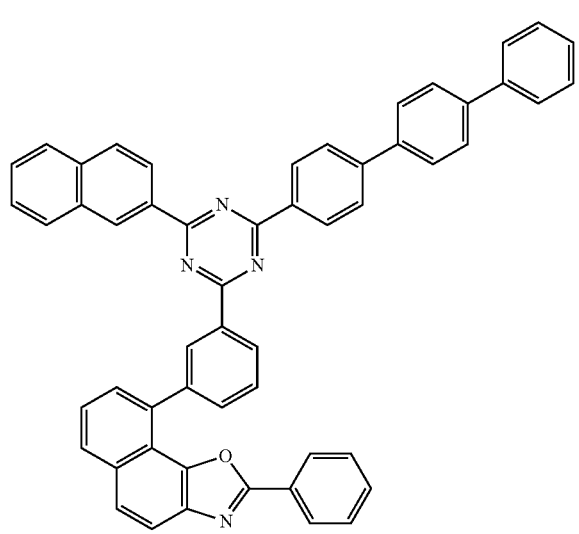
118
-continued
216
217
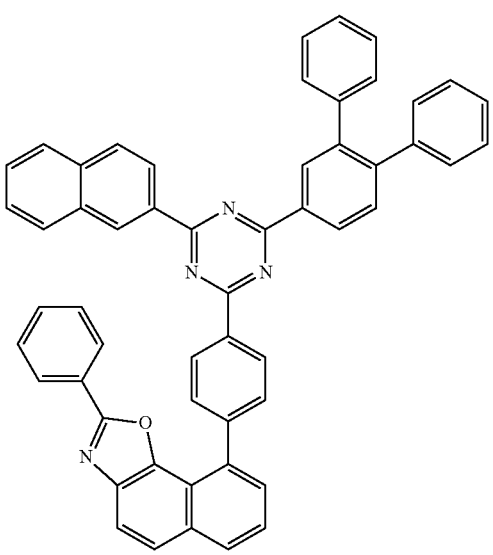
218

119
-continued
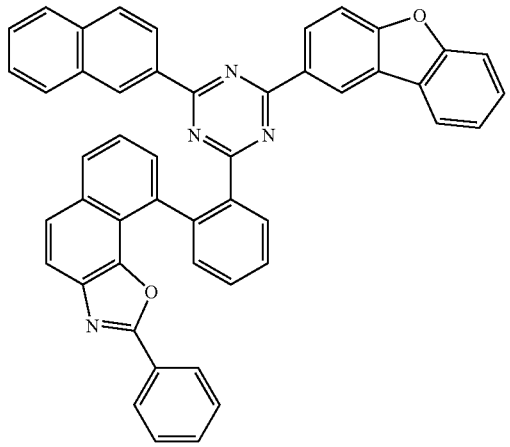
219
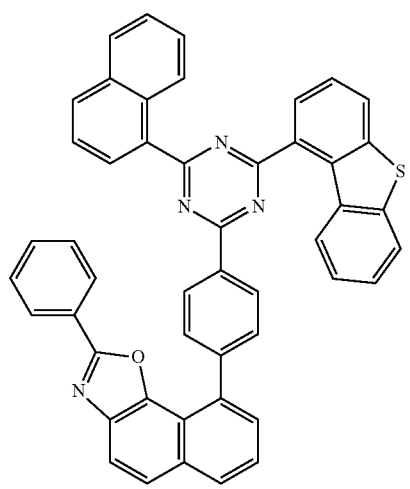
220
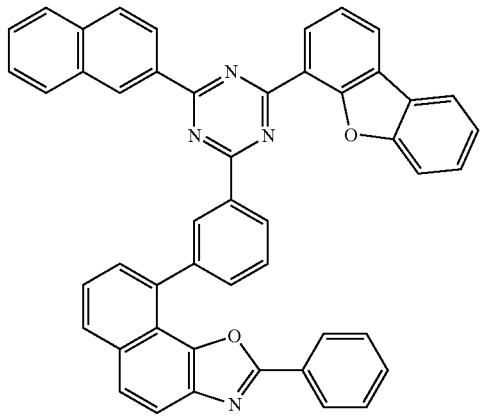
221
120
-continued
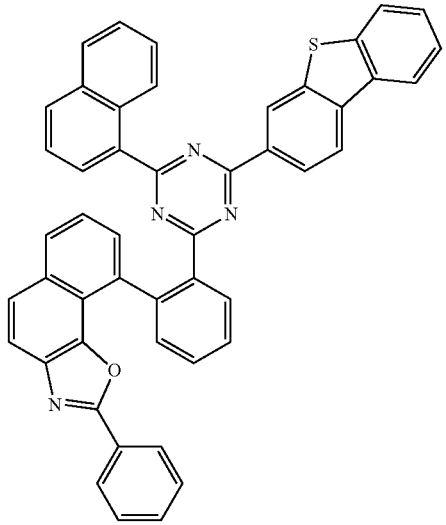
222
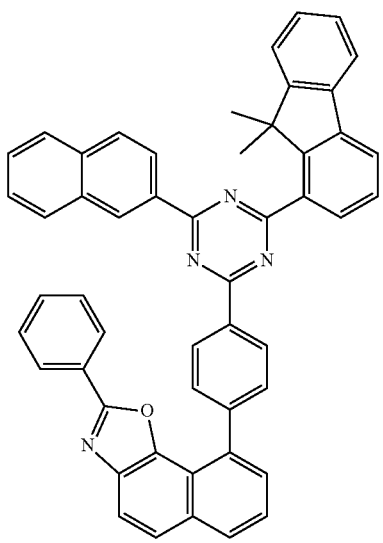
223
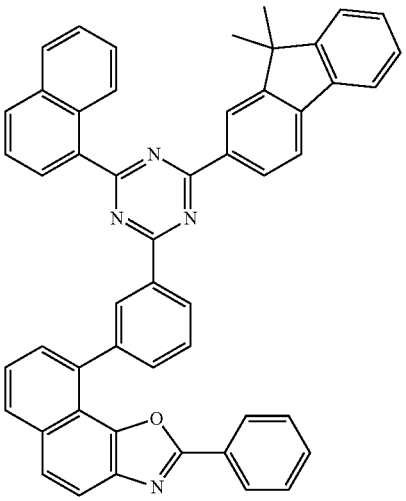
224

225
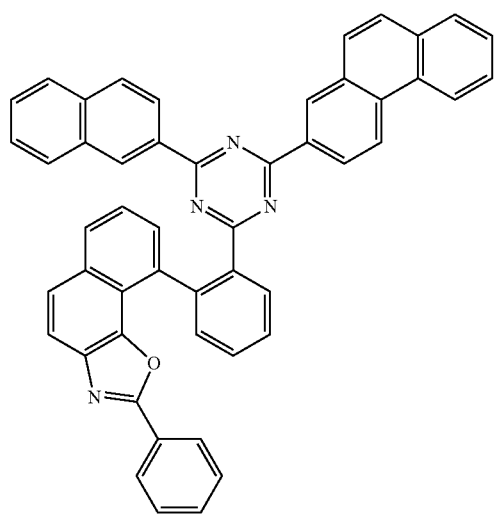
228
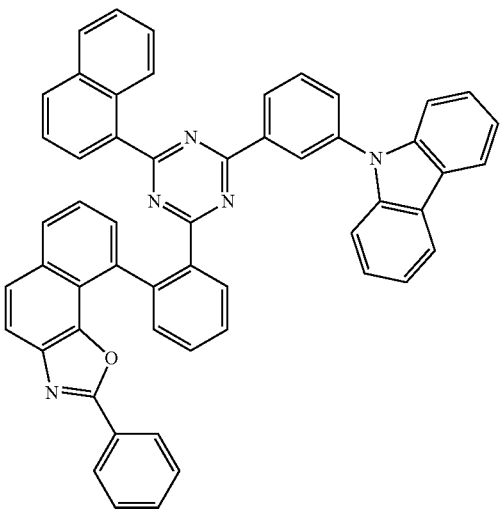
226
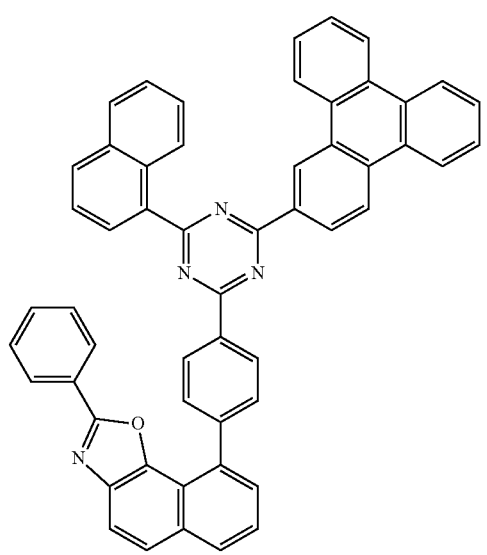
229
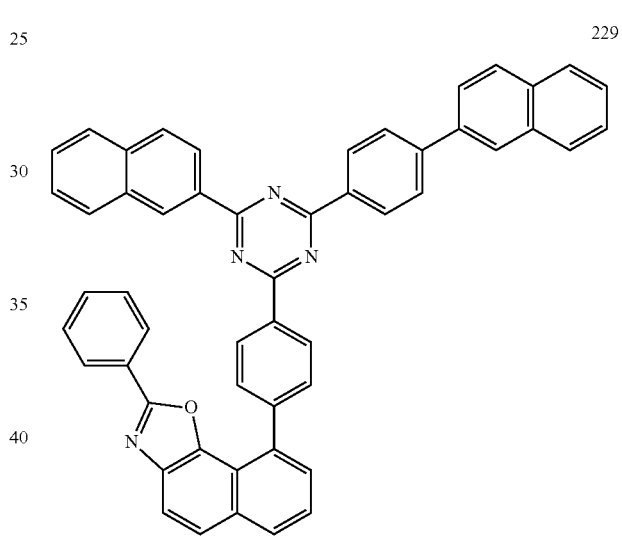
227
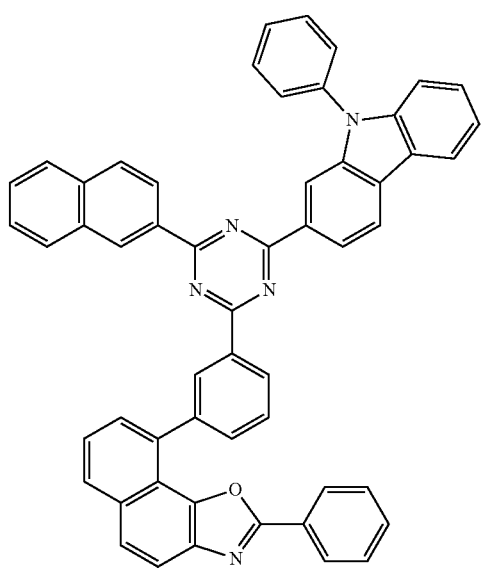
230
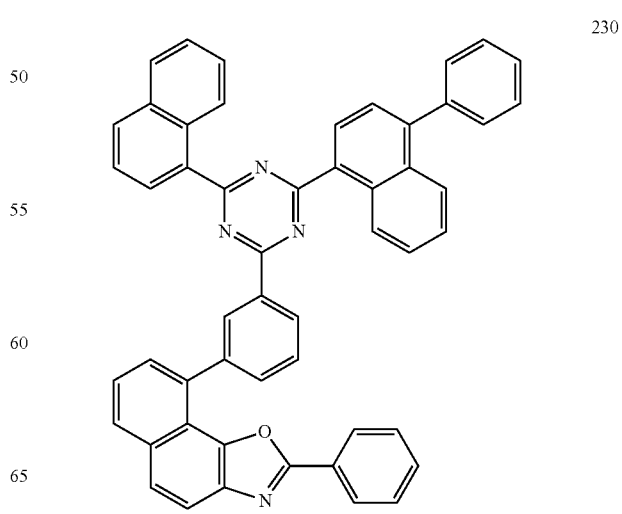

123
231
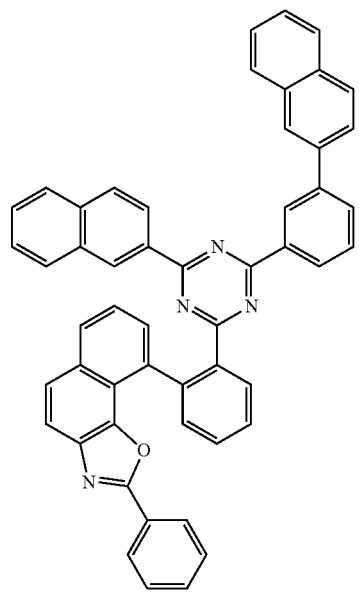
232
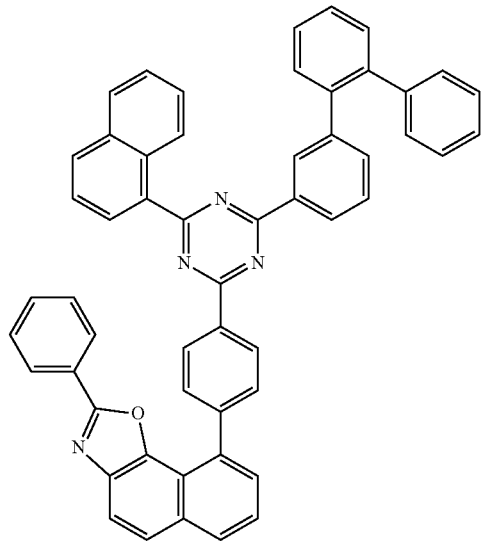
124
233
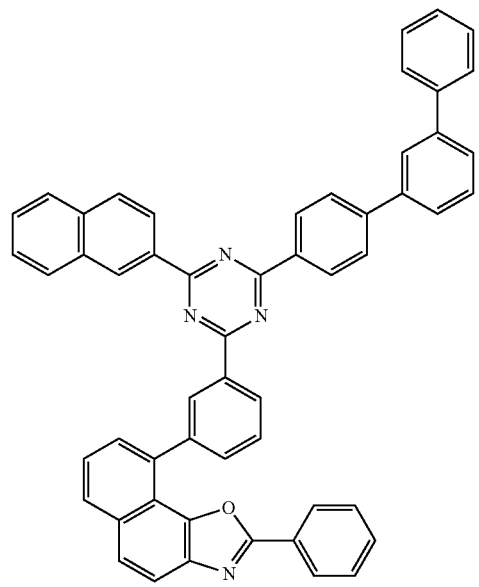
234
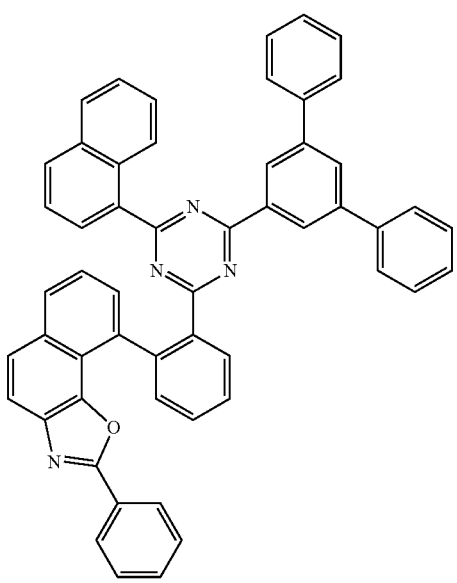

235 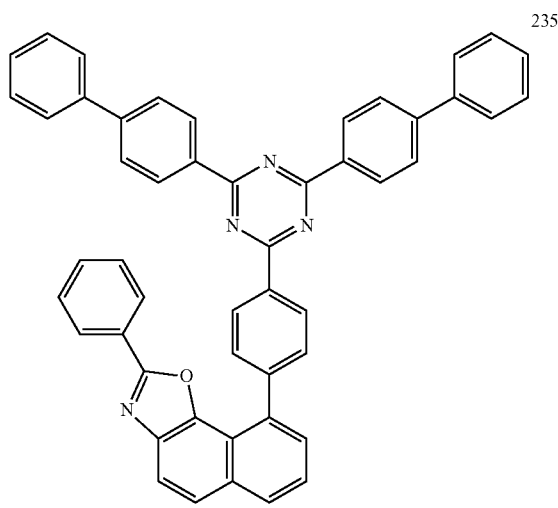
236 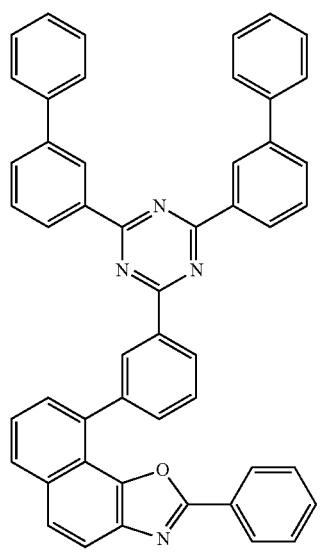
237 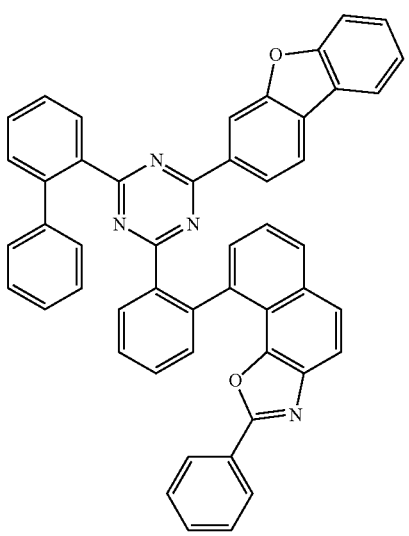
238 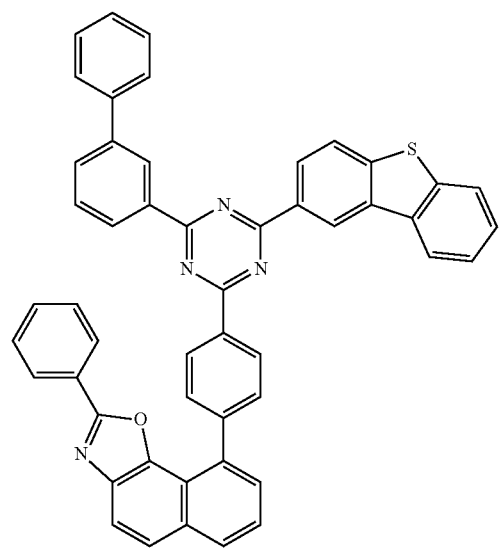
239 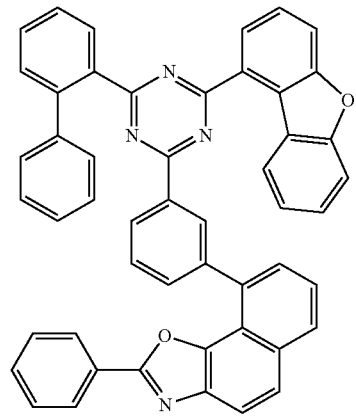
240 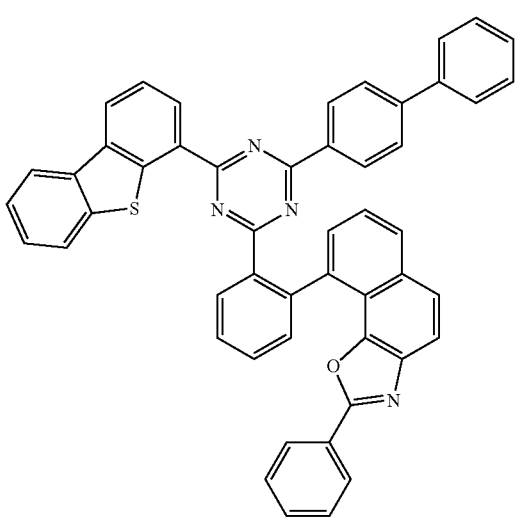

241
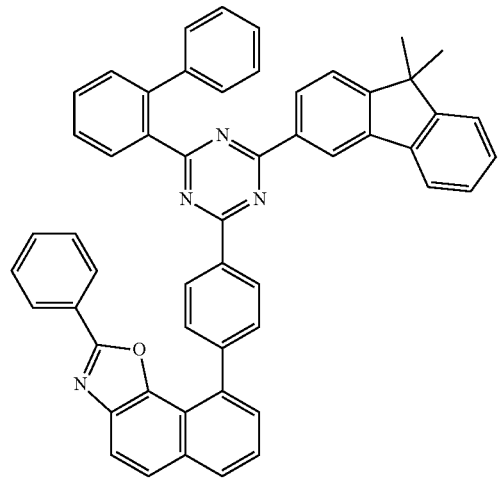
242
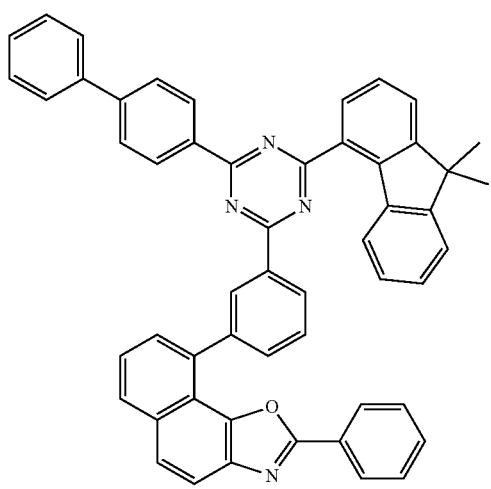
243
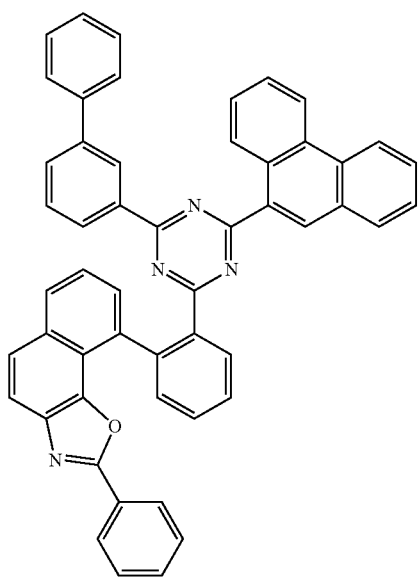
244
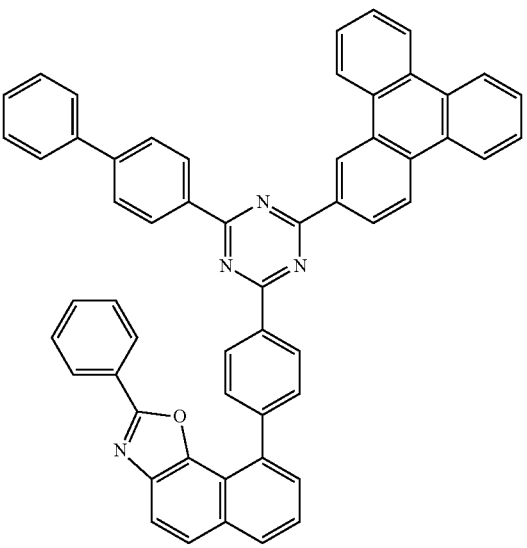
245
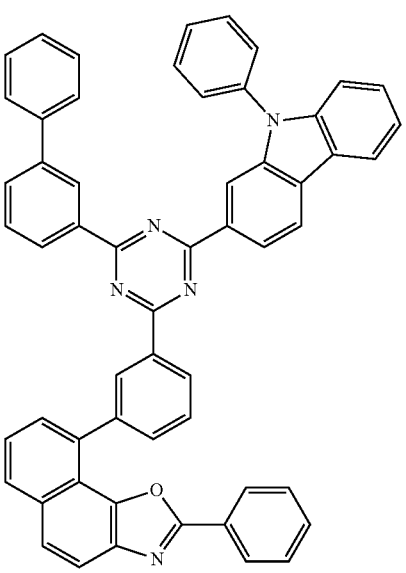

129
-continued
246
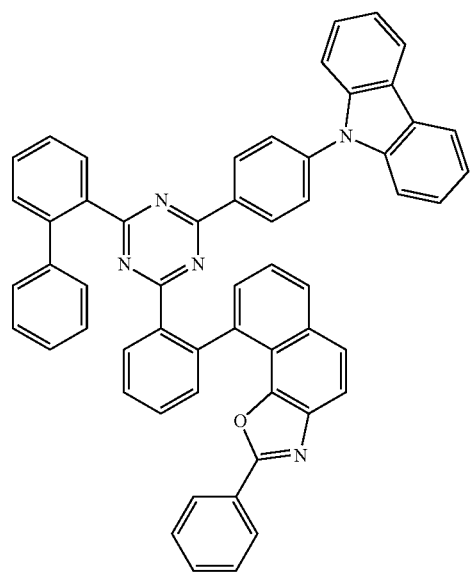
247
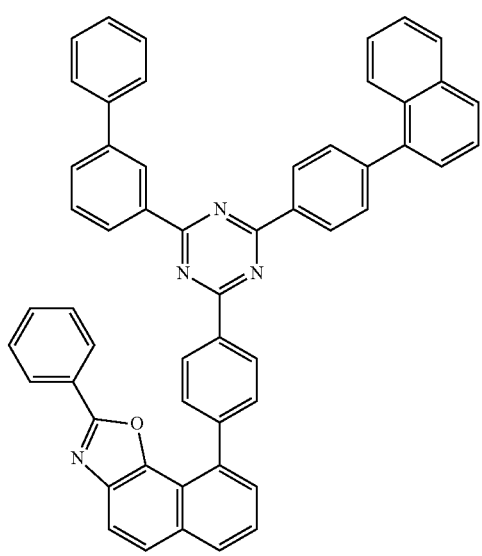
248
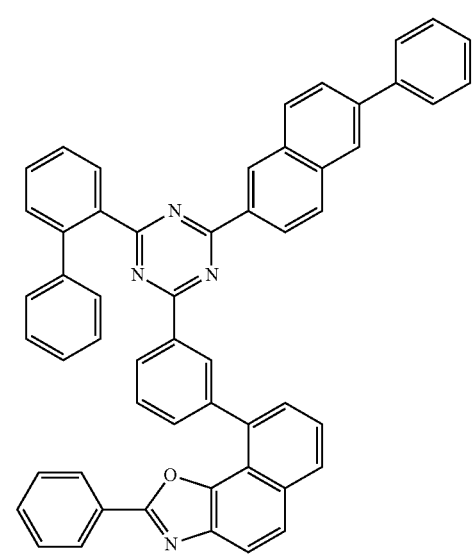
130
-continued
249
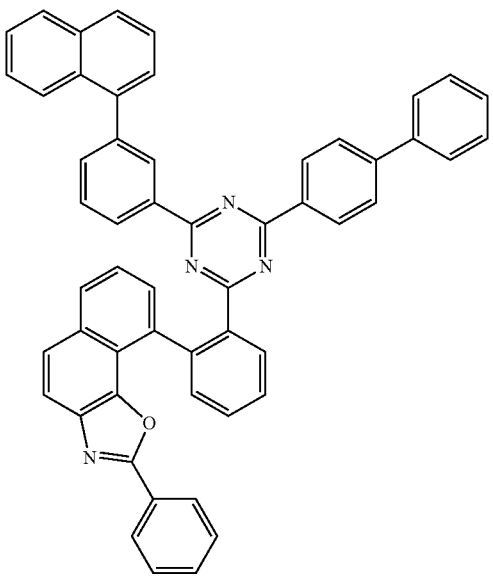
250
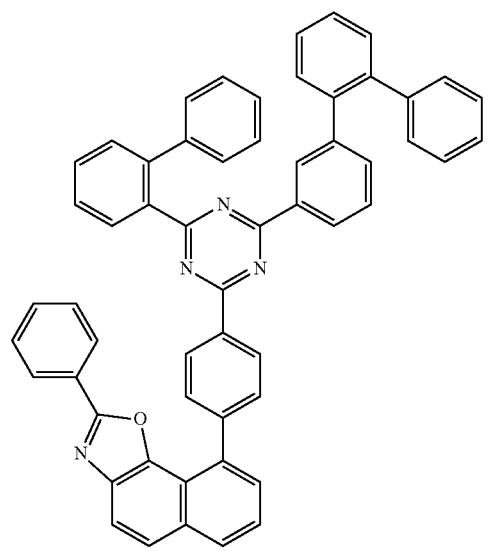

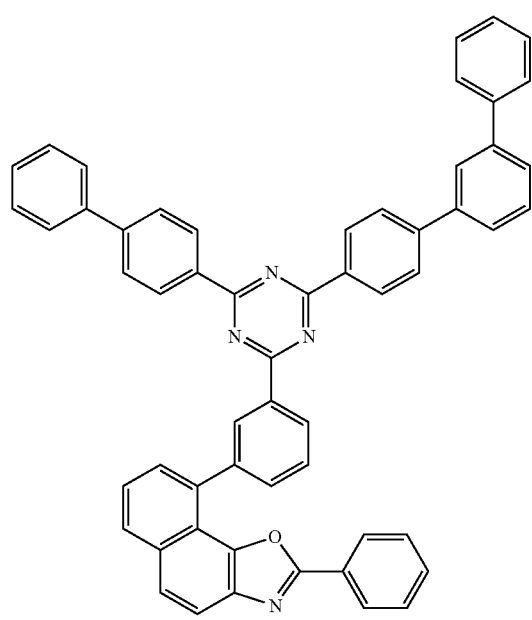
251
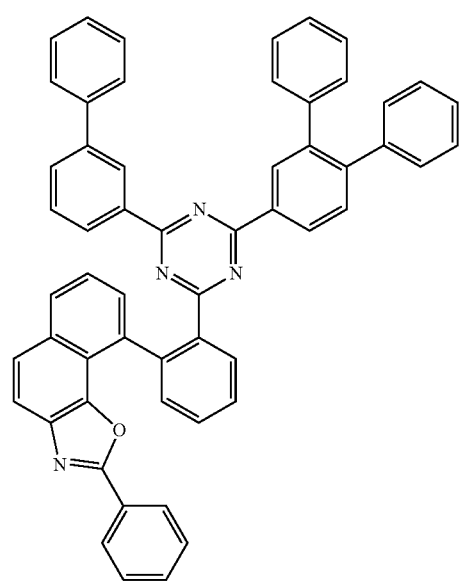
252
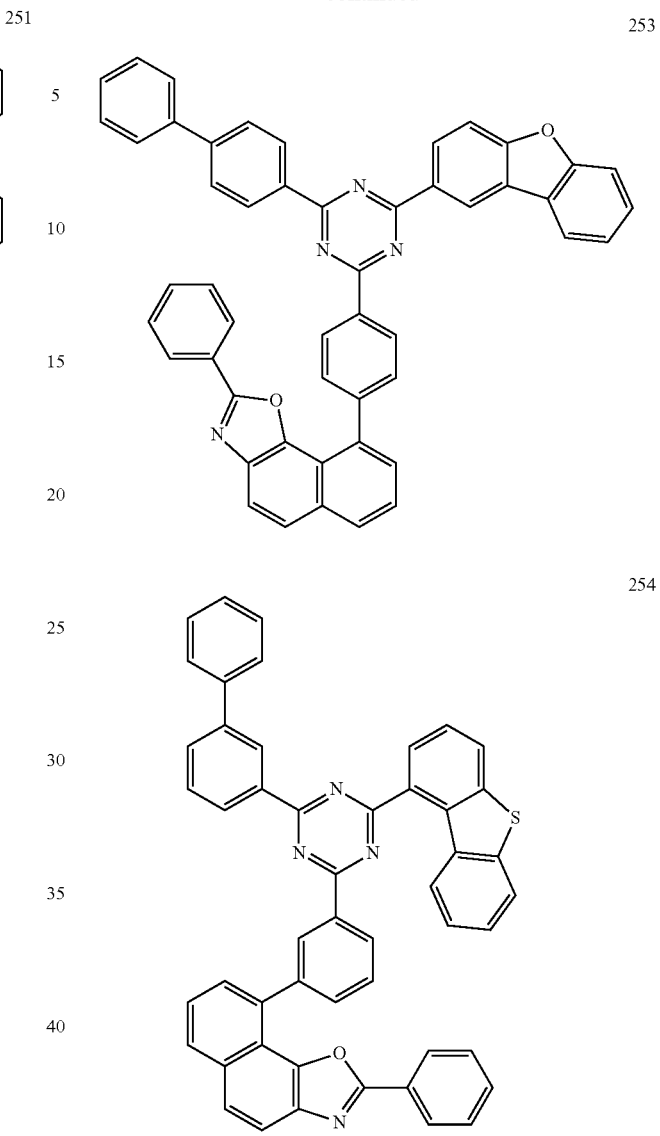
253
254
255

133
-continued
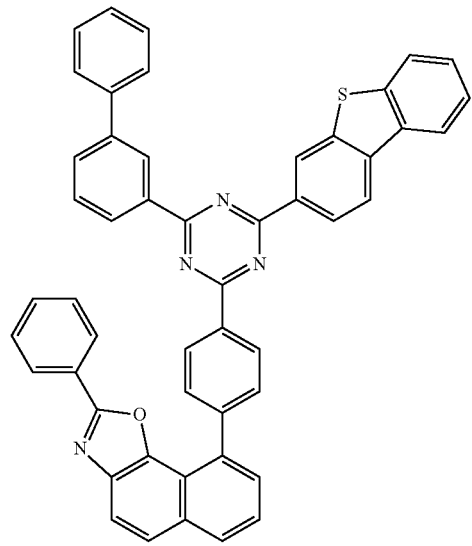
256
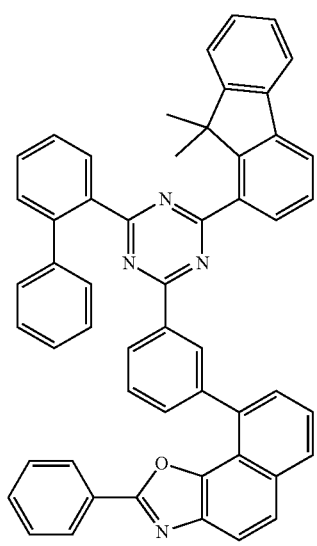
257
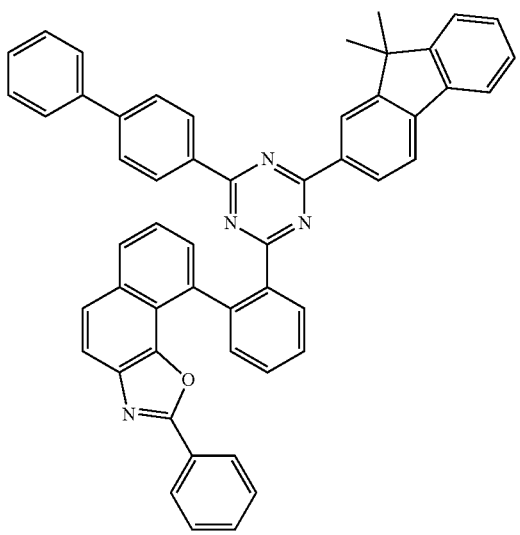
258
134
-continued
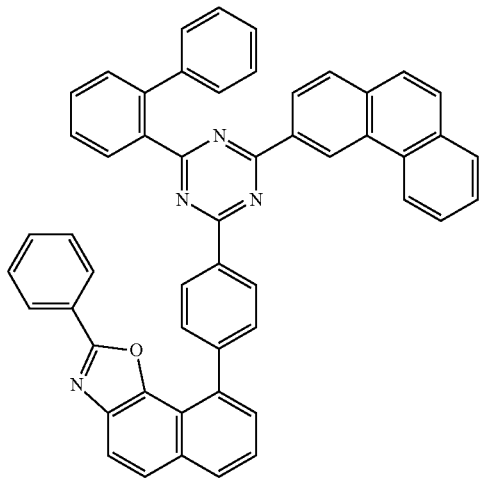
259
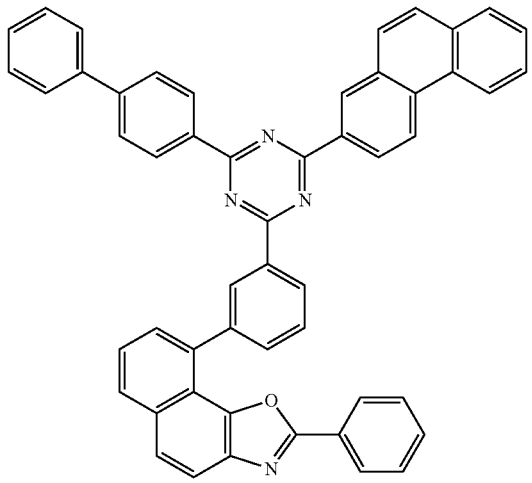
260
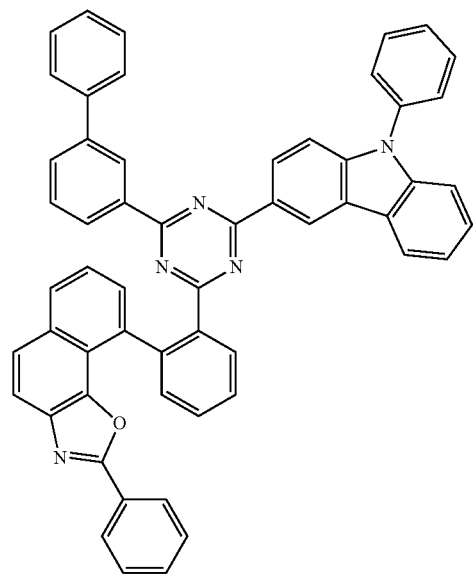
261

262
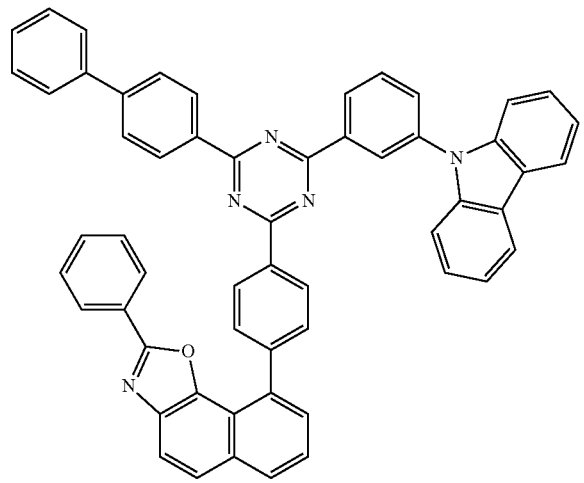
263
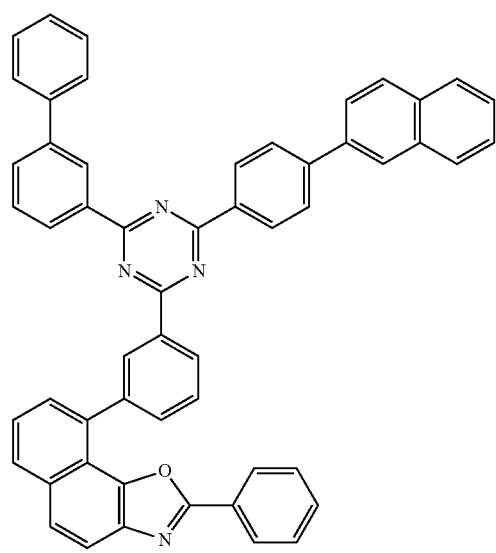
264
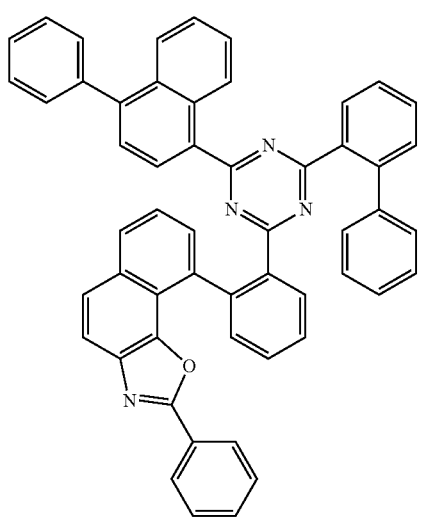
265
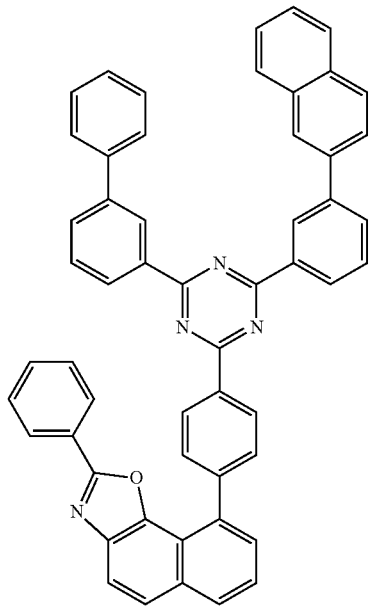
266
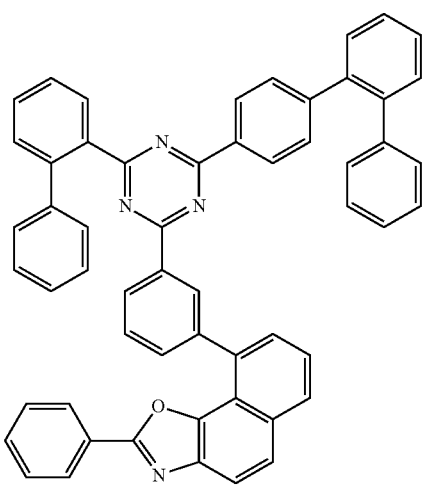
267
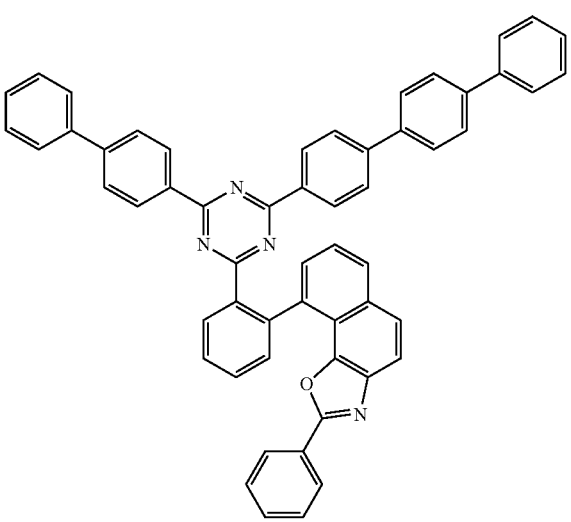

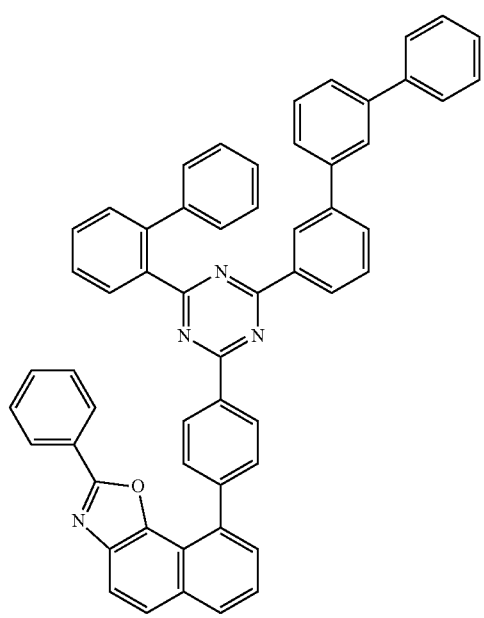
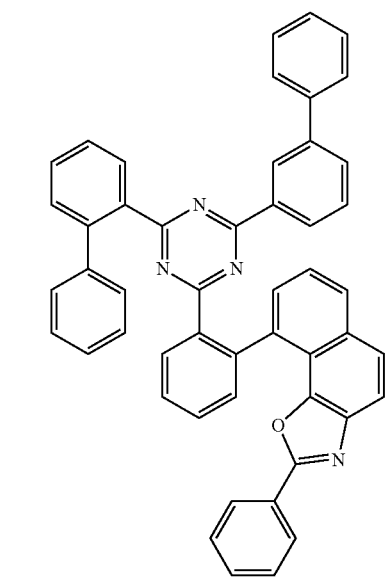
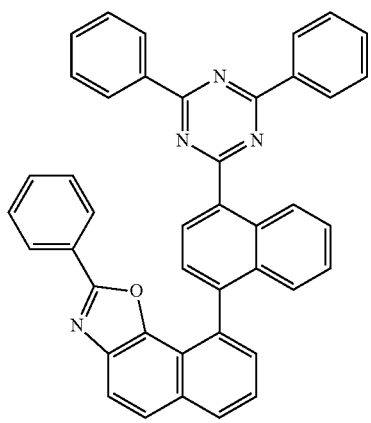

274
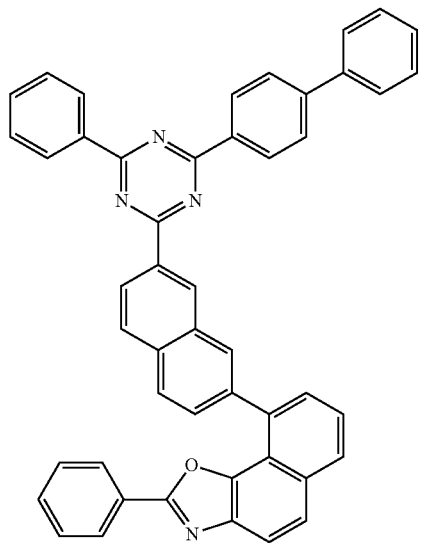
275
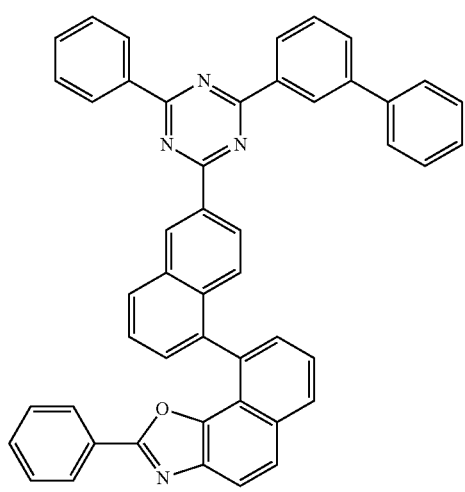
276
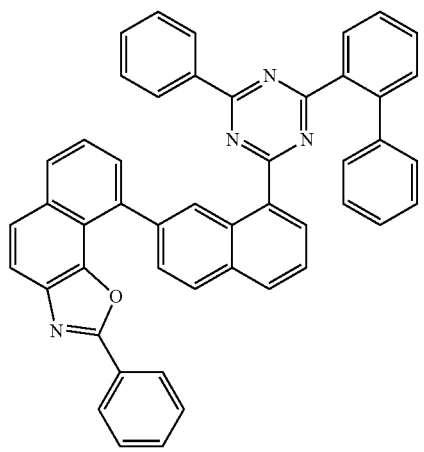
277
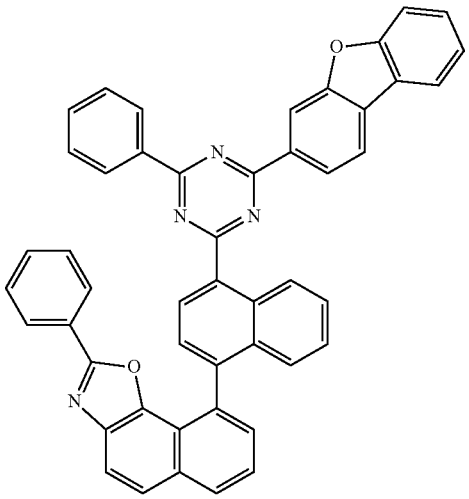
278
279
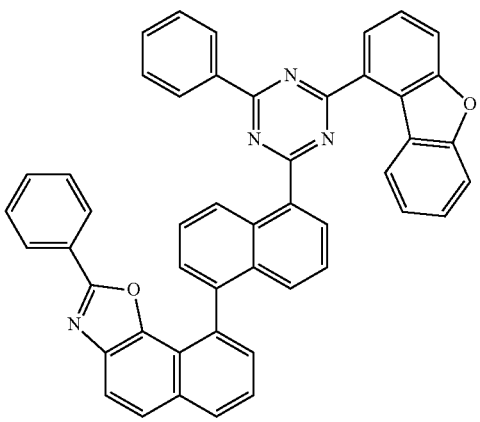

280
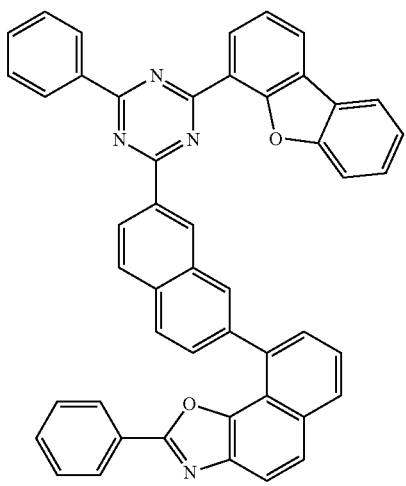
281
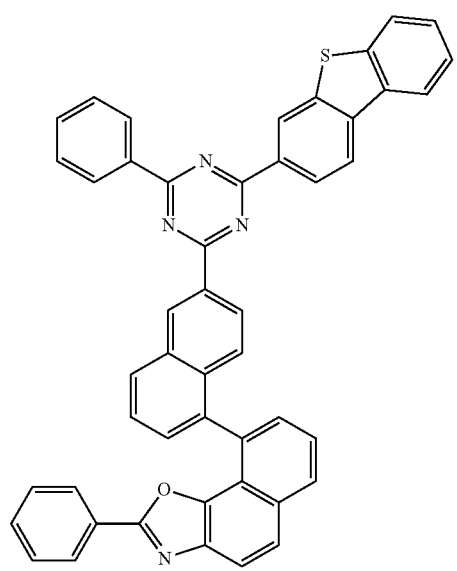
282
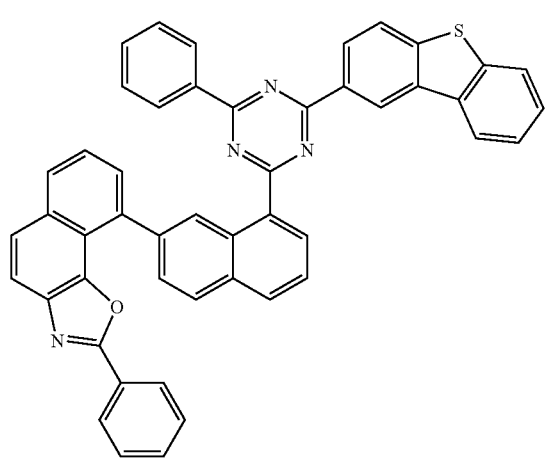
283
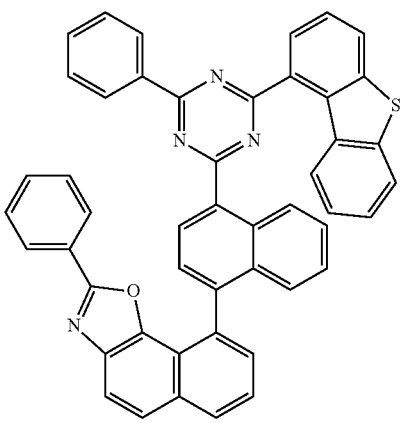
284
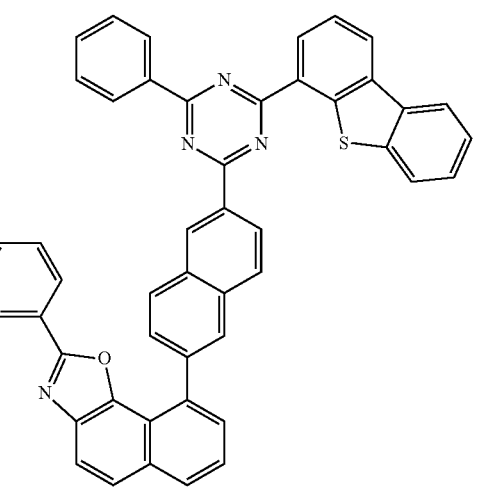
285
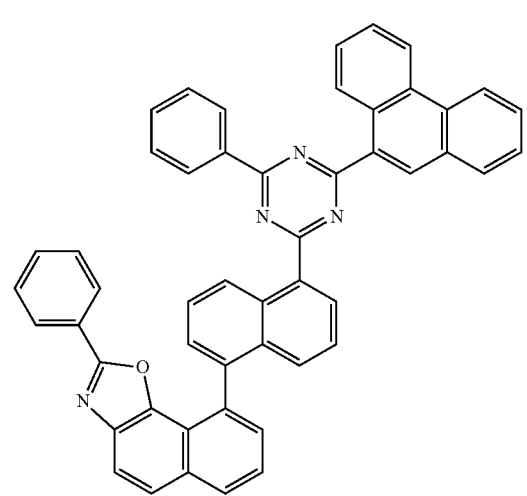

286
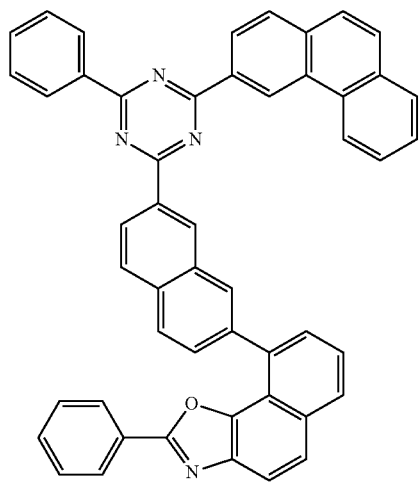
287
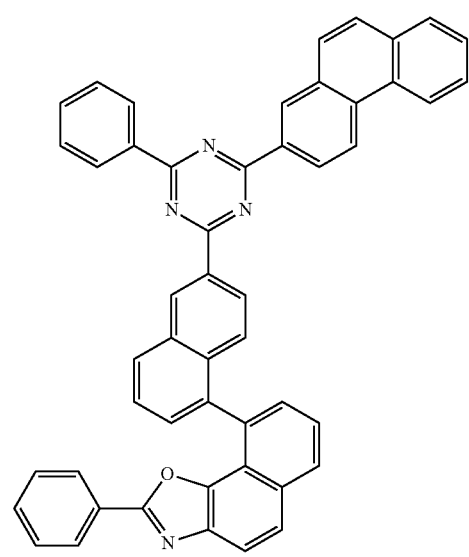
288
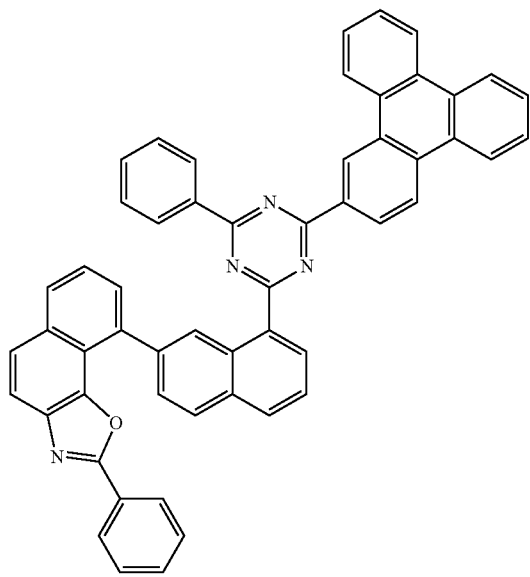
289
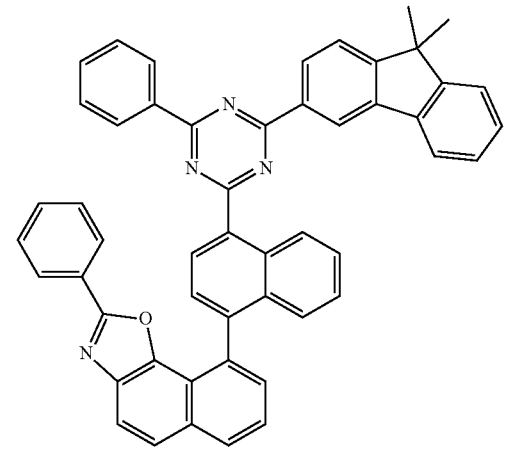
290
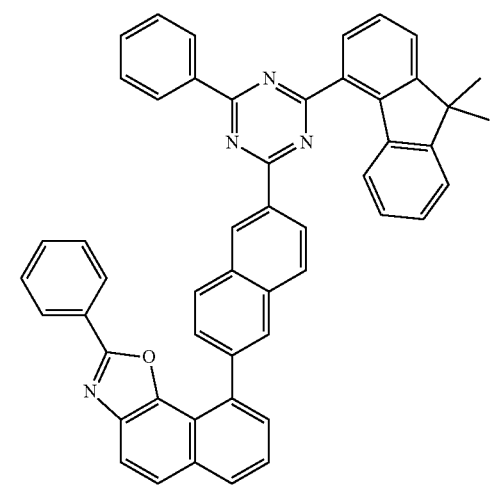
291
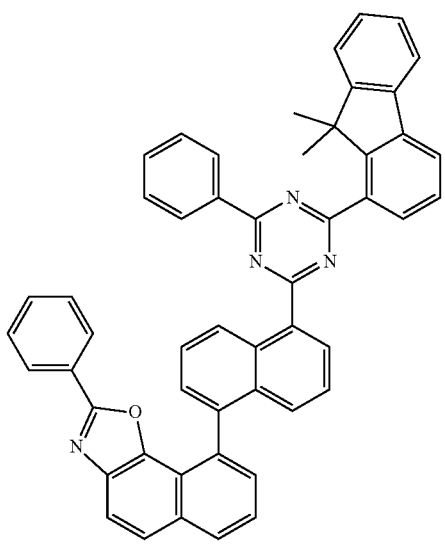

145
-continued
292
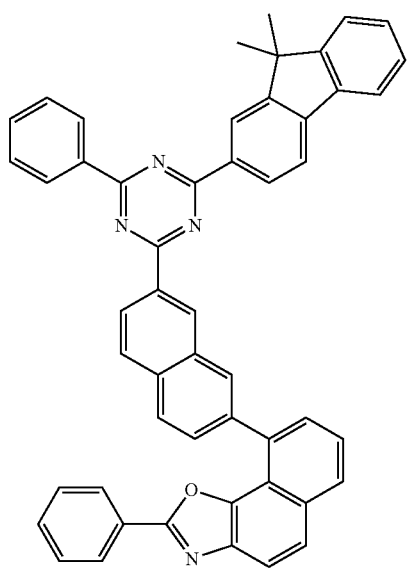
293
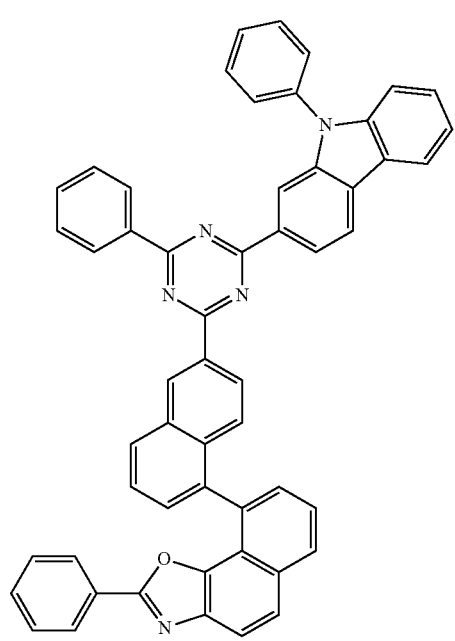
146
-continued
294
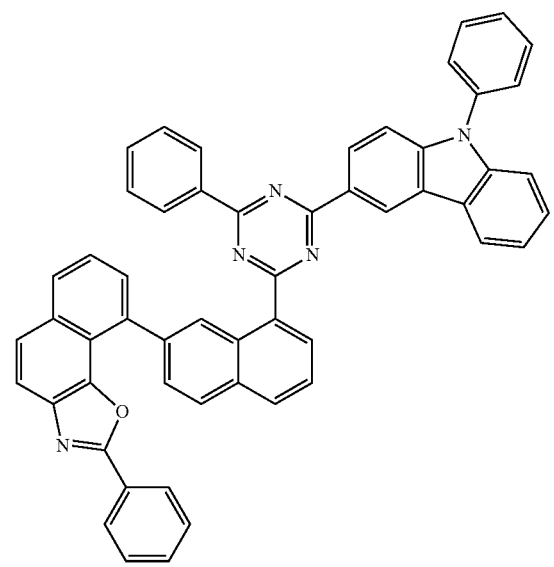
295
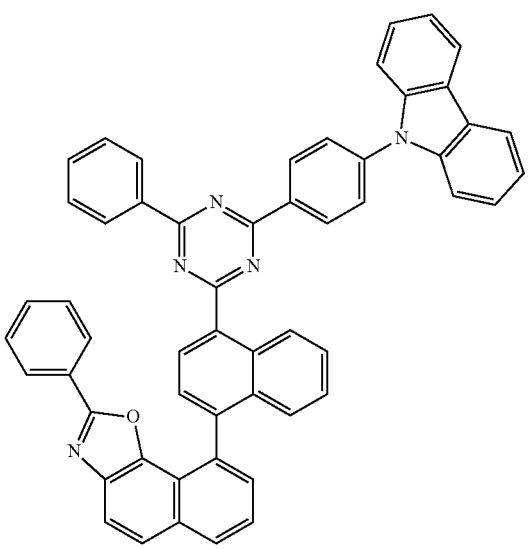

296
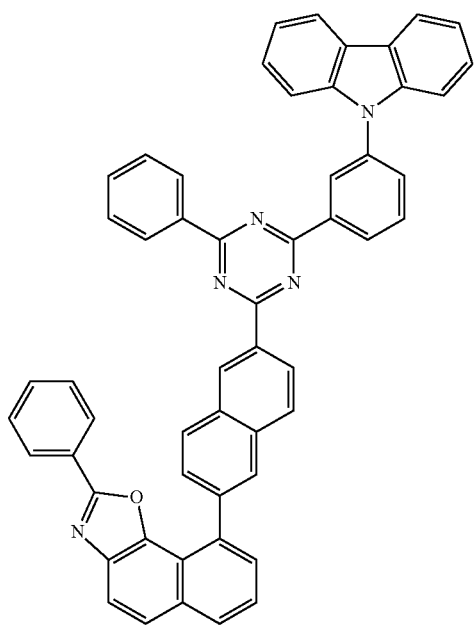
297
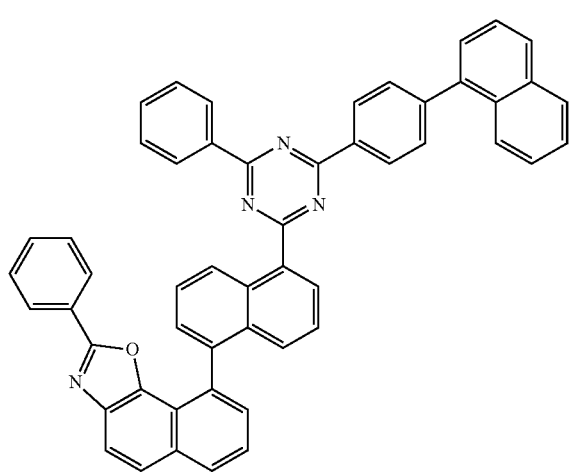
298
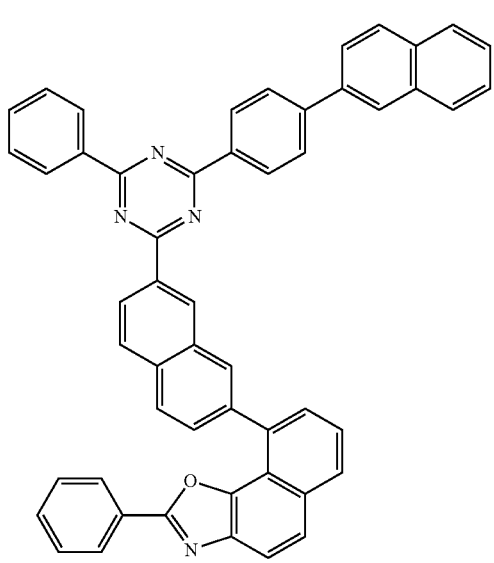
299
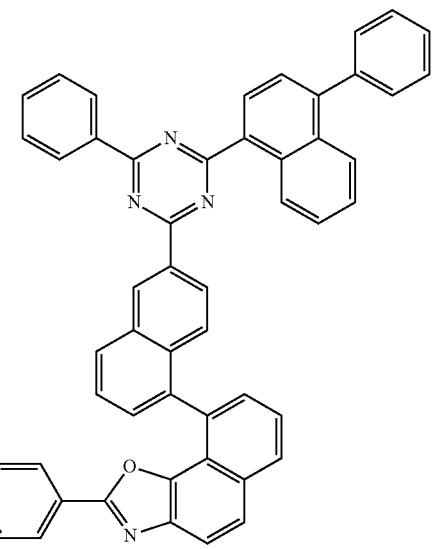
300
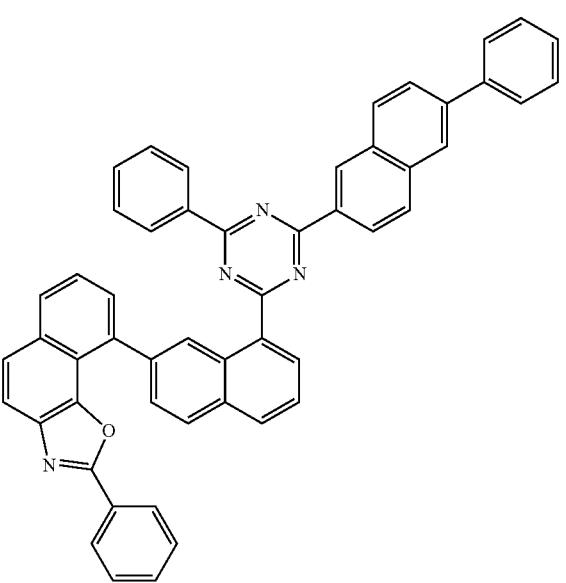

-continued
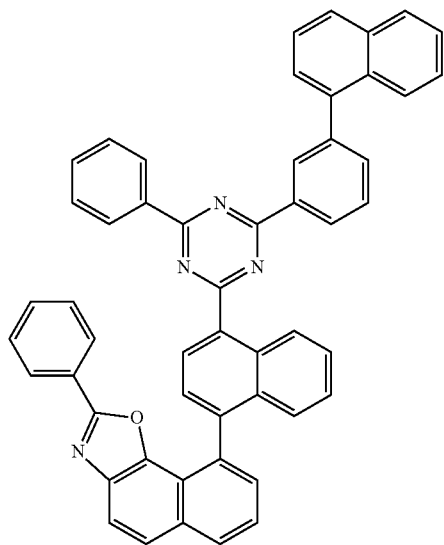
301
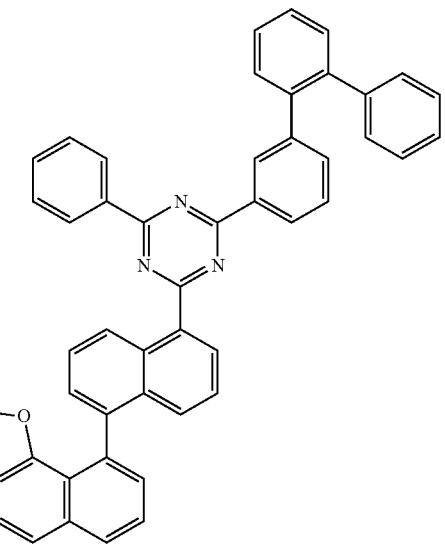
303
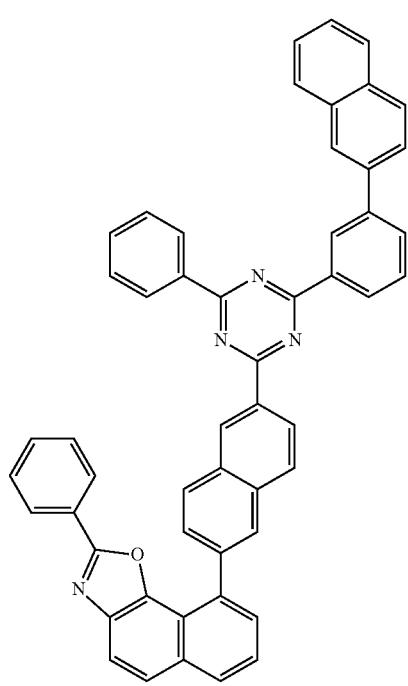
302
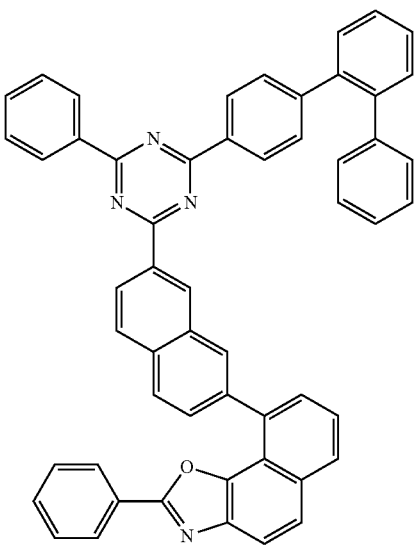
304

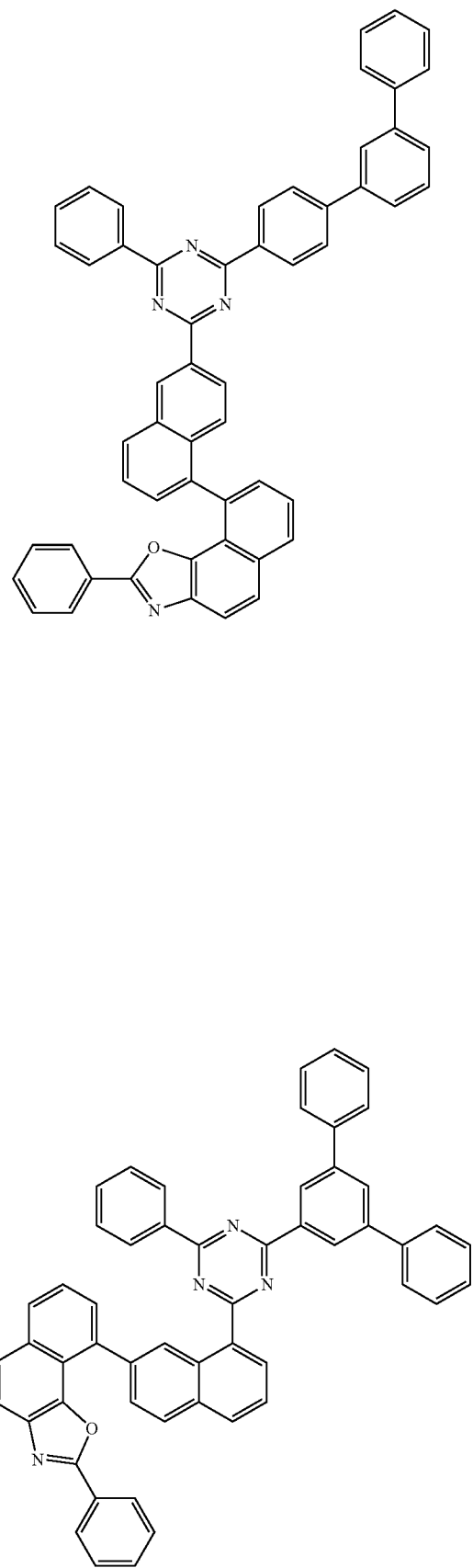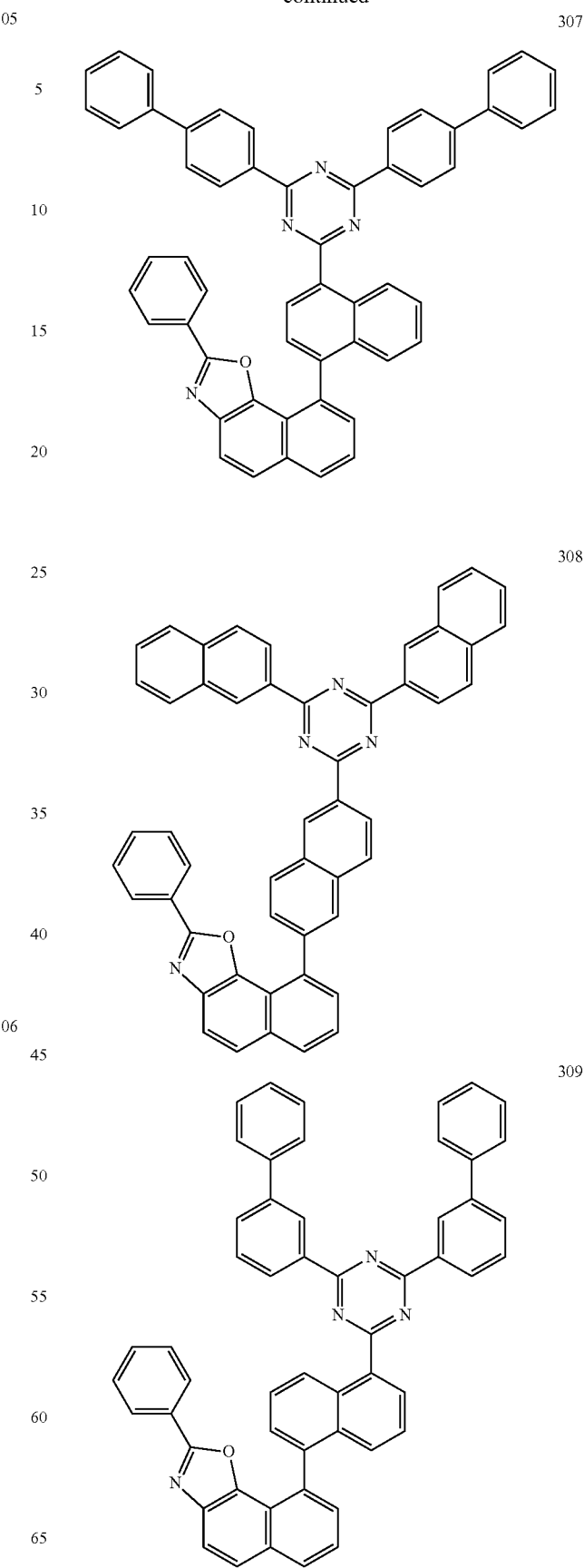

153
-continued
310
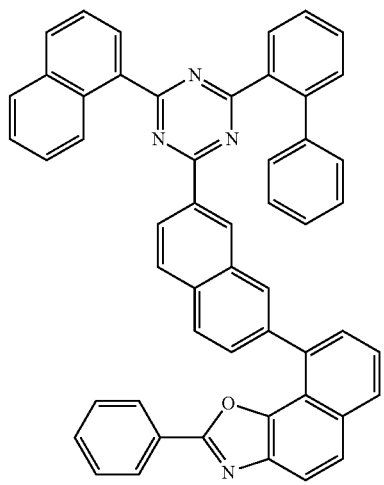
311
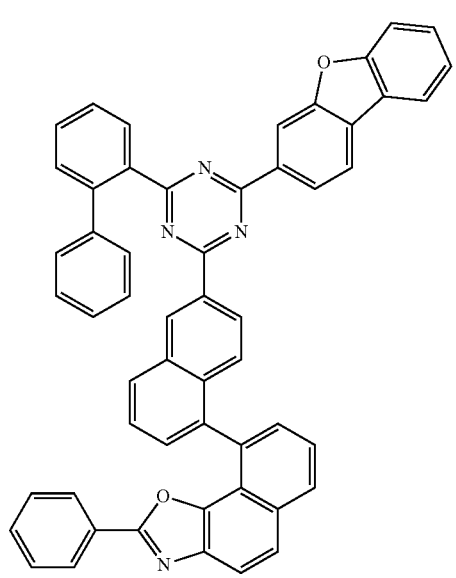
312
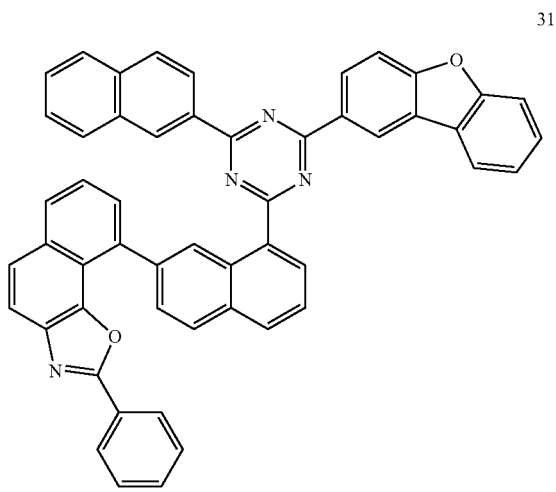
154
-continued
313
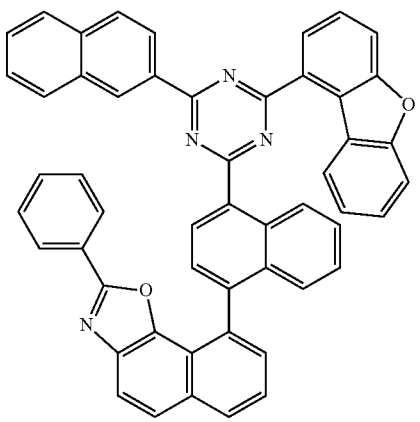
314
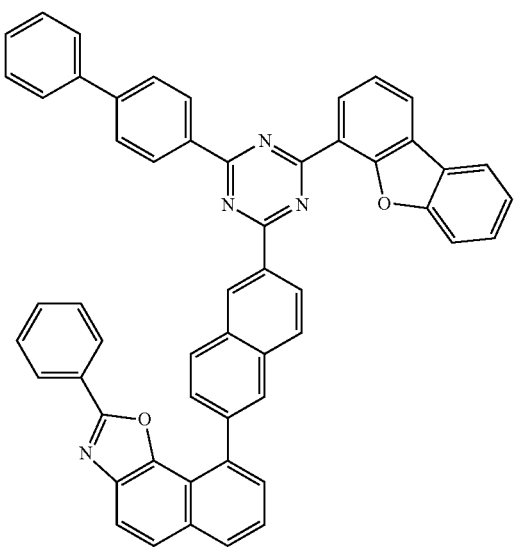
315
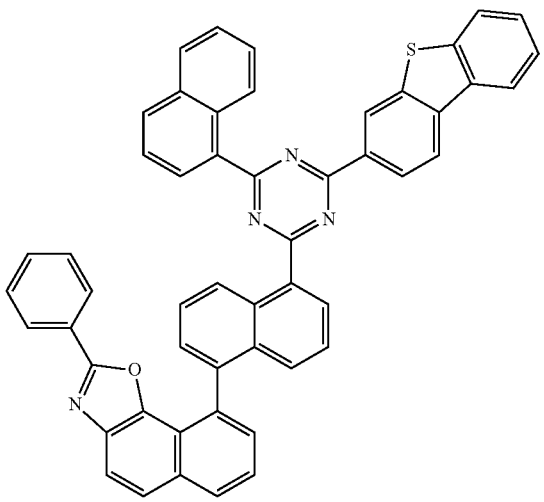

316
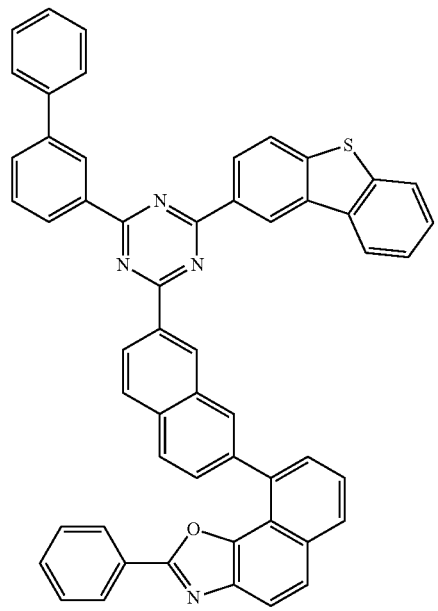
317
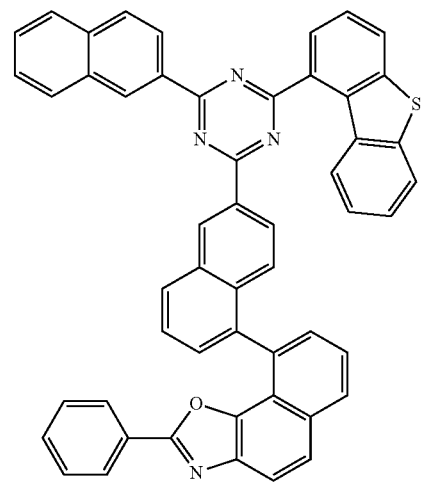
318
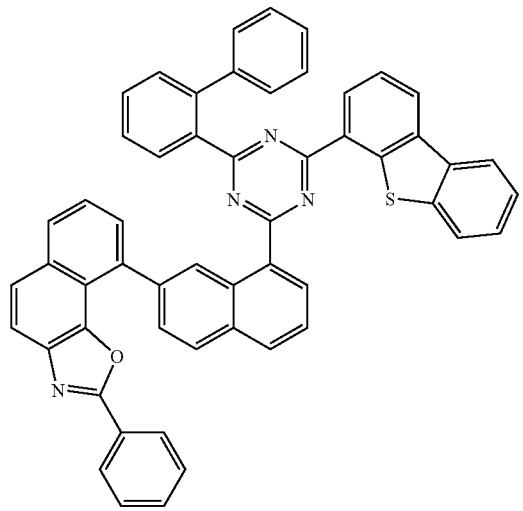
319
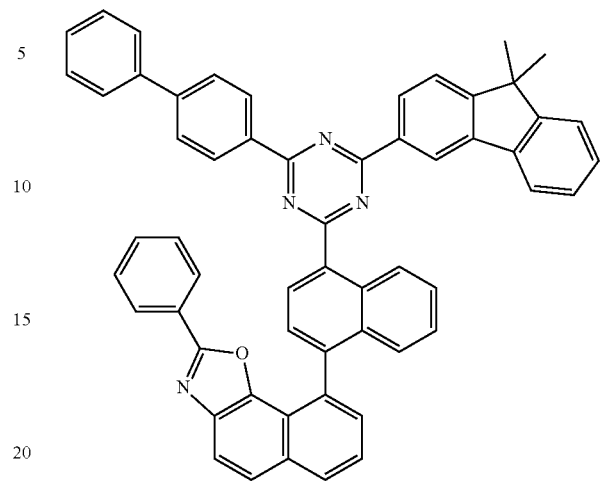
320
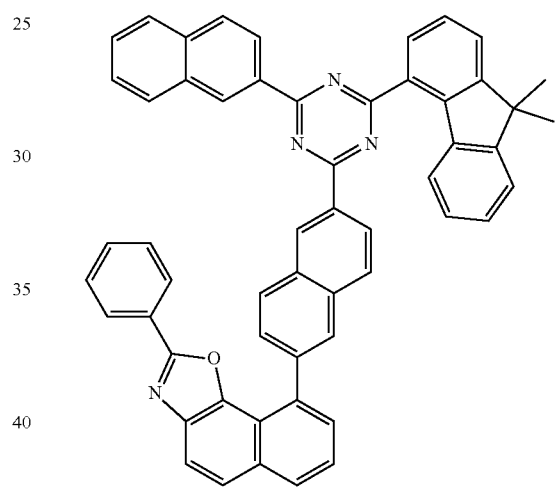
321
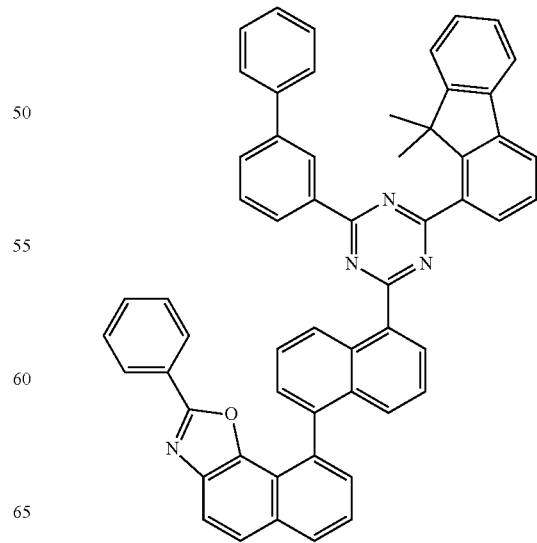

322
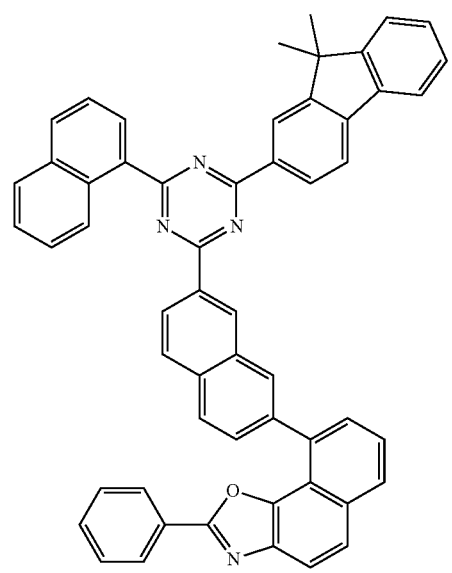
323
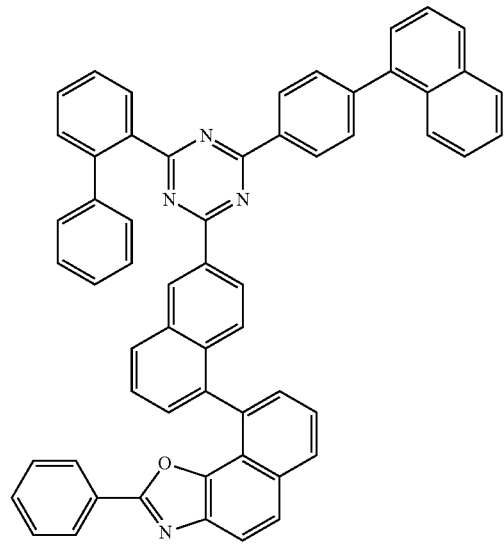
324
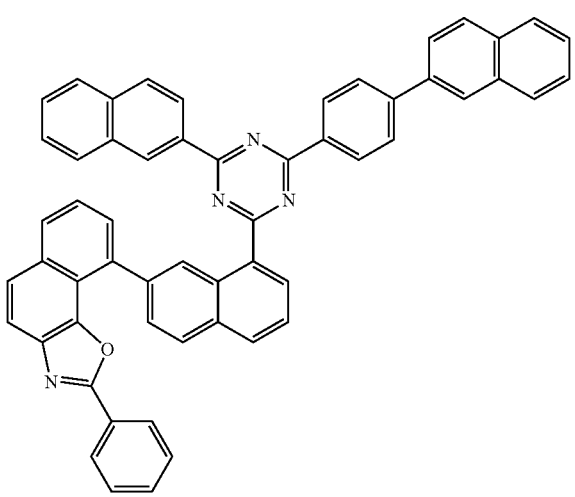
325
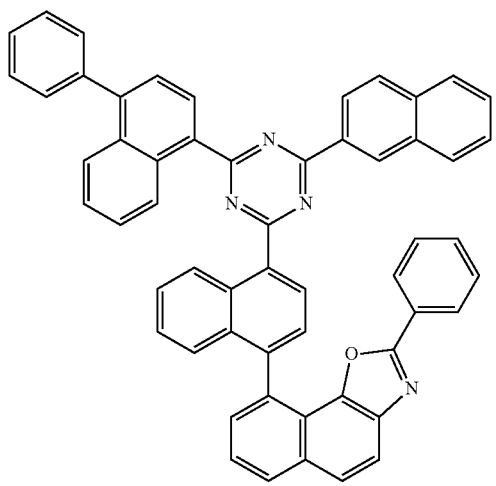
326
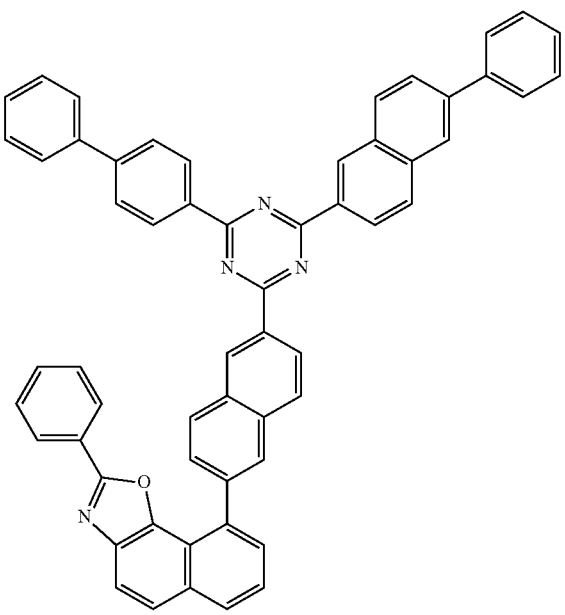
327

159
-continued
328
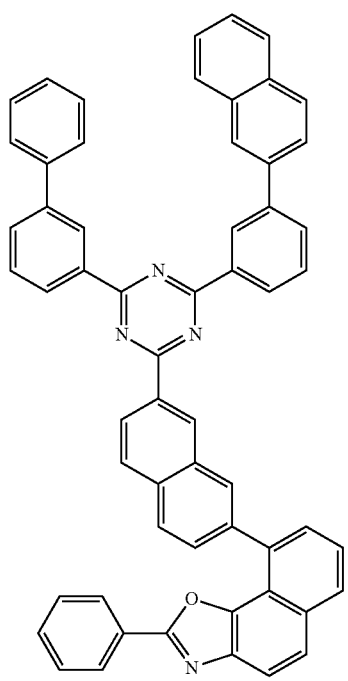
329
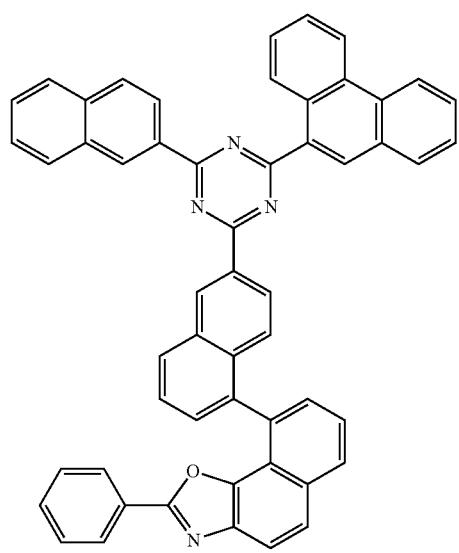
160
-continued
330
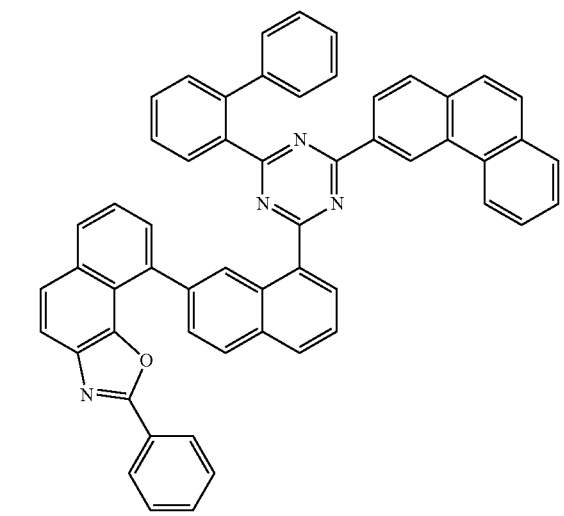
331
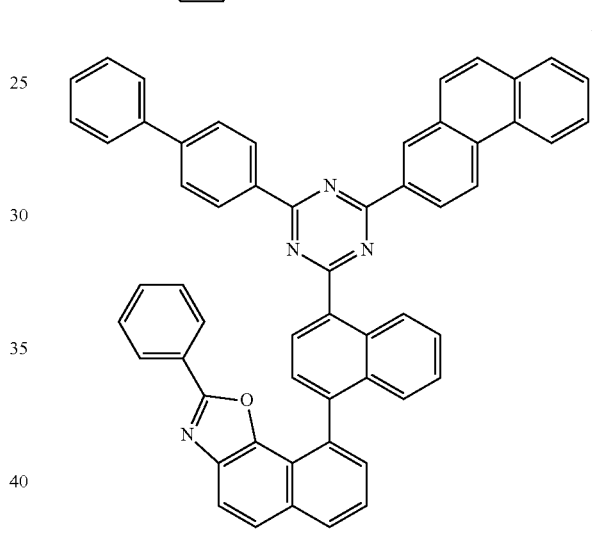
332
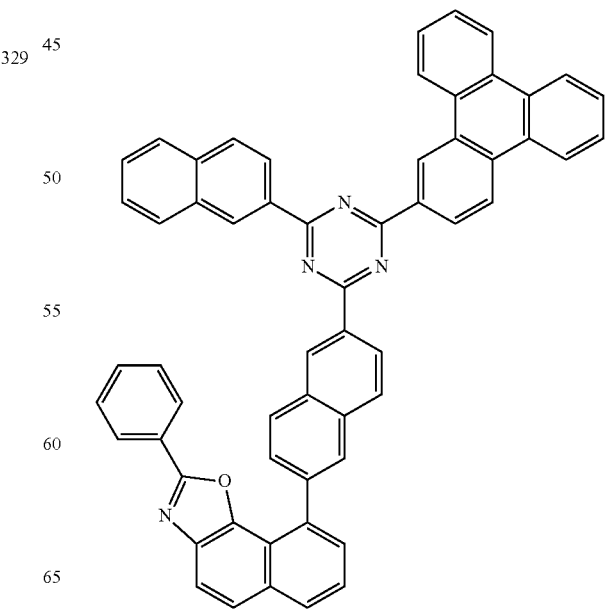

-continued
333
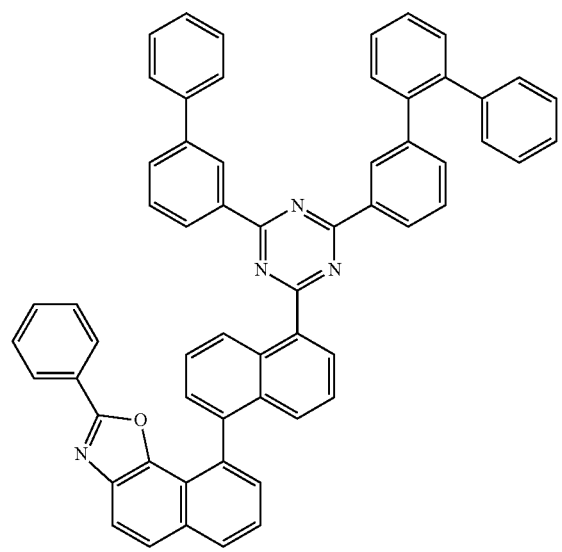
334
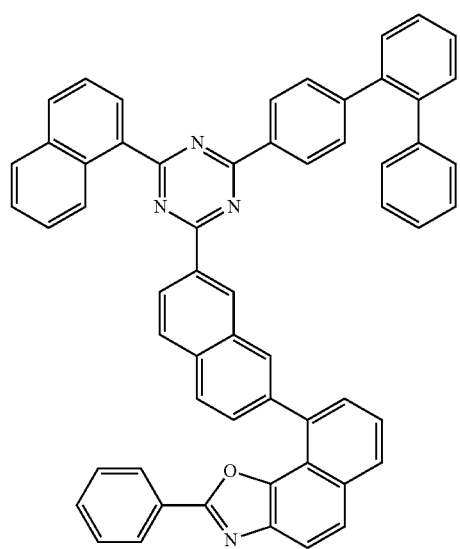
-continued
335
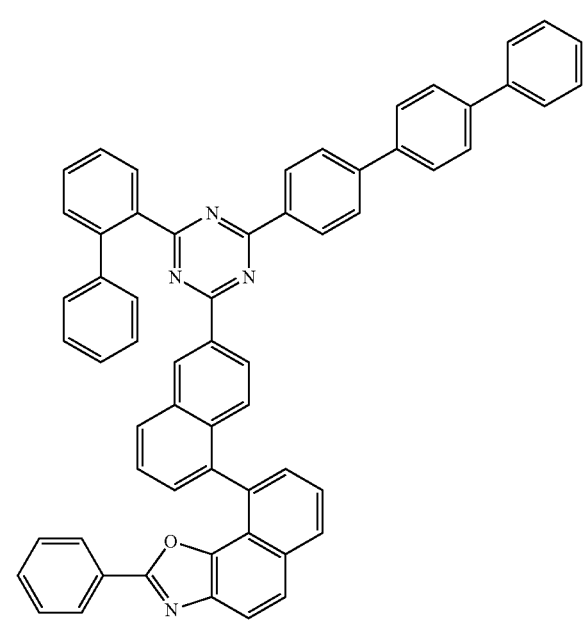
336
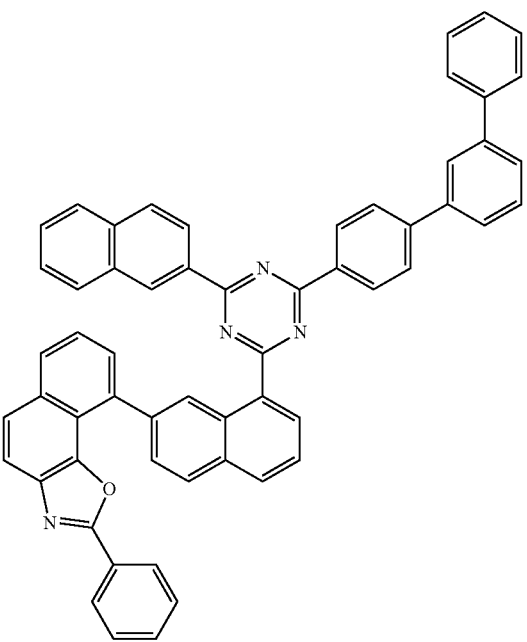

337
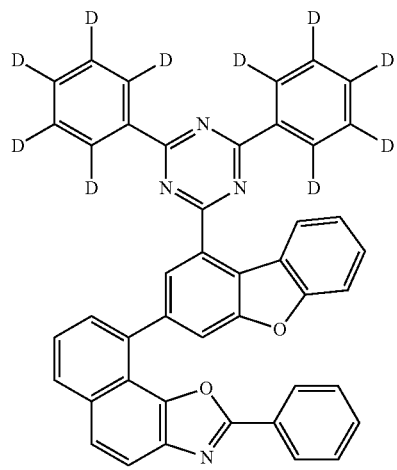
340
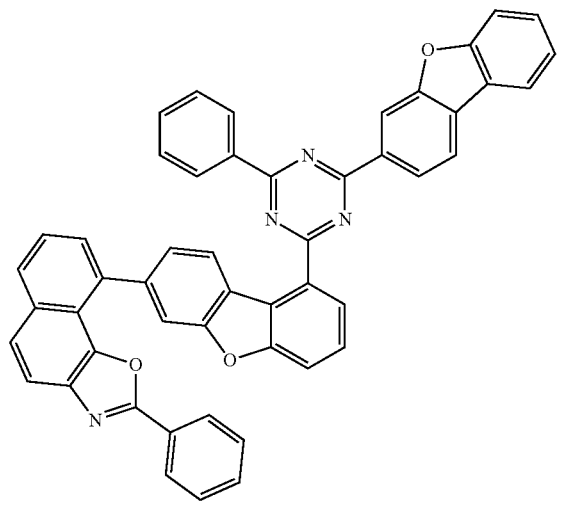
338
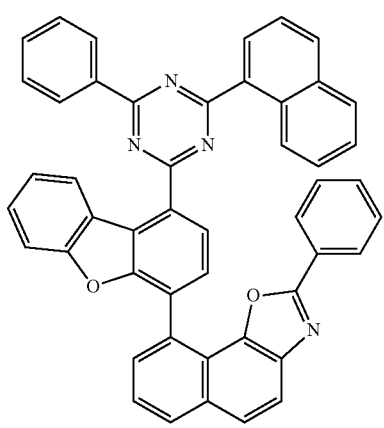
341
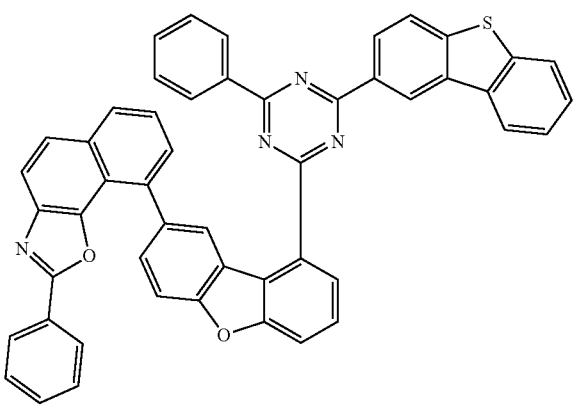
339
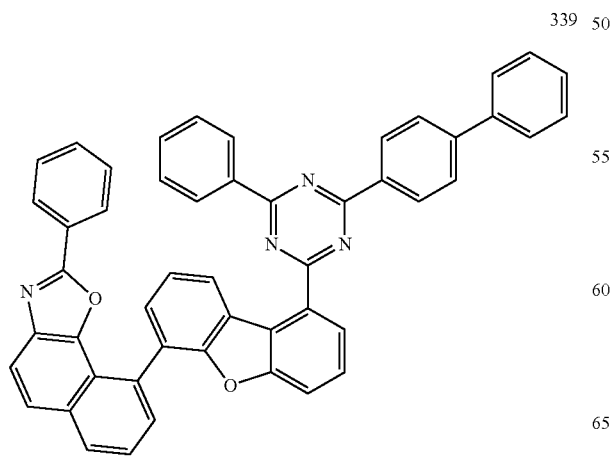
342
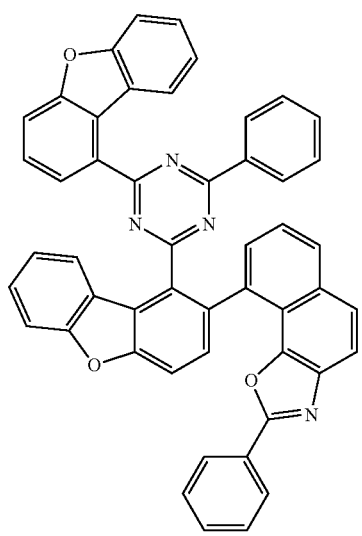

343
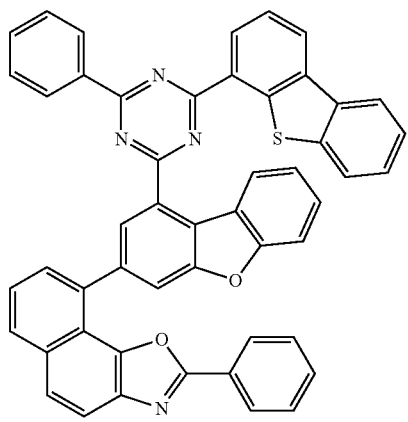
344
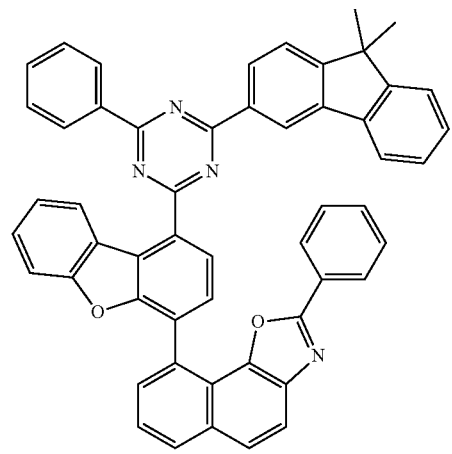
345
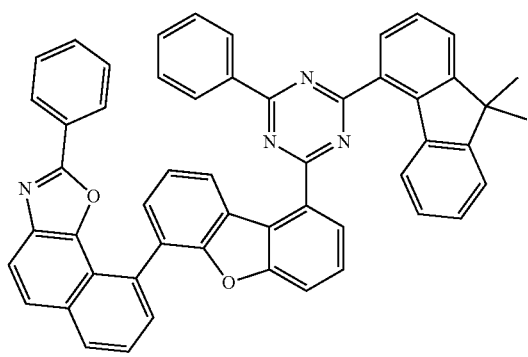
346
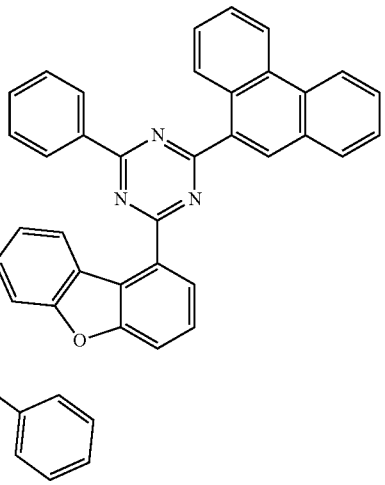
347
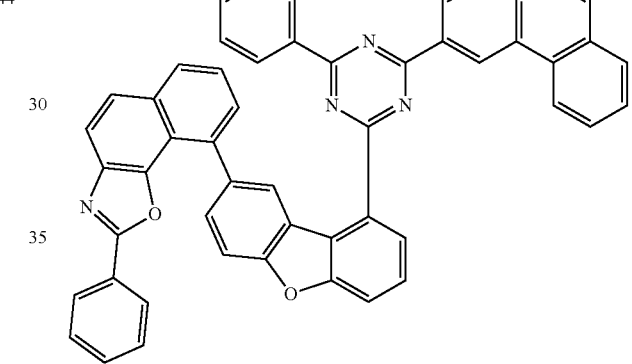
348
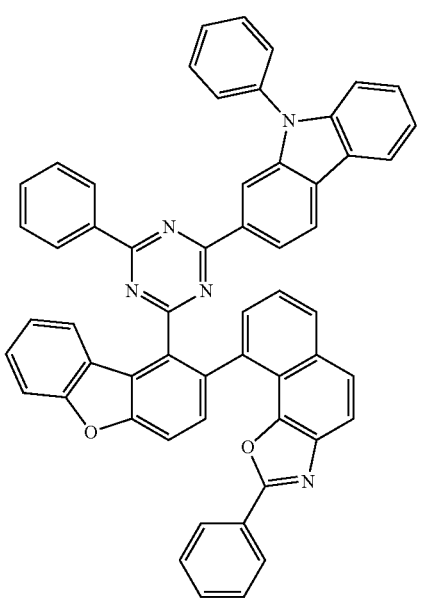

349
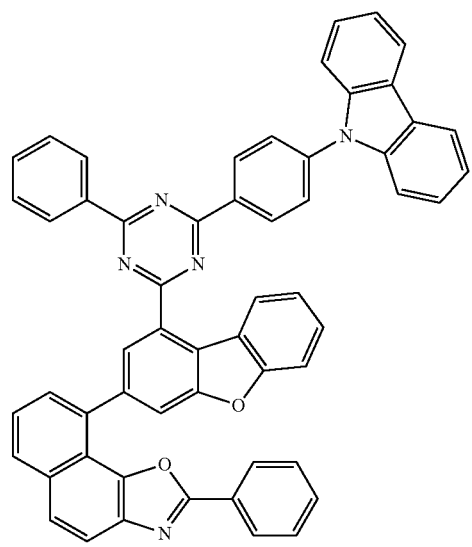
350
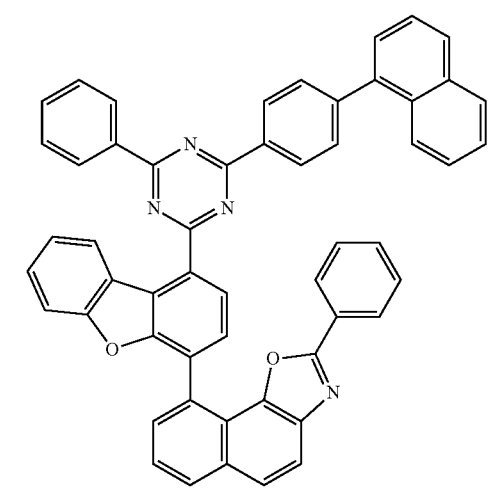
351
352
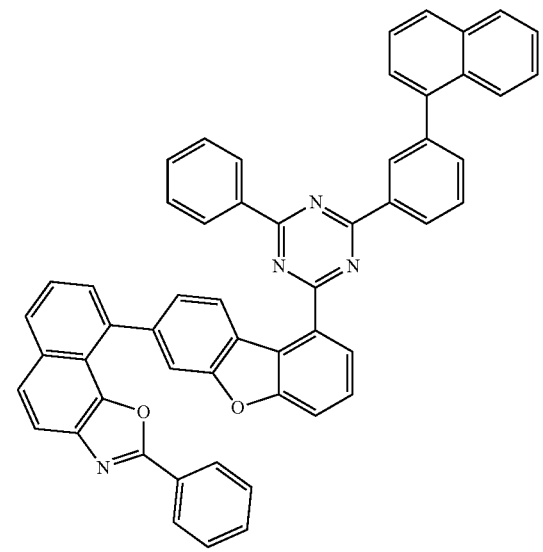
353
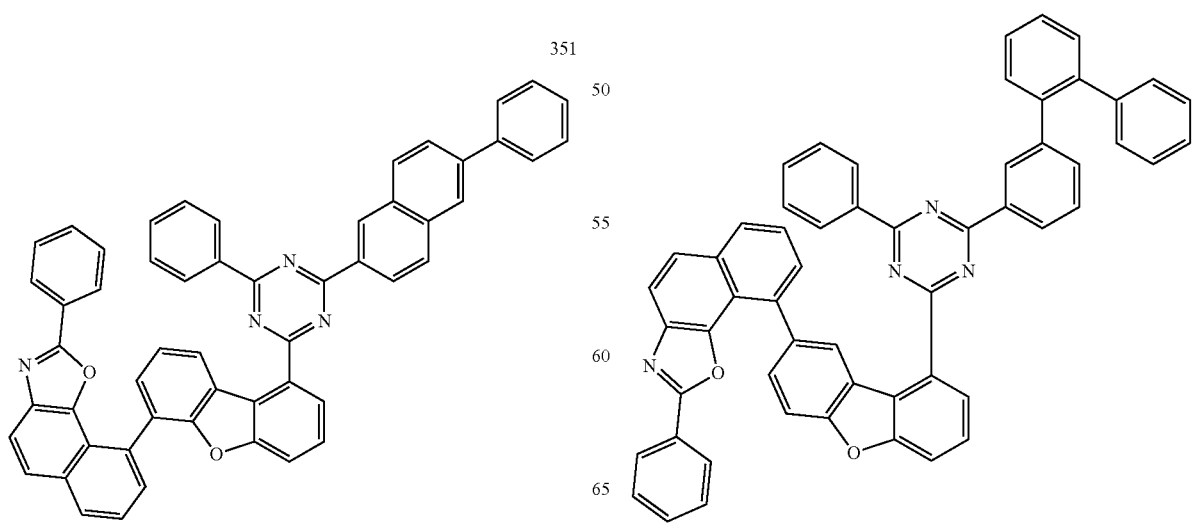

354
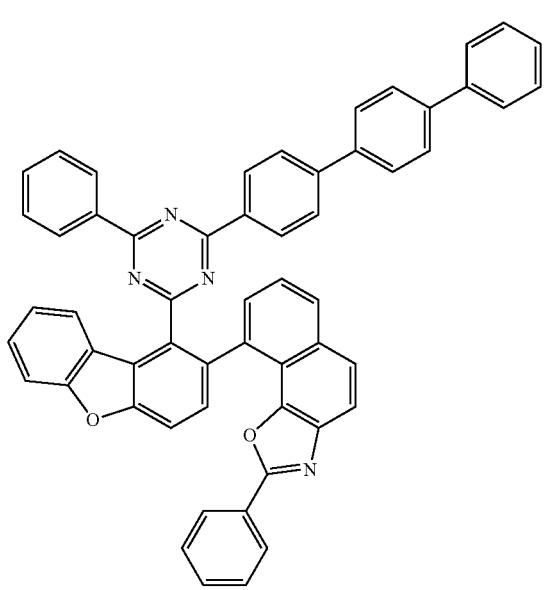
355
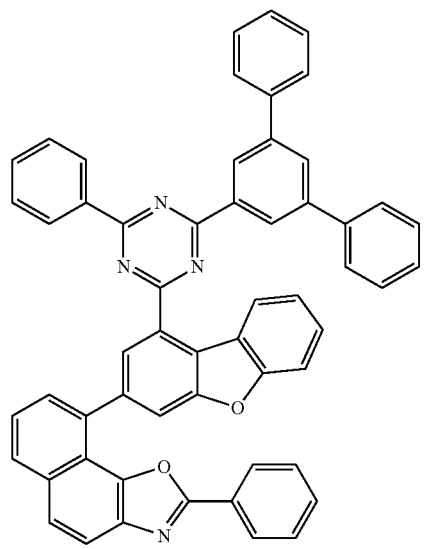
356
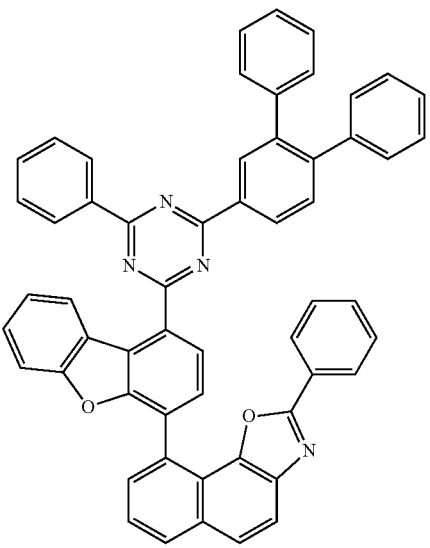
357
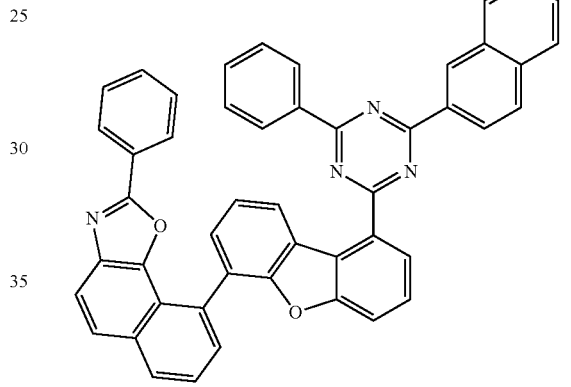
358
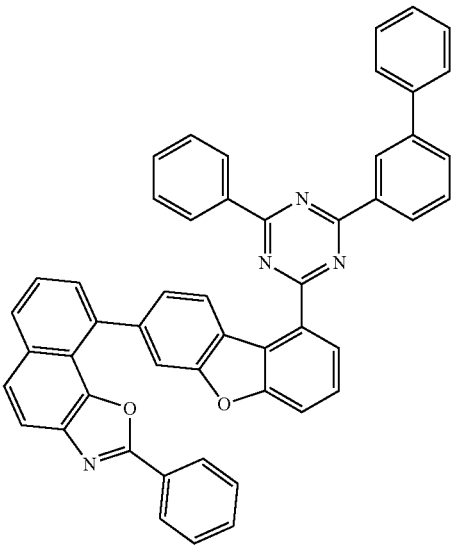

359
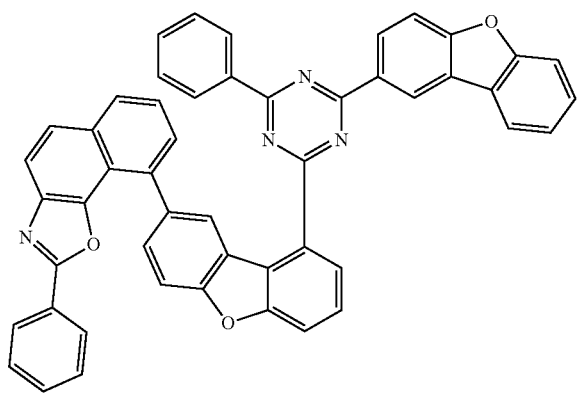
360
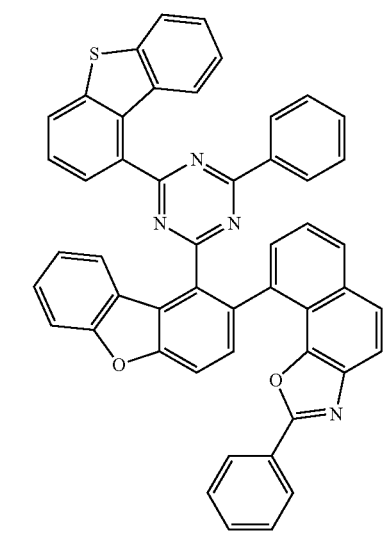
361
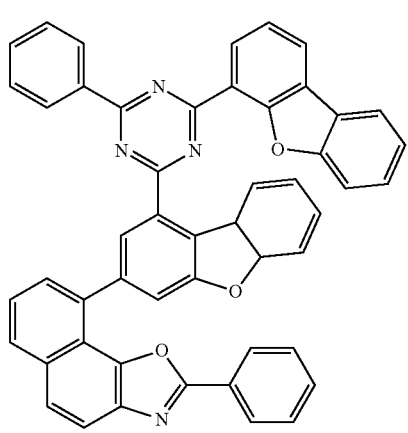
362
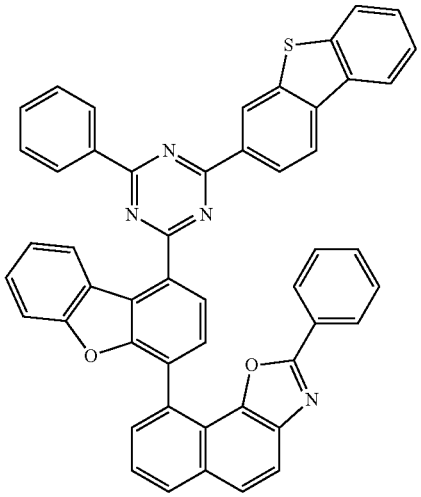
363
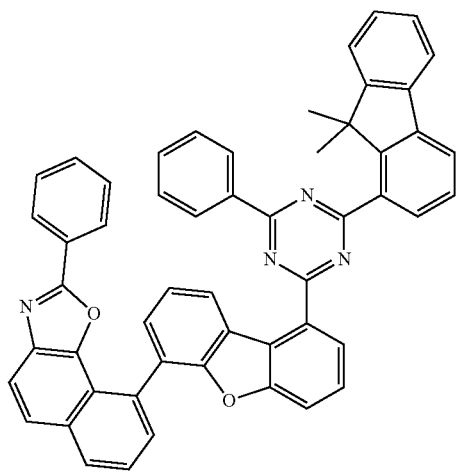
364
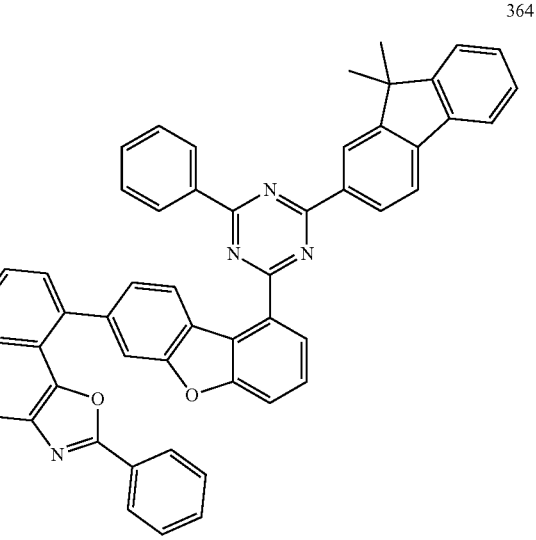

365
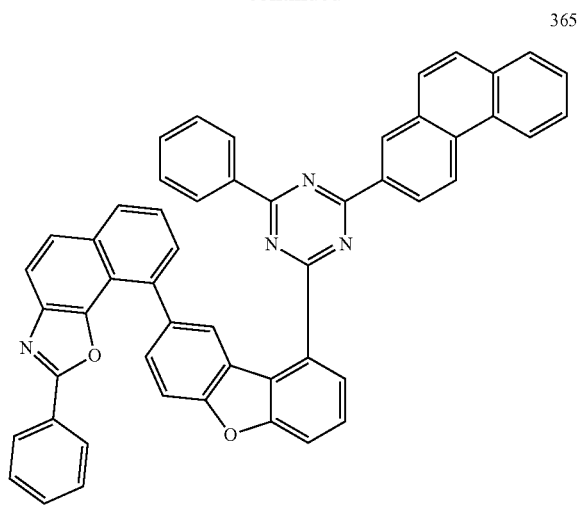
366
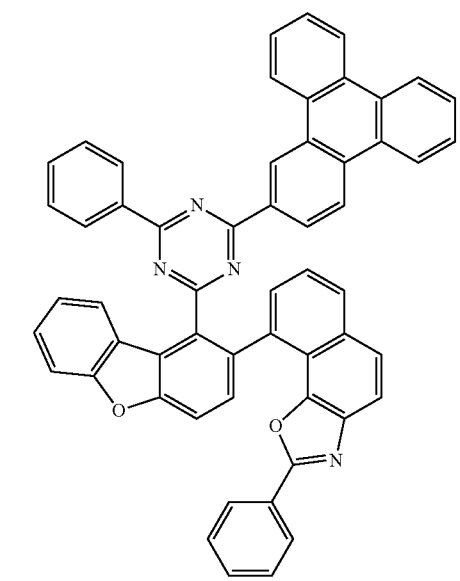
367
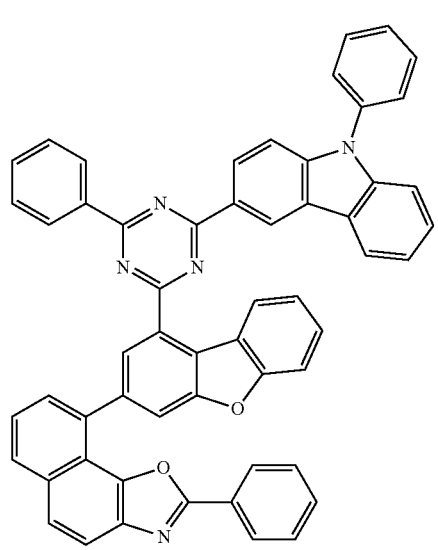
368
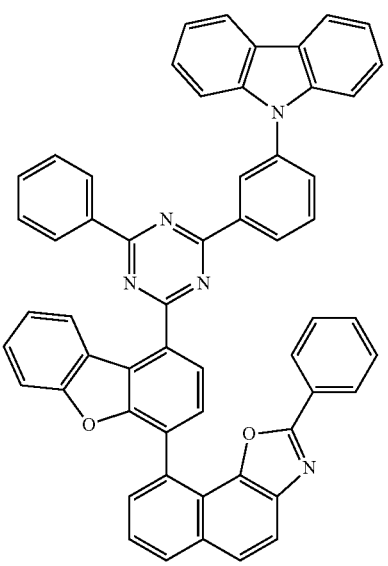
369
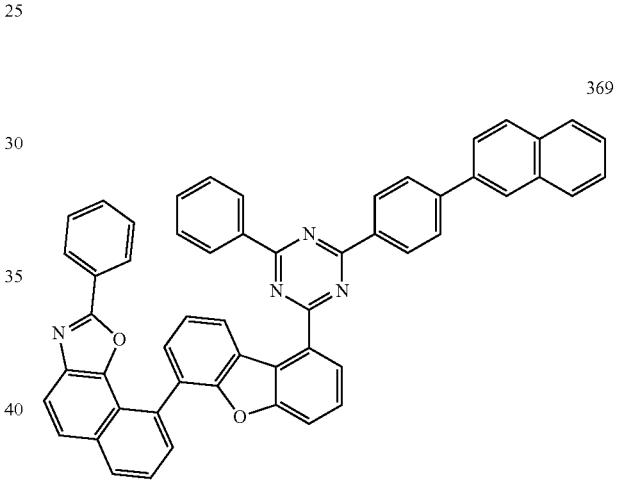
370
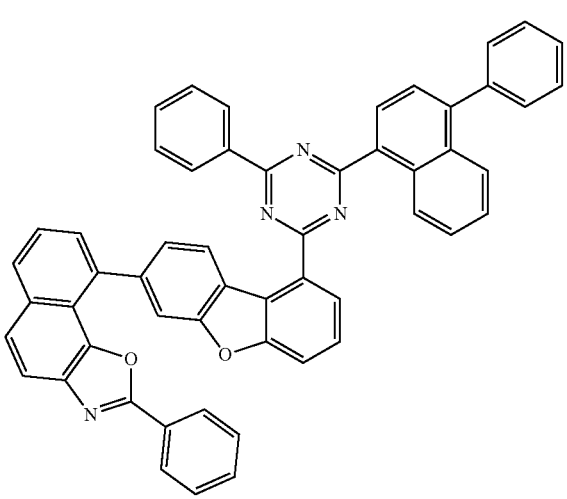

371
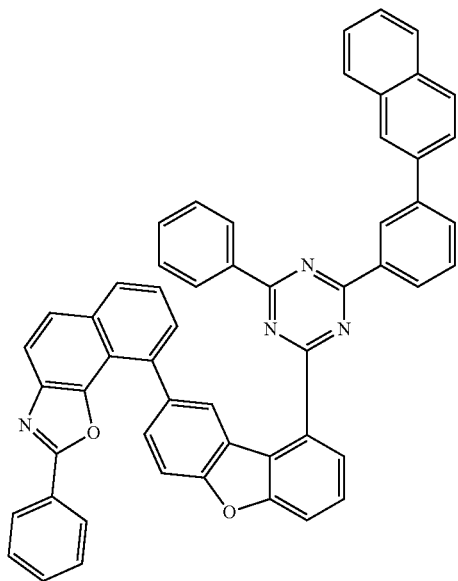
373
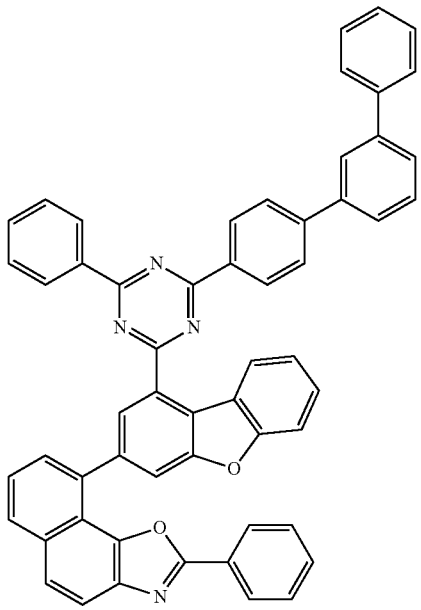
374
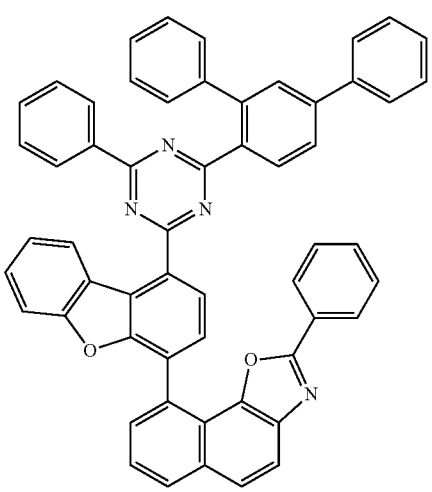
372
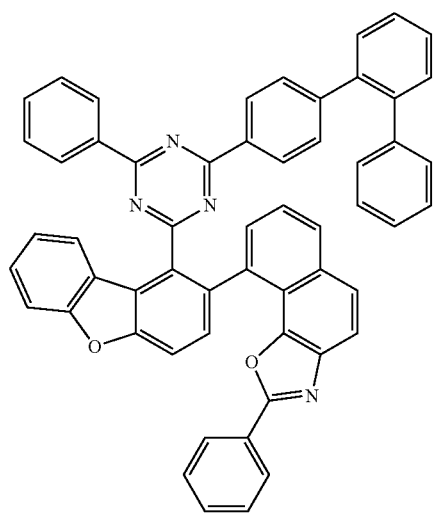
375
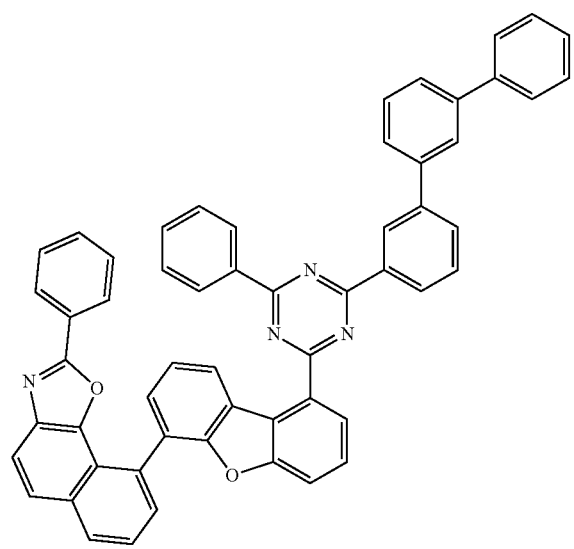

-continued
376
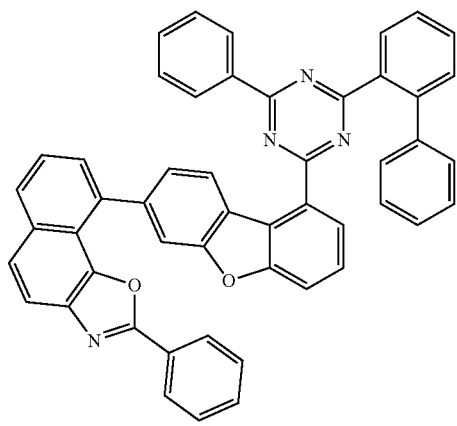
377
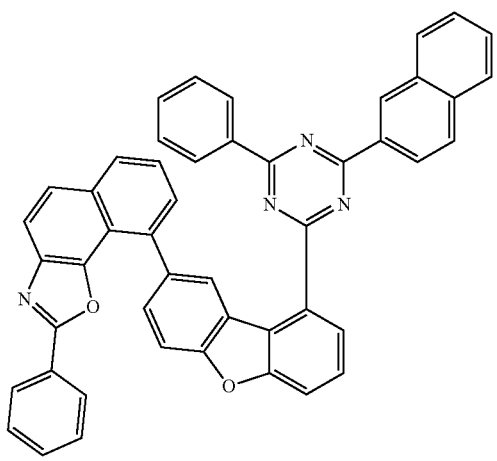
378
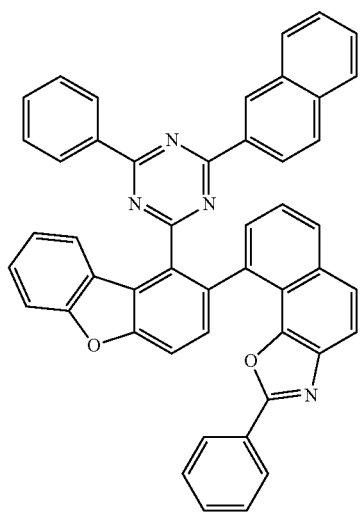
-continued
379
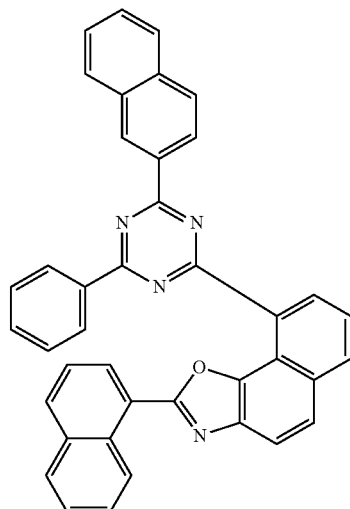
380
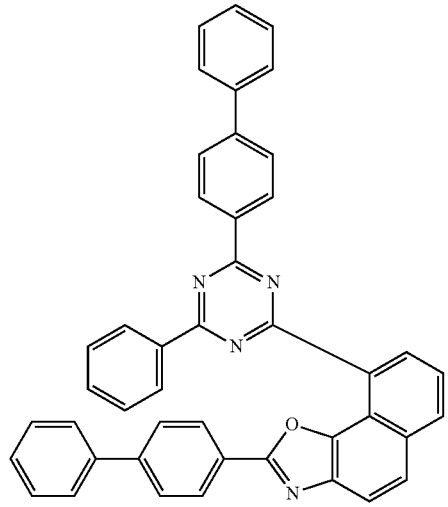
381
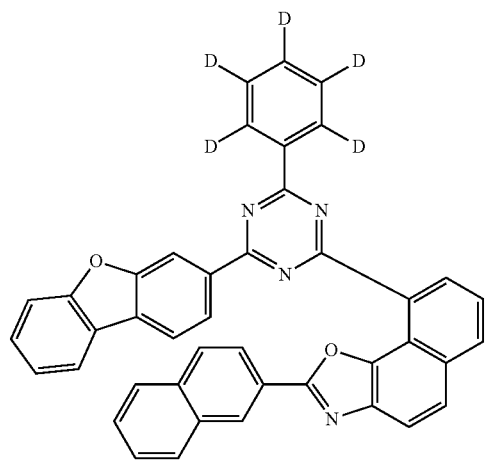

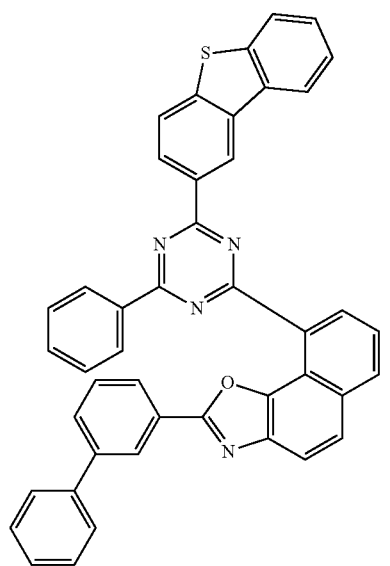
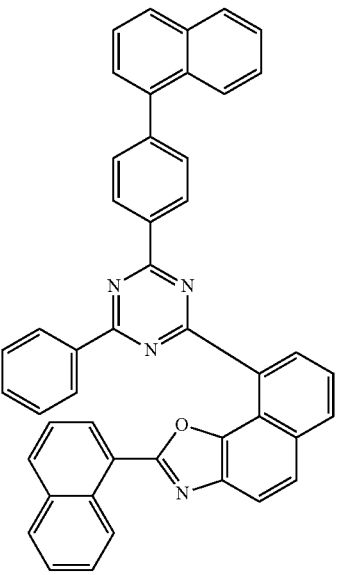

387
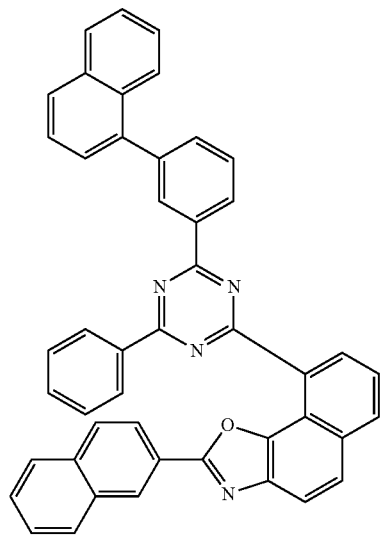
388
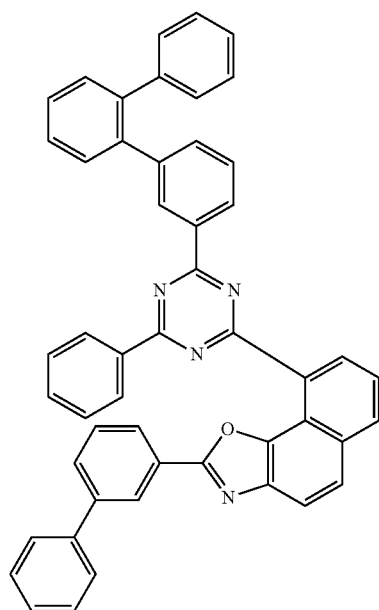
389
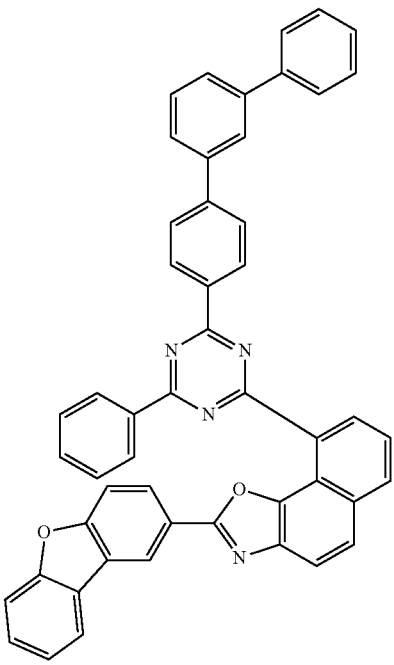
390
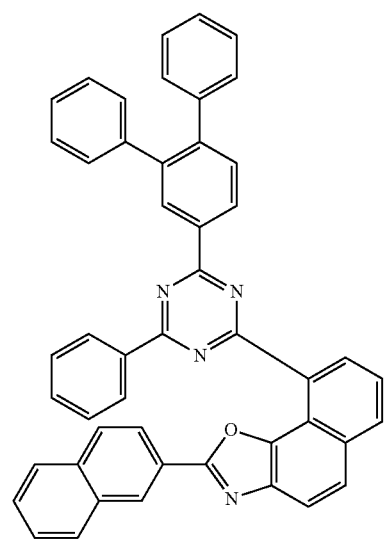

391
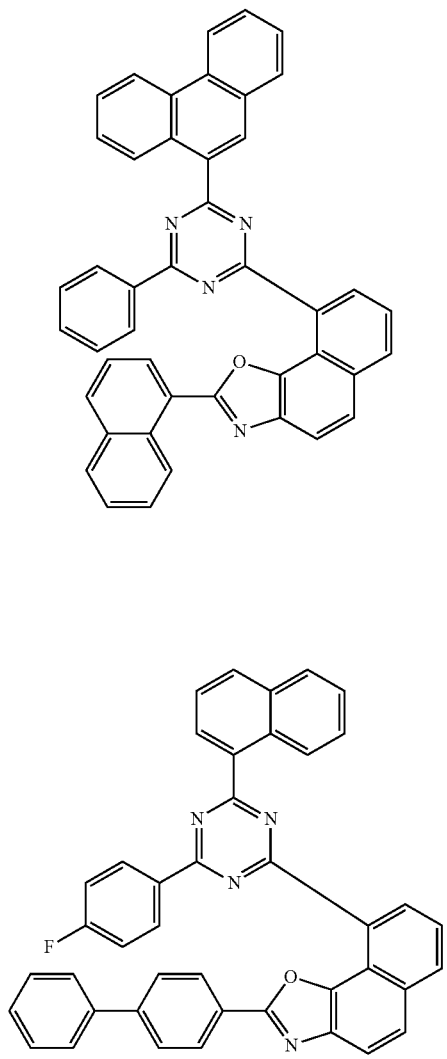
392
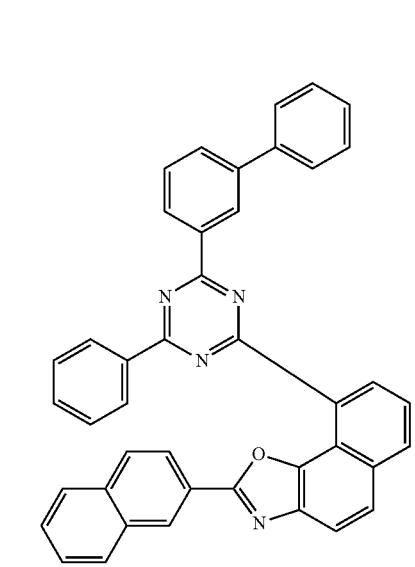
393
394
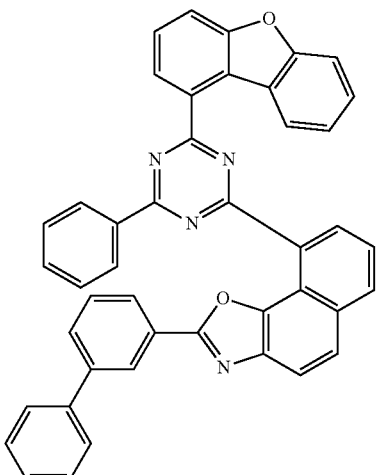
395
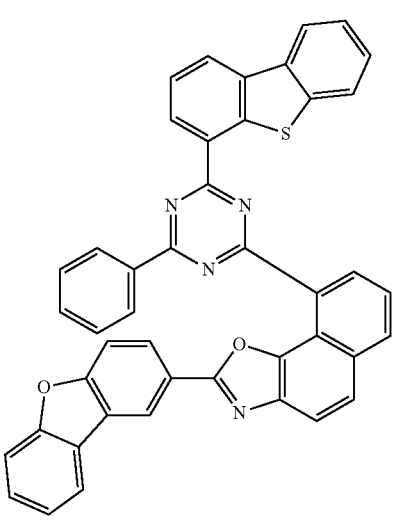
396
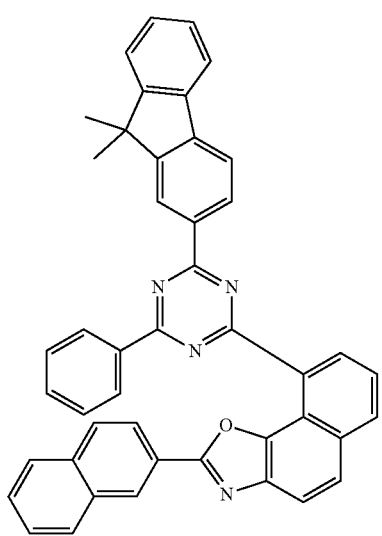

397
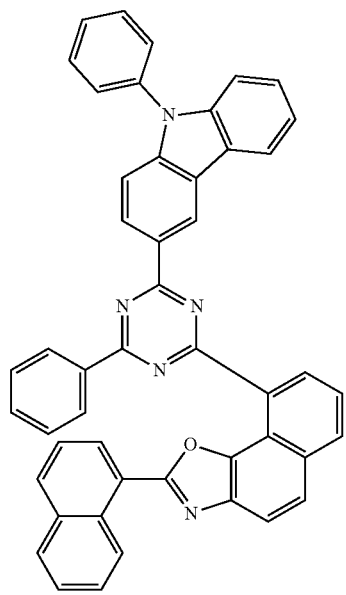
398
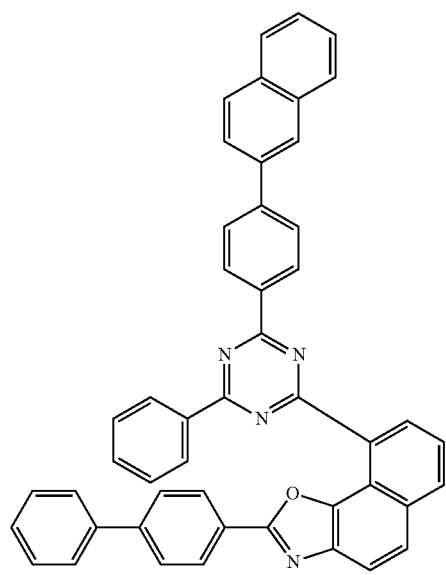
399
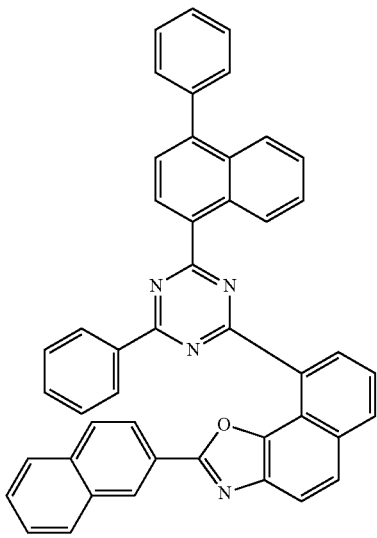
400
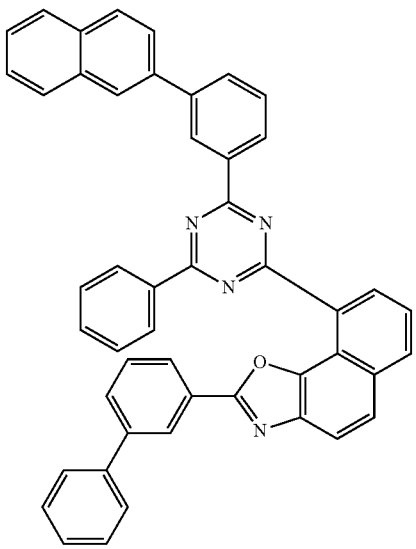

401 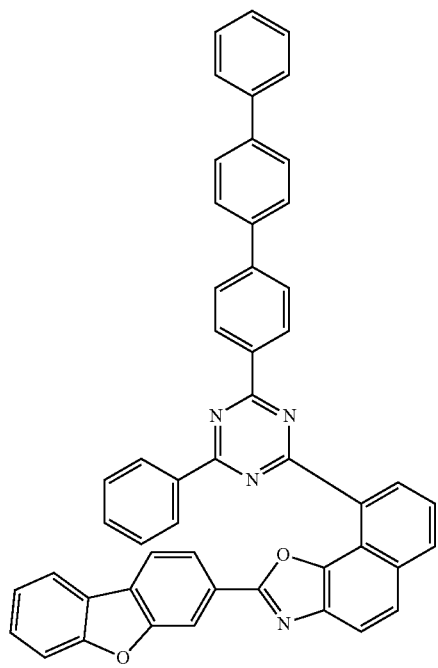
402 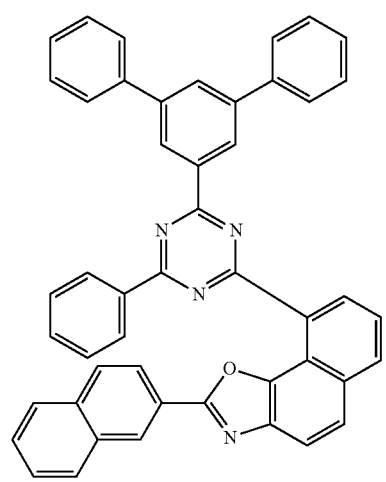
403 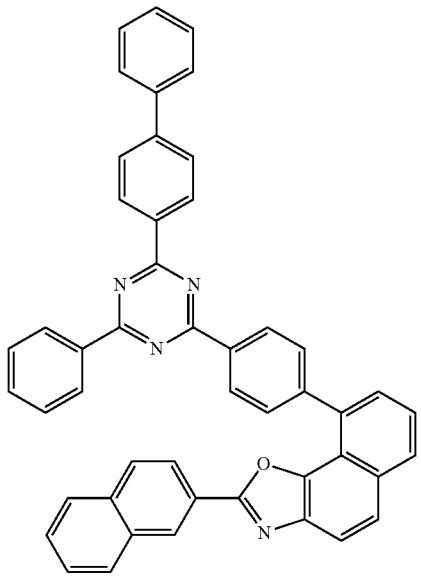
404 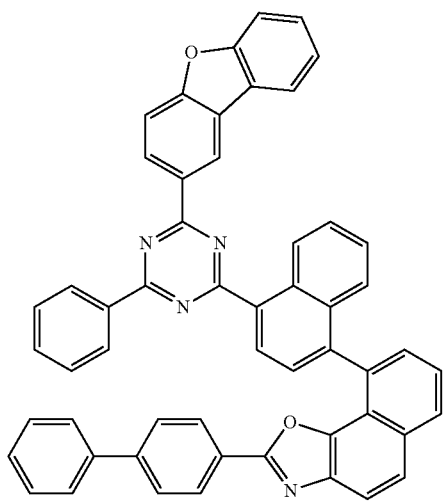
405 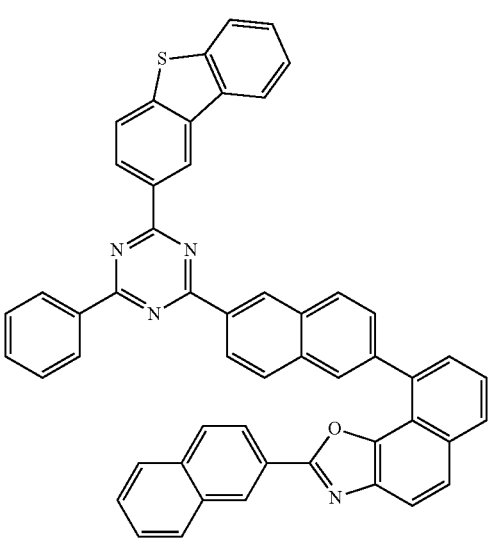

-continued
406
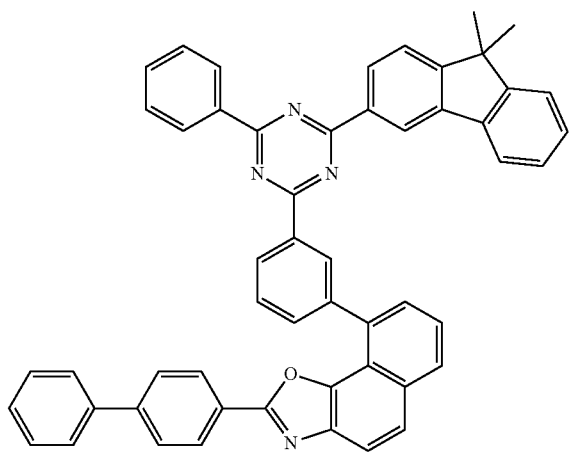
407
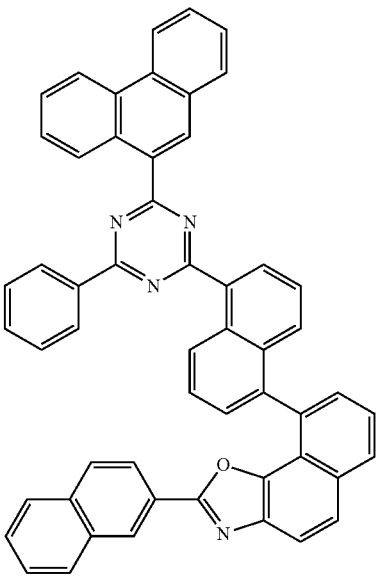
408
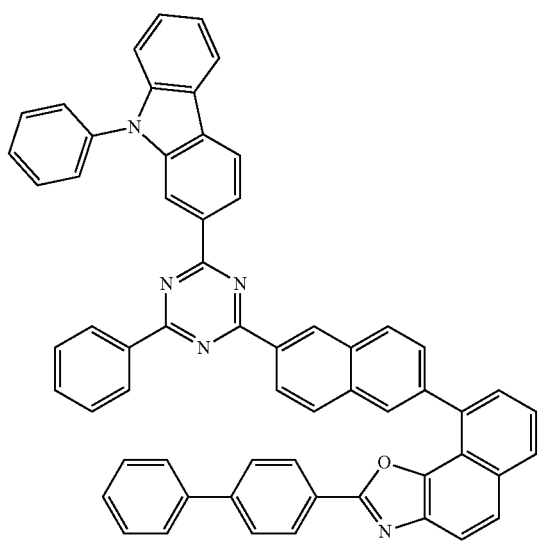
-continued
409
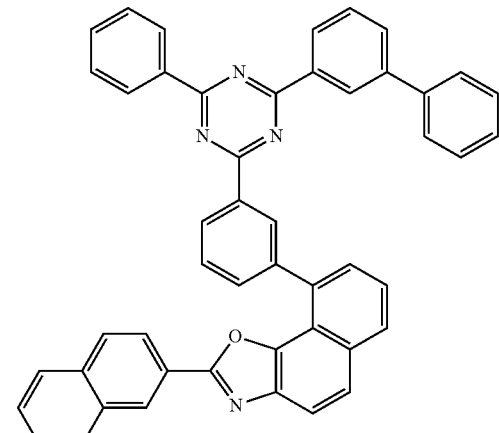
410
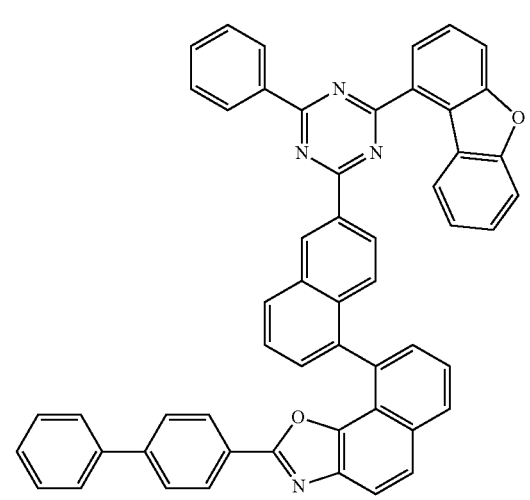
411
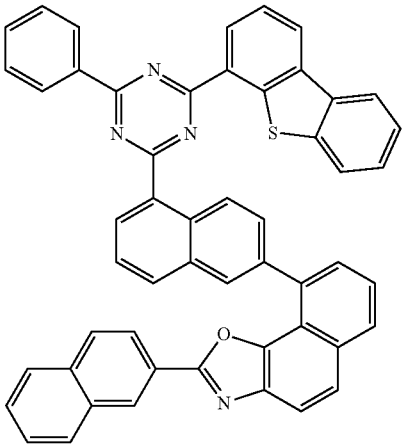

-continued
412
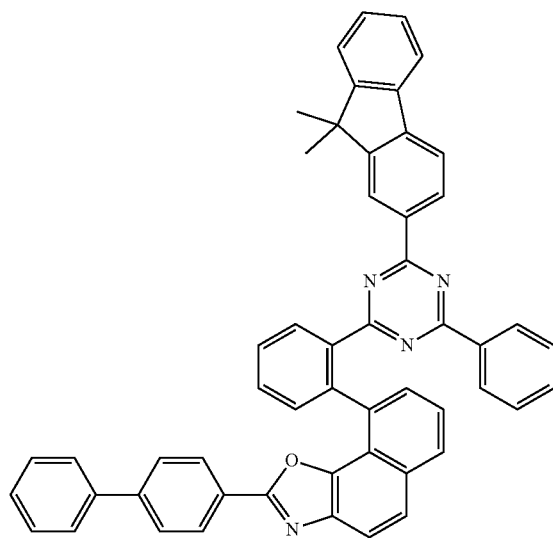
413
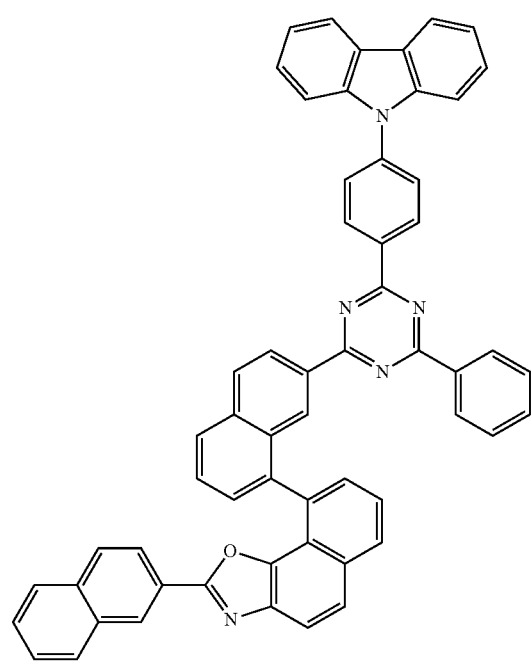
-continued
414
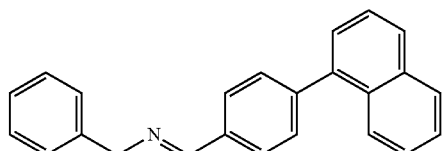
415
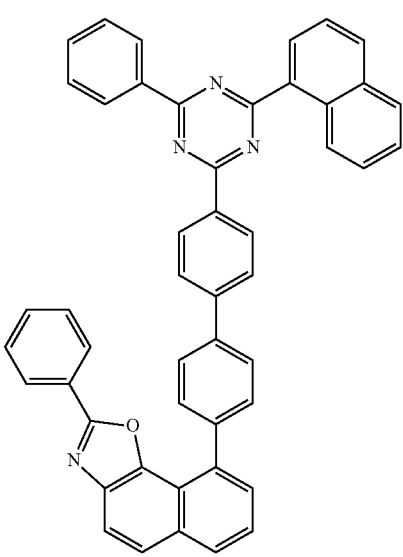
416
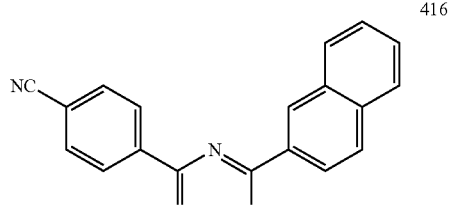
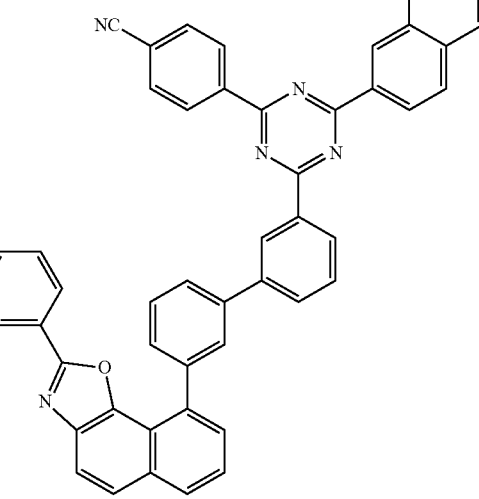

-continued
417
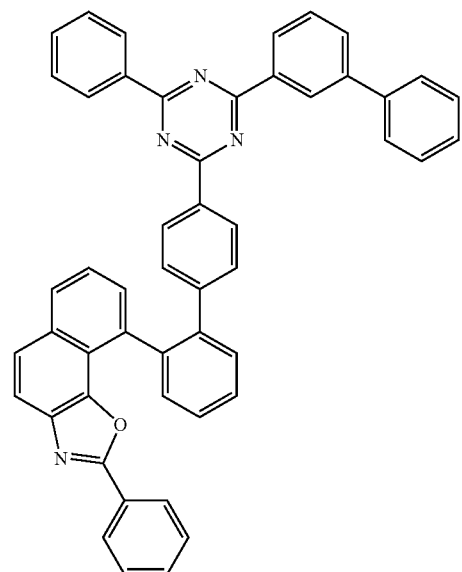
418
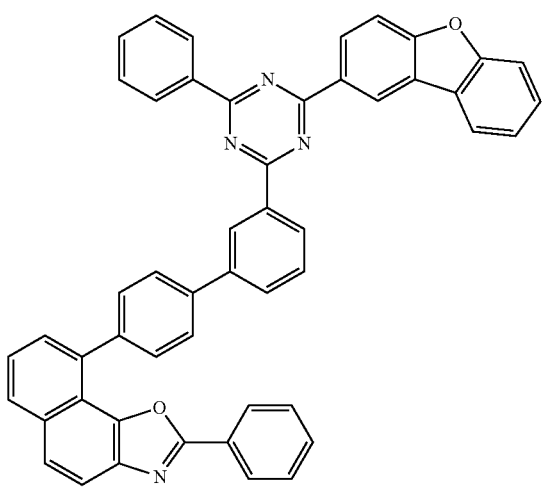
419
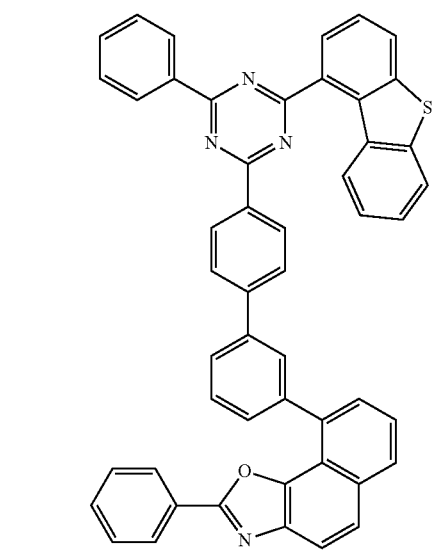
-continued
420
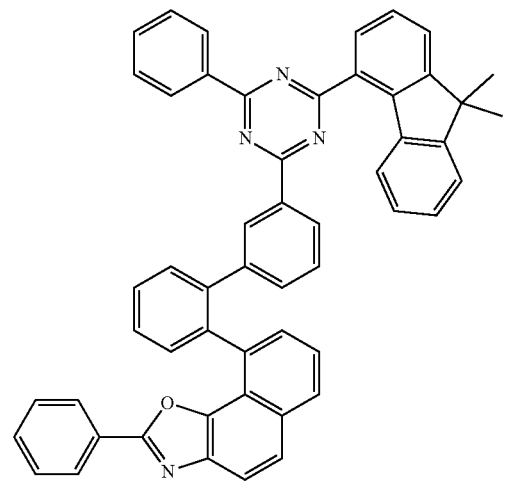
421
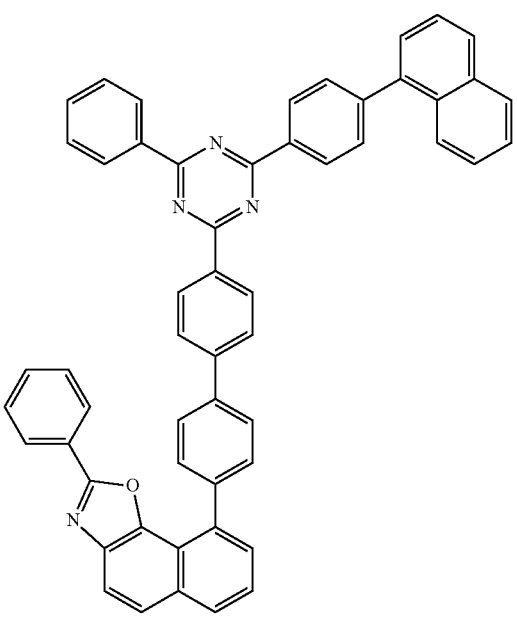
422
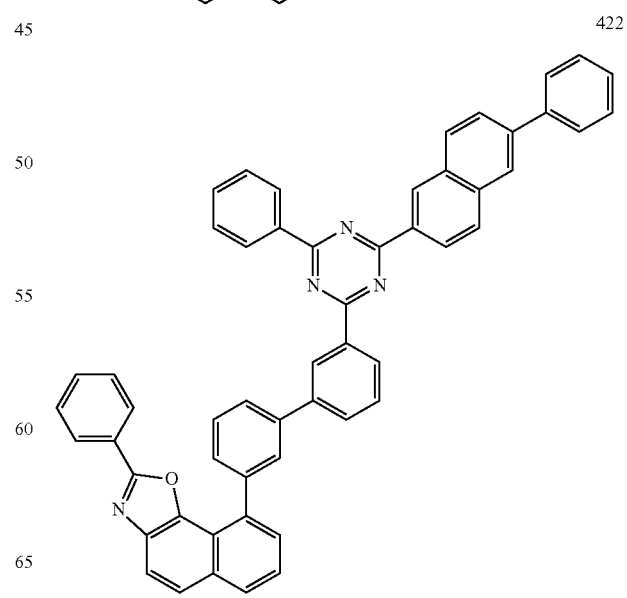

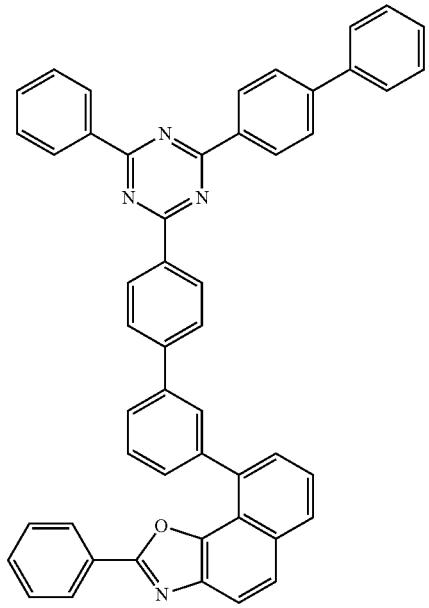
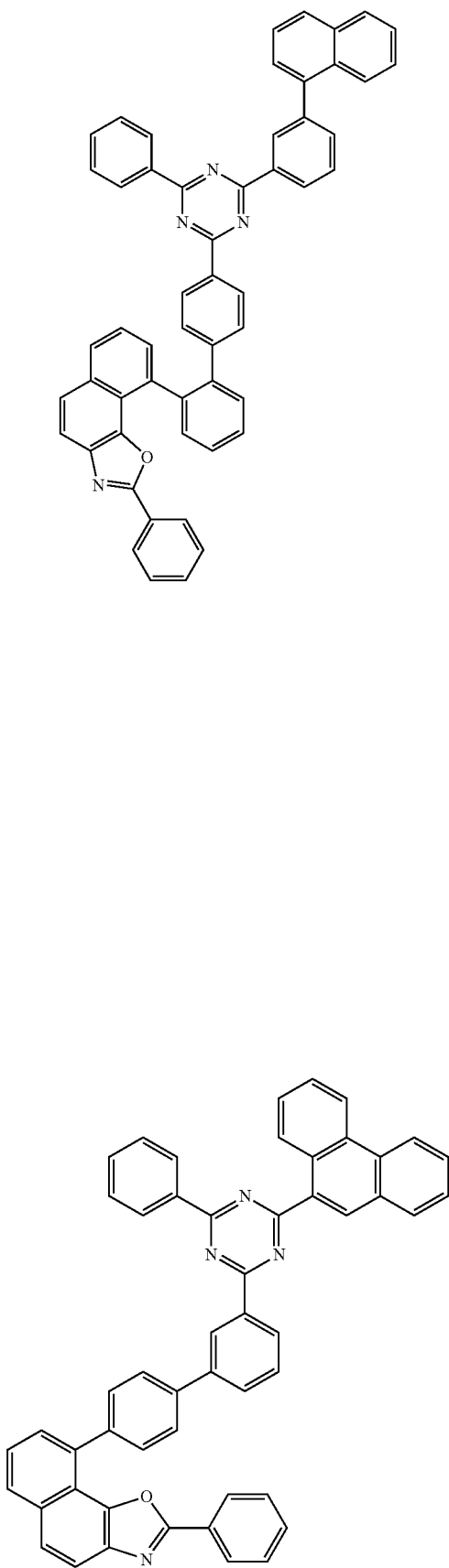
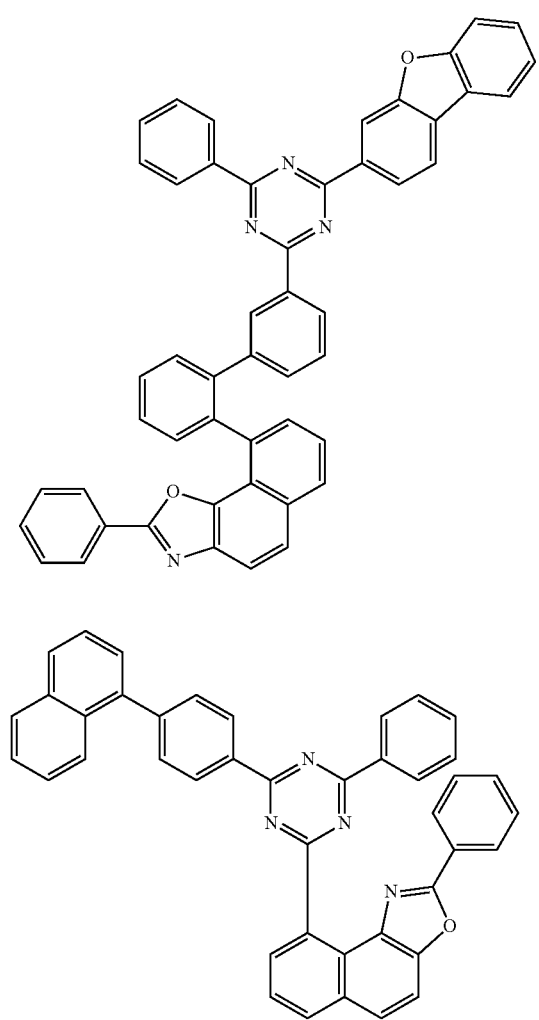

428
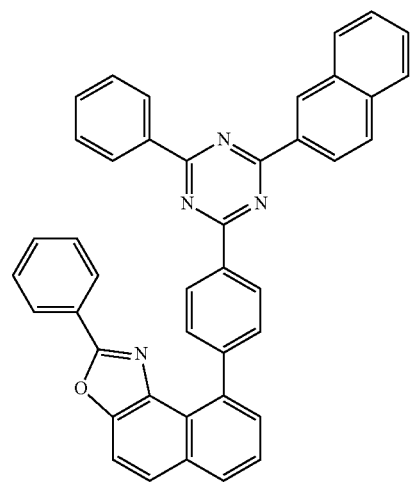
429
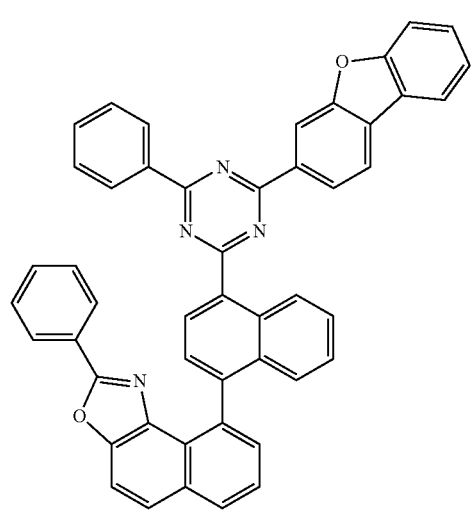
430
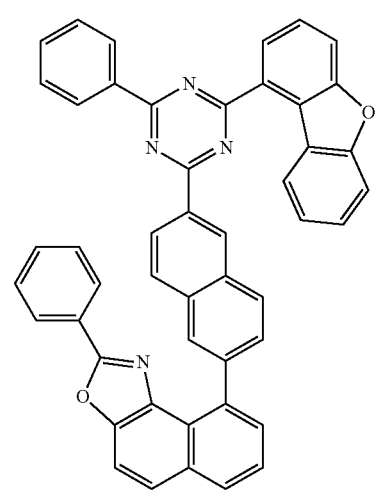
431
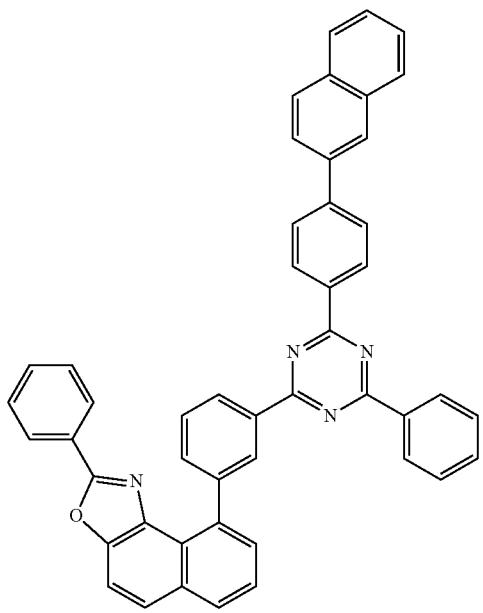
432
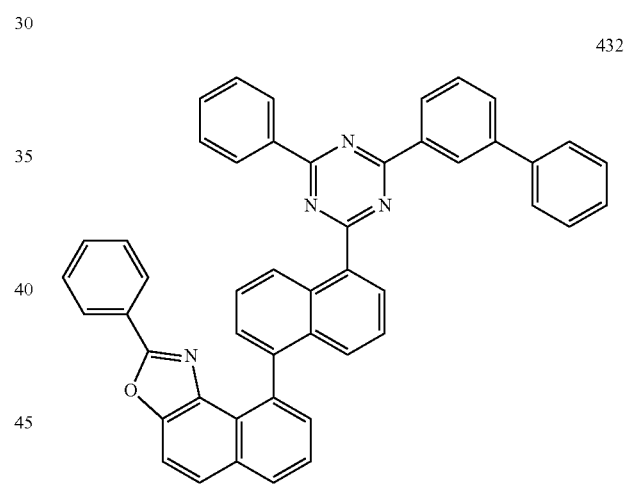
433
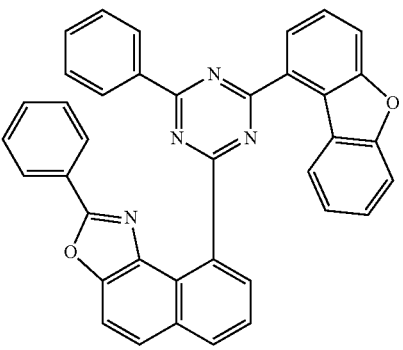

199
-continued
434
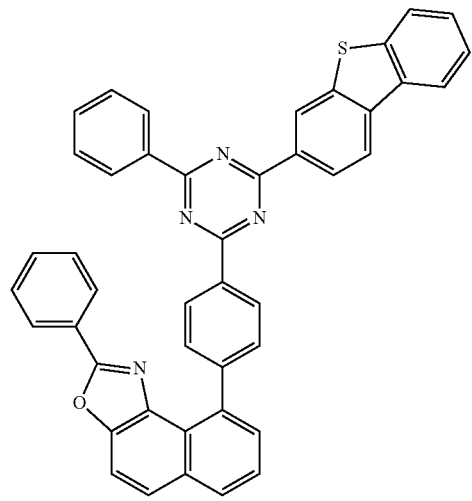
435
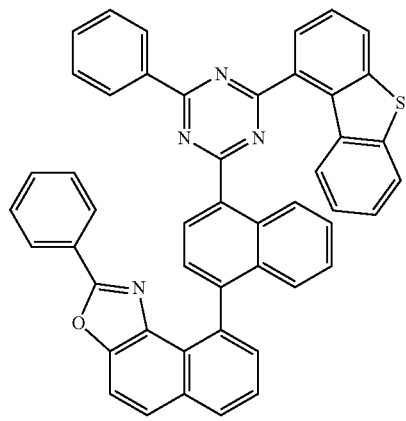
436
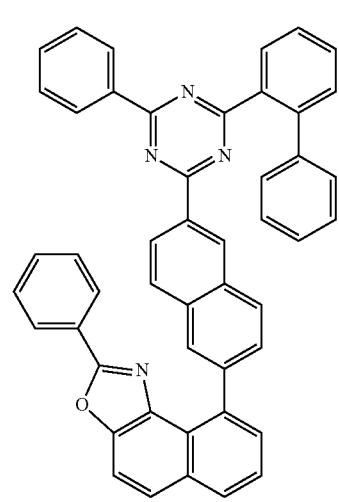
200
-continued
437
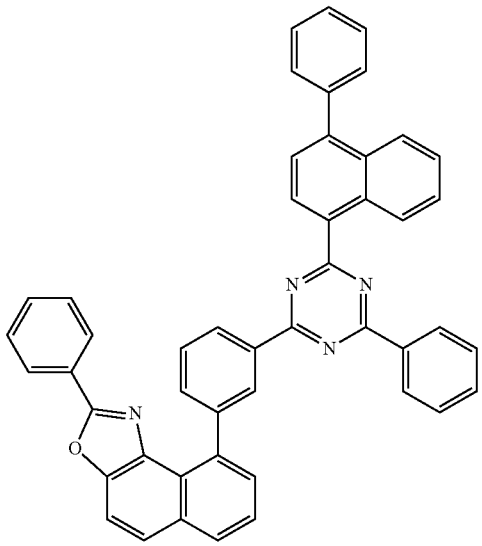
438
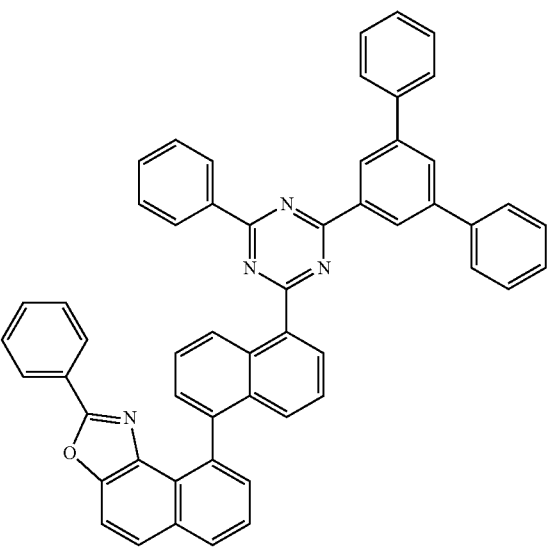

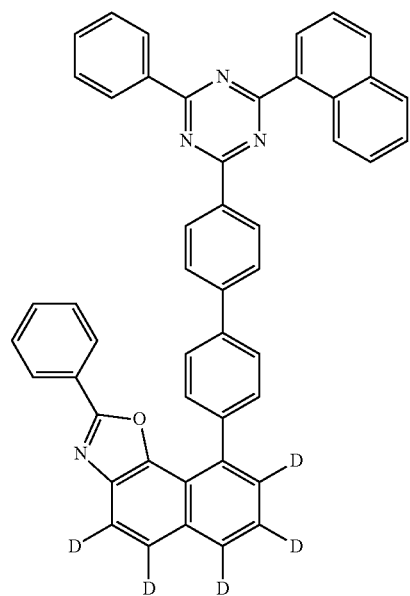
439
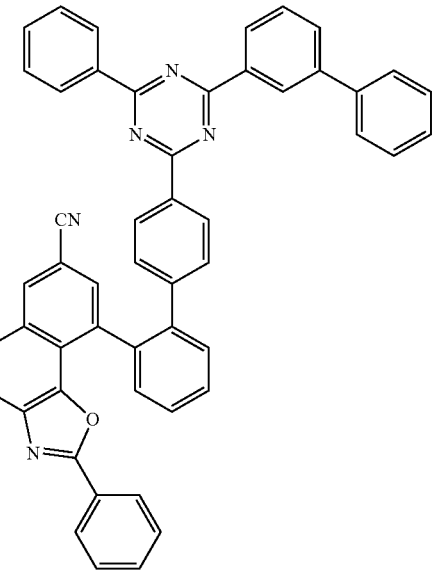
441
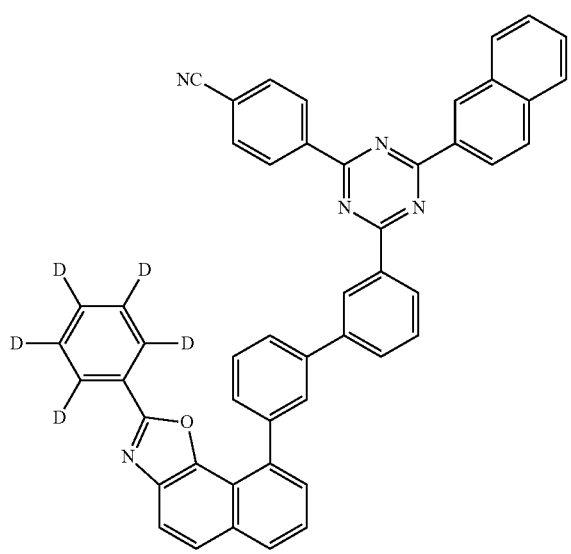
440
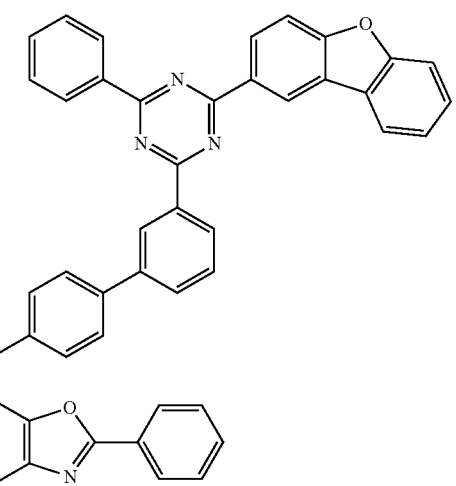
442
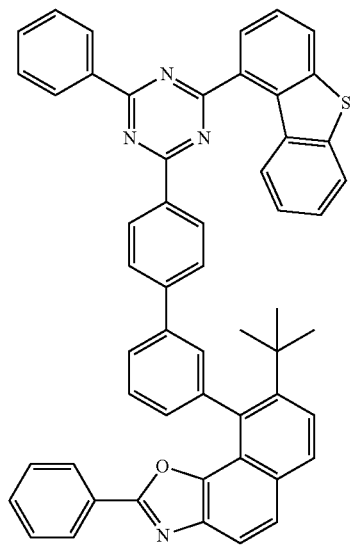
443

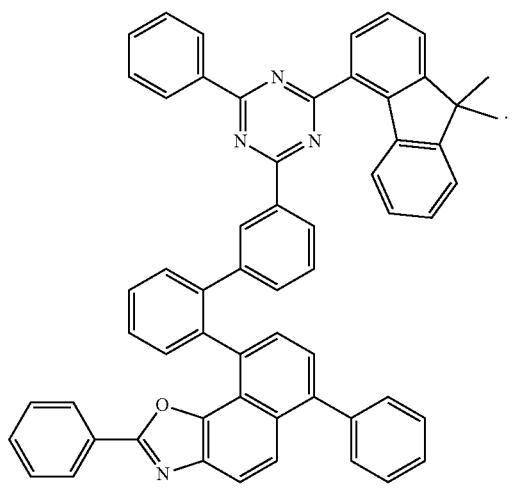

444

A second aspect of the disclosure provides an organic electroluminescent device, including an anode, a cathode, and a functional layer arranged between the anode and the cathode, where the functional layer comprises the nitrogen-containing compound described in the first aspect of the disclosure.

The nitrogen-containing compound provided in the disclosure can be used for forming at least one organic film layer in the functional layer to improve the properties of the organic electroluminescent device, such as luminous efficiency, lifetime, etc.

Optionally, the functional layer includes an organic emitting layer, which includes the nitrogen-containing compound. Where the organic emitting layer may be composed of either the nitrogen-containing compound provided in the disclosure, or may be composed of the nitrogen-containing compound provided in the disclosure and other materials.

According to a specific embodiment, the organic electroluminescent device, as shown in FIG. 1, may include an anode 100, a hole injection layer 310, a first hole transport layer 321, a second hole transport layer (also known as a hole assist layer) 322, an organic light-emitting layer 330, an electron transport layer 340, an electron injection layer 350, and a cathode 200 laminated in sequence.

In the disclosure, the anode 100 includes an anode material, which is preferably a material with a large work function that facilitates hole injection into the functional layer. Specific examples of the anode material include, but are not limited to, metals such as nickel, platinum, vanadium, chromium, copper, zinc, and gold, or alloys thereof; metal oxides such as zinc oxide, indium oxide, indium tin oxide (ITO), and indium zinc oxide (IZO); combined metals and oxides, such as ZnO:Al or $SnO_2$:Sb; or conducting polymers, such as poly(3-methylthiophene), poly[3,4-(ethylidene-1,2-dioxy)thiophene] (PEDT), polypyrrole, and polyaniline. A transparent electrode containing indium tin oxide (ITO) as the anode is preferably included.

In the disclosure, the first hole transport layer may include one or more hole transport materials. The material of the first hole transport layer may be selected from carbazole multimers, carbazole linked triarylamine compounds, or other types of compounds, and specifically, the material of the first hole transport layer may be selected from the following compounds or any combination thereof:

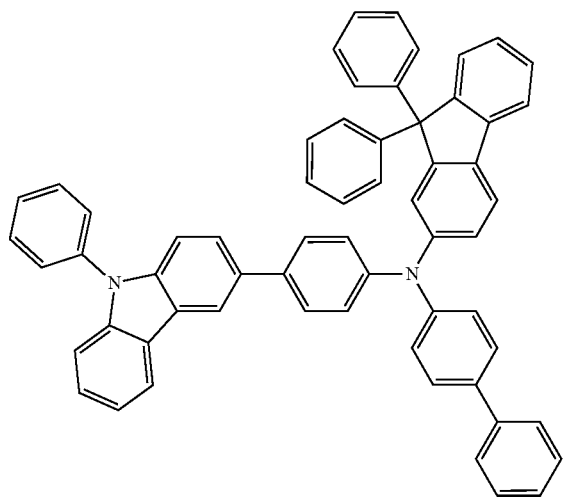

HT-1

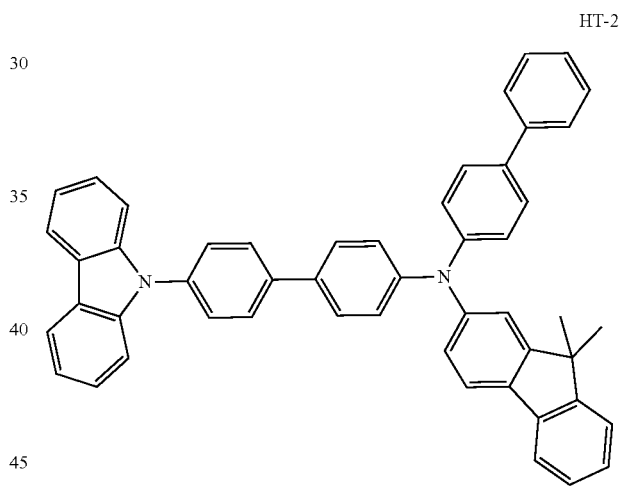

HT-2

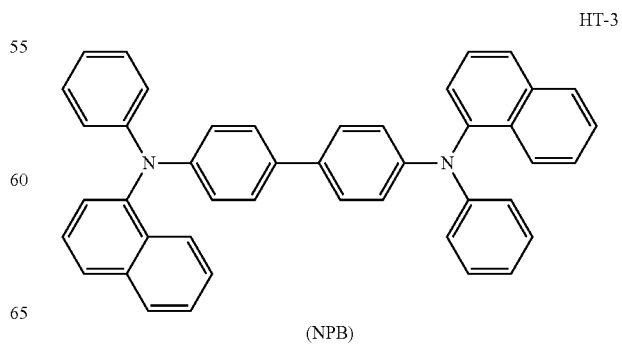

HT-3

(NPB)

HT-4
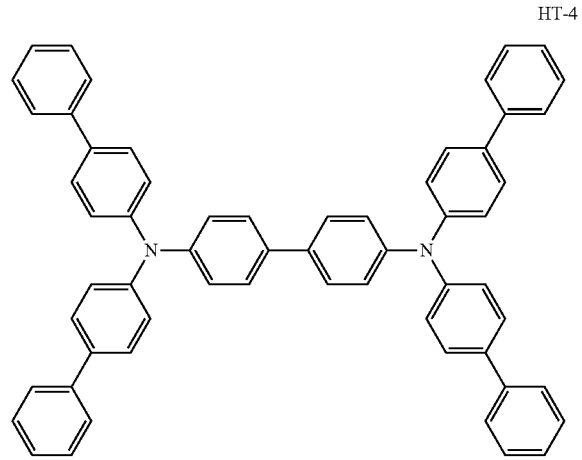
HT-7
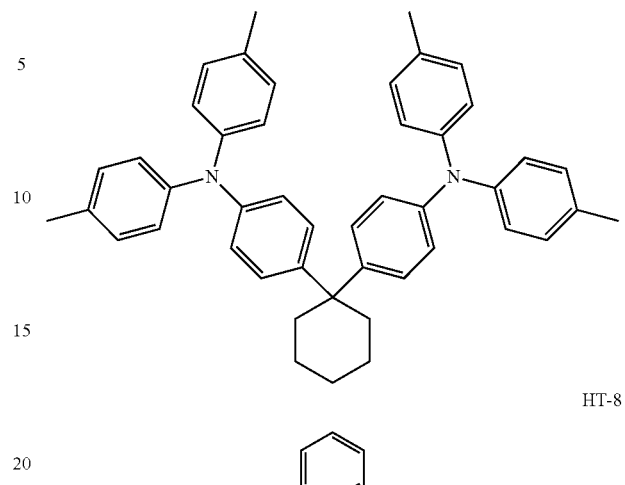
HT-5
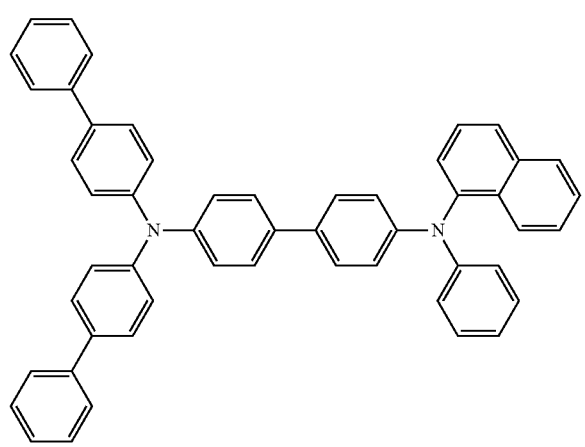
HT-8
HT-9
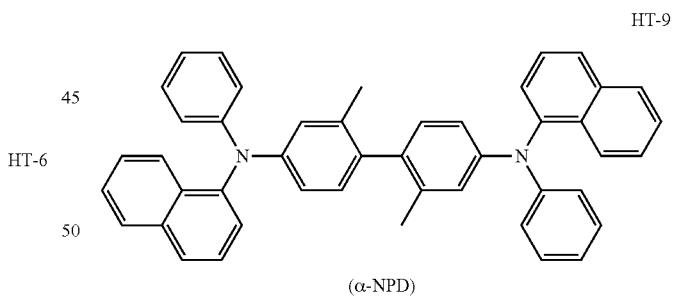
(α-NPD)
HT-6
HT-10
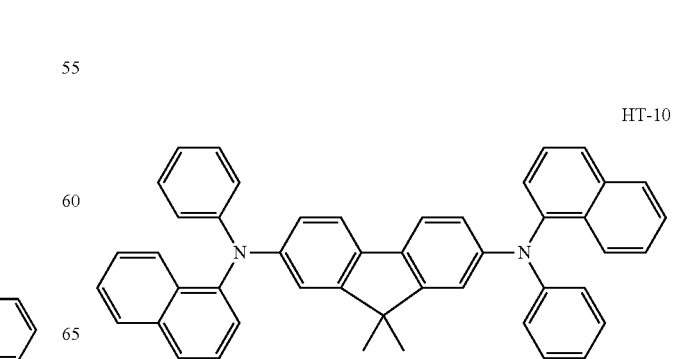

-continued

HT-11
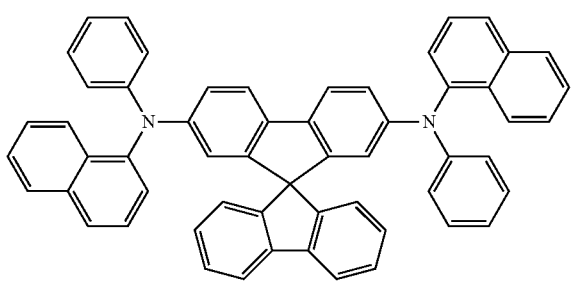

HT-12
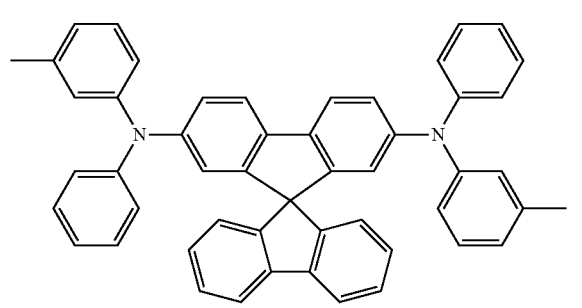

HT-13
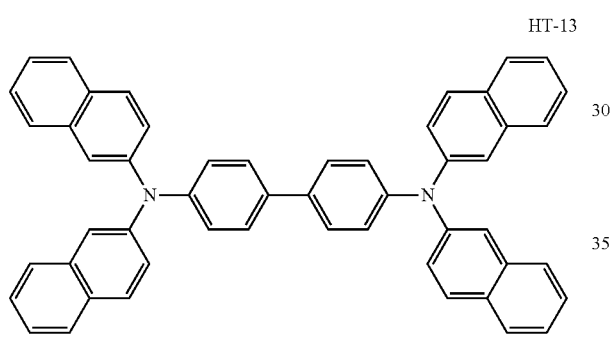

HT-14
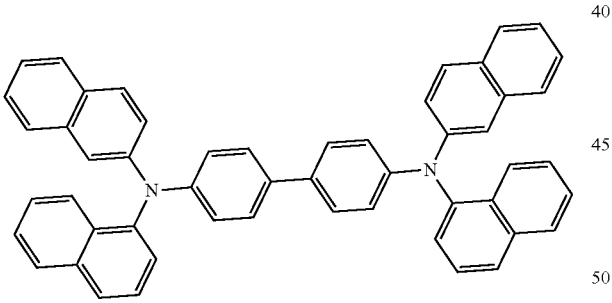

HT-15
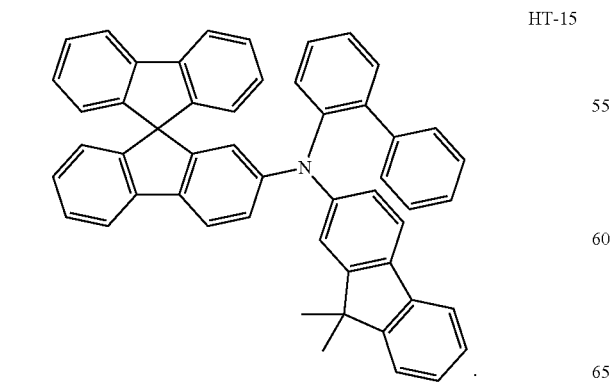

In one embodiment, the first hole transport layer 321 is composed of HT-1.

In one embodiment, the second hole transport layer 322 is composed of HT-2.

Optionally, the hole injection layer 310 is further arranged between the anode 100 and the first hole transport layer 321 to enhance the capability of injecting holes into the first hole transport layer 321. The hole injection layer 310 may be selected from benzidine derivatives, starburst arylamine compounds, phthalocyanine derivatives, or other materials, which are not particularly limited in the disclosure. The material of the hole injection layer 310 is, for example, selected from the following compounds or any combination thereof:

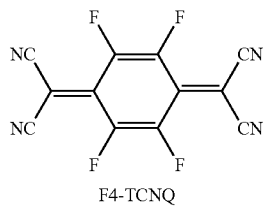

F4-TCNQ

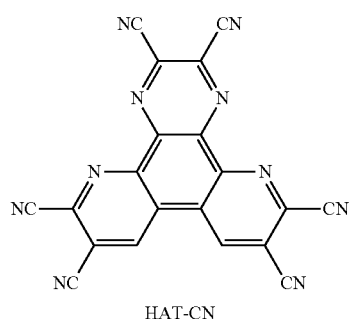

HAT-CN

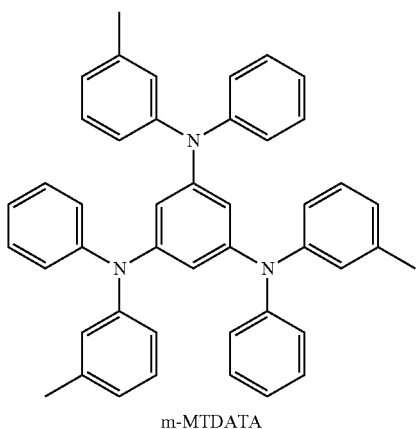

m-MTDATA

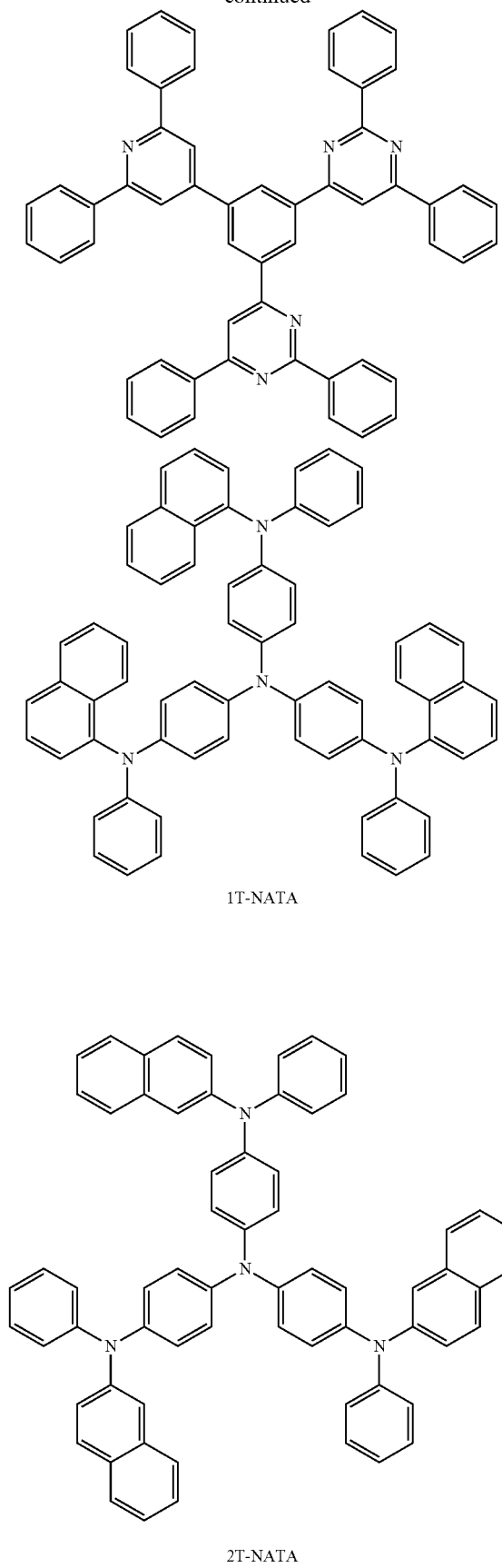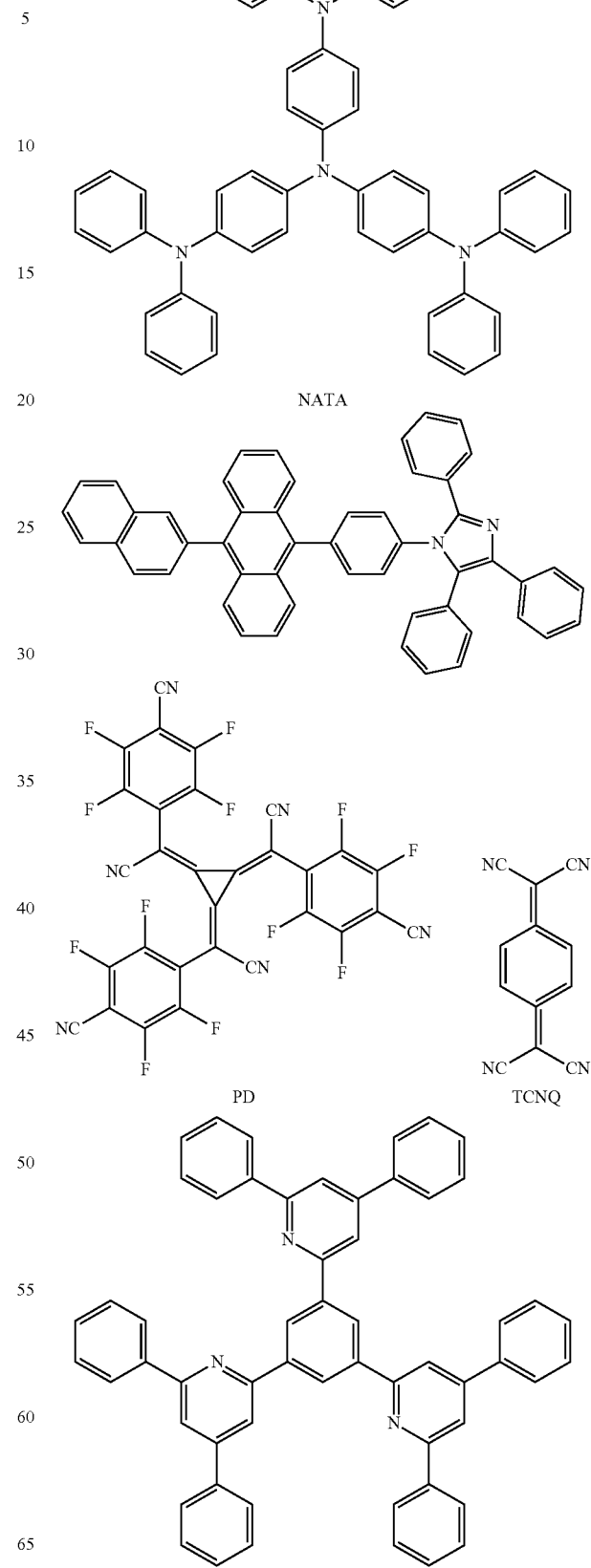

-continued

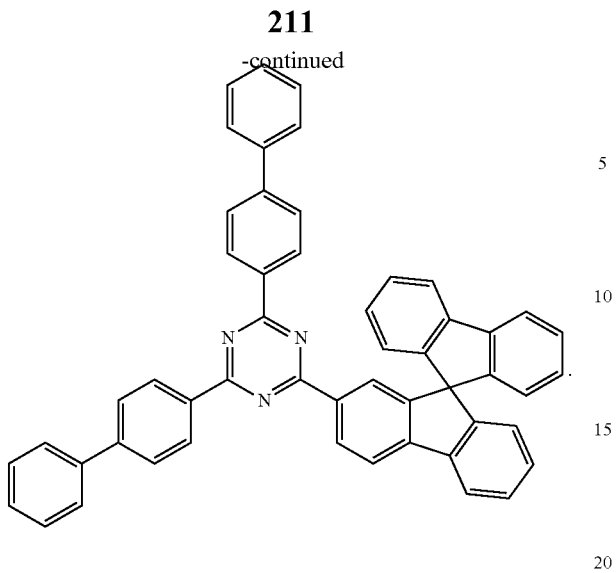

In one embodiment, the hole injection layer 310 is composed of PD and HT-1.

In the disclosure, the organic light-emitting layer 330 may be composed of a single electroluminescent material, or may also include a host material and a guest material. Optionally, the organic light-emitting layer 330 is composed of a host material and a guest material, holes injected into the organic light-emitting layer 330 and electrons injected into the organic light-emitting layer 330 can recombine in the organic light-emitting layer 330 to form excitons, the excitons transfer energy to the host material, and the host material transfers energy to the guest material, so that the guest material can emit light.

The host material of the organic light-emitting layer 330 may include metalchelated compounds, distyryl derivatives, aromatic amine derivatives, dibenzofuran derivatives, or other types of materials. Optionally, the host material includes the nitrogen-containing compound of the disclosure.

The guest material of the organic light-emitting layer 330 may be a compound having a condensed aryl ring or derivatives thereof, a compound having a heteroaryl ring or derivatives thereof, aromatic amine derivatives, or other materials, which are not particularly limited in the disclosure. The guest material is also known as a doping material or dopant. According to the type of luminescence, the dopant may include fluorescent dopants and phosphorescent dopants. Specific examples of the phosphorescent dopants include, but are not limited to,

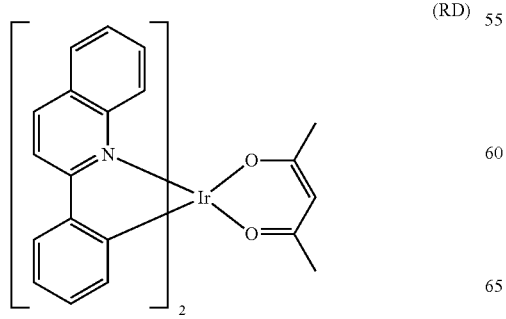

(RD)

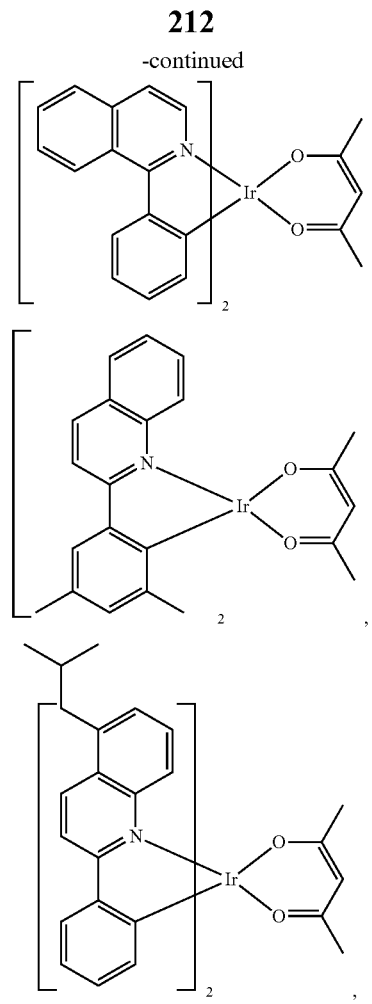

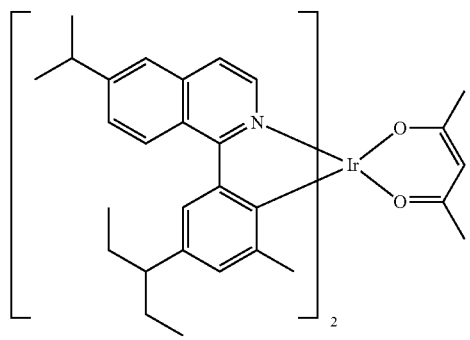

(RD)

213
-continued
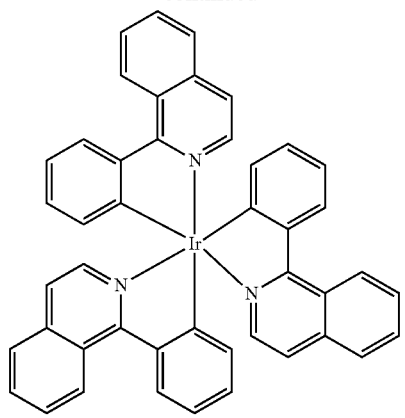
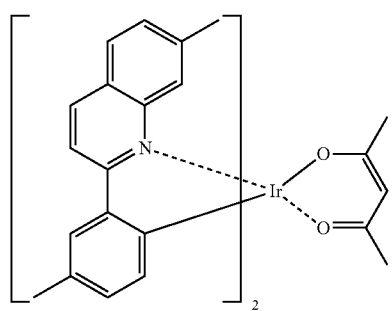
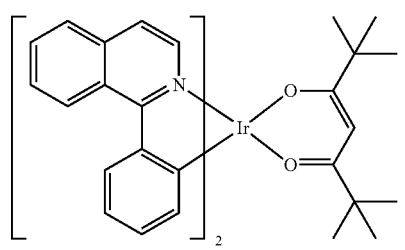
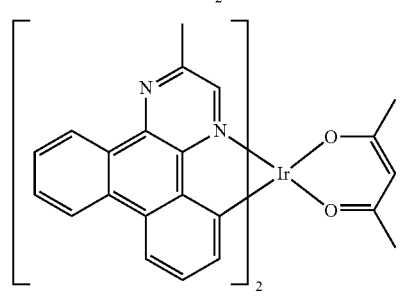
Ir(MDQ)2(acac)
214
-continued
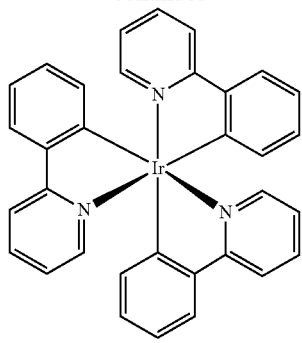
fac-Ir(ppy)3
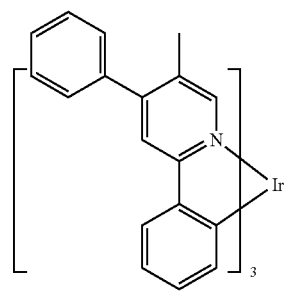

-continued

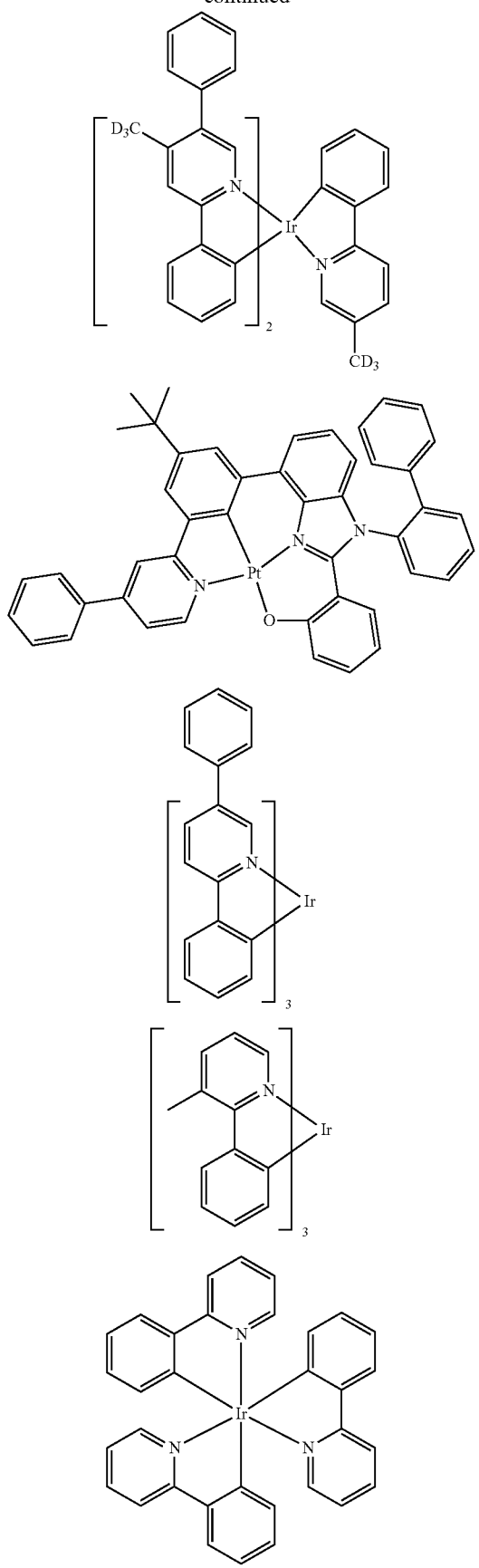

-continued

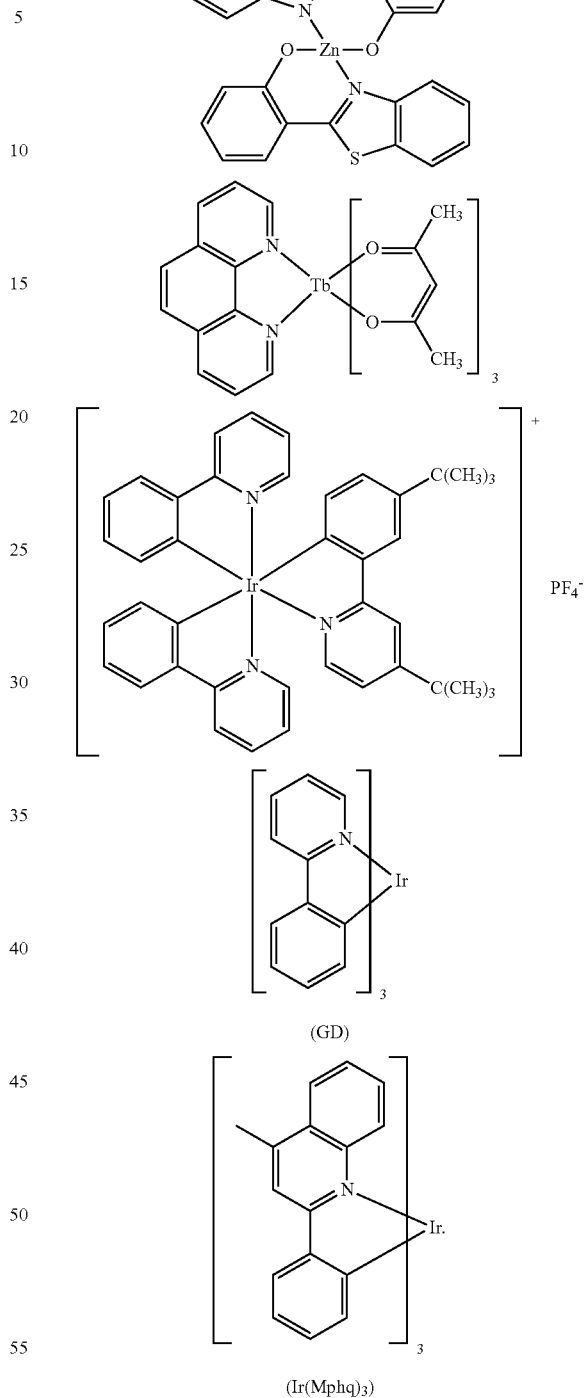

(GD)

(Ir(Mphq)₃)

In one embodiment of the disclosure, the organic electroluminescent device is a red organic electroluminescent device. In one embodiment, the host material of the organic light-emitting layer 330 includes the nitrogen-containing compound of the disclosure. The guest material is, for example, RD. In another embodiment, the host material of the organic light-emitting layer 330 includes the nitrogen-containing compound of the disclosure and RH—P

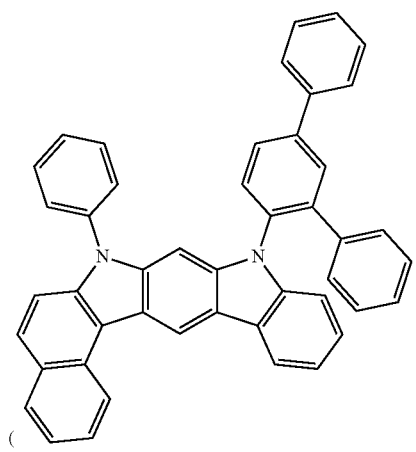

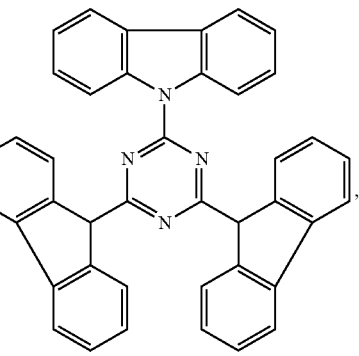

The guest material is, for example, RD.

In one embodiment of the disclosure, the organic electroluminescent device is a green organic electroluminescent device. In a more specific embodiment, the host material of the organic light-emitting layer 330 includes the nitrogen-containing compound of the disclosure. The guest material is, for example, fac-Ir(ppy)$_3$.

The electron transport layer 340 may be of a single-layer structure or a multi-layer structure, which may include one or more electron transport materials, and the electron transport materials may be selected from but are not limited to, BTB, LiQ, benzimidazole derivatives, oxadiazole derivatives, quinoxaline derivatives, or other electron transport materials, which are not particularly limited in the disclosure. The material of the electronic transport layer 340 includes but is not limited to the following compounds:

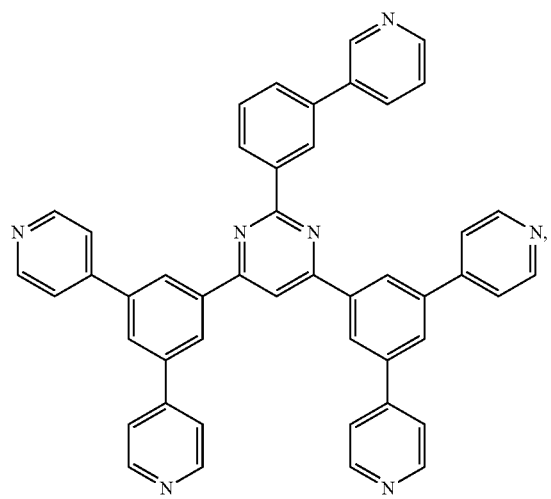

(ET-1)

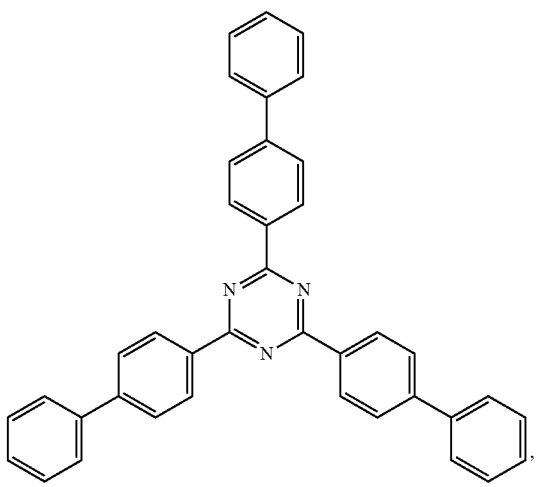

(BTB)

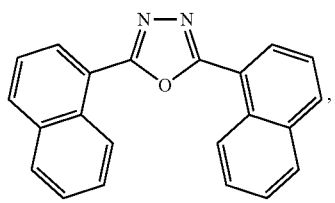

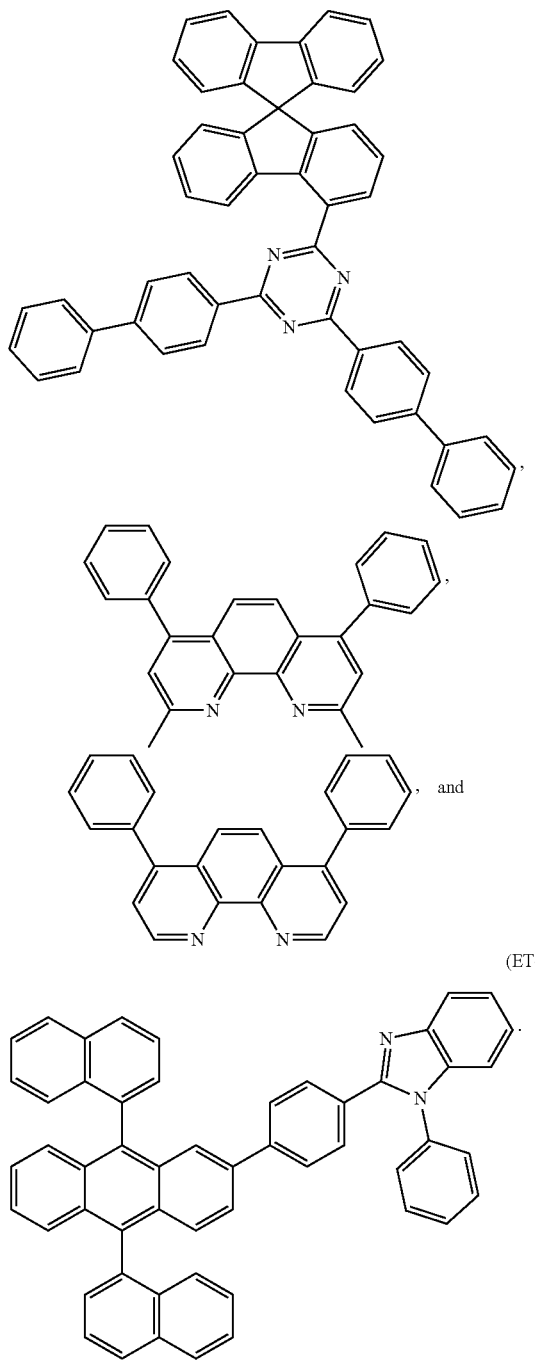

In one embodiment of the disclosure, the electron transport layer 340 may be composed of ET and LiQ.

In the disclosure, the cathode 200 may include a cathode material, which is a material having a small work function that facilitates electron injection into the functional laye. Specific examples of the cathode material include, but are not limited to, metals such as magnesium, calcium, sodium, potassium, titanium, indium, yttrium, lithium, gadolinium, aluminum, silver, tin, and lead, or alloys thereof; or multilayer materials such as LiF/Al, Liq/Al, LiO$_2$/Al, LiF/Ca, LiF/Al, and BaF$_2$/Ca. A metal electrode containing magnesium and silver is preferably included as the cathode.

Optionally, the electron injection layer 350 is further arranged between the cathode 200 and the electron transport layer 340 to enhance the capability of injecting electrons into the electron transport layer 340. The electron injection layer 350 may include an inorganic material such as an alkali metal sulfide and an alkali metal halide, or may include a complex compound of an alkali metal and an organic substance. In an embodiment of the present disclosure, the electron injection layer 350 may include ytterbium (Yb).

A third aspect of the disclosure provides an electronic apparatus, including the organic electroluminescent device described in the second aspect of the disclosure.

Figure 2:
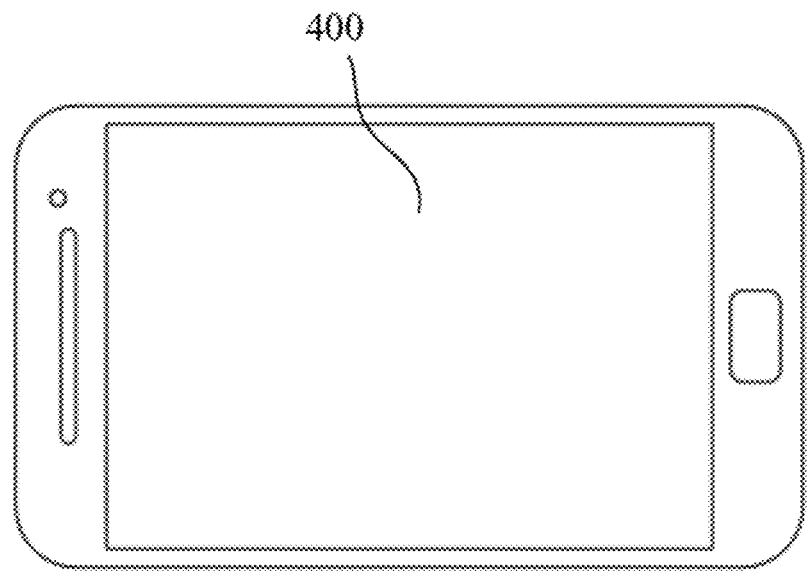
FIG. 2 is a schematic structural diagram of an electronic apparatus in an embodiment of the disclosure.

According to one embodiment, as shown in FIG. 2, the provided electronic apparatus is an electronic apparatus 400, which includes the aforementioned organic electroluminescent device. The electronic apparatus 400 may be, for example, a display apparatus, a lighting apparatus, an optical communication apparatus, or other types of electronic apparatuses, such as but not limited to a computer screen, a mobile phone screen, a television, electronic paper, an emergency lamp, an optical module, etc.

Synthesis methods for the nitrogen-containing compound of the disclosure is specifically illustrated below with reference to synthesis examples, but the present disclosure is not limited thereby in any way.

Examples of Synthesis

Those skilled in the art should recognize that the chemical reactions described in the disclosure can be used for suitably preparing many organic compounds of the disclosure, and other methods for preparing the compounds of the disclosure are considered to fall within the scope of the disclosure. For example, the synthesis of those non-exemplified compounds according to the disclosure can be successfully accomplished by those skilled in the art by modifying methods, such as appropriately protecting interfering groups, using other known reagents in addition to those described in the disclosure, or making some routine modifications on the reaction conditions. The compounds in the synthesis methods that are not mentioned in the disclosure are all raw materials obtained through commercial channels.

Synthesis of Sub-a1

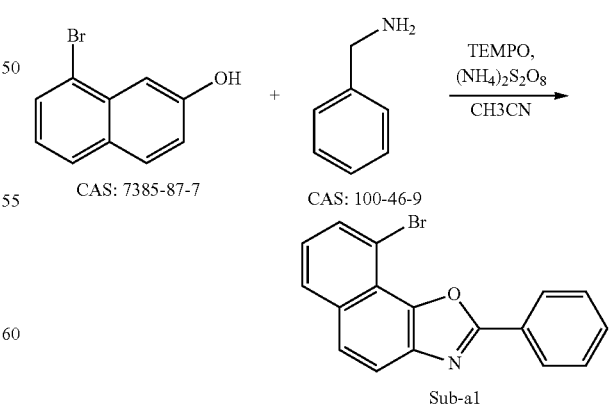

Under nitrogen atmosphere, 8-bromo-2-hydroxynaphthalene (11.1 g, 50 mmol), benzylamine (10.71 g, 100 mmol), ammonium persulfate (22.82 g, 100 mmol), 2,2,6,6-tetramethylpiperidine oxide (TEMPO, 15.63 g, 100 mmol), and acetonitrile (150 mL) were sequentially added to a 250 mL three-necked flask, stirring and heating were started, heating was performed to 50° C. to react with stirring for 24 hours. After the system was cooled to room temperature, the resulting reaction solution was extracted with dichloromethane (100 mL× 3 times), organic phases were combined and dried with anhydrous magnesium sulfate, filtration was performed, and the filtrate was concentrated in vacuum to obtain a crude product. The crude product was purified by silica gel column chromatography using ethyl acetate/n-heptane as a mobile phase to obtain a gray white solid Sub-a1 (8.24 g, yield 51%).

With reference to the synthesis of Sub-a1, reactants A shown in Table 1 were used instead of benzylamine to synthesize Sub-a2 and Sub-a3.

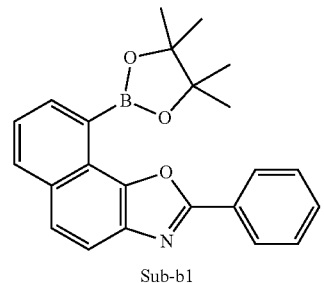
Sub-b1

Under nitrogen atmosphere, Sub-a1 (16.21 g, 50 mmol), bisdiboron bis (pinacolato)diboron (14.0 g, 55 mmol), potassium acetate (10.8 g, 110 mmol), and 1,4-dioxane (160 mL) were sequentially added to a 500 mL three-necked flask, stirring and heating were started, when the system is heated to 40° C., tris (dibenzylideneacetone) dipalladium (Pd$_2$(dba)$_3$, 0.46 g, 0.50 mmol) and 2-dicyclohexylphosphine-2',4',6'-triisopropylbiphenyl (XPhos, 0.48 g, 1.0 mmol) were quickly added, the heating was performed to reflux, and the reaction was carried out overnight with stirring. After the system was cooled to room temperature, 200 ml of water was added to the system, well stirring was performed for 30 minutes, suction filtration was performed under reduced pressure, the filter cake was washed with deionized water until neutral, and then rinsed with 100 mL of anhydrous ethanol to obtain a gray solid. The crude product was pulped once with n-heptane and then dissolved in 200 mL of toluene, followed by purification through a silica gel column and concentration to obtain a white solid Sub-b1 (13.55 g, yield 73%).

With reference to the synthesis of Sub-b1, reactants B shown in Table 2 were used instead of Sub-a1 to synthesize Sub-b2 and Sub-b3.

TABLE 1

Synthesis of Sub-a2 and Sub-a3

| Sub-a number | Reactant A | Sub-a structure | Yield (%) |
|---|---|---|---|
| Sub-a2 | CAS: 712-76-5 | | 49 |
| Sub-a3 | CAS: 2018-90-8 | | 44 |

Synthesis of Sub-b1

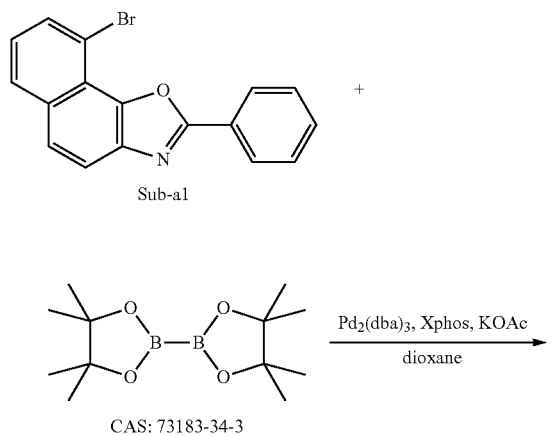

TABLE 2

Synthesis of Sub-b2 to Sub-b3

| Sub-b number | Reactant B | Sub-b structure | Yield (%) |
|---|---|---|---|
| Sub-b2 | | | 67 |
| Sub-b3 | | | 63 |

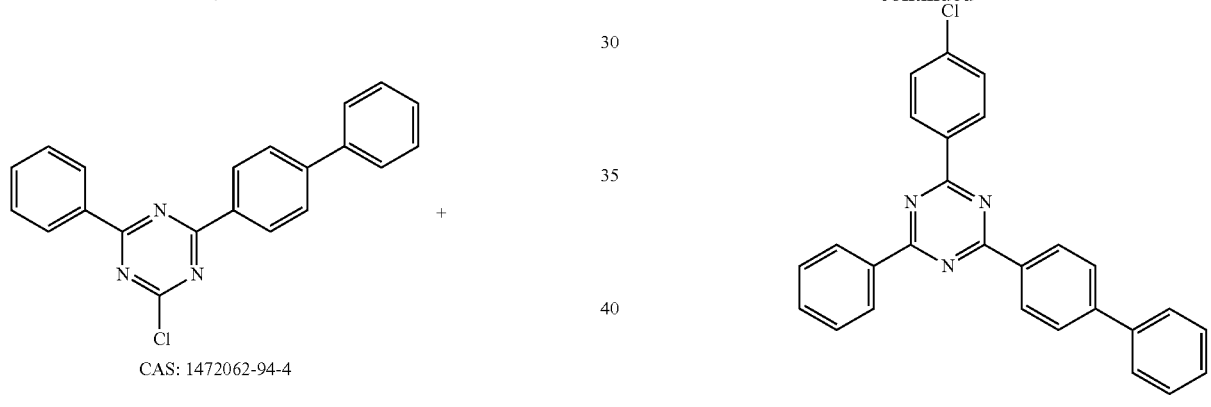

Synthesis of Sub-c1

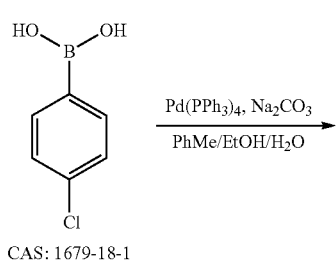

CAS: 1472062-94-4

+

HO-B-OH, Cl-phenyl
CAS: 1679-18-1

Pd(PPh₃)₄, Na₂CO₃
PhMe/EtOH/H₂O
→

-continued

Sub-c1

Under nitrogen atmosphere, 2-chloro-4-(biphen-4-yl)-6-phenyl-1,3,5-triazine (17.20 g, 50 mmol), 4-chlorobenzeneboronic acid (8.60 g, 55 mmol), tetrakis (triphenylphosphine) palladium (0.58 g, 0.5 mmol), anhydrous sodium carbonate (10.60 g, 100 mmol), toluene (140 mL), anhydrous ethanol (35 mL), and deionized water (35 mL) were sequentially added to a 500 mL three-necked flask, stirring and heating were started, and heating was performed to reflux, and a reaction was carried out for 8 hours. After the system was cooled to room temperature, the resulting reaction solution was extracted with dichloromethane (100 mL× 3 times), organic phases were combined and dried with anhydrous magnesium sulfate, filtration was performed, and the filtrate was distilled under reduced pressure to remove the solvent, so as to obtain a crude product. The crude product was purified by silica gel column chromatography using dichloromethane/n-heptane as a mobile phase to obtain an orange-yellow solid Sub-c1 (18.26 g, yield 87%).

With reference to the synthesis of Sub-c1, reactants C shown in Table 3 were used instead of 2-chloro-4-(biphen-4-yl)-6-phenyl-1,3,5-triazine and reactants D therein were used instead of (4-chlorophenyl) boronic acid to synthesize Sub-c2 to Sub-c28.

TABLE 3
Synthesis of Sub-c2 to Sub-c28
| Sub-c number | Reactant C | Reactant D | Sub-c structure | Yield (%) |
|---|---|---|---|---|
| Sub-c2 | 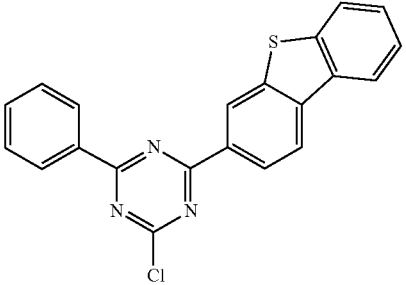<br>CAS: 2142681-84-1 | 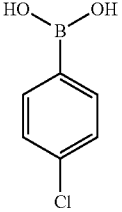<br>CAS: 1679-18-1 | 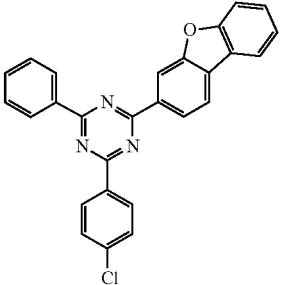 [SMILES: Clc1ccc(-c2nc(-c3ccccc3)nc(-c3ccc4c(c3)oc3ccccc34)n2)cc1] | 86 |
| Sub-c3 | 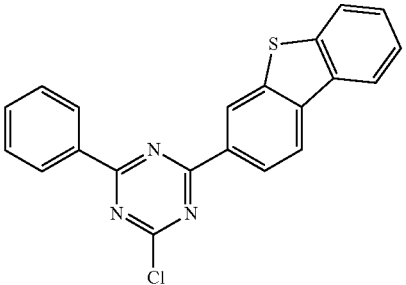 [SMILES: Clc1nc(-c2ccccc2)nc(-c2ccc3c(c2)sc2ccccc23)n1]<br>CAS: 2172889-29-9 | 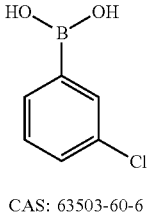<br>CAS: 63503-60-6 | 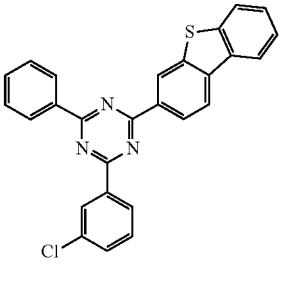 [SMILES: Clc1cccc(-c2nc(-c3ccccc3)nc(-c3ccc4c(c3)sc3ccccc34)n2)c1] | 72 |
| Sub-c4 | 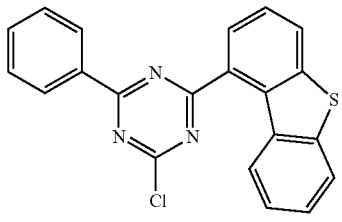 [SMILES: Clc1nc(-c2ccccc2)nc(-c2cccc3sc4ccccc4c23)n1]<br>CAS: 1883265-40-4 | 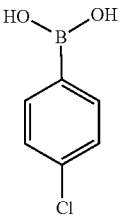<br>CAS: 1679-18-1 | 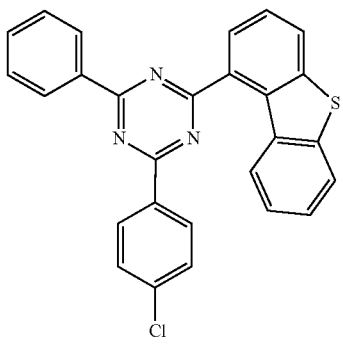 [SMILES: Clc1ccc(-c2nc(-c3ccccc3)nc(-c3cccc4sc5ccccc5c34)n2)cc1] | 78 |
| Sub-c5 | 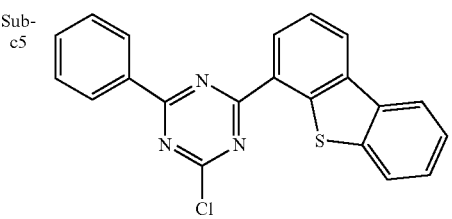<br>CAS: 1476735-48-4 | 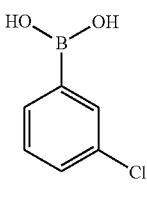<br>CAS: 63503-60-6 | 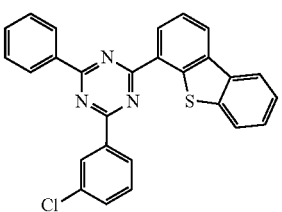 [SMILES: Clc1cccc(-c2nc(-c3ccccc3)nc(-c3cccc4c3sc3ccccc34)n2)c1] | 82 |

TABLE 3-continued

Synthesis of Sub-c2 to Sub-c28

| Sub-c number | Reactant C | Reactant D | Sub-c structure | Yield (%) |
|---|---|---|---|---|
| Sub-c6 | CAS: 2396648-13-6 | CAS: 1679-18-1 | | 78 |
| Sub-c7 | CAS: 2600635-28-5 | CAS: 1679-18-1 | | 82 |
| Sub-c8 | CAS: 1247124-77-1 | CAS: 1679-18-1 | | 74 |
| Sub-c9 | CAS: 2138467-53-3 | CAS: 63503-60-6 | | 75 |

TABLE 3-continued
Synthesis of Sub-c2 to Sub-c28
| Sub-c number | Reactant C | Reactant D | Sub-c structure | Yield (%) |
|---|---|---|---|---|
| Sub-c10 | 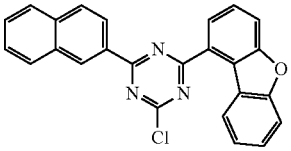 [SMILES: Clc1nc(-c2ccc3ccccc3c2)nc(-c2cccc3oc4ccccc4c23)n1]<br>CAS: 2418528-30-8 | 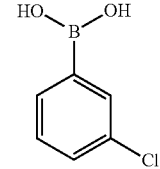<br>CAS: 63503-60-6 | 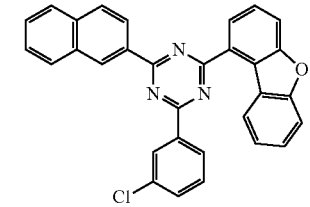 [SMILES: Clc1cccc(-c2nc(-c3ccc4ccccc4c3)nc(-c3cccc4oc5ccccc5c34)n2)c1] | 83 |
| Sub-c11 | 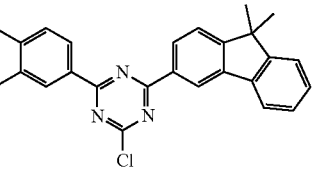<br>CAS: 2691136-09-9 | 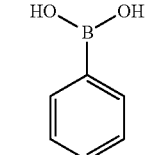<br>CAS: 1679-18-1 | 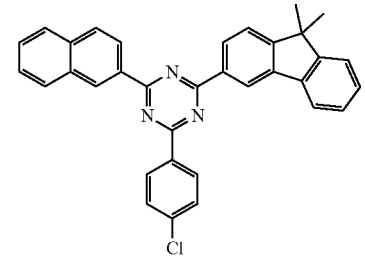 [SMILES: CC1(C)c2ccccc2-c2cc(-c3nc(-c4ccc(Cl)cc4)nc(-c4ccc5ccccc5c4)n3)ccc21] | 82 |
| Sub-c12 | 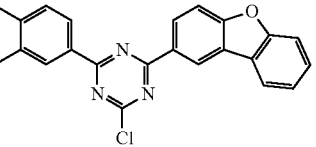<br>CAS: 2412580-40-4 | 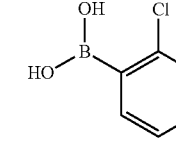<br>CAS: 3900-89-8 | 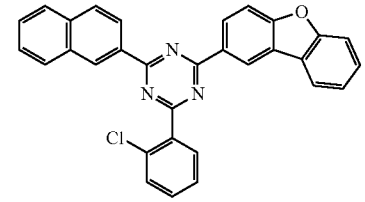 [SMILES: Clc1ccccc1-c1nc(-c2ccc3ccccc3c2)nc(-c2ccc3oc4ccccc4c3c2)n1] | 58 |
| Sub-c13 | 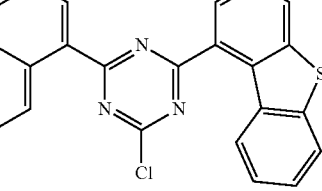<br>CAS: 2446167-09-3 | 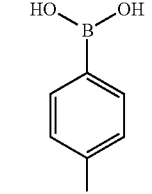<br>CAS: 1679-18-1 | 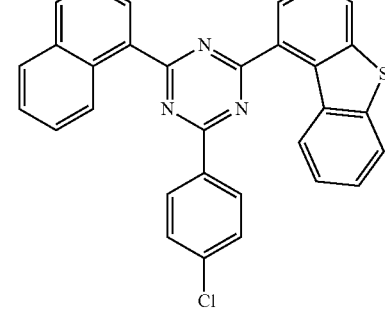 | 75 |
| Sub-c14 | 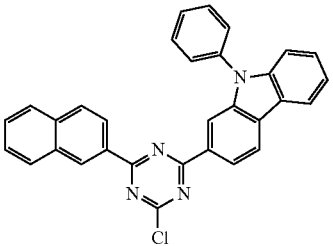 [SMILES: Clc1nc(-c2ccc3ccccc3c2)nc(-c2ccc3c4ccccc4n(-c4ccccc4)c3c2)n1]<br>CAS: 2412060-98-9 | 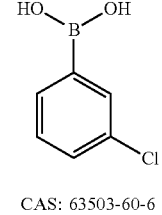<br>CAS: 63503-60-6 | 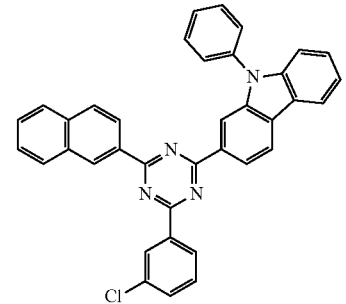 [SMILES: Clc1cccc(-c2nc(-c3ccc4ccccc4c3)nc(-c3ccc4c5ccccc5n(-c5ccccc5)c4c3)n2)c1] | 82 |

TABLE 3-continued

Synthesis of Sub-c2 to Sub-c28

| Sub-c number | Reactant C | Reactant D | Sub-c structure | Yield (%) |
|---|---|---|---|---|
| Sub-c15 | CAS: 2243406-96-2 | CAS: 63503-60-6 | | 86 |
| Sub-c16 | CAS: 2864453-17-6 | CAS: 1679-18-1 | | 83 |
| Sub-c17 | CAS: 1342819-12-8 | CAS: 2142655-40-9 | | 81 |
| Sub-c18 | CAS: 1835683-68-5 | CAS: 2309283-15-4 | | 77 |

TABLE 3-continued

Synthesis of Sub-c2 to Sub-c28

| Sub-c number | Reactant C | Reactant D | Sub-c structure | Yield (%) |
|---|---|---|---|---|
| Sub-c19 | CAS: 2142681-84-1 | CAS: 147102-97-4 | | 87 |
| Sub-c20 | CAS: 1883265-32-4 | CAS: 2142655-40-9 | | 86 |
| Sub-c21 | CAS: 1472729-25-1 | CAS: 2118958-50-0 | | 74 |
| Sub-c22 | CAS: 1821147-80-1 | CAS: 2142655-40-9 | | 74 |

TABLE 3-continued

Synthesis of Sub-c2 to Sub-c28

| Sub-c number | Reactant C | Reactant D | Sub-c structure | Yield (%) |
|---|---|---|---|---|
| Sub-c23 | CAS: 1476735-48-4 | CAS: 870822-86-9 | | 75 |
| Sub-c24 | CAS: 2173555-98-9 | CAS: 2142655-40-9 | | 84 |
| Sub-c25 | CAS: 2418528-30-8 | CAS: 147102-97-4 | | 85 |
| Sub-c26 | CAS: 1300115-09-6 | CAS: 2634757-57-4 | | 65 |

TABLE 3-continued

Synthesis of Sub-c2 to Sub-c28

| Sub-c number | Reactant C | Reactant D | Sub-c structure | Yield (%) |
|---|---|---|---|---|
| Sub-c27 | CAS: 2142681-84-1 | CAS: 2173555-53-6 | | 62 |
| Sub-c28 | CAS: 2568464-79-7 | CAS: 1107603-42-8 | | 81 |

Synthesis of Compound 22

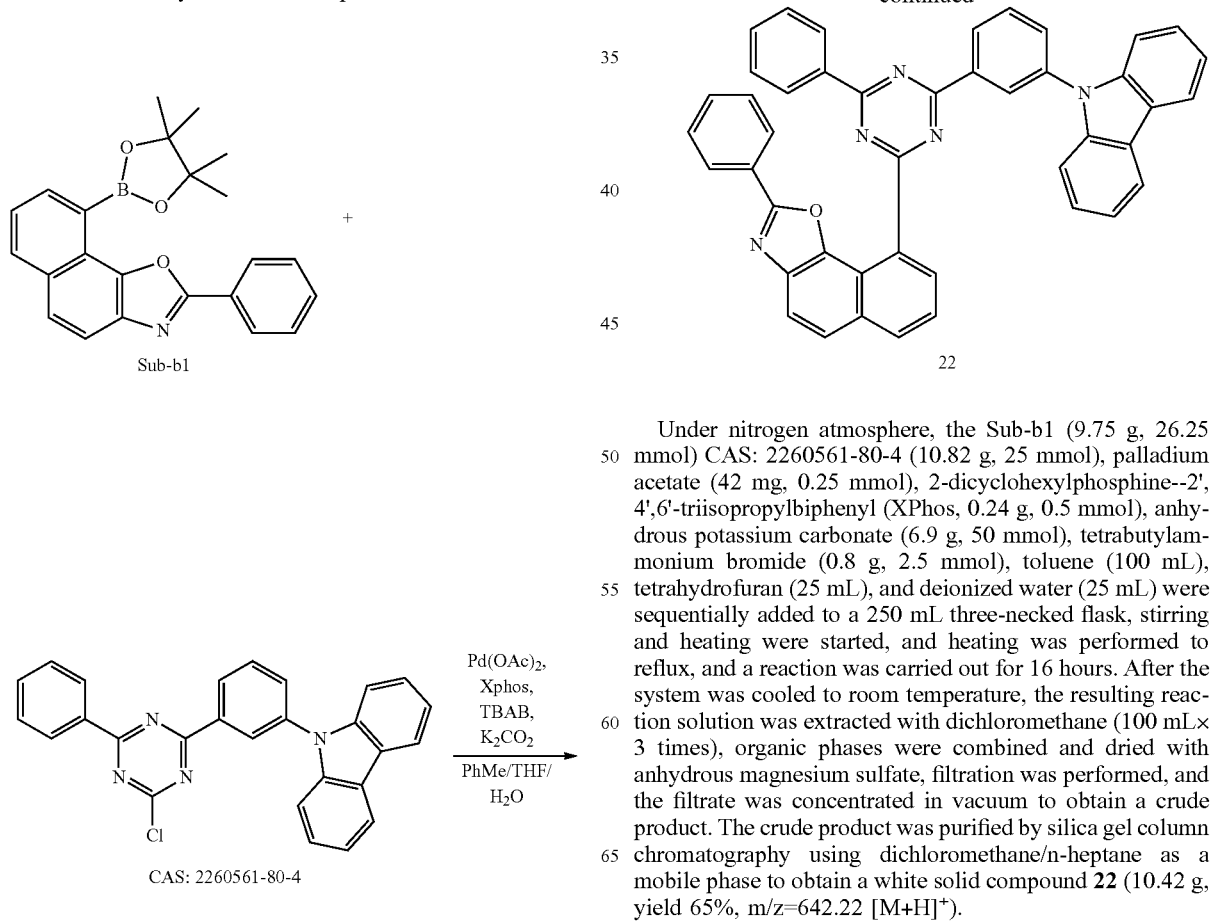

Under nitrogen atmosphere, the Sub-b1 (9.75 g, 26.25 mmol) CAS: 2260561-80-4 (10.82 g, 25 mmol), palladium acetate (42 mg, 0.25 mmol), 2-dicyclohexylphosphine--2', 4',6'-triisopropylbiphenyl (XPhos, 0.24 g, 0.5 mmol), anhydrous potassium carbonate (6.9 g, 50 mmol), tetrabutylammonium bromide (0.8 g, 2.5 mmol), toluene (100 mL), tetrahydrofuran (25 mL), and deionized water (25 mL) were sequentially added to a 250 mL three-necked flask, stirring and heating were started, and heating was performed to reflux, and a reaction was carried out for 16 hours. After the system was cooled to room temperature, the resulting reaction solution was extracted with dichloromethane (100 mL× 3 times), organic phases were combined and dried with anhydrous magnesium sulfate, filtration was performed, and the filtrate was concentrated in vacuum to obtain a crude product. The crude product was purified by silica gel column chromatography using dichloromethane/n-heptane as a mobile phase to obtain a white solid compound 22 (10.42 g, yield 65%, m/z=642.22 [M+H]$^+$).

With reference to the synthesis of compound 22, reactants E shown in Table 4 were used instead of the Sub-b1 and reactants F therein were used instead of CAS: 2260561-80-4 to synthesize the compounds of the disclosure listed in Table 4.

TABLE 4

Synthesis of some compounds in the disclosure

| Reactant E | Reactant F | Structure and number of compound | m/z ([M + H]⁺) | Yield (%) |
|---|---|---|---|---|
| Sub-b1 | CAS:1836145-06-2 | 26 | 627.21 | 64 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | CAS: 1835683-69-6 | 27 | 717.26 | 63 |
| Sub-b1 | CAS: 2596187-88-9 | | 717.26 | 53 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | CAS: 1644054-71-6 | 29 | 715.24 | 51 |
| Sub-b1 | CAS: 2229752-36-5 | 34 | 603.21 | 64 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | CAS: 2476829-04-4 | 37 | 603.21 | 62 |
| Sub-b1 | CAS: 2421105-91-9 | 39 | 603.21 | 58 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | CAS: 2173555-94-5 | 42 | 629.23 | 65 |
| Sub-b1 | CAS: 2600635-24-1 | 43 | 629.23 | 62 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | CAS: 1616231-57-2 | 46 | 629.23 | 51 |
| Sub-b1 | CAS: 2596188-54-2 | | 629.23 | 62 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | CAS: 2305965-24-4 | 55 | 653.23 | 52 |

48

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | CAS: 2137919-56-1 | 59 | 643.21 | 50 |
| Sub-b1 | CAS: 2861990-98-7 | 60 | 643.21 | 60 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | CAS: 2226747-96-0 | 65 | 643.21 | 57 |

TABLE 4-continued
Synthesis of some compounds in the disclosure
| Reactant E | Reactant F | Structure and number of compound | m/z ([M + H]+) | Yield (%) |
|---|---|---|---|---|
| 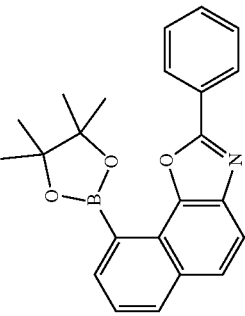 Sub-b1 | 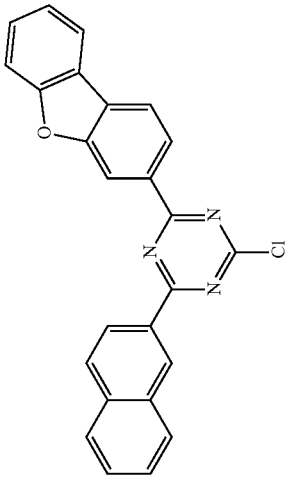 CAS: 2226747-69-7 | 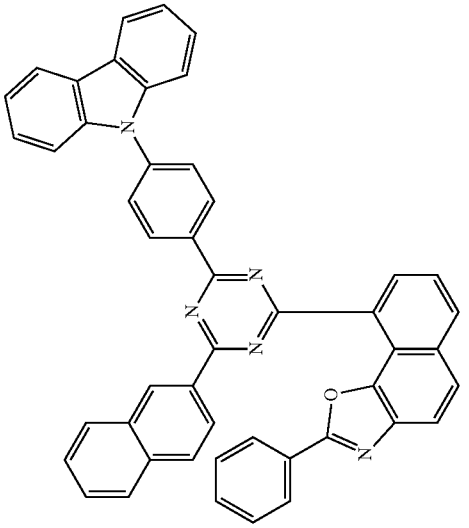 69 | 617.19 | 51 |
| 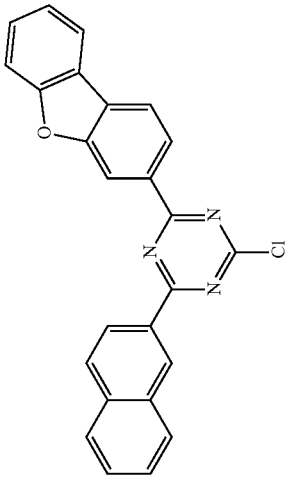 Sub-b1 | 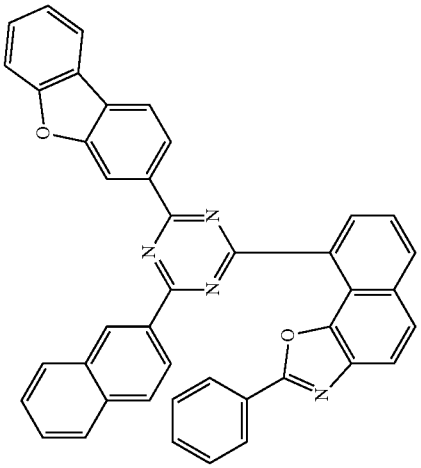 CAS: 2454450-90-7 | 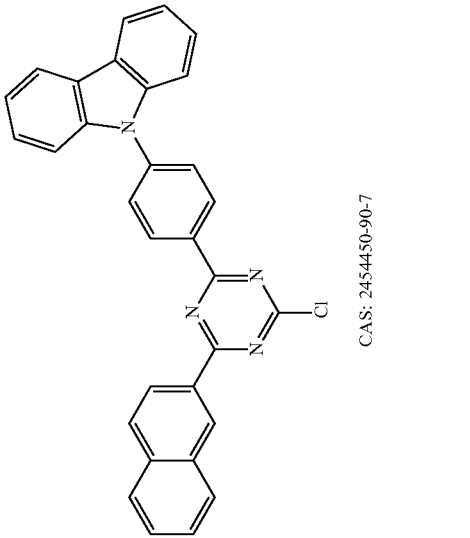 75 | 692.24 | 64 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | CAS: 2855211-57-1 | 80 | 653.23 | 58 |
| Sub-b1 | CAS: 2583051-59-4 | 90 | 633.17 | 65 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | CAS: 2304695-00-7 | 97 | 653.23 | 59 |
| Sub-b1 | CAS: 2700204-22-2 | 101 | 679.24 | 53 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | CAS: 1205748-61-3 | 110 | 629.23 | 65 |
| Sub-b1 | CAS: 2761222-01-7 |  | 679.24 | 62 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | CAS: 2374740-77-7 | 122 | 679.24 | 53 |
| Sub-b1 | CAS: 2437221-70-8 | 123 (labeled 150 in structure) | 735.22 | 57 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | Sub-c1 | 154 | 629.23 | 61 |
| Sub-b1 | Sub-c2 | | 643.21 | 60 |

TABLE 4-continued

Synthesis of some compounds in the disclosure

| Reactant E | Reactant F | Structure and number of compound | m/z ([M + H]⁺) | Yield (%) |
|---|---|---|---|---|
| Sub-b1 | Sub-c3 | 157 | 659.19 | 53 |
| Sub-b1 | Sub-c4 | 161 | 659.19 | 58 |

TABLE 4-continued
Synthesis of some compounds in the disclosure
| Reactant E | Reactant F | Structure and number of compound | m/z ([M + H]+) | Yield (%) |
|---|---|---|---|---|
| 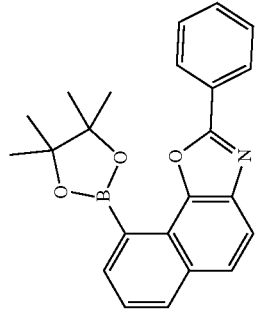 Sub-b1 | 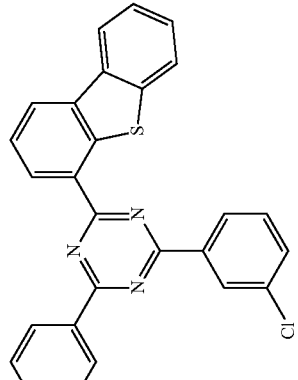 Sub-c5 | 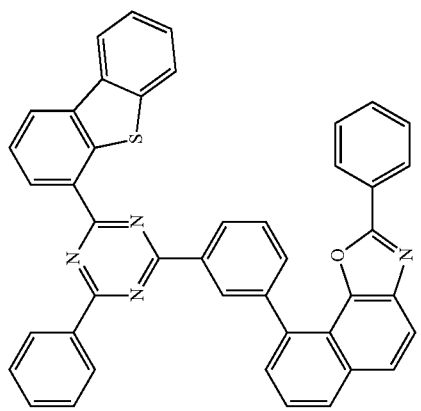 163 | 659.19 | 58 |
| 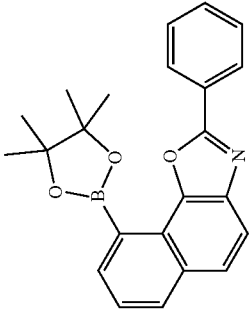 Sub-b1 | 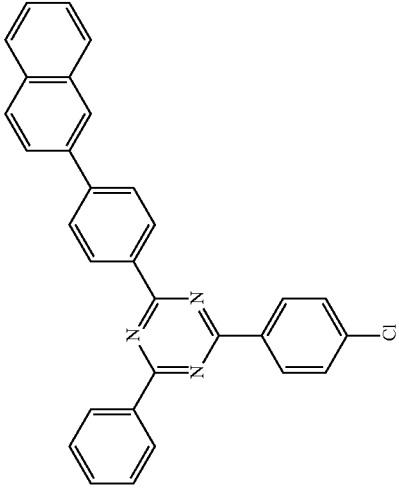 Sub-c6 | 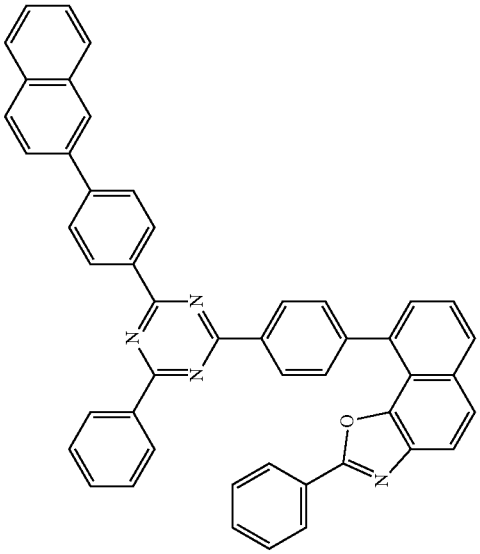 164 | 679.24 | 51 |

TABLE 4-continued

Synthesis of some compounds in the disclosure

| Reactant E | Reactant F | Structure and number of compound | m/z ([M + H]⁺) | Yield (%) |
|---|---|---|---|---|
| Sub-b1 | Sub-c7 | 178 | 679.24 | 54 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | Sub-c8 | 199 | 653.23 | 50 |
| Sub-b1 | Sub-c9 | | 679.24 | 61 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | Sub-c10 | 200 | 693.22 | 57 |
| Sub-b1 | Sub-c11 | 203 | 719.28 | 65 |

TABLE 4-continued

Synthesis of some compounds in the disclosure

| Reactant E | Reactant F | Structure and number of compound | m/z ([M + H]$^+$) | Yield (%) |
|---|---|---|---|---|
| Sub-b1 | Sub-c12 | 219 | 693.22 | 45 |
| Sub-b1 | Sub-c13 | 220 | 709.20 | 60 |

TABLE 4-continued
Synthesis of some compounds in the disclosure
| Reactant E | Reactant F | Structure and number of compound | m/z ([M + H]+) | Yield (%) |
|---|---|---|---|---|
| 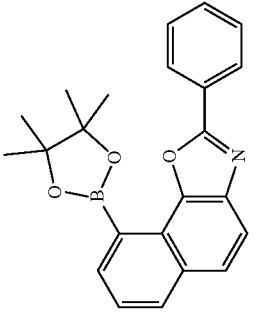 Sub-b1 | 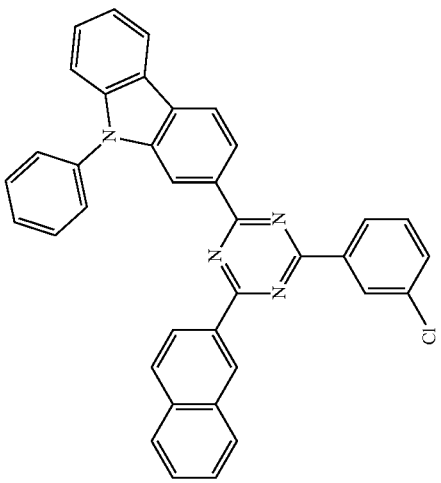 Sub-c14 | 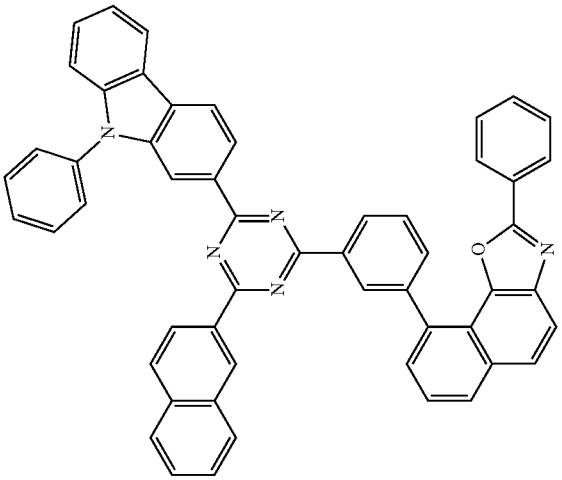 227 | 768.27 | 61 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | Sub-c15 | 242 | 745.29 | 58 |
| Sub-b1 | Sub-c16 | | 729.26 | 55 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | Sub-c17 | 273 | 653.23 | 56 |

TABLE 4-continued
Synthesis of some compounds in the disclosure
| Reactant E | Reactant F | Structure and number of compound | m/z ([M + H]+) | Yield (%) |
|---|---|---|---|---|
| 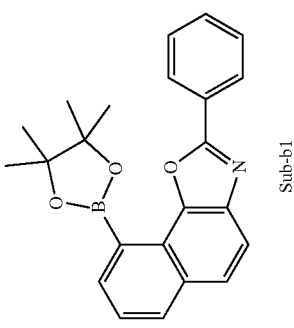 Sub-b1 | 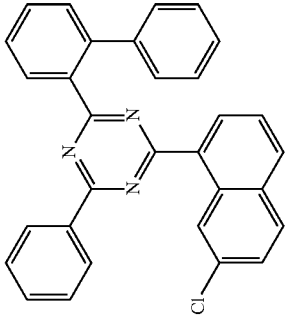 Sub-c18 | 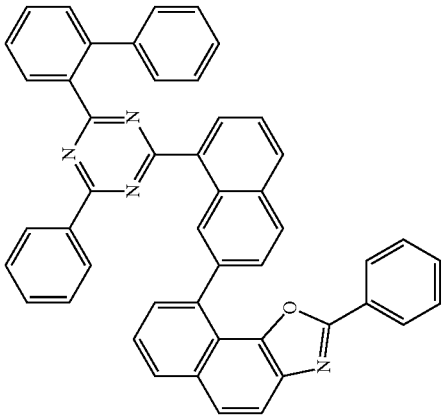 276 | 679.24 | 64 |
| 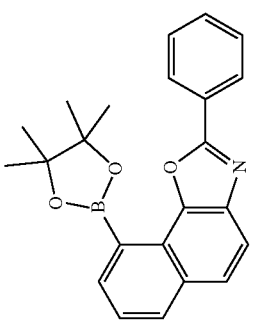 Sub-b1 | 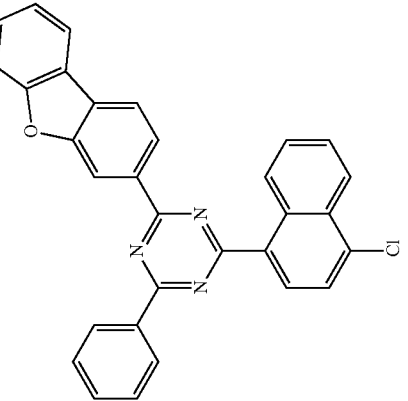 Sub-c19 | 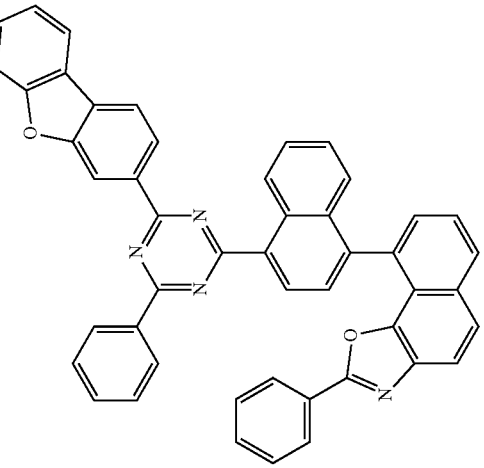 | 693.23 | 57 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | Sub-c20 | 277 | 693.23 | 62 |
| Sub-b1 | Sub-c22 | 279 | 703.24 | 58 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | Sub-c23 | 285 / 284 | 709.20 | 64 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | Sub-c24 | 291 | 719.28 | 62 |
| Sub-b1 | Sub-c25 | | 743.24 | 50 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | Sub-c26 | 313 337 | 653.27 | 54 |

TABLE 4-continued

Synthesis of some compounds in the disclosure

| Reactant E | Reactant F | Structure and number of compound | m/z ([M + H]+) | Yield (%) |
|---|---|---|---|---|
| Sub-b1 | Sub-c27 | 299 | 733.22 | 52 |
| Sub-b3 | CAS: 2226747-65-3 | 340 | 622.23 | 53 |

TABLE 4-continued

Synthesis of some compounds in the disclosure

| Reactant E | Reactant F | Structure and number of compound | m/z ([M + H]⁺) | Yield (%) |
|---|---|---|---|---|
| Sub-b2 | CAS: 2763201-83-6 | 392 | 621.21 | 52 |

TABLE 4-continued
Synthesis of some compounds in the disclosure
| Reactant E | Reactant F | Structure and number of compound | m/z ([M + H]+) | Yield (%) |
|---|---|---|---|---|
| 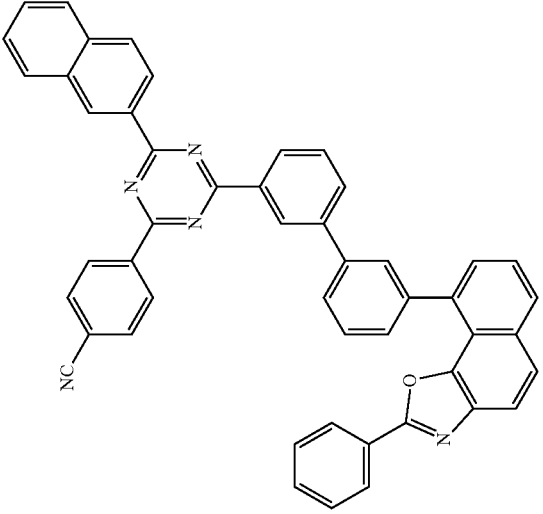 Sub-b1 | 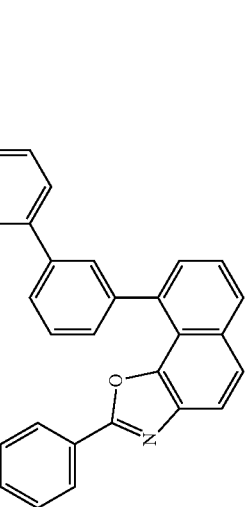 Sub-c28 | 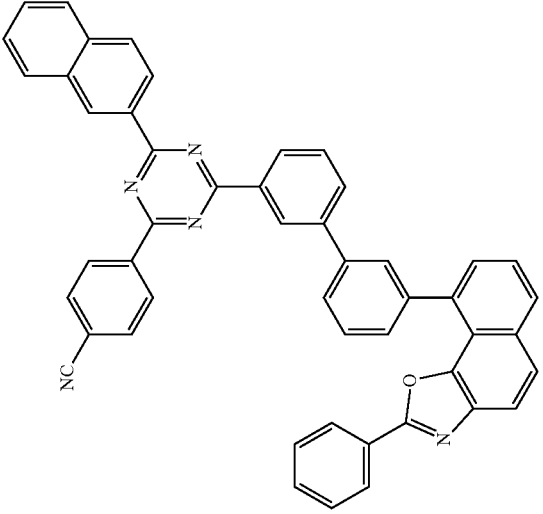 416 | 704.24 | 60 |

TABLE 4-continued
Synthesis of some compounds in the disclosure
| Reactant E | Reactant F | Structure and number of compound | m/z ([M + H]+) | Yield (%) |
|---|---|---|---|---|
| 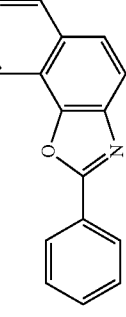 Sub-b1 | 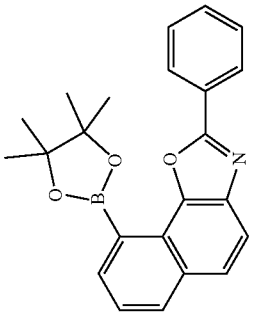 Sub-c21 | 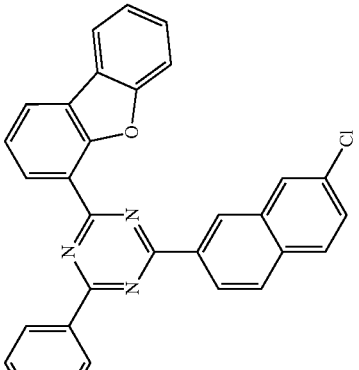 280 | 693.22 | 62 |

Compound 277 NMR: $^{1}$H-NMR (400 MHZ, $CD_2Cl_2$) δ ppm 9.31 (d, 1H), 9.01 (s, 1H), 8.96-8.86 (m, 3H), 8.71 (d, 1H), 8.22-8.13 (m, 2H), 8.08 (d, 1H), 7.96 (d, 1H), 7.86 (d, 1H), 7.80-7.51 (m, 10H), 7.41 (t, 1H), 7.35-7.28 (m, 3H), 7.20-7.10 (m, 3H).

Fabrication and Evaluation of Organic Electroluminescent Devices:

Example 1: Red Organic Electroluminescent Device

First, an anode was pre-treated by the following process: surface treatment was performed on ITO/Ag/ITO substrates with thicknesses of 100 Å, 1000 Å, and 100 Å in sequence using ultraviolet ozone and $O_2$:$N_2$ plasma to increase the work function of the anode, and the surface of an ITO substrate was cleaned with an organic solvent to remove impurities and oil stains therefrom.

On the experimental substrate (anode), PD:HT-1 were co-evaporated at rate ratio of 2%: 98% to form a hole injection layer (HIL) with a thickness of 100 Å, and then HT-1 was vacuum-evaporated on the hole injection layer to form a first hole transport layer with a thickness of 1065 Å. The compound HT-2 was vacuum-evaporated on the first hole transport layer to form a second hole transport layer with a thickness of 890 Å.

Next, on the second hole transport layer, the compound 22:RH—P: RD was co-evaporated at a rate ratio of 49%: 49%: 2% to form a red electroluminescent layer (EML) with a thickness of 410 Å.

The compound ET and LiQ were co-evaporated at a rate ratio of 1:1 to form an electron transport layer (ETL) with a thickness of 350 Å, Yb was evaporated on the electron transport layer to form an electron injection layer (EIL) with a thickness of 10 Å, and then magnesium (Mg) and silver (Ag) were mixed at an evaporation rate ratio of 1:9 and vacuum-evaporated on the electron injection layer to form a cathode with a thickness of 130 Å.

In addition, CP was evaporated in vacuum on the cathode to form a capping layer (CPL) with a thickness of 800 Å, thereby completing the fabrication of a red organic electroluminescent device.

Examples 2 to 56

Organic electroluminescent devices were fabricated using the same method as Example 1, except that compounds X in Table 5 were used instead of compound 22 in Example 1 when the electroluminescent layer was produced.

Comparative Examples 1 to 4

Organic electroluminescent devices were fabricated using the same method as Example 1, except that compound A, compound B, compound C, and compound D were respectively used instead of compound 22 in Example 1 when the electroluminescent layer was produced.

The structures of compound used in each example and comparative example are as follows:

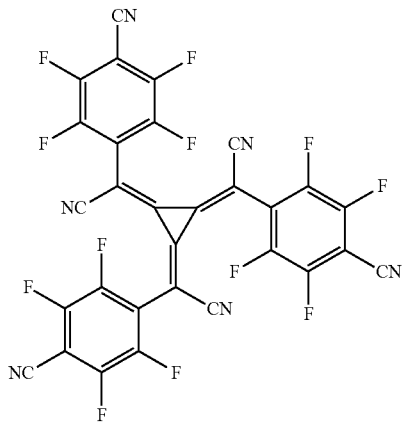

PD

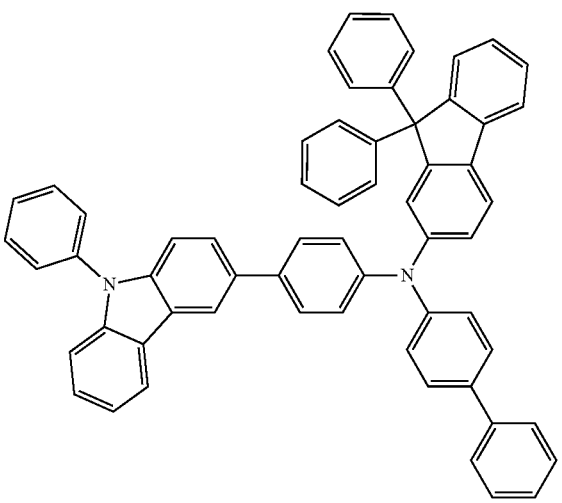

HT-1

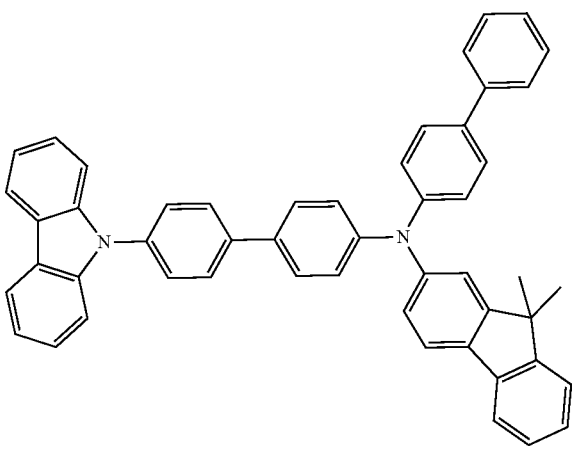

HT-2

309
-continued
310
-continued
RD
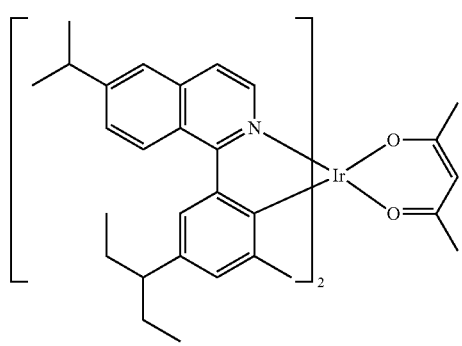
RH-P
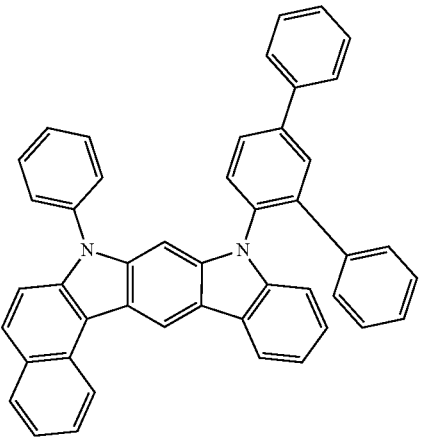
ET
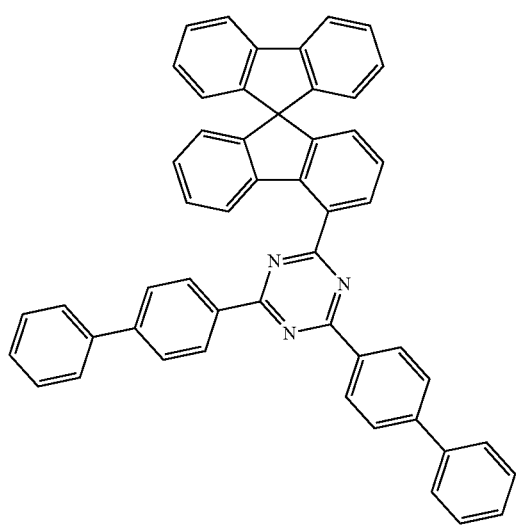
compound A
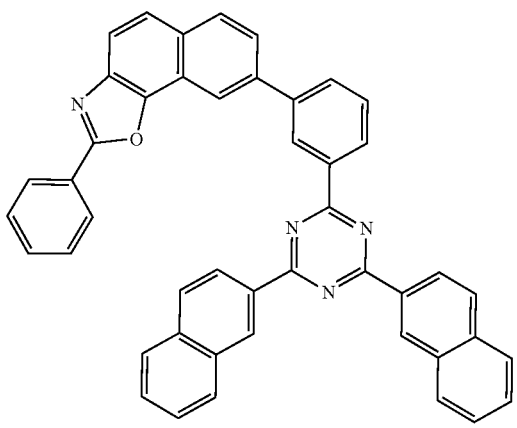
compound B
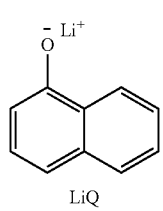
LiQ
compound C
CP
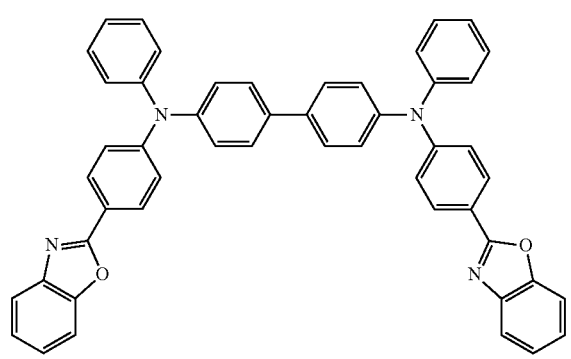
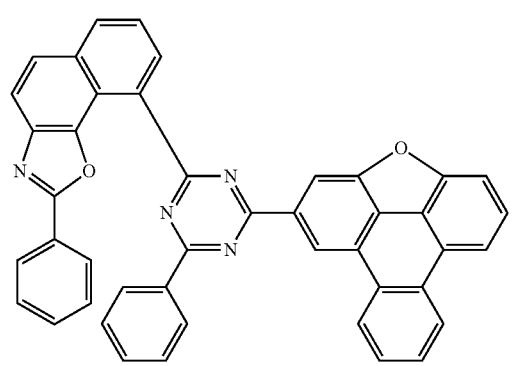

-continued compound D

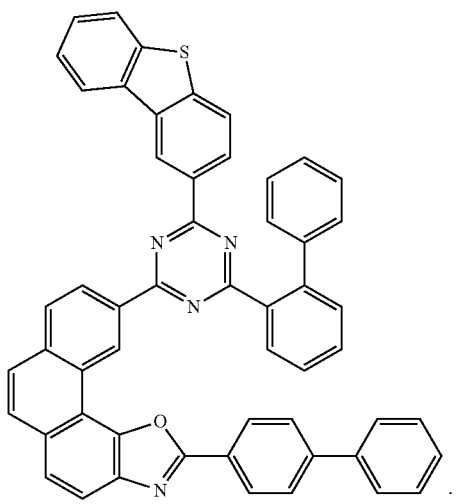

The red organic electroluminescent devices fabricated in Examples 1-56 and Comparative Examples 1~4 were subjected to performance tests. Specifically, IVL performances of the devices were tested under the condition of 10 mA/cm², and $T_{95}$ lifetimes of the devices were tested under the condition of 20 mA/cm². The test results were shown in Table 5 below.

TABLE 5

| Example number | Electroluminescent layer Compound X: RH-P:RD | Operating voltage Volt (V) | Cd/A | CIEx | CIEy | T95(h) @20 mA/cm² |
|---|---|---|---|---|---|---|
| Example 1 | Compound 22 | 3.48 | 60.1 | 0.680 | 0.320 | 529 |
| Example 2 | Compound 26 | 3.46 | 60.7 | 0.680 | 0.320 | 531 |
| Example 3 | Compound 27 | 3.42 | 60.3 | 0.680 | 0.320 | 533 |
| Example 4 | Compound 29 | 3.43 | 60.4 | 0.680 | 0.320 | 535 |
| Example 5 | Compound 32 | 3.46 | 61.0 | 0.680 | 0.320 | 532 |
| Example 6 | Compound 34 | 3.43 | 60.9 | 0.680 | 0.320 | 534 |
| Example 7 | Compound 37 | 3.44 | 61.2 | 0.680 | 0.320 | 533 |
| Example 8 | Compound 39 | 3.44 | 59.8 | 0.680 | 0.320 | 534 |
| Example 9 | Compound 42 | 3.48 | 60.7 | 0.680 | 0.320 | 529 |
| Example 10 | Compound 43 | 3.42 | 60.6 | 0.680 | 0.320 | 537 |
| Example 11 | Compound 46 | 3.42 | 61.3 | 0.680 | 0.320 | 533 |
| Example 12 | Compound 48 | 3.46 | 61.1 | 0.680 | 0.320 | 526 |
| Example 13 | Compound 55 | 3.46 | 60.5 | 0.680 | 0.320 | 527 |
| Example 14 | Compound 59 | 3.48 | 59.7 | 0.680 | 0.320 | 523 |
| Example 15 | Compound 61 | 3.47 | 61.4 | 0.680 | 0.320 | 532 |
| Example 16 | Compound 65 | 3.42 | 61.2 | 0.680 | 0.320 | 536 |
| Example 17 | Compound 69 | 3.42 | 61.3 | 0.680 | 0.320 | 538 |
| Example 18 | Compound 75 | 3.46 | 60.8 | 0.680 | 0.320 | 530 |
| Example 19 | Compound 80 | 3.46 | 59.6 | 0.680 | 0.320 | 537 |
| Example 20 | Compound 90 | 3.47 | 61.0 | 0.680 | 0.320 | 535 |
| Example 21 | Compound 97 | 3.47 | 61.6 | 0.680 | 0.320 | 520 |
| Example 22 | Compound 101 | 3.43 | 59.9 | 0.680 | 0.320 | 527 |
| Example 23 | Compound 110 | 3.43 | 61.2 | 0.680 | 0.320 | 534 |
| Example 24 | Compound 122 | 3.44 | 61.5 | 0.680 | 0.320 | 526 |
| Example 25 | Compound 123 | 3.45 | 60.7 | 0.680 | 0.320 | 533 |
| Example 26 | Compound 150 | 3.45 | 59.3 | 0.680 | 0.320 | 520 |
| Example 27 | Compound 154 | 3.45 | 65.3 | 0.680 | 0.320 | 488 |
| Example 28 | Compound 157 | 3.48 | 65.4 | 0.680 | 0.320 | 489 |
| Example 29 | Compound 161 | 3.42 | 65.1 | 0.680 | 0.320 | 487 |
| Example 30 | Compound 163 | 3.42 | 65.3 | 0.680 | 0.320 | 481 |
| Example 31 | Compound 164 | 3.47 | 65.0 | 0.680 | 0.320 | 480 |
| Example 32 | Compound 178 | 3.48 | 65.7 | 0.680 | 0.320 | 485 |
| Example 33 | Compound 181 | 3.46 | 65.7 | 0.680 | 0.320 | 486 |
| Example 34 | Compound 199 | 3.48 | 65.1 | 0.680 | 0.320 | 484 |
| Example 35 | Compound 200 | 3.48 | 65.2 | 0.680 | 0.320 | 483 |
| Example 36 | Compound 203 | 3.45 | 65.6 | 0.680 | 0.320 | 481 |

TABLE 5-continued

| Example number | Electroluminescent layer Compound X: RH-P:RD | Operating voltage Volt (V) | Cd/A | CIEx | CIEy | T95(h) @20 mA/cm² |
|---|---|---|---|---|---|---|
| Example 37 | Compound 205 | 3.44 | 65.8 | 0.680 | 0.320 | 485 |
| Example 38 | Compound 219 | 3.44 | 65.7 | 0.680 | 0.320 | 477 |
| Example 39 | Compound 220 | 3.46 | 65.4 | 0.680 | 0.320 | 488 |
| Example 40 | Compound 227 | 3.46 | 65.9 | 0.680 | 0.320 | 485 |
| Example 41 | Compound 242 | 3.42 | 65.3 | 0.680 | 0.320 | 483 |
| Example 42 | Compound 259 | 3.45 | 65.2 | 0.680 | 0.320 | 488 |
| Example 43 | Compound 273 | 3.45 | 65.7 | 0.680 | 0.320 | 491 |
| Example 44 | Compound 276 | 3.44 | 65.5 | 0.680 | 0.320 | 474 |
| Example 45 | Compound 277 | 3.46 | 65.6 | 0.680 | 0.320 | 473 |
| Example 46 | Compound 279 | 3.45 | 65.7 | 0.680 | 0.320 | 483 |
| Example 47 | Compound 280 | 3.47 | 65.6 | 0.680 | 0.320 | 484 |
| Example 48 | Compound 284 | 3.47 | 66.0 | 0.680 | 0.320 | 472 |
| Example 49 | Compound 285 | 3.45 | 65.3 | 0.680 | 0.320 | 479 |
| Example 50 | Compound 291 | 3.44 | 65.7 | 0.680 | 0.320 | 474 |
| Example 51 | Compound 313 | 3.45 | 65.8 | 0.680 | 0.320 | 482 |
| Example 52 | Compound 337 | 3.43 | 66.2 | 0.680 | 0.320 | 489 |
| Example 53 | Compound 340 | 3.47 | 65.5 | 0.680 | 0.320 | 481 |
| Example 54 | Compound 381 | 3.45 | 61.5 | 0.680 | 0.320 | 525 |
| Example 55 | Compound 392 | 3.44 | 60.2 | 0.680 | 0.320 | 522 |
| Example 56 | Compound 416 | 3.45 | 65.7 | 0.680 | 0.320 | 476 |
| Comparative Example 1 | Compound A | 3.51 | 49.3 | 0.680 | 0.320 | 386 |
| Comparative Example 2 | Compound B | 3.49 | 52.5 | 0.680 | 0.320 | 375 |
| Comparative Example 3 | Compound C | 3.49 | 47.2 | 0.680 | 0.320 | 410 |
| Comparative Example 4 | Compound D | 3.63 | 43.7 | 0.680 | 0.320 | 399 |

From Table 5 above, it can be seen that when the compound of the disclosure was used as a host material of the red organic electroluminescent device, the luminous efficiency (Cd/A) is increased by at least 12.9%, and the $T_{95}$ lifetime is prolonged by at least 15.1%. When the compound of the disclosure is used as an electron transport material in a hybrid host material, the balance of carriers in a electroluminescent layer can be improved, the carrier utilization rate can be improved, and a recombination region of carriers can be broadened, exciton generation and utilization efficiency can be improved, and the efficiency and service life of devices can be improved.

The preferred embodiments of the present invention are described in detail above with reference to the accompanying drawings. However, the present invention is not limited to the specific details in the above embodiments. Various simple modifications can be made to the technical solutions of the present invention within the technical idea scope of the present invention, and these simple modifications fall within the protection scope of the present invention.

The invention claimed is:

1. A nitrogen-containing compound, having a structure represented by formula 1 below:

formula 1

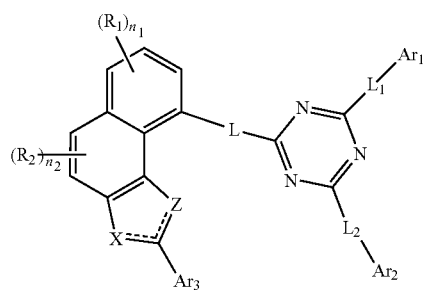

X is —N=, Z is O;

L$_1$ and L$_2$ are each independently selected from a single bond, substituted or unsubstituted arylene with 6 to 20 carbon atoms, and substituted or unsubstituted heteroarylene with 3 to 18 carbon atoms;

L is selected from a single bond, substituted or unsubstituted arylene with 6 to 20 carbon atoms, and substituted or unsubstituted heteroarylene with 3 to 12 carbon atoms;

the substituent(s) in L, L$_1$, and L$_2$ are the same or different, and are each independently selected from deuterium, fluorine, cyano, methyl, ethyl, isopropyl, tert-butyl, trifluoromethyl, trideuteromethyl, trimethylsilyl, pentadeuterophenyl, and phenyl;

Ar$_1$, Ar$_2$, and Ar$_3$ are the same or different, and are each independently selected from substituted or unsubstituted phenyl, substituted or unsubstituted naphthyl, substituted or unsubstituted biphenyl, substituted or unsubstituted terphenyl, substituted or unsubstituted fluorenyl, substituted or unsubstituted phenanthryl, substituted or unsubstituted pyrenyl, substituted or unsubstituted triphenylene, substituted or unsubstituted spirobifluorenyl, and the following groups;

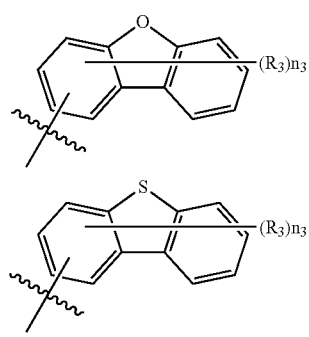

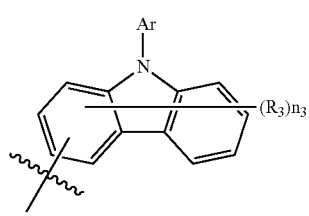

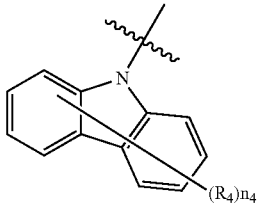

wherein, Ar is selected from unsubstituted phenyl, unsubstituted naphthyl, unsubstituted biphenyl, unsubstituted terphenyl, and unsubstituted phenanthryl;

each of R$_3$ and R$_4$ is independently selected from deuterium, fluorine, cyano, trimethylsilyl, trideuteromethyl, trifluoromethyl, cyclopentyl, cyclohexyl, methyl, ethyl, isopropyl, tert-butyl, phenyl, pentadeuterophenyl, naphthyl and biphenyl;

the substituent(s) in Ar$_1$, Ar$_2$, and Ar$_3$ are the same or different, and are each independently selected from deuterium, fluorine, cyano, trimethylsilyl, trideuteromethyl, trifluoromethyl, cyclopentyl, cyclohexyl, methyl, ethyl, isopropyl, tert-butyl, phenyl, pentadeuterophenyl, naphthyl and biphenyl;

R$_1$ and R$_2$ are the same or different, and are each independently selected from hydrogen, deuterium, fluorine, cyano, trimethylsilyl, trideuteromethyl, trifluoromethyl, cyclopentyl, cyclohexyl, methyl, ethyl, isopropyl, tert-butyl, phenyl, pentadeuterophenyl, and naphthyl;

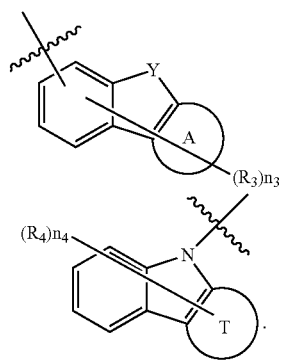

n$_1$ represents the number of R$_1$, and n$_1$ is selected from 0, 1, 2, and 3;

n$_2$ represents the number of R$_2$, and n$_2$ is selected from 0, 1, and 2;

n$_3$ represents the number of R$_3$, and n$_3$ is selected from 0, 1, 2, 3, 4, 5, 6, and 7; and n$_4$ represents the number of R$_4$, and n$_4$ is selected from 0, 1, 2, 3, 4, 5, 6, 7, and 8.

2. The nitrogen-containing compound according to claim 1, wherein L is selected from a single bond, substituted or unsubstituted phenylene, substituted or unsubstituted naphthylene, substituted or unsubstituted biphenylene, substituted or unsubstituted pyridylidene, substituted or unsubstituted dibenzothiophenylene, and substituted or unsubstituted dibenzofuranylene; and the substituent(s) in L are the same or different, and are each independently selected from deuterium, fluorine, cyano, methyl, ethyl, isopropyl, tert-butyl, trifluoromethyl, trideuteromethyl, trimethylsilyl, pentadeuterophenyl, and phenyl.

3. The nitrogen-containing compound according to claim 1, wherein L is selected from a single bond and the group consisting of the following groups:

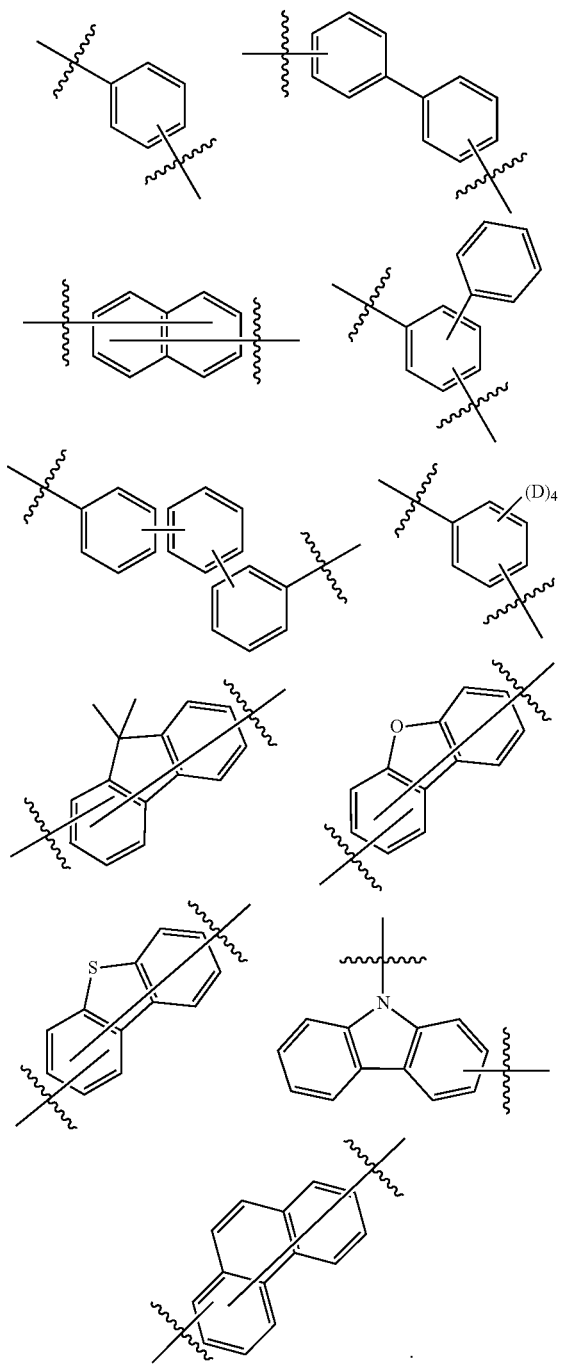

4. The nitrogen-containing compound according to claim 1, wherein $L_1$ and $L_2$ are each independently selected from a single bond, substituted or unsubstituted phenylene, substituted or unsubstituted naphthylene, substituted or unsubstituted biphenylene, substituted or unsubstituted fluorenylene, substituted or unsubstituted phenanthrylene, substituted or unsubstituted dibenzothiophenylene, substituted or unsubstituted dibenzofuranylene, substituted or unsubstituted carbazolylene, and substituted or unsubstituted pyridylidene; and the substituent(s) in $L_1$ and $L_2$ are the same or different, and are each independently selected from deuterium, fluorine, cyano, methyl, ethyl, isopropyl, tert-butyl, trifluoromethyl, trideuteromethyl, trimethylsilyl, pentadeuterophenyl, and phenyl.

5. The nitrogen-containing compound according to claim 1, wherein $L_1$ and $L_2$ are each independently selected from a single bond and the group consisting of the following groups:

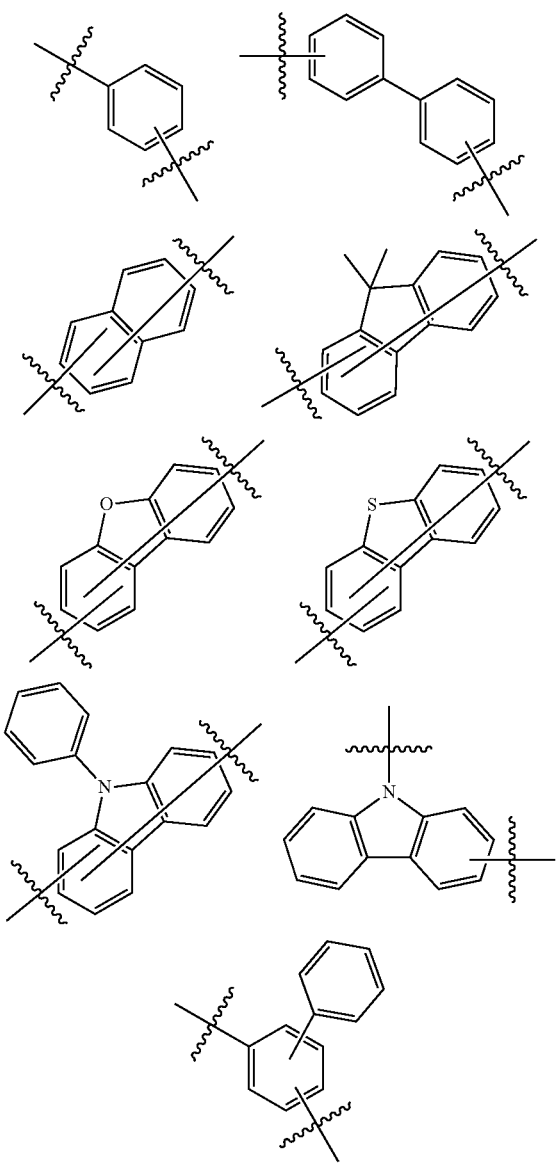

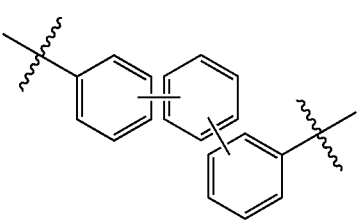

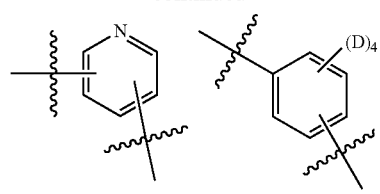
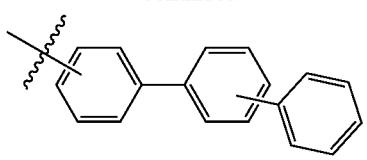
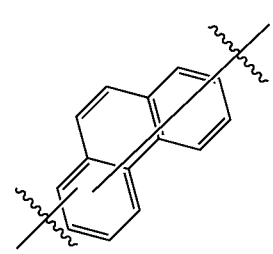
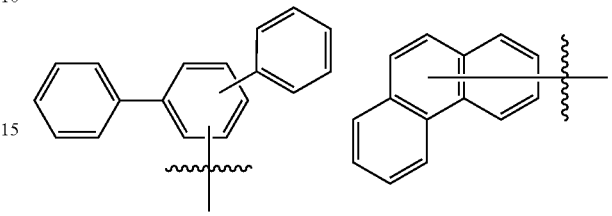
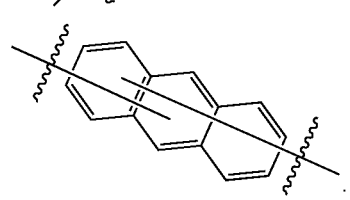
6. The nitrogen-containing compound according to claim 1, wherein Ar₁ and Ar₂ are the same or different, and are each independently selected from the following groups:
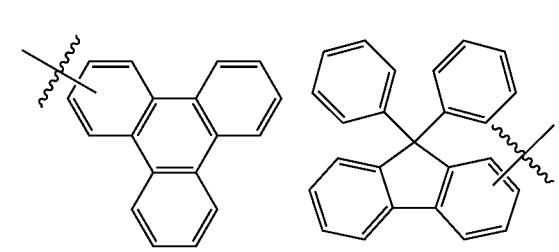
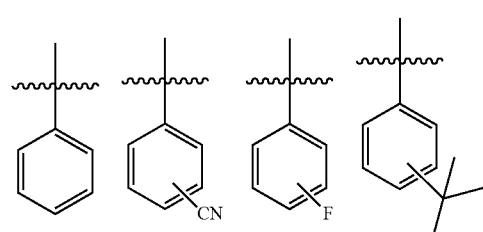
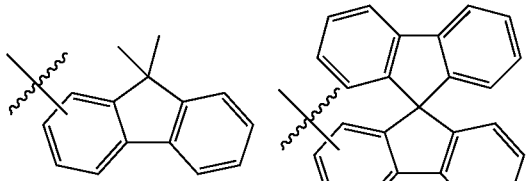
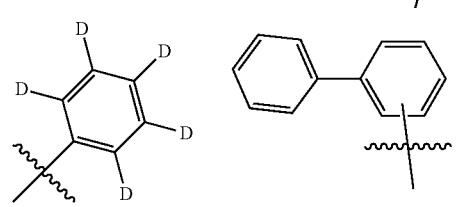
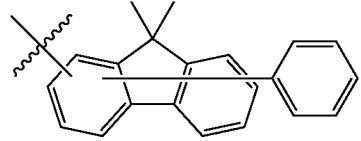
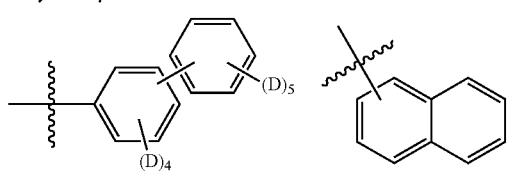
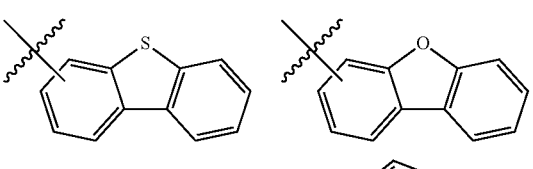
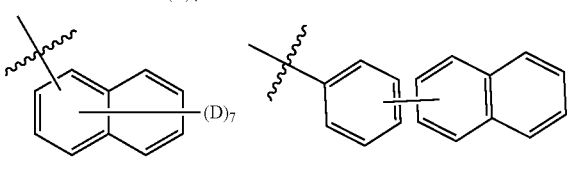
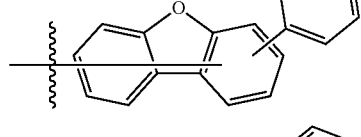
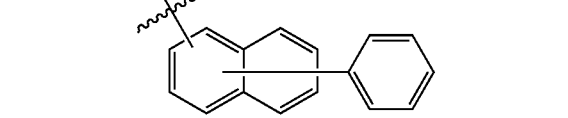
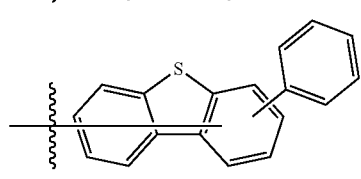

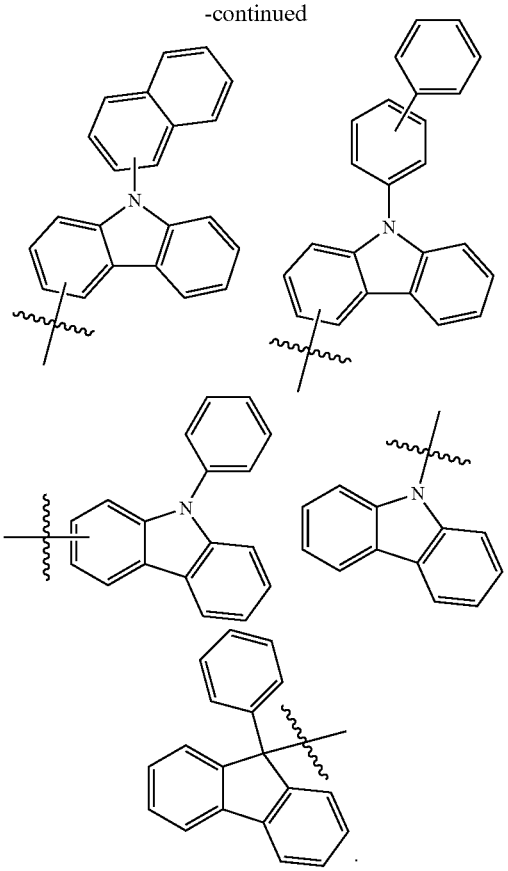
7. The nitrogen-containing compound according to claim 1, wherein Ar₃ is selected from the following groups:
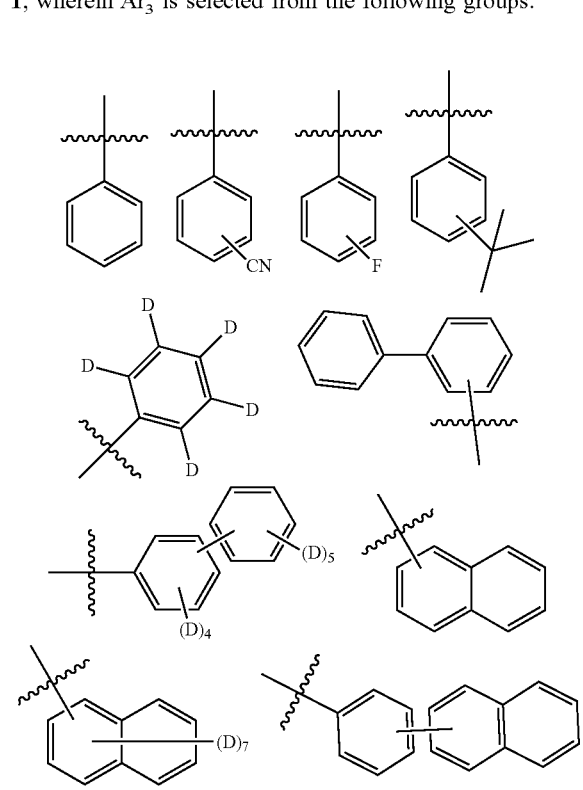
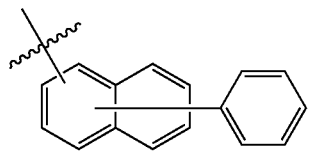
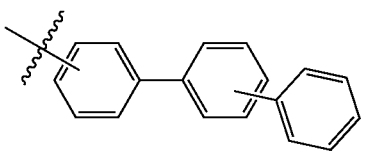
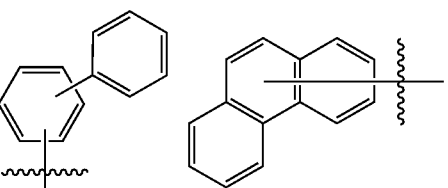
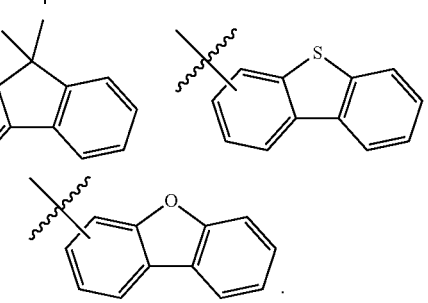
8. The nitrogen-containing compound according to claim 1, wherein
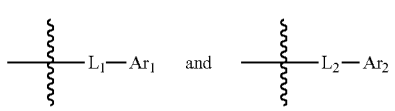
are the same or different, and are each independently selected from the following groups:
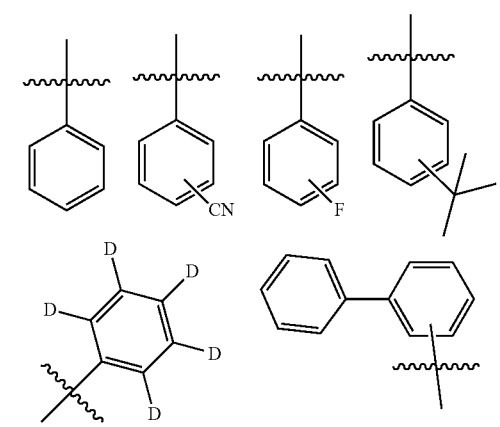

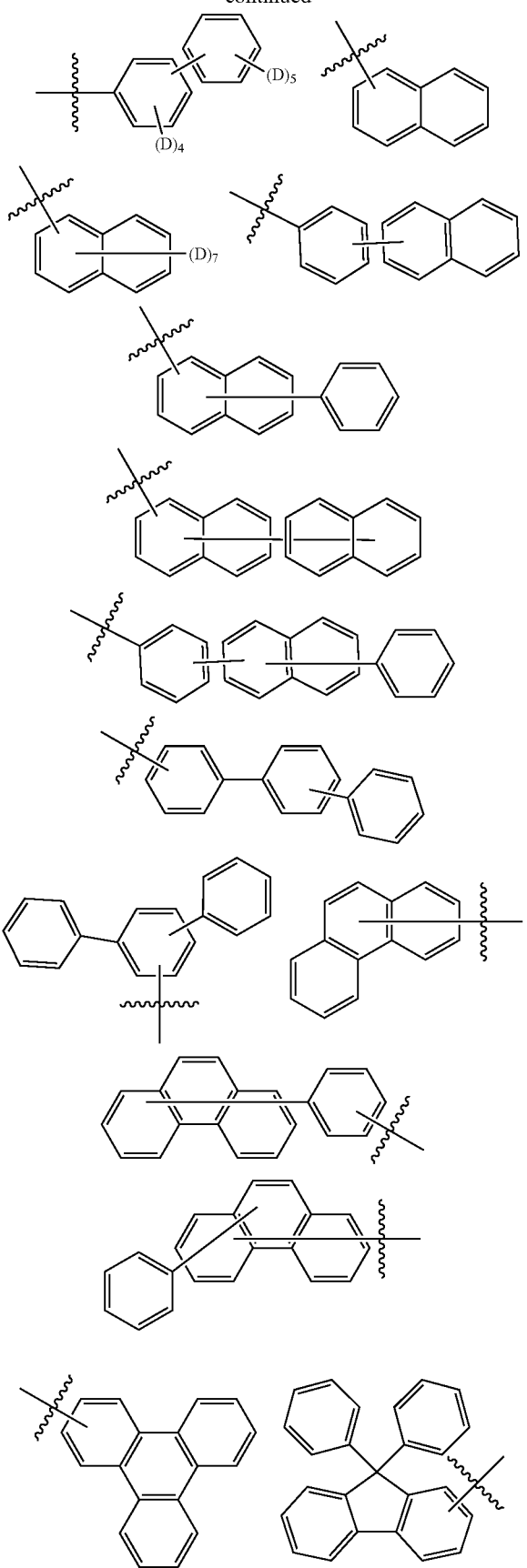
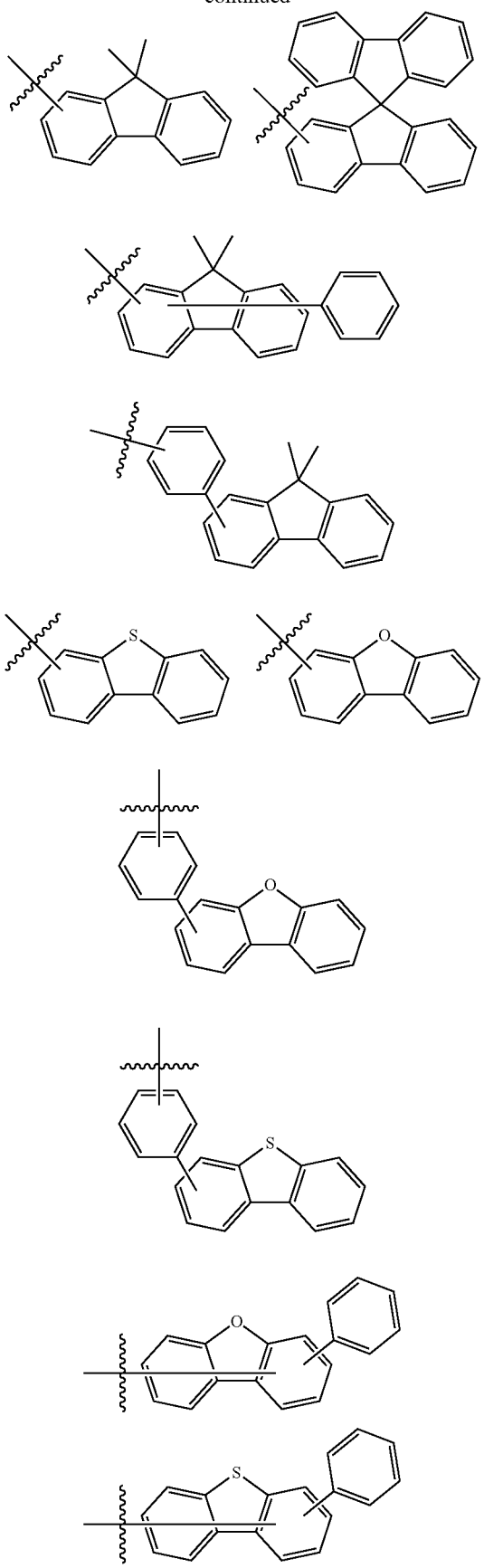

323
-continued

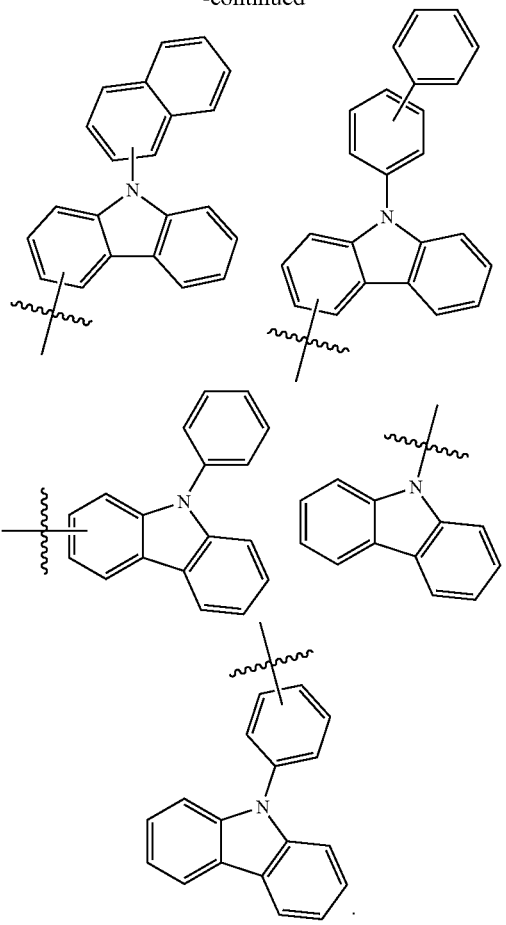

9. An organic electroluminescent device, comprising an anode and a cathode which are oppositely arranged, and a functional layer arranged between the anode and the cathode, wherein the functional layer comprises the nitrogen-containing compound according to claim 1.

10. An electronic apparatus, comprising the organic electroluminescent device according to claim 9.

11. The organic electroluminescent device according to claim 9, wherein, the functional layer comprises an organic light-emitting layer, which comprises the nitrogen-containing compound.

12. A nitrogen-containing compound, wherein the nitrogen-containing compound is selected from the group consisting of the following compounds:

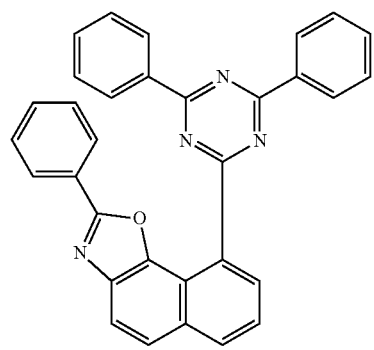

324
-continued

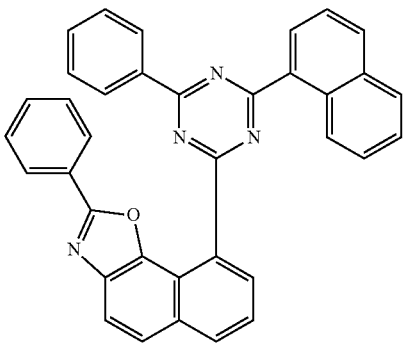

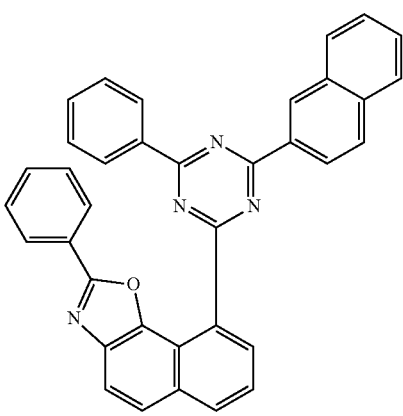

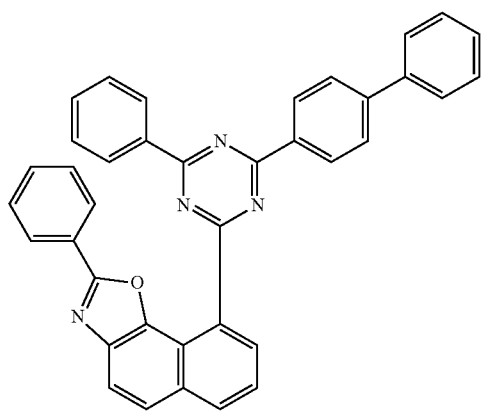

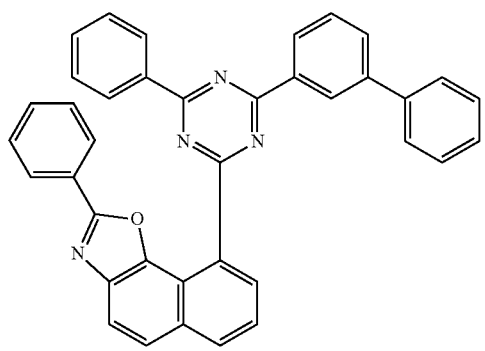

325
-continued
| | |
|---|---|
| 6 | 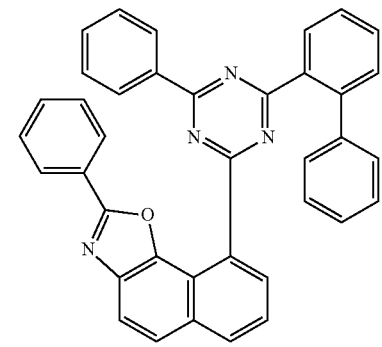 |
| 7 | 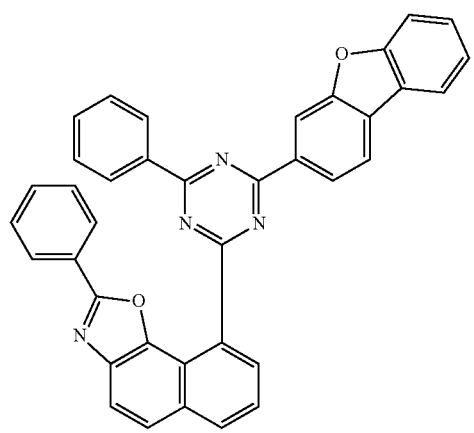 |
| 8 | 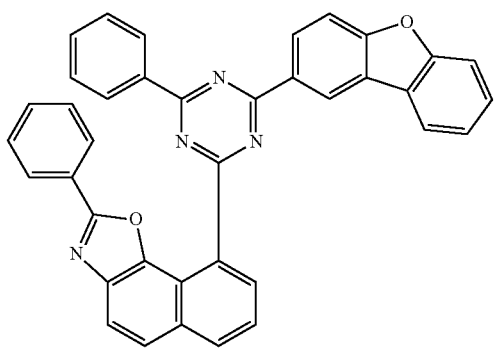 |
| 9 | 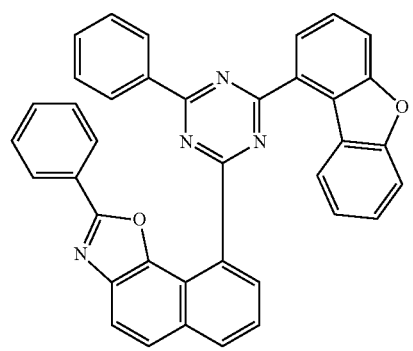 |
326
-continued
| | |
|---|---|
| 10 | 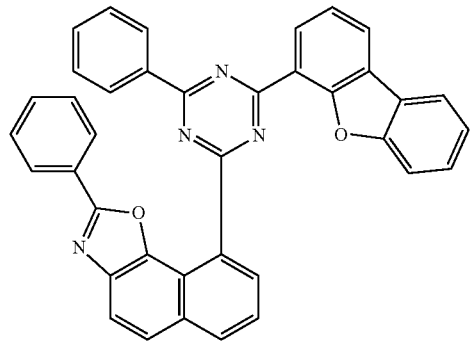 |
| 11 | 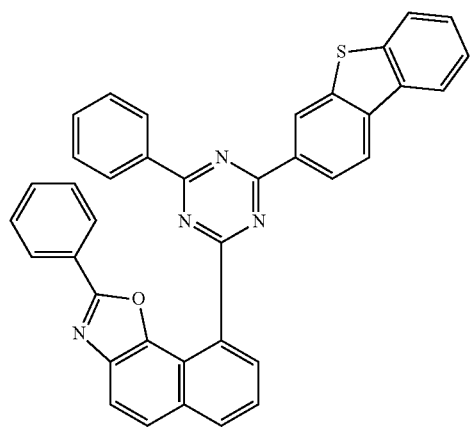 |
| 12 | 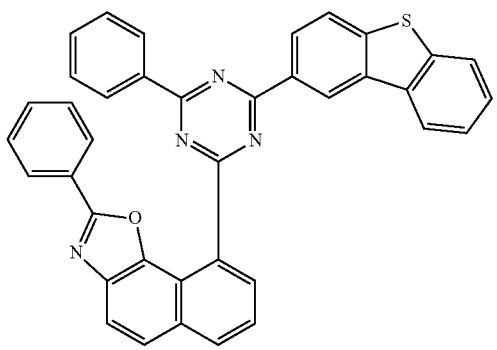 |
| 109 | 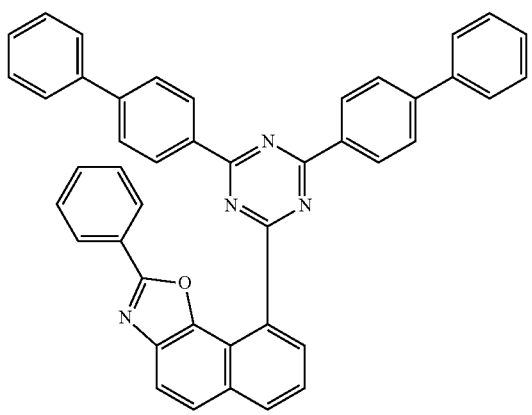 |

327
-continued
110
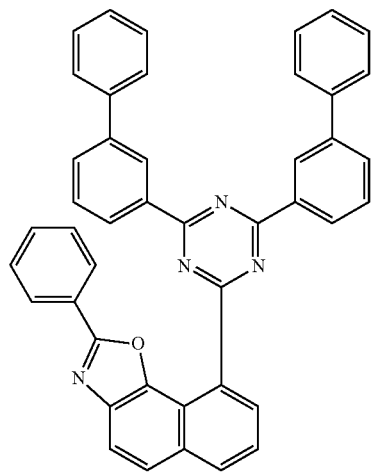
111
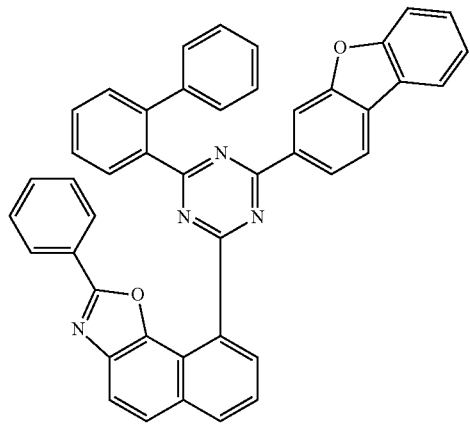
112
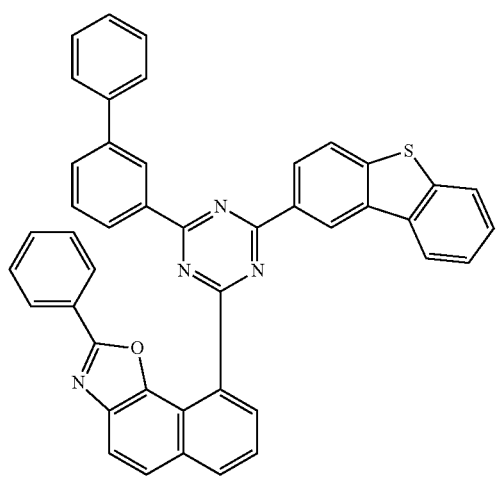
328
-continued
113
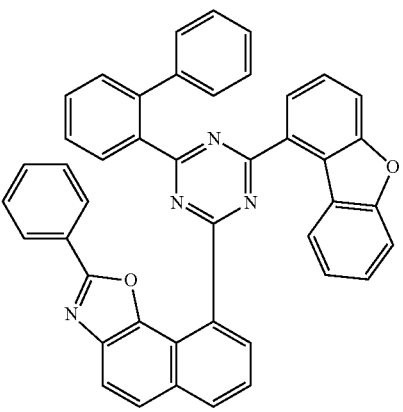
114
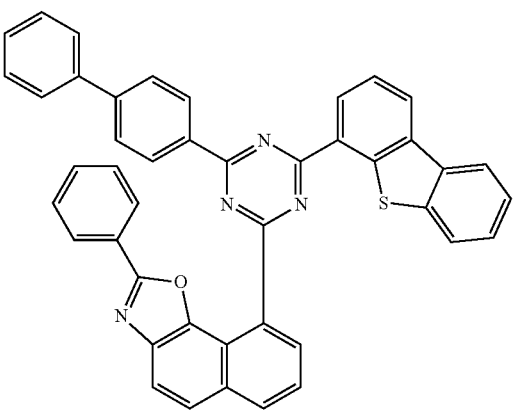
115
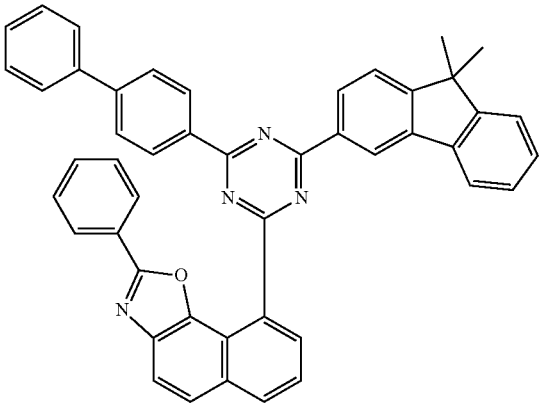

329
-continued
116
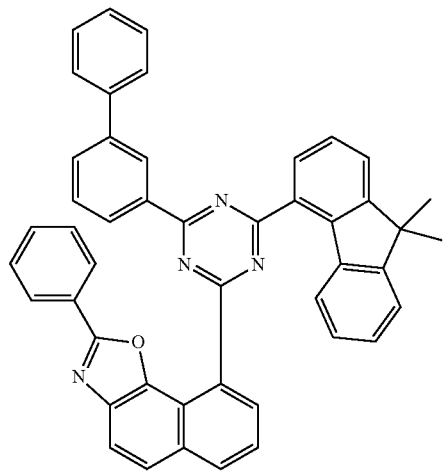
117
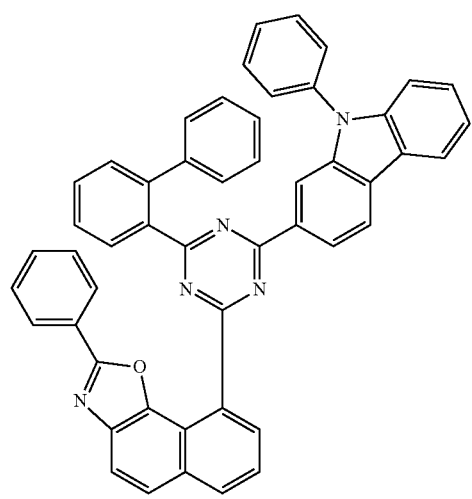
118
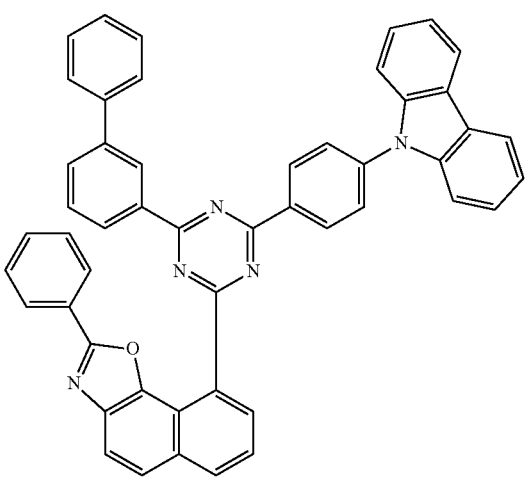
330
-continued
119
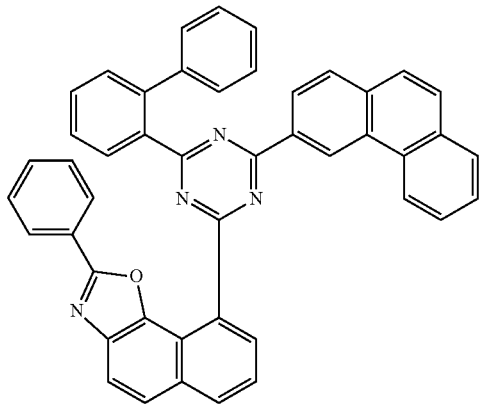
120
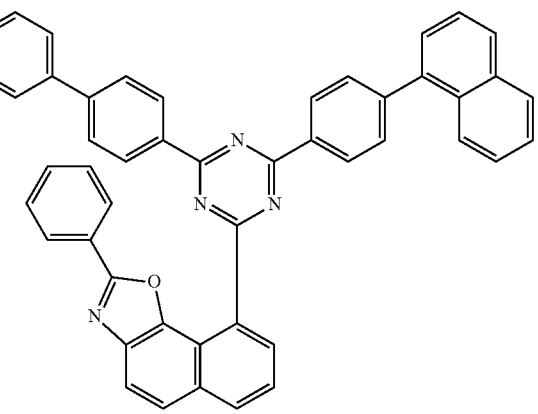
121

331
-continued
122
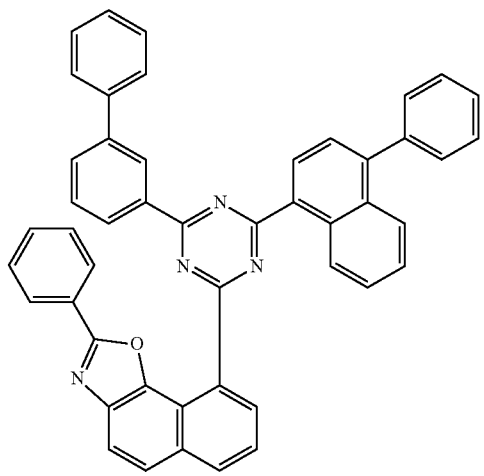
123
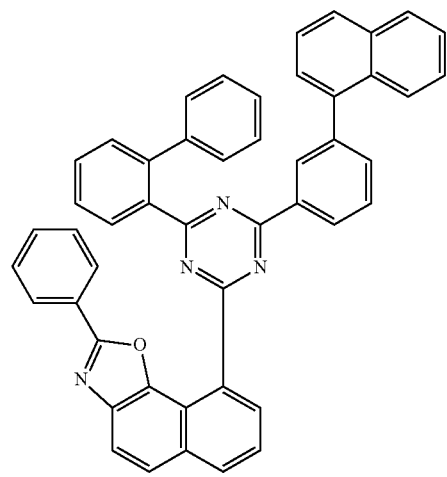
124
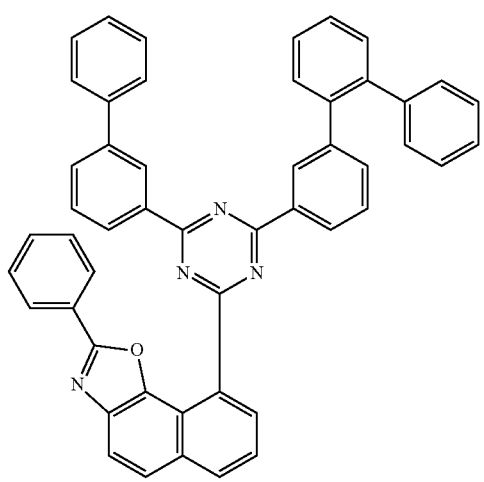
332
-continued
125
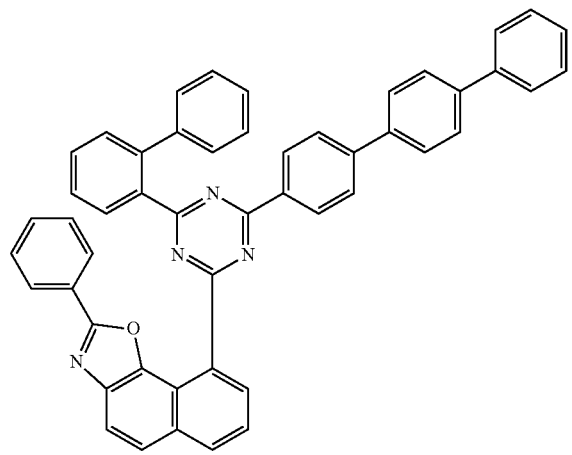
126
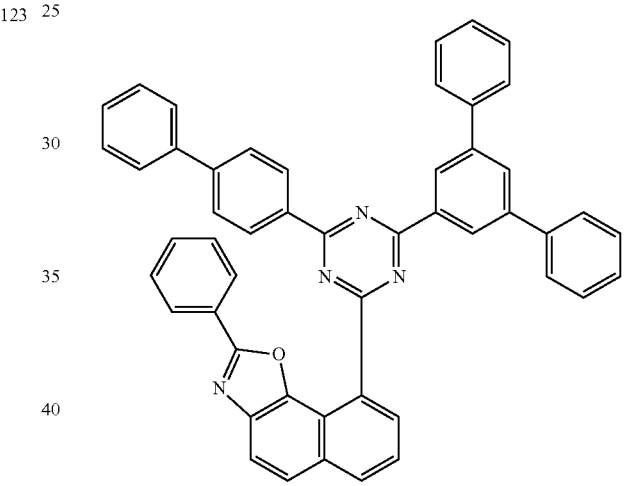
127
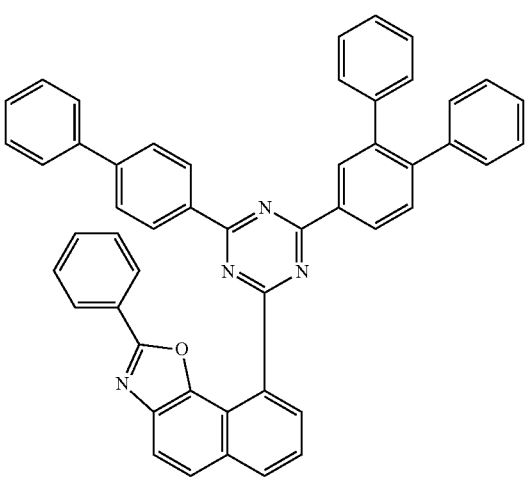

128
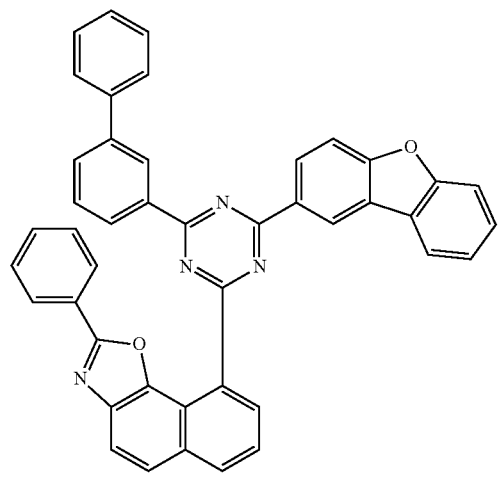
129
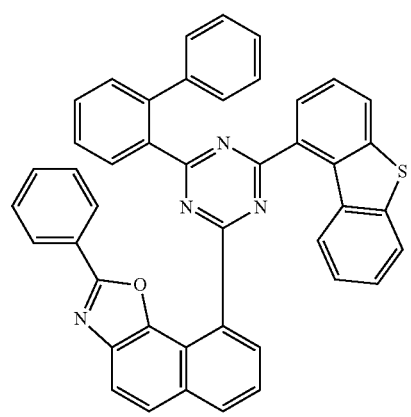
130
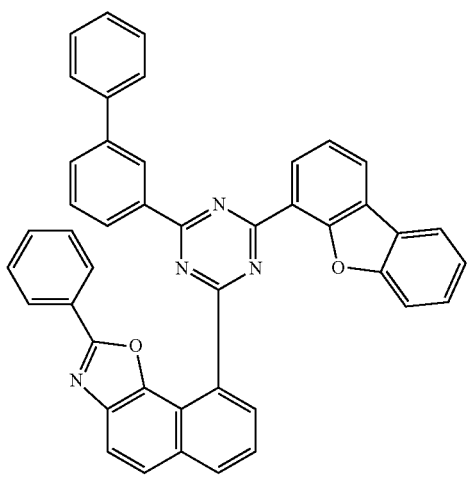
131
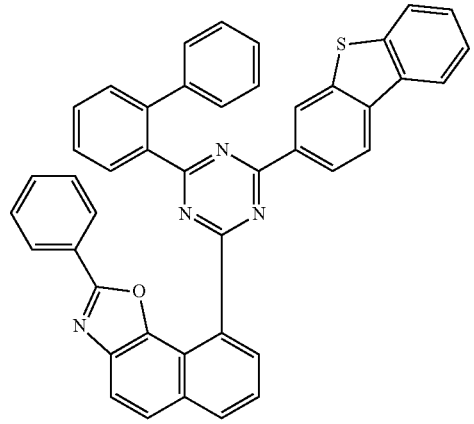
132
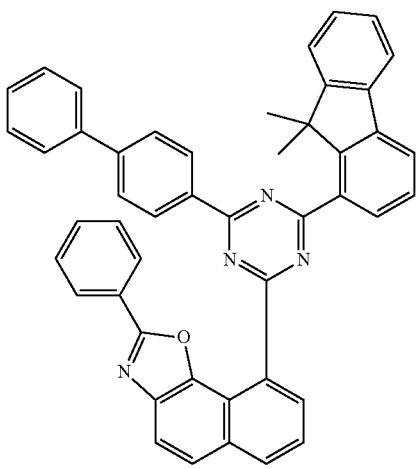
133
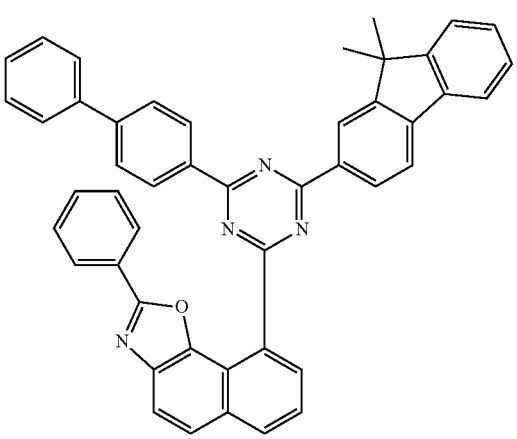

| 134 | 137 |
|---|---|
| 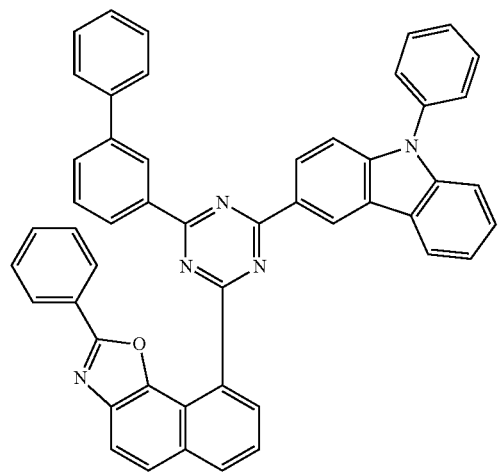 | 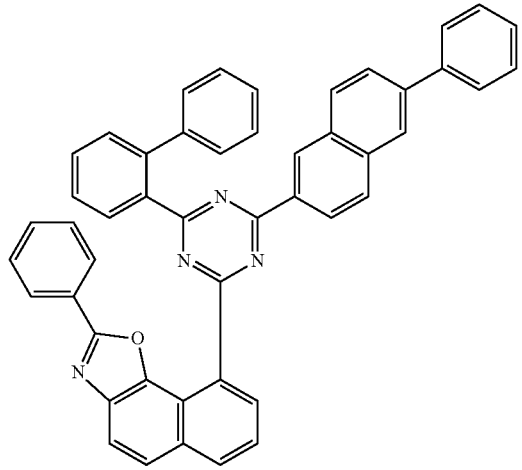 |
| 135 | 138 |
| 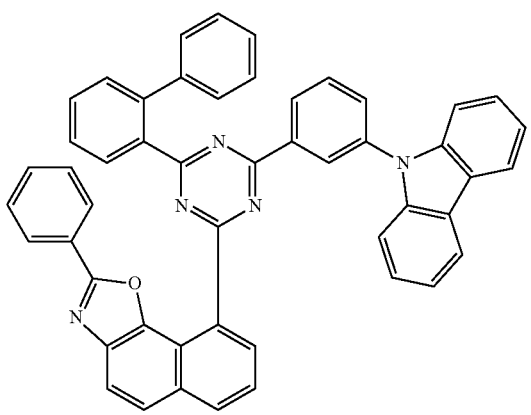 | 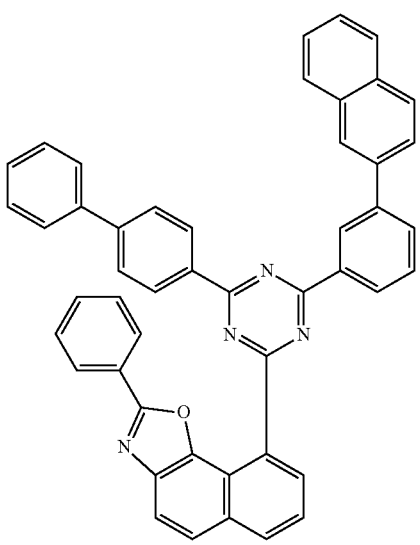 |
| 136 | 139 |
| 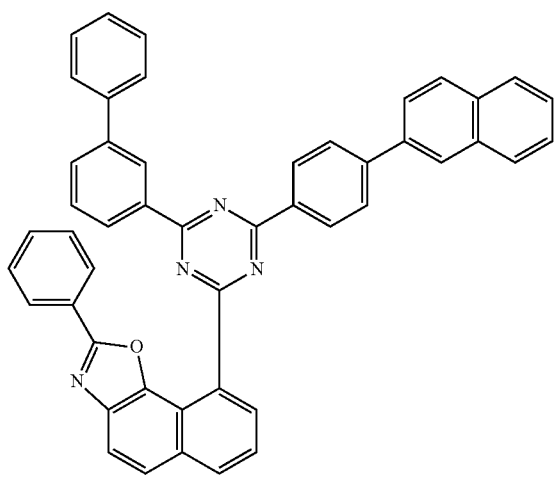 | 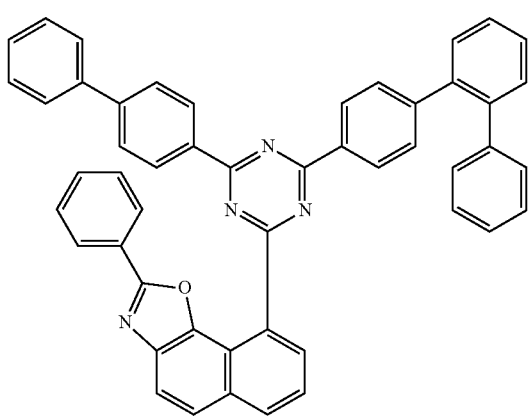 |

337
-continued
140
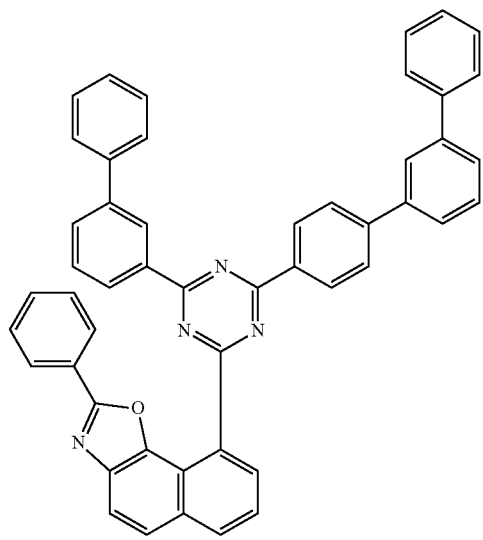
141
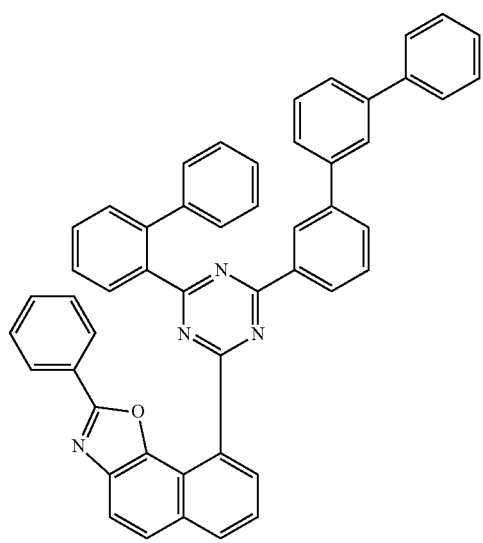
142
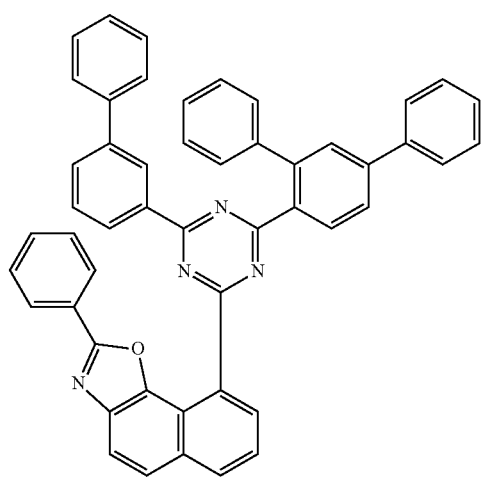
338
-continued
143
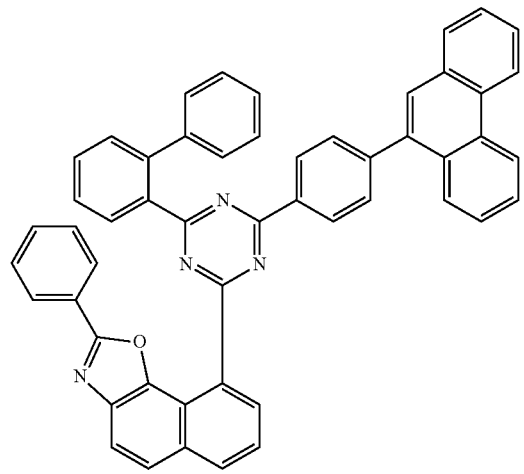
144
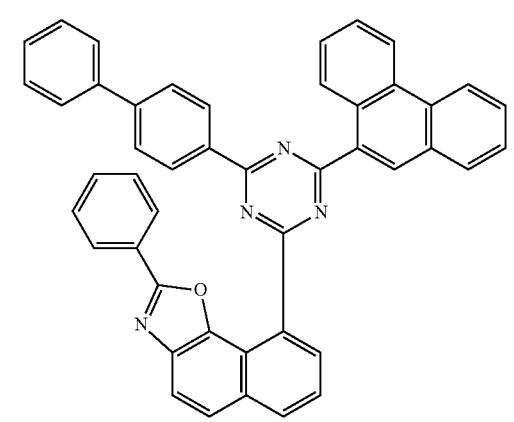
439
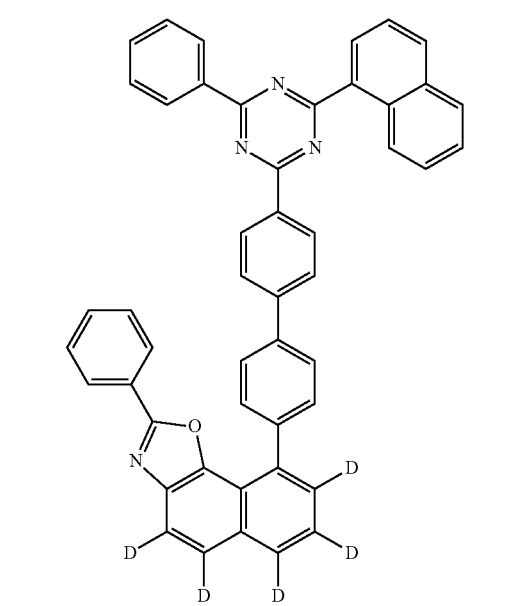

440
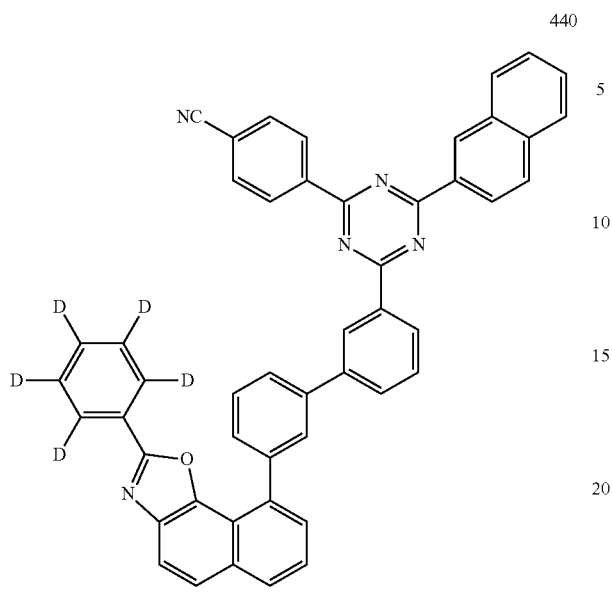
441
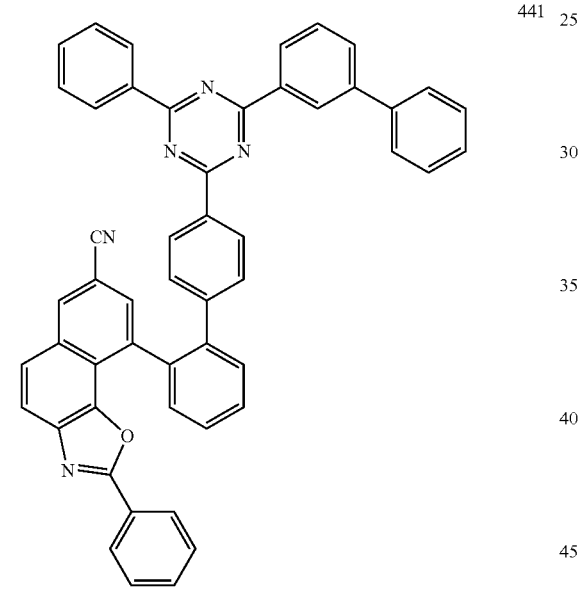
442
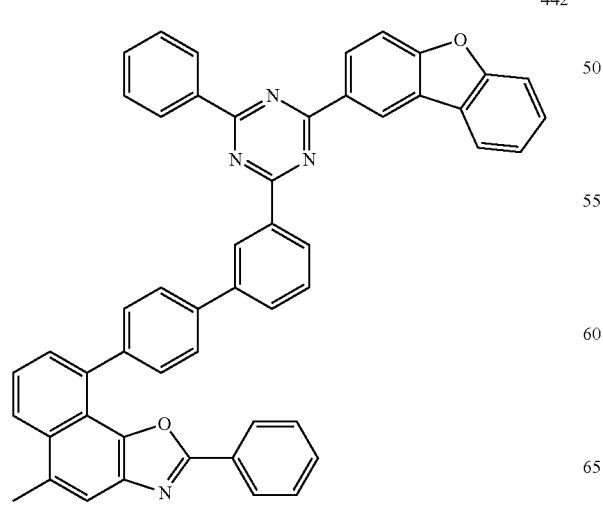
443
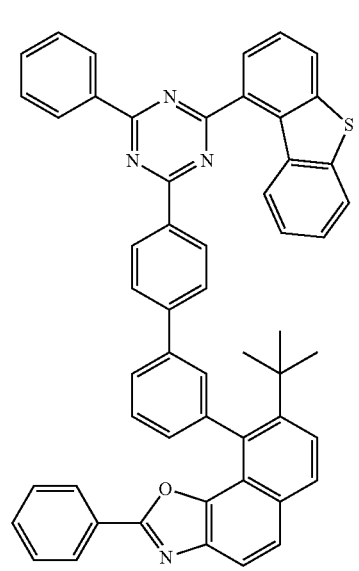
444
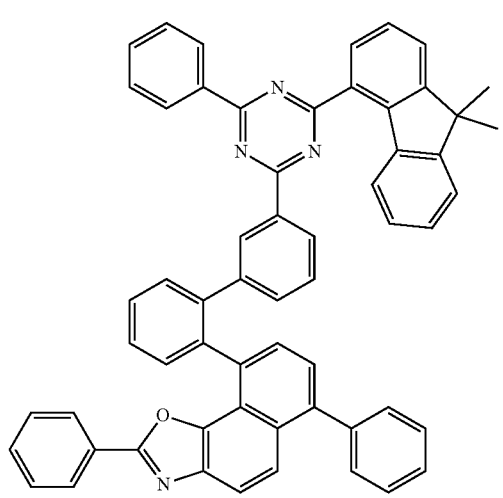
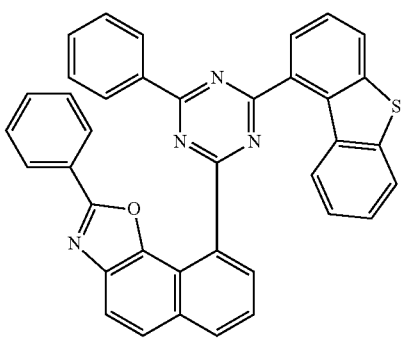

341
-continued
14
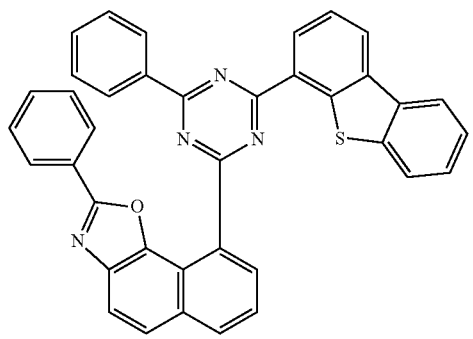
15
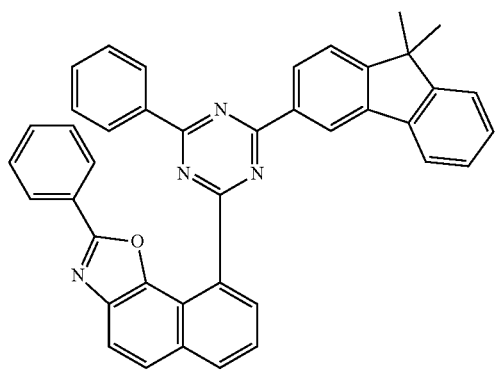
16
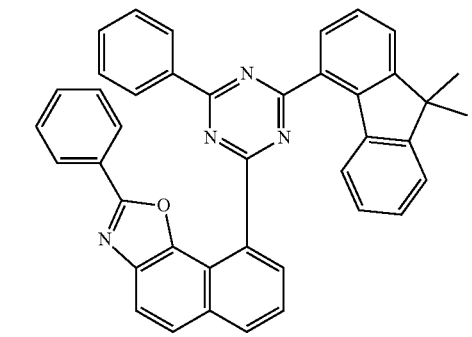
17
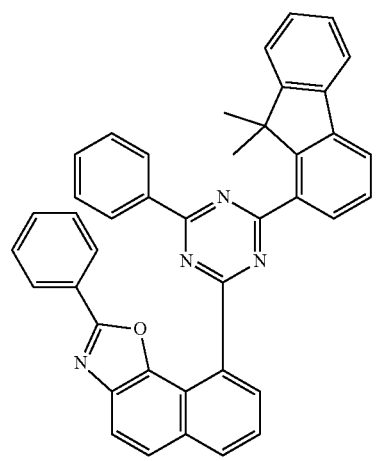
342
-continued
18
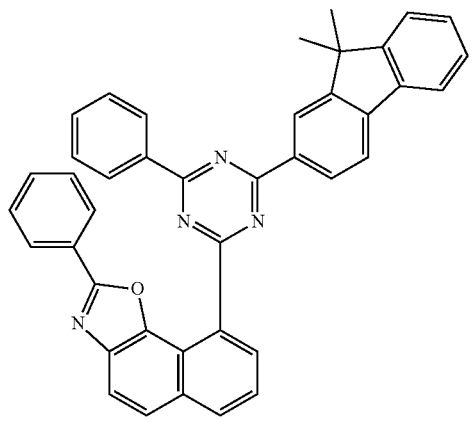
19
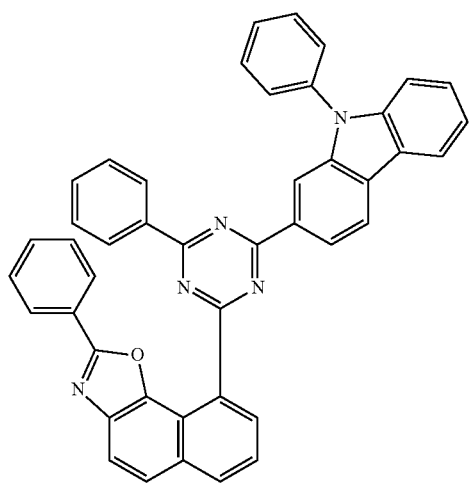
20
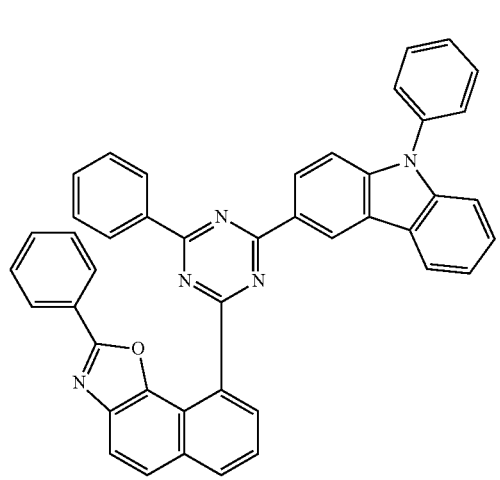

21
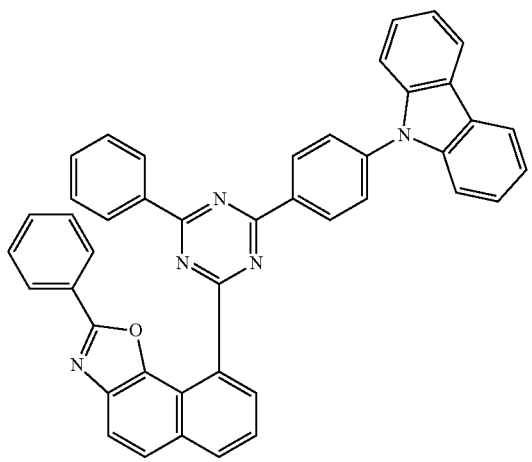
22
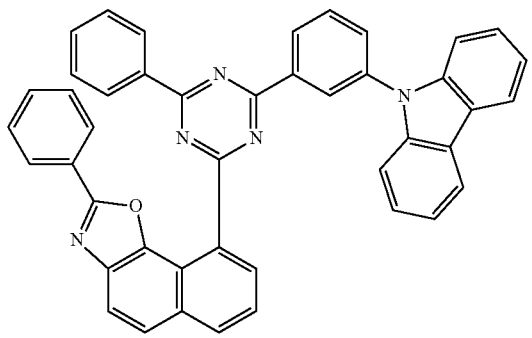
23
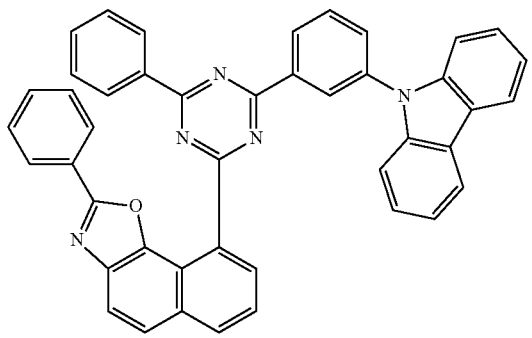
24
25
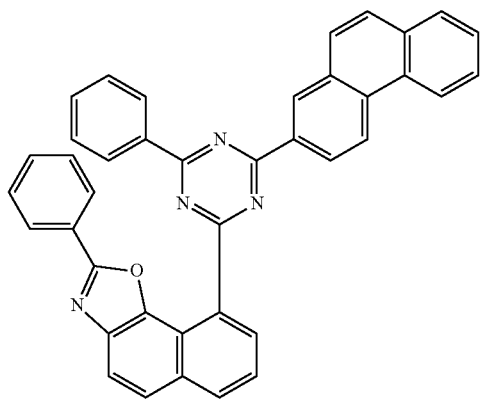
26
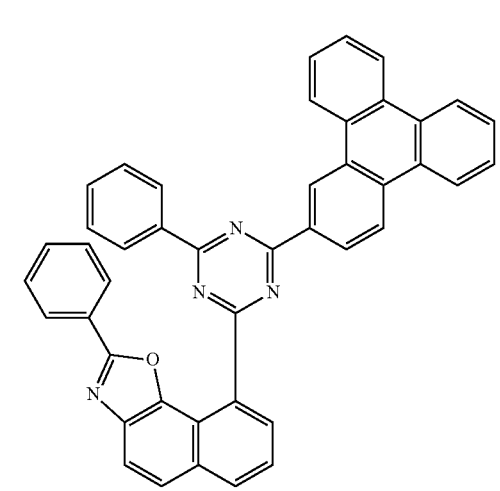
27
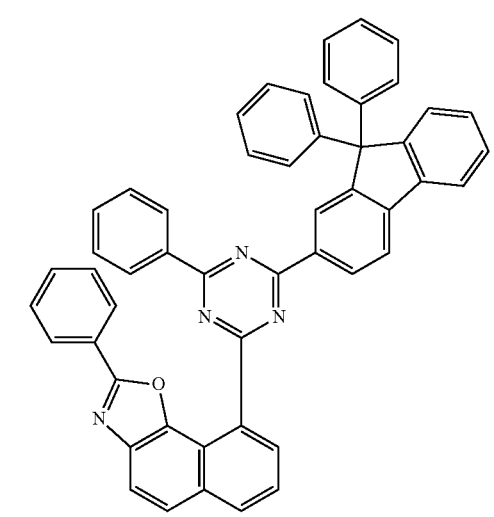

28
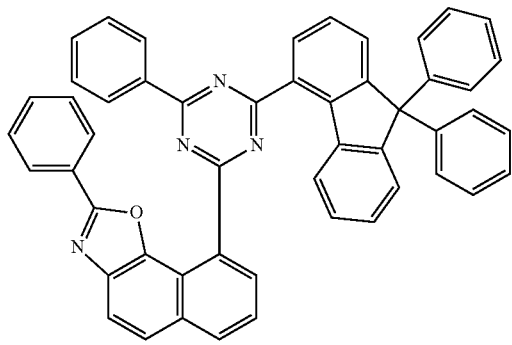
29
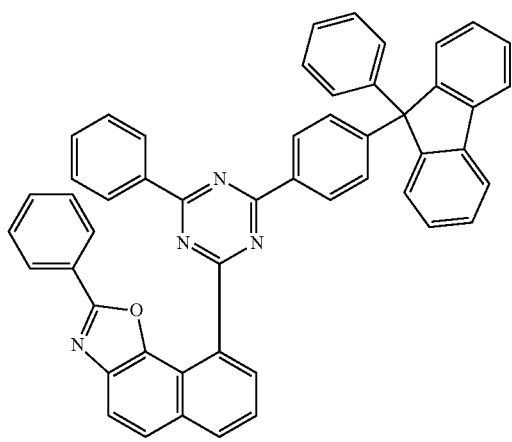
30
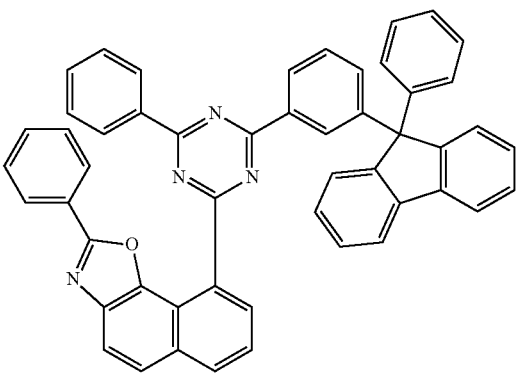
31
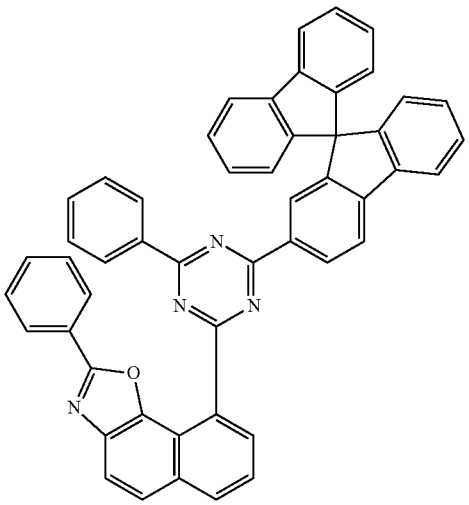
32
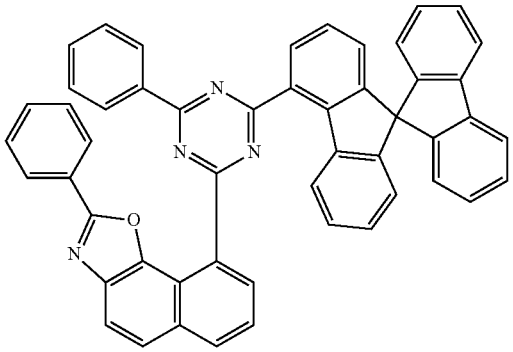
33
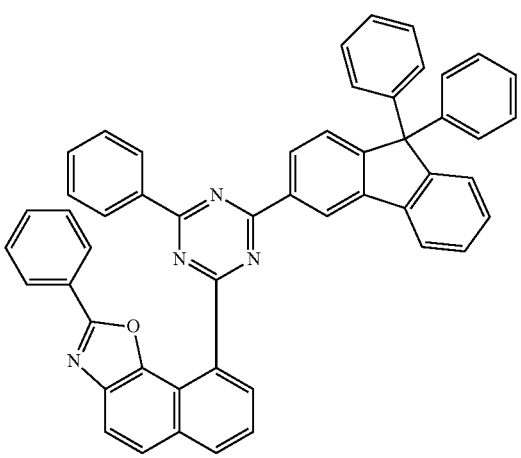

34
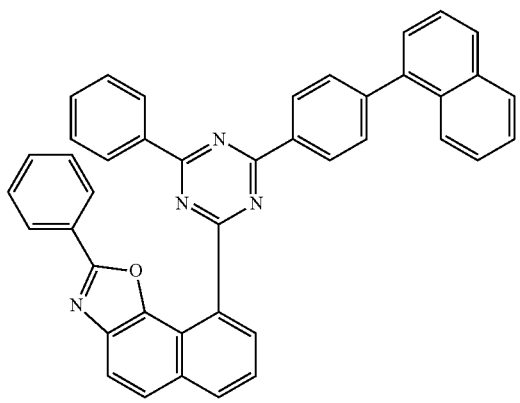
35
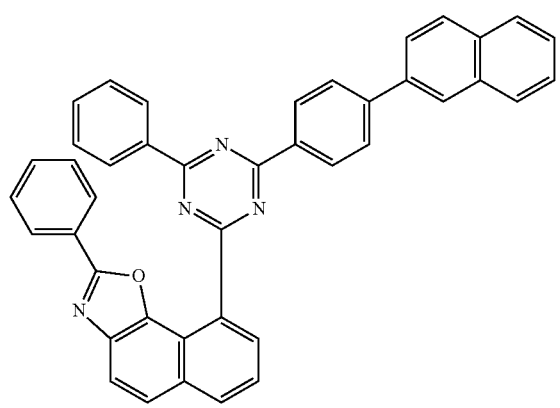
36
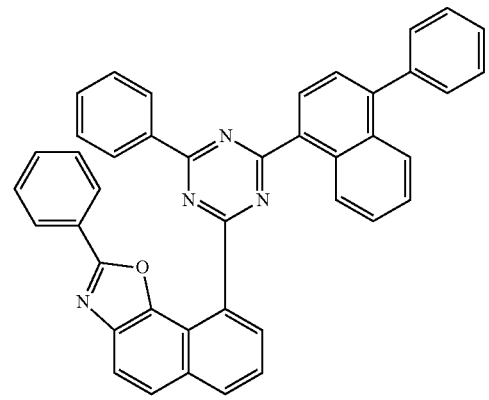
37
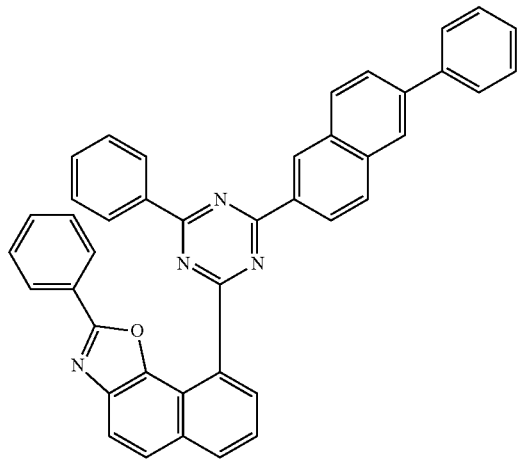 [SMILES: c1ccc(-c2ccc3cc(-c4nc(-c5ccccc5)nc(-c5cccc6ccc7nc(-c8ccccc8)oc7c56)n4)ccc3c2)cc1]
38
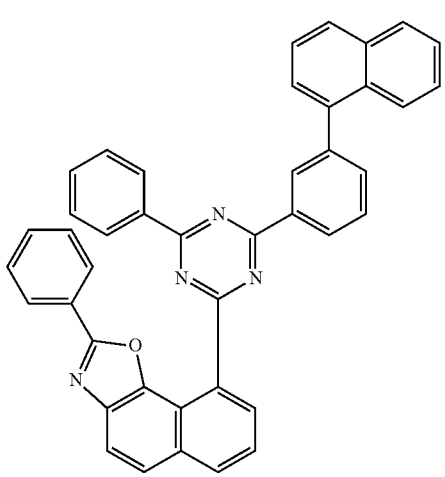
39
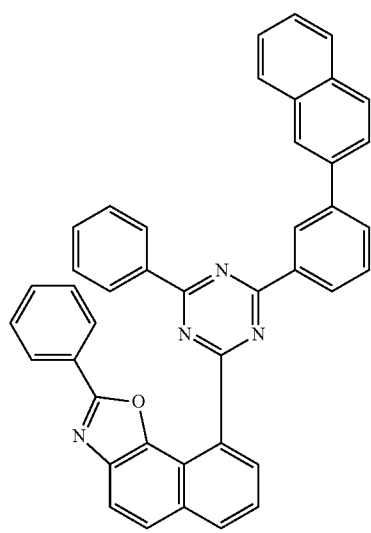

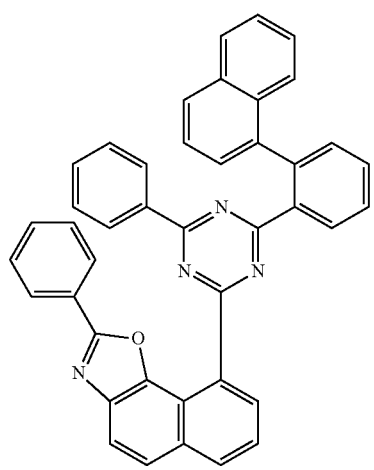
40
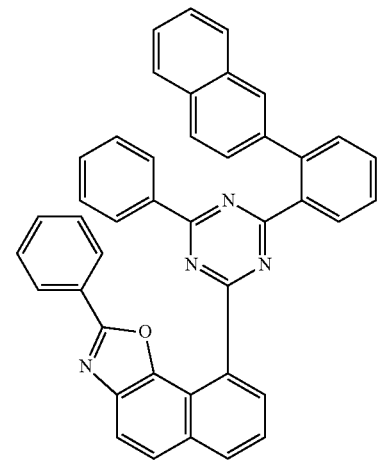
41
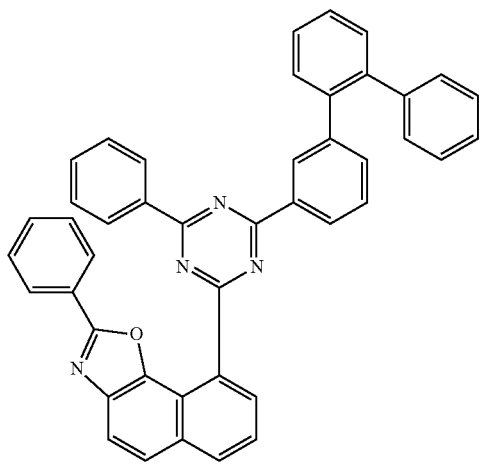 [SMILES: c1ccc(-c2nc(-c3cccc(-c4ccccc4-c4ccccc4)c3)nc(-c3cccc4ccc5nc(-c6ccccc6)oc5c34)n2)cc1]
42
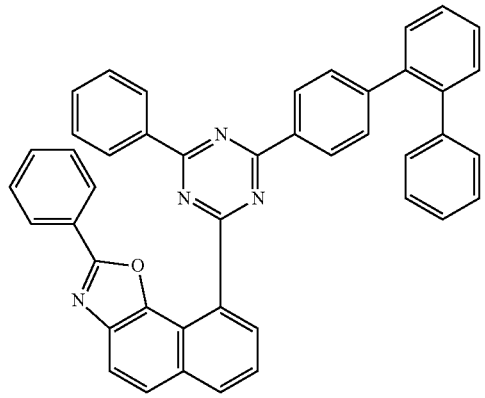 [SMILES: c1ccc(-c2nc(-c3ccc(-c4ccccc4-c4ccccc4)cc3)nc(-c3cccc4ccc5nc(-c6ccccc6)oc5c34)n2)cc1]
43
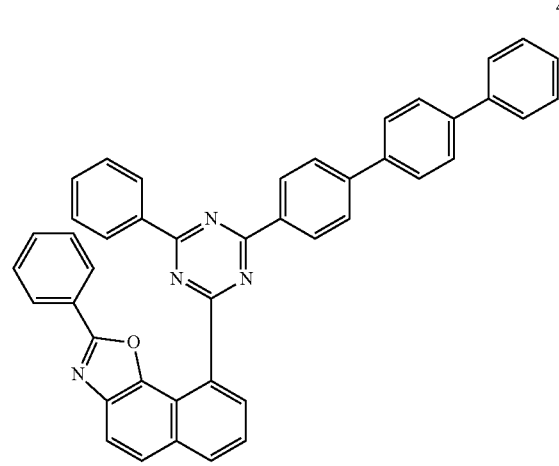
44
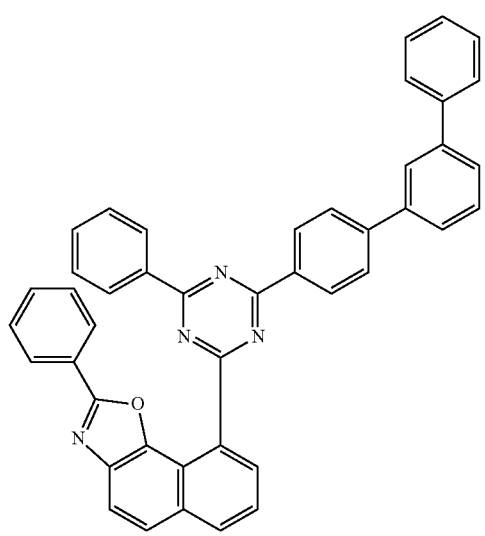
45

351
46
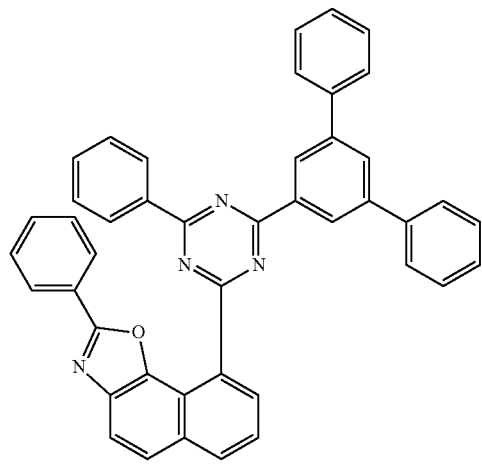 [SMILES: c1ccc(-c2cc(-c3ccccc3)cc(-c3nc(-c4ccccc4)nc(-c4cccc5ccc6nc(-c7ccccc7)oc6c45)n3)c2)cc1]
47
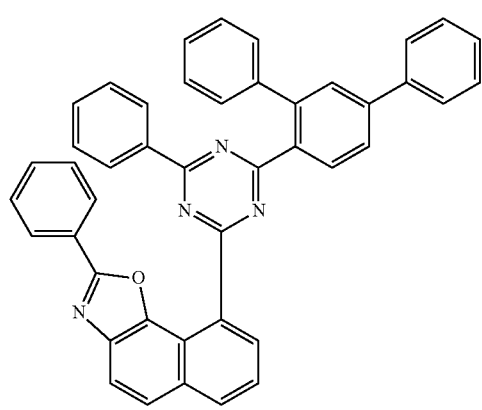
48
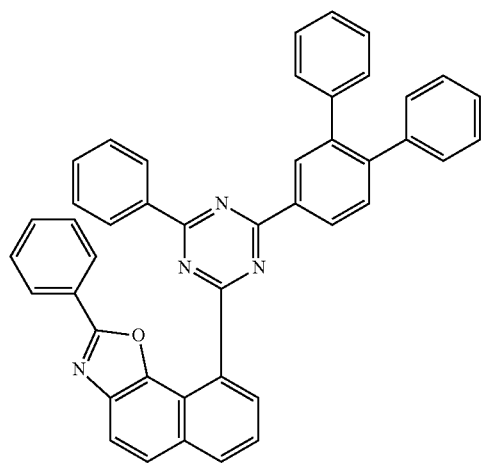
352
49
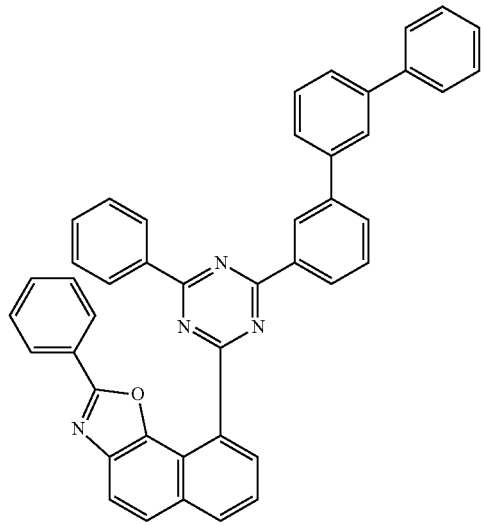
50
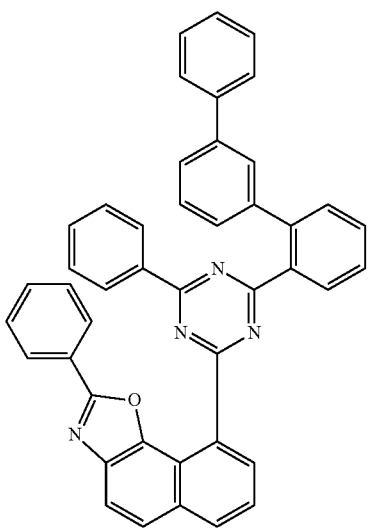
51
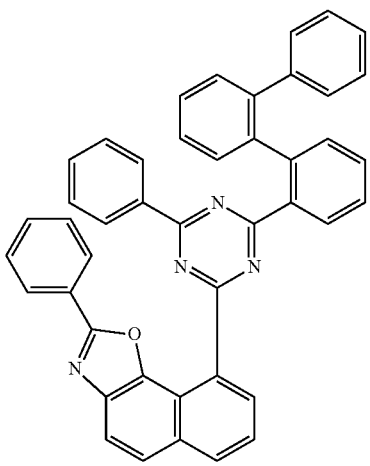

353
-continued
52
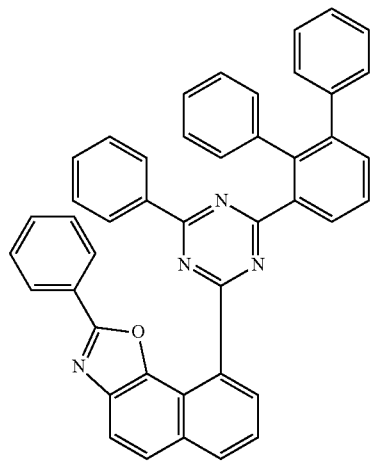
53
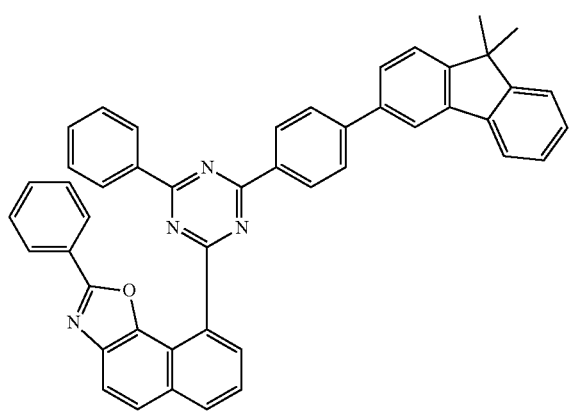
54
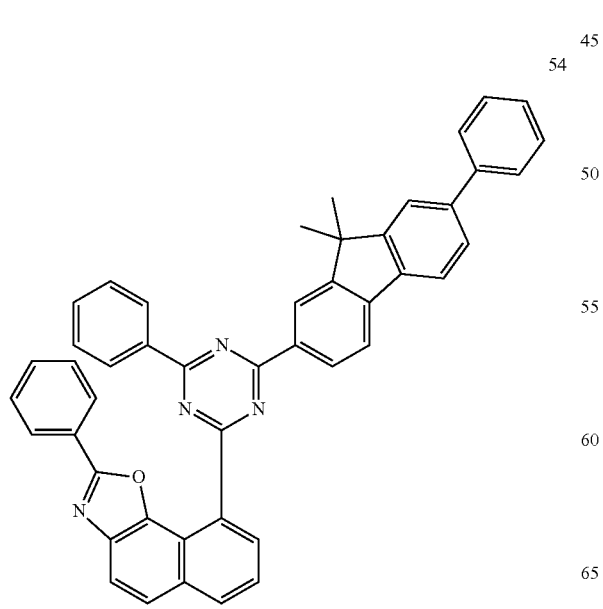
354
-continued
55
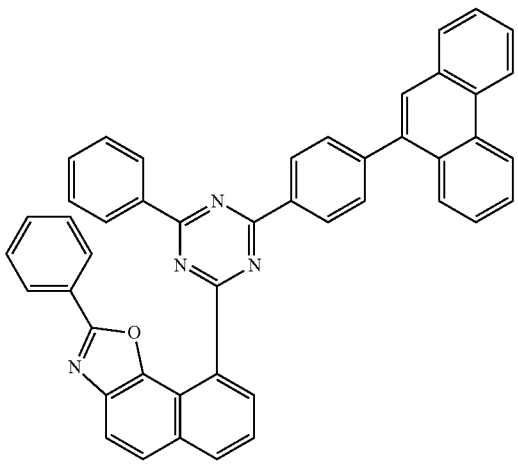
56
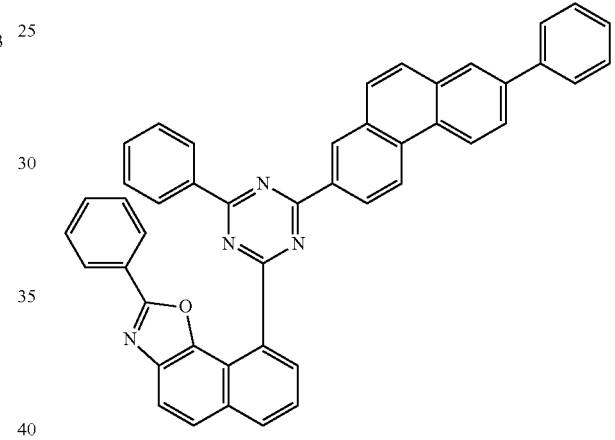
57
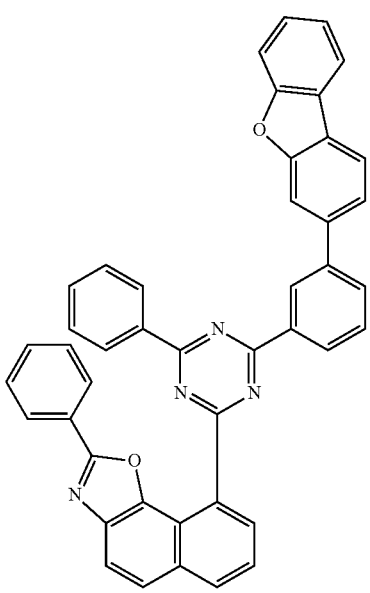

-continued
58
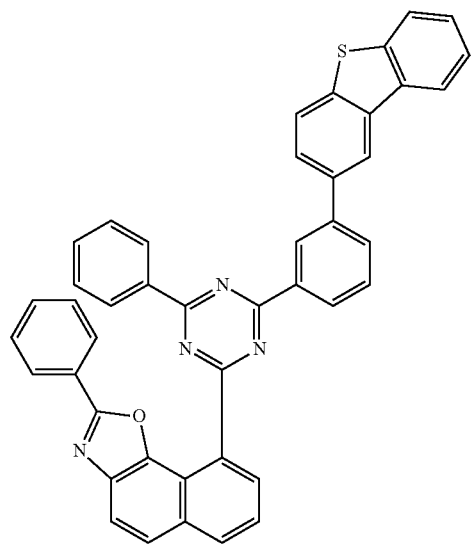
59
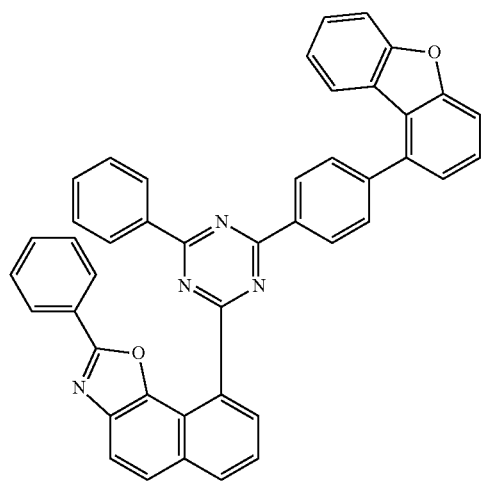
60
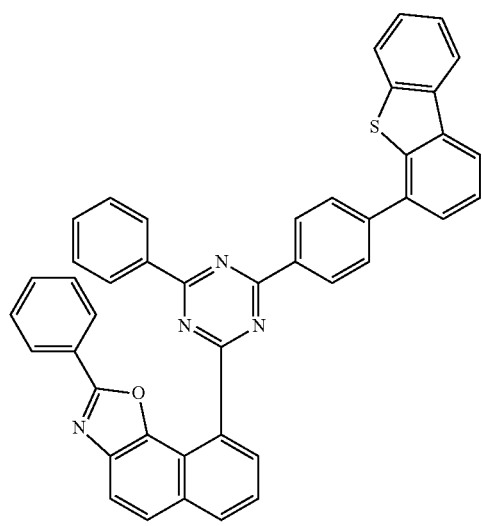
-continued
61
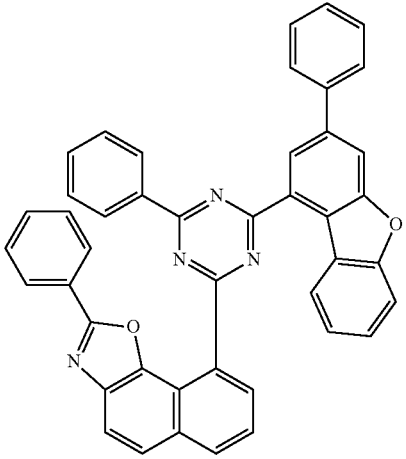
62
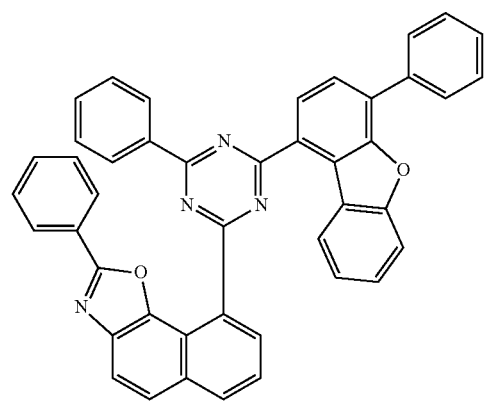
63
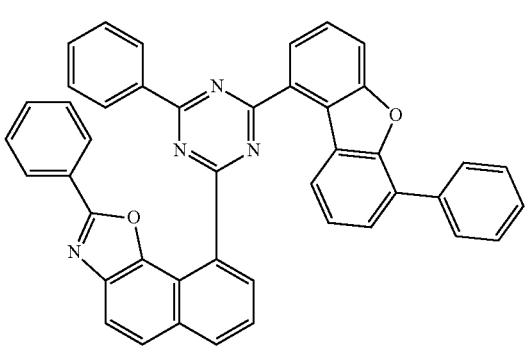
64
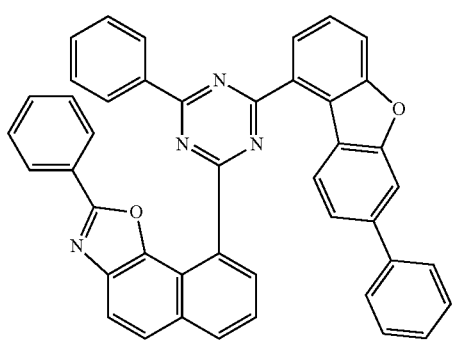

357
-continued
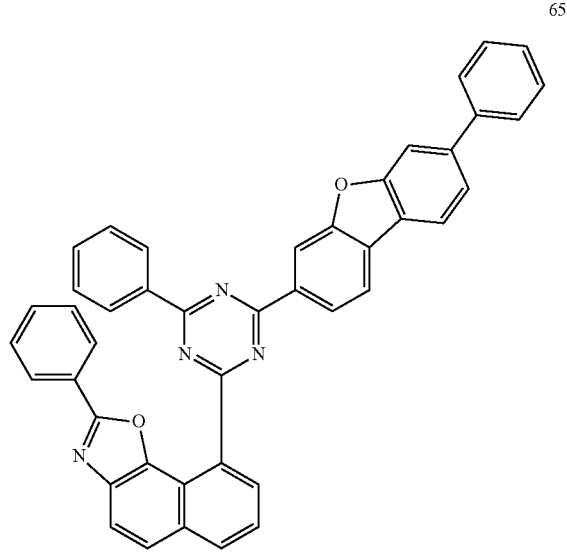
65
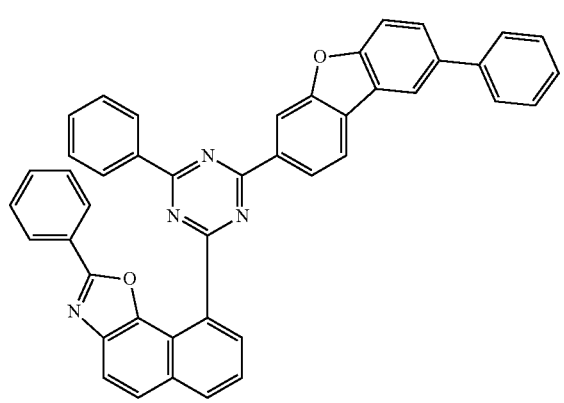
66
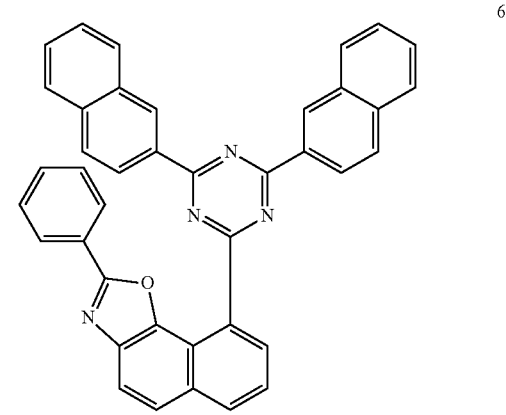
67
358
-continued
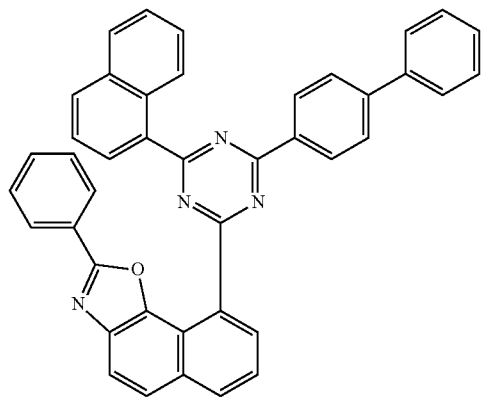
68
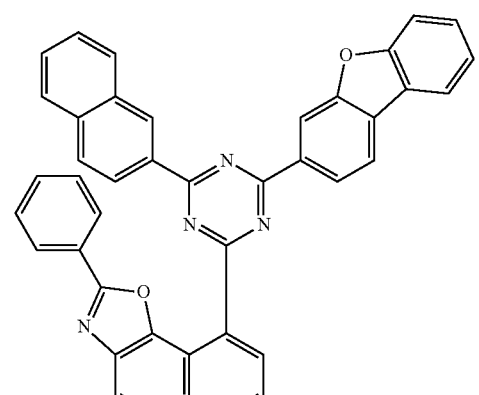
69
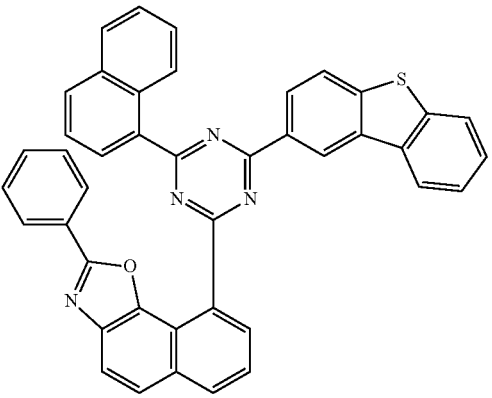
70
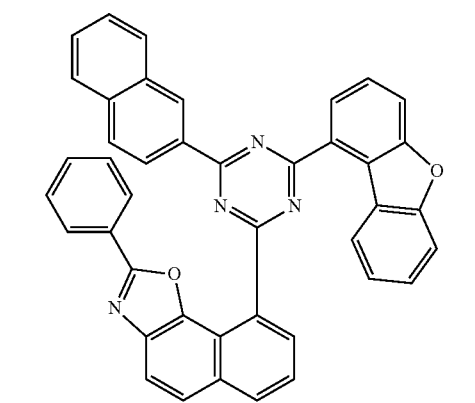
71

359
-continued

72

73

74

360
-continued

75

76

77

78
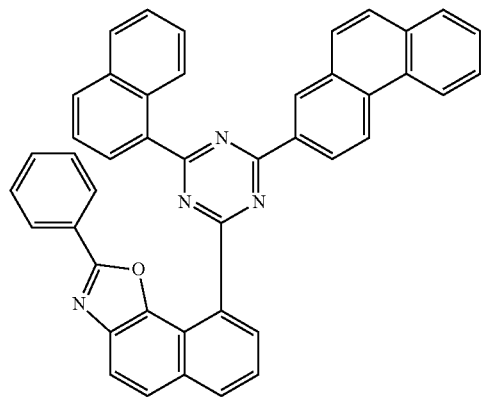
79
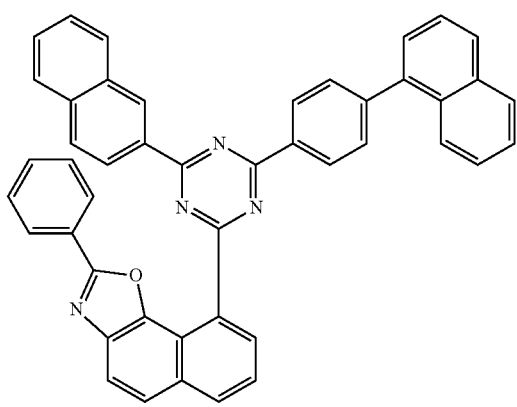
80
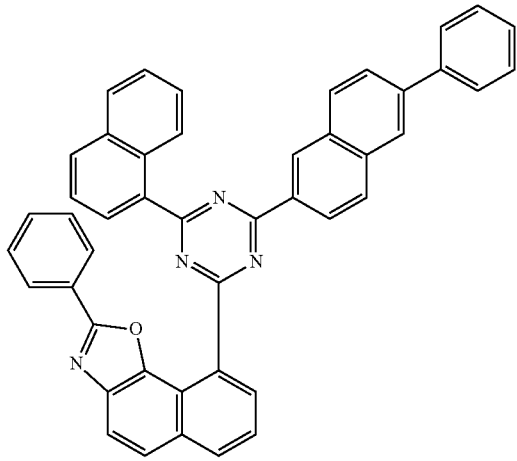
81
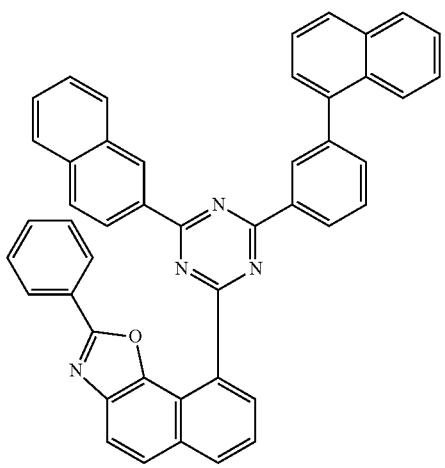
82
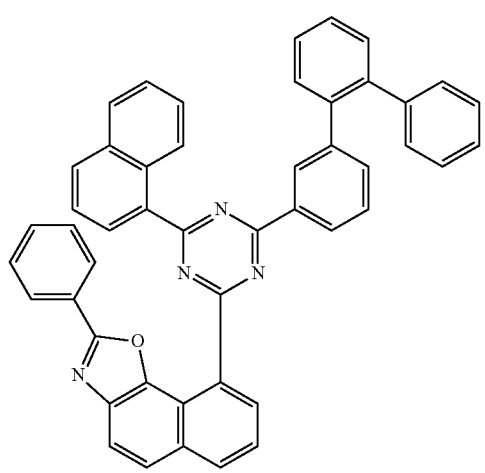
83
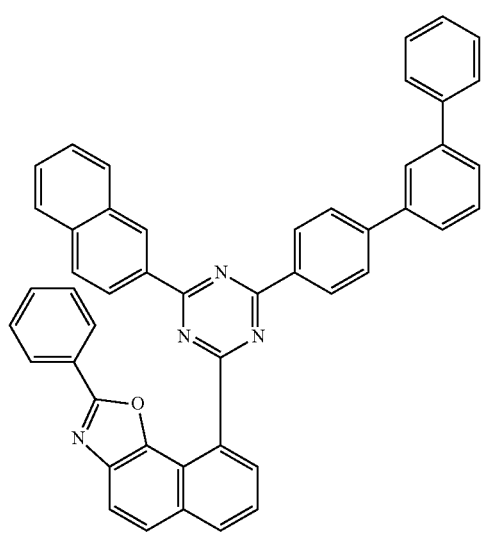

84
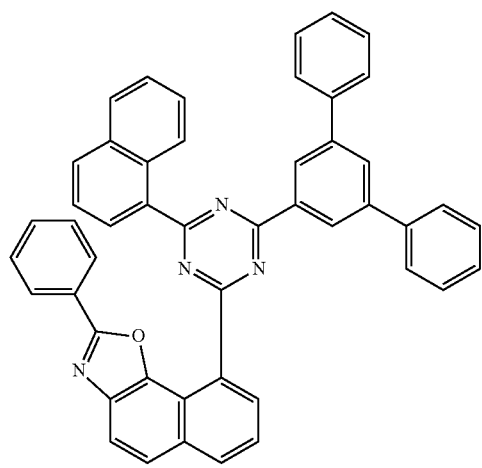
85
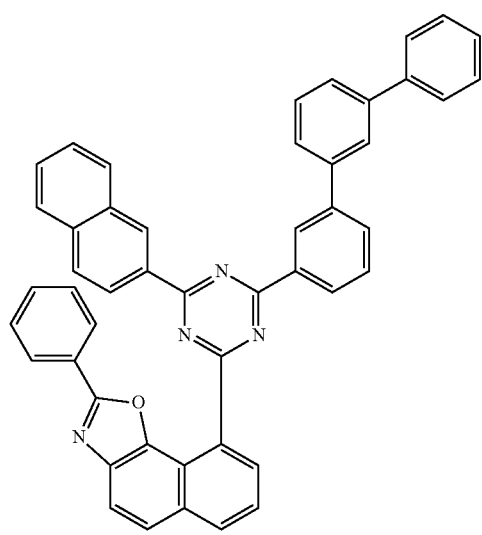
86
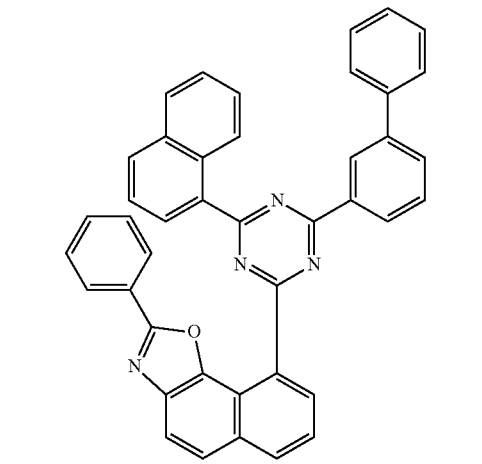
87
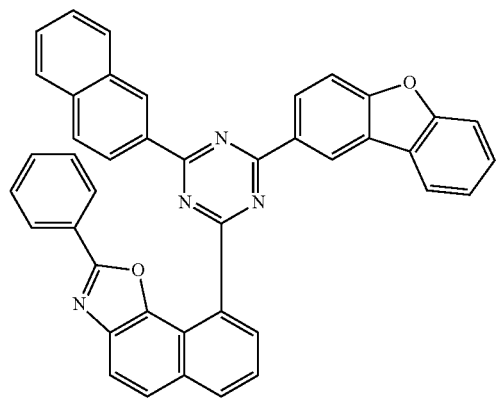
88
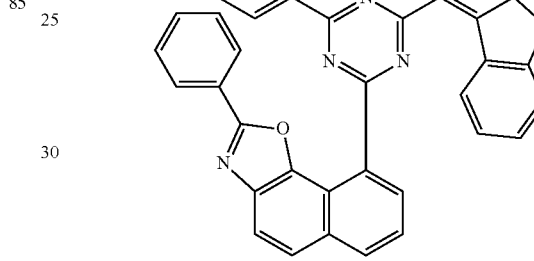
89
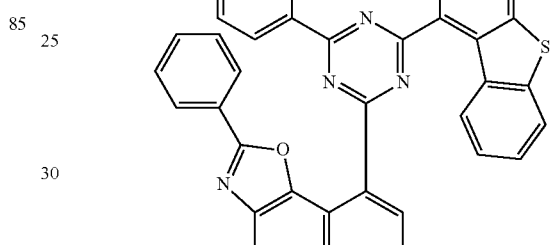
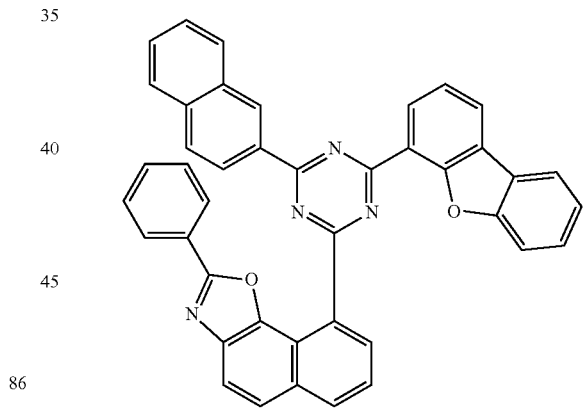
90
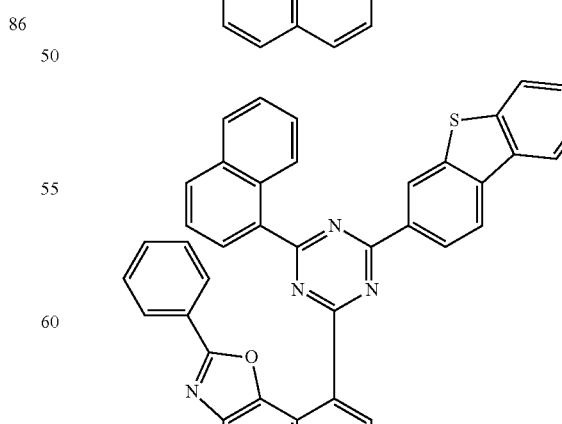

365
-continued
91
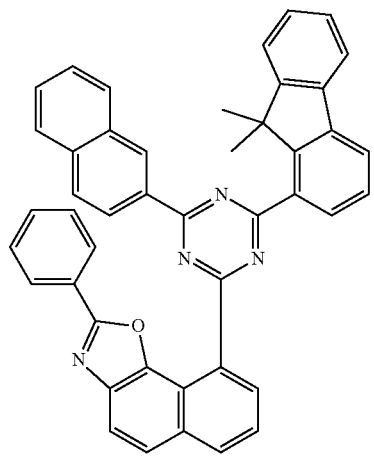
92
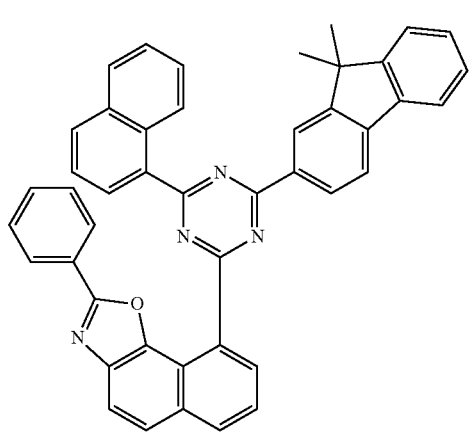
93
366
-continued
94
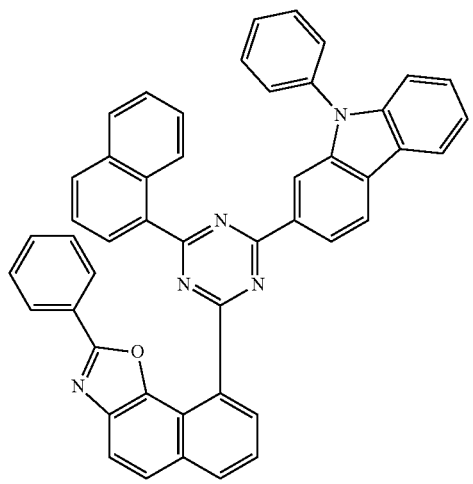
95
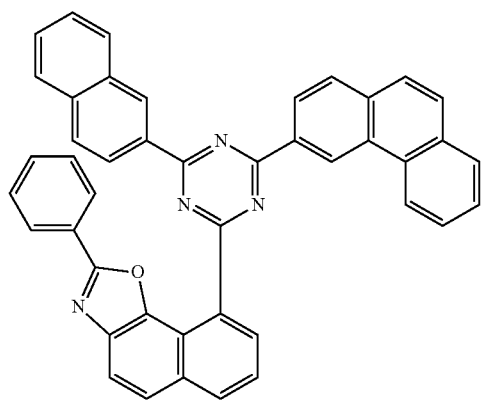
96
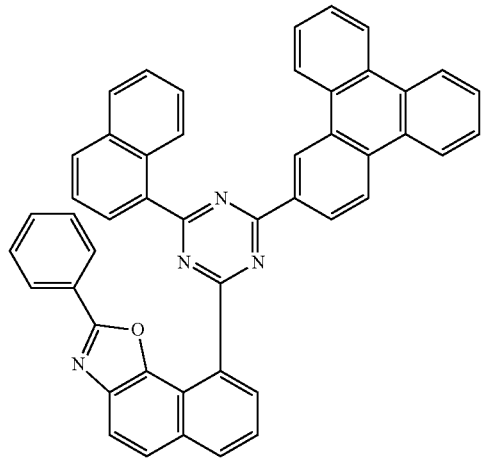

-continued
97
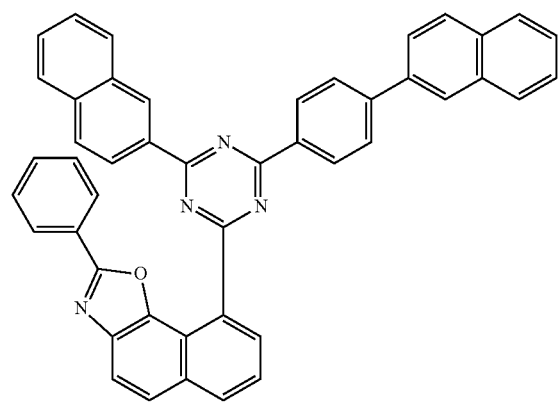 [SMILES: c1ccc(-c2nc3ccc4cccc(-c5nc(-c6ccc(-c7ccc8ccccc8c7)cc6)nc(-c6ccc7ccccc7c6)n5)c4c3o2)cc1]
98
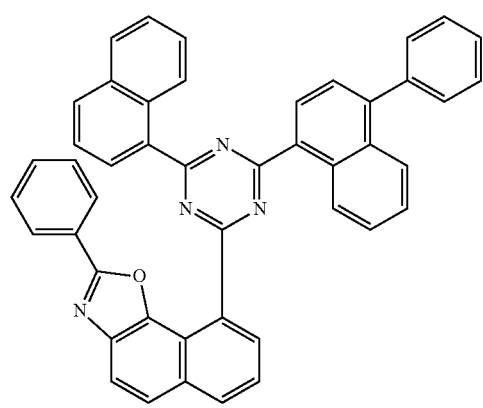
99
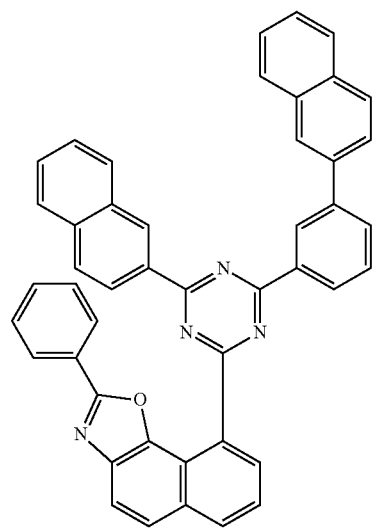
-continued
100
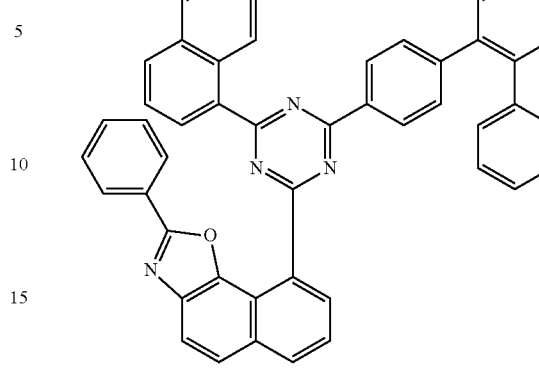
101
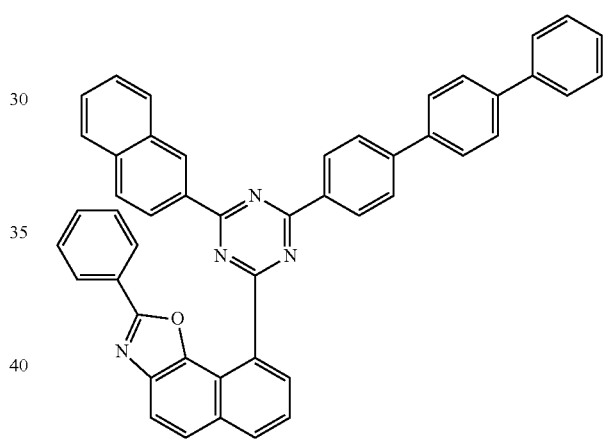
102
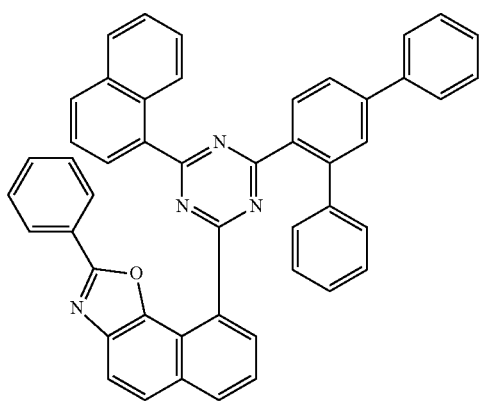

369
-continued
103
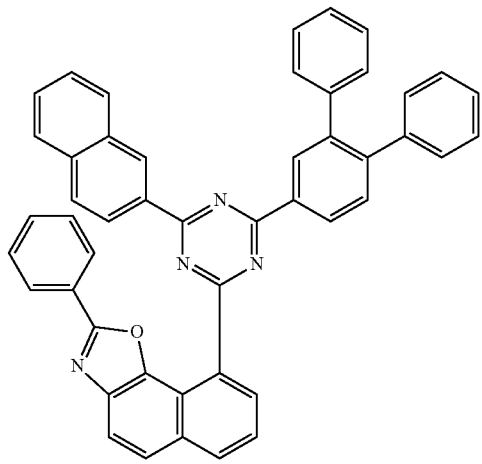
104
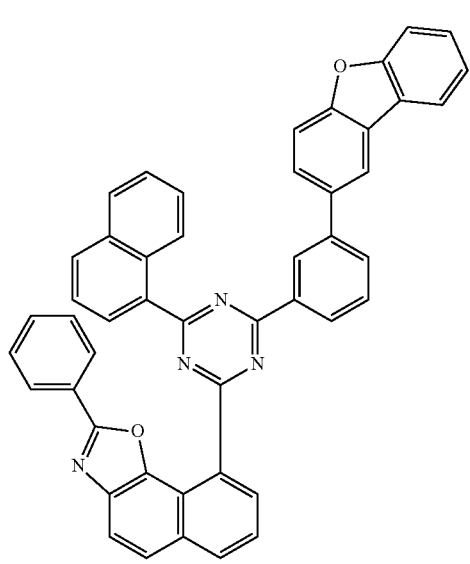
105
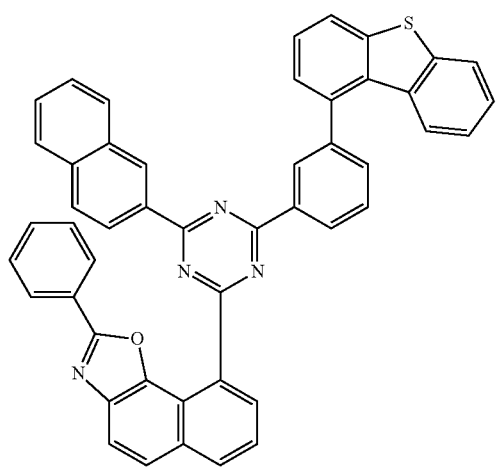
370
-continued
106
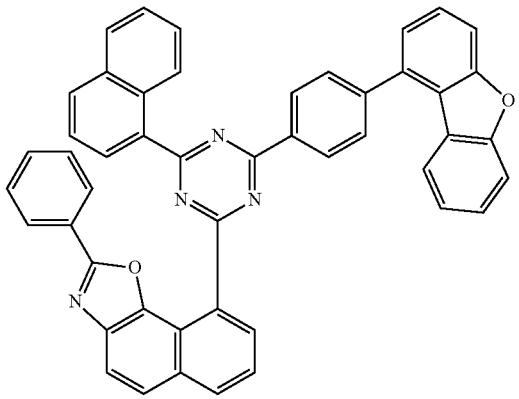
107
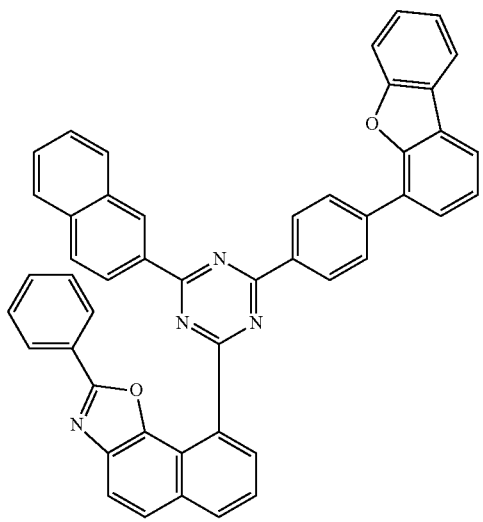
108
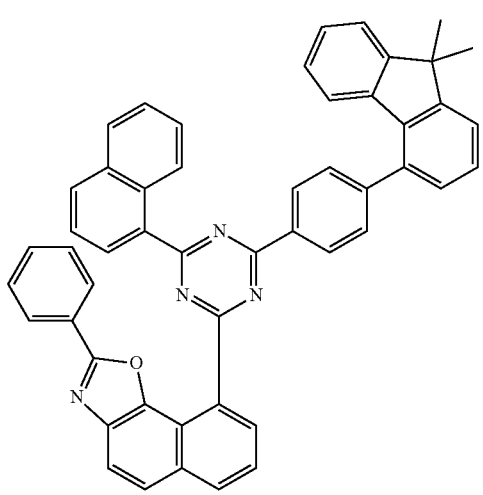

145
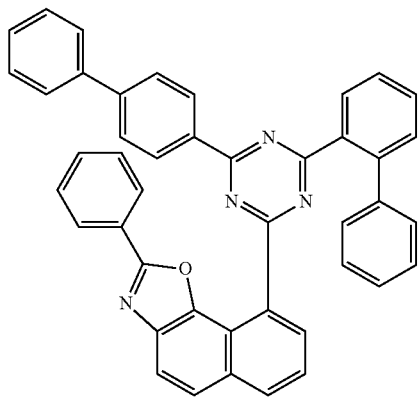
146
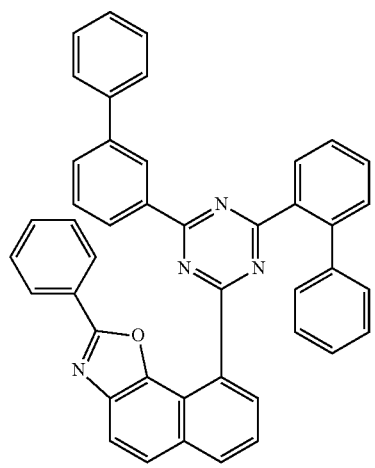
147
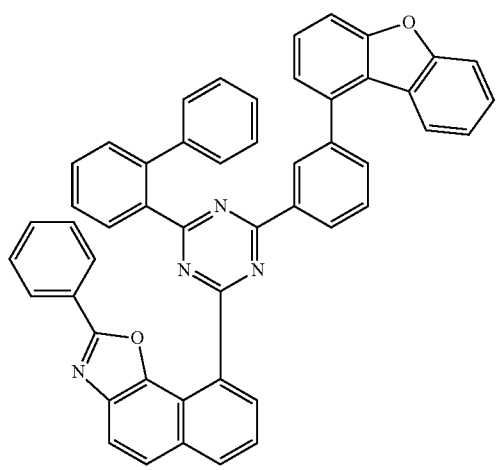
148
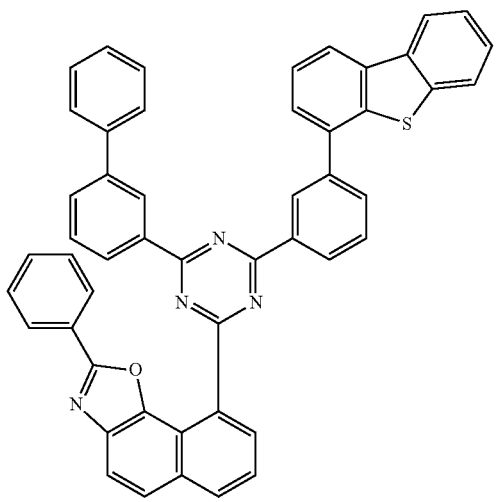
149
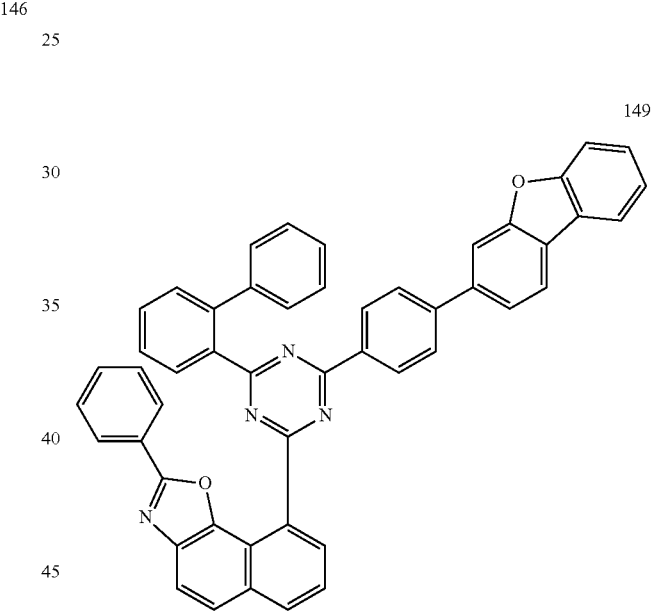
150
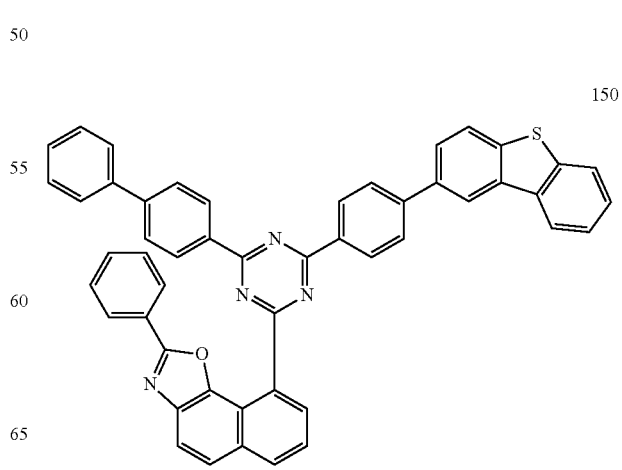

-continued
151
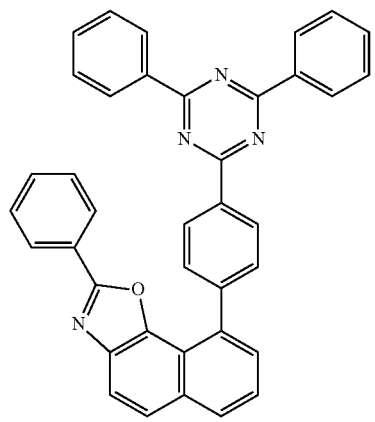
152
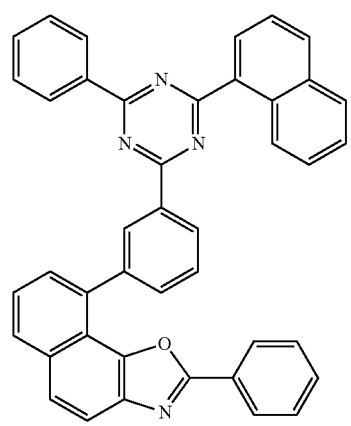
153
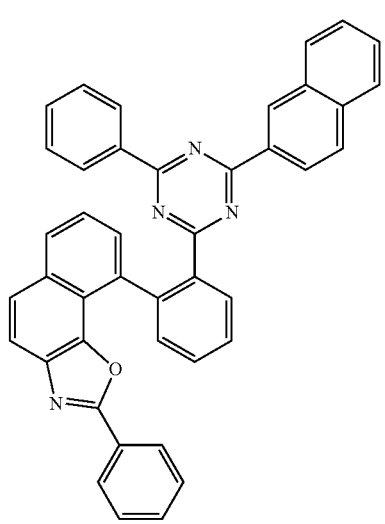
-continued
154
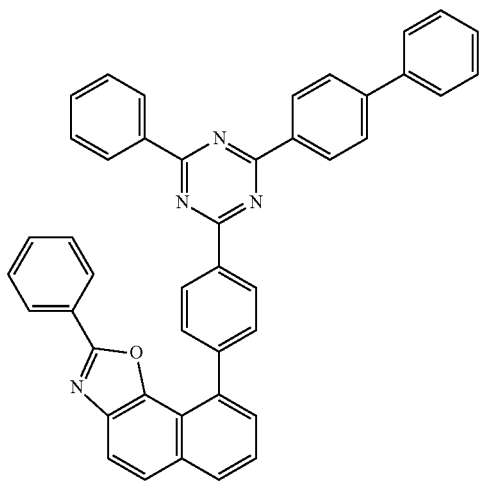 [SMILES: c1ccc(-c2ccc(-c3nc(-c4ccccc4)nc(-c4ccc(-c5cccc6ccc7nc(-c8ccccc8)oc7c56)cc4)n3)cc2)cc1]
155
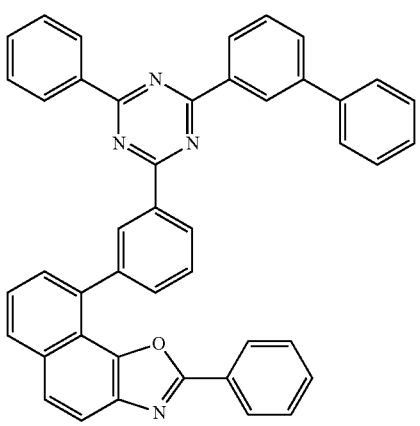
156
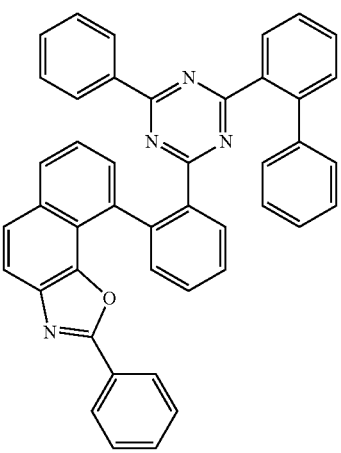

157
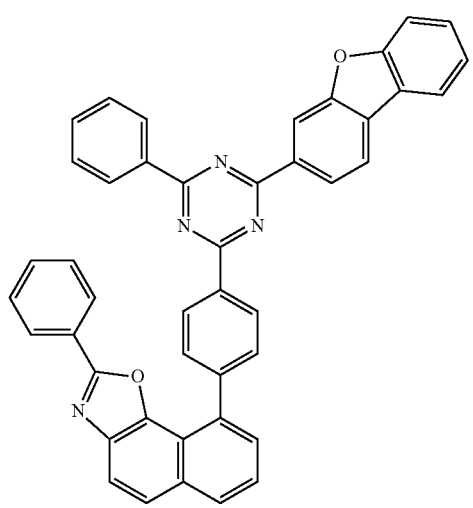 [SMILES: c1ccc(-c2nc(-c3ccc(-c4cccc5ccc6nc(-c7ccccc7)oc6c45)cc3)nc(-c3ccc4c(c3)oc3ccccc34)n2)cc1]
158
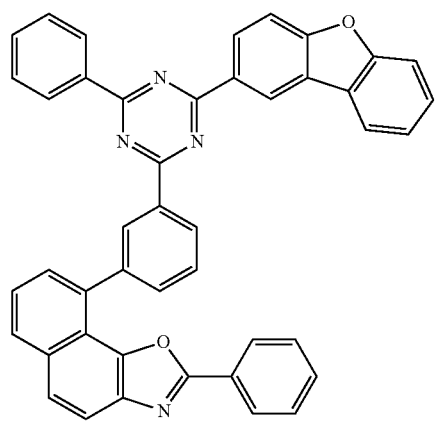
159
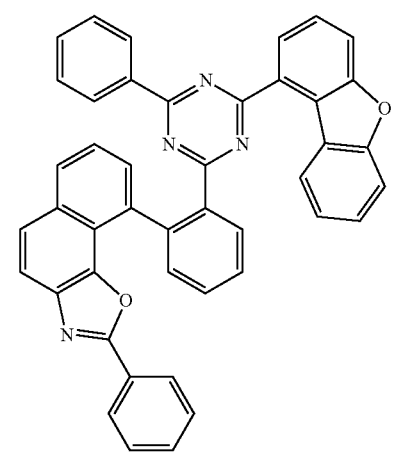
160
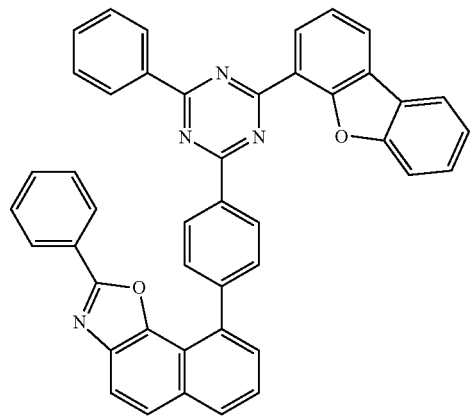
161
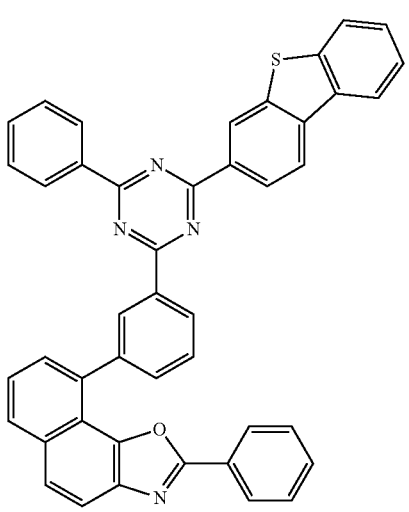 [SMILES: c1ccc(-c2nc(-c3cccc(-c4cccc5ccc6nc(-c7ccccc7)oc6c45)c3)nc(-c3ccc4c(c3)sc3ccccc34)n2)cc1]
162
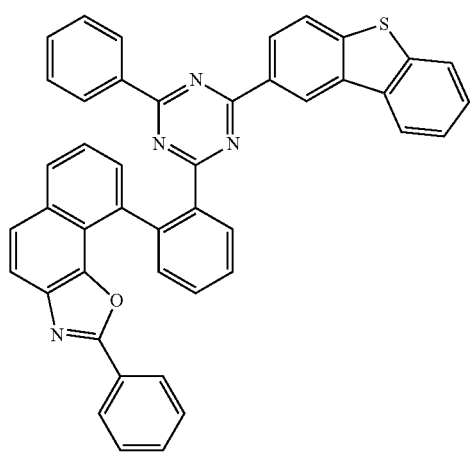

377
-continued
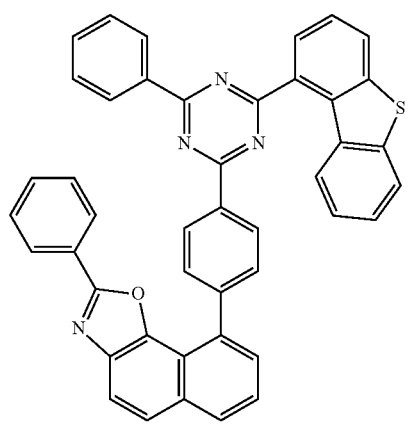 [SMILES: c1ccc(-c2nc(-c3ccc(-c4cccc5ccc6nc(-c7ccccc7)oc6c45)cc3)nc(-c3cccc4sc5ccccc5c34)n2)cc1]
163
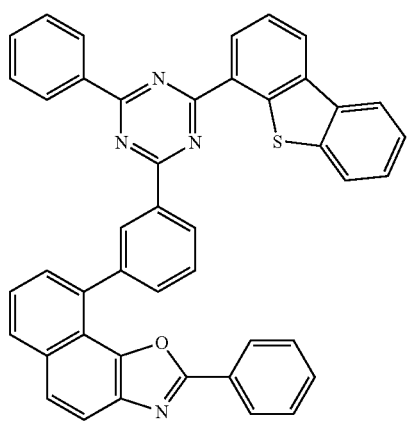 [SMILES: c1ccc(-c2nc(-c3cccc(-c4cccc5ccc6nc(-c7ccccc7)oc6c45)c3)nc(-c3cccc4c3sc3ccccc34)n2)cc1]
164
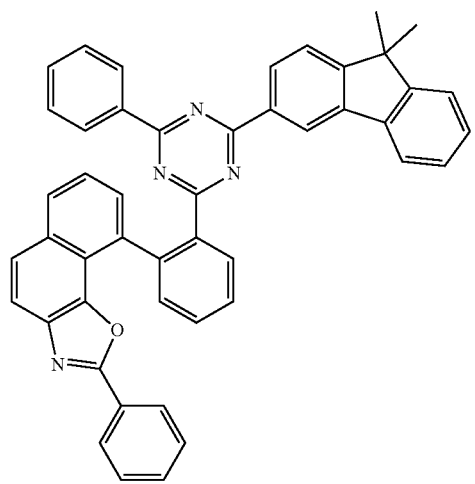
165
378
-continued
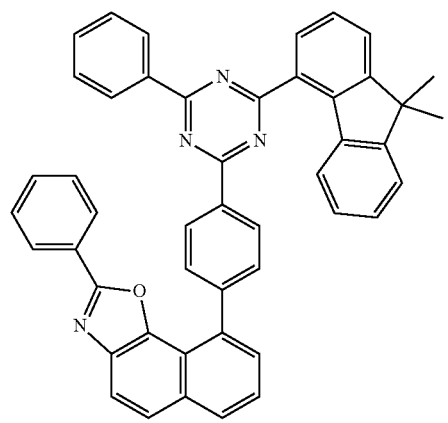
166
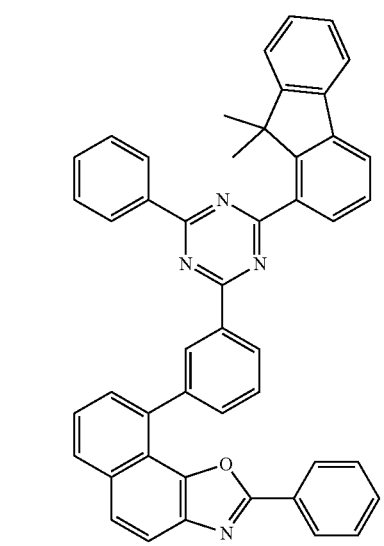
167
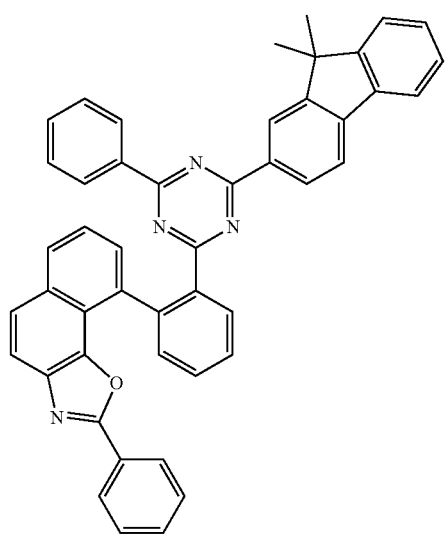
168

-continued
169
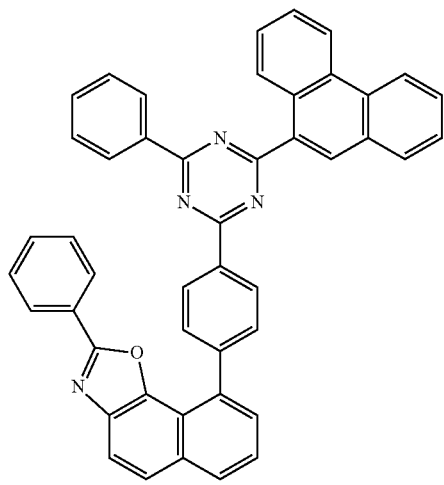
170
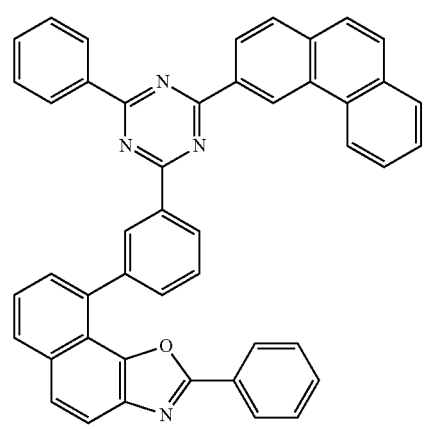
171
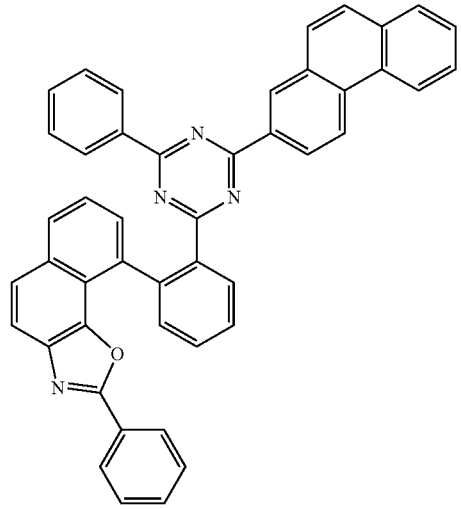
-continued
172
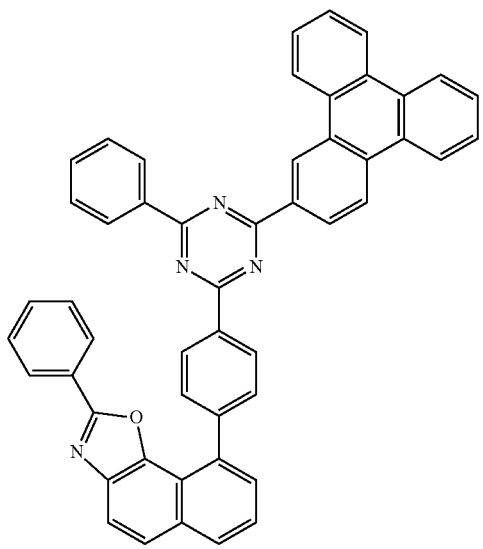
173
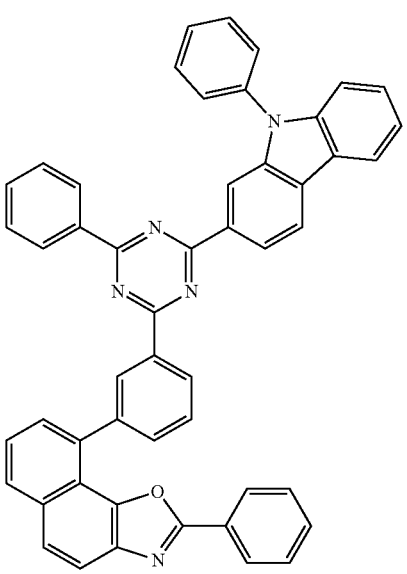
174
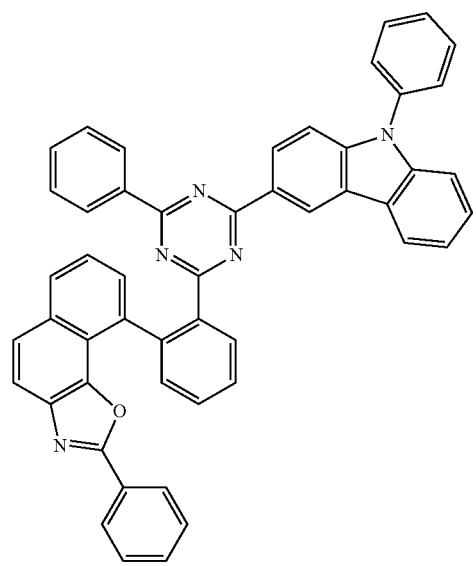

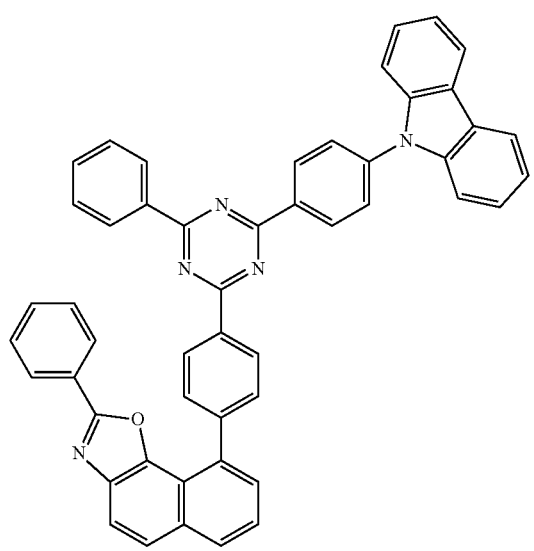
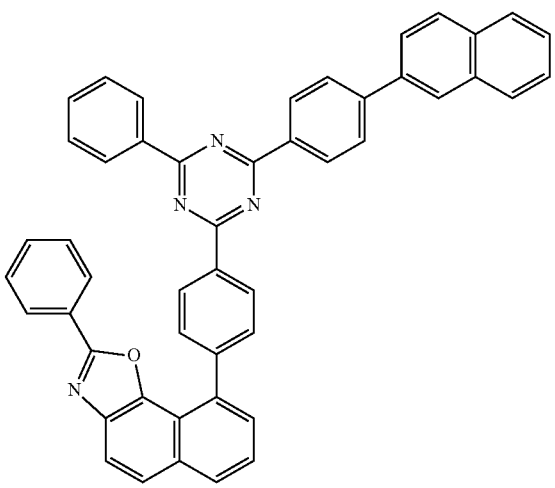 [SMILES: c1ccc(-c2nc(-c3ccc(-c4ccc5ccccc5c4)cc3)nc(-c3ccc(-c4cccc5ccc6nc(-c7ccccc7)oc6c45)cc3)n2)cc1]

181
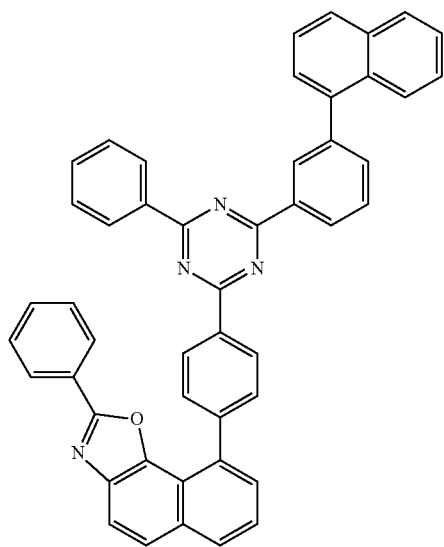
182
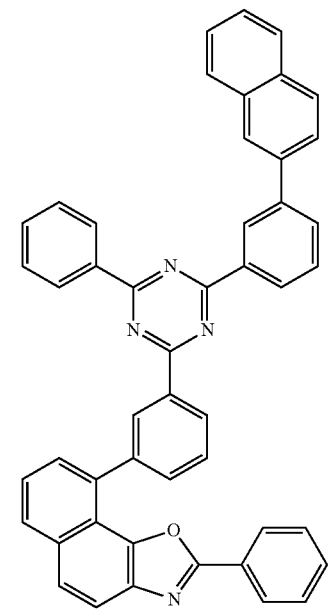
183
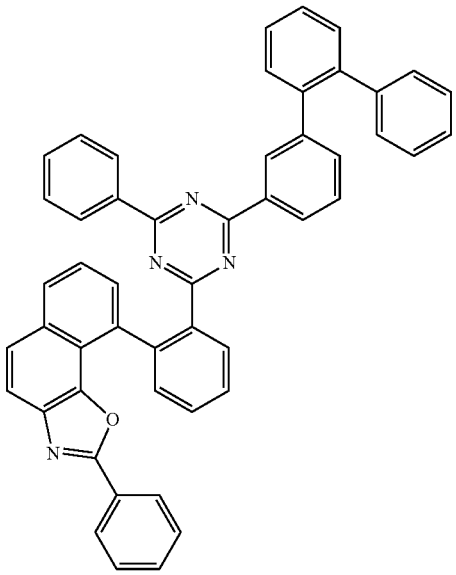
184
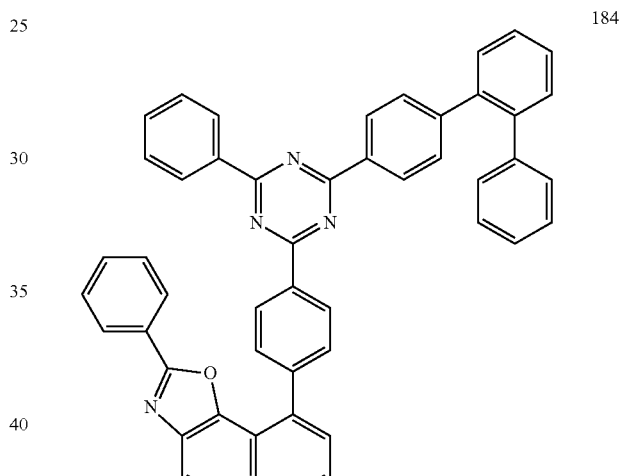
185
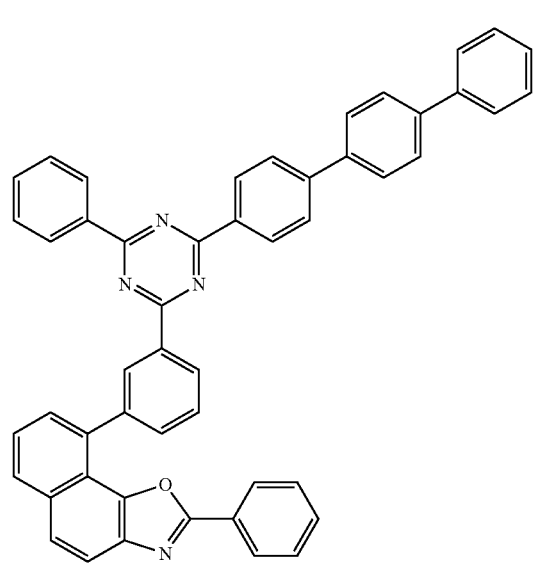

186
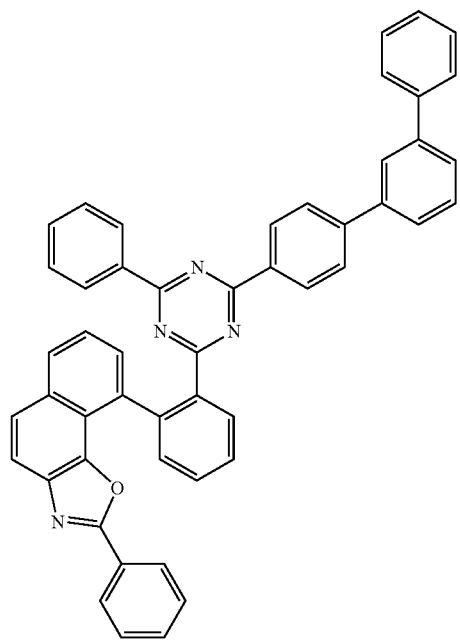
187
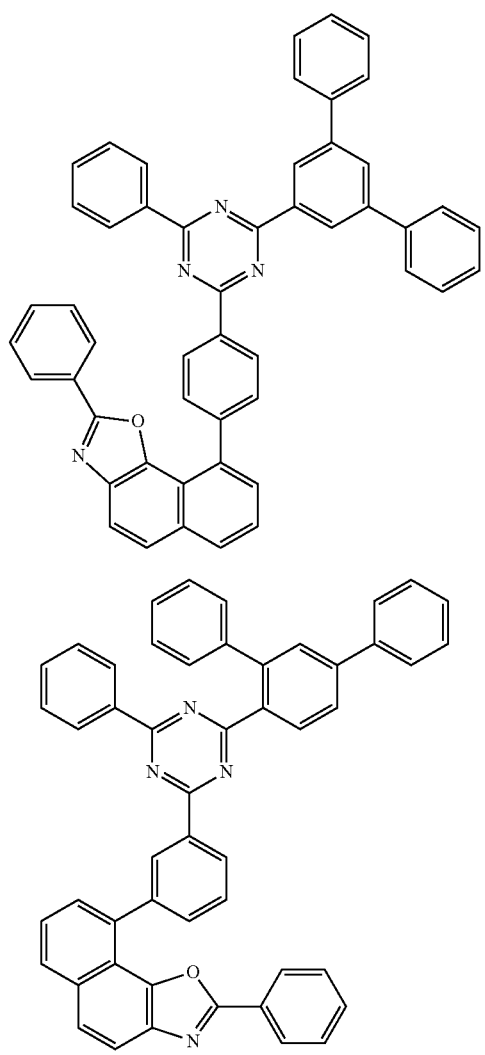
188
189
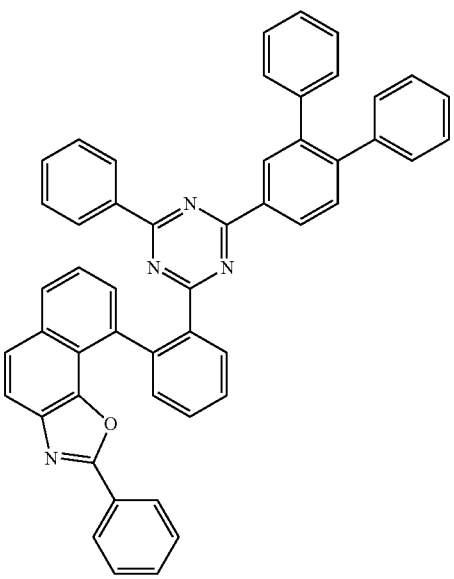
190
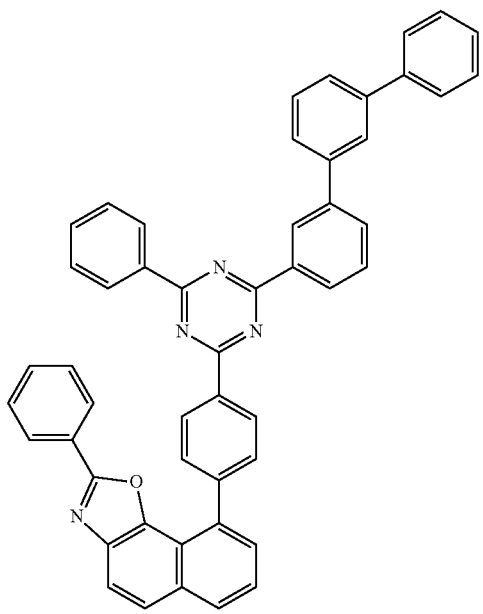

191
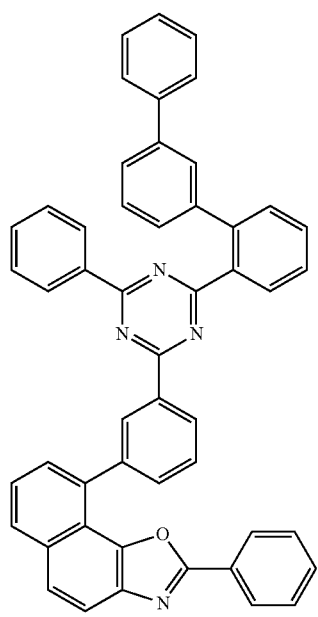
192
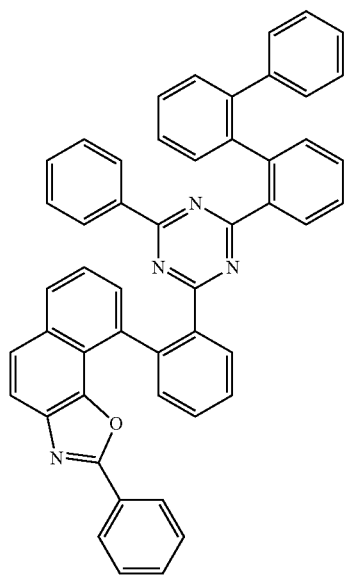
193
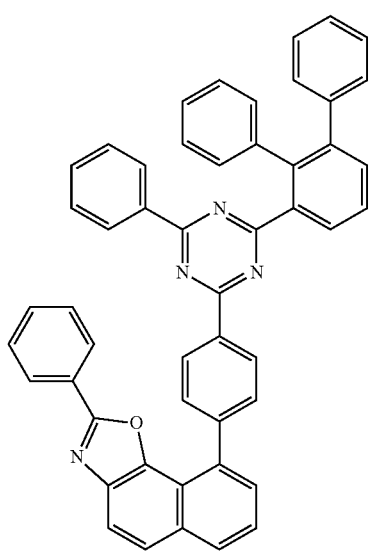
194
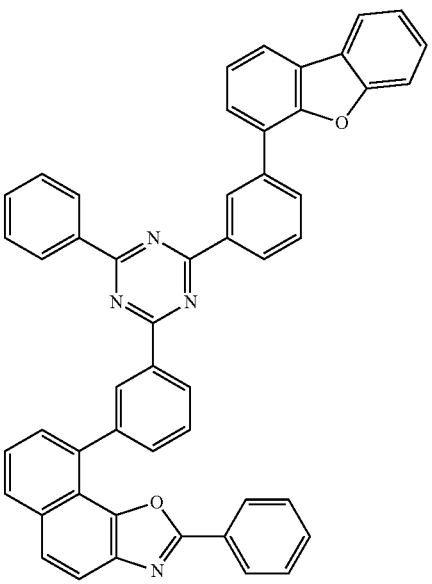

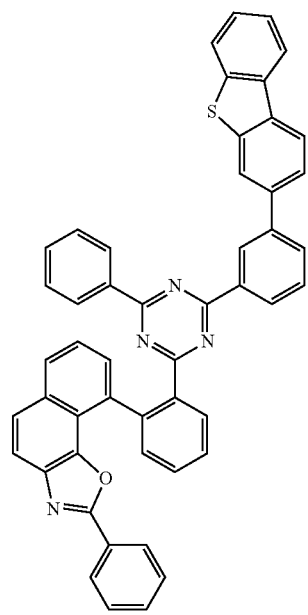
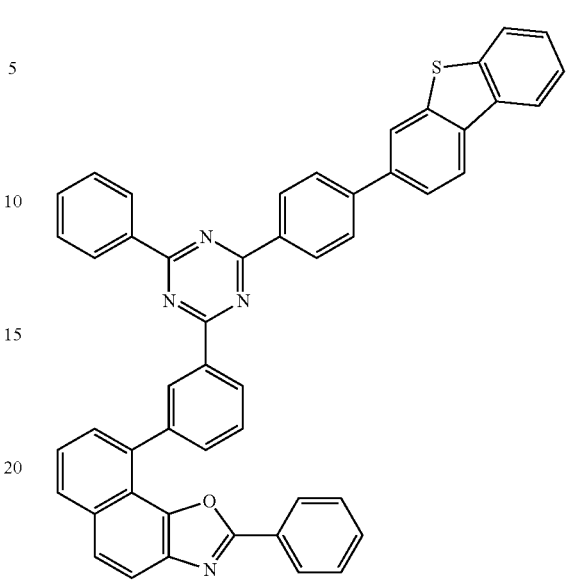
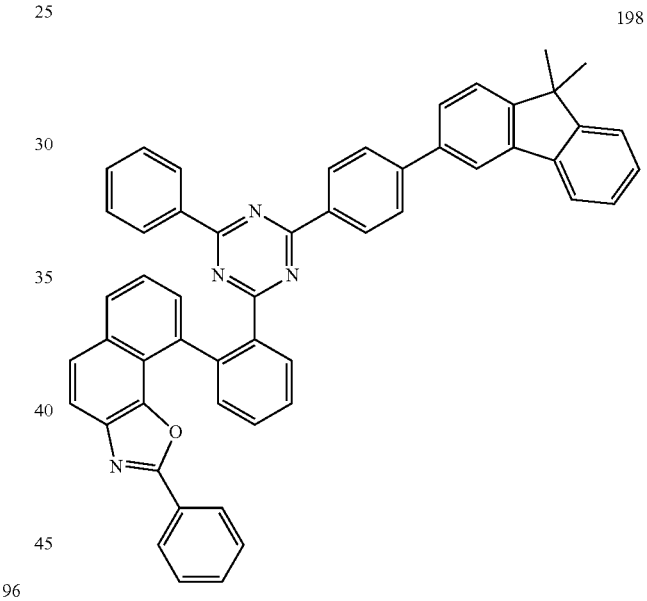
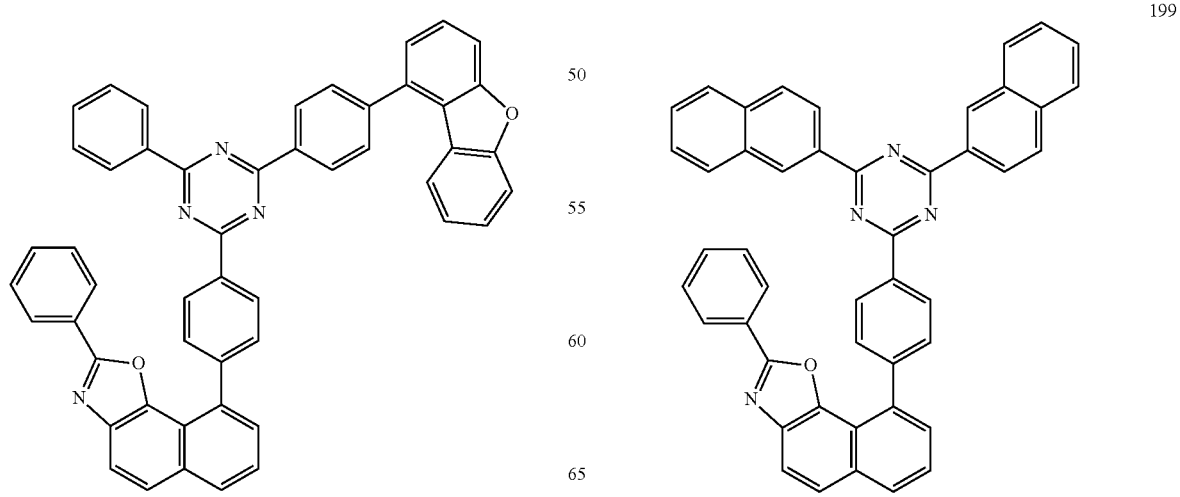

391
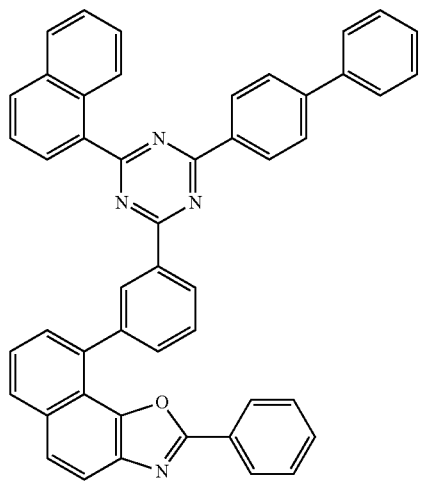 [SMILES: c1ccc(-c2ccc(-c3nc(-c4cccc(-c5cccc6ccc7nc(-c8ccccc8)oc7c56)c4)nc(-c4cccc5ccccc45)n3)cc2)cc1]
200
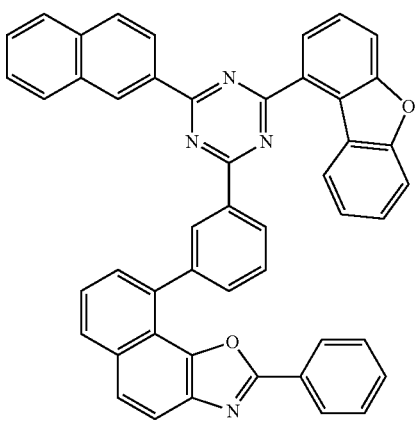 [SMILES: c1ccc(-c2nc3ccc4cccc(-c5cccc(-c6nc(-c7ccc8ccccc8c7)nc(-c7cccc8oc9ccccc9c78)n6)c5)c4c3o2)cc1]
203
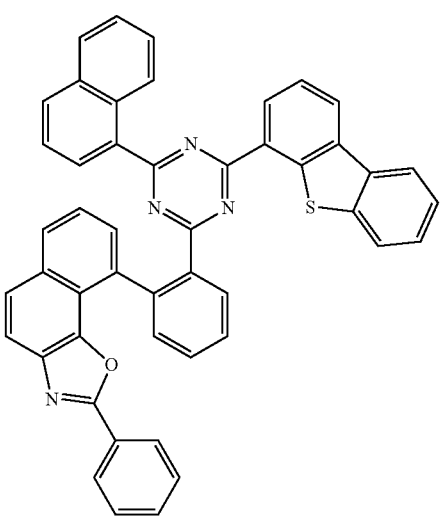
204
392
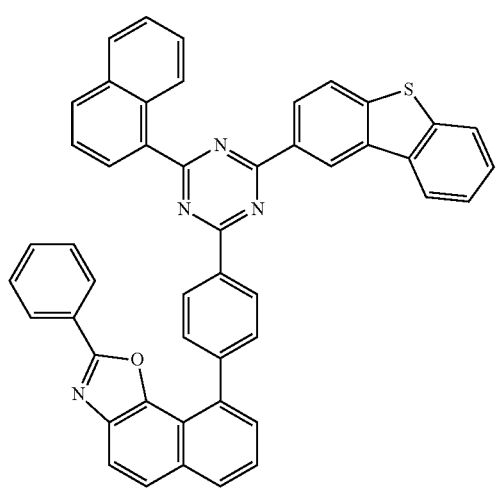
201
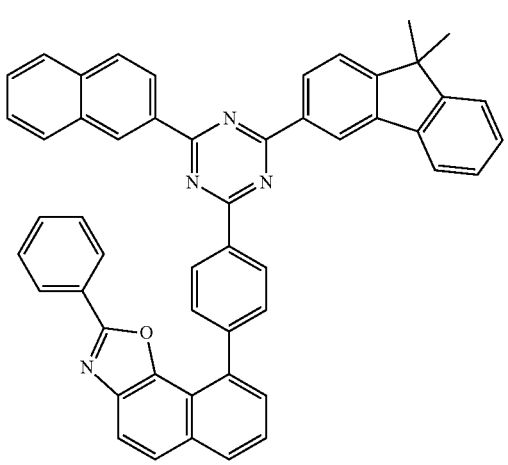 [SMILES: CC1(C)c2ccccc2-c2cc(-c3nc(-c4ccc(-c5cccc6ccc7nc(-c8ccccc8)oc7c56)cc4)nc(-c4ccc5ccccc5c4)n3)ccc21]
202
205

206
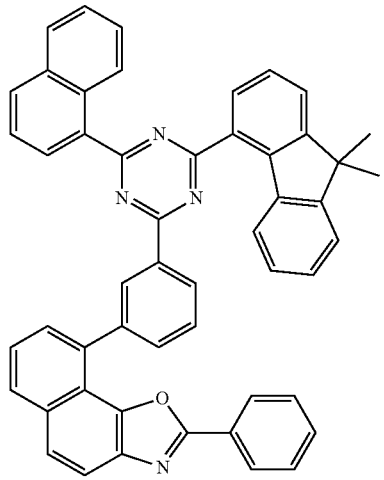
207
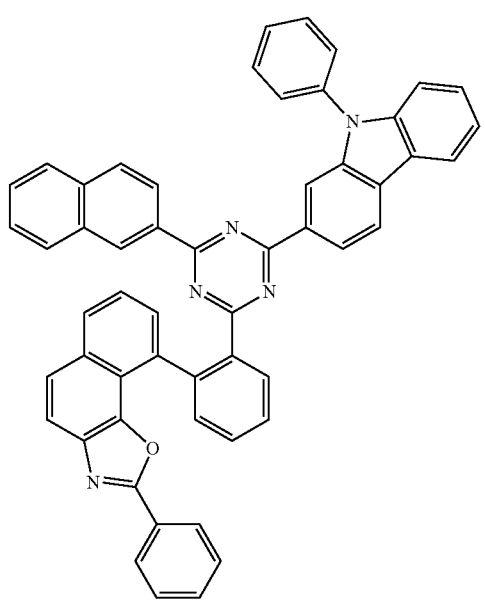
208
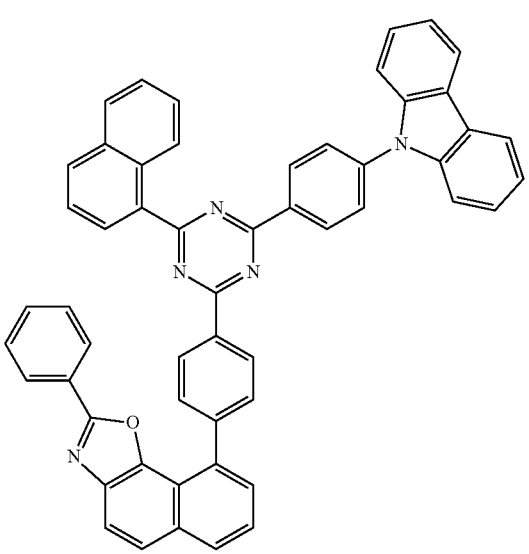
209
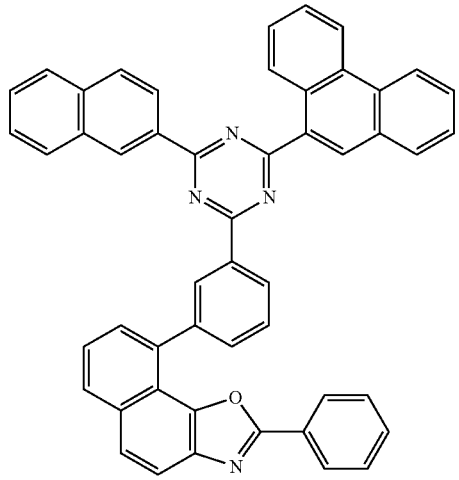
210
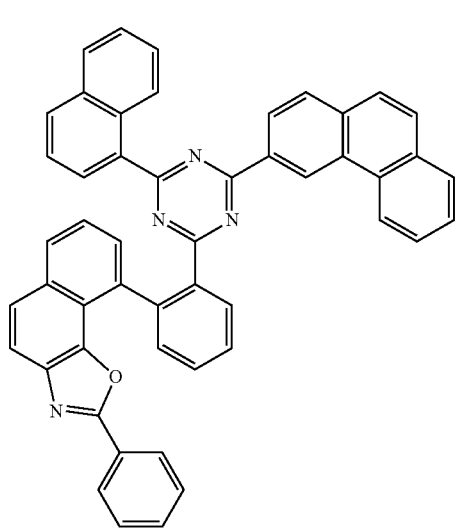
211
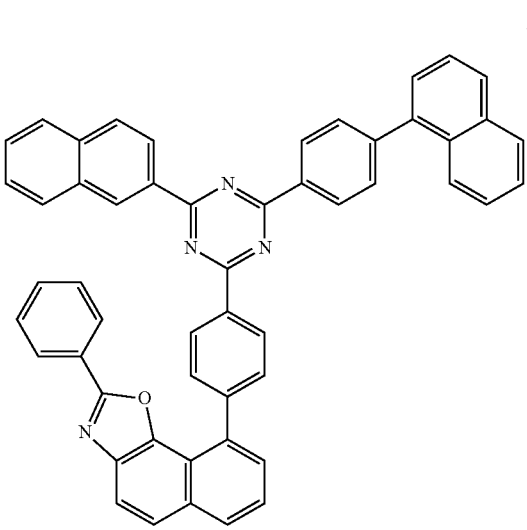

395
-continued
212
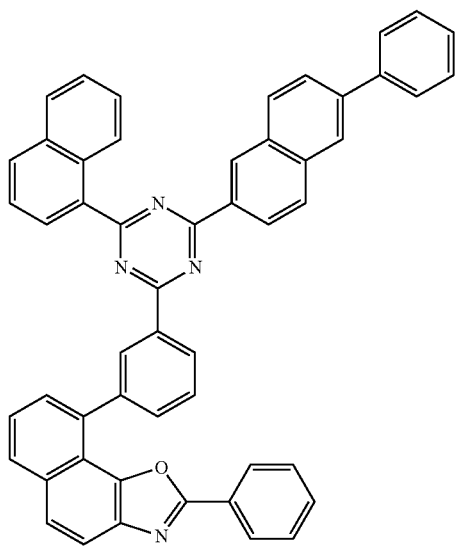
213
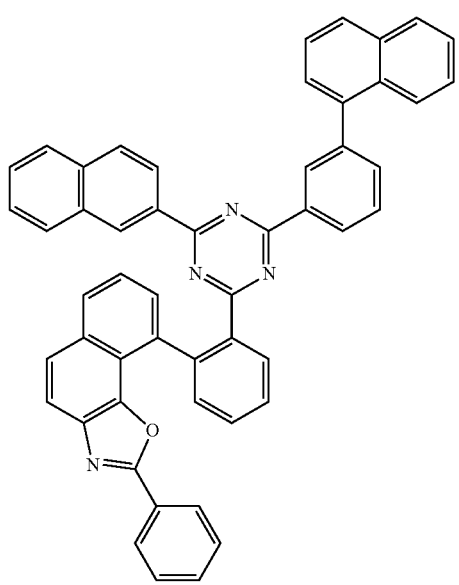
214
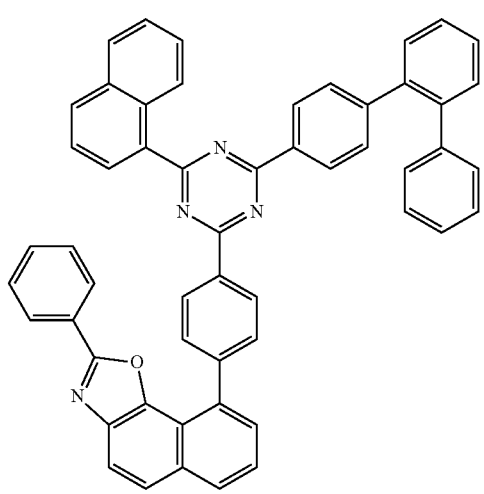
396
-continued
215
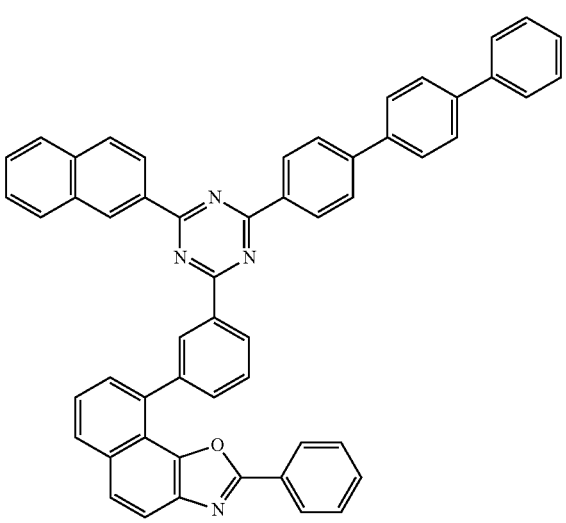
216
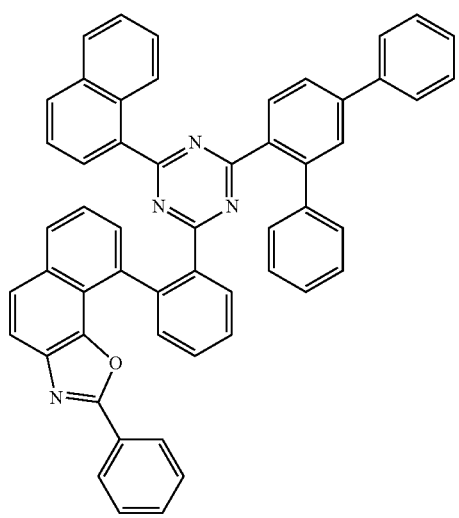
217
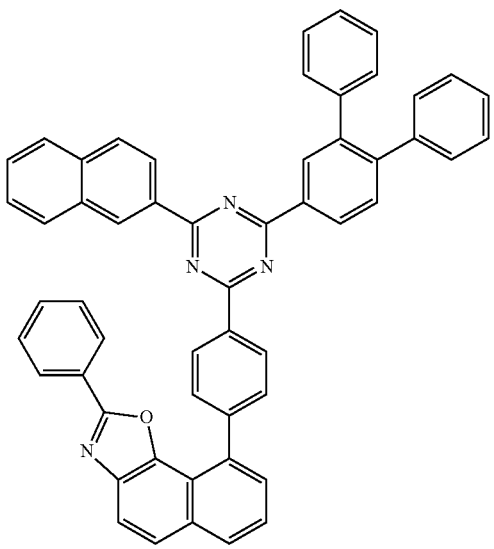

218
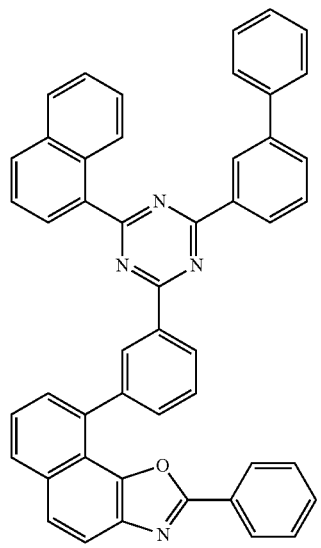
219
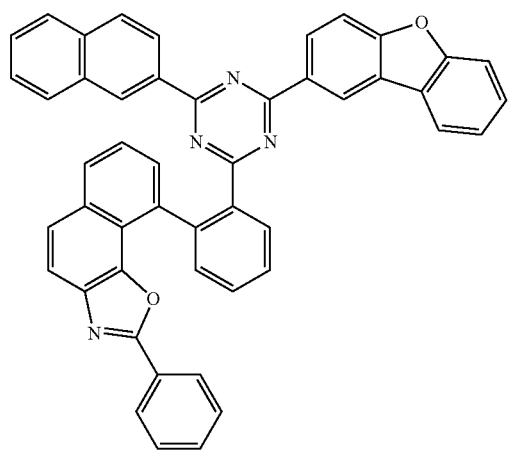 [SMILES: c1ccc(-c2nc3ccc4cccc(-c5ccccc5-c5nc(-c6ccc7ccccc7c6)nc(-c6ccc7oc8ccccc8c7c6)n5)c4c3o2)cc1]
220
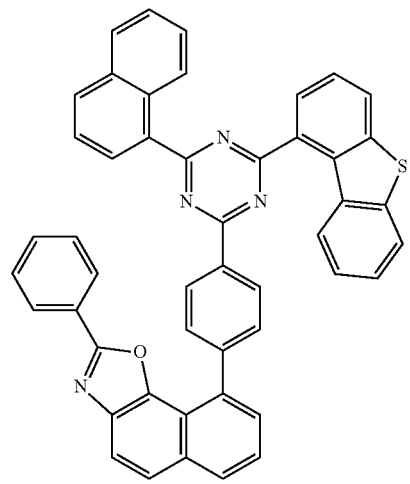
221
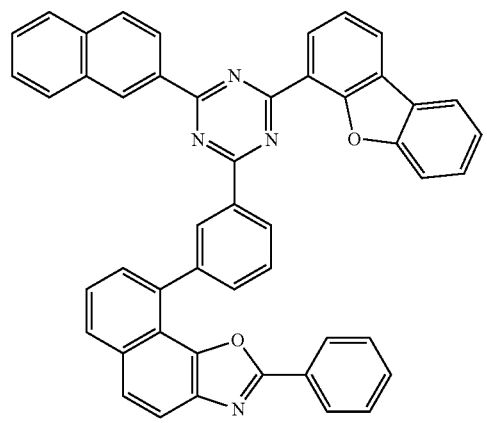
222
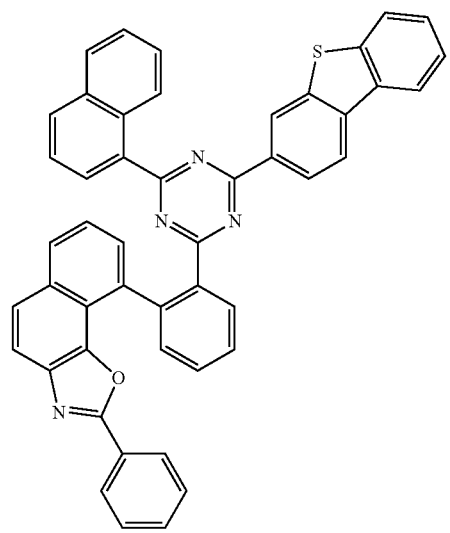
223
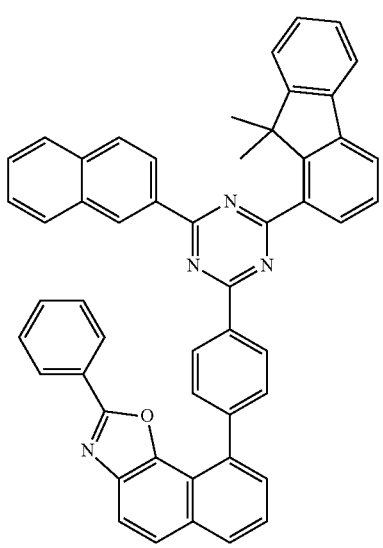

399
-continued
224
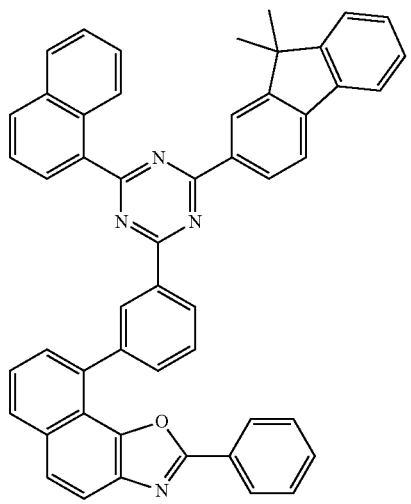
225
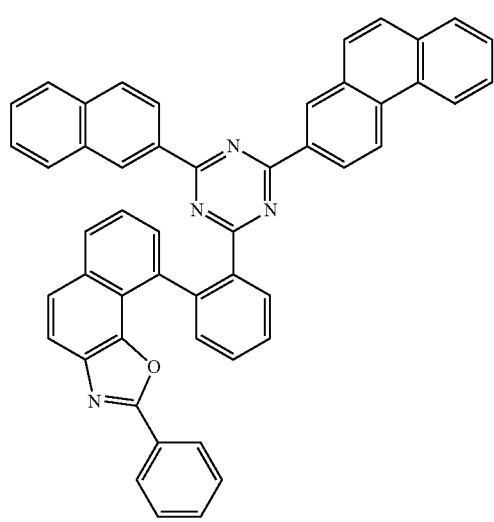
226
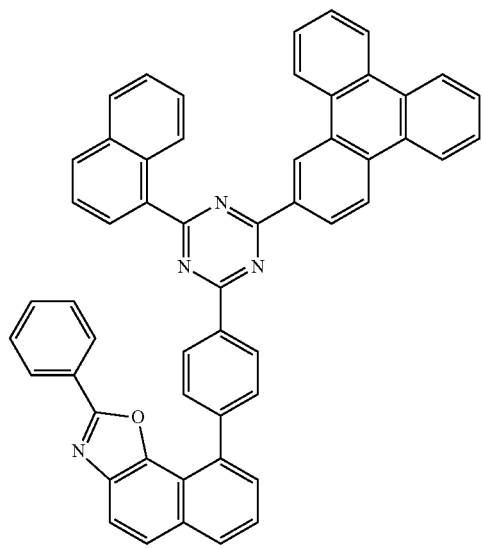
400
-continued
227
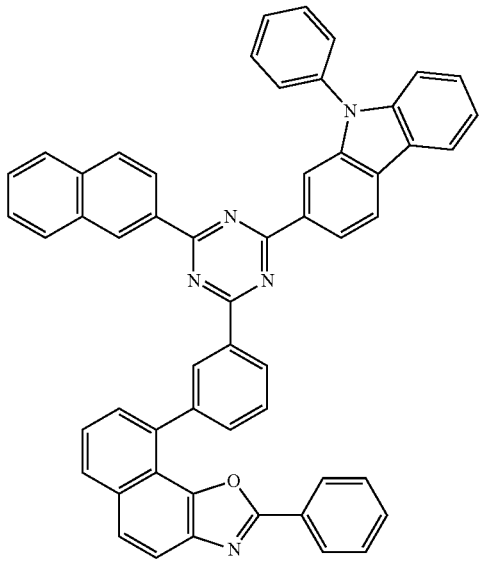 [SMILES: c1ccc(-c2nc3ccc4cccc(-c5cccc(-c6nc(-c7ccc8ccccc8c7)nc(-c7ccc8c9ccccc9n(-c9ccccc9)c8c7)n6)c5)c4c3o2)cc1]
228
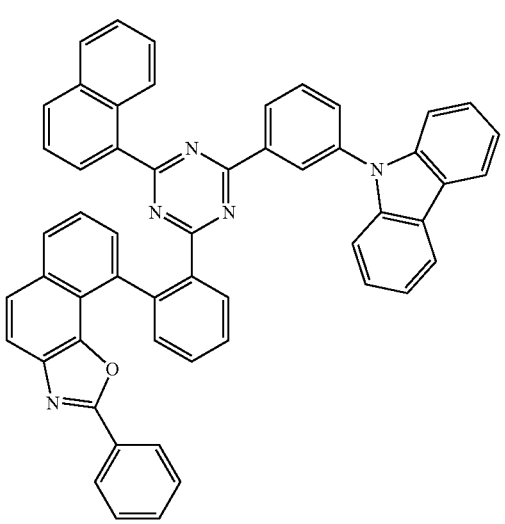
229
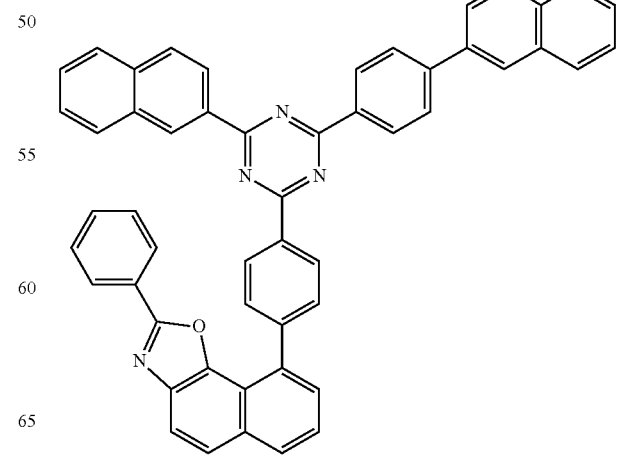

401
-continued
402
-continued
230
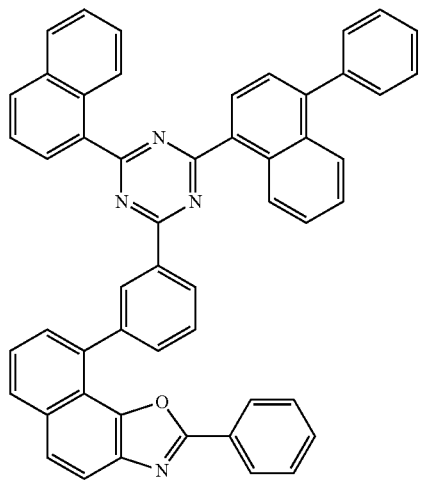
232
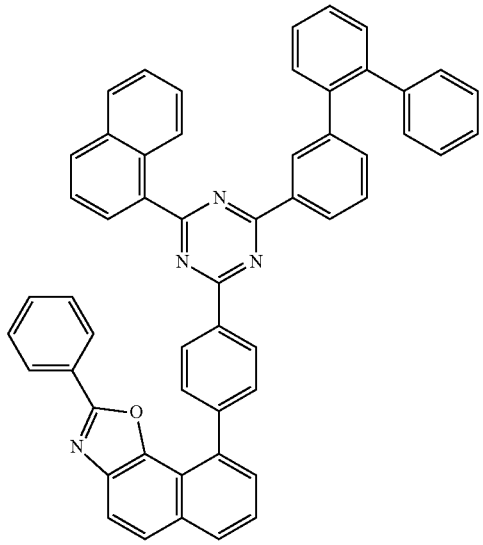
231
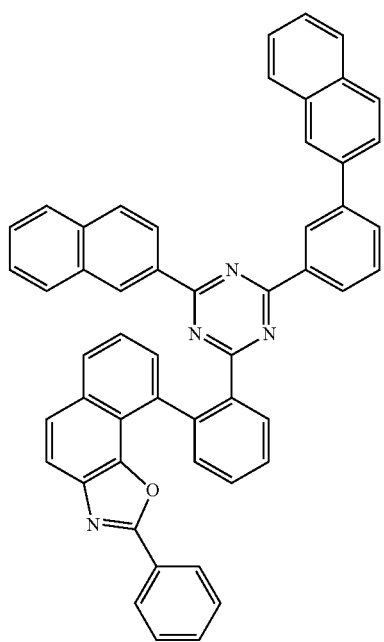
233
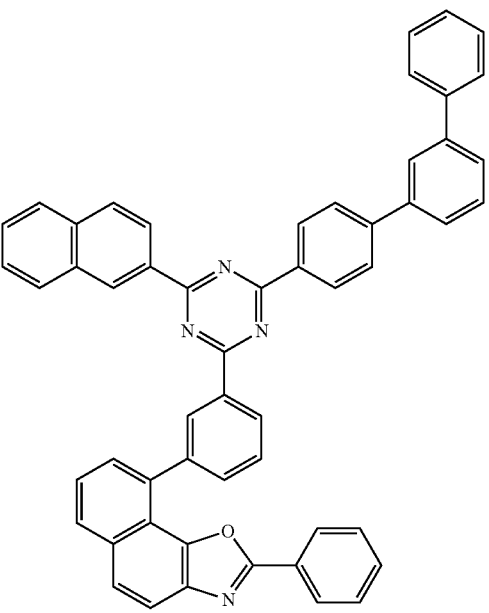

403
-continued
234
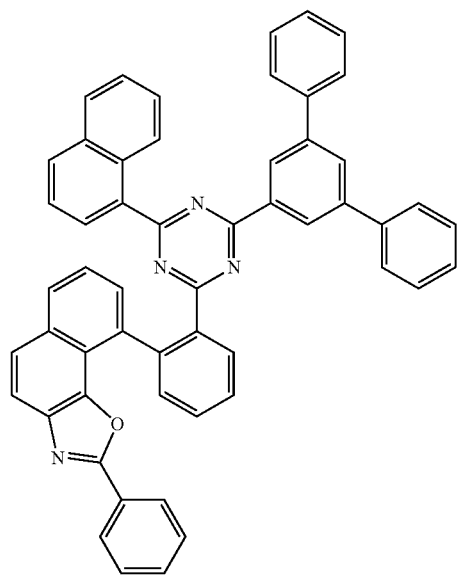
235
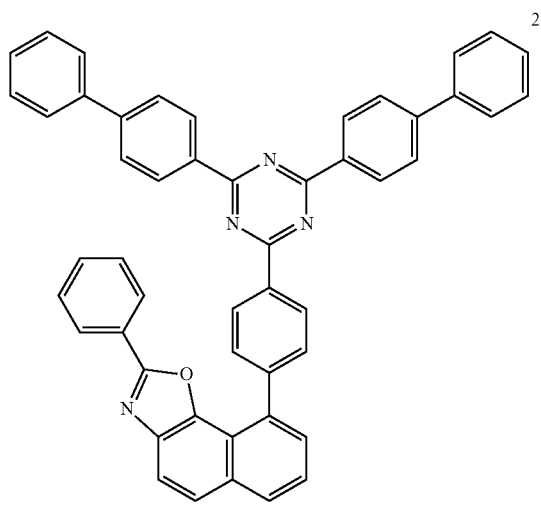
404
-continued
236
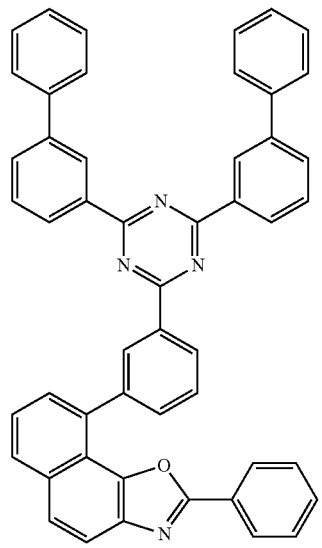
237
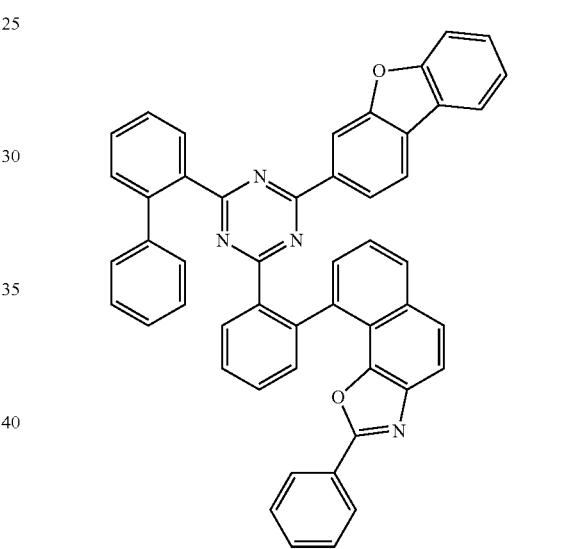
238
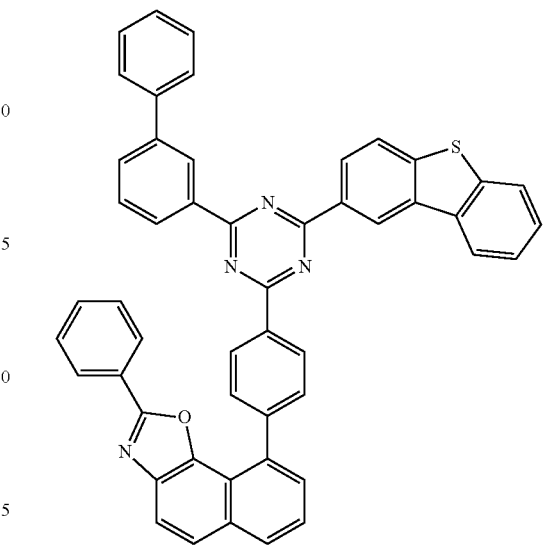

239
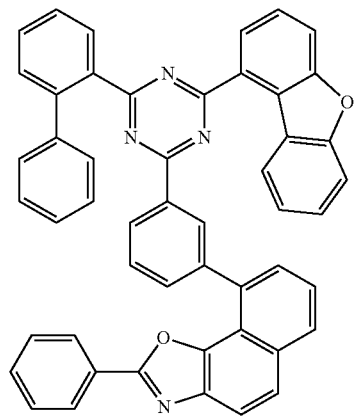
240
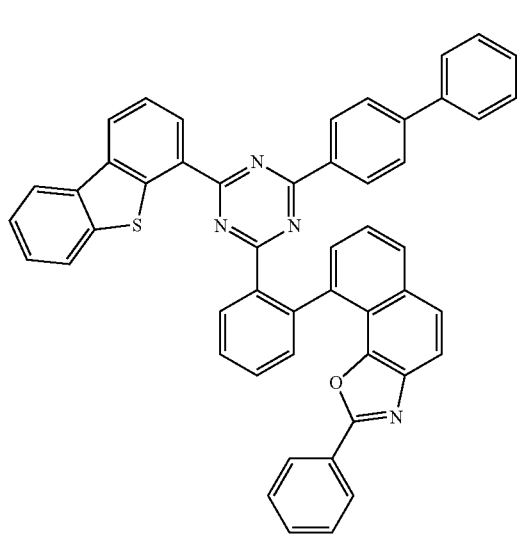
241
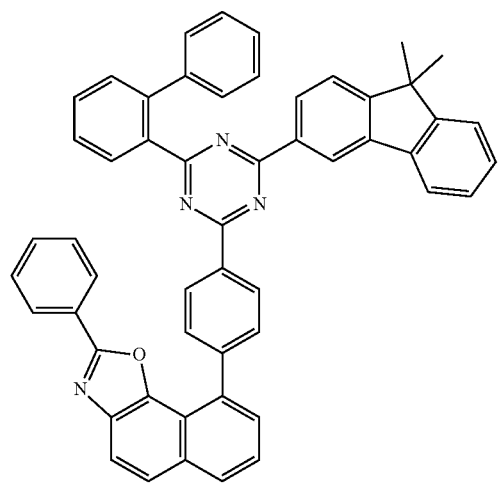
242
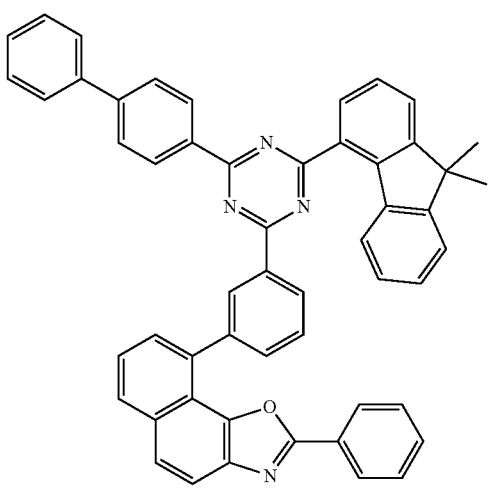 [SMILES: CC1(C)c2ccccc2-c2c(-c3nc(-c4ccc(-c5ccccc5)cc4)nc(-c4cccc(-c5cccc6ccc7nc(-c8ccccc8)oc7c56)c4)n3)cccc21]
243
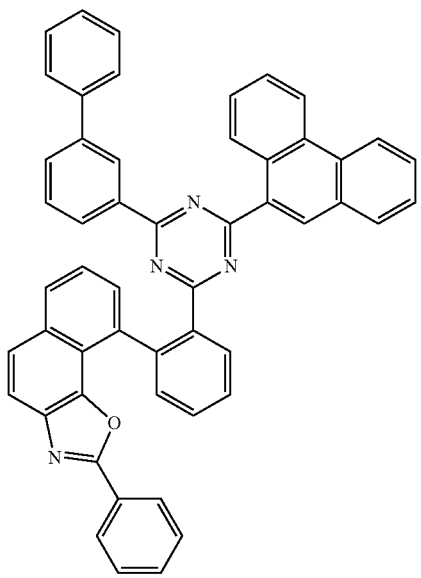
244
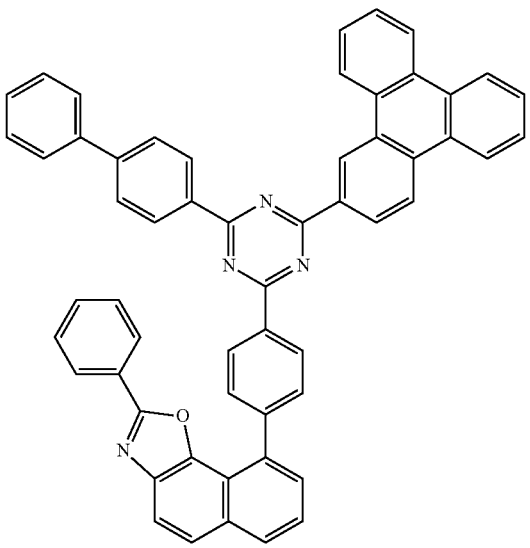

407
-continued
245
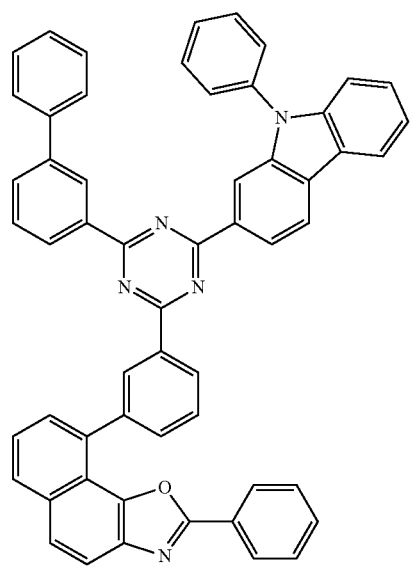
246
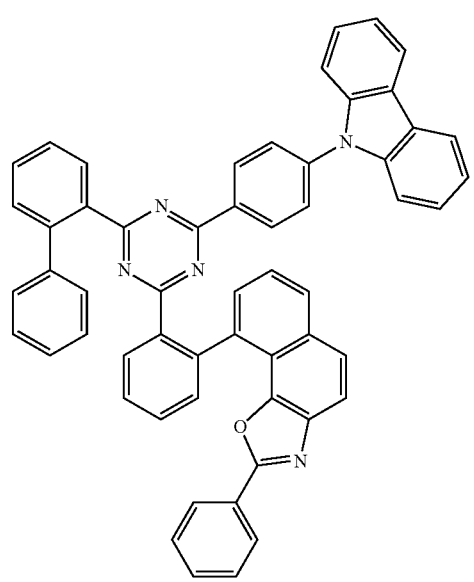
408
-continued
247
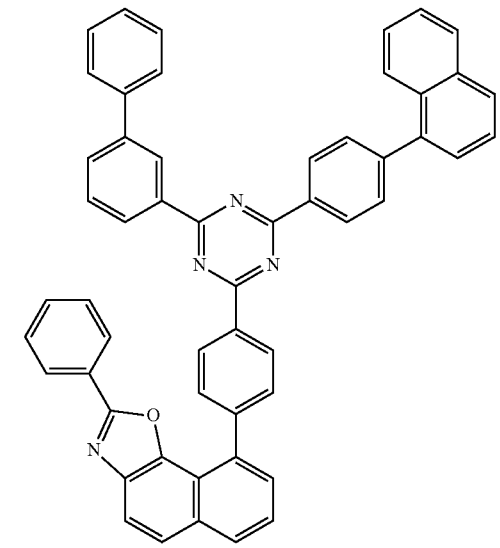
248
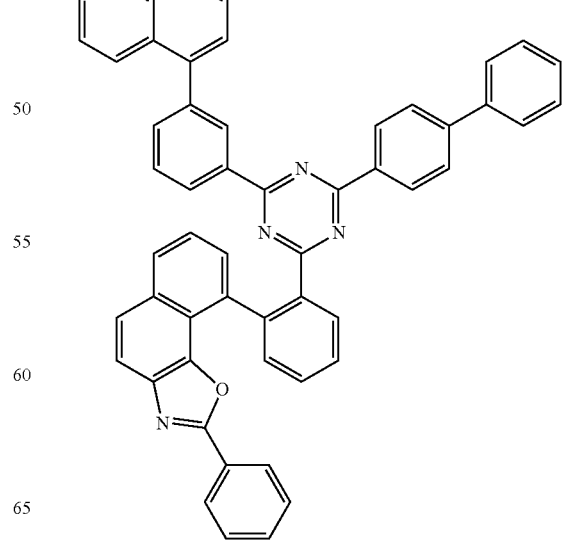
249

409
-continued
250
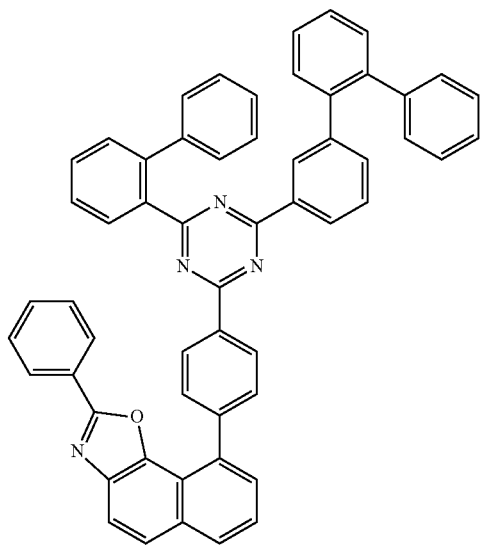
251
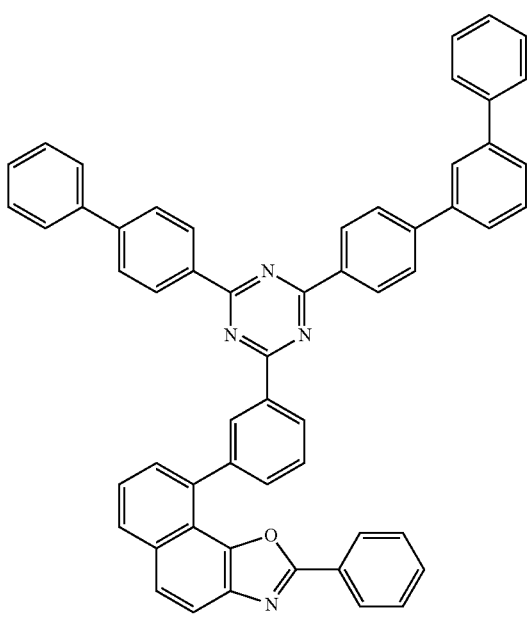
410
-continued
252
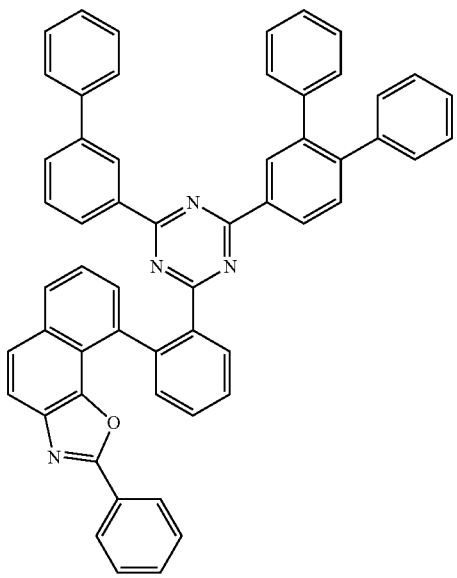
253
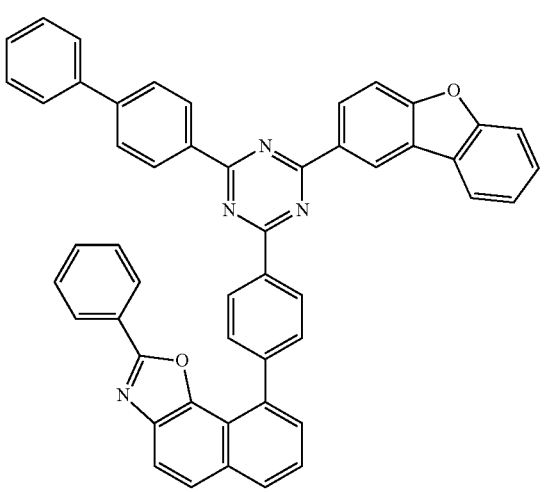
254
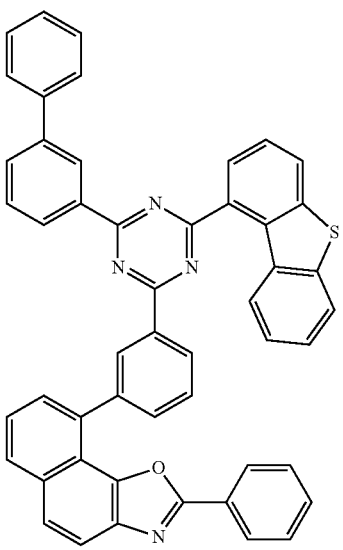

411
-continued
255
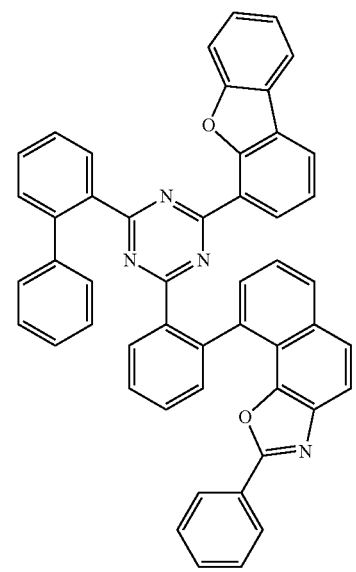
256
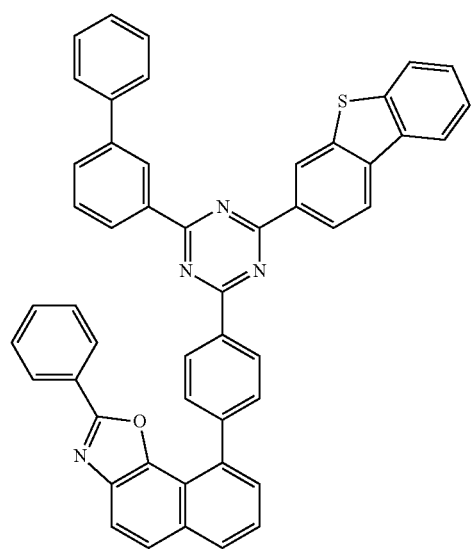
257
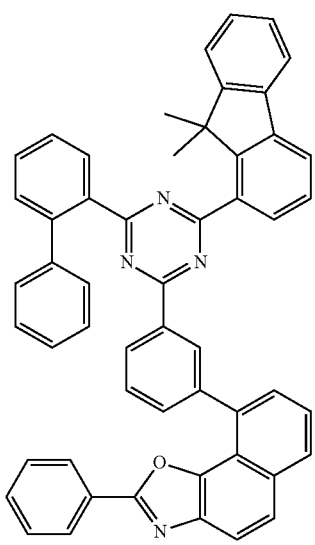
412
-continued
258
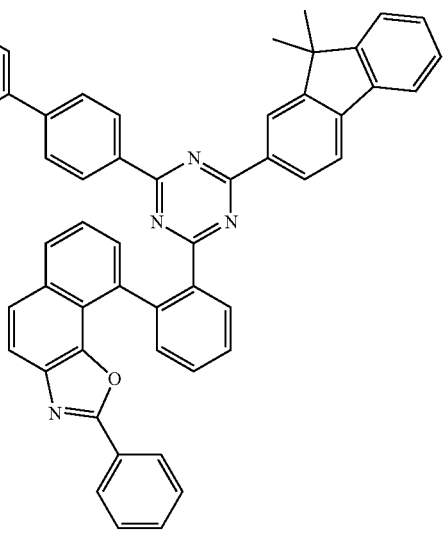
259
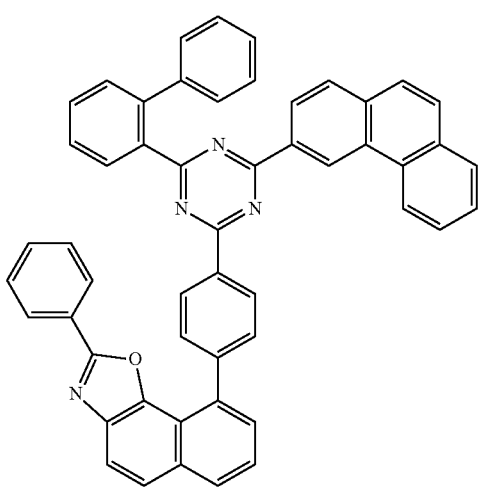 [SMILES: c1ccc(-c2nc3ccc4cccc(-c5ccc(-c6nc(-c7ccc8ccc9ccccc9c8c7)nc(-c7ccccc7-c7ccccc7)n6)cc5)c4c3o2)cc1]
260
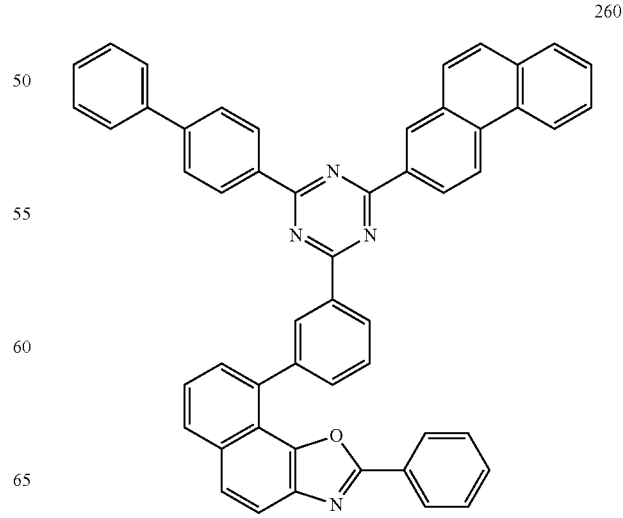

413
-continued
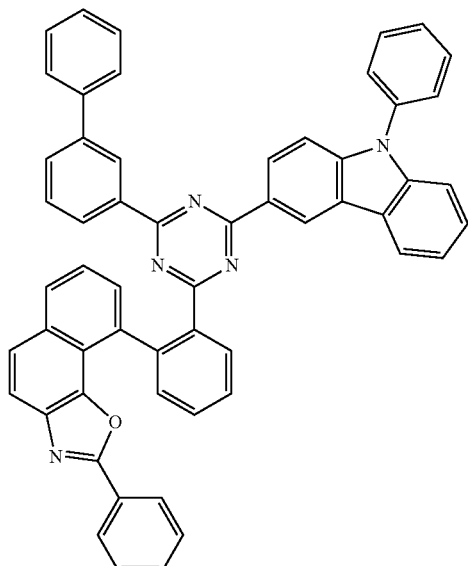
261
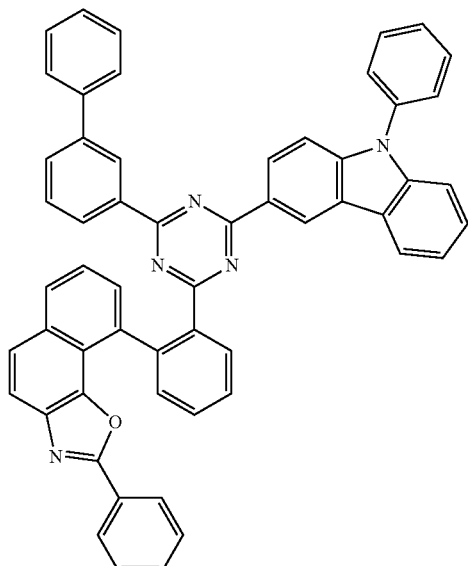
262
414
-continued
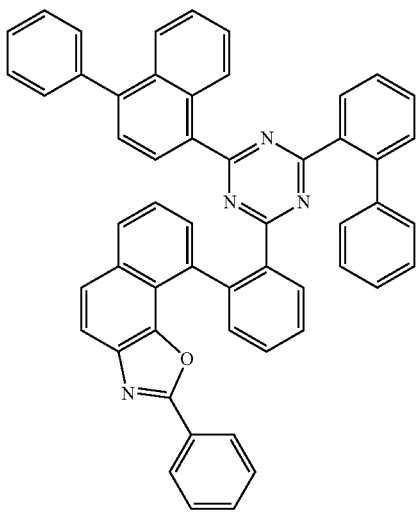
264
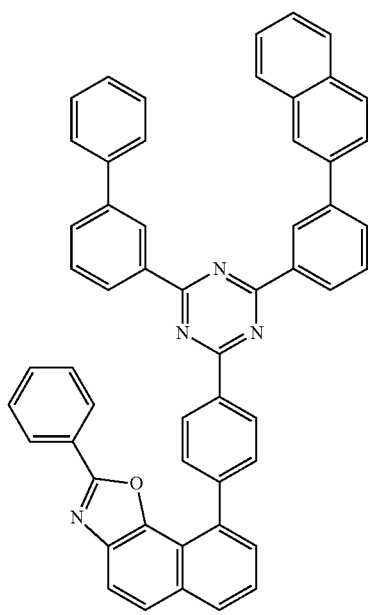
265
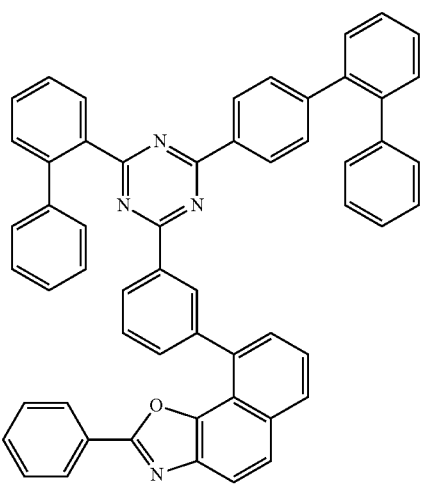
266

267
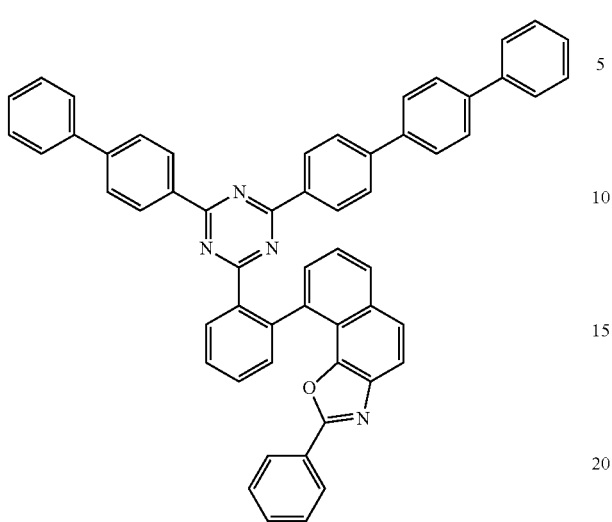
268
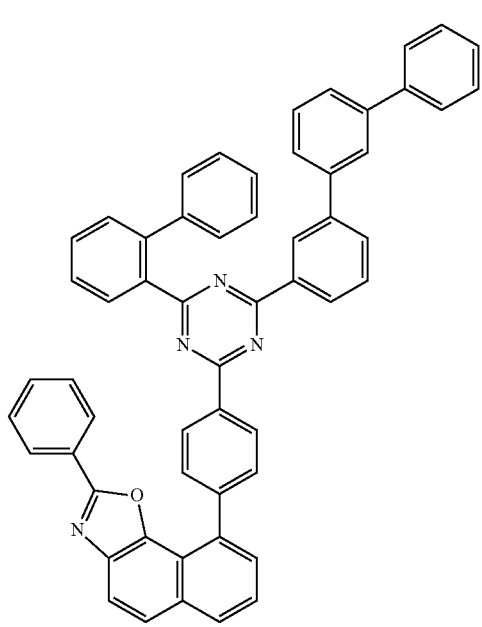
269
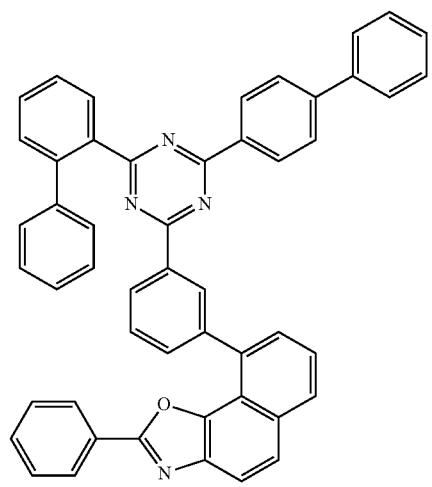
270
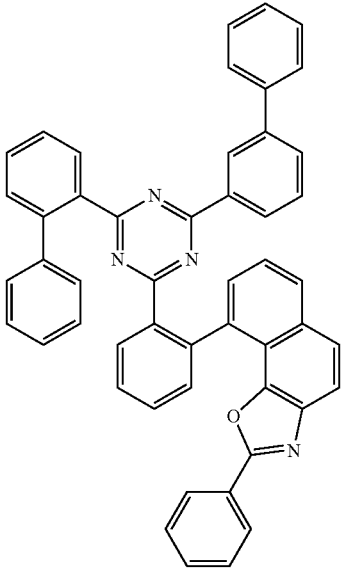
271
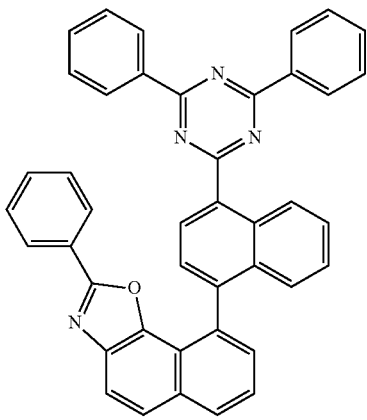
272
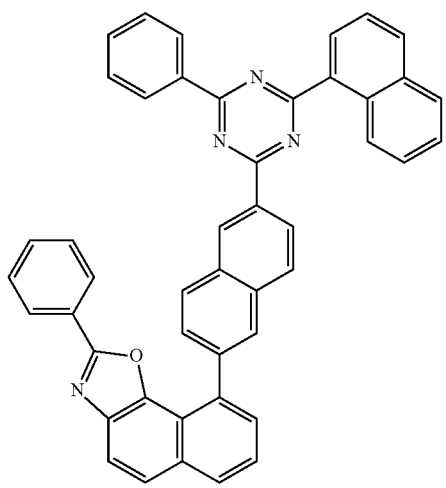

417
-continued
273
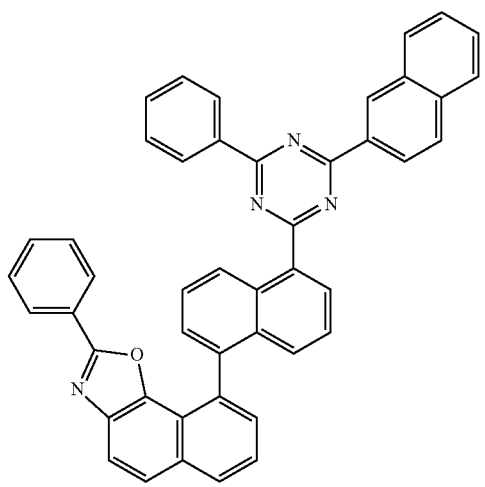 [SMILES: c1ccc(-c2nc(-c3ccc4ccccc4c3)nc(-c3cccc4c(-c5cccc6ccc7nc(-c8ccccc8)oc7c56)cccc34)n2)cc1]
274
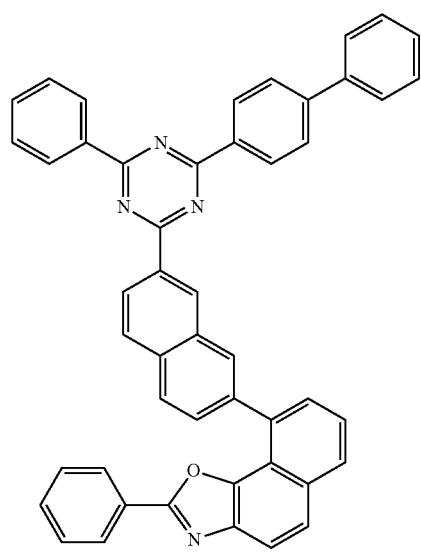
275
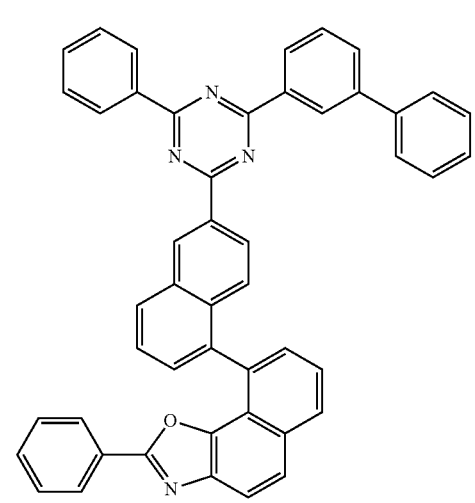
418
-continued
276
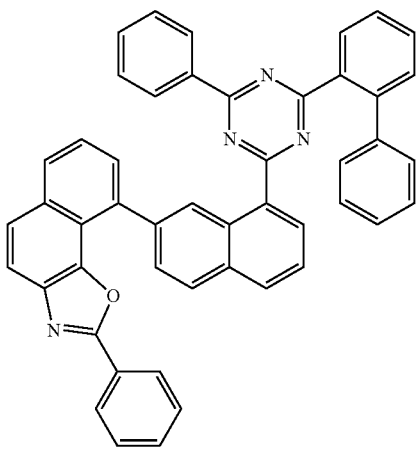 [SMILES: c1ccc(-c2nc(-c3ccccc3-c3ccccc3)nc(-c3cccc4ccc(-c5cccc6ccc7nc(-c8ccccc8)oc7c56)cc34)n2)cc1]
277
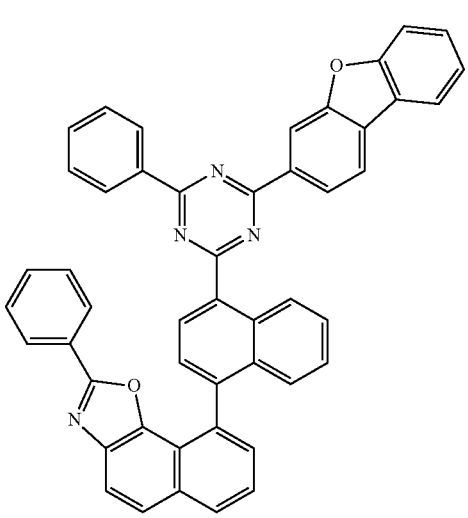 [SMILES: c1ccc(-c2nc(-c3ccc4c(c3)oc3ccccc34)nc(-c3ccc(-c4cccc5ccc6nc(-c7ccccc7)oc6c45)c4ccccc34)n2)cc1]
278
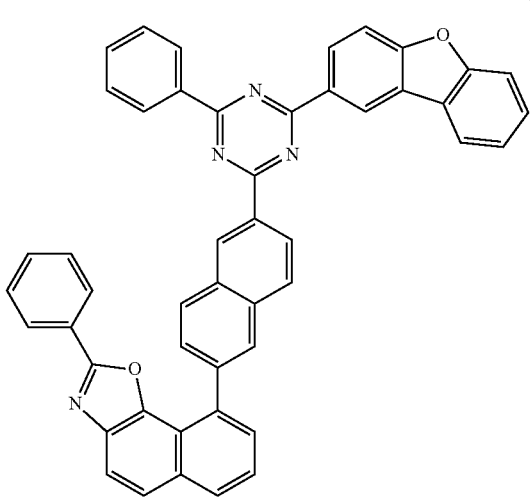

279
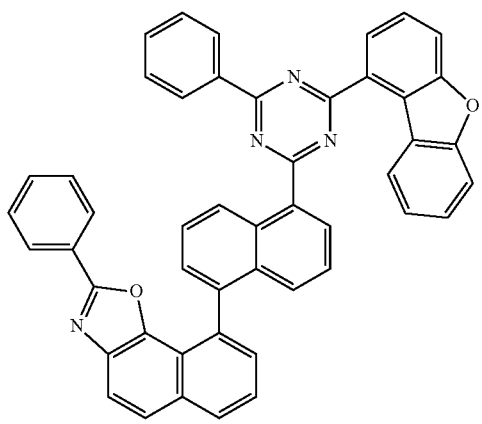 [SMILES: c1ccc(-c2nc(-c3cccc4c(-c5cccc6ccc7nc(-c8ccccc8)oc7c56)cccc34)nc(-c3cccc4oc5ccccc5c34)n2)cc1]
280
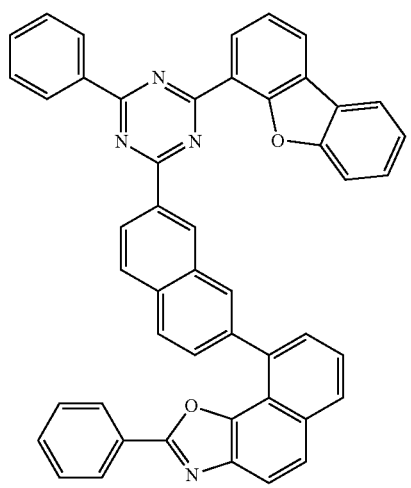
281
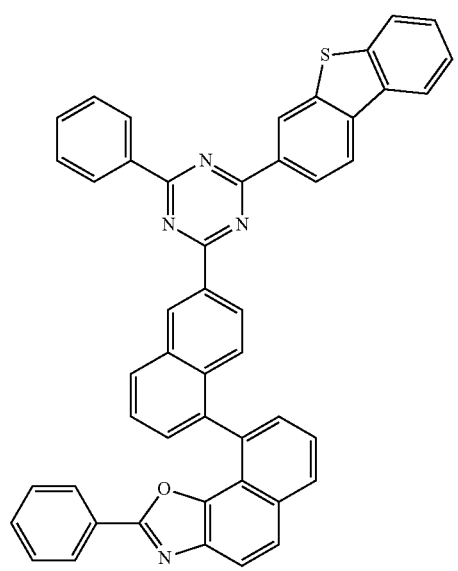
282
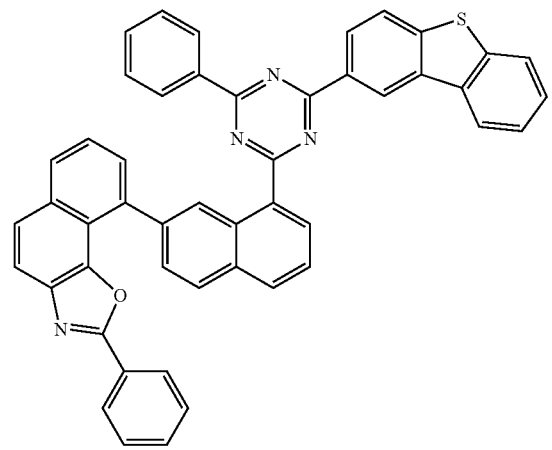
283
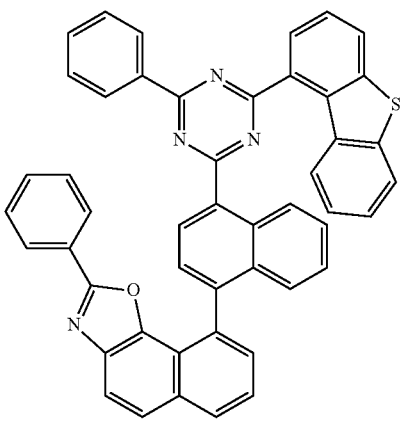
284
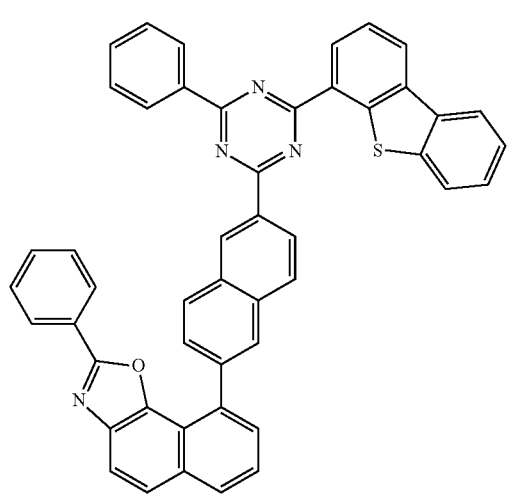

-continued
285
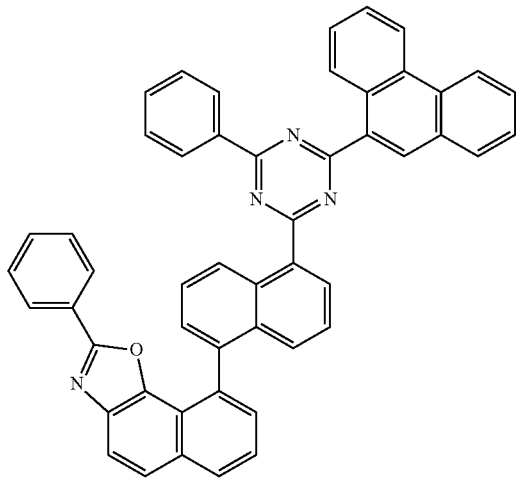 [SMILES: c1ccc(-c2nc(-c3cccc4c(-c5cccc6ccc7nc(-c8ccccc8)oc7c56)cccc34)nc(-c3cc4ccccc4c4ccccc34)n2)cc1]
286
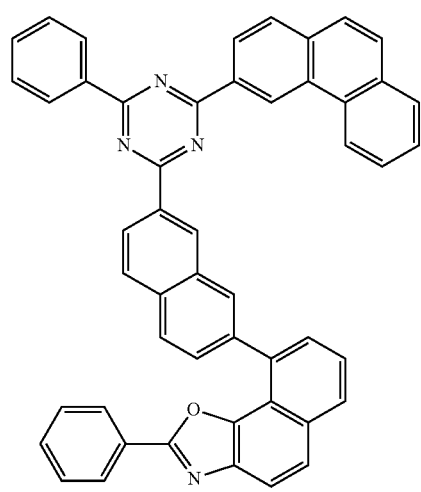
287
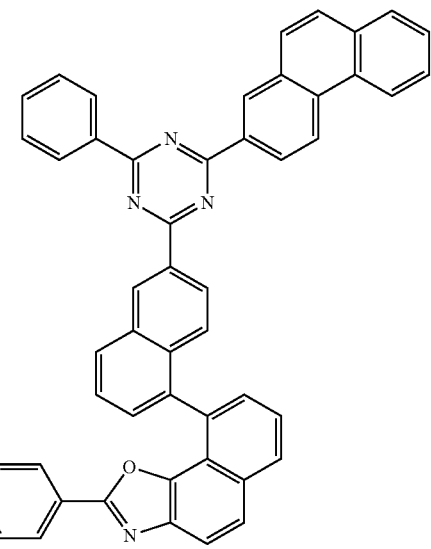
-continued
288
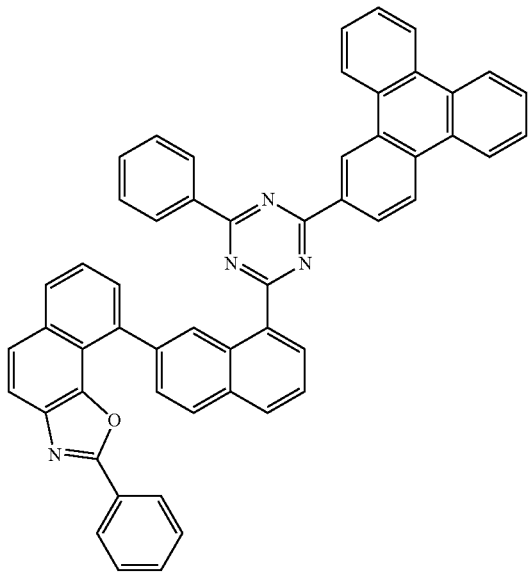
289
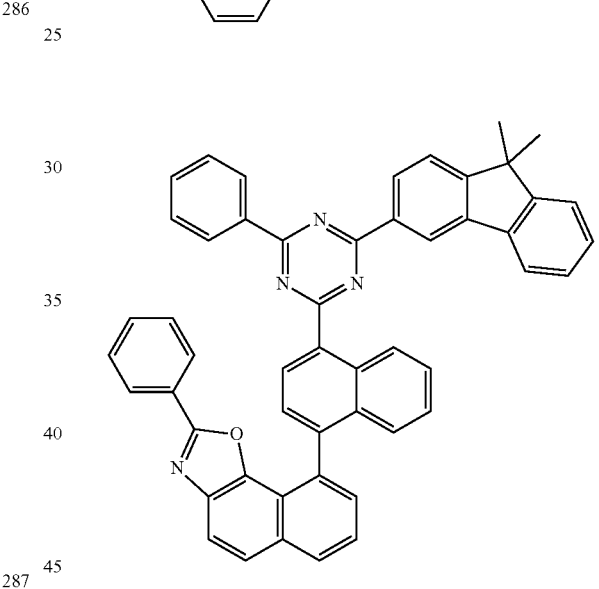
290
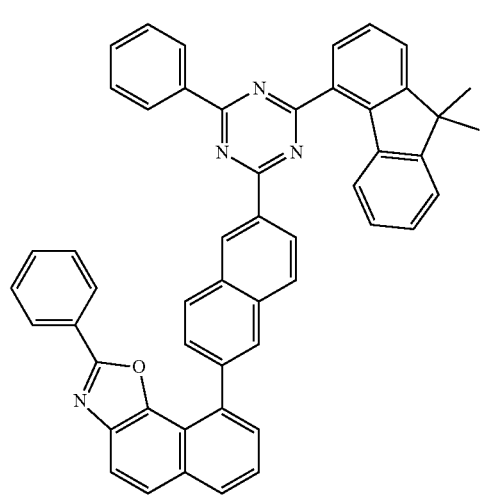

423
-continued
291
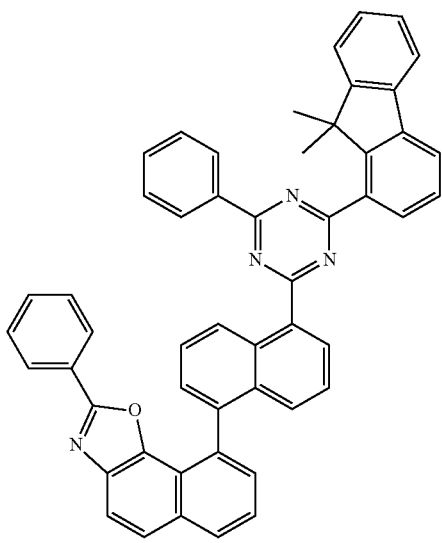 [SMILES: CC1(C)c2ccccc2-c2cccc(-c3nc(-c4ccccc4)nc(-c4cccc5c(-c6cccc7ccc8nc(-c9ccccc9)oc8c67)cccc45)n3)c21]
292
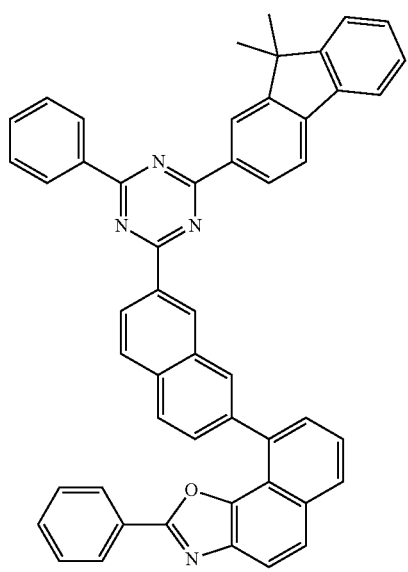
424
-continued
293
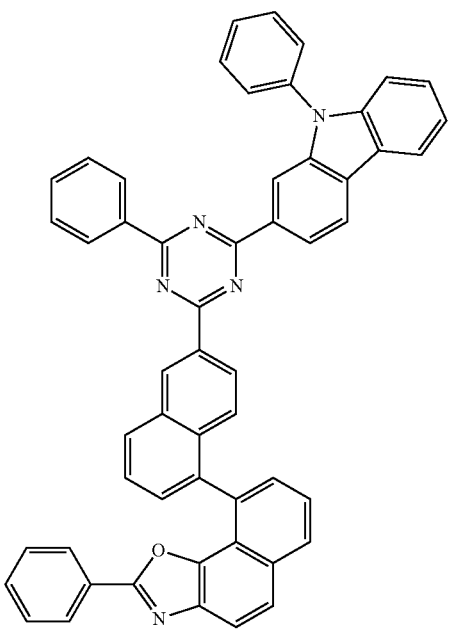
294
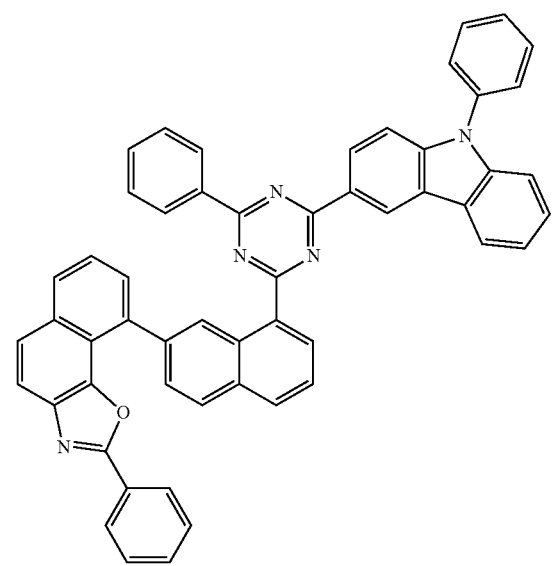

425
-continued
295
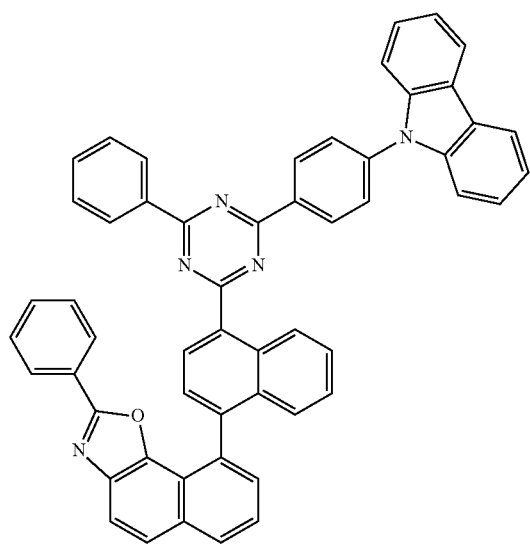
296
297
426
-continued
298
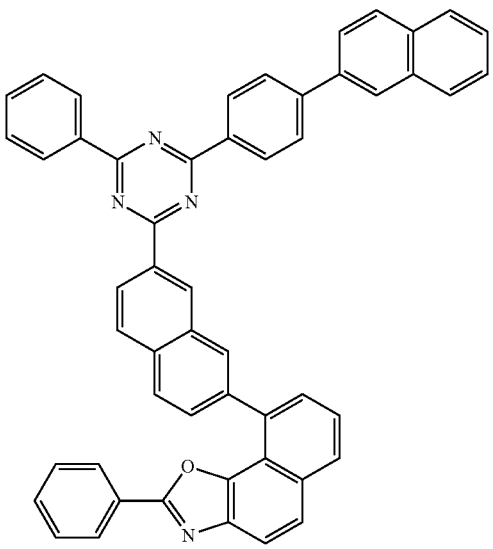
299
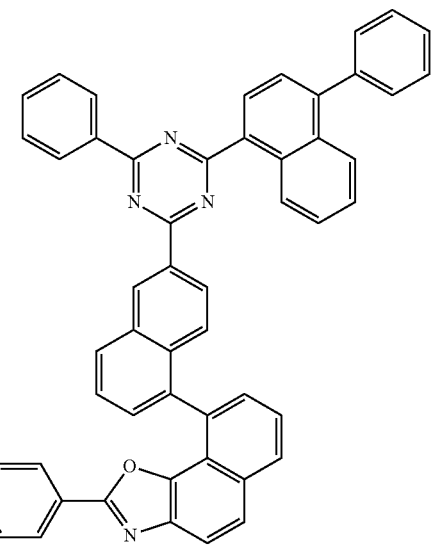

-continued
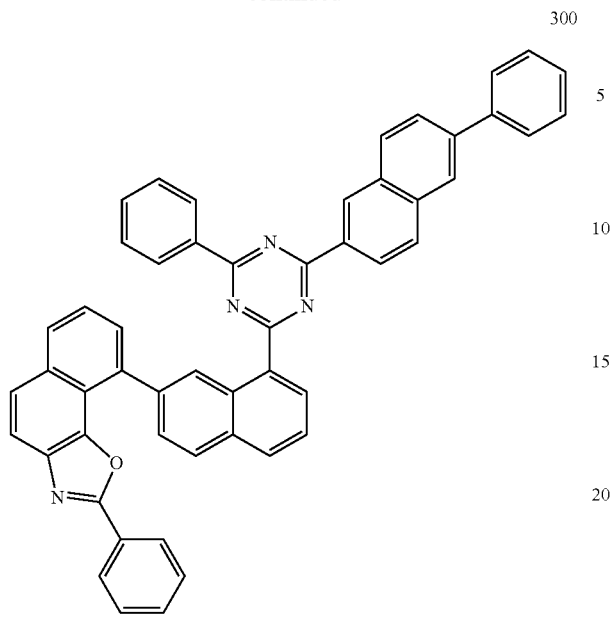
300
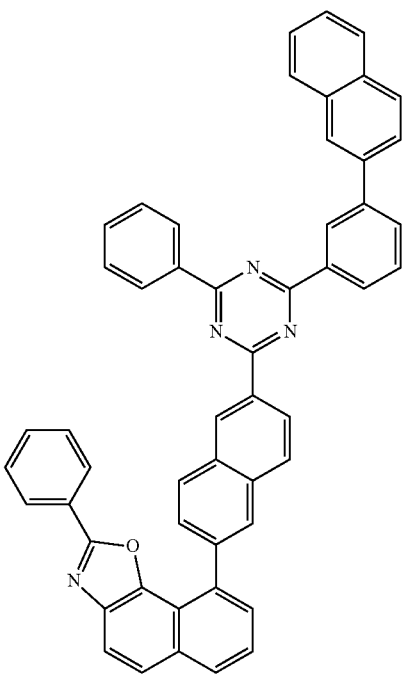
302
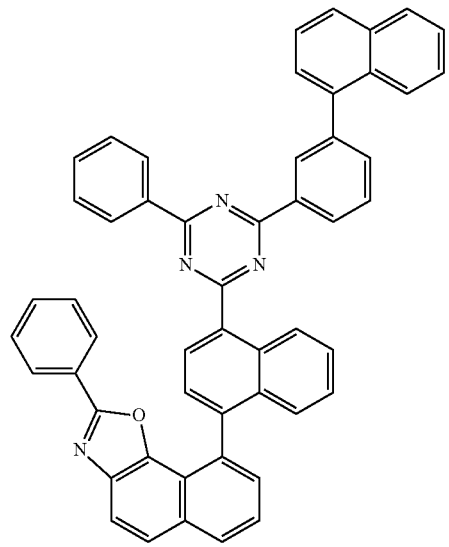
301
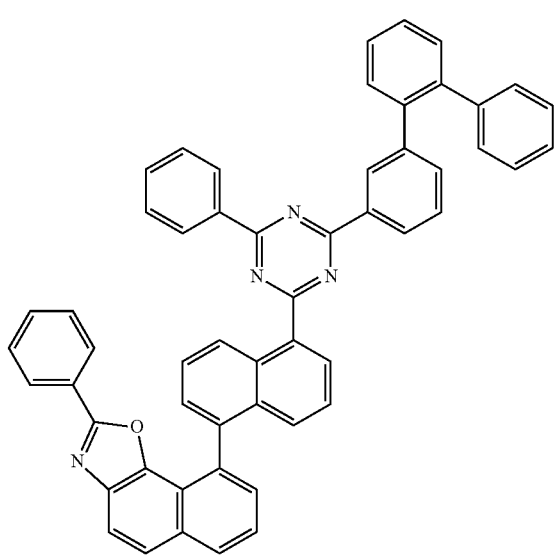
303

429
-continued
304
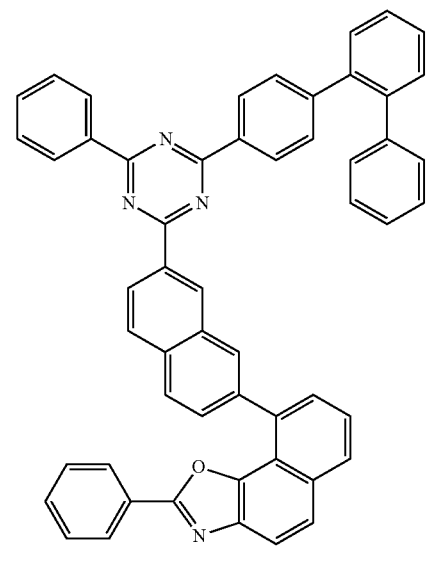
305
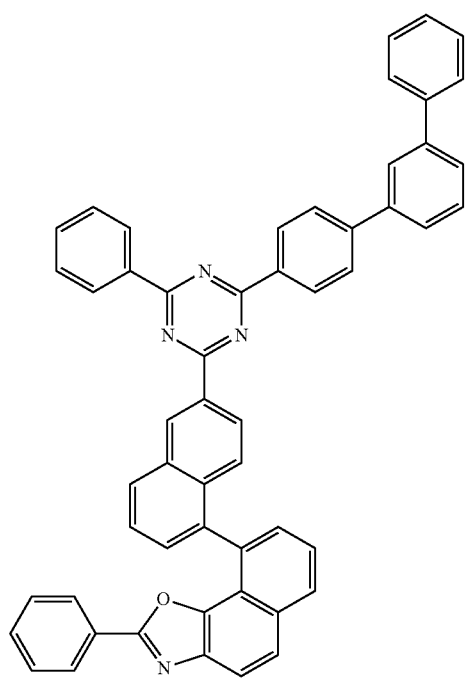
430
-continued
306
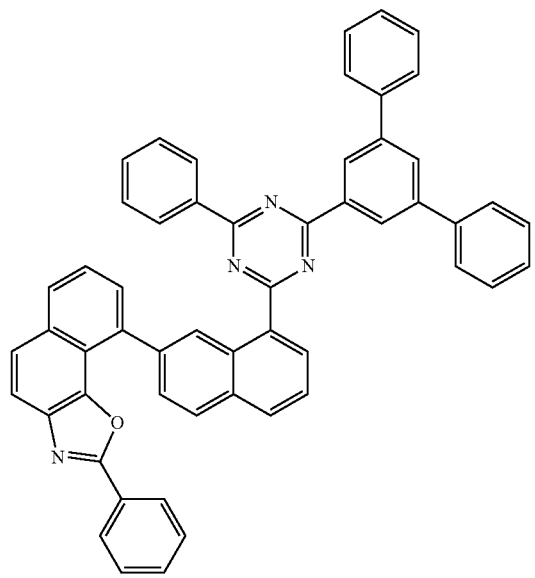
307
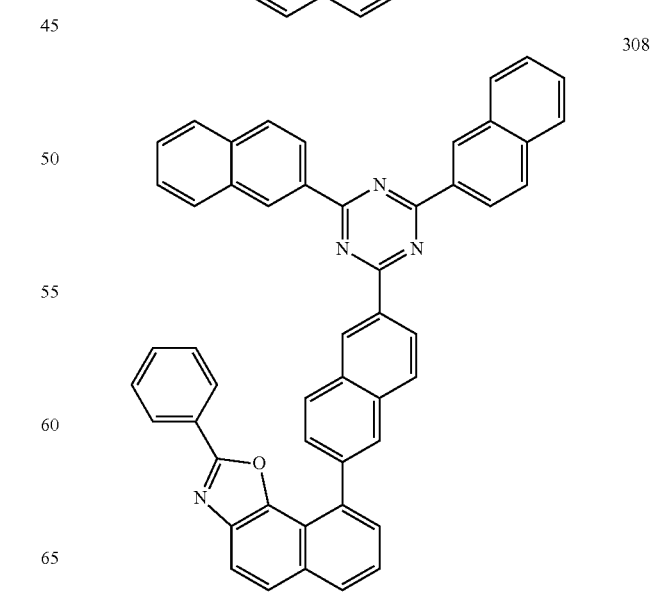
308

431
-continued
432
-continued
309
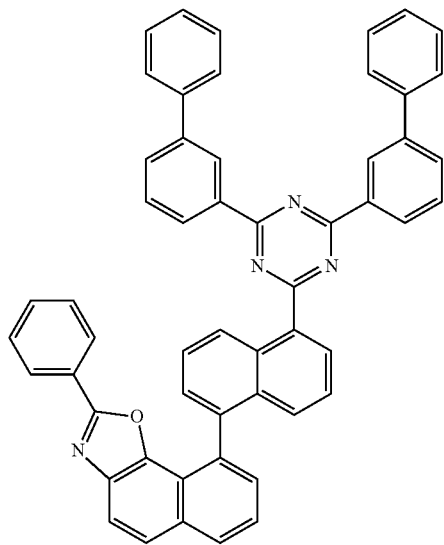
312
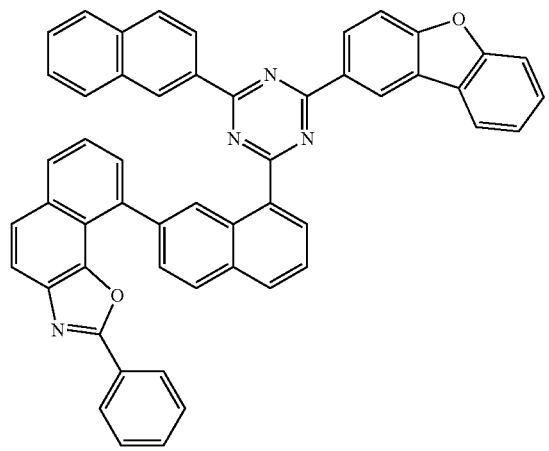
310
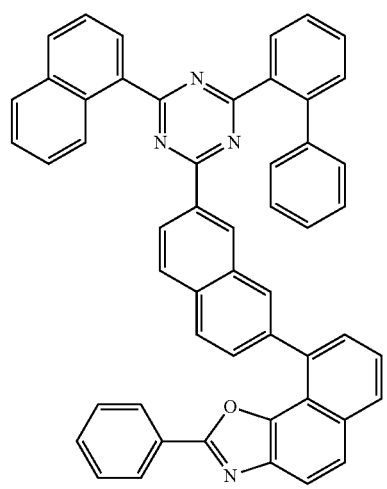
313
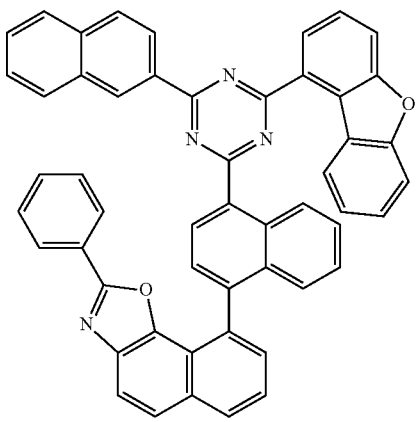 [SMILES: c1ccc(-c2nc3ccc4cccc(-c5ccc(-c6nc(-c7ccc8ccccc8c7)nc(-c7cccc8oc9ccccc9c78)n6)c6ccccc56)c4c3o2)cc1]
311
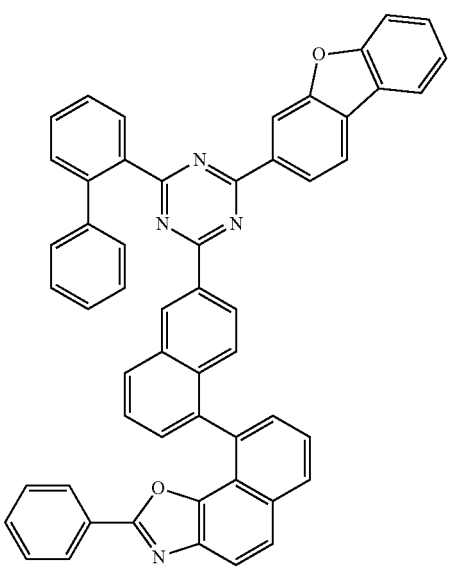
314
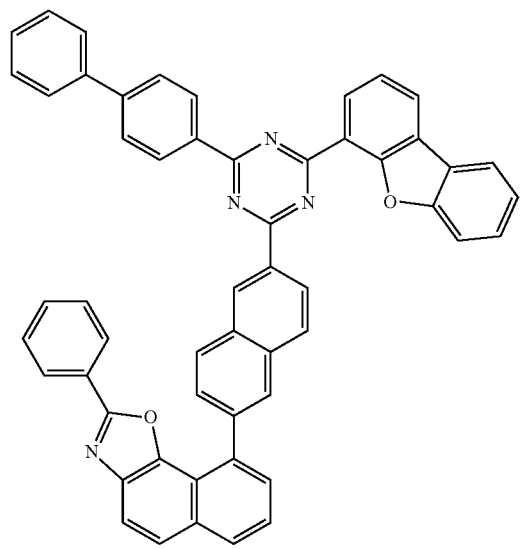

315
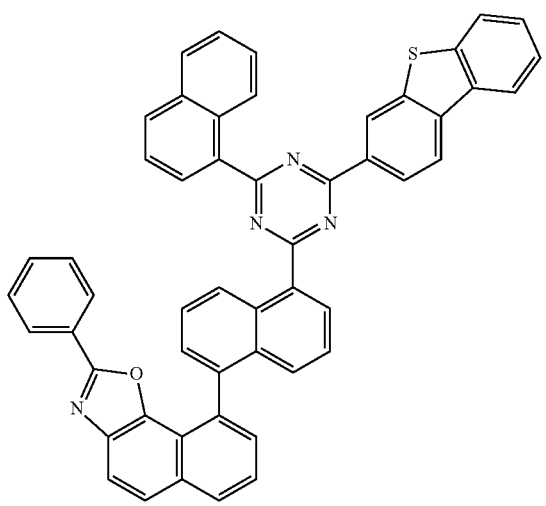
318
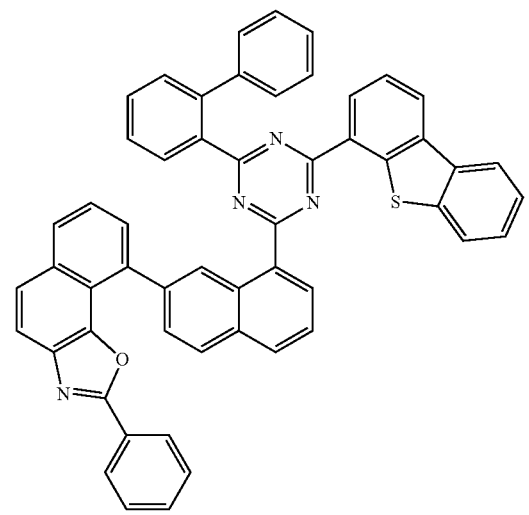
316
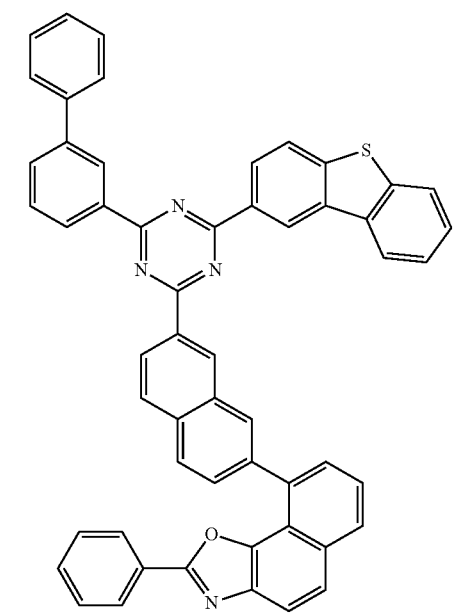
319
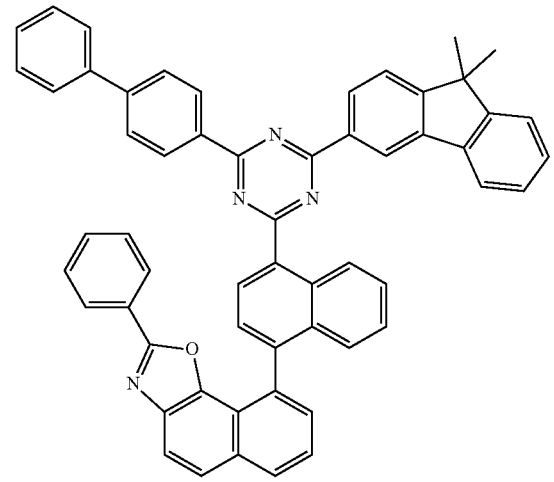
317
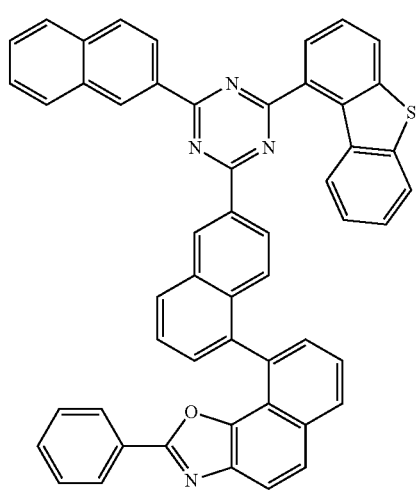
320
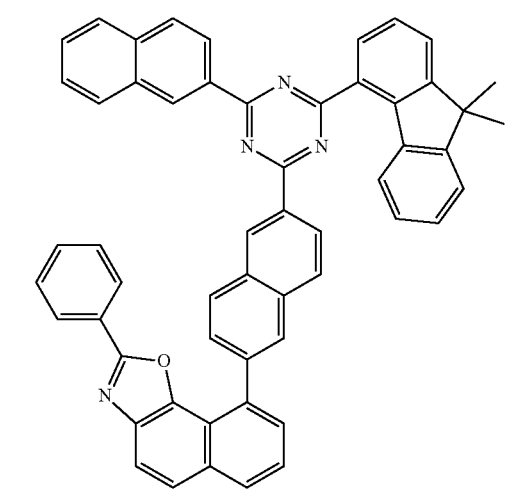

435
-continued
321
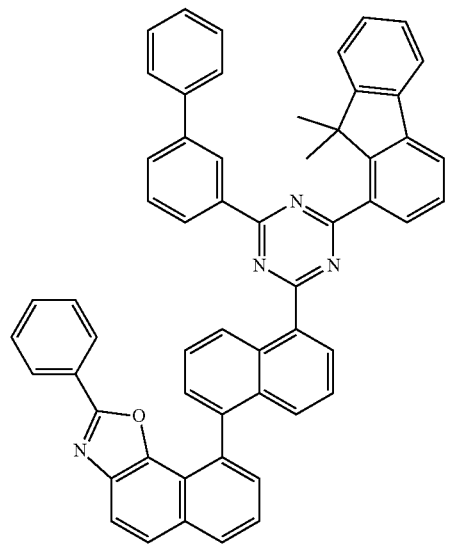
322
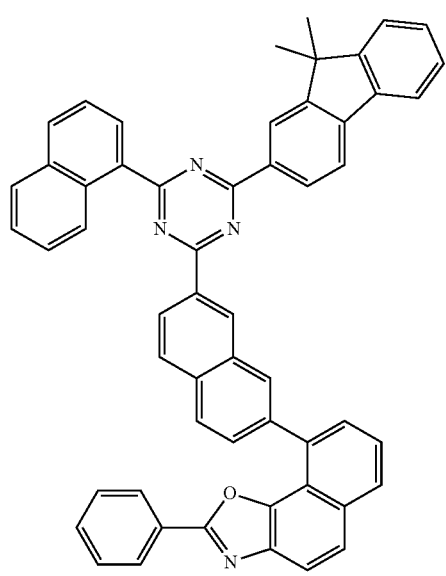
323
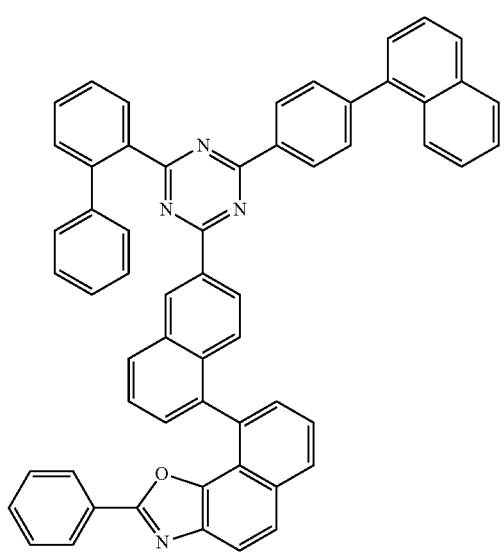
436
-continued
324
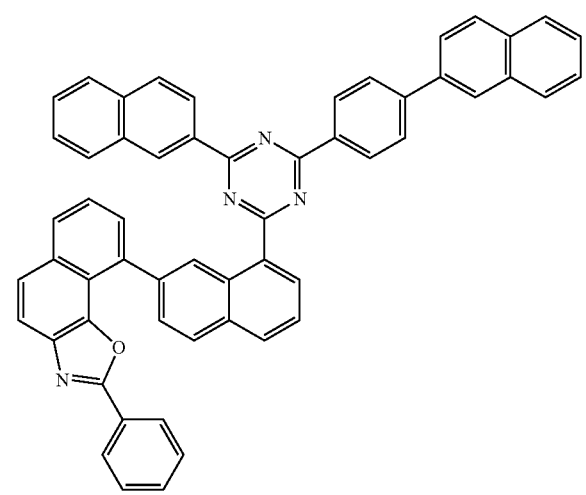
325
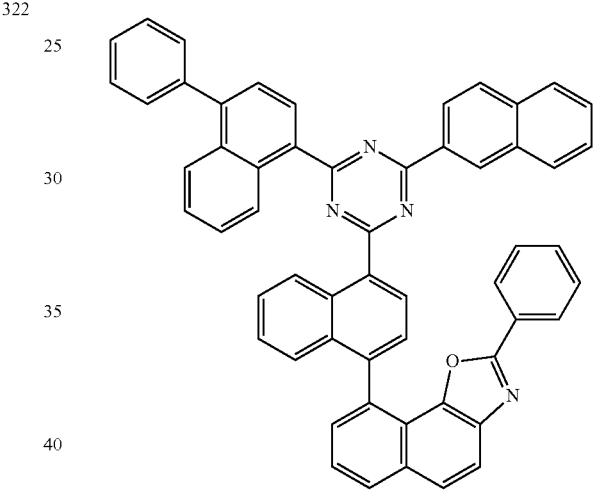
326
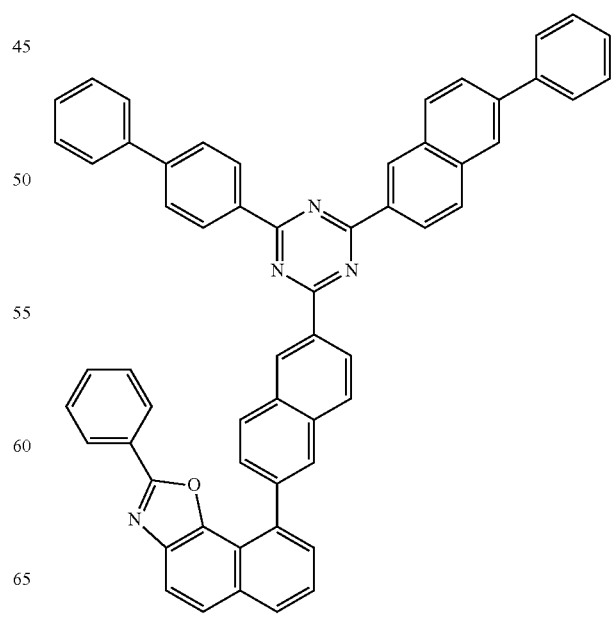

437
-continued
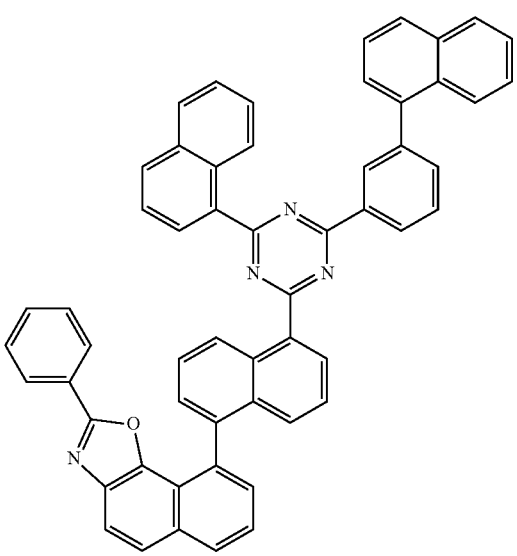
327
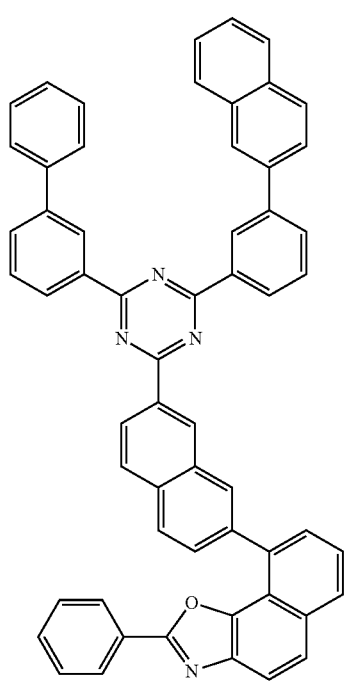
328
438
-continued
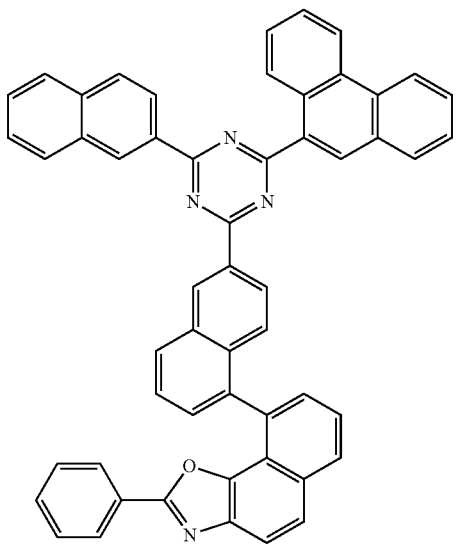
329
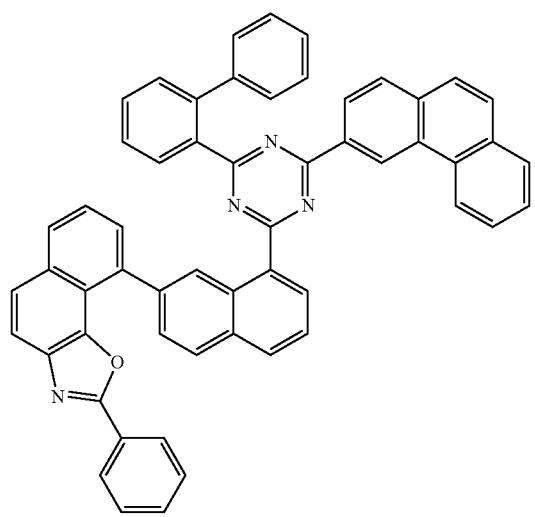
330
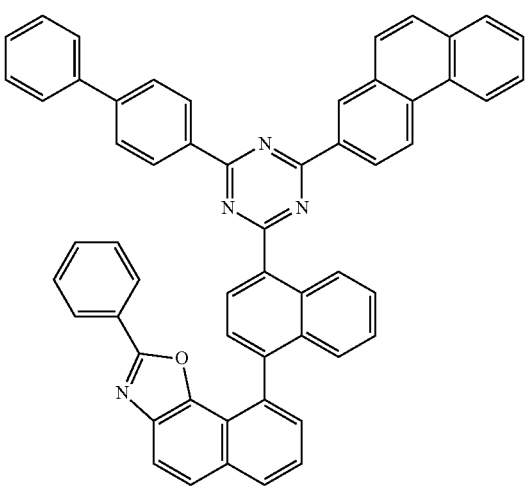
331

332
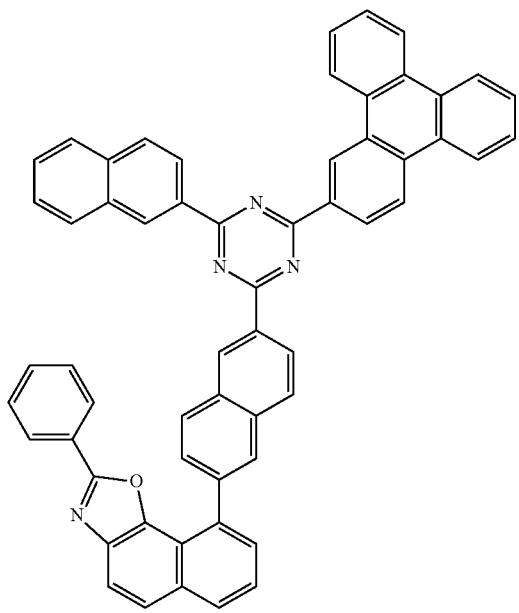
333
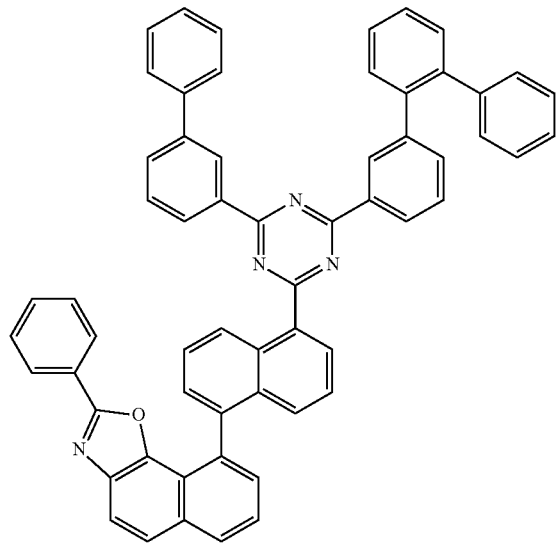
334
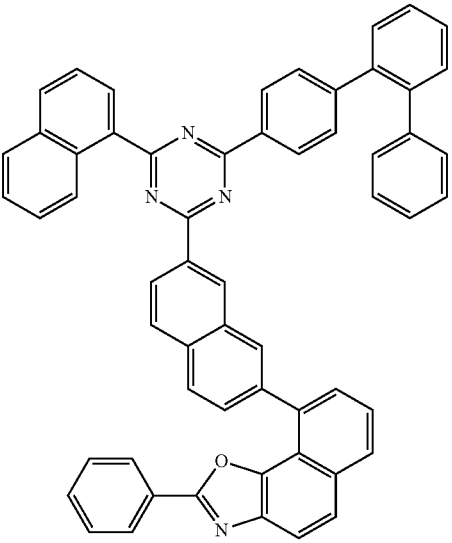
335
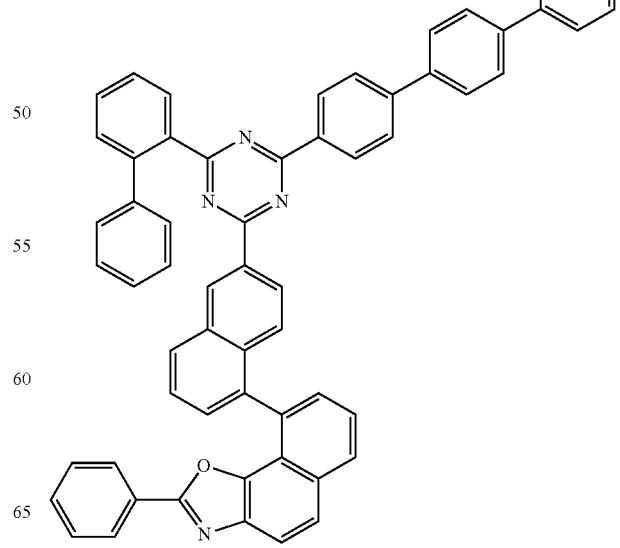

336
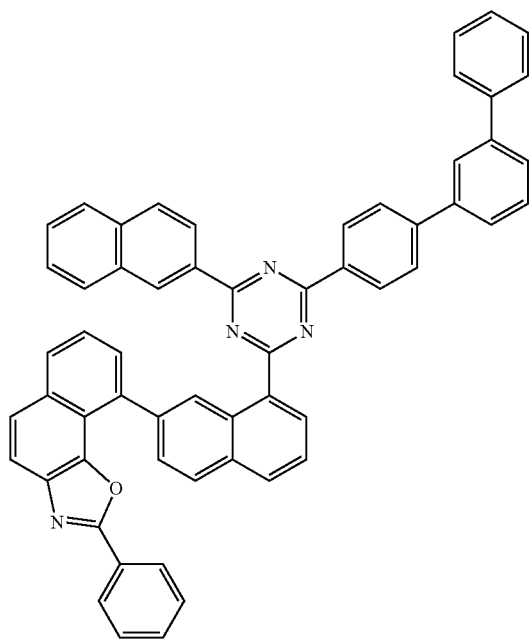
337
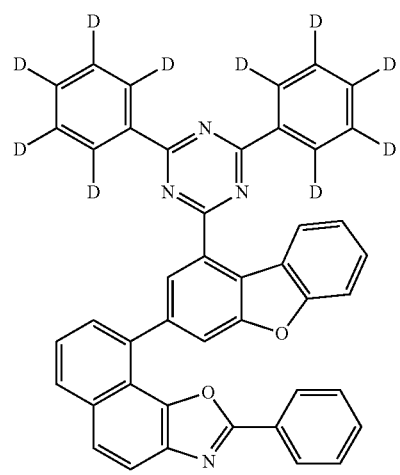 [SMILES: [2H]c1c([2H])c([2H])c(-c2nc(-c3c([2H])c([2H])c([2H])c([2H])c3[2H])nc(-c3cc(-c4cccc5ccc6nc(-c7ccccc7)oc6c45)cc4oc5ccccc5c34)n2)c([2H])c1[2H]]
338
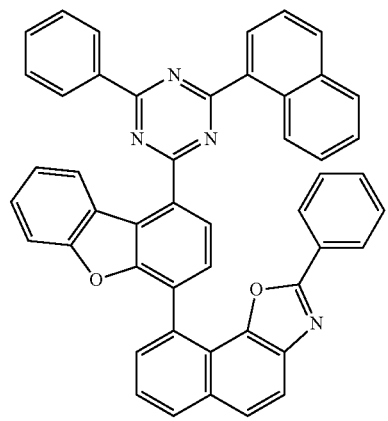
339
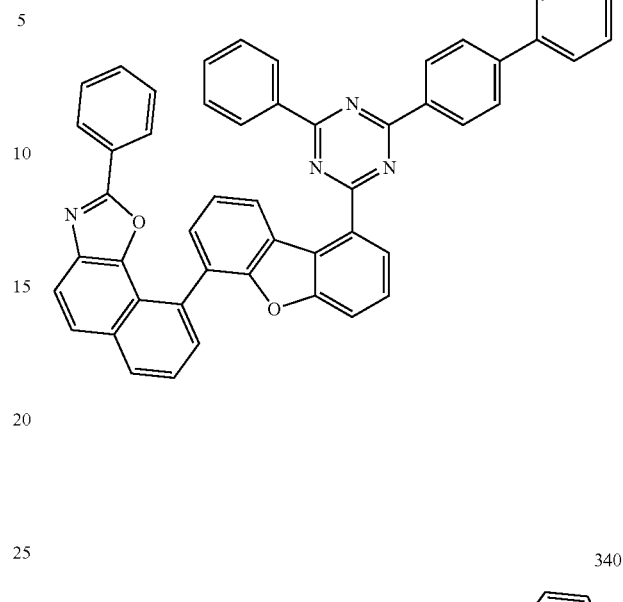
340
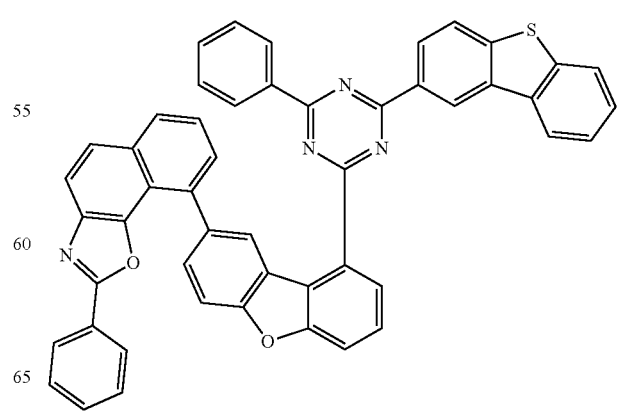
341

342
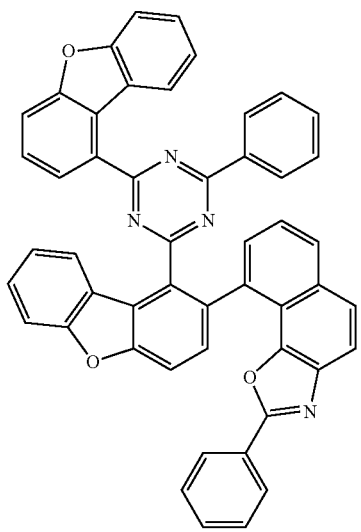
343
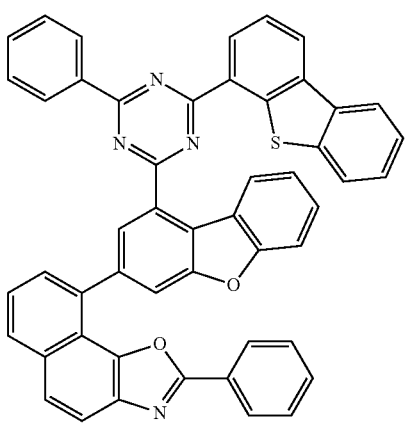
344
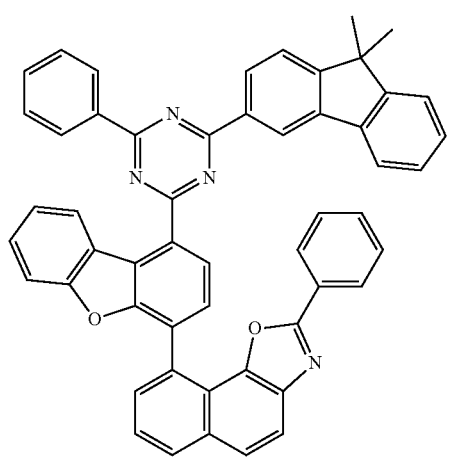
345
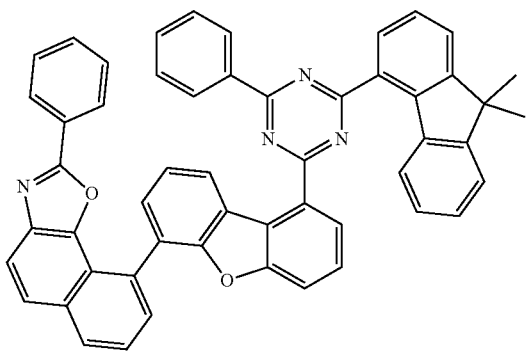
346
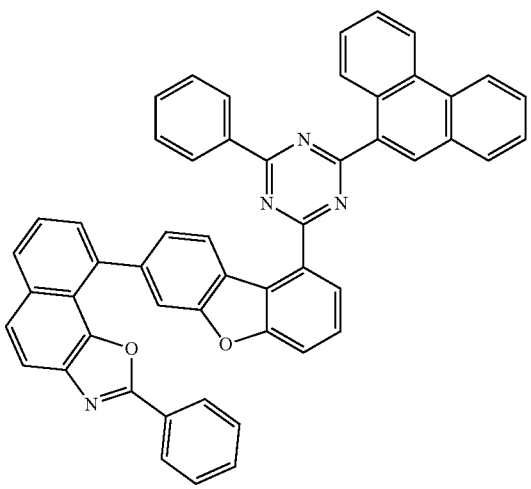
347
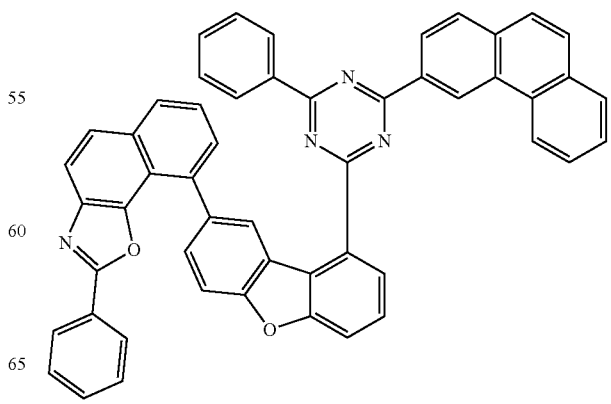

445
-continued
348
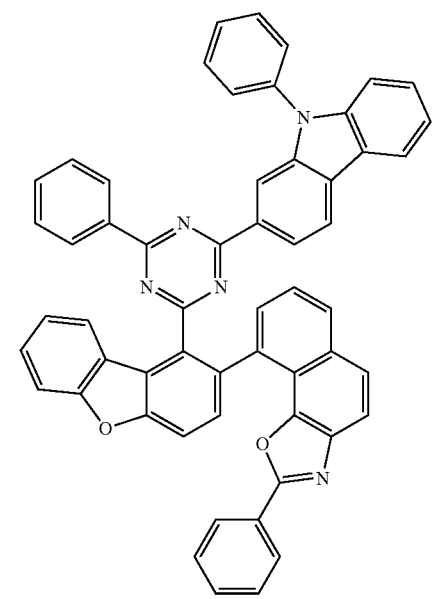
349
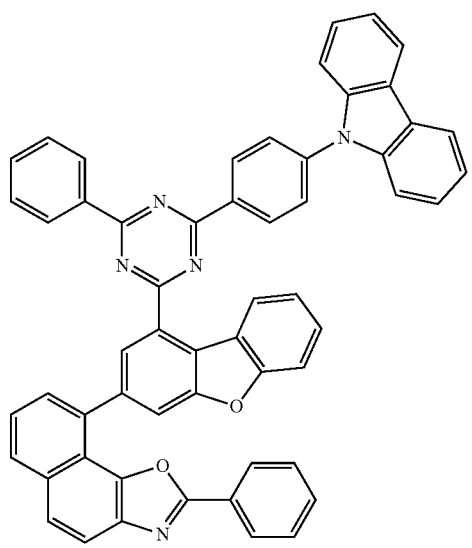
350
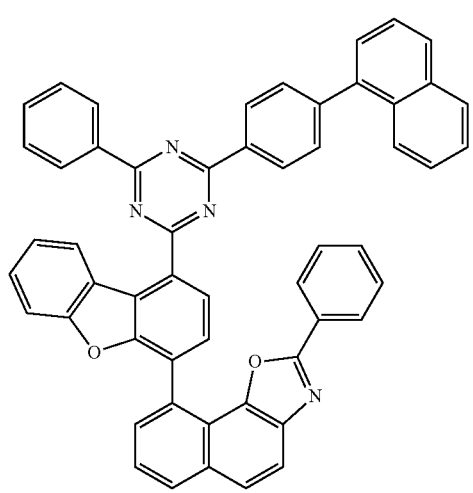
446
-continued
351
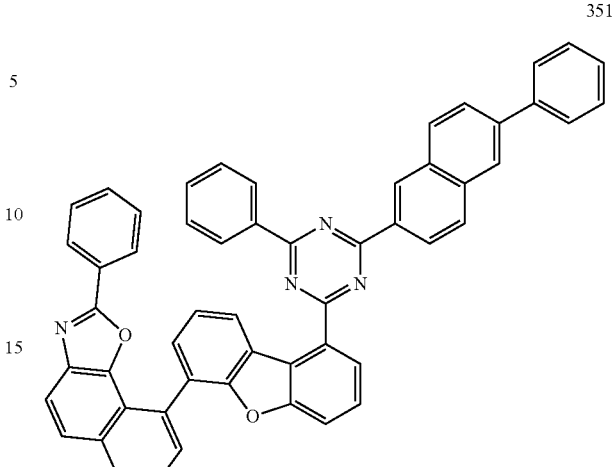
352
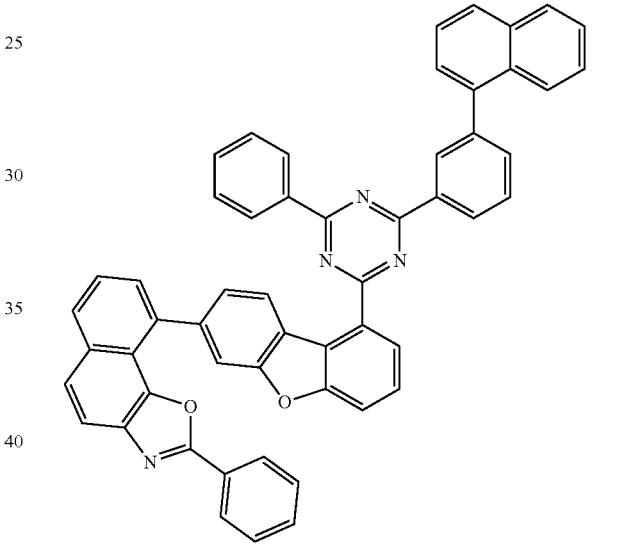
353
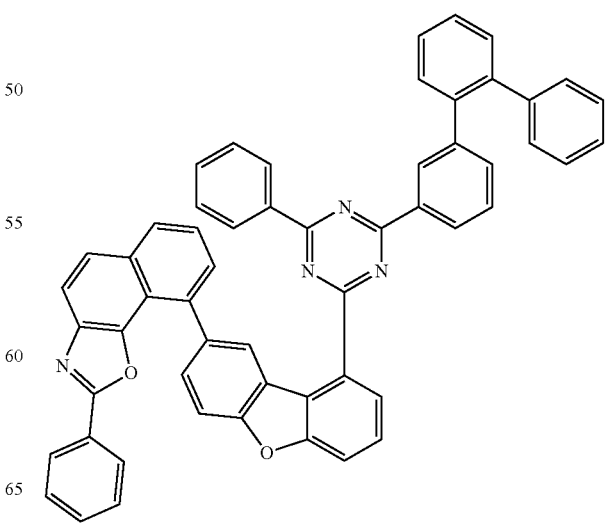

354
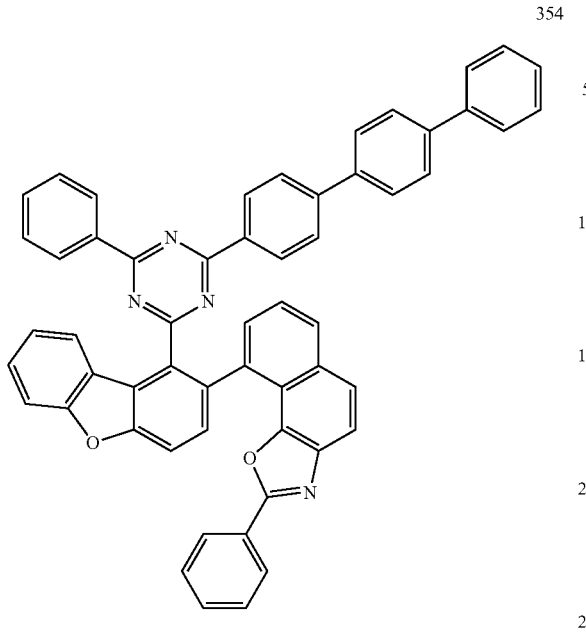
356
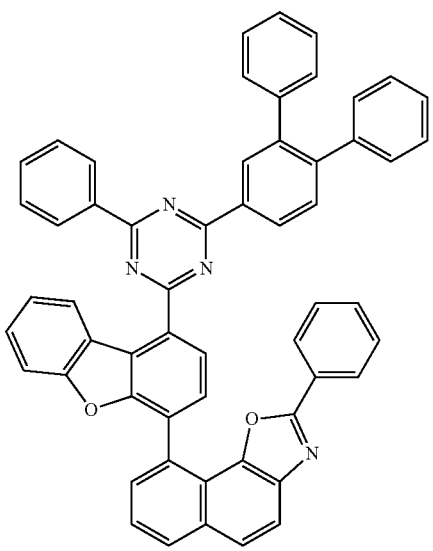
357
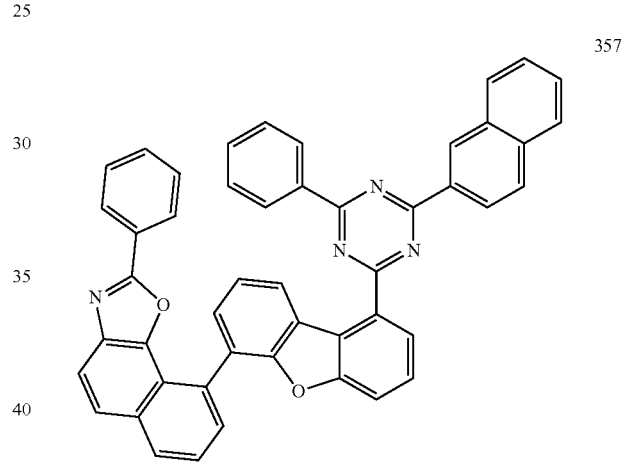
355
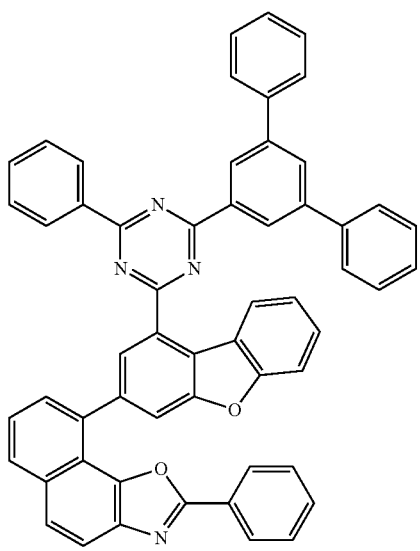
358
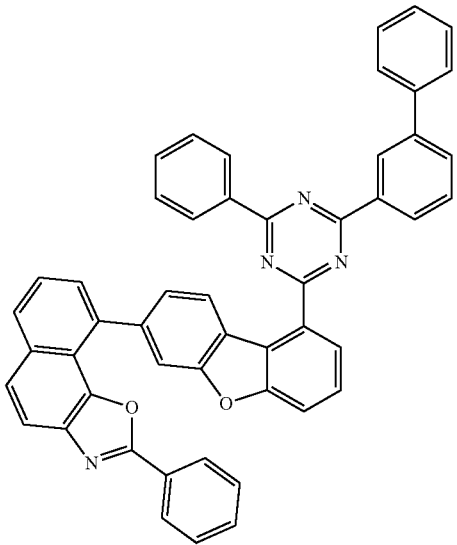

359
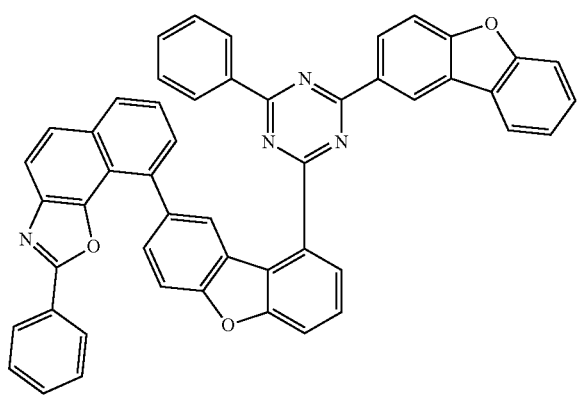
362
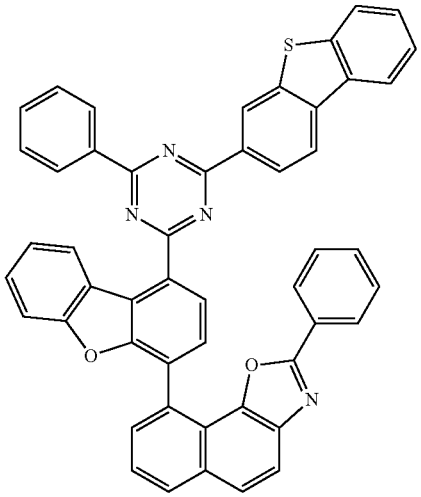
360
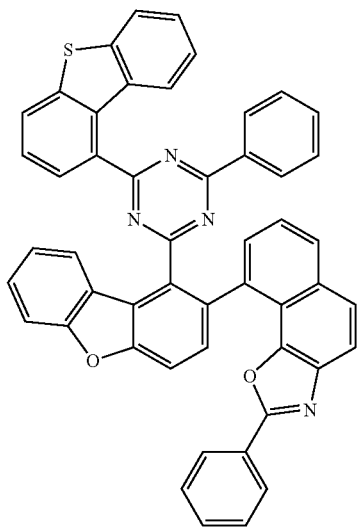
363
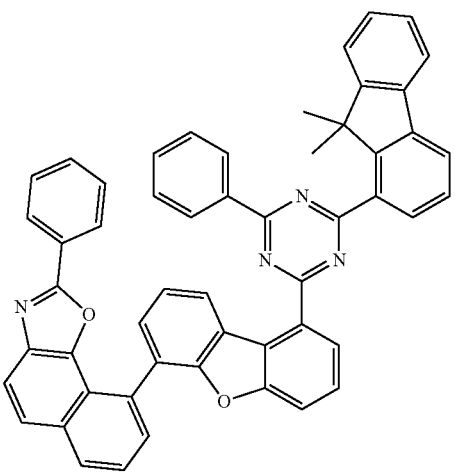
361
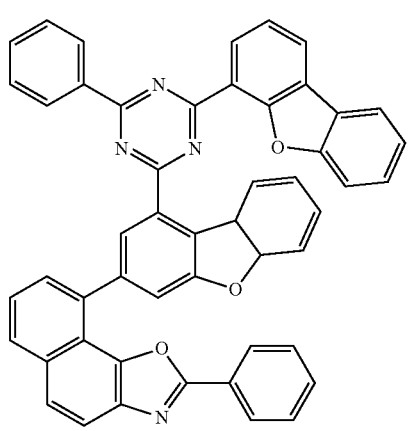
364
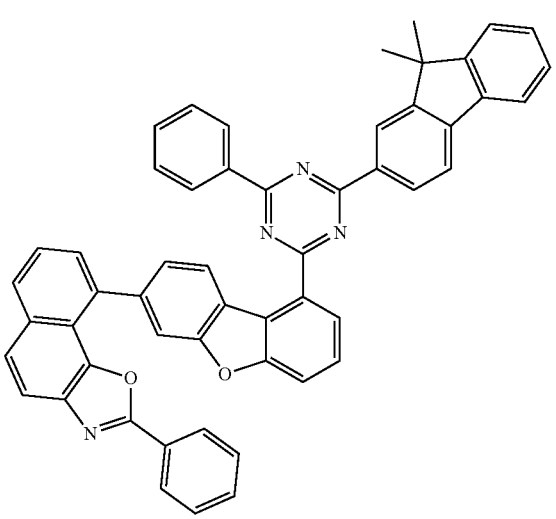 [SMILES: c1ccc(-c2nc(-c3ccc4c(c3)oc3ccccc34)nc(-c3cccc4oc5cc(-c6cccc7ccc8nc(-c9ccccc9)oc8c67)ccc5c34)n2)cc1]

451
-continued
365
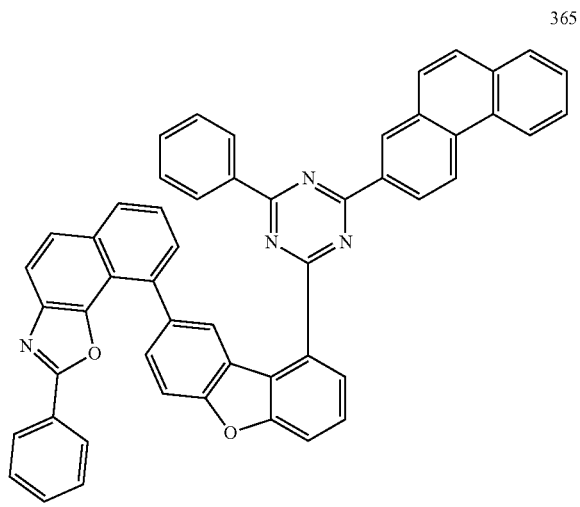
366
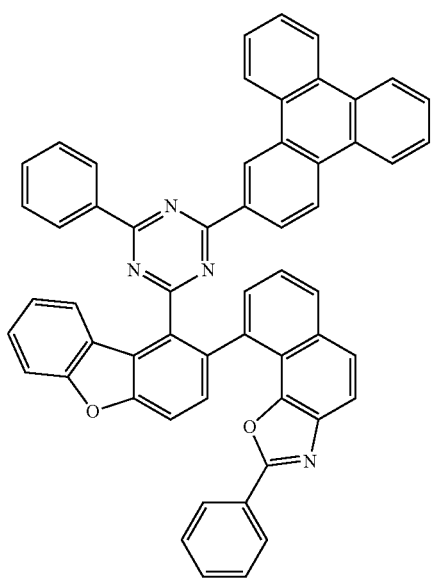
367
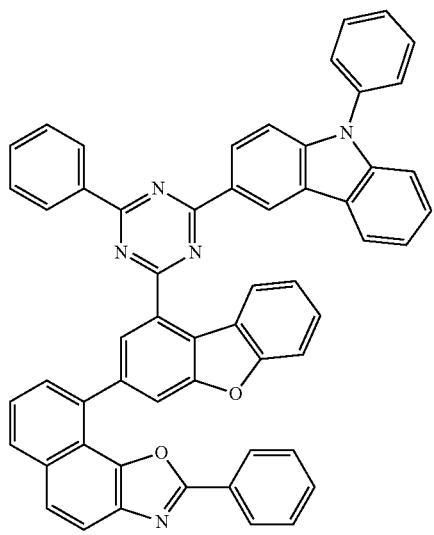
452
-continued
368
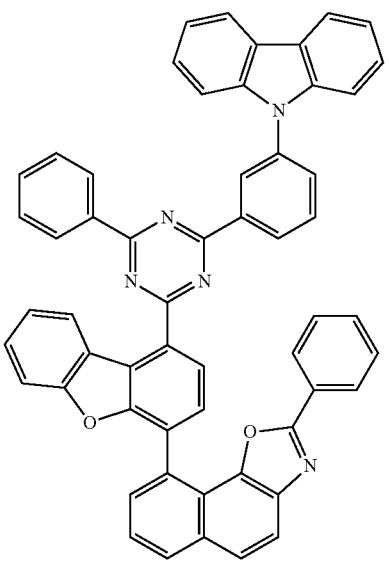
369
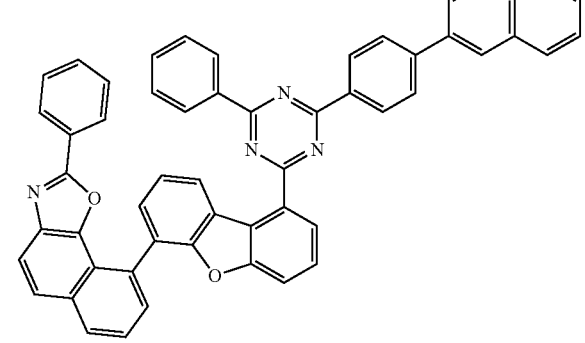
370

-continued
371
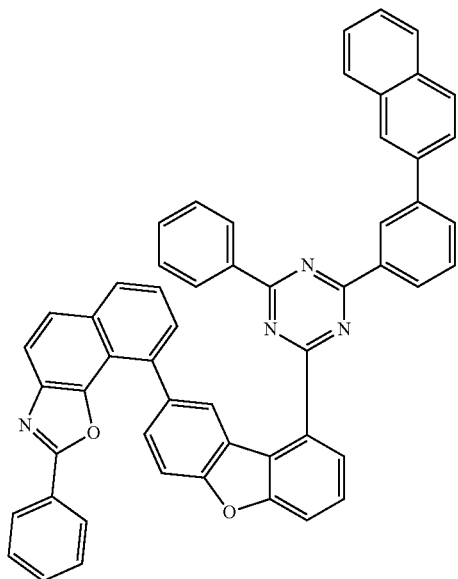
372
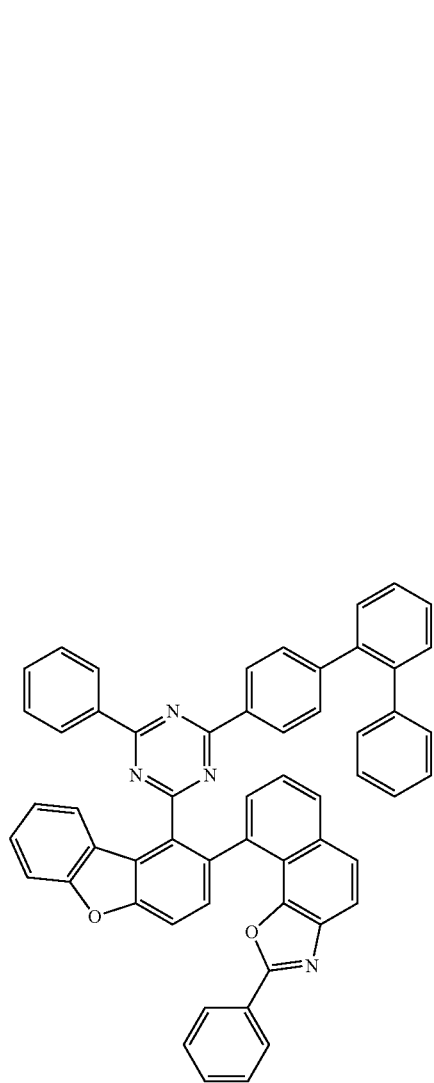
-continued
373
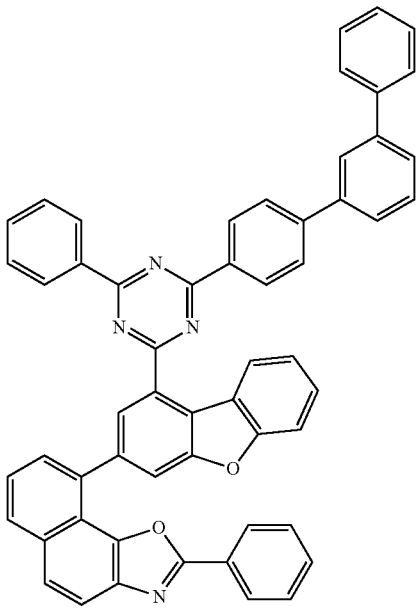
374
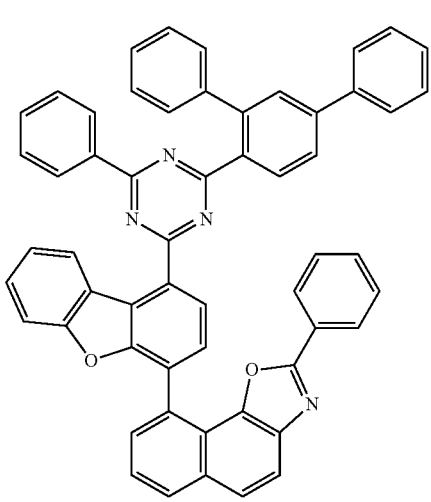
375
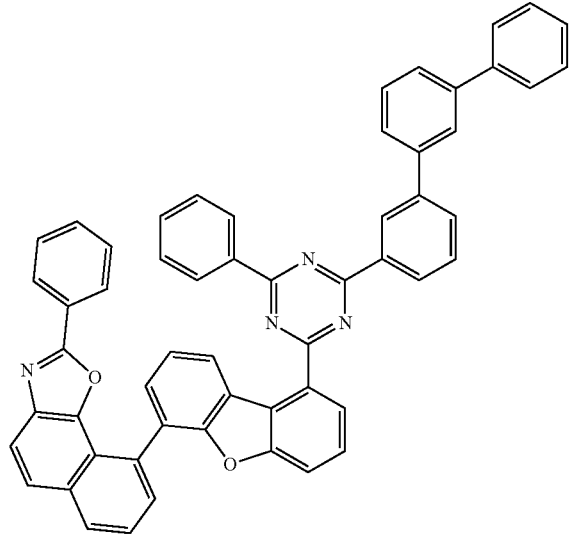

376 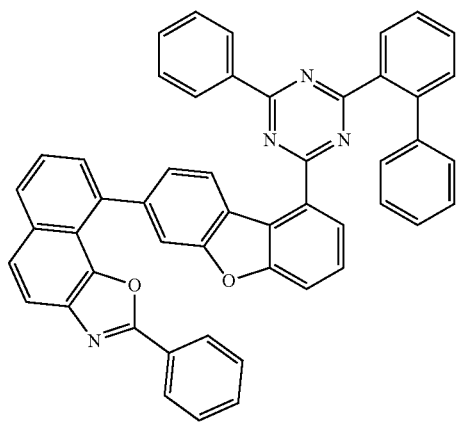
377 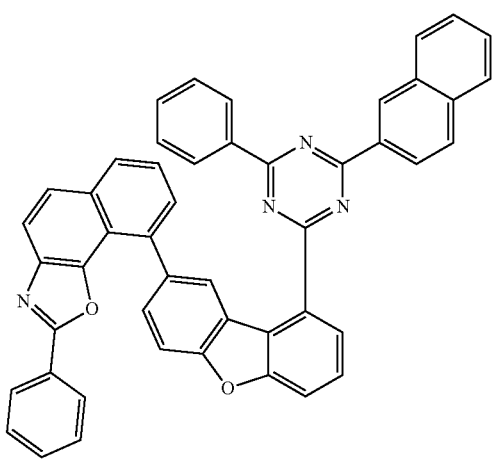
378 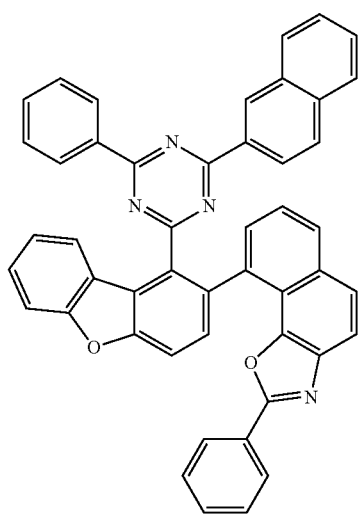
379 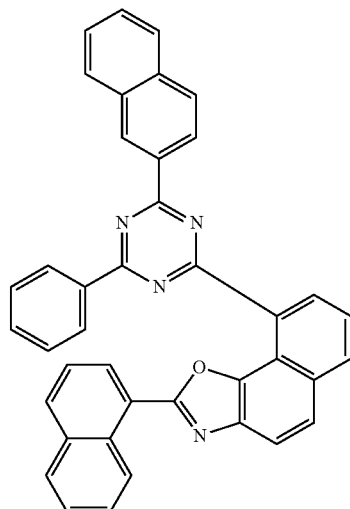
380 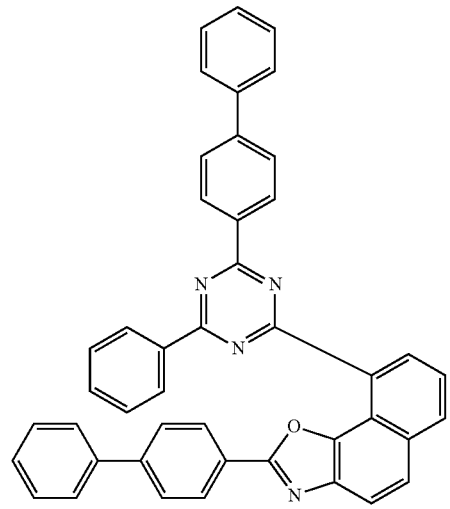
381 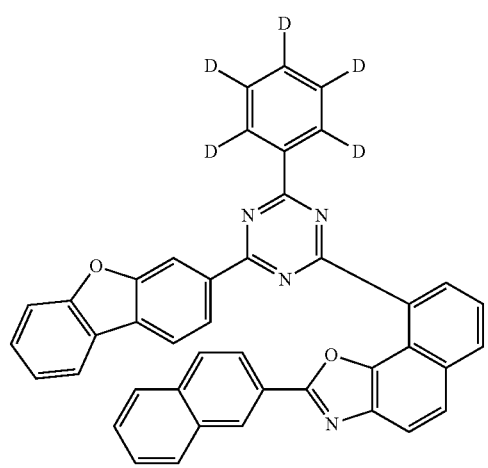 [SMILES: [2H]c1c([2H])c([2H])c(-c2nc(-c3ccc4c(c3)oc3ccccc34)nc(-c3cccc4ccc5nc(-c6ccc7ccccc7c6)oc5c34)n2)c([2H])c1[2H]]

382
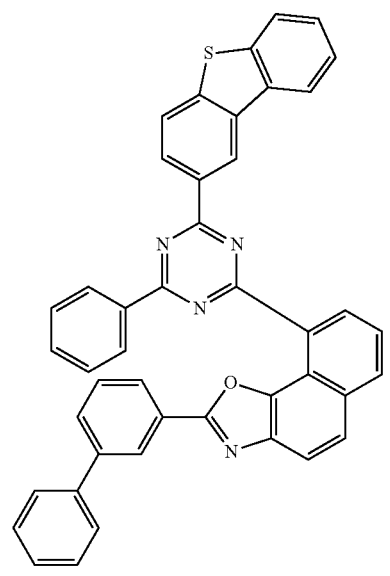
383
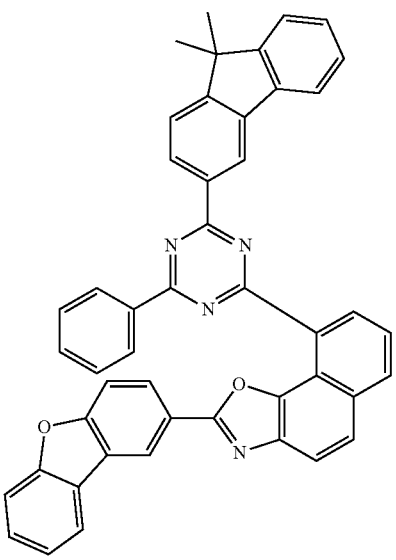
384
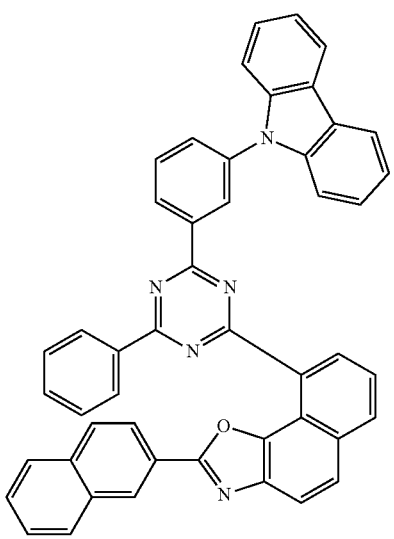
385
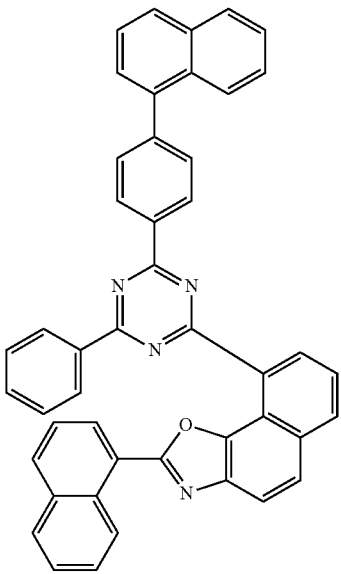
386
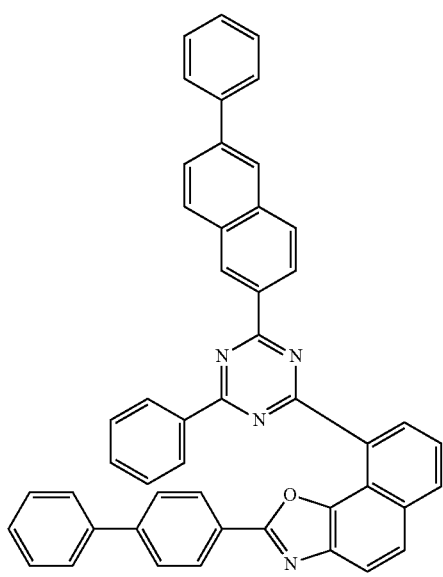

459
-continued
387
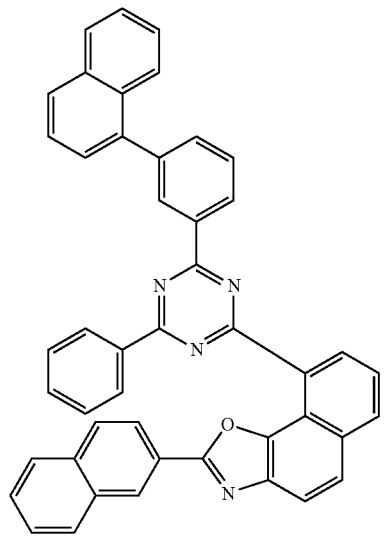
388
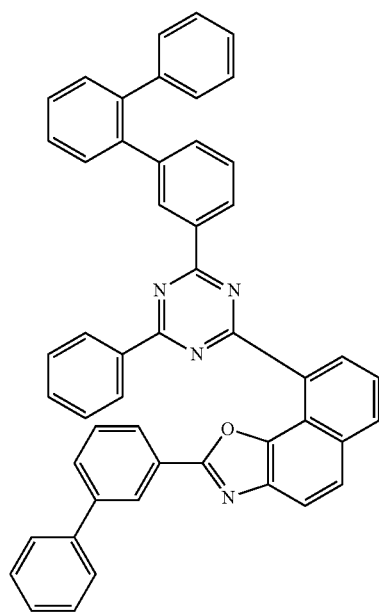
460
-continued
389
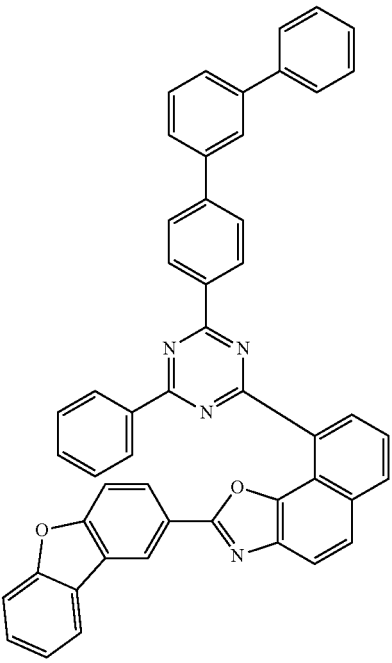
390
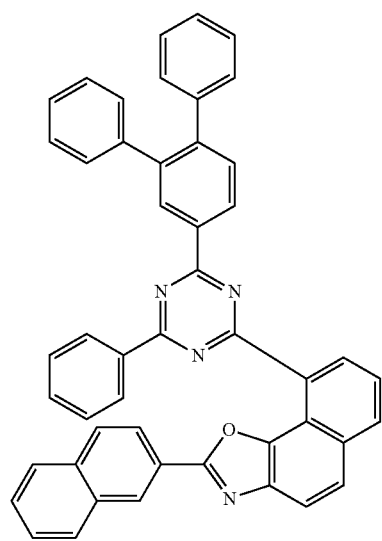

391 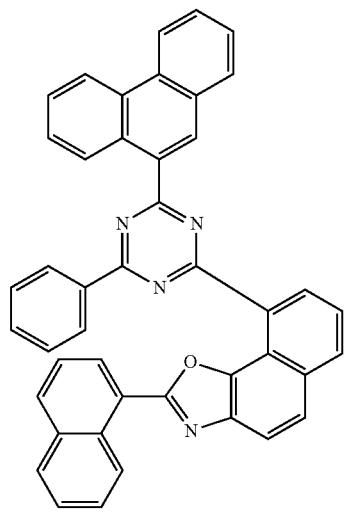
392 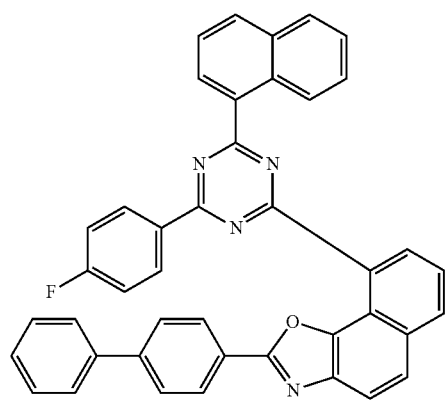
393 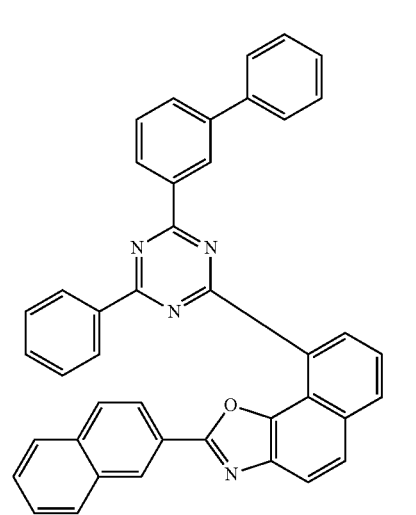
394 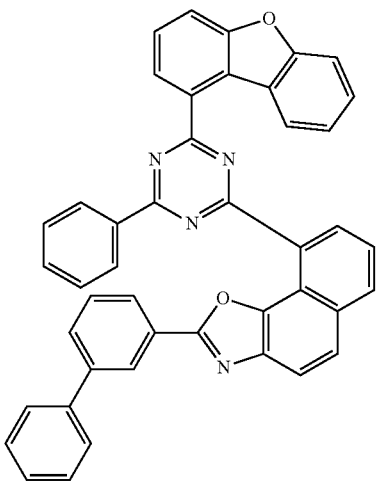
395 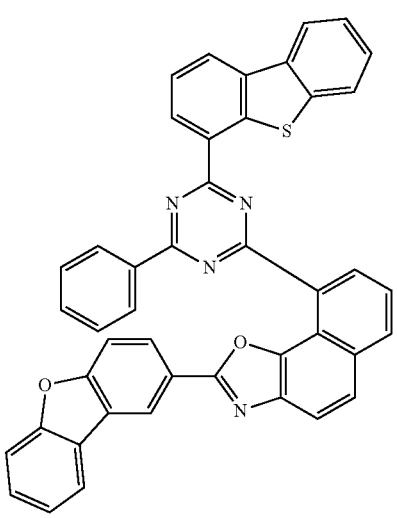
396 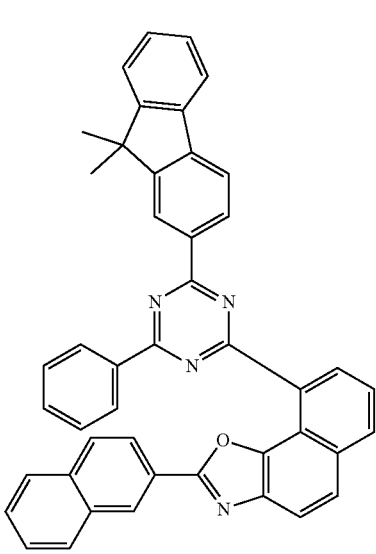

463
-continued

397

398

464
-continued

399

400

465
-continued
401
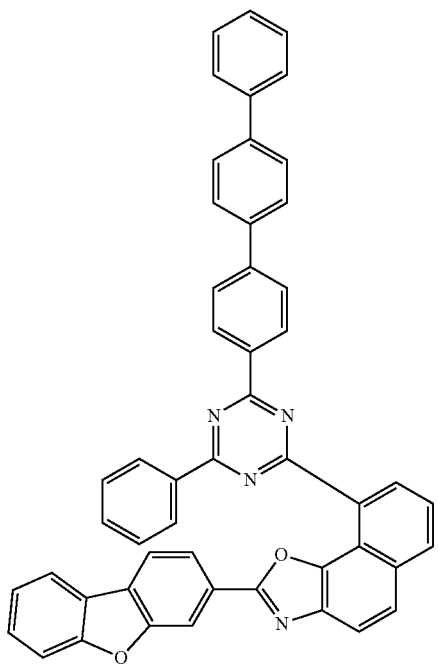
402
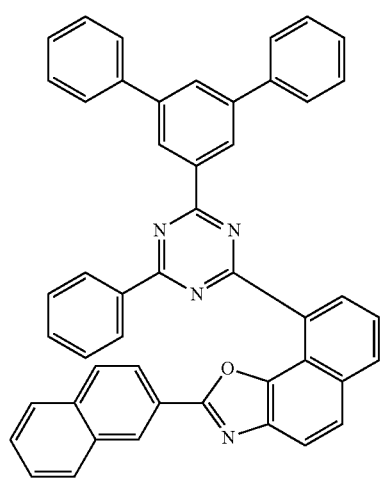
466
-continued
403
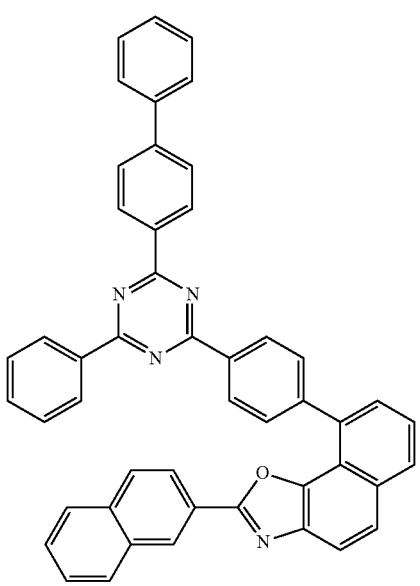
404
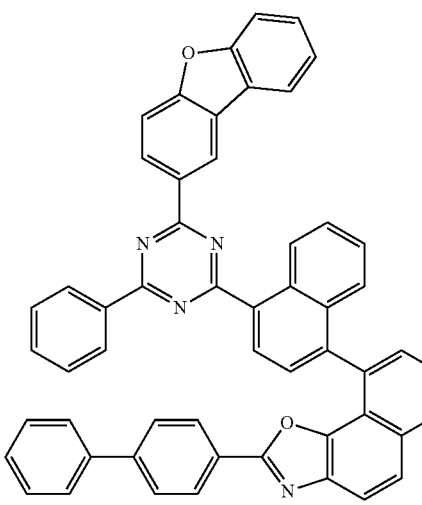
405
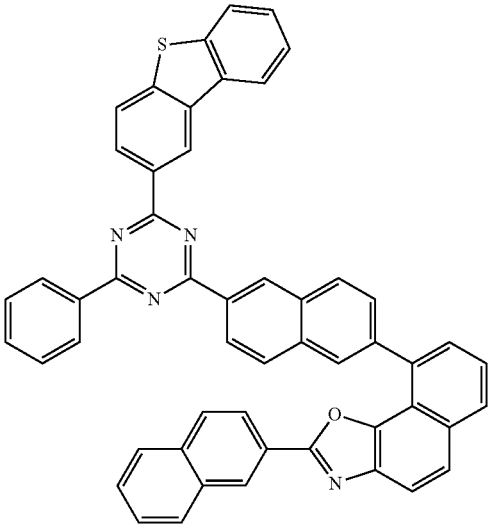

-continued
406
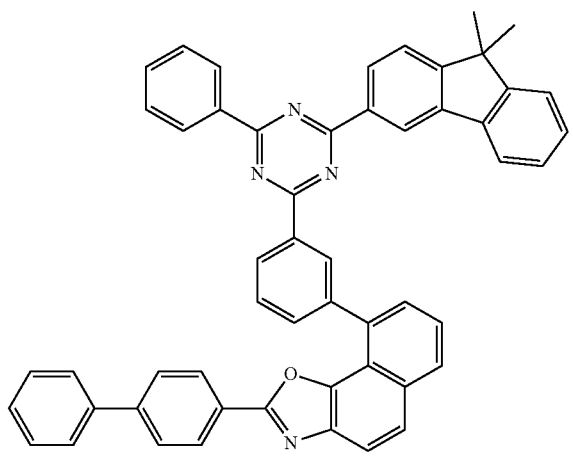
407
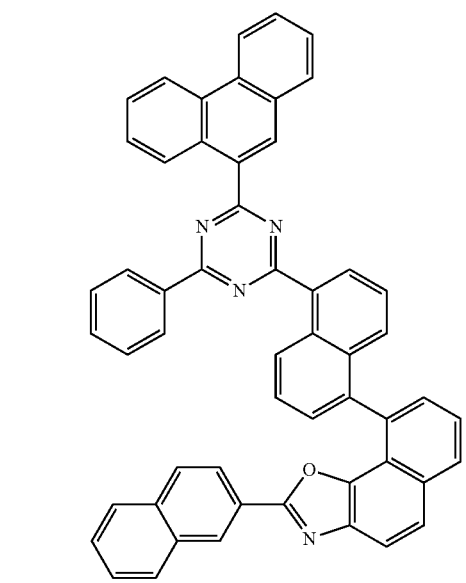
408
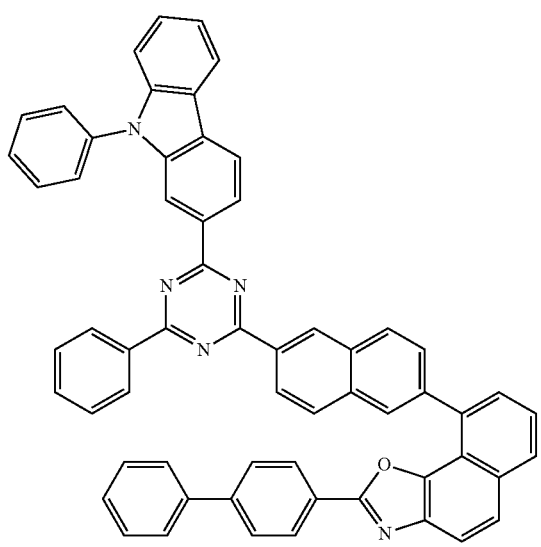
-continued
409
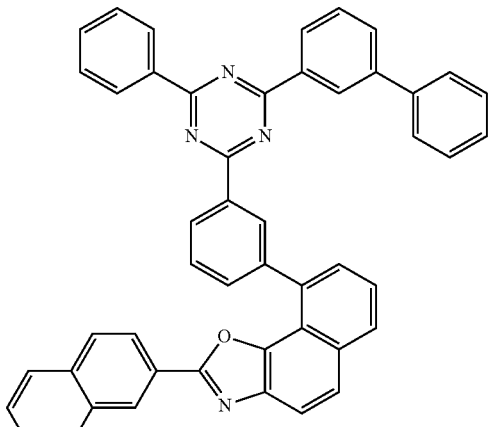
410
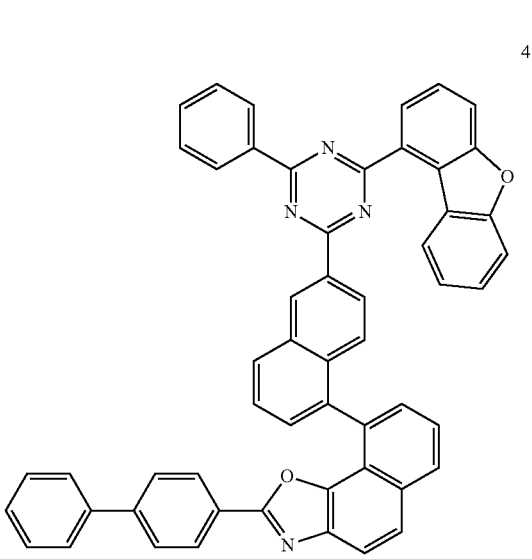
411
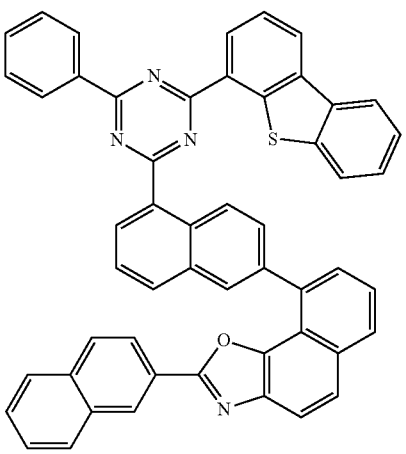

469
-continued
412
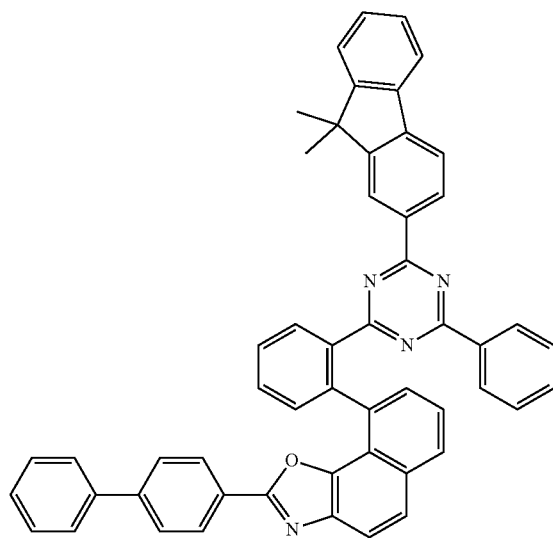
413
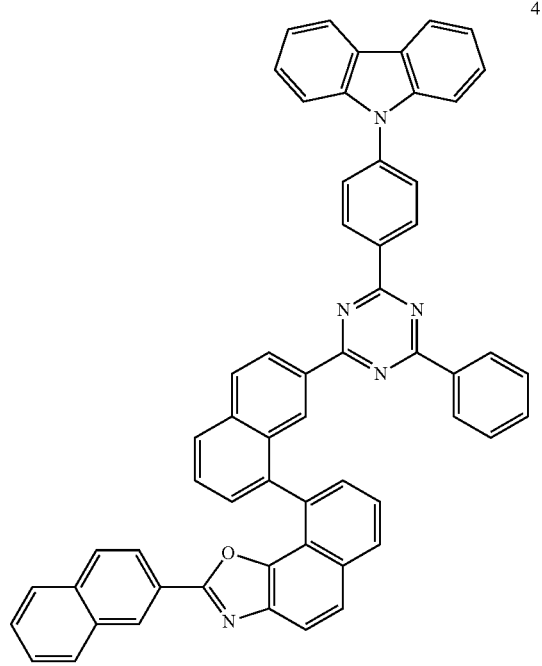
470
-continued
414
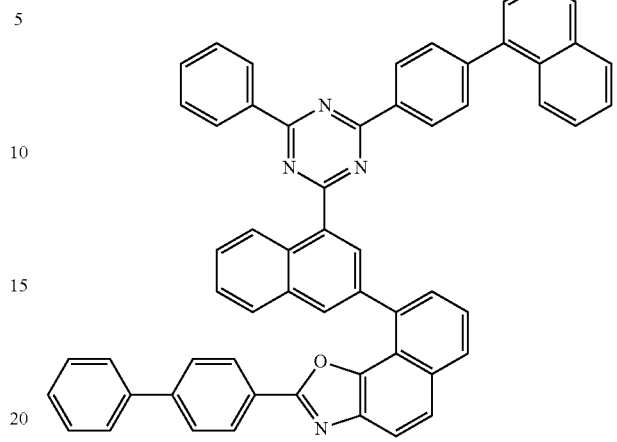
415
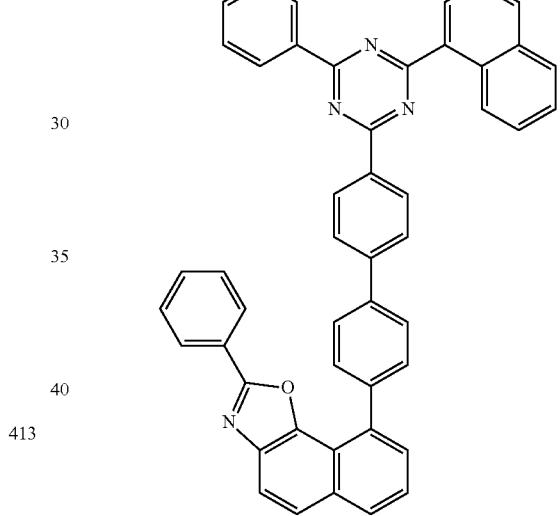
416
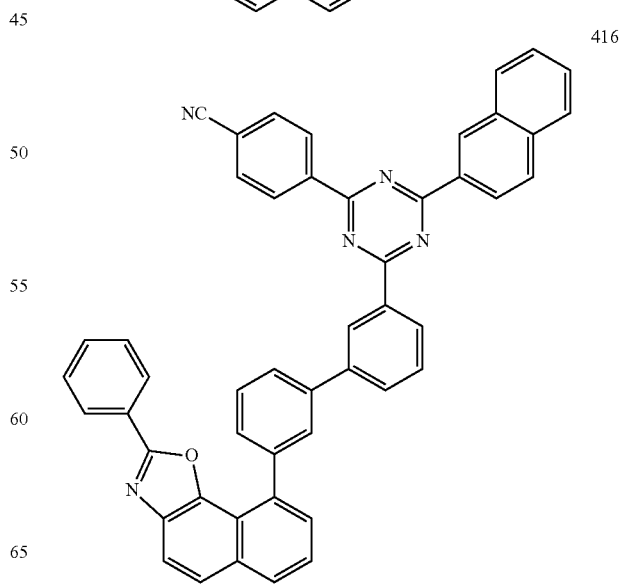

417
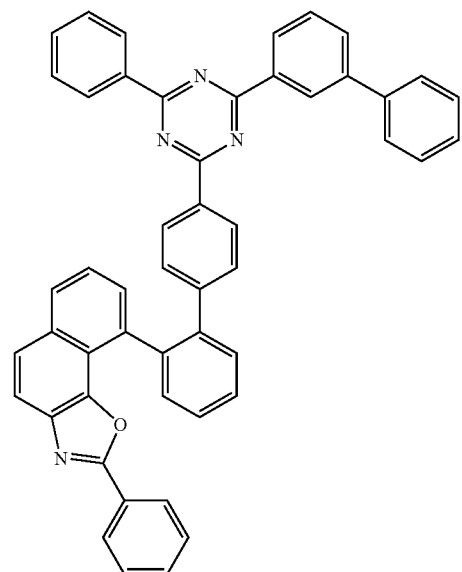
418
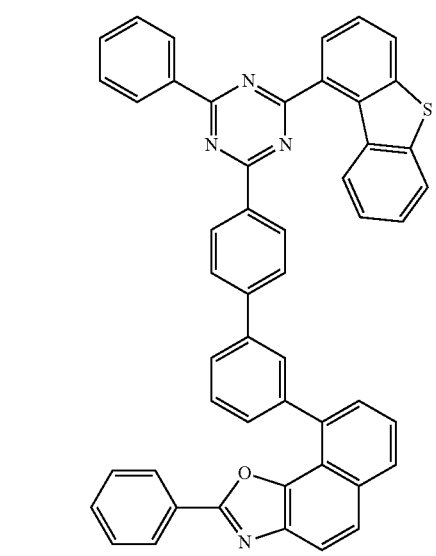
420
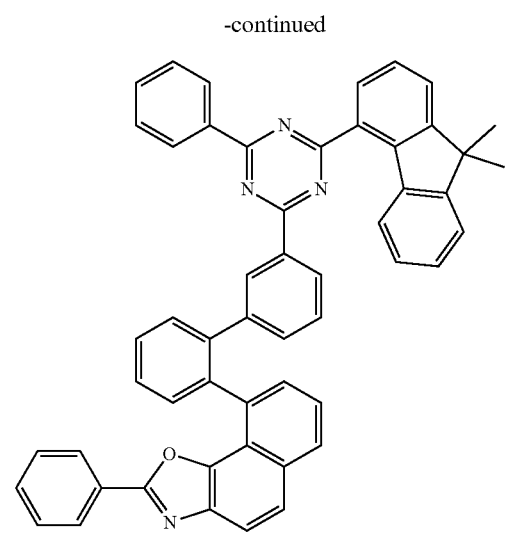
421
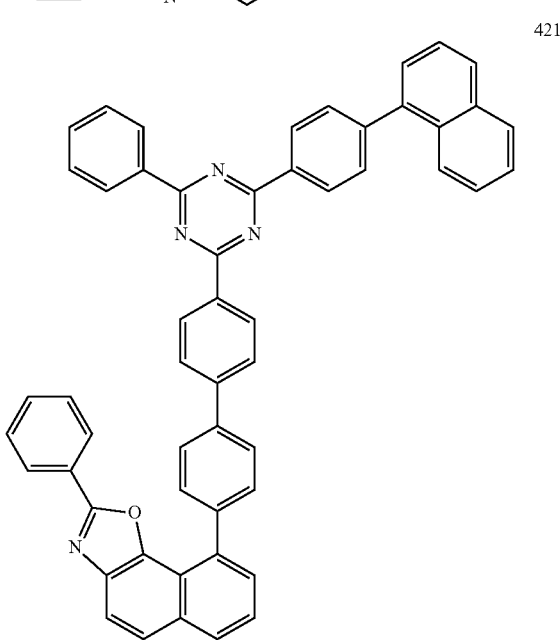
422
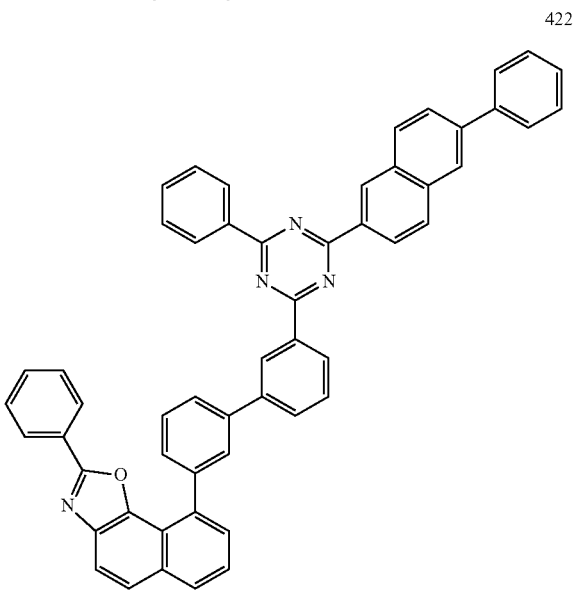

473
-continued
423
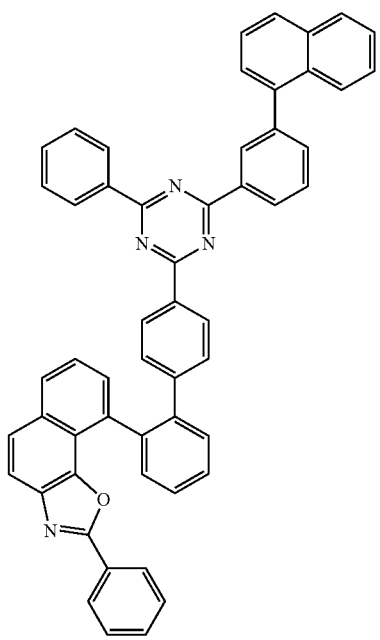
424
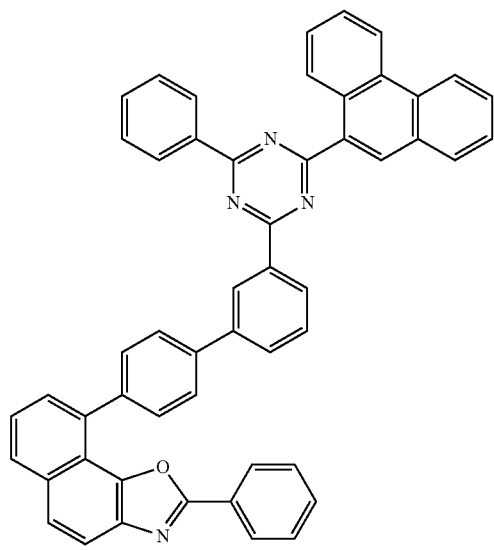
474
-continued
425
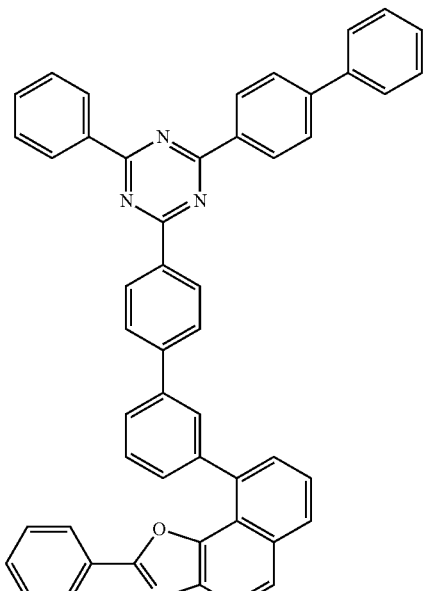
426
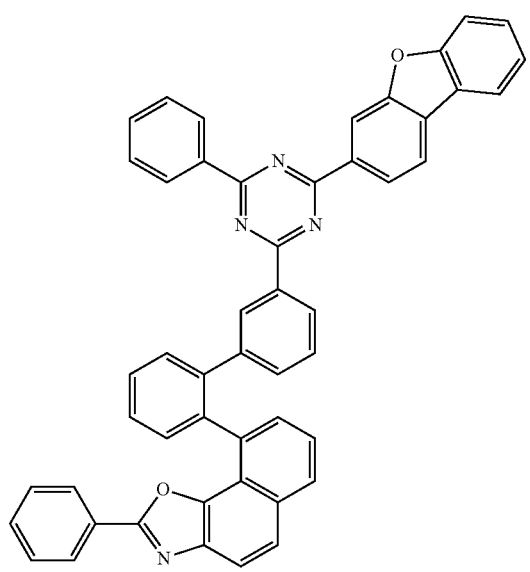
* * * * *